United States Patent
Beigelman et al.

(10) Patent No.: US 11,485,753 B2
(45) Date of Patent: *Nov. 1, 2022

(54) SUBSTITUTED NUCLEOSIDES, NUCLEOTIDES AND ANALOGS THEREOF

(71) Applicant: JANSSEN PHARMACEUTICA NV, Beerse (BE)

(72) Inventors: Leonid Beigelman, San Mateo, CA (US); Guangyi Wang, Carlsbad, CA (US); David Bernard Smith, San Mateo, CA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 17/063,545

(22) Filed: Oct. 5, 2020

(65) Prior Publication Data
US 2021/0139523 A1 May 13, 2021

Related U.S. Application Data

(63) Continuation of application No. 16/692,858, filed on Nov. 22, 2019, now Pat. No. 10,793,591, which is a continuation of application No. 16/161,705, filed on Oct. 16, 2018, now Pat. No. 10,487,104, which is a continuation of application No. 15/256,337, filed on Sep. 2, 2016, now Pat. No. 10,112,966, which is a continuation of application No. 14/836,896, filed on Aug. 26, 2015, now abandoned, which is a continuation of application No. 14/135,484, filed on Dec. 19, 2013, now Pat. No. 9,243,022.

(60) Provisional application No. 61/890,125, filed on Oct. 11, 2013, provisional application No. 61/745,466, filed on Dec. 21, 2012.

(51) Int. Cl.
| | |
|---|---|
| *A61K 31/7076* | (2006.01) |
| *C07H 19/10* | (2006.01) |
| *C07H 19/06* | (2006.01) |
| *C07H 19/20* | (2006.01) |
| *C07H 19/173* | (2006.01) |
| *C07H 19/213* | (2006.01) |
| *A61P 31/14* | (2006.01) |
| *C07H 19/16* | (2006.01) |
| *C07H 19/207* | (2006.01) |

(52) U.S. Cl.
CPC ......... *C07H 19/10* (2013.01); *A61K 31/7076* (2013.01); *A61P 31/14* (2018.01); *C07H 19/06* (2013.01); *C07H 19/16* (2013.01); *C07H 19/173* (2013.01); *C07H 19/20* (2013.01); *C07H 19/207* (2013.01); *C07H 19/213* (2013.01)

(58) Field of Classification Search
None
See application file for complete search history.

(56) References Cited

U.S. PATENT DOCUMENTS

| | | | |
|---|---|---|---|
| 3,817,978 | A | 6/1974 | Verheyden |
| 3,852,267 | A | 12/1974 | Robins |
| 4,713,383 | A | 12/1987 | Francis |
| 5,679,342 | A | 10/1997 | Houghton |
| 5,712,088 | A | 1/1998 | Houghton |
| 5,714,596 | A | 2/1998 | Houghton |
| 5,863,719 | A | 1/1999 | Houghton |
| 6,027,729 | A | 2/2000 | Houghton |
| 6,074,816 | A | 6/2000 | Houghton |
| 6,096,541 | A | 8/2000 | Houghton |
| 6,171,782 | B1 | 1/2001 | Houghton |
| 6,348,587 | B1 | 2/2002 | Schinazi |
| 6,495,677 | B1 | 12/2002 | Ramasamy |
| 6,777,395 | B2 | 8/2004 | Bhat |
| 6,787,525 | B1 | 9/2004 | Schott |
| 6,812,219 | B2 | 11/2004 | Lacolla |
| 6,911,424 | B2 | 6/2005 | Schinazi |
| 7,138,376 | B2 | 11/2006 | Gosselin |
| 7,307,065 | B2 | 12/2007 | Schinazi |
| 7,429,572 | B2 | 9/2008 | Clark |
| 7,608,597 | B2 | 10/2009 | Sommadossi |
| 7,608,600 | B2 | 10/2009 | Storer |
| 7,790,366 | B1 | 9/2010 | Houghton |
| 7,964,580 | B2 | 6/2011 | Sofia |
| 8,168,583 | B2 | 5/2012 | Schinazi |
| 8,173,621 | B2 | 5/2012 | Du |
| 8,334,270 | B2 | 12/2012 | Sofia |
| 8,415,322 | B2 | 4/2013 | Clark |
| 8,563,530 | B2 | 10/2013 | Chang |
| 8,580,765 | B2 | 11/2013 | Sofia |
| 8,609,627 | B2 | 12/2013 | Cho |

(Continued)

FOREIGN PATENT DOCUMENTS

| | | |
|---|---|---|
| AU | 5181998 | 11/1998 |
| CA | 2026131 A1 | 3/1991 |

(Continued)

OTHER PUBLICATIONS

Alexandrova, L.L. et al. (2011). "Cheminform Abstract: 4'-C-Nuceloside Derivatives: Synthesis and Antiviral Properties," Russian Journal of Bioorganic Chemistry. 37(6):651-671.

(Continued)

*Primary Examiner* — Traviss C McIntosh, III
(74) *Attorney, Agent, or Firm* — Morrison & Foerster LLP

(57) ABSTRACT

Disclosed herein are nucleotide analogs, methods of synthesizing nucleotide analogs and methods of treating diseases and/or conditions such as a HCV infection with one or more nucleotide analogs.

20 Claims, 62 Drawing Sheets

Specification includes a Sequence Listing.

(56) References Cited

U.S. PATENT DOCUMENTS

| | | |
|---|---|---|
| 8,629,263 B2 | 1/2014 | Ross |
| 8,716,263 B2 | 5/2014 | Chun |
| 8,735,372 B2 | 5/2014 | Du |
| 8,759,510 B2 | 6/2014 | Du |
| 8,877,731 B2 | 11/2014 | Beigelman et al. |
| 9,045,520 B2 | 6/2015 | Chun |
| 9,073,960 B2 | 7/2015 | Beigelman et al. |
| 9,090,642 B2 | 7/2015 | Cho |
| 9,173,893 B2 | 11/2015 | Cho |
| 9,180,138 B2 | 11/2015 | Schinazi |
| 9,211,300 B2 | 12/2015 | Mayes |
| 9,243,022 B2 * | 1/2016 | Beigelman ............. C07H 19/10 |
| 9,249,174 B2 | 2/2016 | Beigelman |
| 9,328,199 B2 | 5/2016 | García Pérez et al. |
| 9,346,848 B2 | 5/2016 | Beigelman et al. |
| 9,422,322 B2 | 8/2016 | Dyatkina et al. |
| 9,441,007 B2 | 9/2016 | Wang et al. |
| 9,603,863 B2 | 3/2017 | Blatt |
| 9,603,864 B2 * | 3/2017 | Blatt .................... A61P 31/14 |
| 9,724,351 B2 | 8/2017 | Wang et al. |
| 9,815,864 B2 | 11/2017 | Beigelman |
| 9,862,743 B2 | 1/2018 | Beigelman et al. |
| 9,890,188 B2 | 2/2018 | Wang et al. |
| 9,908,914 B2 | 3/2018 | Serebryany et al. |
| 9,932,363 B2 | 4/2018 | Dyatkina et al. |
| 10,052,342 B2 | 8/2018 | Blatt et al. |
| 10,112,966 B2 * | 10/2018 | Beigelman ............. C07H 19/10 |
| 10,144,755 B2 | 12/2018 | Beigelman |
| 10,183,945 B2 | 1/2019 | Welch et al. |
| 10,208,045 B2 | 2/2019 | Hendricks et al. |
| 10,251,882 B2 | 4/2019 | Hendricks et al. |
| 10,307,439 B2 * | 6/2019 | Blatt .................... A61P 31/14 |
| 10,358,453 B2 | 7/2019 | Wang et al. |
| 10,364,226 B2 | 7/2019 | Beigelman et al. |
| 10,370,401 B2 * | 8/2019 | Beigelman ......... A61K 31/7072 |
| 10,464,965 B2 | 11/2019 | Beigelman et al. |
| 10,485,815 B2 | 11/2019 | Wang |
| 10,487,104 B2 * | 11/2019 | Beigelman ........... C07H 19/173 |
| 10,519,185 B2 | 12/2019 | Serebryany |
| 10,683,320 B2 | 6/2020 | Beigelman et al. |
| 10,696,708 B2 | 6/2020 | Dyatkina et al. |
| 10,702,523 B2 | 7/2020 | Hendricks |
| RE48,171 E | 8/2020 | Wang et al. |
| 10,745,427 B2 | 8/2020 | Beigelman |
| 10,780,105 B2 | 9/2020 | Blatt |
| 10,793,591 B2 * | 10/2020 | Beigelman ............. C07H 19/06 |
| 2003/0087873 A1 | 5/2003 | Stuyver |
| 2003/0129712 A1 | 7/2003 | Poechlauer |
| 2003/0236216 A1 | 12/2003 | Devos |
| 2004/0002596 A1 | 1/2004 | Hong |
| 2004/0006002 A1 | 1/2004 | Sommadossi |
| 2004/0181052 A1 | 9/2004 | Sourena |
| 2004/0209904 A1 | 10/2004 | Dunn |
| 2004/0229839 A1 | 11/2004 | Babu |
| 2004/0259934 A1 | 12/2004 | Olsen |
| 2005/0009737 A1 | 1/2005 | Clark |
| 2006/0205685 A1 | 9/2006 | Phiasivongsa |
| 2007/0042988 A1 | 2/2007 | Klumpp |
| 2008/0070861 A1 | 3/2008 | Clark |
| 2008/0255038 A1 | 10/2008 | Hopkins |
| 2009/0076062 A1 | 3/2009 | Maibaum |
| 2009/0162292 A1 | 6/2009 | Thompson |
| 2009/0176732 A1 | 7/2009 | Beigelman |
| 2010/0016251 A1 | 1/2010 | Sofia |
| 2010/0151001 A1 | 6/2010 | Schott |
| 2010/0240604 A1 | 9/2010 | Beigelman |
| 2010/0279973 A1 | 11/2010 | Chun |
| 2010/0286083 A1 | 11/2010 | Bao |
| 2010/0298257 A1 | 11/2010 | Ross |
| 2010/0331397 A1 | 12/2010 | Beigelman |
| 2011/0015146 A1 | 1/2011 | Sofia |
| 2011/0091943 A1 | 4/2011 | Gallou |
| 2011/0171192 A1 | 7/2011 | Tomiyama |
| 2011/0257121 A1 | 10/2011 | Chang |
| 2011/0287927 A1 | 11/2011 | Grasset |
| 2011/0288308 A1 | 11/2011 | Grasset |
| 2012/0040924 A1 | 2/2012 | Cho |
| 2012/0041184 A1 | 2/2012 | Beigelman |
| 2012/0070411 A1 | 3/2012 | Beigelman |
| 2012/0070415 A1 | 3/2012 | Beigelman |
| 2012/0071434 A1 | 3/2012 | Smith |
| 2012/0157511 A1 | 6/2012 | Manoharan |
| 2012/0165286 A1 | 6/2012 | Beigelman |
| 2012/0165515 A1 | 6/2012 | Bhat |
| 2012/0219568 A1 | 8/2012 | Liu |
| 2012/0258928 A1 | 10/2012 | Du |
| 2012/0263678 A1 | 10/2012 | Cho |
| 2012/0316327 A1 | 12/2012 | Chun |
| 2013/0017171 A1 | 1/2013 | Sommadossi |
| 2013/0029929 A1 | 1/2013 | Sofia |
| 2013/0078217 A1 | 3/2013 | Wang |
| 2013/0137143 A1 | 5/2013 | Gallou |
| 2013/0164261 A1 | 6/2013 | Wang |
| 2013/0165400 A1 | 6/2013 | Beigelman |
| 2013/0252920 A1 | 9/2013 | Blatt |
| 2013/0253181 A1 | 9/2013 | Serebryany |
| 2013/0281686 A1 | 10/2013 | Cho |
| 2013/0281687 A1 | 10/2013 | Serebryany |
| 2013/0315862 A1 | 11/2013 | Sommadossi |
| 2013/0315868 A1 | 11/2013 | Mayes |
| 2013/0323836 A1 | 12/2013 | Manoharan |
| 2014/0057863 A1 | 2/2014 | Stuyver |
| 2014/0057864 A1 | 2/2014 | Kim |
| 2014/0088117 A1 | 3/2014 | Burch |
| 2014/0178336 A1 | 6/2014 | Link et al. |
| 2014/0178338 A1 | 6/2014 | Mayes |
| 2014/0179627 A1 | 6/2014 | Beigelman |
| 2014/0179667 A1 | 6/2014 | Edwards et al. |
| 2014/0179910 A1 | 6/2014 | Beigelman |
| 2014/0206608 A1 | 7/2014 | Haack et al. |
| 2014/0213554 A1 | 7/2014 | Wu et al. |
| 2014/0213591 A1 | 7/2014 | Chen et al. |
| 2014/0288020 A1 | 9/2014 | Du |
| 2014/0303108 A1 | 10/2014 | Beigelman |
| 2014/0303113 A1 | 10/2014 | Krop |
| 2014/0315852 A1 | 10/2014 | Du |
| 2014/0329794 A1 | 11/2014 | Duncan et al. |
| 2014/0341847 A1 | 11/2014 | Smith |
| 2015/0005251 A1 | 1/2015 | Dyatkina et al. |
| 2015/0011497 A1 | 1/2015 | Beigelman |
| 2015/0038451 A1 | 2/2015 | Smith |
| 2015/0051167 A1 | 2/2015 | Wang |
| 2015/0065504 A1 | 3/2015 | Wang et al. |
| 2015/0072982 A1 | 3/2015 | Hendricks et al. |
| 2015/0105341 A1 | 4/2015 | Beigelman |
| 2015/0141363 A1 | 5/2015 | Wang |
| 2015/0183818 A1 | 7/2015 | Tran |
| 2015/0183819 A1 | 7/2015 | Beigelman |
| 2015/0238498 A1 | 8/2015 | Wang et al. |
| 2015/0284434 A1 | 10/2015 | Bissantz et al. |
| 2015/0307471 A1 | 10/2015 | Willand et al. |
| 2015/0315228 A1 | 11/2015 | Beigelman |
| 2015/0344432 A1 | 12/2015 | Jordan et al. |
| 2015/0361020 A1 | 12/2015 | Van Tilborg |
| 2015/0366887 A1 | 12/2015 | Blatt |
| 2015/0366888 A1 | 12/2015 | Blatt |
| 2016/0002208 A1 | 1/2016 | Maue et al. |
| 2016/0016987 A1 | 1/2016 | Beigelman |
| 2016/0022724 A1 | 1/2016 | Chanda |
| 2016/0024136 A1 | 1/2016 | Beigelman |
| 2016/0039858 A1 | 2/2016 | Beigelman |
| 2016/0045528 A1 | 2/2016 | Blatt et al. |
| 2016/0115190 A1 | 4/2016 | Serebryany |
| 2016/0221963 A1 | 8/2016 | Beigelman et al. |
| 2016/0228438 A1 | 8/2016 | Hendricks et al. |
| 2016/0244460 A1 | 8/2016 | Wang et al. |
| 2016/0264581 A1 | 9/2016 | Hendricks et al. |
| 2016/0264610 A1 | 9/2016 | Beigelman |
| 2016/0318967 A1 | 11/2016 | Dyatkina |
| 2016/0331770 A1 | 11/2016 | Wang |
| 2017/0037075 A1 | 2/2017 | Beigelman |
| 2017/0037077 A1 | 2/2017 | Beigelman |
| 2017/0143749 A1 | 5/2017 | Blatt |
| 2017/0143751 A1 | 5/2017 | Blatt |

(56) References Cited

U.S. PATENT DOCUMENTS

| | | |
|---|---|---|
| 2017/0260189 A1 | 9/2017 | Welch et al. |
| 2017/0283429 A1 | 10/2017 | Wang et al. |
| 2018/0044369 A1 | 2/2018 | Beigelman |
| 2018/0065932 A1 | 3/2018 | Wang et al. |
| 2018/0079774 A1 | 3/2018 | Beigelman |
| 2018/0117042 A1 | 5/2018 | Chanda |
| 2018/0186825 A1 | 7/2018 | Serebryany |
| 2018/0194793 A1 | 7/2018 | Dyatkina |
| 2019/0031703 A1 | 1/2019 | Beigelman |
| 2019/0054108 A1 | 2/2019 | Blatt |
| 2019/0055273 A1 | 2/2019 | Beigelman |
| 2019/0085011 A1 | 3/2019 | Beigelman |
| 2019/0263754 A1 | 8/2019 | Wang |
| 2019/0314373 A1 | 10/2019 | Hendricks et al. |
| 2019/0381081 A1 | 12/2019 | Wang |
| 2020/0024297 A1 | 1/2020 | Beigelman et al. |
| 2020/0030328 A1 | 1/2020 | Hendricks et al. |
| 2020/0079813 A1 | 3/2020 | Beigelman |
| 2020/0392169 A1 | 12/2020 | Beigelman et al. |

FOREIGN PATENT DOCUMENTS

| | | |
|---|---|---|
| CA | 2087967 A1 | 1/1992 |
| CA | 2600359 A1 | 9/2006 |
| CL | 200800902 A1 | 11/2008 |
| CL | 2008003431 A1 | 11/2008 |
| CL | 201001407 A1 | 5/2011 |
| CL | 201403168 A1 | 5/2015 |
| CL | 2015001702 A1 | 8/2015 |
| CL | 2015001751 A1 | 9/2015 |
| CL | 2015001790 A1 | 9/2015 |
| CL | 2015001724 A1 | 10/2015 |
| CL | 2015001733 A1 | 10/2015 |
| CL | 2015001785 A1 | 10/2015 |
| CL | 2015001754 A1 | 11/2015 |
| CL | 2015001881 A1 | 11/2015 |
| CL | 2015001640 | 1/2016 |
| CL | 2015001771 A1 | 1/2016 |
| CL | 2015003357 A1 | 11/2016 |
| CN | 1816558 A | 8/2006 |
| CN | 101918425 A | 12/2010 |
| CN | 102119167 A | 7/2011 |
| CN | 103201345 A | 5/2013 |
| CN | 105307662 A | 2/2016 |
| DE | 4232852 A1 | 3/1994 |
| DE | 19855963 A1 | 6/2000 |
| DE | 20121305 U1 | 9/2002 |
| EA | 201190178 A1 | 6/2012 |
| EP | 1178049 A1 | 2/2002 |
| EP | 1323830 A2 | 7/2003 |
| EP | 1980568 A1 | 10/2008 |
| EP | 2264169 A1 | 12/2010 |
| EP | 2388069 A1 | 11/2011 |
| EP | 2392580 A1 | 12/2011 |
| FR | 2977586 A1 | 10/2008 |
| IL | 242605 A | 8/2018 |
| IN | 167775 A1 | 12/1990 |
| JP | 05069681 A | 3/1993 |
| JP | 07242544 A | 9/1995 |
| JP | 2004520367 A | 7/2004 |
| JP | 2004532184 A | 10/2004 |
| JP | 2008214305 A | 9/2008 |
| JP | 2010505902 A | 2/2010 |
| JP | 2010532747 A | 10/2010 |
| JP | 2011503234 A | 10/2011 |
| JP | 2012502956 A | 2/2012 |
| JP | 2016505595 A | 2/2016 |
| JP | 2016514104 A | 5/2016 |
| JP | 2016536288 A | 11/2016 |
| JP | 6284547 B2 | 2/2018 |
| JP | 6637023 B2 | 12/2019 |
| KR | 20140108290 A | 9/2014 |
| KR | 20150013825 A | 2/2015 |
| WO | 199316075 A1 | 8/1993 |
| WO | 199428715 A1 | 12/1994 |
| WO | 199508540 A1 | 3/1995 |
| WO | 199515332 A1 | 6/1995 |
| WO | 199726883 A1 | 7/1997 |
| WO | 199816184 A2 | 4/1998 |
| WO | 199816186 A2 | 4/1998 |
| WO | 199914226 A2 | 3/1999 |
| WO | 199961583 A2 | 12/1999 |
| WO | 200034276 A1 | 6/2000 |
| WO | 200066604 A2 | 11/2000 |
| WO | 200168663 A1 | 9/2001 |
| WO | 200203997 A1 | 1/2002 |
| WO | 2002057287 A2 | 7/2002 |
| WO | 2002057425 A2 | 7/2002 |
| WO | 2002100415 A2 | 12/2002 |
| WO | 2003022859 A2 | 3/2003 |
| WO | 2003026589 A2 | 4/2003 |
| WO | 2003039523 A2 | 5/2003 |
| WO | 2003048315 A2 | 6/2003 |
| WO | 2003068244 A1 | 8/2003 |
| WO | 2003073989 A2 | 9/2003 |
| WO | 2003099840 A1 | 12/2003 |
| WO | 2004002999 A2 | 1/2004 |
| WO | 2004003138 A2 | 1/2004 |
| WO | 2004007512 A2 | 1/2004 |
| WO | 2004014312 A2 | 2/2004 |
| WO | 2004037159 A2 | 5/2004 |
| WO | 2004080466 A1 | 9/2004 |
| WO | 2004091499 A2 | 10/2004 |
| WO | 2004106356 A1 | 12/2004 |
| WO | 2005003147 A1 | 1/2005 |
| WO | 2005007810 A2 | 1/2005 |
| WO | 2005009418 A2 | 2/2005 |
| WO | 2005020884 A2 | 3/2005 |
| WO | 2005021568 A2 | 3/2005 |
| WO | 2005034878 A2 | 4/2005 |
| WO | 2006000922 A2 | 1/2006 |
| WO | 2006012078 A2 | 2/2006 |
| WO | 2006063717 A2 | 6/2006 |
| WO | 2006094347 A1 | 9/2006 |
| WO | 2006105440 A2 | 10/2006 |
| WO | 2006116512 A1 | 11/2006 |
| WO | 2007113538 A1 | 10/2007 |
| WO | 2008012555 A2 | 1/2008 |
| WO | 2008043704 A | 4/2008 |
| WO | 2008089439 A2 | 7/2008 |
| WO | 2008095040 A2 | 8/2008 |
| WO | 2008117047 A1 | 10/2008 |
| WO | 2008121634 A2 | 10/2008 |
| WO | 2009001097 A2 | 12/2008 |
| WO | 2009003042 A1 | 12/2008 |
| WO | 2009010299 A1 | 1/2009 |
| WO | 2009040269 A1 | 4/2009 |
| WO | 2009058800 A2 | 5/2009 |
| WO | 2009067409 A1 | 5/2009 |
| WO | 2009086201 A1 | 7/2009 |
| WO | 2009105712 A1 | 8/2009 |
| WO | 2009129120 A2 | 10/2009 |
| WO | 2009152095 A2 | 12/2009 |
| WO | 2010002877 A2 | 1/2010 |
| WO | 2010026153 A1 | 3/2010 |
| WO | 2010027005 A1 | 3/2010 |
| WO | 2010031829 A1 | 3/2010 |
| WO | 2010075554 A1 | 7/2010 |
| WO | 2010084115 A2 | 7/2010 |
| WO | 2010088924 A1 | 8/2010 |
| WO | 2010089128 A2 | 8/2010 |
| WO | 2010091386 A2 | 8/2010 |
| WO | 2010108140 A1 | 9/2010 |
| WO | 2011005860 A2 | 1/2011 |
| WO | 2011029537 A1 | 3/2011 |
| WO | 2011039221 A2 | 4/2011 |
| WO | 2011057204 A2 | 5/2011 |
| WO | 2011119869 A1 | 9/2011 |
| WO | 2011133871 A2 | 10/2011 |
| WO | 2012012465 A1 | 1/2012 |
| WO | 2012012776 A1 | 1/2012 |
| WO | 2012025857 A1 | 3/2012 |
| WO | 2012037038 A1 | 3/2012 |
| WO | 2012040124 A1 | 3/2012 |

(56) References Cited

FOREIGN PATENT DOCUMENTS

| WO | 2012041965 A1 | 4/2012 |
|---|---|---|
| WO | 2012074547 A2 | 6/2012 |
| WO | 2012088155 A1 | 6/2012 |
| WO | 2012094248 A1 | 7/2012 |
| WO | 2012099630 A1 | 7/2012 |
| WO | 2012142085 A1 | 10/2012 |
| WO | 2012167133 A2 | 12/2012 |
| WO | 2013019874 A1 | 2/2013 |
| WO | 2013072466 A1 | 5/2013 |
| WO | 2013087765 A1 | 6/2013 |
| WO | 2013092481 A1 | 6/2013 |
| WO | 2013096679 A1 | 6/2013 |
| WO | 2013138210 A1 | 9/2013 |
| WO | 2013142124 A1 | 9/2013 |
| WO | 2013142159 A1 | 9/2013 |
| WO | 2013142525 A1 | 9/2013 |
| WO | 2013177219 A1 | 11/2013 |
| WO | 2014008236 A1 | 1/2014 |
| WO | 2014031784 A1 | 2/2014 |
| WO | 2014047117 A1 | 3/2014 |
| WO | 2014048532 A1 | 4/2014 |
| WO | 2014070771 A1 | 5/2014 |
| WO | 2014099941 A1 | 6/2014 |
| WO | 2014100498 A1 | 6/2014 |
| WO | 2014100505 A1 | 6/2014 |
| WO | 2014134251 A1 | 9/2014 |
| WO | 2014135439 A1 | 9/2014 |
| WO | 2014164533 A1 | 10/2014 |
| WO | 2014186637 A1 | 11/2014 |
| WO | 2014209979 A1 | 12/2014 |
| WO | 2014209983 A1 | 12/2014 |
| WO | 2015026792 A1 | 2/2015 |
| WO | 2015038655 A1 | 3/2015 |
| WO | 2015038660 A1 | 3/2015 |
| WO | 2015054465 A1 | 4/2015 |
| WO | 2015200205 A1 | 12/2015 |
| WO | 2015200219 A1 | 12/2015 |
| WO | 2016014398 A1 | 1/2016 |
| WO | 2016022464 A1 | 2/2016 |
| WO | 2016069489 A1 | 5/2016 |
| WO | 2016138158 A1 | 9/2016 |
| WO | 2016145103 A1 | 9/2016 |
| WO | 2017156262 A1 | 9/2017 |
| WO | 2017156407 A1 | 9/2017 |
| WO | 2017223231 A1 | 12/2017 |
| WO | 2018081449 A1 | 5/2018 |
| WO | 2018222774 A1 | 12/2018 |
| WO | 2020121122 A1 | 6/2020 |
| WO | 2020121123 A2 | 6/2020 |

OTHER PUBLICATIONS

Arnold, J.J. et al. (2012). "Sensitivity of Mitochondrial Transcription and Resistance of RNA Polymerase II Dependent Nuclear Transcription to Antiviral Ribonucleosides" PLOS Pathogens 8(11)e1003030, 12 pages.
Article 94(3) Examination Report dated Jul. 28, 2017 for European Application No. 13864403.4, filed Dec. 19, 2013.
Decision on Rejection for Chinese Patent Application No. 201380072742.9 dated Nov. 1, 2017. (Translation).
Examination Report for Singapore Application No. 11201504554U dated Jan. 11, 2018.
Extended European Search Report dated Nov. 30, 2018 for European Application No. 18168337.6, filed Apr. 19, 2018.
Extended Search Report dated Jul. 13, 2016 for European Application No. 13864403.4 filed Dec. 19, 2013.
Final Office Action dated Oct. 24, 2017, for Japanese Application No. 2015-549476, filed Jun. 19, 2015 (translation).
First Examination Report dated May 16, 2017 for Australian Application No. 2013361200 filed Jul. 7, 2015.
Georgian Order No. 387/01 dated May 4, 2017 for Georgia Application No. N 13892/01 filed Dec. 19, 2013 (translation).

International Preliminary Report on Patentability dated Jun. 23, 2015 for PCT Application No. PCT/US2013/076740 filed Dec. 19, 2013.
International Search Report and Written Opinion dated Mar. 3, 2014 for PCT Application No. PCT/US2013/076740 filed Dec. 19, 2013.
Ivanov, M.A. et al. (2010). "Synthesis and Biological Properties of Pyrimidine 4' Fluoronucleosides and 4' Fluorouridine 5' 0 Triphosphate" Russian Journal of Bioorganic Chemistry 36(4):488-496.
Jonckers, T.H.M. et al. (May 14, 2016). "Discovery of 1-((2R,4aR,6R,7R,7aR)-2-Isopropoxy-2-oxidodihydro-4H,6H-spiro[furo[3,2-d][1,3,2]dioxaphosphinine-7,2'-oxetan]-6-yl)pyrimidine-2,4(1H,3H)-dione (JNJ-54257099), a 3'-5'-Cyclic Phosphate Ester Prodrug of 2'-Deoxy-2'-Spirooxetane Uridine Triphosphate Useful for HCV Inhibition" J. Med. Chem. 59:5790-5798.
Lee, S. et al. (2007, e-pub. Nov. 2, 2007). "A Concise Synthesis of 4'-Fluoro Nucleosides" Organic Letters 9 (24):5007-5009.
Lewis, W.L. et al. (Oct. 2003). "Mitochondrial Toxicity of NRTI Antiviral Drugs: An Integrated Cellular Perspective," Nature Reviews Drug Discovery 2:812-822.
Moyle, G. et al. (2000). "Clinical Manifestations and Management of Antiretroviral Nucleoside Analog-Related Mitochondrial Toxicity," Clin. Ther. 22(8):911-936.
Notice of Allowance dated Jan. 11, 2018 for Singapore Application No. 11201504554U filed Dec. 19, 2013.
Notice of Favorable Decision dated Jan. 20, 2017 for Georgia Application No. N 13892/01 filed Dec. 19, 2013 (Translation).
Office Action and Search Report in Taiwan Patent Application 102147608 dated Dec. 14, 2017, with an English Translation.
Office Action dated Apr. 15, 2018 for Israeli Application No. 239324 filed Jun. 10, 2015 (translation).
Office Action dated Apr. 18, 2018 for Indonesian Application No. P00201503822 filed Jun. 23, 2015 (translation).
Office Action dated Apr. 22, 2019 for Uzbekistan Patent Application No. IAP20150295 field Jul. 21, 2015. (Translation).
Office Action dated Apr. 30, 2017 for Israeli Application No. 239324 filed Dec. 19, 2013 (Translation).
Office Action dated Aug. 11, 2015 for Colombian Application No. 15141920 filed Dec. 19, 2013 (Translation).
Office Action dated Aug. 19, 2016 for Chinese Application No. 201380072742.9 filed Aug. 11, 2015. (translation).
Office Action dated Aug. 3, 2017 for Colombian Application No. 1514920 filed Dec. 19, 2013 (Translation).
Office Action dated Dec. 18, 2018 for Chilean Patent Application No. 2017-001769 filed Jul. 4, 2017. (Translation).
Office Action dated Feb. 2, 2016 for Georgia Application No. 13892/01 filed Dec. 19, 2013 (Translation).
Office Action dated Feb. 27, 2019 for Australian Patent Application No. 201820337 filed May 14, 2018.
Office Action dated Jan. 13, 2017 for Chilean Application No. 1699-2015 filed Jun. 17, 2015 (Translation).
Office Action dated Jan. 17, 2019 for Indian Patent Application No. 5505/DELNP/2015 filed Jun. 15, 2019.
Office Action dated Jan. 23, 2017 for Thai Application No. 1501003547 filed Jun. 19, 2015 (Translation).
Office Action dated Jul. 13, 2018 for Uzbekistan Application No. IAP20150295, filed Jun. 21, 2015 (translation).
Office Action dated Jul. 4, 2017 for Japanese Application No. 2015-549746 filed Jun. 19, 2015 (Translation).
Office Action dated Jul. 6, 2016 for Chilean Application No. 1699-2015 filed Dec. 19, 2016 (Translation).
Office Action dated Jul. 6, 2016 for Eurasian Application No. 201590943 filed Dec. 19, 2013 (Translation).
Office Action dated Jun. 11, 2019 for European Application No. 13864403.4, filed Dec. 19, 2013.
Office Action dated Jun. 12, 2018 for Ukrainian No. a 2015 05947, filed Jun. 16, 2015 (translation).
Office Action dated Jun. 12, 2019 for Mexican Application No. Mx/A/2015/007925 filed Jun. 18, 2015. (Translation).
Office Action dated Jun. 22, 2017 for Chinese Application No. 201380072742.9 filed Aug. 11, 2015 (Translation).
Office Action dated Jun. 30, 2016 for Israeli Application No. 239324 filed Dec. 19, 2013 (Translation).

(56) References Cited

OTHER PUBLICATIONS

Office Action dated Jun. 4, 2019 for Israeli Application No. 239324, filed Dec. 19, 2013. (Translation).
Office Action dated Mar. 25, 2020 for Israeli Patent Application No. 239324, Filed Jun. 10, 2015 (Translation).
Office Action dated Mar. 25, 2020 for Korean Patent Application No. 10-2015-7019672, Filed Jul. 20, 2015 (Translation).
Office Action dated May 21, 2020 for Canadian Patent Application No. 2894542, Filed Jun. 9, 2015.
Office Action dated May 26, 2020 for Australian Patent Application No. 2020200499, Filed Jan. 23, 2020.
Office Action dated May 7, 2019 for Japanese Patent Application No. 2017-243925 filed Dec. 20, 2017. (Translation).
Office Action dated Nov. 1, 2018, for Indonesian Application No. P00201503822 filed Jun. 23, 2015, (translation).
Office Action dated Nov. 30, 2016 for Colombian Application No. 15141920 filed Dec. 19, 2013 (translation).
Office Action dated Sep. 27, 2018, for Mexican Application No. MX/a/2015/007925 filed Jun. 18, 2015. (translation).
Office Action dated Sep. 4, 2018 for Japanese Application No. 2017-243925, filed Dec. 20, 2017 (translation).
Office Action dated Apr. 6, 2017 for Colombian Application No. 15141920 filed Dec. 19, 2013 (Translation).
Owen, G.R. et al. (1976). "4'-Substituted Nucleosides. Synthesis of Some 4'-Fluorouridine Derivatives," J. Org. Chem. 41(18):3010-3017.
Reexamination Decision dated Dec. 13, 2018 for Chinese Application No. 201380072742.9 filed Aug. 11, 2015. (Translation).
Reexamination Decision dated May 5, 2019 for Chinese Application No. 201380072742.9 filed Aug. 11, 2015. (Translation).
Search and Examination Report, and Notification Form 18 dated May 21, 2018 for ARIPO Application No. AP/P/2015/008533. (Translation).
Search Report and Documentary Conclusion dated Sep. 29, 2016 in Georgian Application No. 13892/01, filed Dec. 19, 2013 (Translation).
Search Report and Written Opinion dated May 19, 2016 for Singapore Application No. 11201504554U filed Dec. 19, 2016.
Second Examination Report dated Aug. 15, 2017 for Australian Application No. 2013361200 filed Jul. 7, 2015.
Sofia, M.J. (2011). "Review Nucleotide Prodrugs for HCV Therapy," Anitviral Chemistry et Chemotherapy 22:23-49.
Written Opinion dated Mar. 24, 2017 for Singapore Application No. 11201504554U filed Dec. 19, 2013.

\* cited by examiner

Figure 1: HCV Protease Inhibitors

Figure 1 (cont.): HCV Protease Inhibitors

| # | Name | Structure |
|---|---|---|
| 1006 | BMS-650032<br>BM032<br>Asunaprevir | 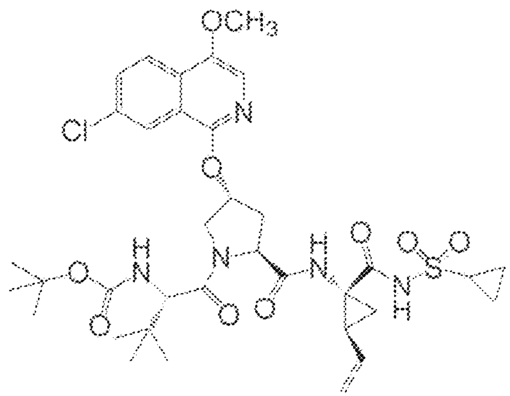 |
| 1007 | Boceprevir<br>SCH 503034 | 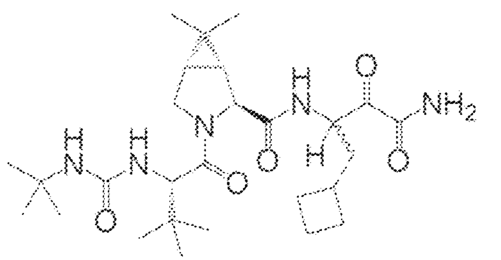 |
| 1008 | GS-9256 | |
| 1009 | GS-9451 | |
| 1010 | IDX-320 | |
| 1011 | ACH-1625 | |
| 1012 | ACH-2684 | |
| 1013 | TMC-435<br>TMC-435350 | |
| 1014 | Danoprevir<br>ITMN-191<br>RG7227<br>RO5190591 | |

Figure 1 (cont.): HCV Protease Inhibitors
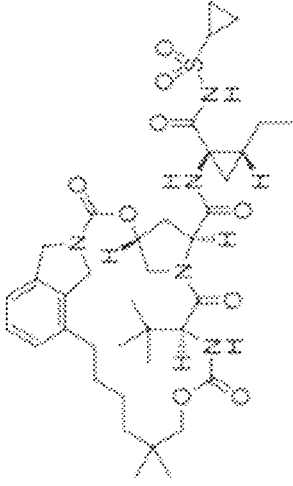
| # | Name | Structure |
|---|---|---|
| 1015 | MK-7009 Vaniprevir | 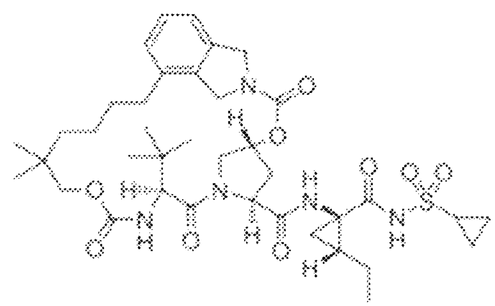 |
| 1016 | PHX1766 | |

Figure 2: HCV Polymerase Inhibitors – Nucleosides, Nucleotides and Analogs Thereof

| # | Name | Structure |
|---|---|---|
| 2001 | RG7128 Mericitabine | 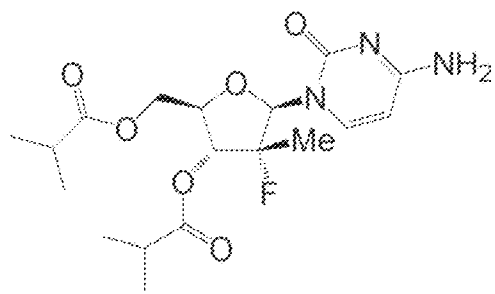 |
| 2002 | PSI-7851 | 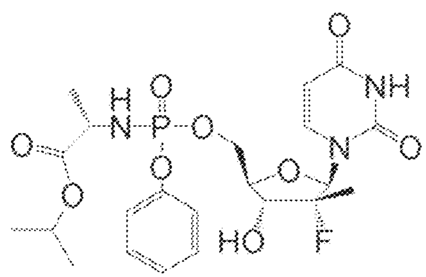 |
| 2003 | PSI-7977 GS-7977, Sofosbuvir | 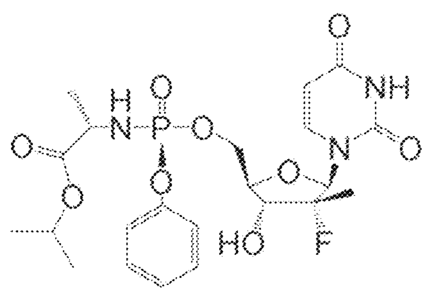 |
| 2004 | PSI-352938 GS-938 | 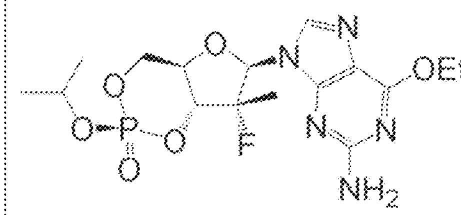 |
| 2005 | 4'-azidouridine and its prodrugs | 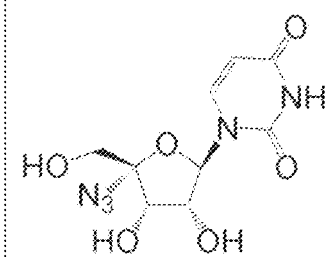 |
| 2006 | PSI-661 | |
| 2007 | GS-6620 | |
| 2008 | TMC649128 | |

Figure 2 (cont.): HCV Polymerase Inhibitors – Nucleosides, Nucleotides and Analogs Thereof

| # | Name | Structure |
|---|------|-----------|
| 2009 | NM283 | (structure shown: cytidine analog with Me, OH, OVal, and HO groups) |
| 2010 | BCX5191 | |
| 2011 | IDX19368 | |
| 2012 | IDX19370 | |

Figure 3: HCV Polymerase Inhibitors – Non-Nucleosides

| # | Name | Structure |
|---|---|---|
| 3004 | HCV-796 | 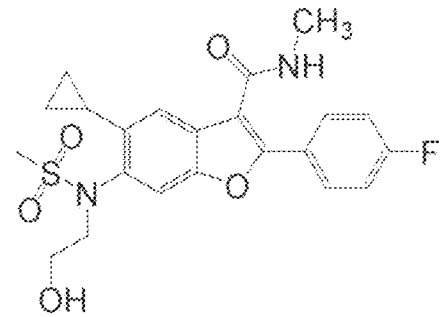 |
| 3005 | BI-207127 | |
| 3006 | GS-9190 | 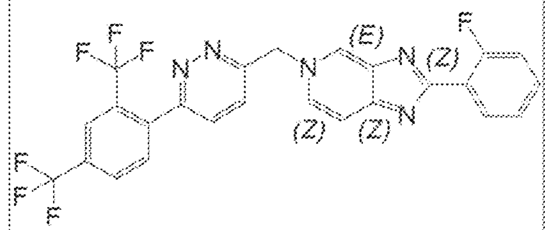 |
| 3007 | Filibuvir PF-00868554 | 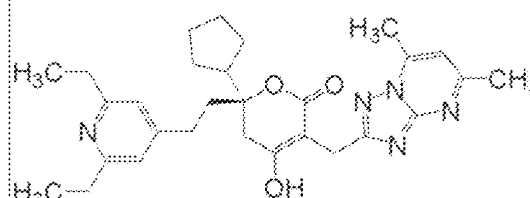 |

| # | Name | Structure |
|---|---|---|
| 3001 | ABT-333 | |
| 3002 | ANA-598 Setrobuvir | 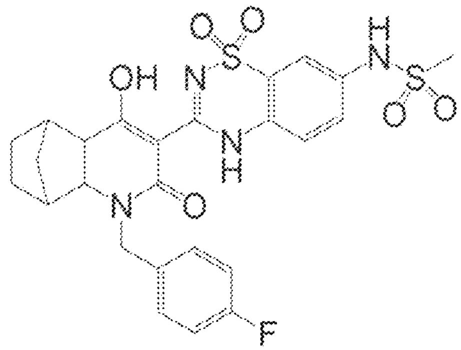 |
| 3003 | VX-222 VCH-222 | 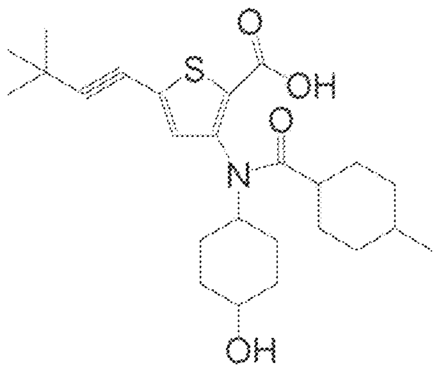 |

Figure 3 (cont.): HCV Polymerase Inhibitors – Non-Nucleosides

| # | Name | Structure |
|---|---|---|
| 3008 | VX-497 | (structure shown) |
| 3009 | ABT-072 | |
| 3010 | MK-3281 | |

| # | Name | Structure |
|---|---|---|
| 3011 | TMC647055 | |
| 3012 | BMS-791325 | |
| 3013 | PPI-383 | |
| 3014 | GS9669 | |

Figure 4: NS5A Inhibitors

| # | Name | Structure |
|---|---|---|
| 4001 | BMS-790052<br>BMS052<br>S1482<br>Daclatasvir | (structure shown) |
| 4002 | PPI-461 | |
| 4003 | ACH-2928 | |
| 4004 | GS-5885 | |
| 4005 | BMS-824393 | |
| 4006 | ABT 267 | |
| 4007 | ACH-3102 | |
| 4008 | AZD-7295 | |
| 4009 | IDX719 | |
| 4010 | PPI-668 | |
| 4011 | MK8742 | |
| 4012 | GSK805 | |

Figure 5: Other Antivirals and Ribavirin

| # | Name | Structure |
|---|---|---|
| 5001 | Debio-025 Alisporivir | |
| 5002 | MIR-122 | |
| 5003 | clemizole | |
| 5004 | ITX 5061 | |
| 5005 | BIT225 | |
| 5006 | NIM811 | |
| 5007 | SCY-635 | |
| 5008 | Nitazoxanide | (structure shown) |
| 5009 | Miravirsen | |

| # | Name | Structure |
|---|---|---|
| 5010 | Celgosivir | (structure shown) |
| 5011 | GS9620 | |
| 5012 | Ribavirin | (structure shown) |

Figure 6: Compounds of Formula (CC) and alpha-thiotriphosphates thereof

| # | Structure |
|---|---|
| 6000 | (structure with $R^{CC1}$, $R^{CC2}$, $R^{CC3a}$, $R^{CC3b}$, $R^{CC4}$, $R^{CC5}$, $R^{CC6}$, $R^{CC7}$, $R^{CC8}$, $R^{CC9}$, $B^{CC1}$) |
| 6001 | (naphthyl phosphoramidate nucleoside structure) |
| 6002 | (phenyl phosphoramidate nucleoside structure) |
| 6003 | (phenyl phosphoramidate nucleoside structure) |
| 6004 | (phenyl phosphoramidate nucleoside structure) |

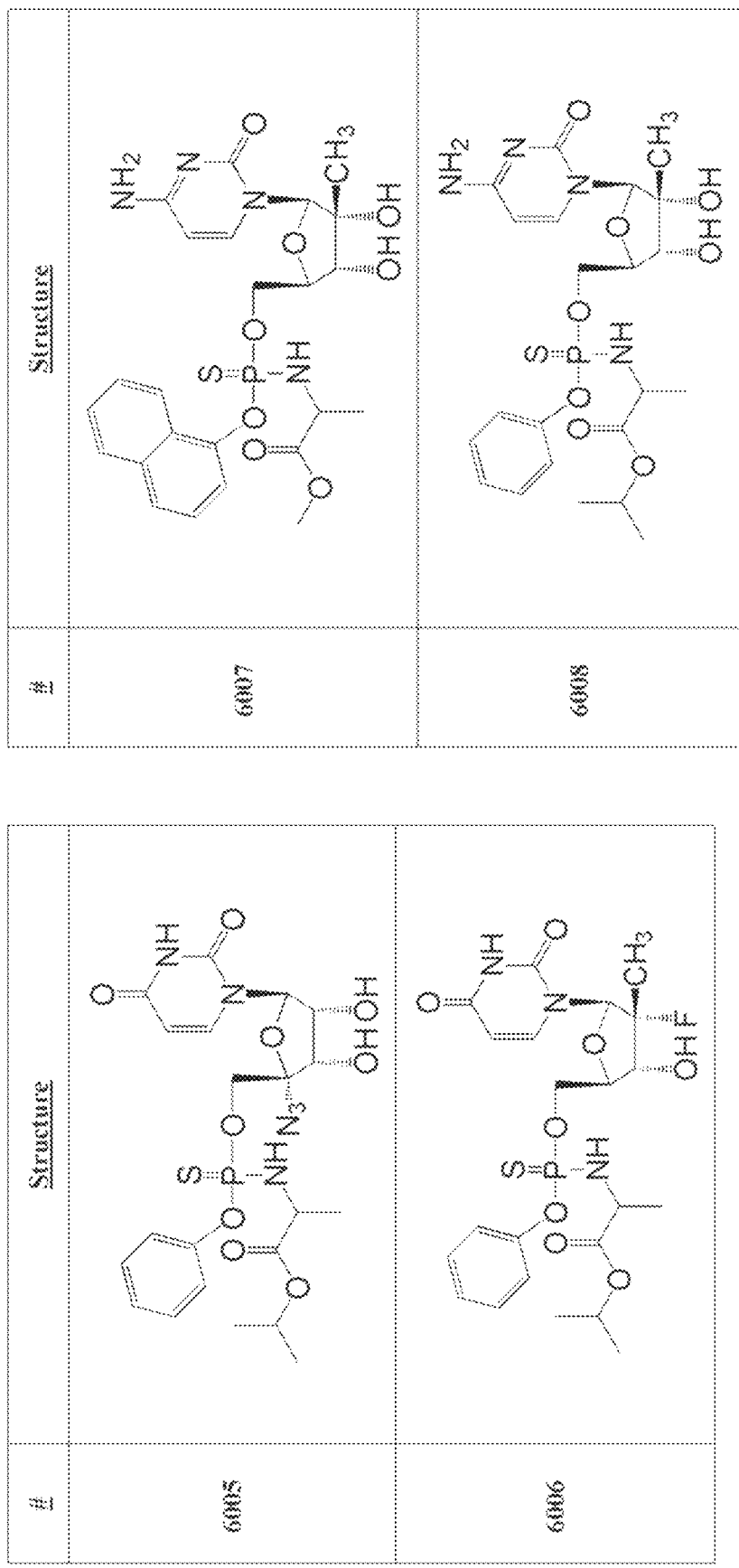
Figure 6 (cont.): Compounds of Formula (CC) and alpha-thiotriphosphates thereof

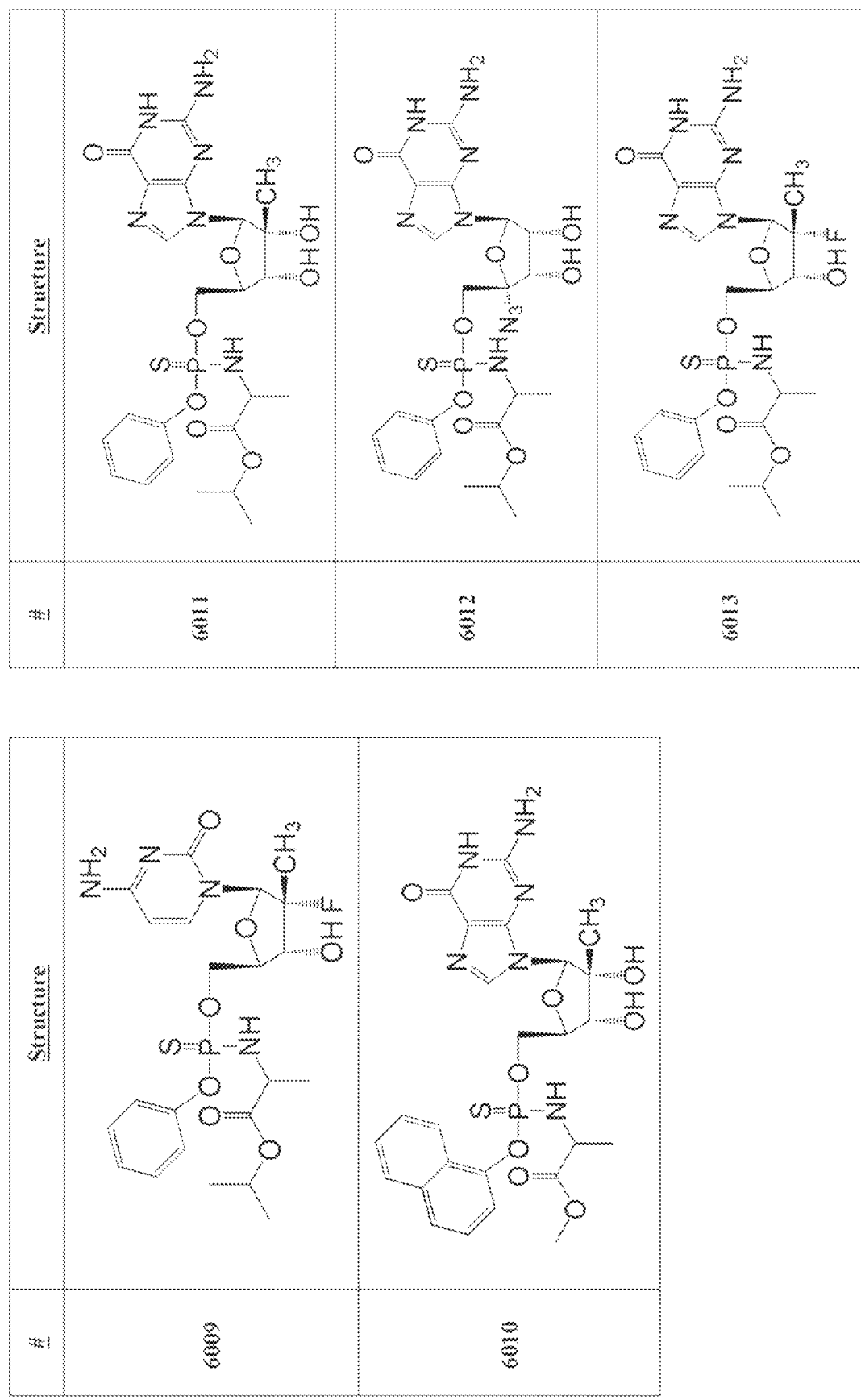
Figure 6 (cont.): Compounds of Formula (CC) and alpha-thiotriphosphates thereof

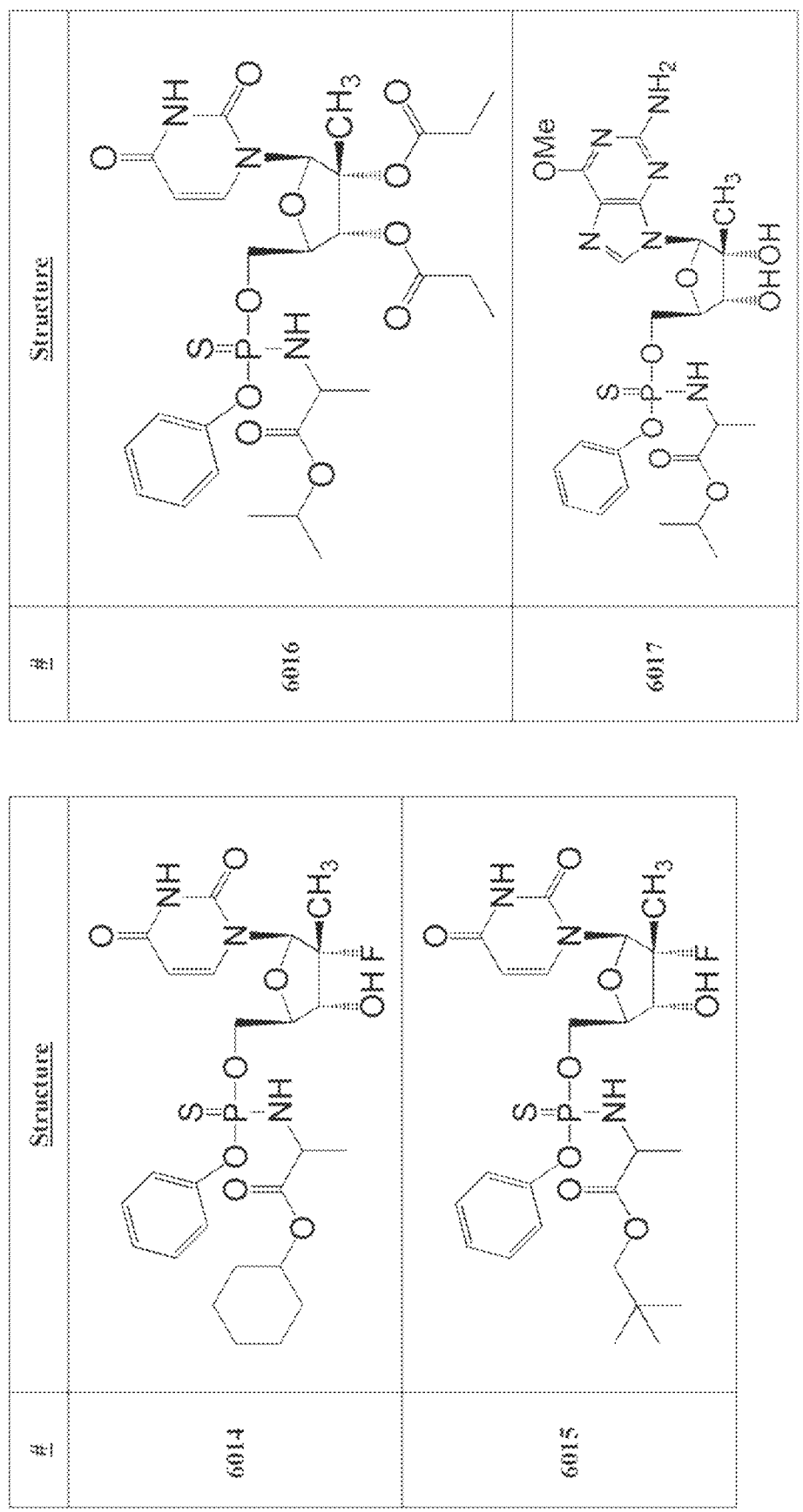
Figure 6 (cont.): Compounds of Formula (CC) and alpha-thiotriphosphates thereof Figure 6 (cont.): Compounds of Formula (CC) and alpha-thiotriphosphates thereof
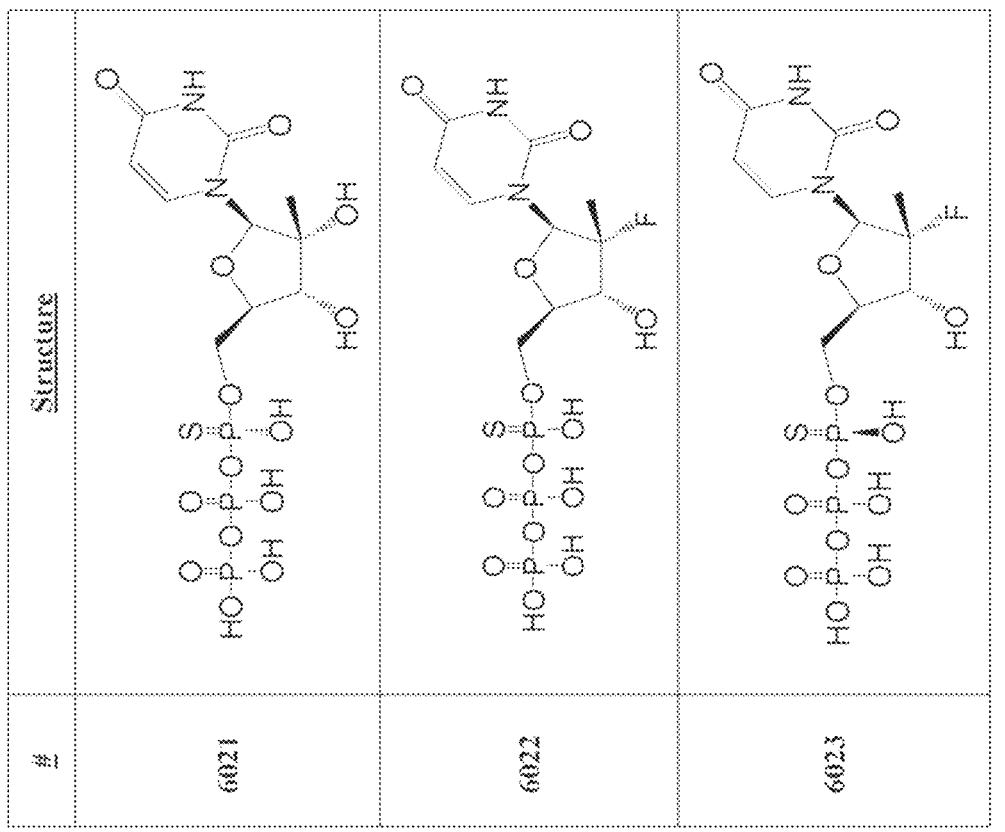
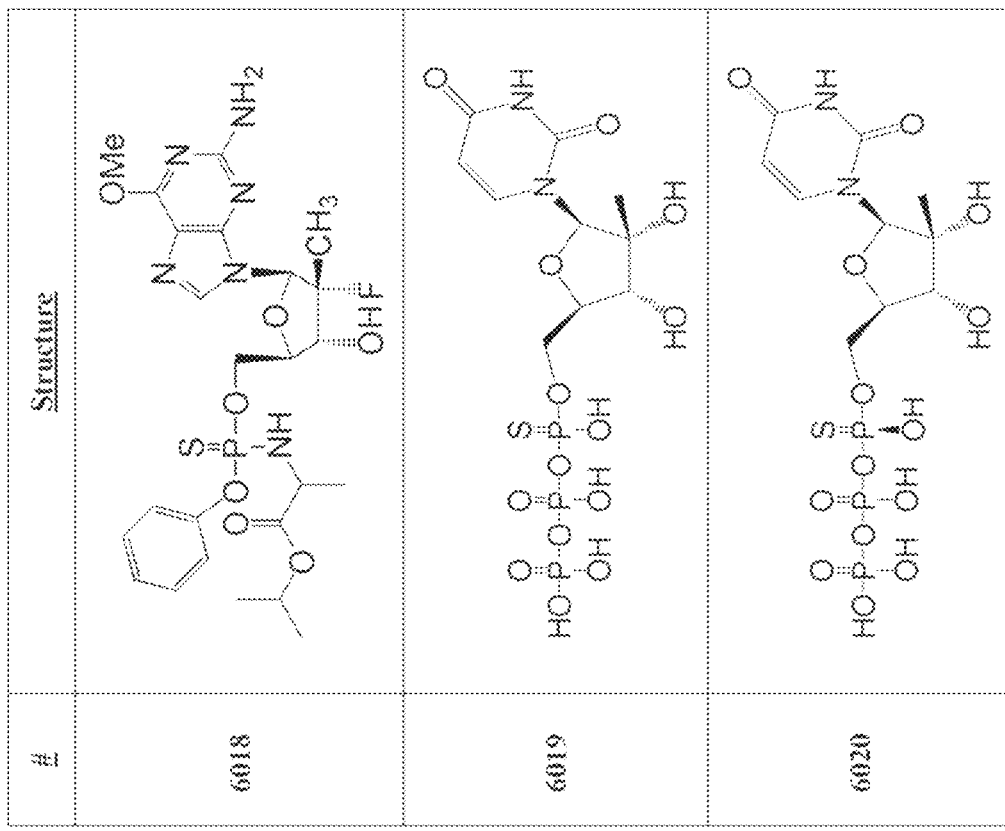

Figure 6 (cont.): Compounds of Formula (CC) and alpha-thiotriphosphates thereof

| # | Structure |
|---|---|
| 6024 | 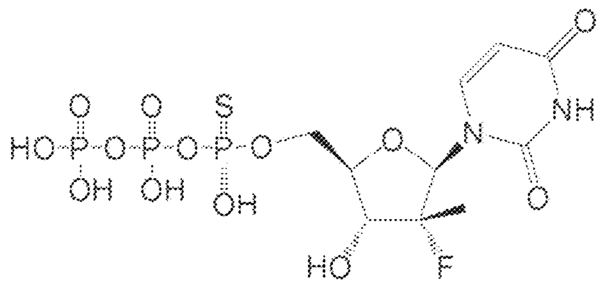 |
| 6025 | 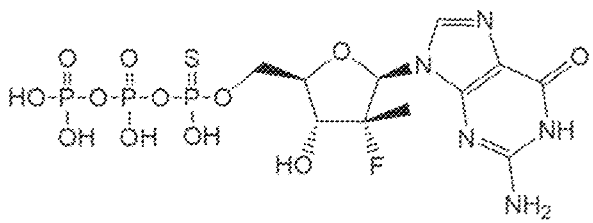 |
| 6026 | 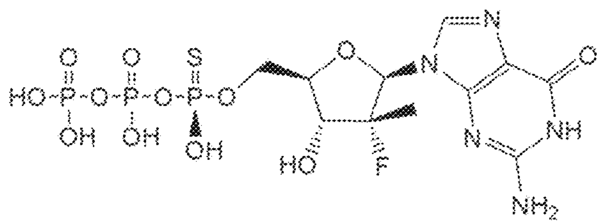 |

| # | Structure |
|---|---|
| 6027 | 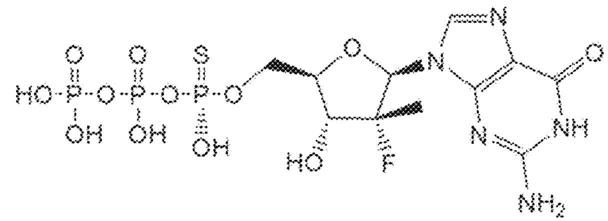 |
| 6028 | 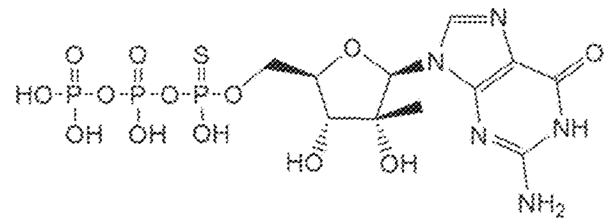 |
| 6029 | 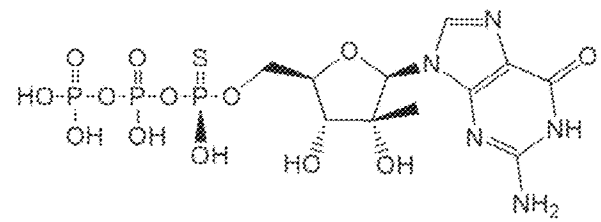 |
| 6030 | 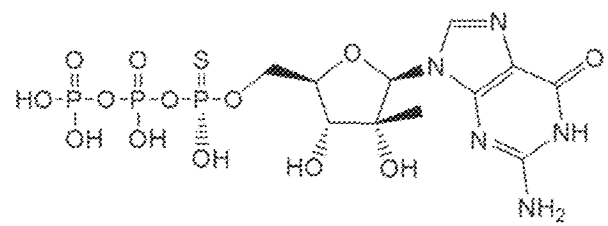 |

Figure 6 (cont.): Compounds of Formula (CC) and alpha-thiotriphosphates thereof
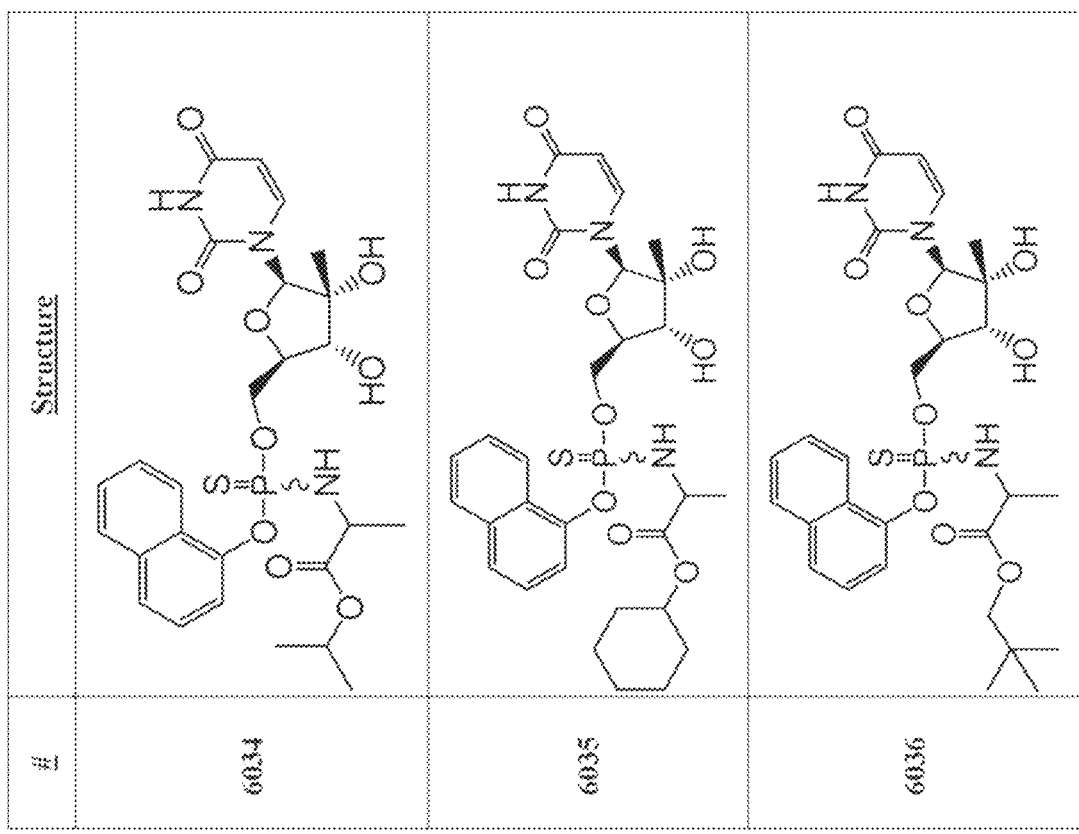
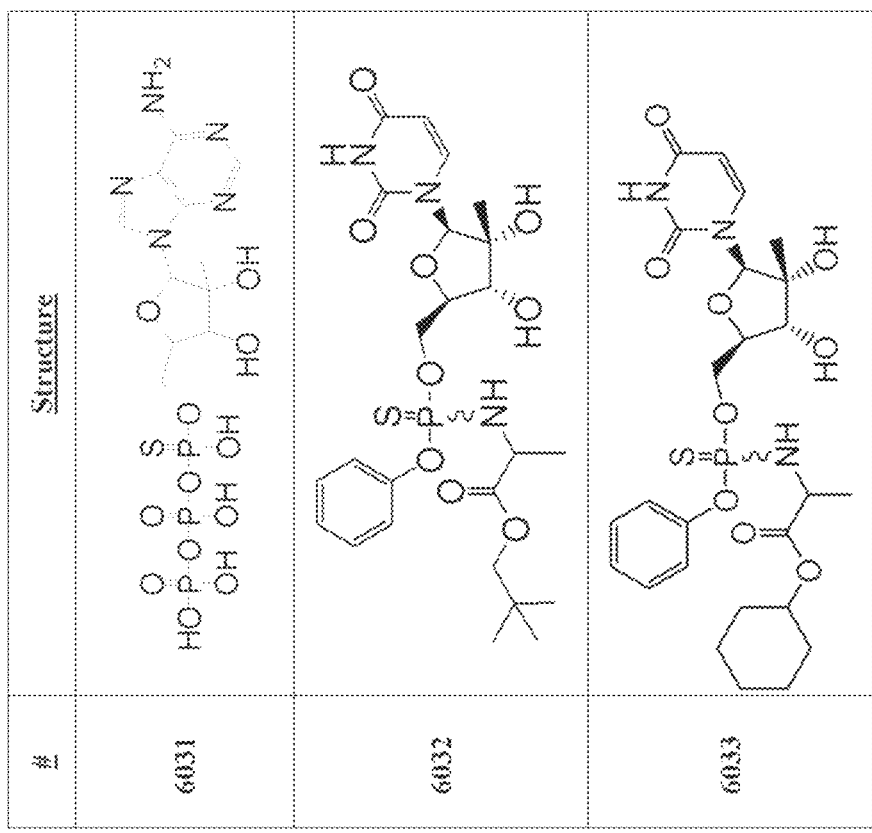

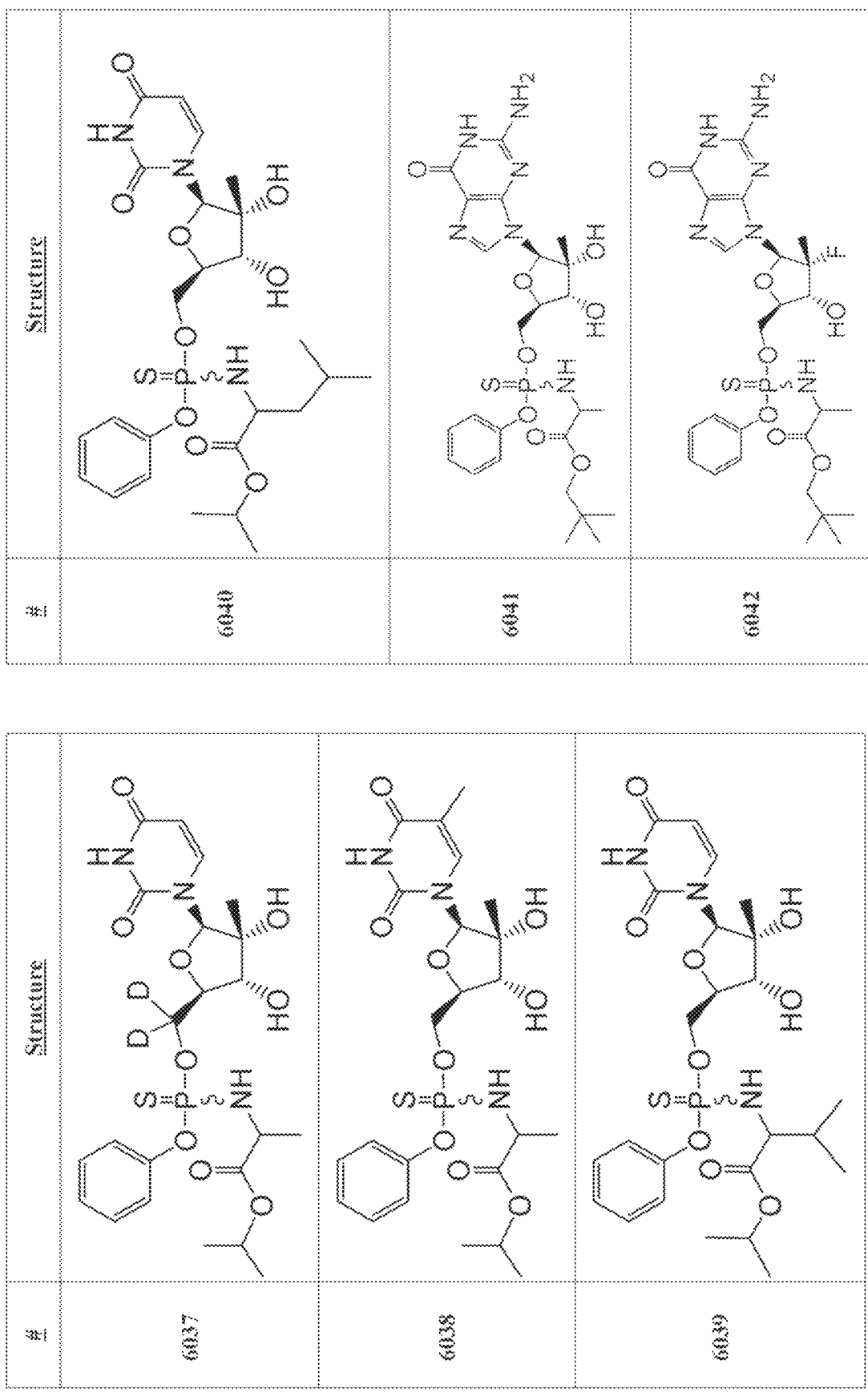
Figure 6 (cont.): Compounds of Formula (CC) and alpha-thiotriphosphates thereof

Figure 6 (cont.): Compounds of Formula (CC) and alpha-thiotriphosphates thereof

| # | Structure |
|---|---|
| 6043 | 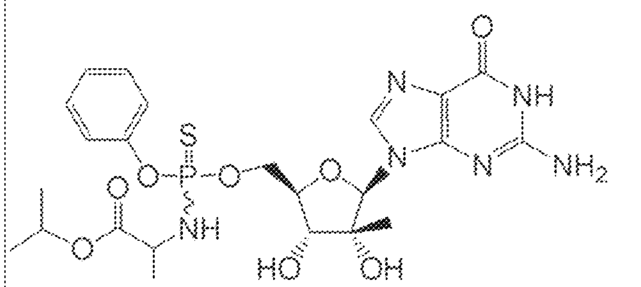 |
| 6044 | 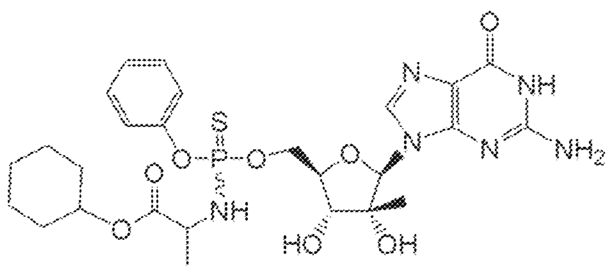 |
| 6045 | 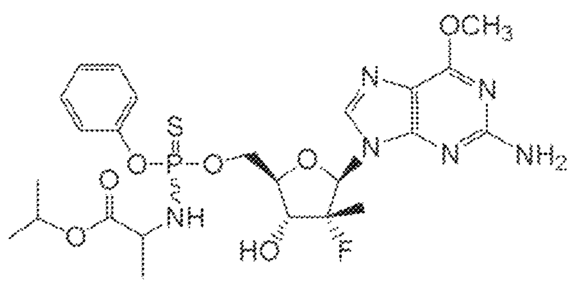 |
| 6046 | |
| 6047 | |
| 6048 | |

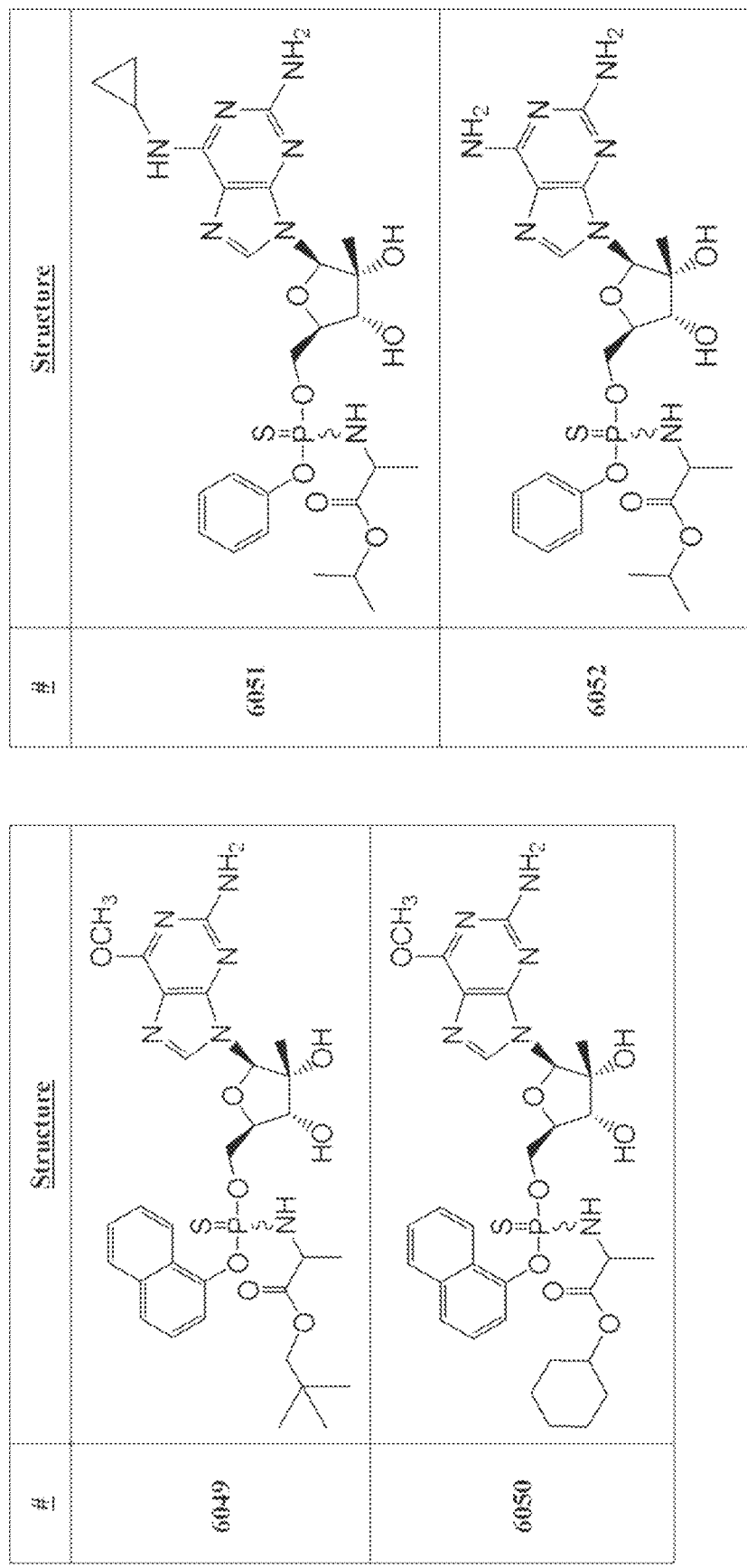
Figure 6 (cont.): Compounds of Formula (CC) and alpha-thiotriphosphates thereof

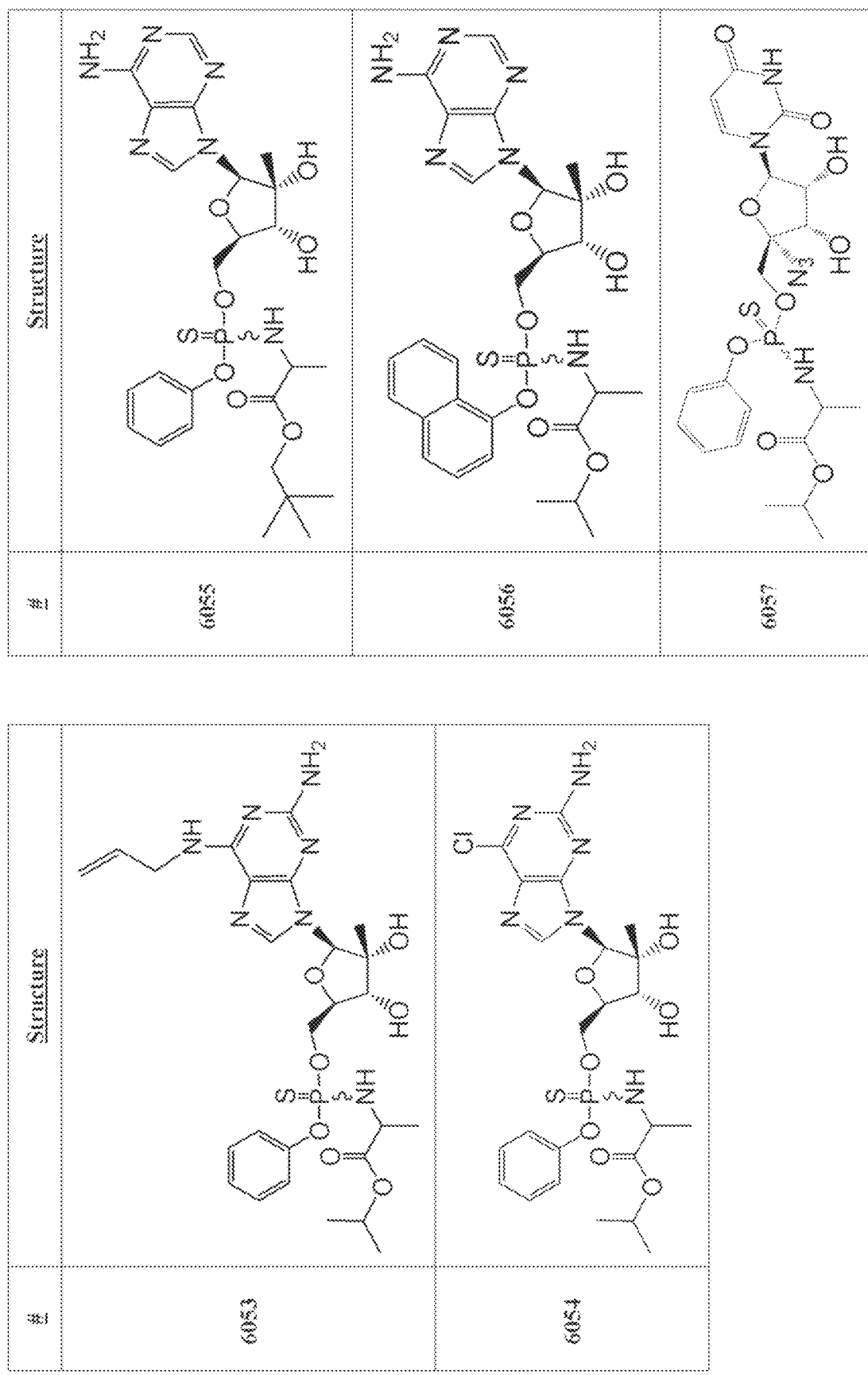
Figure 6 (cont.): Compounds of Formula (CC) and alpha-thiotriphosphates thereof Figure 6 (cont.): Compounds of Formula (CC) and alpha-thiotriphosphates thereof
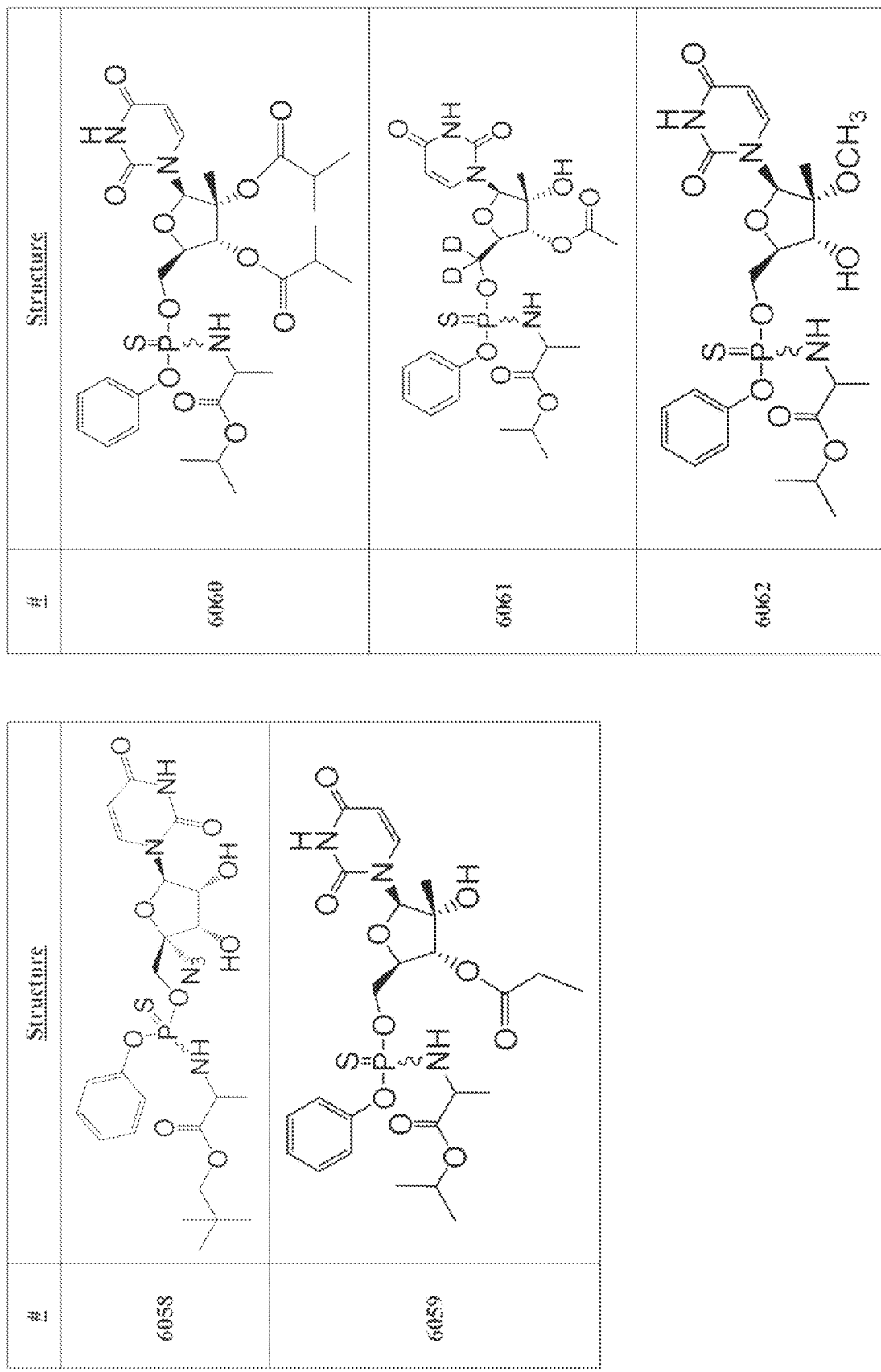

Figure 6 (cont.): Compounds of Formula (CC) and alpha-thiotriphosphates thereof
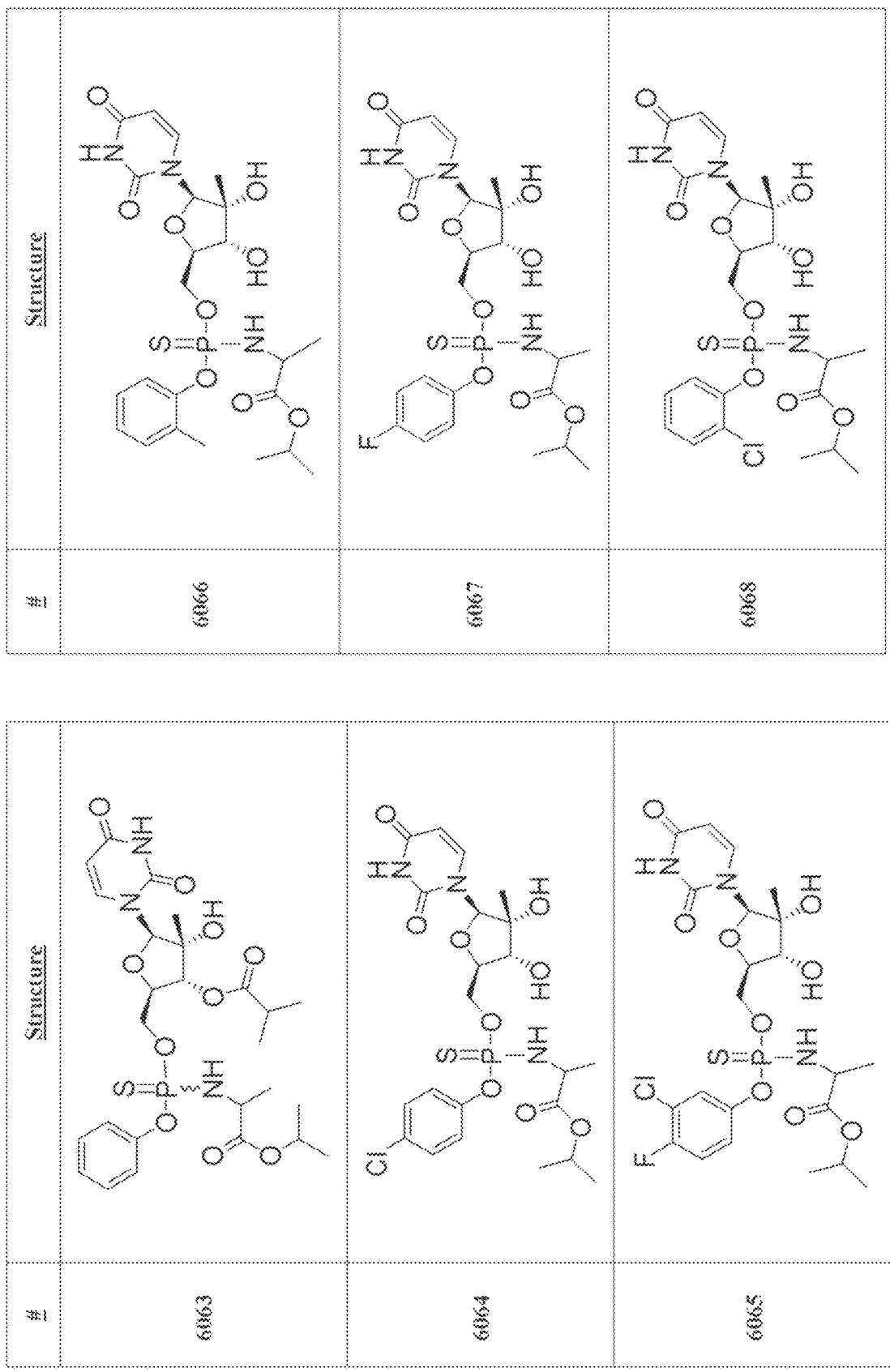

Figure 6 (cont.): Compounds of Formula (CC) and alpha-thiotriphosphates thereof
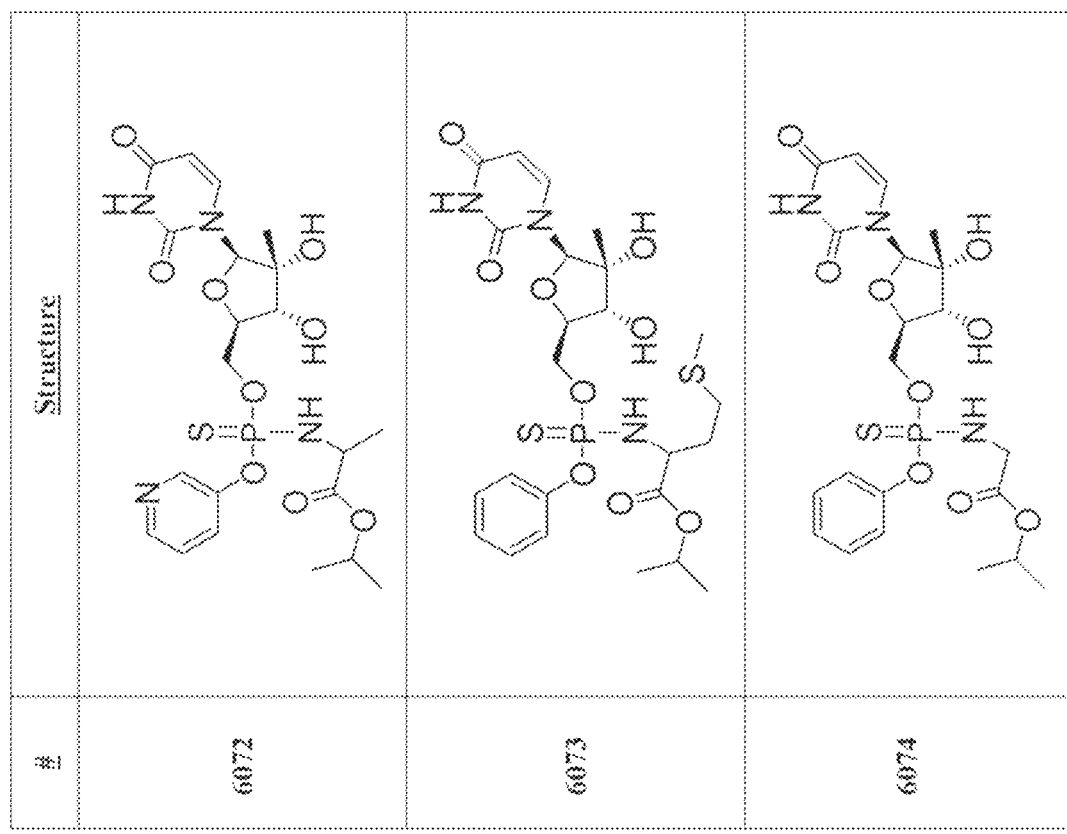
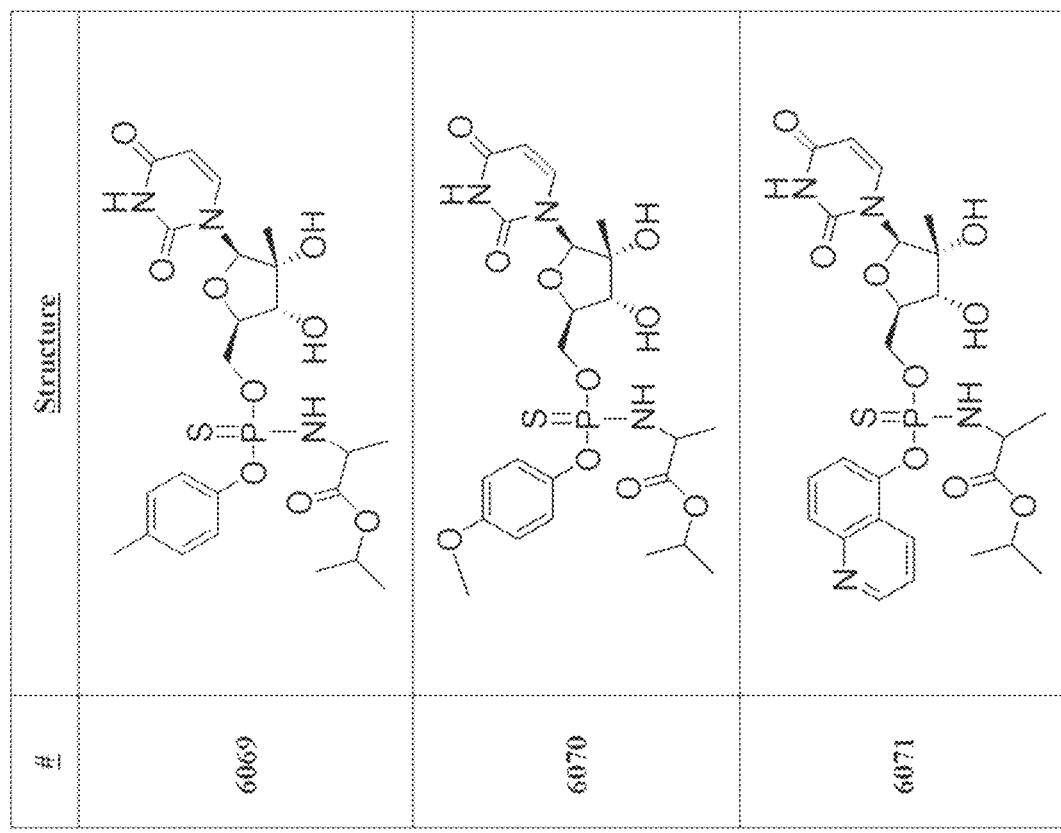

Figure 6 (cont.): Compounds of Formula (CC) and alpha-thiotriphosphates thereof

| # | Structure |
|---|---|
| 6075 | 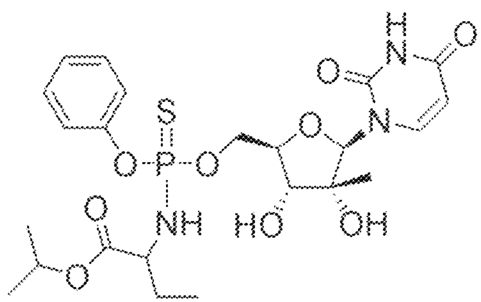 |
| 6076 | 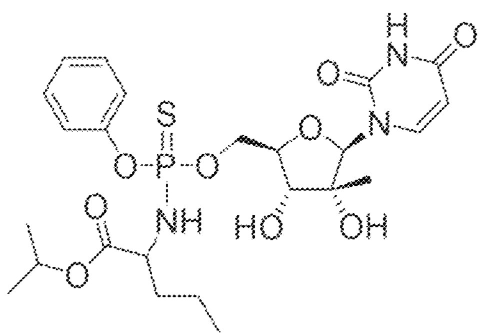 |
| 6077 | |
| 6078 | |

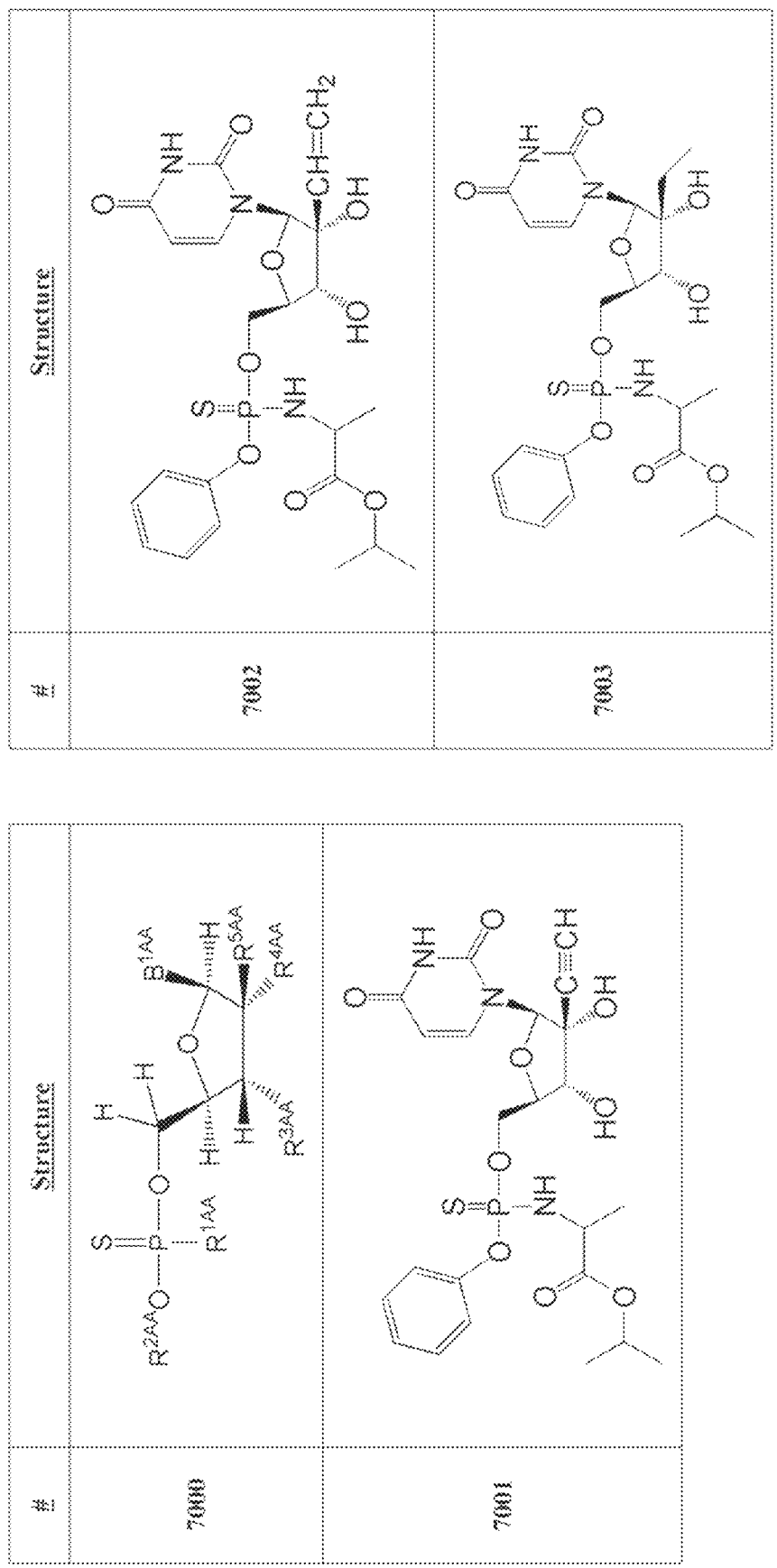
Figure 7: Compounds of Formula (AA)

Figure 7 (cont.): Compounds of Formula (AA)
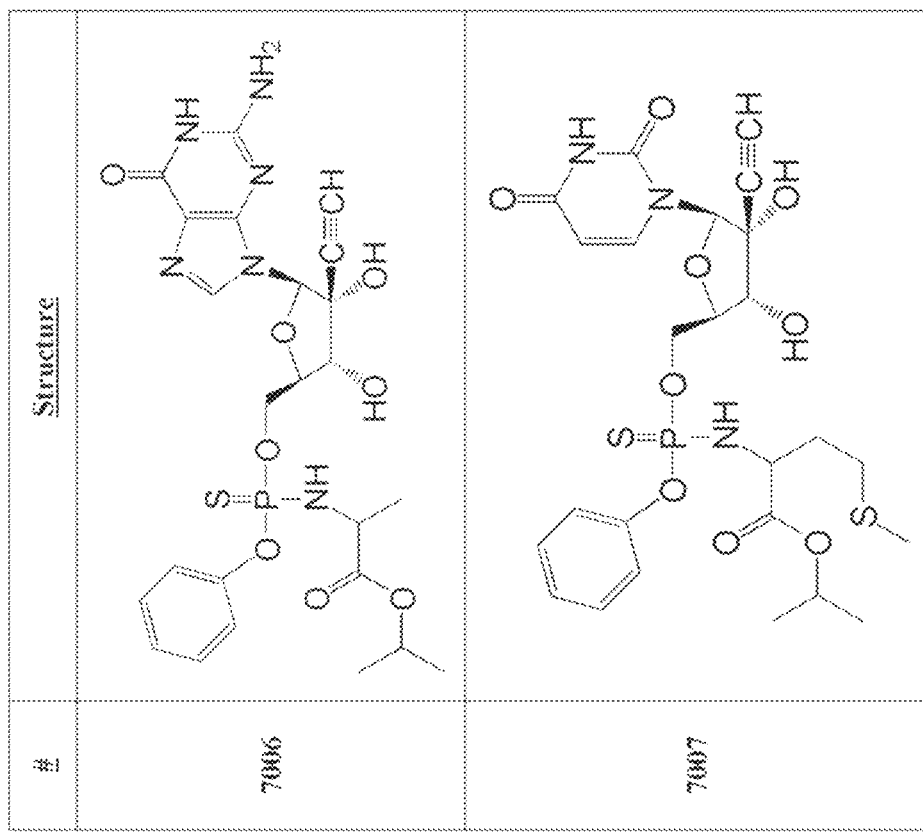
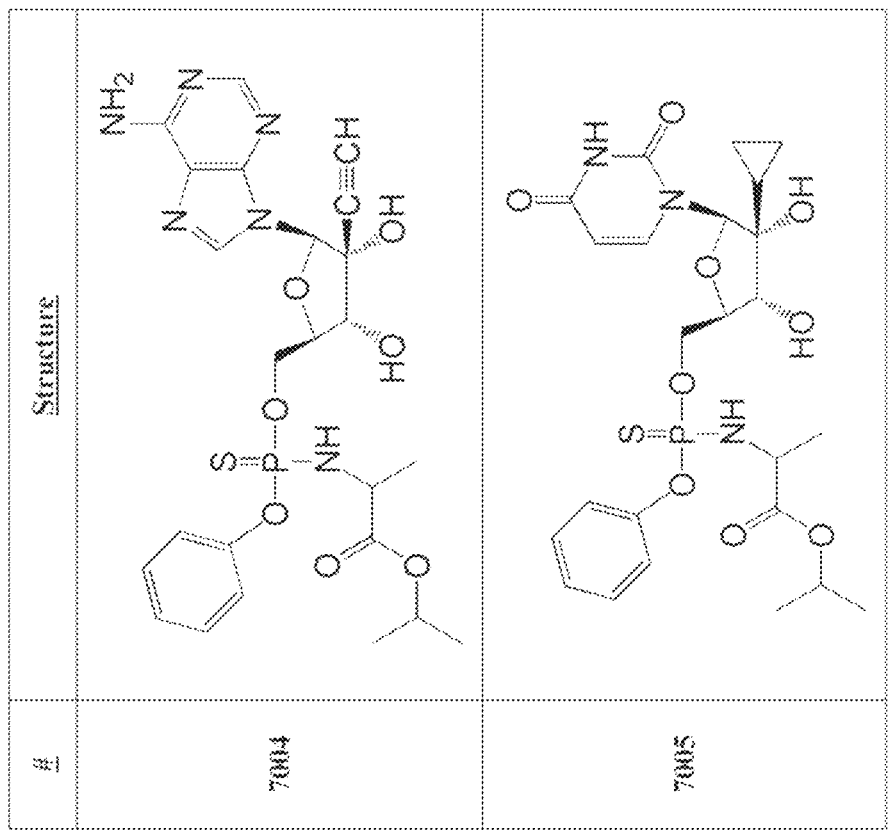

Figure 7 (cont.): Compounds of Formula (AA)
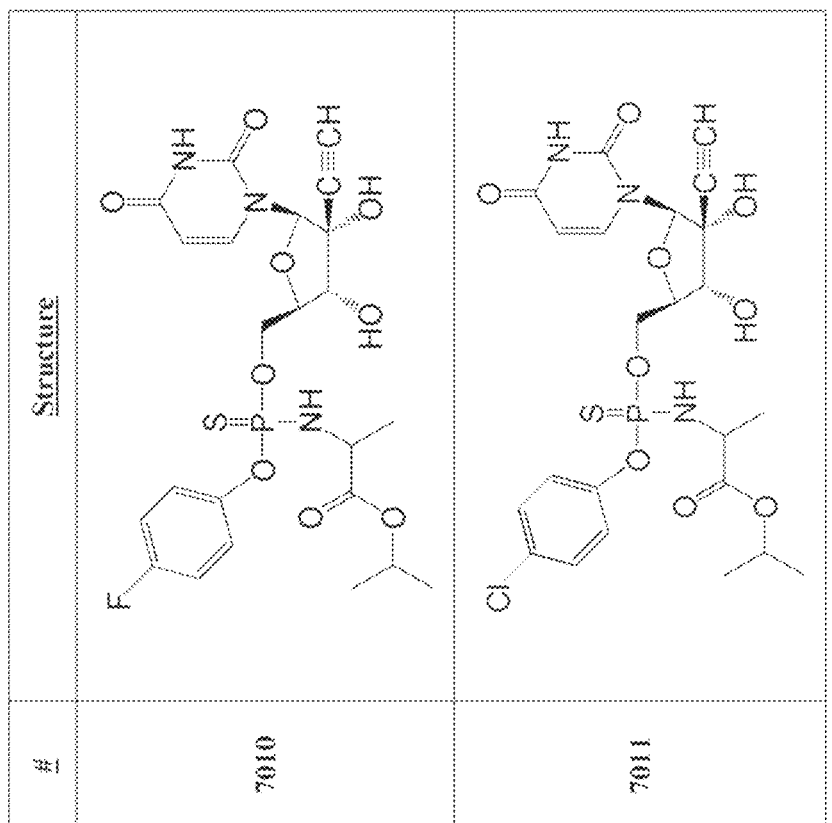
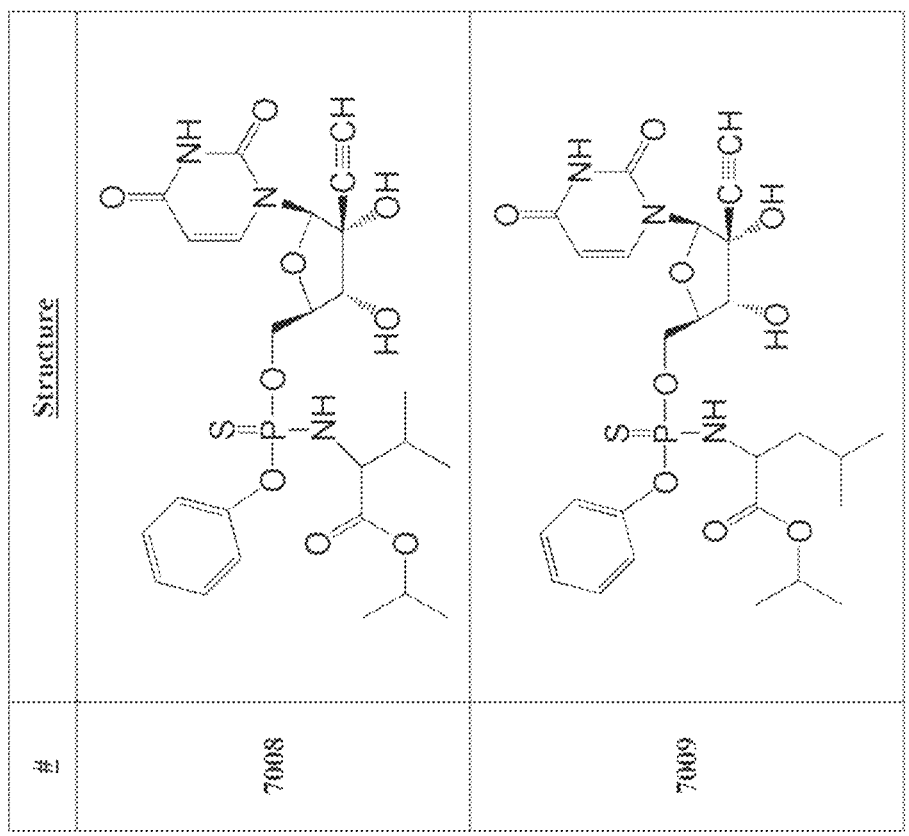

Figure 7 (cont.): Compounds of Formula (AA)
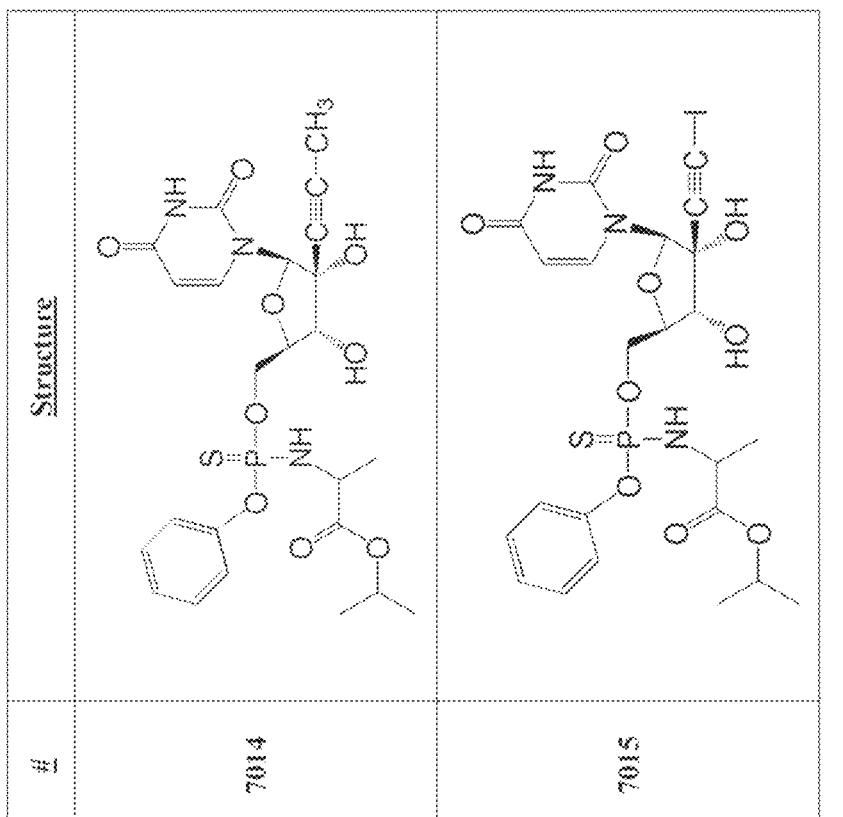
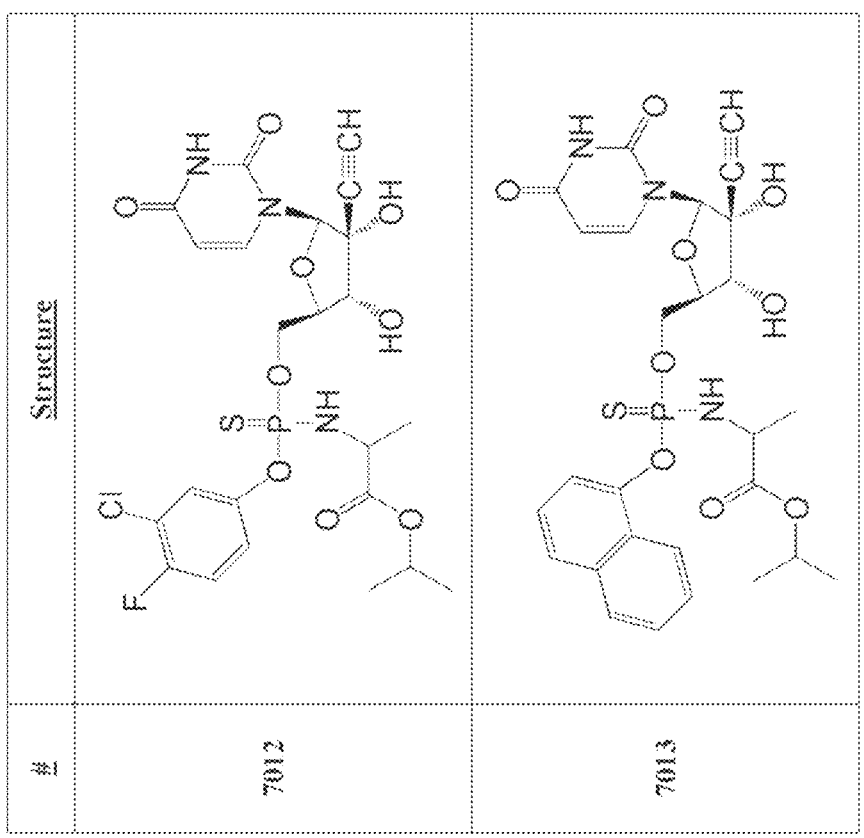

Figure 7 (cont.): Compounds of Formula (AA)
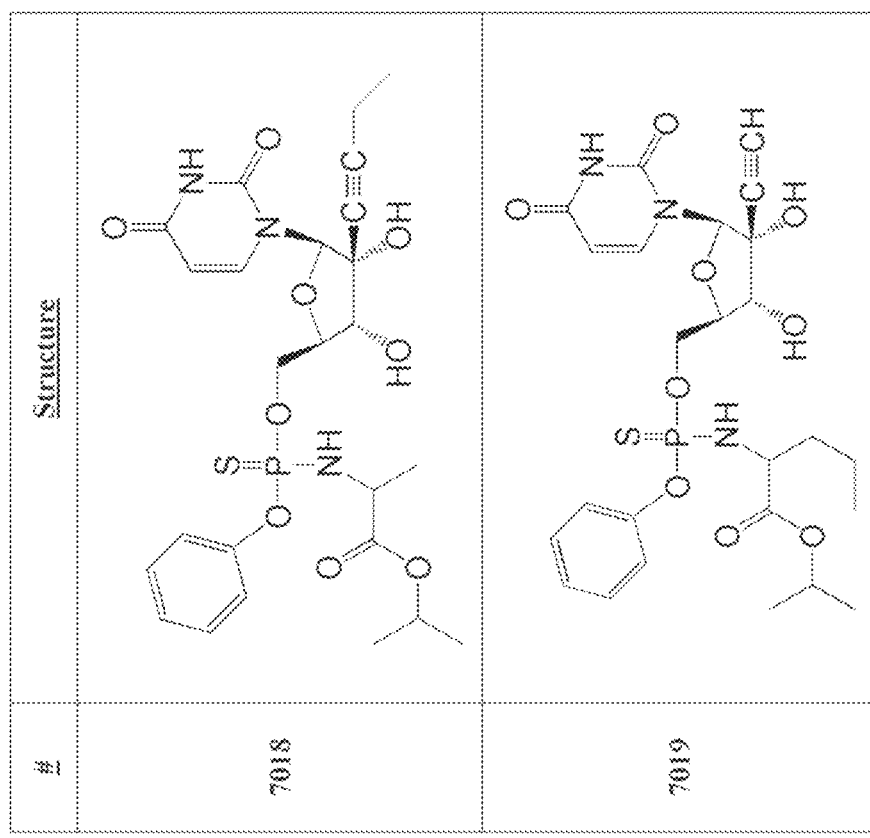
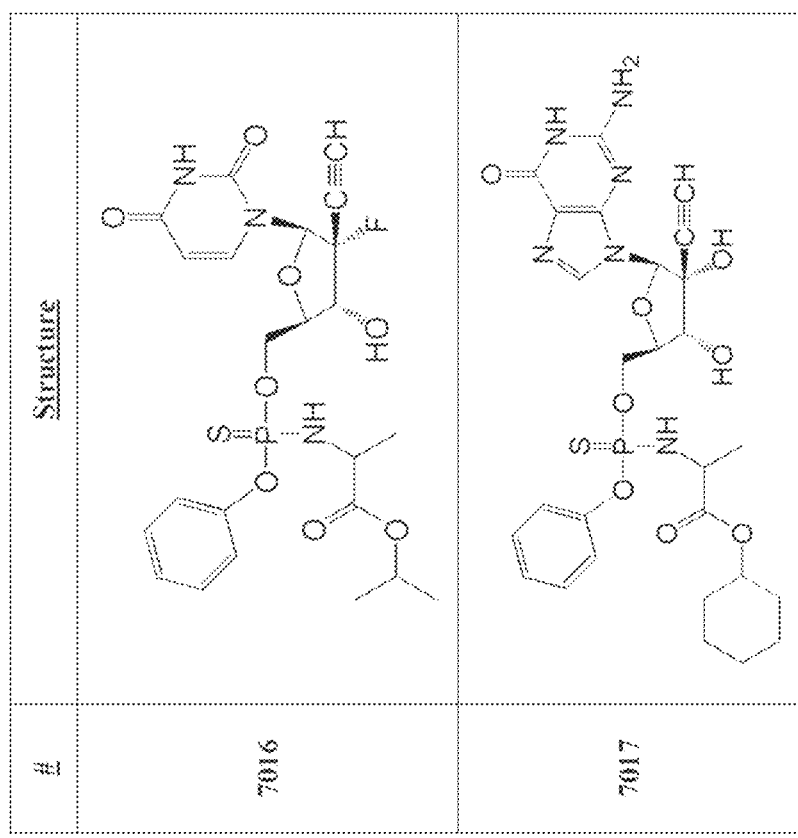

Figure 7 (cont.): Compounds of Formula (AA)
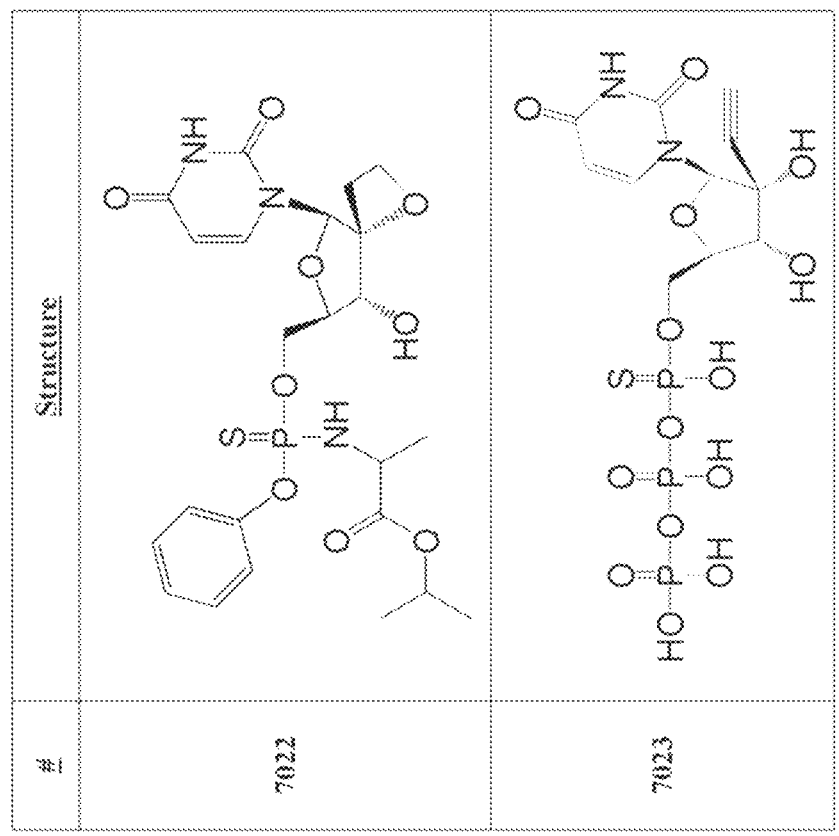
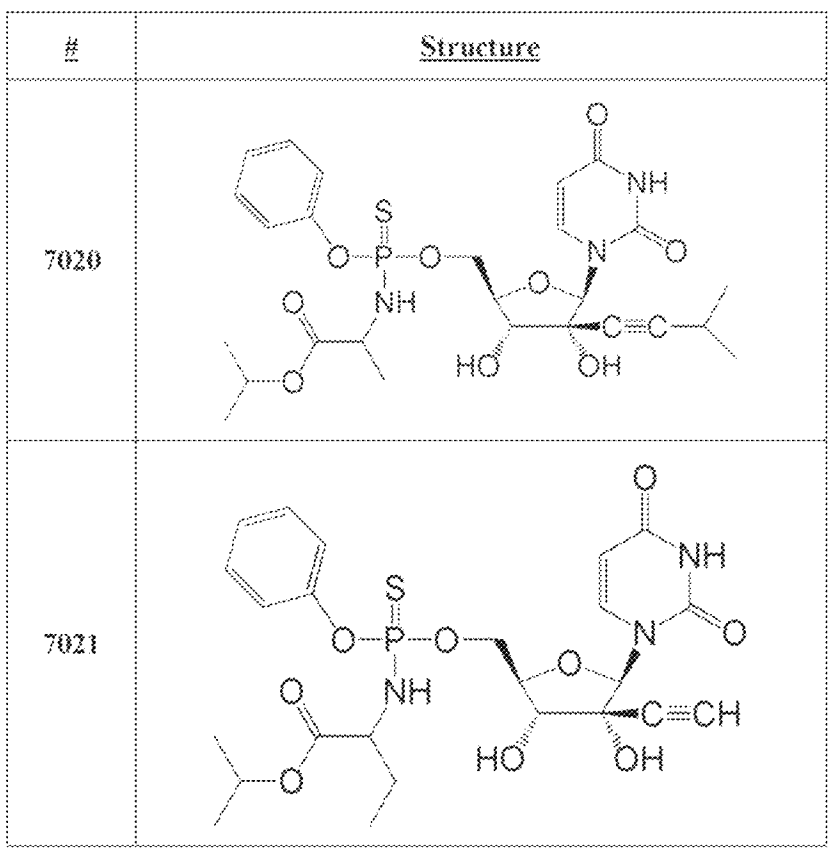

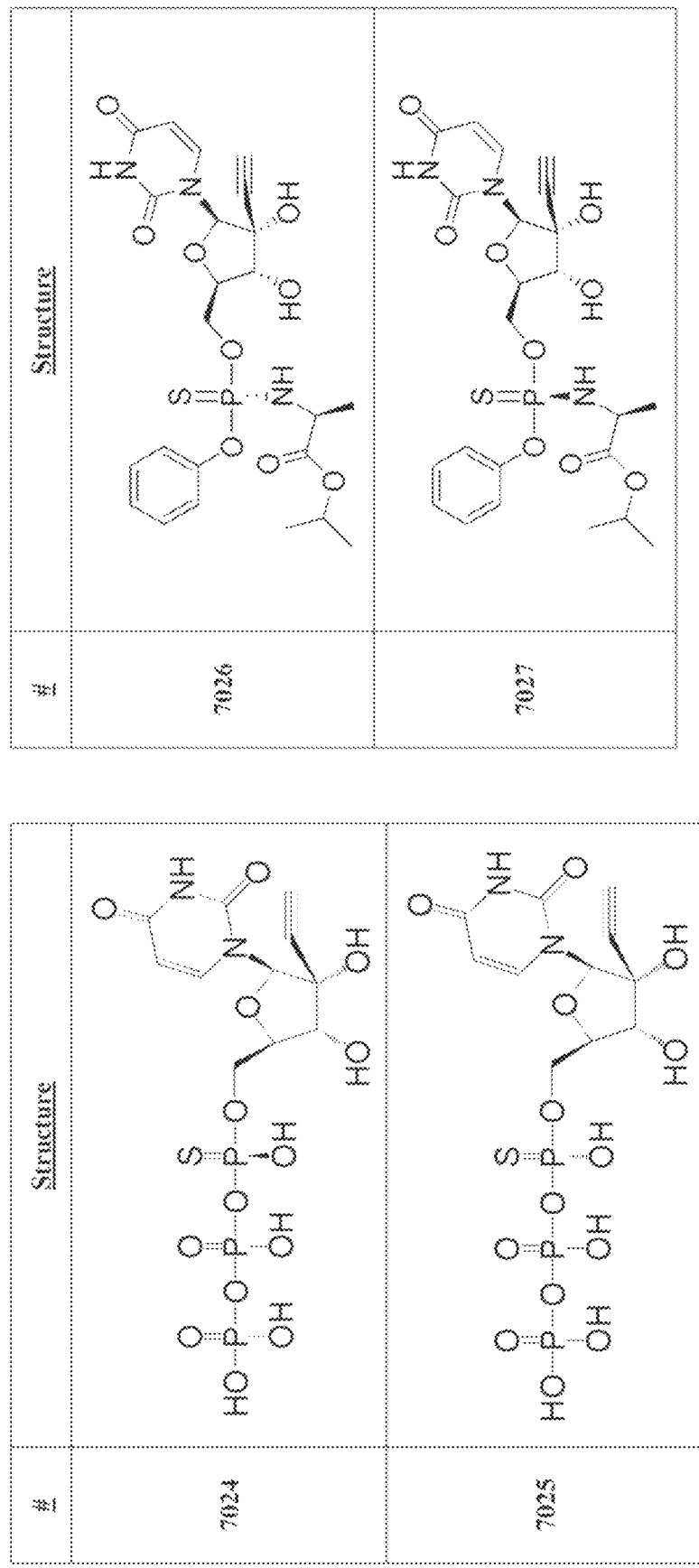
Figure 7 (cont.): Compounds of Formula (AA)

Figure 8: Compounds of Formula (BB)

| # | Structure |
|---|---|
| 8000 | (structure with labels $R^{BB1}$, $R^{BB2}$, $R^{BB3}$, $R^{BB4}$, $R^{BB5}$, $R^{BB6}$, $R^{BB7}$, $R^{BB8}$, $X^{BB}$) |
| 8001 | 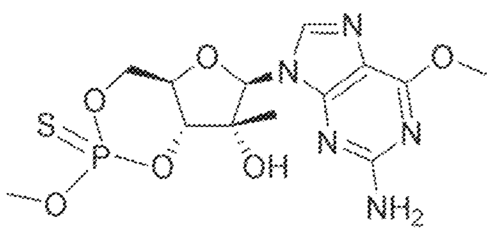 |
| 8002 | 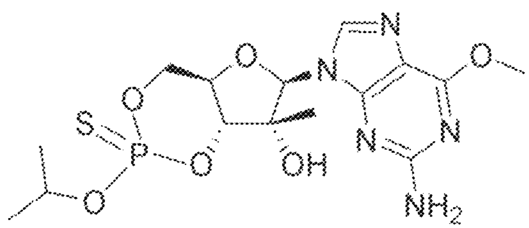 |
| 8003 | |
| 8004 | |
| 8005 | |

Figure 8 (cont.): Compounds of Formula (BB)
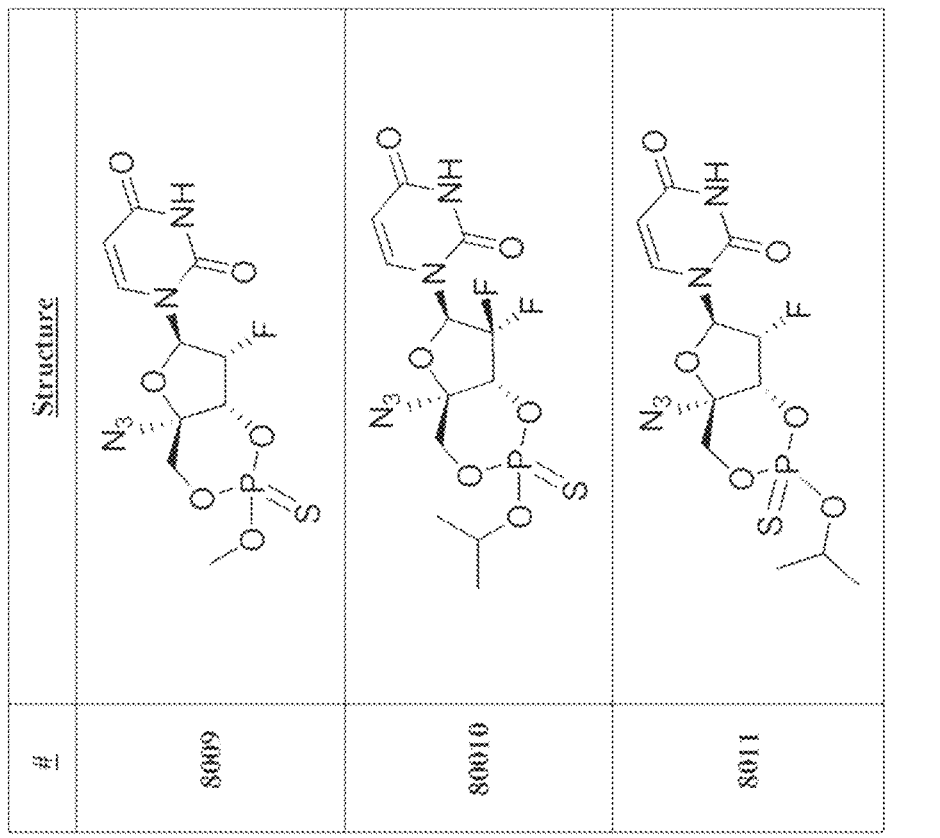
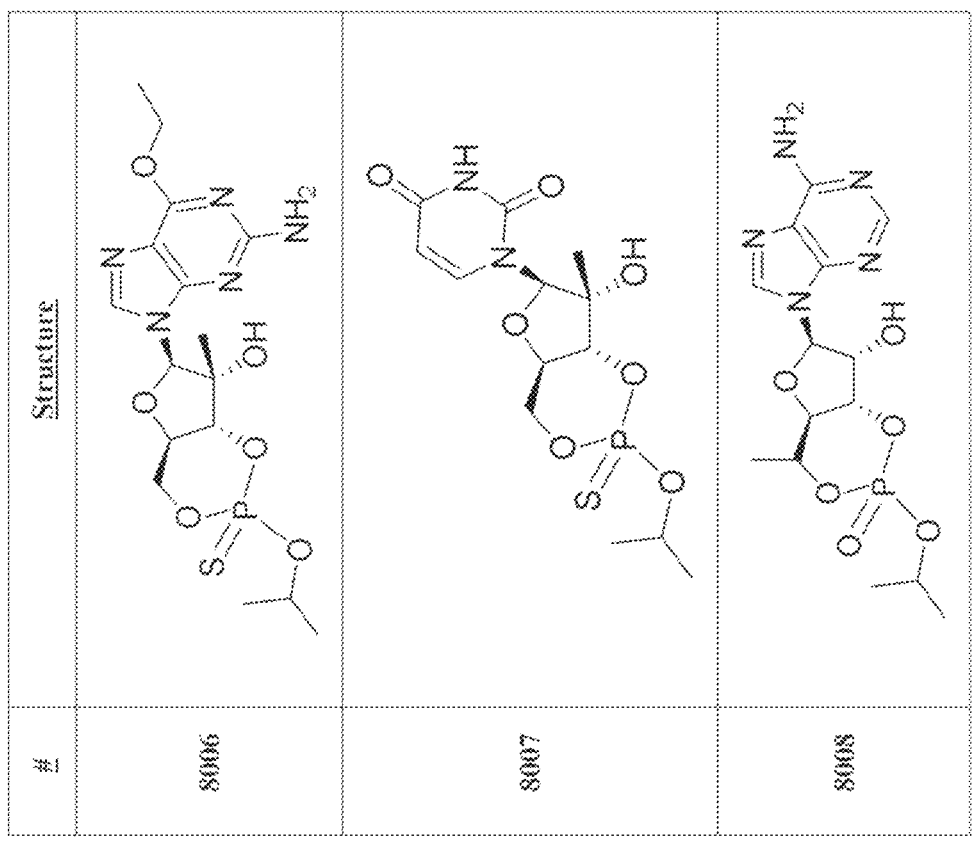

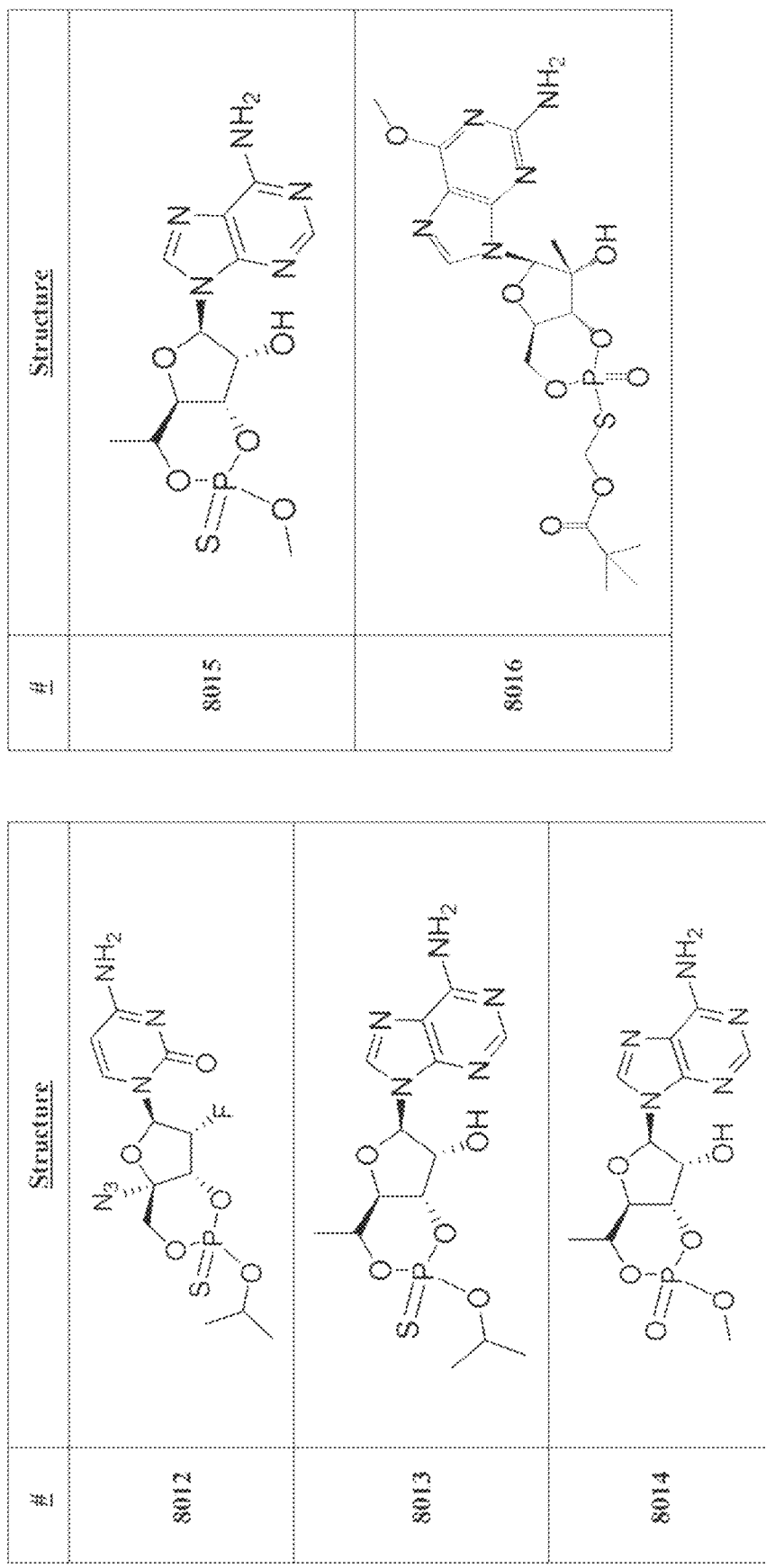

Figure 9: Compounds of Formula (I)
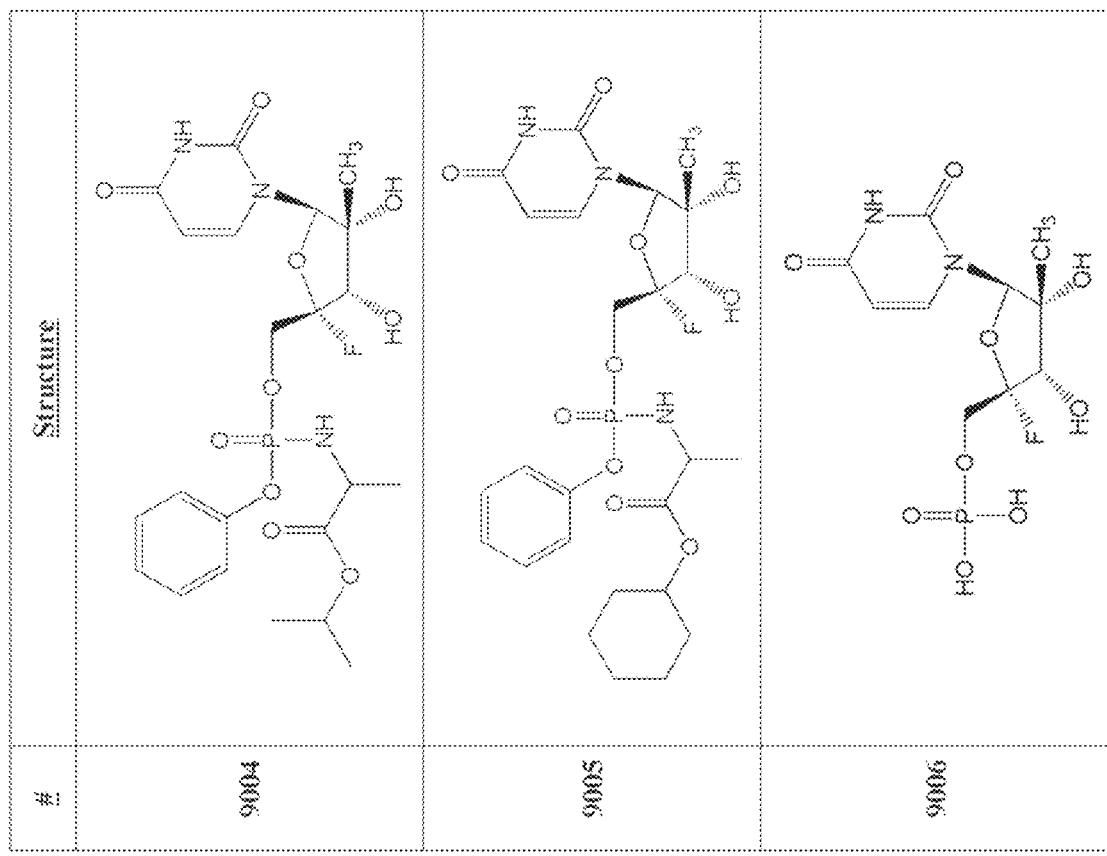
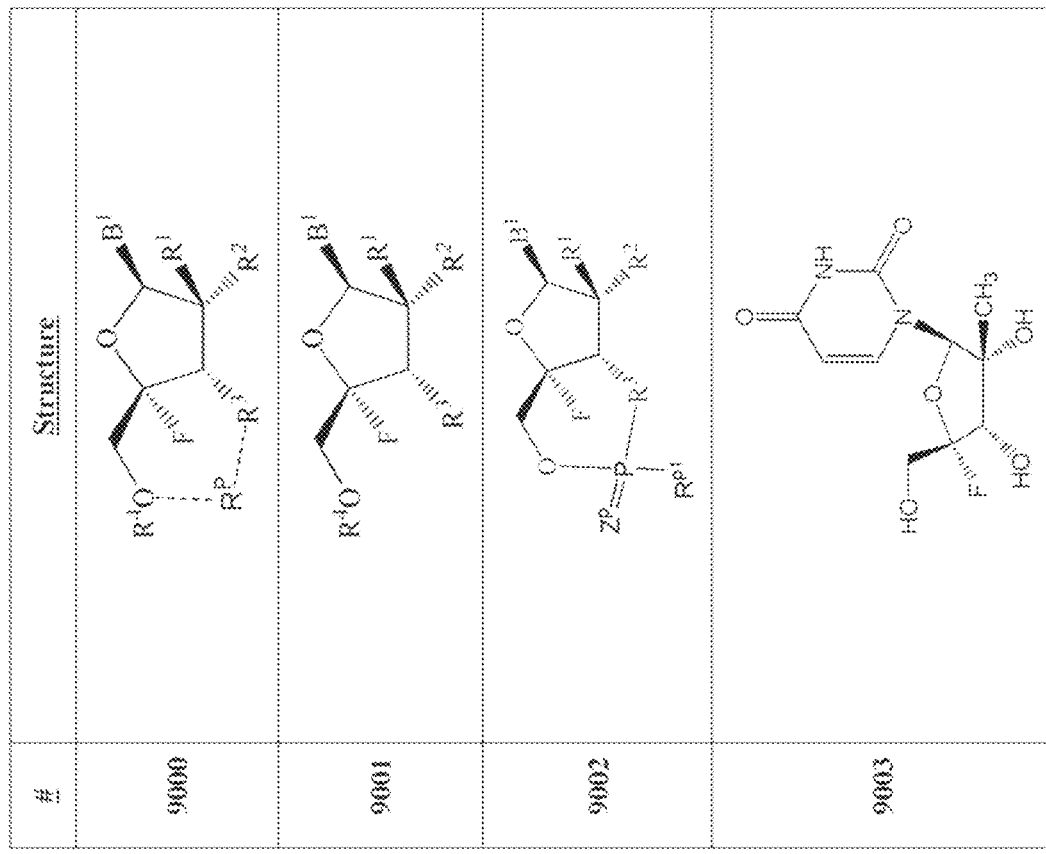

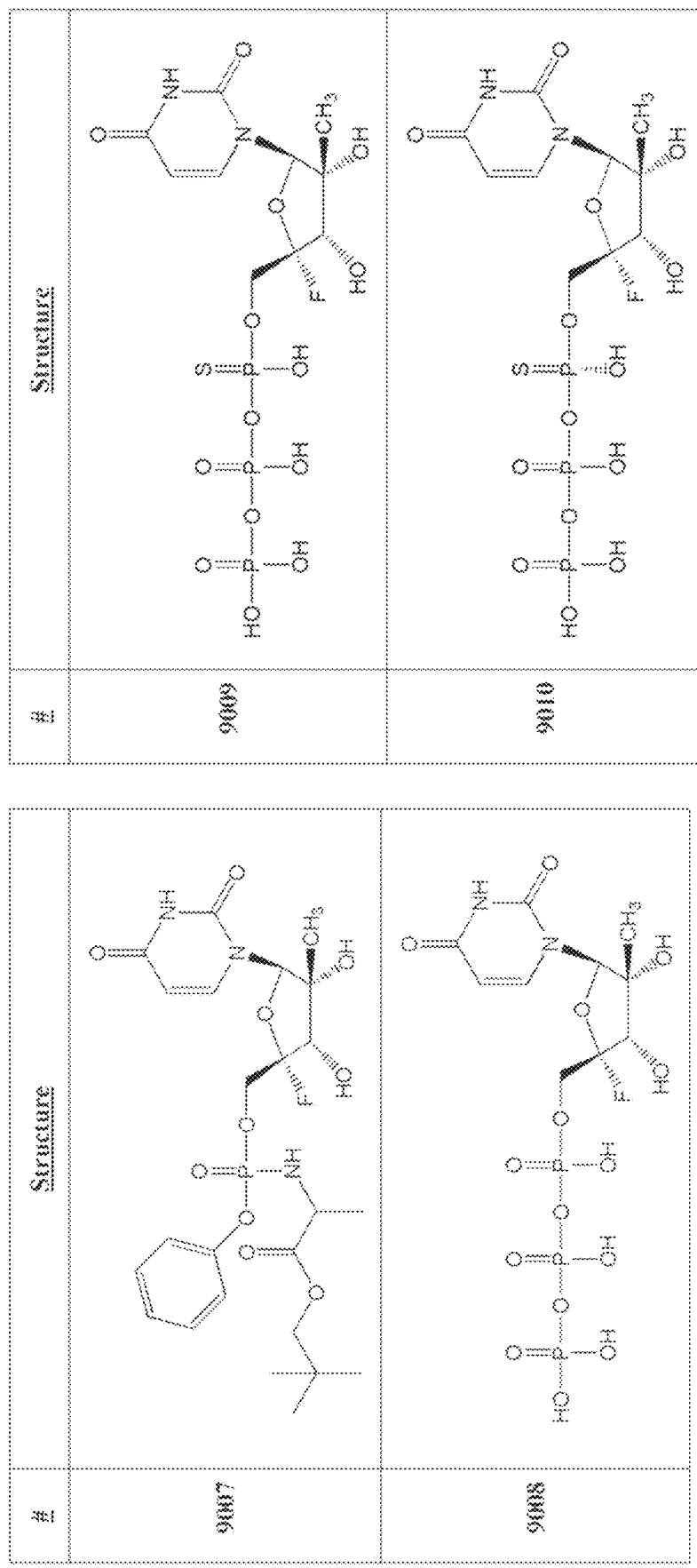

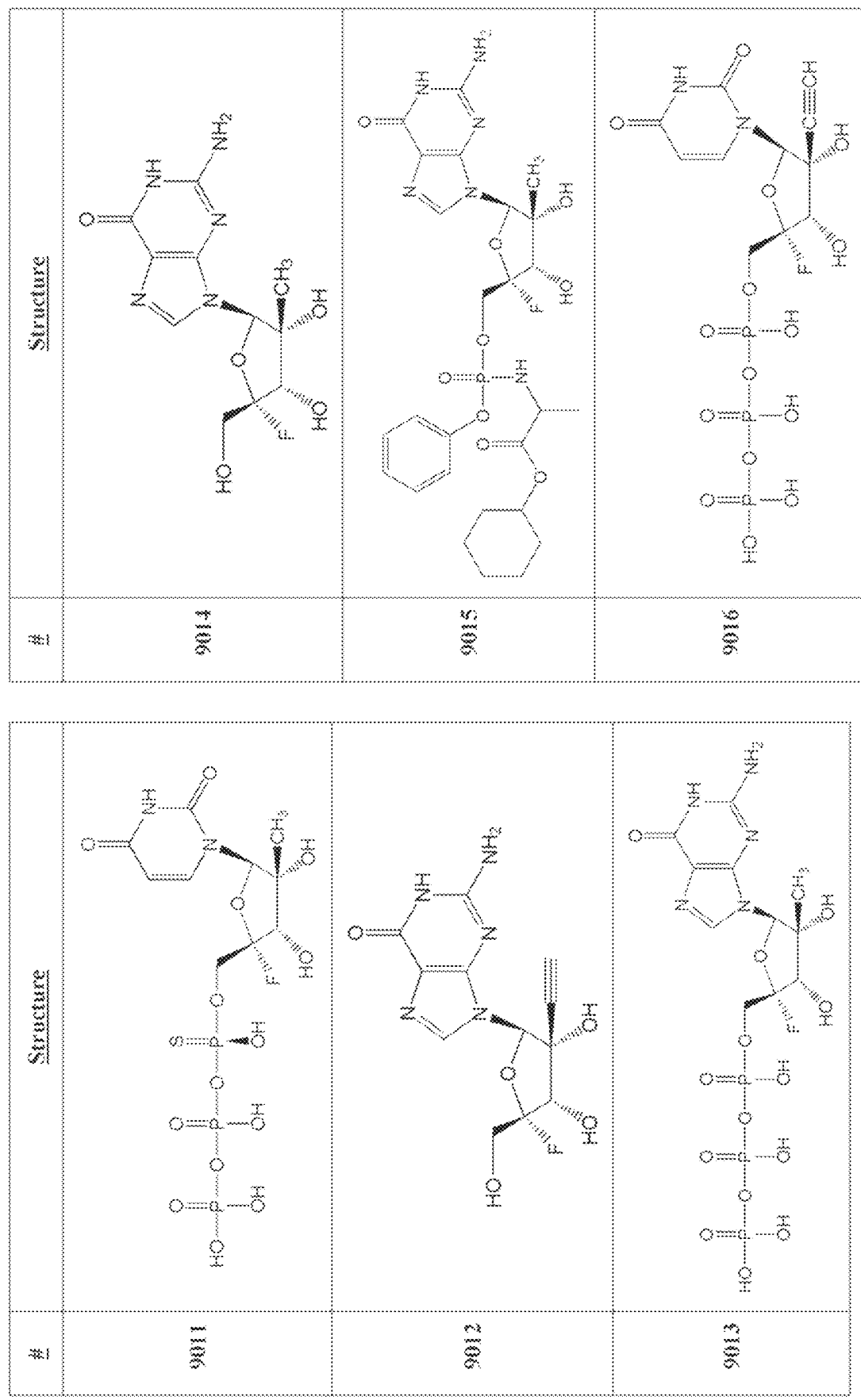
Figure 9 (cont.): Compounds of Formula (I)

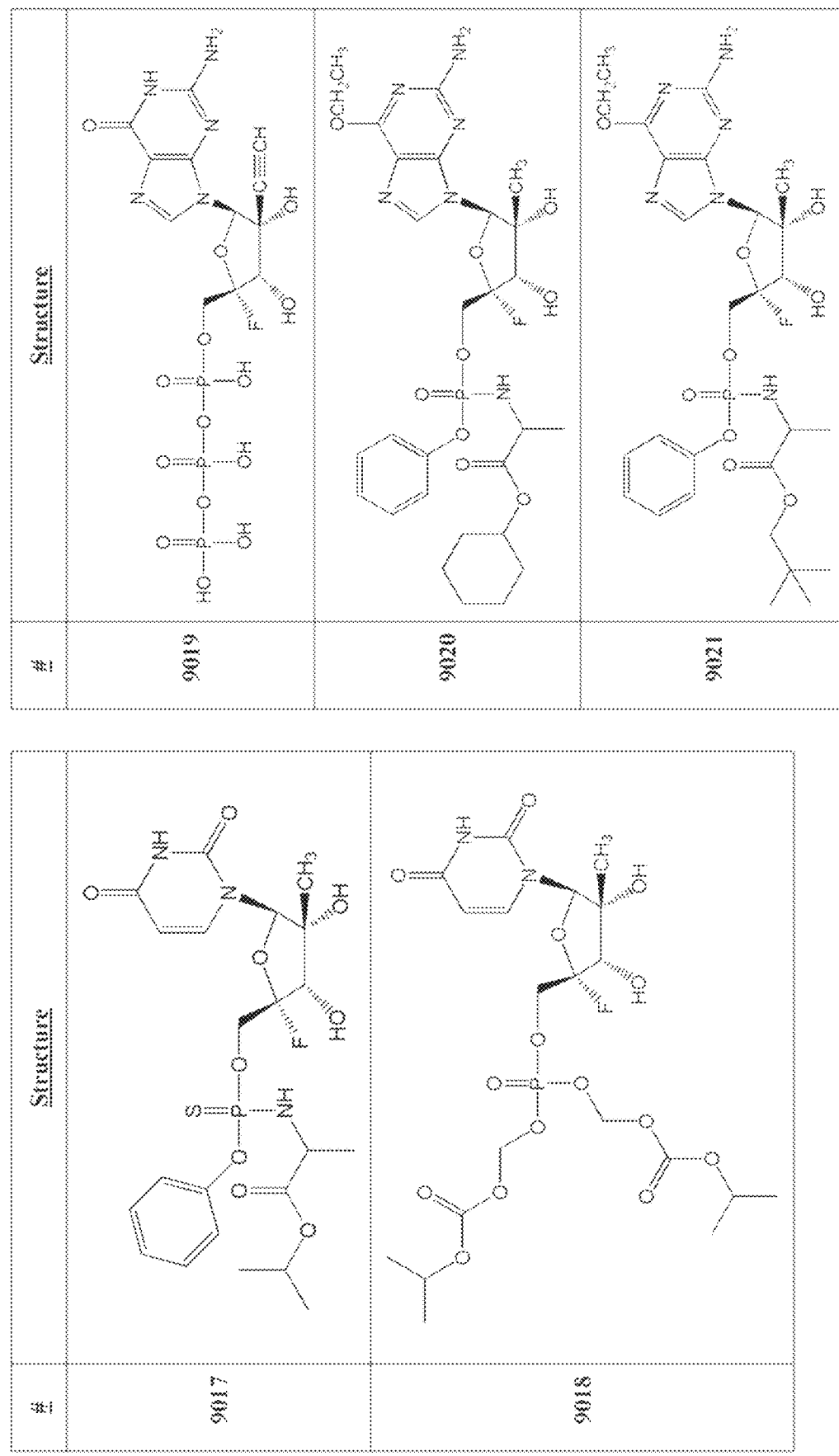
Figure 9 (cont.): Compounds of Formula (II)

Figure 9 (cont.): Compounds of Formula (I)
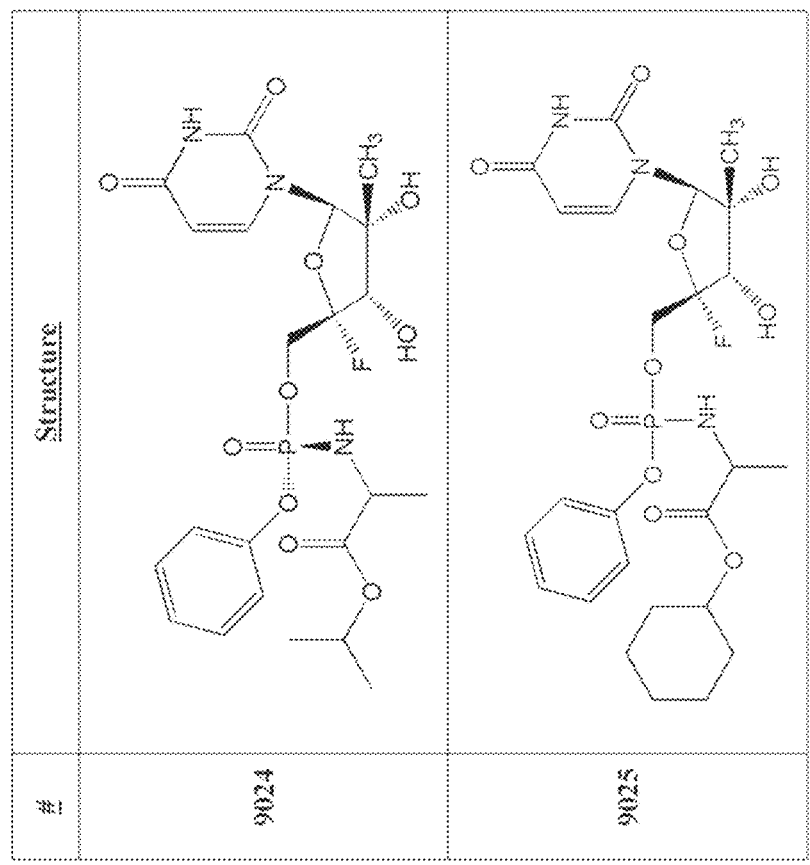
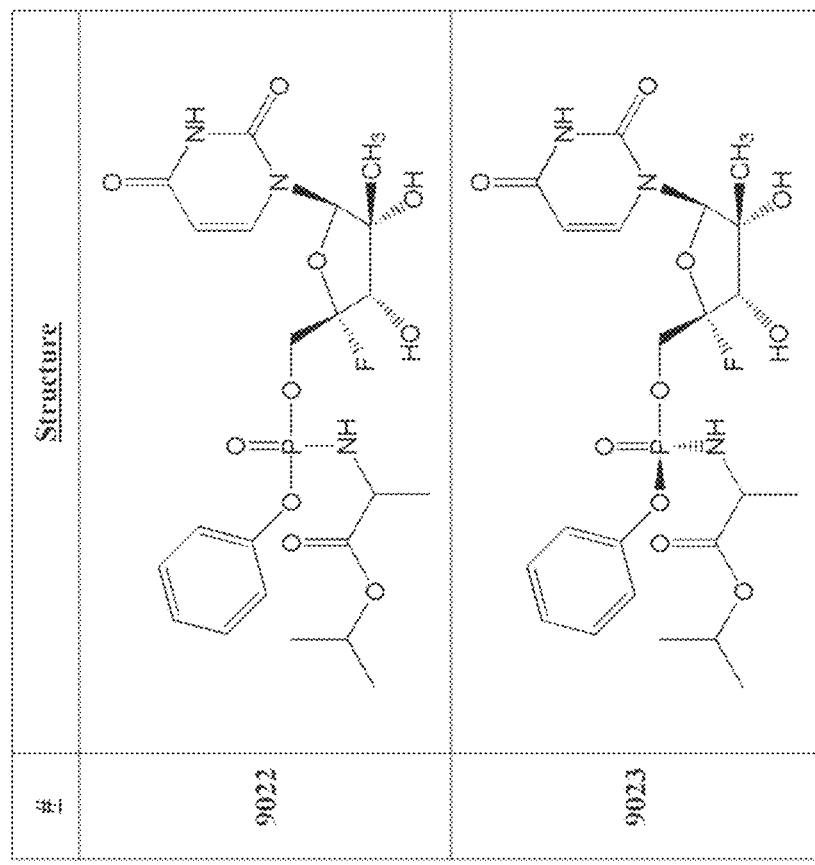

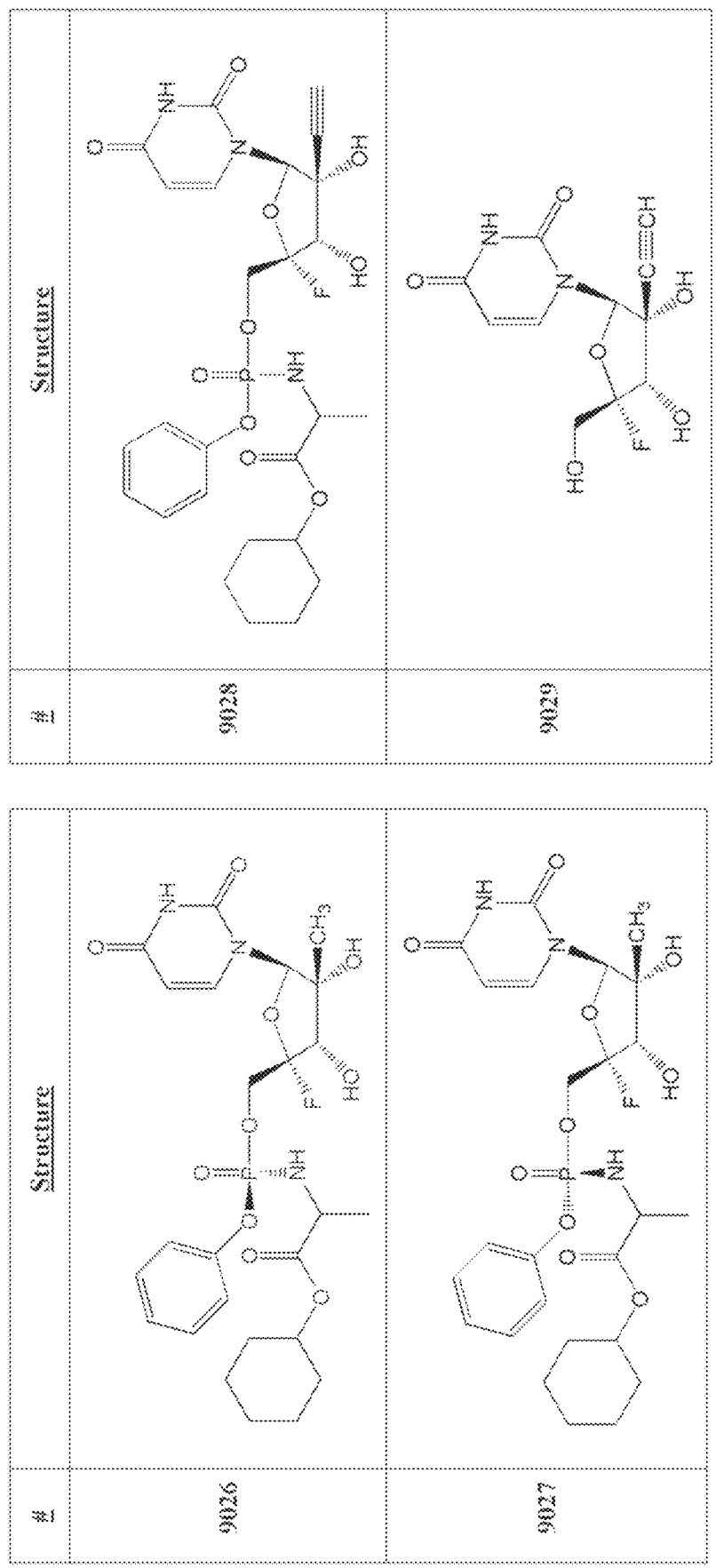
Figure 9 (cont.): Compounds of Formula (II)

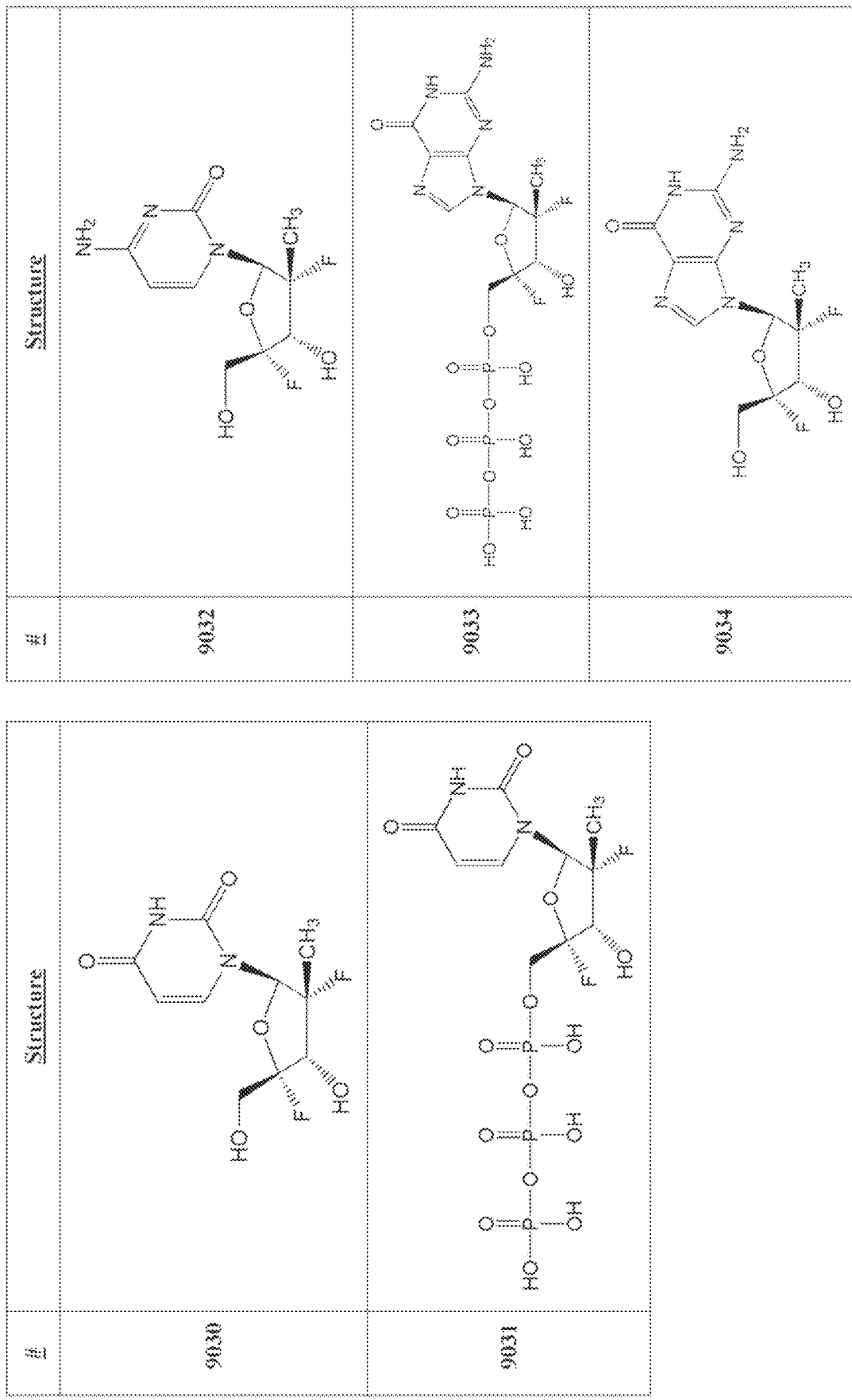
Figure 9 (cont.): Compounds of Formula (I)

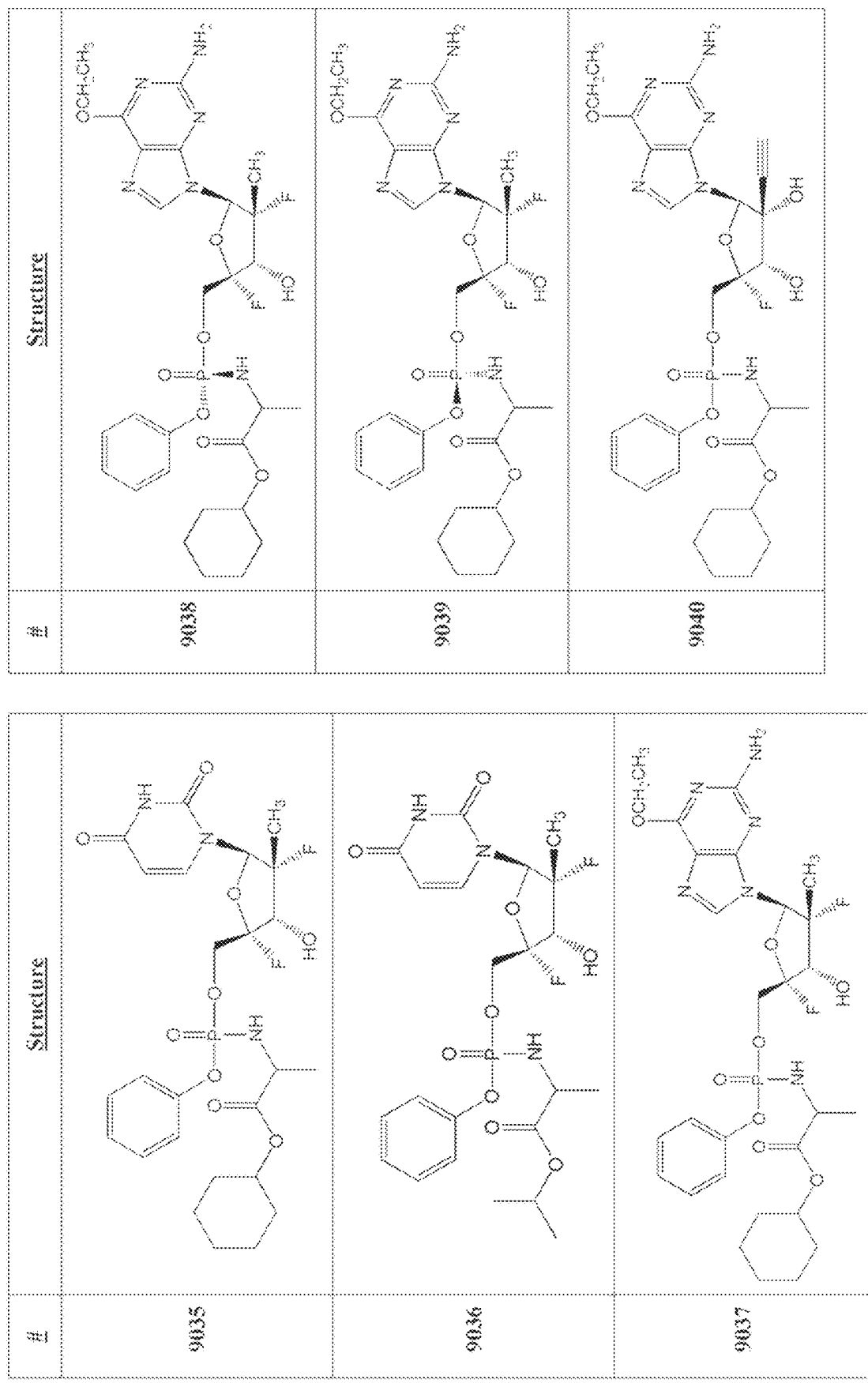
Figure 9 (cont.): Compounds of Formula (I)

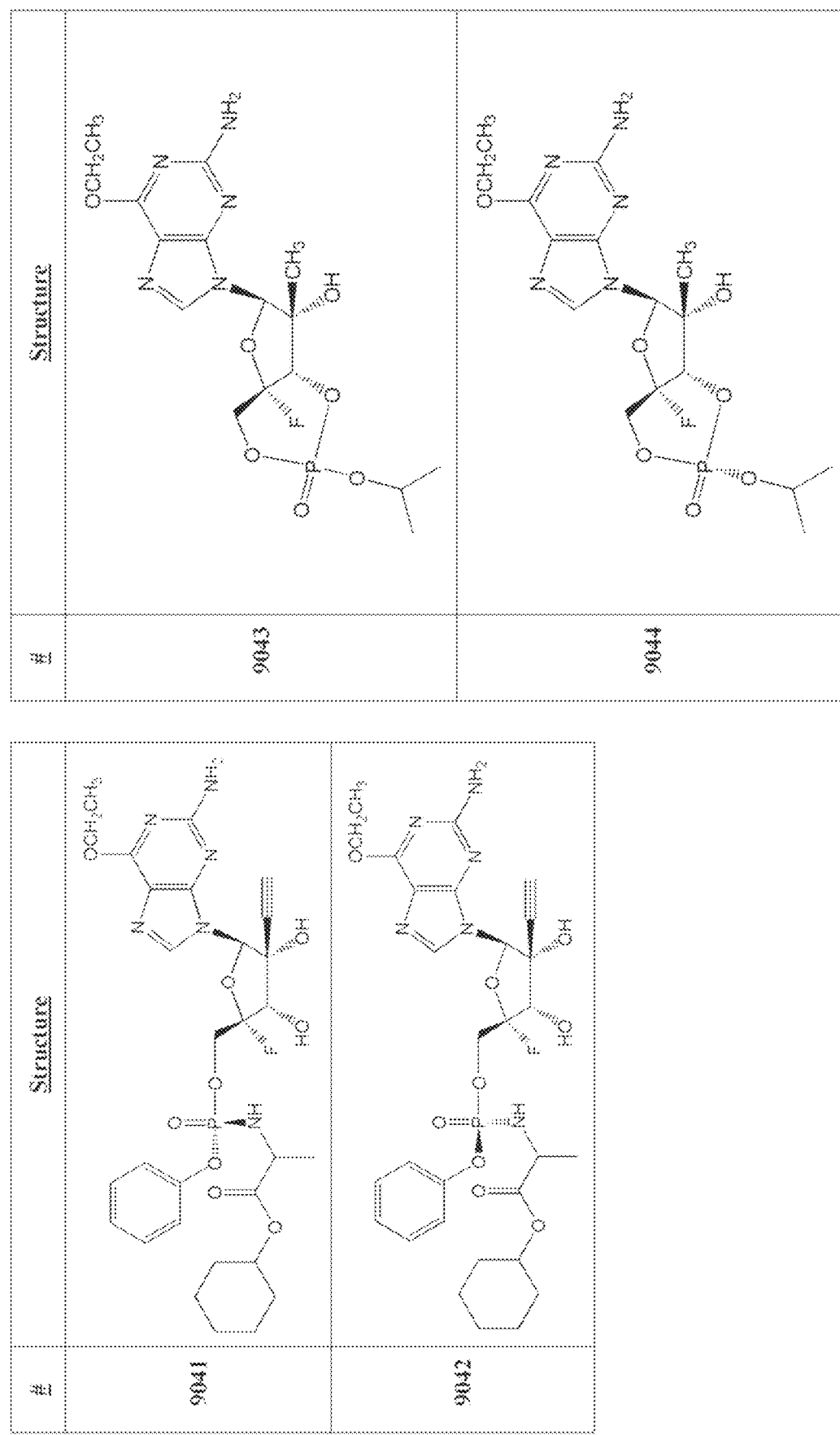
Figure 9 (cont.): Compounds of Formula (I)

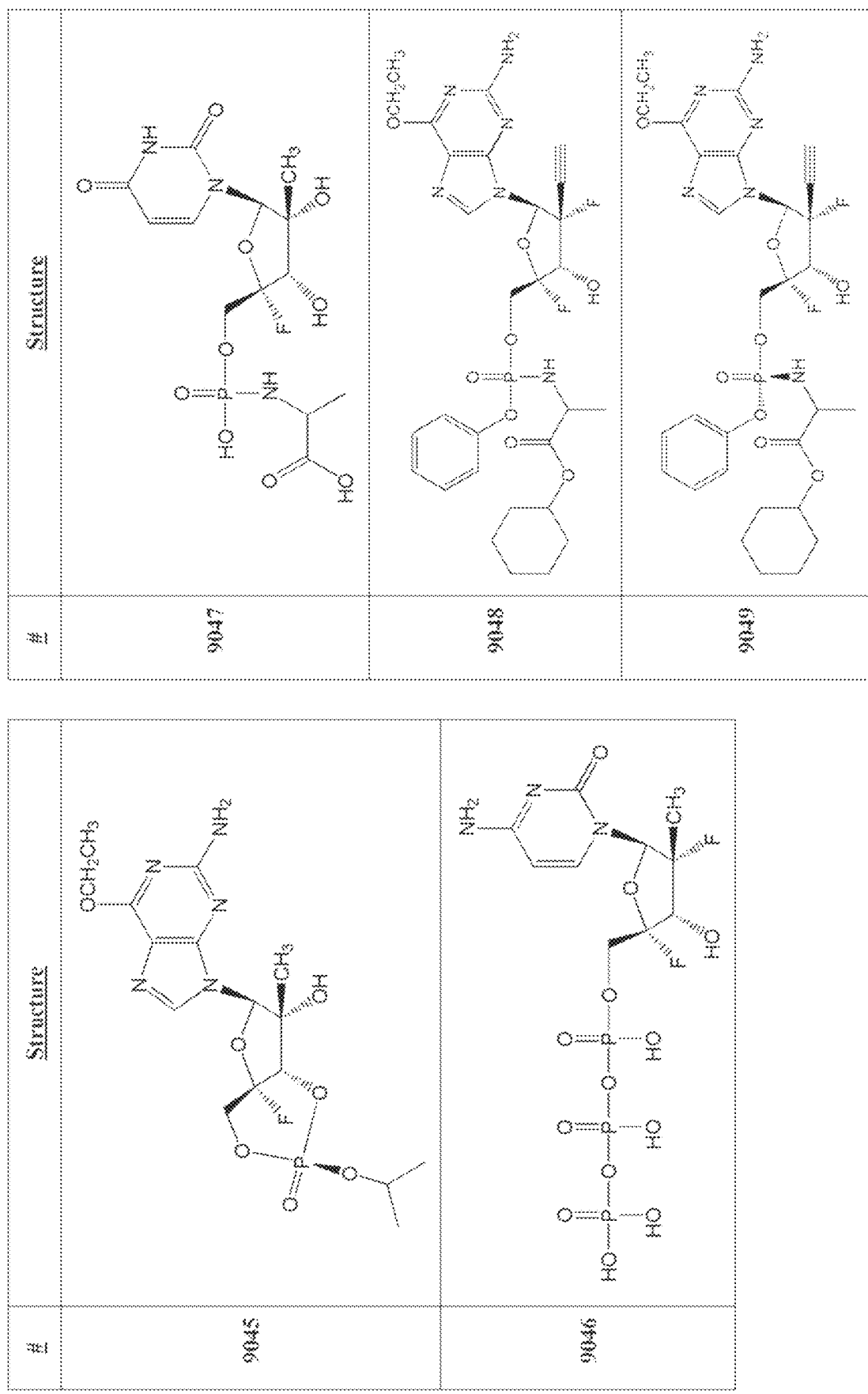
Figure 9 (cont.): Compounds of Formula (I)

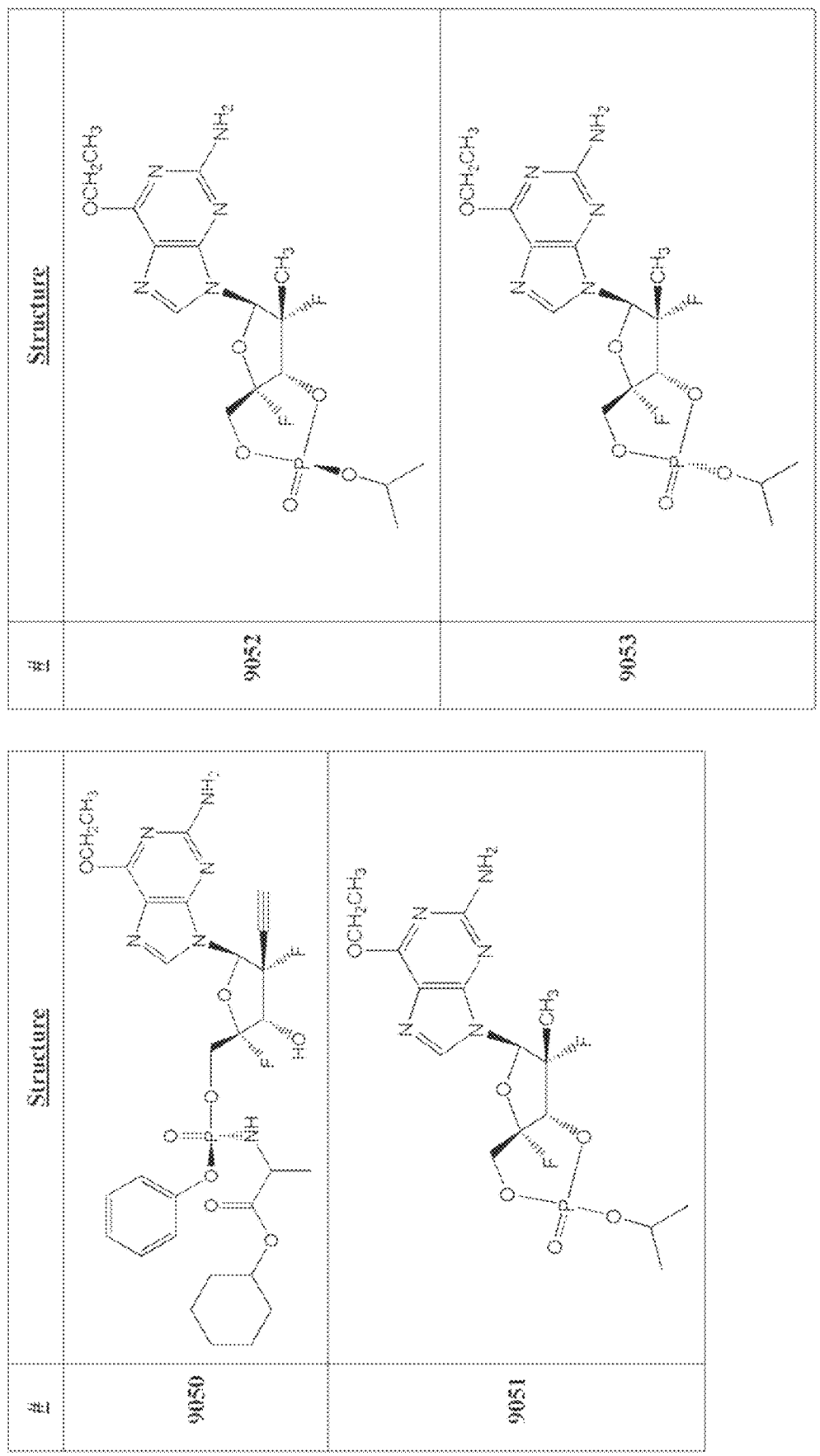

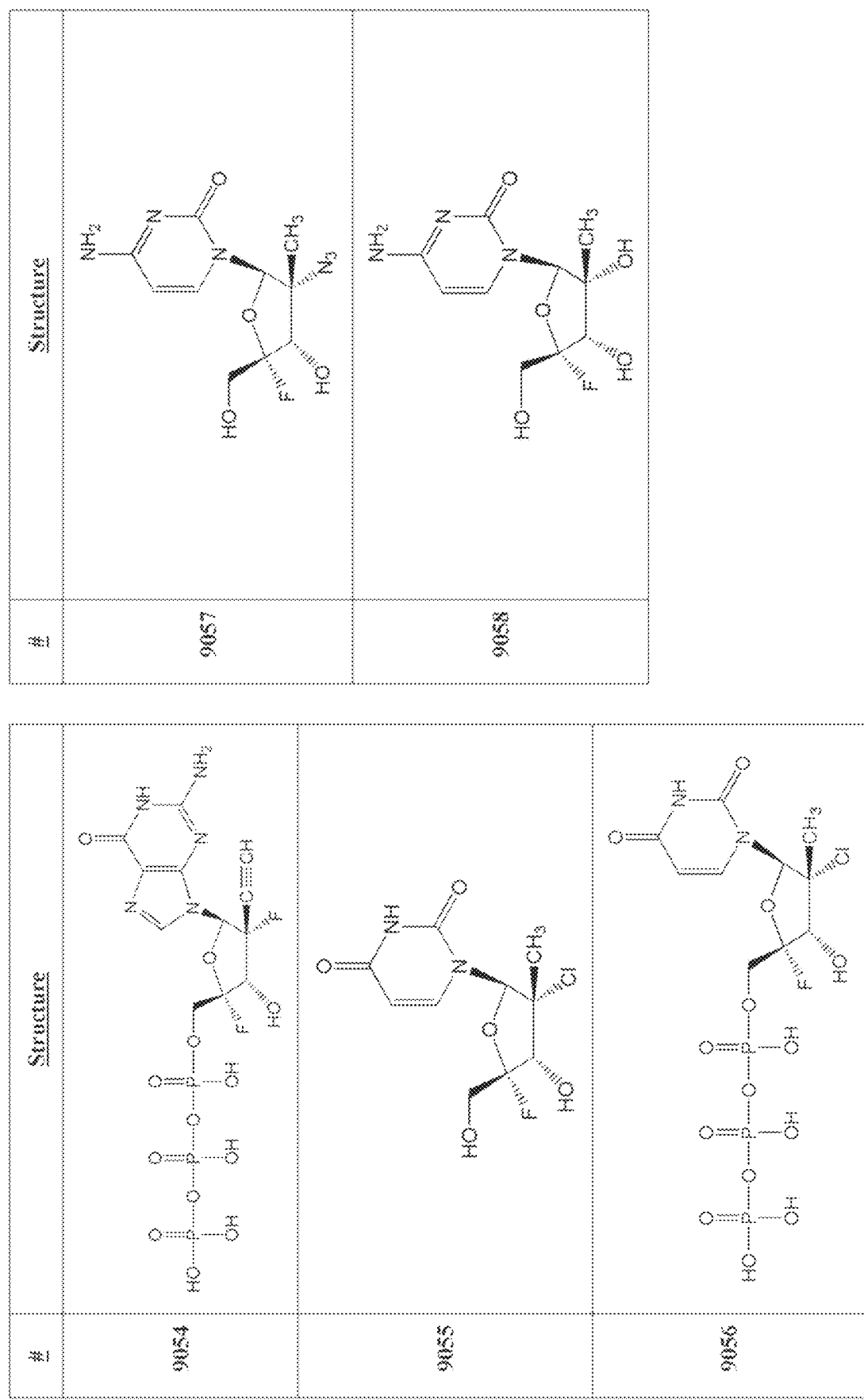
Figure 9 (cont): Compounds of Formula (I)

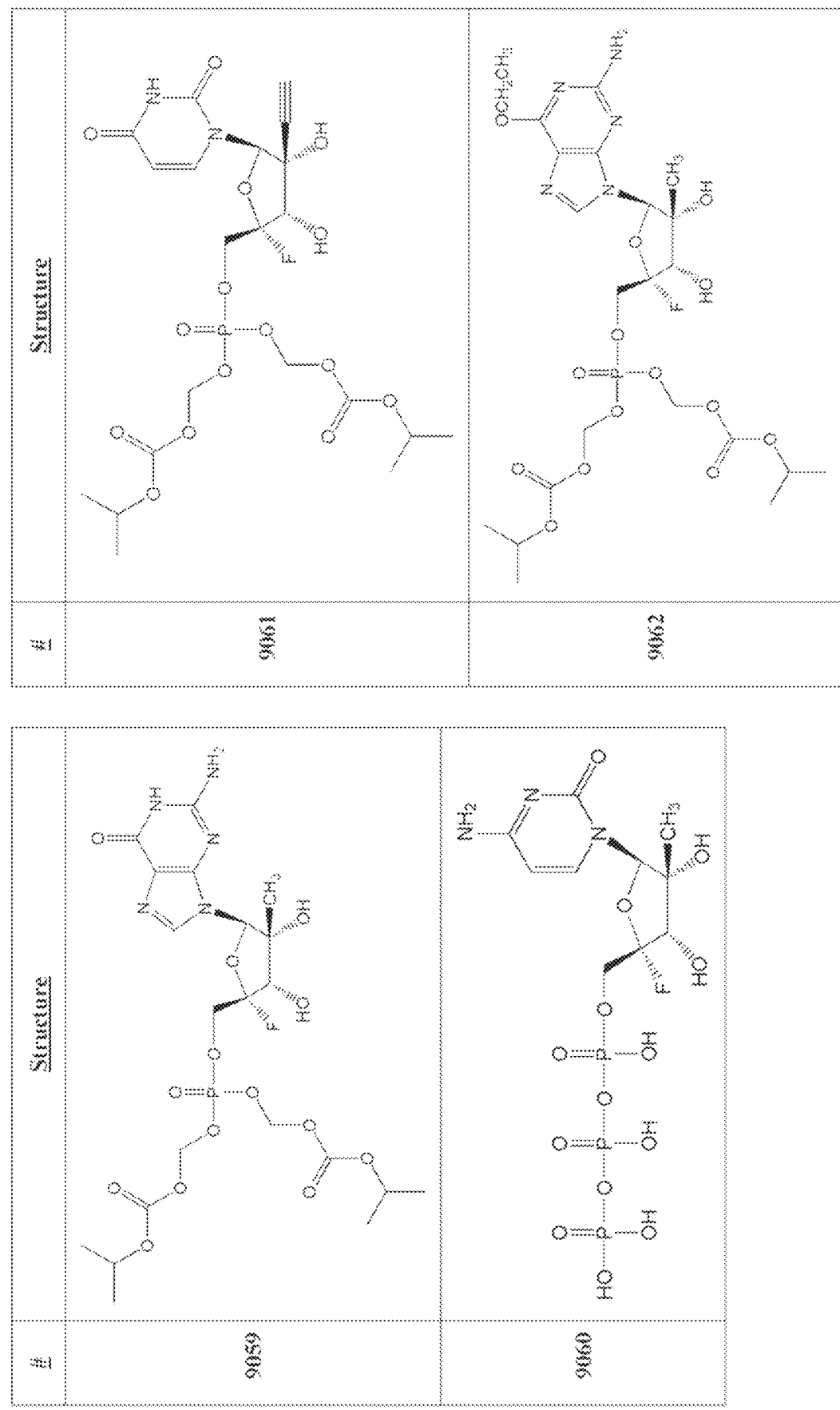

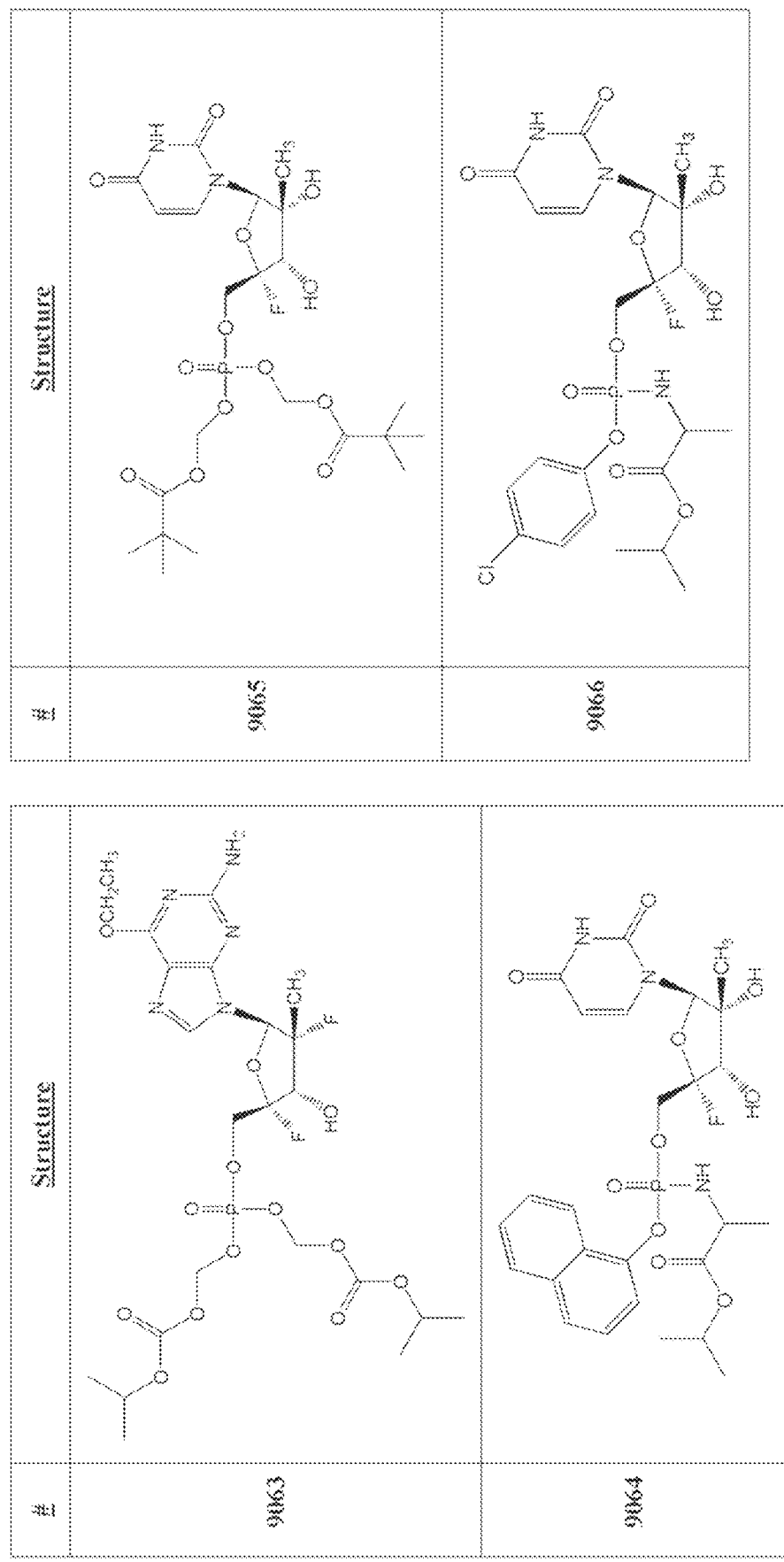

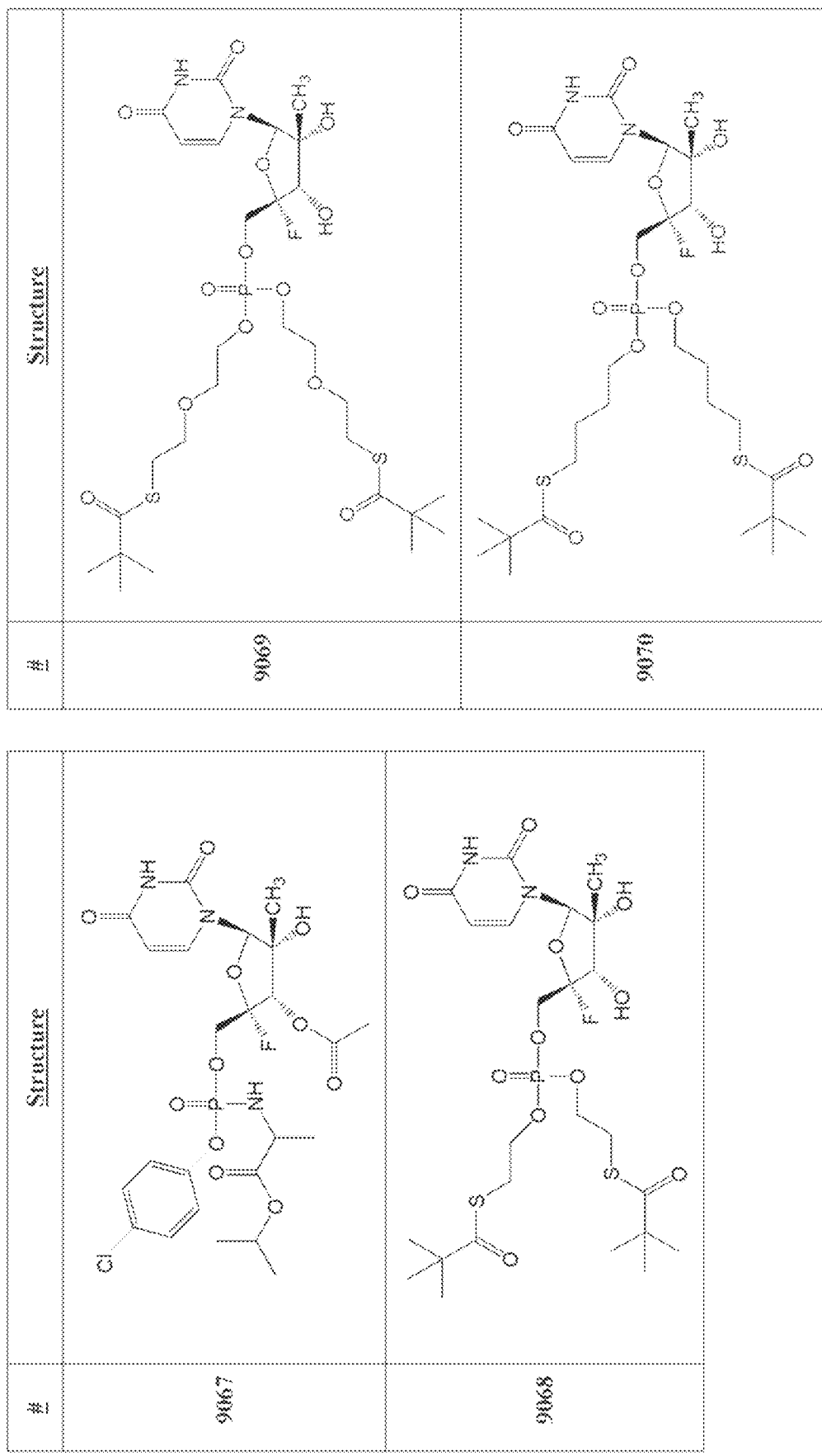

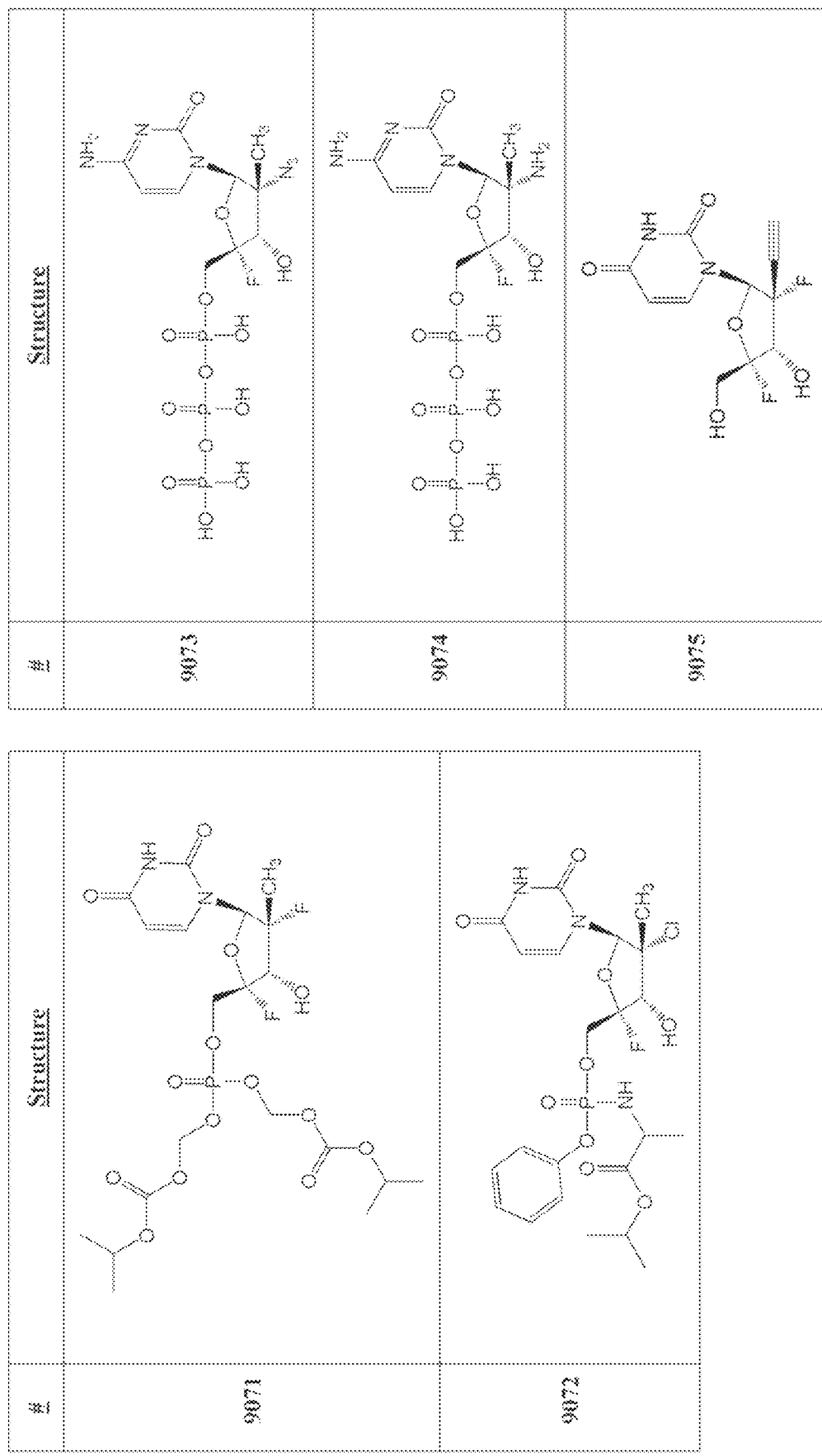
Figure 9 (cont.): Compounds of Formula (I)

Figure 9 (cont.): Compounds of Formula (I)
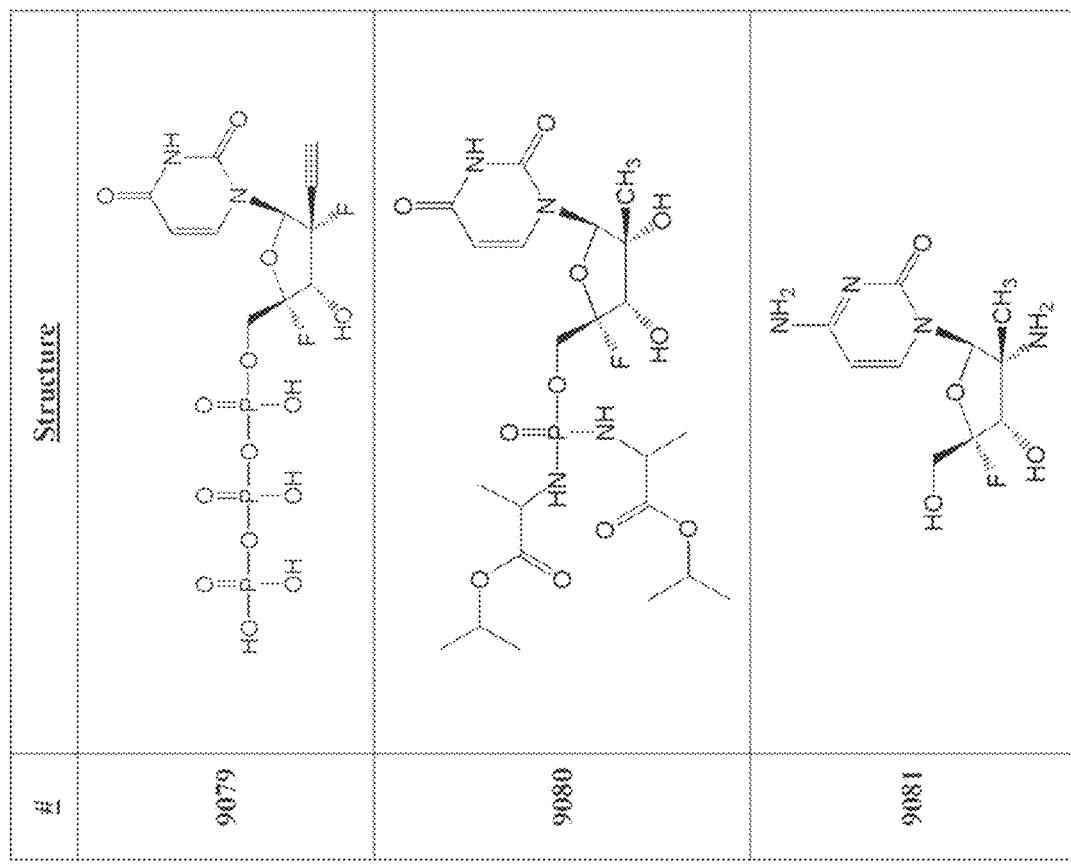
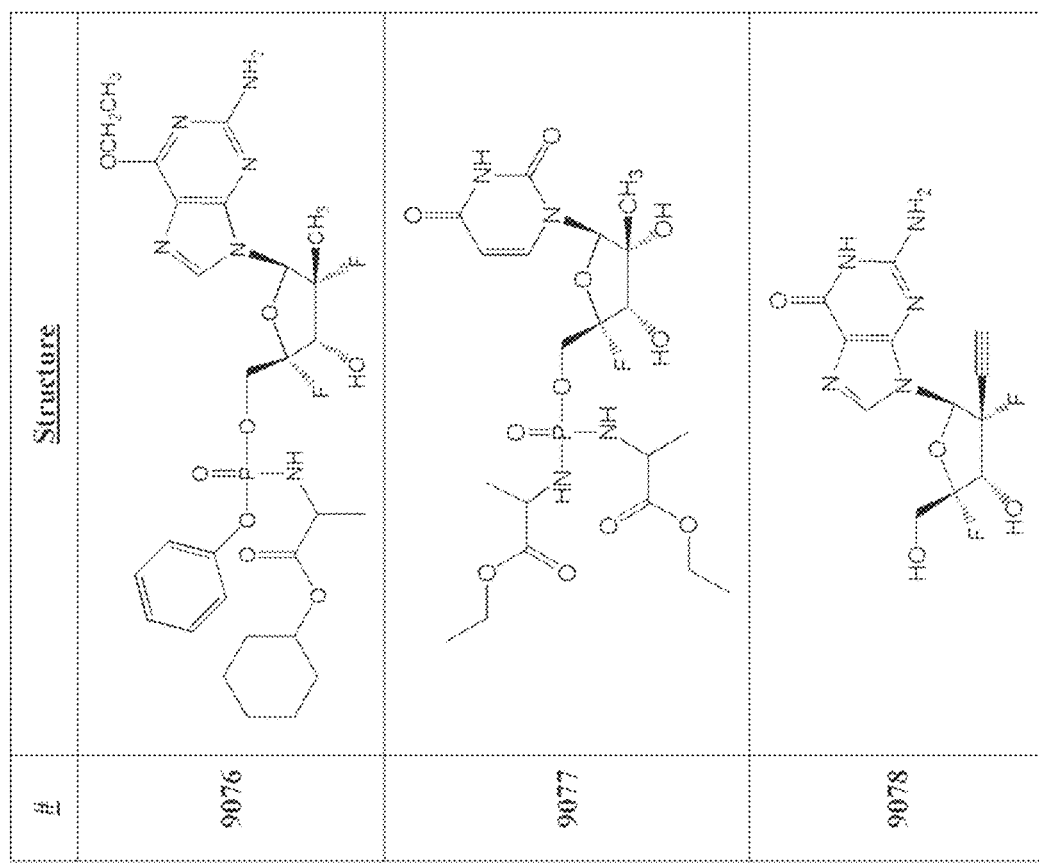

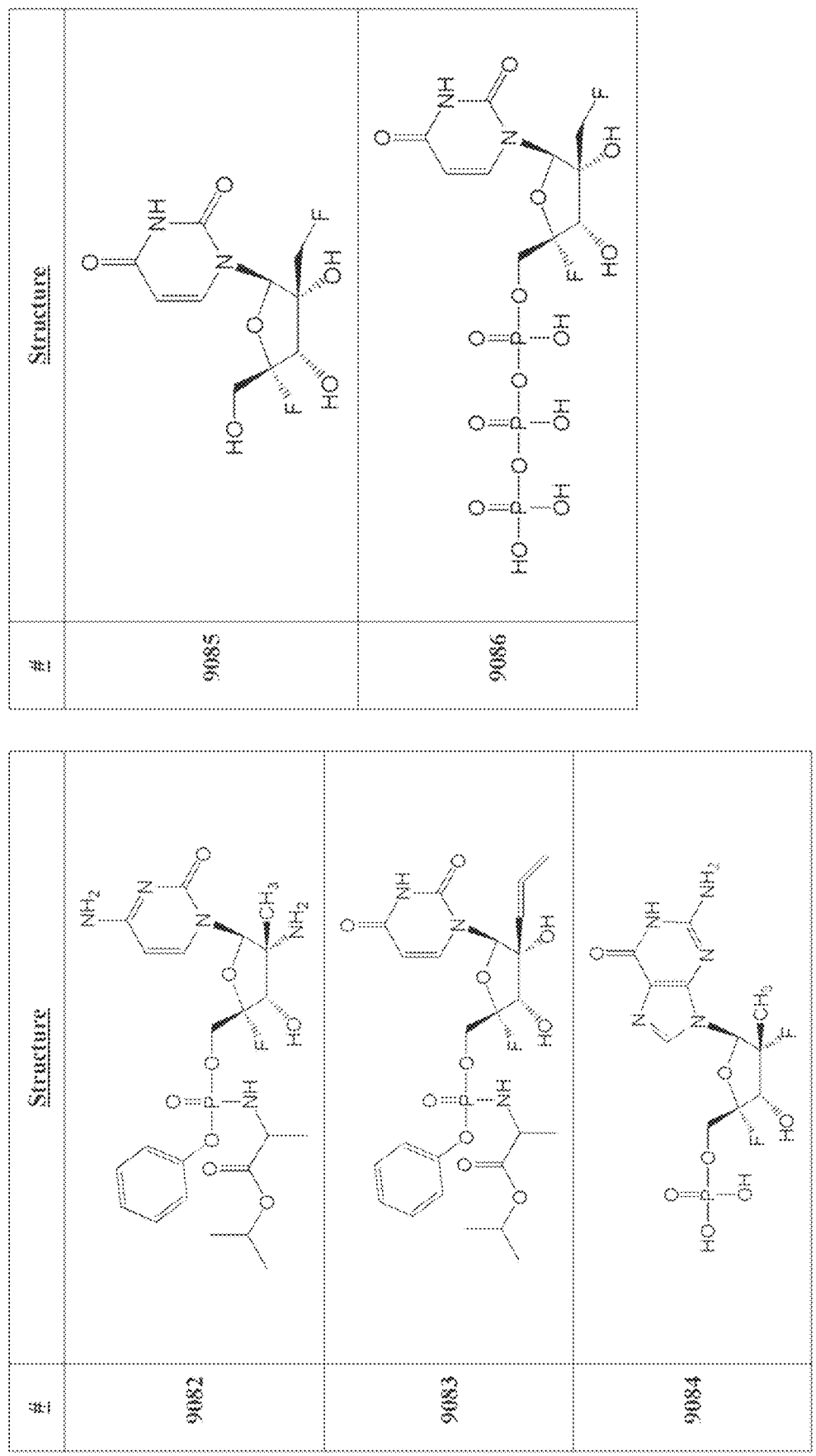
Figure 9 (cont.): Compounds of Formula (I)

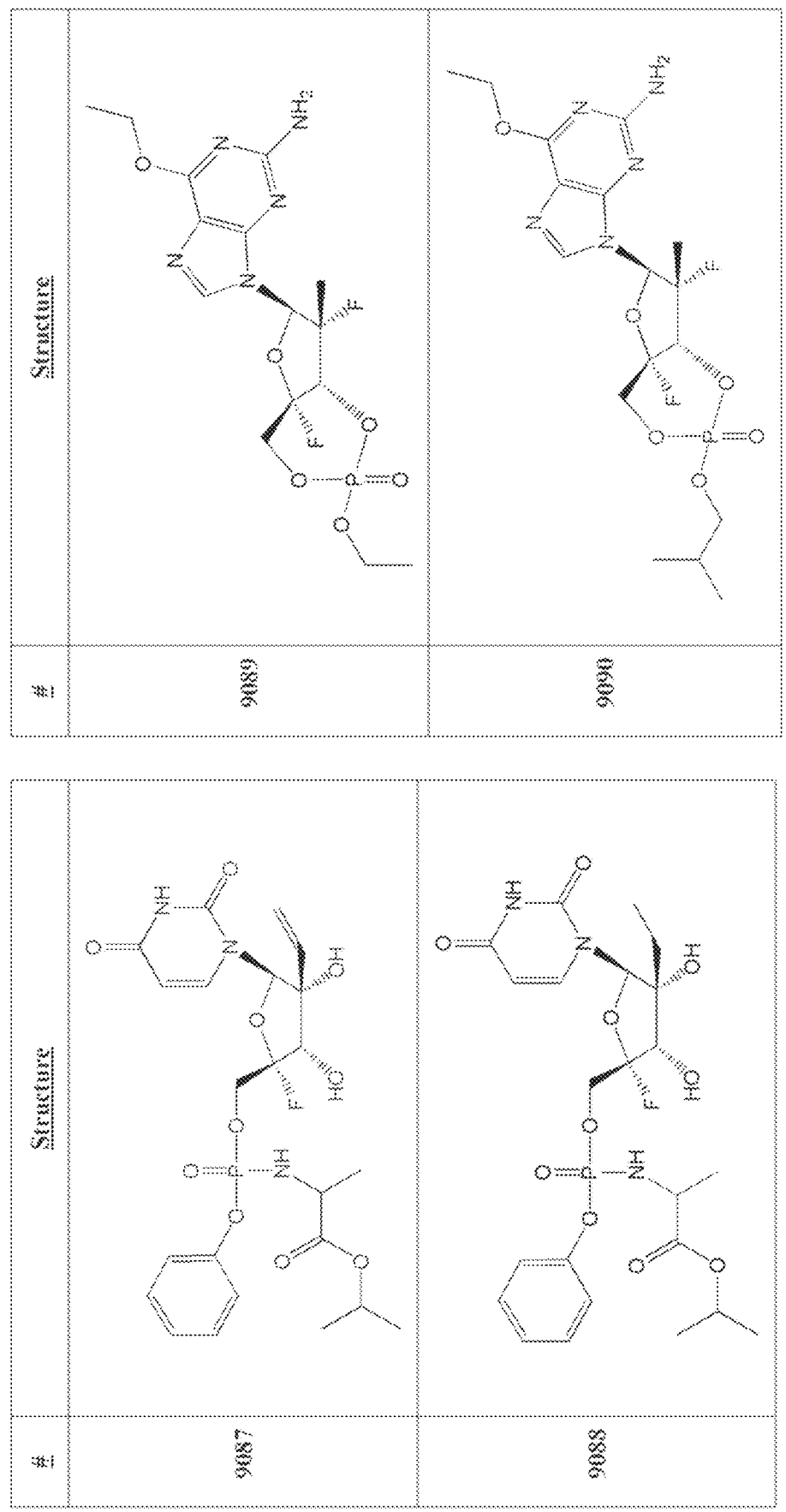
Figure 9 (cont.): Compounds of Formula (I)

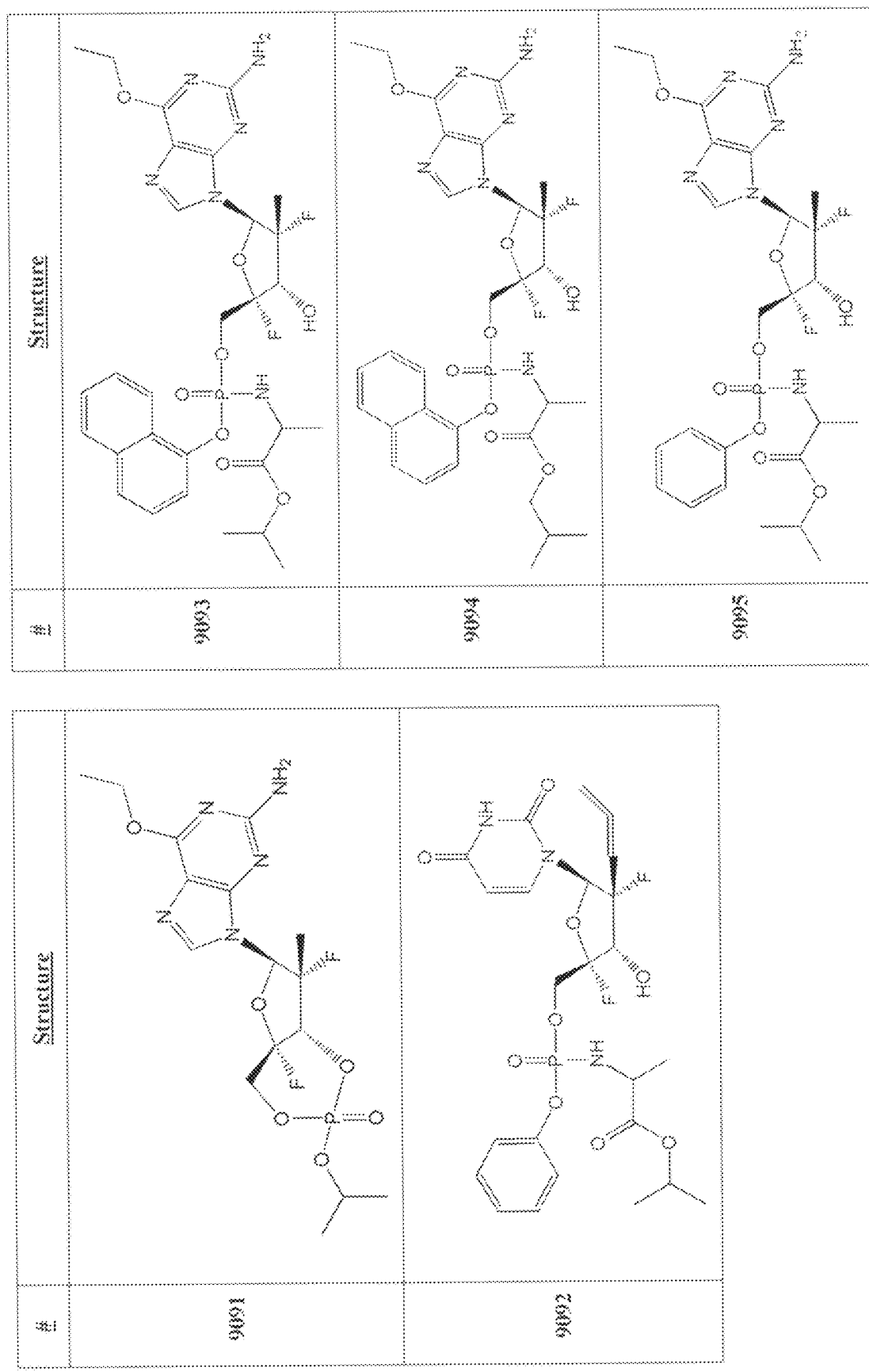
Figure 9 (cont.): Compounds of Formula (I)

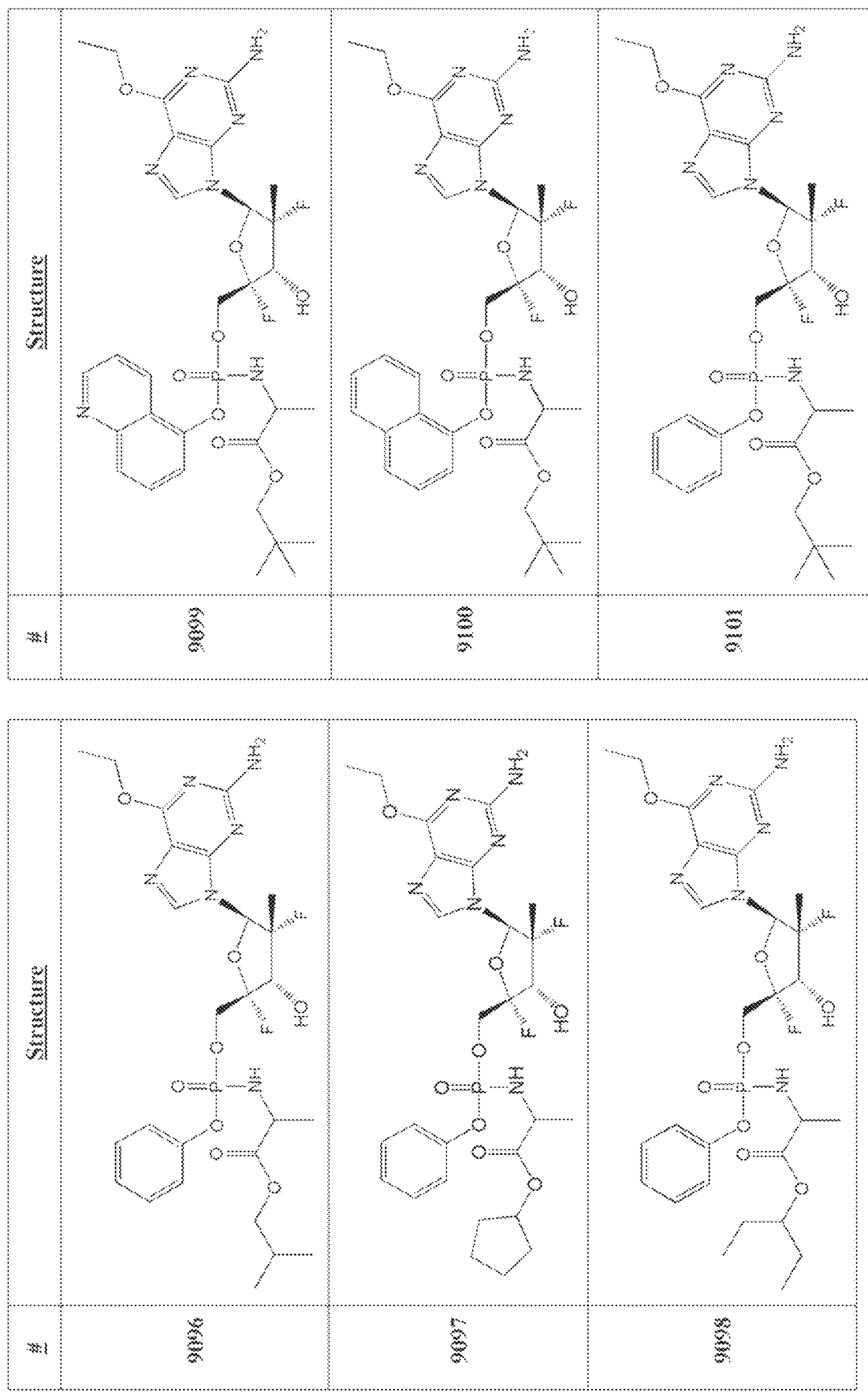
Figure 9 (cont.): Compounds of Formula (I)

Figure 9 (cont.): Compounds of Formula (I)
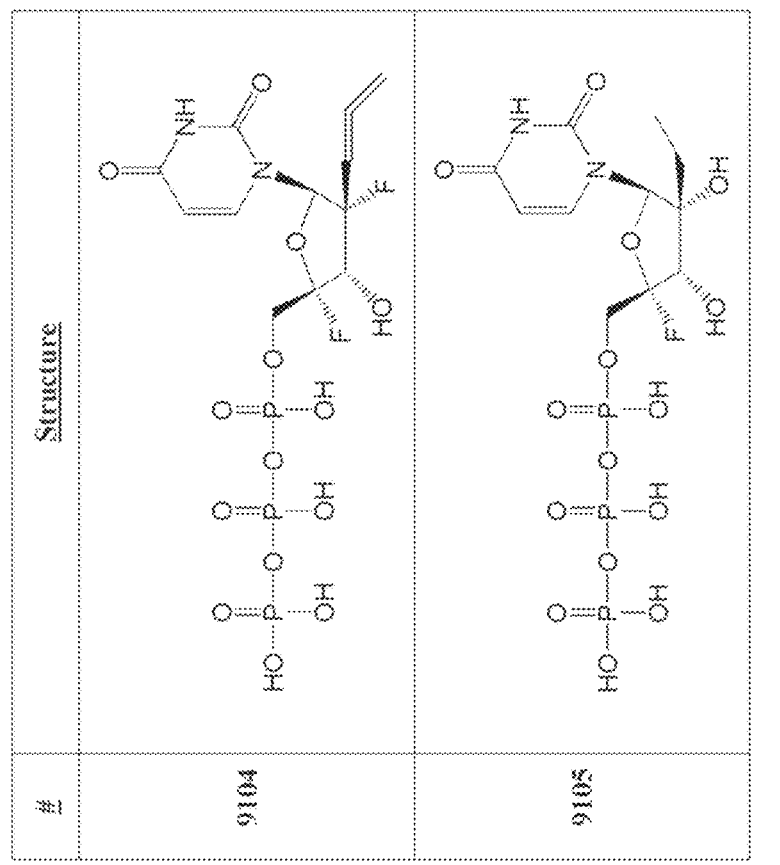
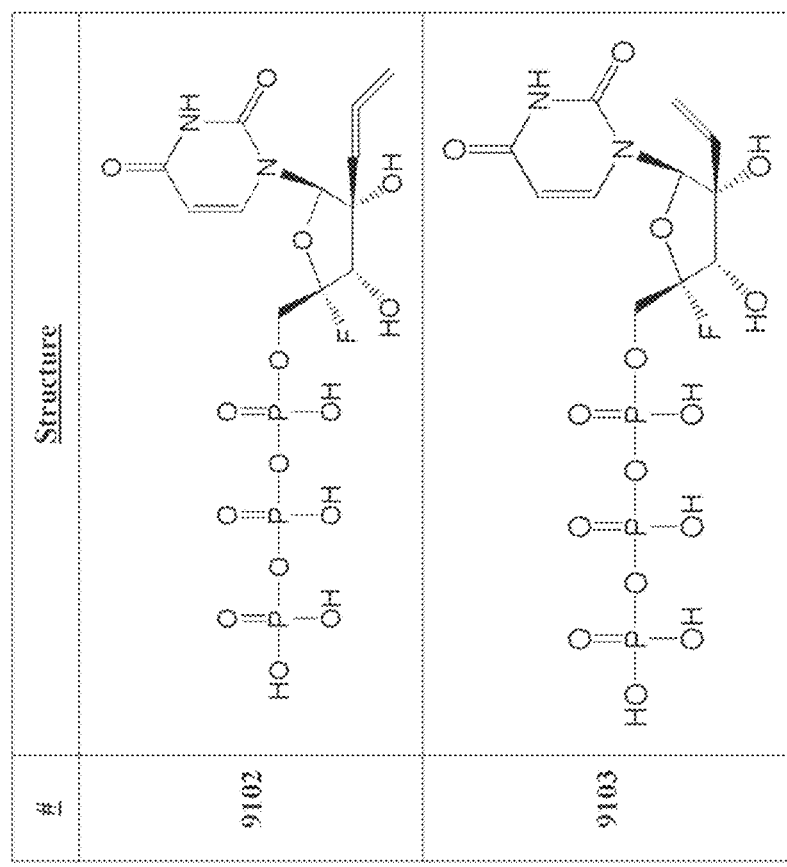

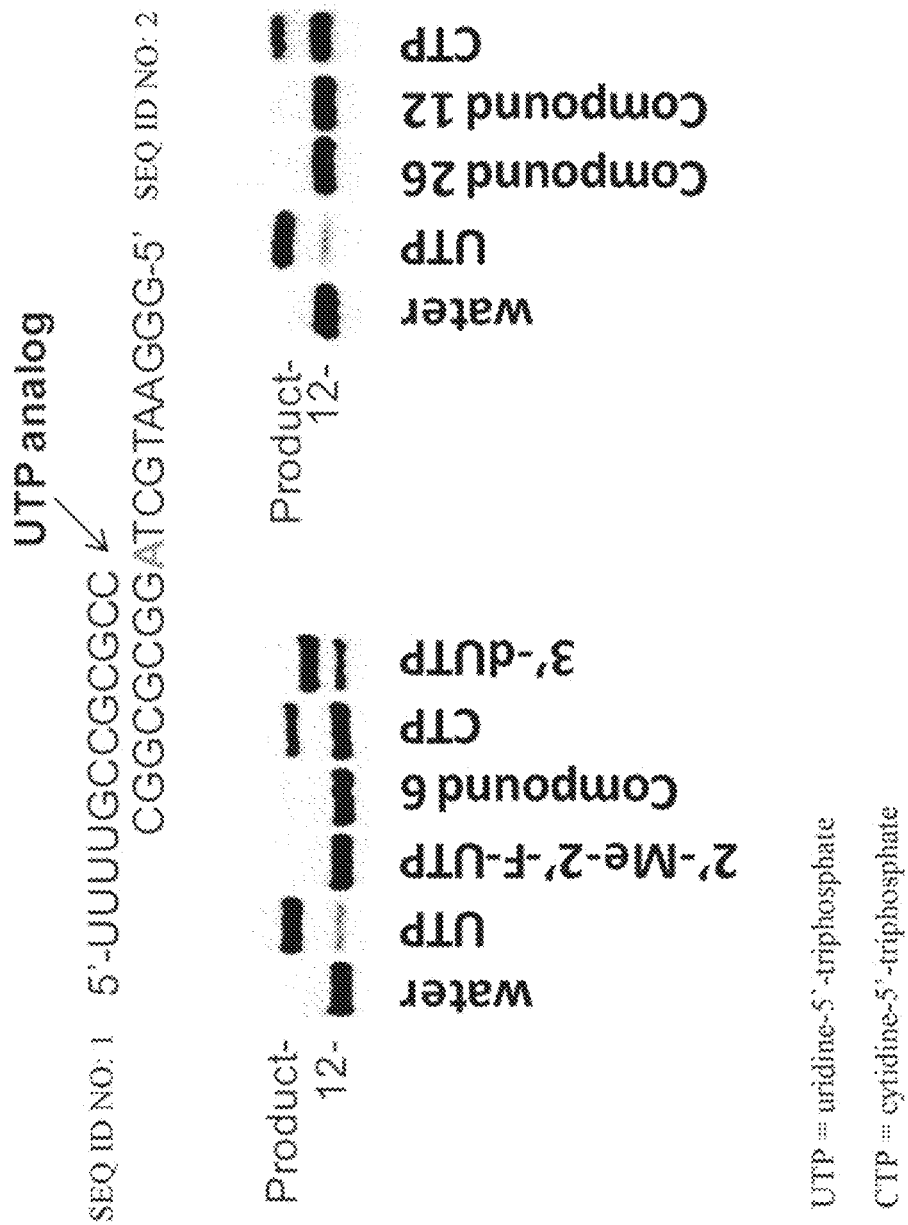

Figure 12A
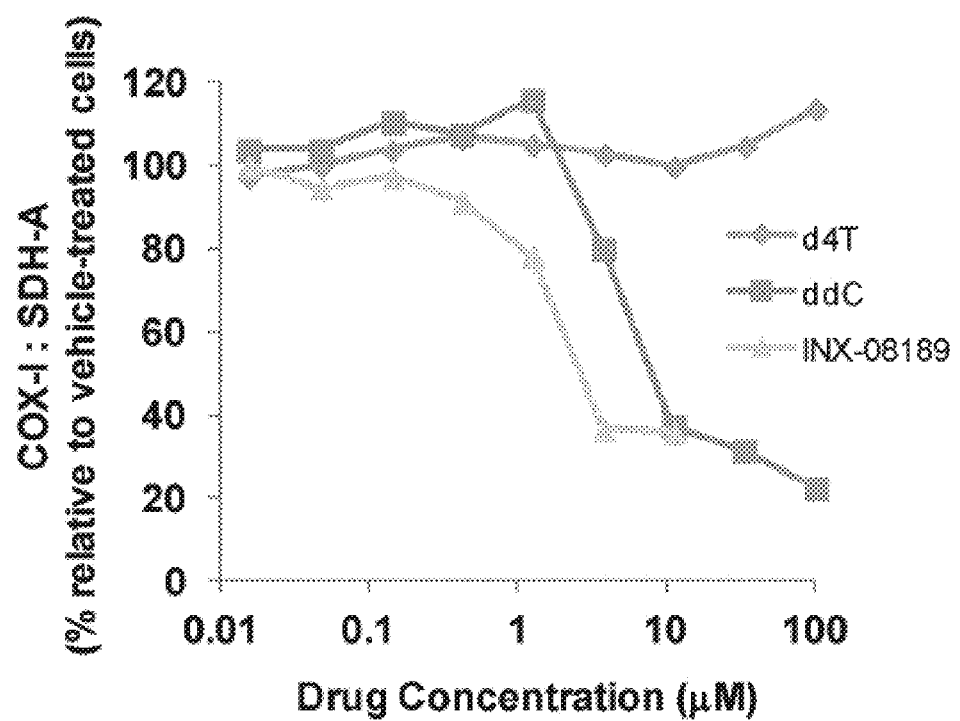
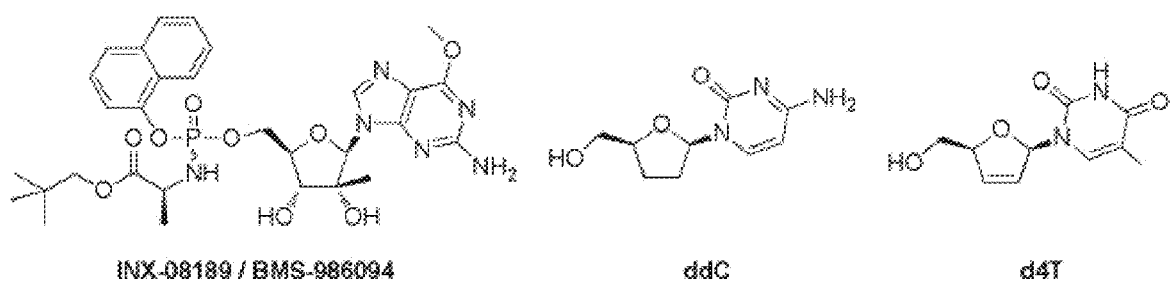

SEQUENCE LISTING

<160> NUMBER OF SEQ ID NOS: 4

<210> SEQ ID NO 1
<211> LENGTH: 12
<212> TYPE: RNA
<213> ORGANISM: Artificial Sequence
<220> FEATURE:
<223> OTHER INFORMATION: synthetic polynucleotides

<400> SEQUENCE: 1
uuuugccgcg cc                                                          12

<210> SEQ ID NO 2
<211> LENGTH: 18
<212> TYPE: DNA
<213> ORGANISM: Artificial Sequence
<220> FEATURE:
<223> OTHER INFORMATION: synthetic polynucleotides

<400> SEQUENCE: 2
gggaatgcta ggcgcggc                                                    18

<210> SEQ ID NO 3
<211> LENGTH: 12
<212> TYPE: RNA
<213> ORGANISM: Artificial Sequence
<220> FEATURE:
<223> OTHER INFORMATION: synthetic polynucleotides

<400> SEQUENCE: 3
uuuugccgcg cc                                                          12

<210> SEQ ID NO 4
<211> LENGTH: 18
<212> TYPE: DNA
<213> ORGANISM: Artificial Sequence
<220> FEATURE:
<223> OTHER INFORMATION: synthetic polynucleotides

<400> SEQUENCE: 4
gggaatgcac ggcgcggc                                                    18

SUBSTITUTED NUCLEOSIDES, NUCLEOTIDES AND ANALOGS THEREOF

CROSS REFERENCE TO RELATED APPLICATIONS

This application is a continuation application of U.S. patent application Ser. No. 16/692,858, filed Nov. 22, 2019, which is a continuation application of U.S. patent application Ser. No. 16/161,705, filed Oct. 16, 2018, now U.S. Pat. No. 10,487,104, which is a continuation application of U.S. patent application Ser. No. 15/256,337, filed Sep. 2, 2016, now U.S. Pat. No. 10,112,966, which is a continuation application of U.S. patent application Ser. No. 14/836,896, filed Aug. 26, 2015, which is a continuation application of U.S. patent application Ser. No. 14/135,484, filed Dec. 19, 2013, now U.S. Pat. No. 9,243,022, which claims priority benefit to U.S. Provisional Application Nos. 61/890,125, filed Oct. 11, 2013, and 61/745,466, filed Dec. 21, 2012, the disclosures of each of which are hereby incorporated by reference in their entireties for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 756982002409SEQLIST.TXT, date recorded: Oct. 5, 2020, size: 2 KB).

BACKGROUND

Field

The present application relates to the fields of chemistry, biochemistry and medicine. More particularly, disclosed herein are nucleotide analogs, pharmaceutical compositions that include one or more nucleotide analogs and methods of synthesizing the same. Also disclosed herein are methods of treating diseases and/or conditions with a nucleotide analog, alone or in combination therapy with one or more other agents.

Description

Nucleoside analogs are a class of compounds that have been shown to exert antiviral and anticancer activity both in vitro and in vivo, and thus, have been the subject of widespread research for the treatment of viral infections. Nucleoside analogs are usually therapeutically inactive compounds that are converted by host or viral enzymes to their respective active anti-metabolites, which, in turn, may inhibit polymerases involved in viral or cell proliferation. The activation occurs by a variety of mechanisms, such as the addition of one or more phosphate groups and, or in combination with, other metabolic processes.

SUMMARY

Some embodiments disclosed herein relate to a compound of Formula (I) or a pharmaceutically acceptable salt thereof. Some embodiments disclosed herein relate to a method of ameliorating and/or treating a hepatitis C viral (HCV) infection that can include administering to a subject identified as suffering from the HCV infection an effective amount of one or more compounds of Formula (I), or a pharmaceutically acceptable salt thereof, or a pharmaceutical composition that includes one or more compounds of Formula (I), or a pharmaceutically acceptable salt thereof. Other embodiments described herein relate to using one or more compounds of Formula (I), or a pharmaceutically acceptable salt thereof, in the manufacture of a medicament for ameliorating and/or treating a HCV infection. Still other embodiments described herein relate to one or more compounds of Formula (I), or a pharmaceutically acceptable salt thereof, or a pharmaceutical composition that includes one or more compounds of Formula (I), or a pharmaceutically acceptable salt thereof, that can be used for ameliorating and/or treating a HCV infection.

Some embodiments disclosed herein relate to a method of ameliorating and/or treating a HCV infection that can include contacting a cell infected with the hepatitis C virus with an effective amount of one or more compounds described herein, or a pharmaceutically acceptable salt of one or more compounds described herein, or a pharmaceutical composition that includes one or more compounds described herein, or a pharmaceutically acceptable salt thereof. Other embodiments described herein relate to using one or more compounds described herein, or a pharmaceutically acceptable salt of one or more compounds described herein, in the manufacture of a medicament for ameliorating and/or treating a HCV infection that can include contacting a cell infected with the hepatitis C virus with an effective amount of said compound(s). Still other embodiments described herein relate to one or more compounds described herein, or a pharmaceutically acceptable salt of one or more compounds described herein, or a pharmaceutical composition that includes one or more compounds described herein, or a pharmaceutically acceptable salt thereof, that can be used for ameliorating and/or treating a HCV infection by contacting a cell infected with the hepatitis C virus with an effective amount of said compound(s).

Some embodiments disclosed herein relate to a method of inhibiting replication of a hepatitis C virus that can include contacting a cell infected with the hepatitis C virus with an effective amount of one or more compounds described herein, or a pharmaceutically acceptable salt of one or more compounds described herein, or a pharmaceutical composition that includes one or more compounds described herein, or a pharmaceutically acceptable salt thereof. Other embodiments described herein relate to using one or more compounds described herein, or a pharmaceutically acceptable salt of one or more compounds described herein, in the manufacture of a medicament for inhibiting replication of a hepatitis C virus that can include contacting a cell infected with the hepatitis C virus with an effective amount of said compound(s). Still other embodiments described herein relate to one or more compounds described herein, or a pharmaceutically acceptable salt of one or more compounds described herein, or a pharmaceutical composition that includes one or more compounds described herein, or a pharmaceutically acceptable salt thereof, that can be used for inhibiting replication of a hepatitis C virus by contacting a cell infected with the hepatitis C virus with an effective amount of said compound(s).

Some embodiments disclosed herein relate to a method of ameliorating and/or treating a HCV infection that can include administering to a subject identified as suffering from the HCV infection an effective amount of a compound described herein or a pharmaceutically acceptable salt thereof (for example, one or more compounds of Formula (I), or a pharmaceutically acceptable salt thereof), or a pharmaceutical composition that includes a compound described herein, or a pharmaceutically acceptable salt thereof, in combination with an agent selected from an interferon, ribavirin, a HCV protease inhibitor, a HCV polymerase inhibitor, a NS5A inhibitor, an other antiviral compound, a compound of Formula (AA), a compound of Formula (BB) and a compound of Formula (CC), or a pharmaceutically acceptable salt of any of the foregoing. Some embodiments disclosed herein relate to a method of ameliorating and/or treating a HCV infection that can include contacting a cell infected with the HCV infection with an effective amount of a compound described herein or a pharmaceutically acceptable salt thereof (for example, one or more compounds of Formula (I), or a pharmaceutically acceptable salt thereof), or a pharmaceutical composition that includes a compound described herein, in combination with an agent selected from an interferon, ribavirin, a HCV protease inhibitor, a HCV polymerase inhibitor, a NS5A inhibitor, an other antiviral compound, a compound of Formula (AA), a compound of Formula (BB) and a compound of Formula (CC), or a pharmaceutically acceptable salt of any of the foregoing. Some embodiments disclosed herein relate to a method of inhibiting replication of a hepatitis C virus that can include administering to a subject identified as suffering from a HCV infection an effective amount of a compound described herein or a pharmaceutically acceptable salt thereof (for example, a compound of Formula (I), or a pharmaceutically acceptable salt thereof), or a pharmaceutical composition that includes a compound described herein, or a pharmaceutically acceptable salt thereof, in combination with an agent selected from an interferon, ribavirin, a HCV protease inhibitor, a HCV polymerase inhibitor, a NS5A inhibitor, another antiviral compound, a compound of Formula (AA), a compound of Formula (BB) and a compound of Formula (CC), or a pharmaceutically acceptable salt of any of the foregoing. In some embodiments, the agent can be a compound, or a pharmaceutically acceptable salt thereof, selected from Compound 1001-1016, 2001-2012, 3001-3014, 4001-4012, 5001-5012, 6001-6078, 7000-7027 and 8000-8016, or a pharmaceutical composition that includes one or more of the aforementioned compounds, or a pharmaceutically acceptable salt of the foregoing. In some embodiments, the method can include administering a second agent selected from an interferon, ribavirin, a HCV protease inhibitor, a HCV polymerase inhibitor, a NS5A inhibitor, an other antiviral compound, a compound of Formula (AA), a compound of Formula (BB) and a compound of Formula (CC), or a pharmaceutically acceptable salt of any of the foregoing.

BRIEF DESCRIPTION OF THE DRAWINGS

FIG. 1 shows example HCV protease inhibitors.

FIG. 2 shows example nucleoside HCV polymerase inhibitors.

FIG. 3 shows example non-nucleoside HCV polymerase inhibitors.

FIG. 4 shows example NS5A inhibitors.

FIG. 5 shows example other antivirals.

FIG. 6 shows example compounds of Formula (CC) and alpha-thiotriphosphates thereof, wherein Formula (CC) and alpha-thiotriphosphates thereof are described herein.

FIG. 7 shows example compounds of Formula (AA), wherein Formula (AA) is described herein.

FIG. 8 shows example compounds of Formula (BB), wherein Formula (BB) is described herein.

FIG. 9 shows example compounds of Formula (I), wherein Formula (I) is described herein.

FIG. 10 shows the gels from the assessment of incorporation of several compound with a uracil base by the human mitochondrial RNA polymerase.

FIGS. 12A-D shows the results of the inhibition of mitochondrial protein synthesis assays.

DETAILED DESCRIPTION

Definitions

Figure 11:
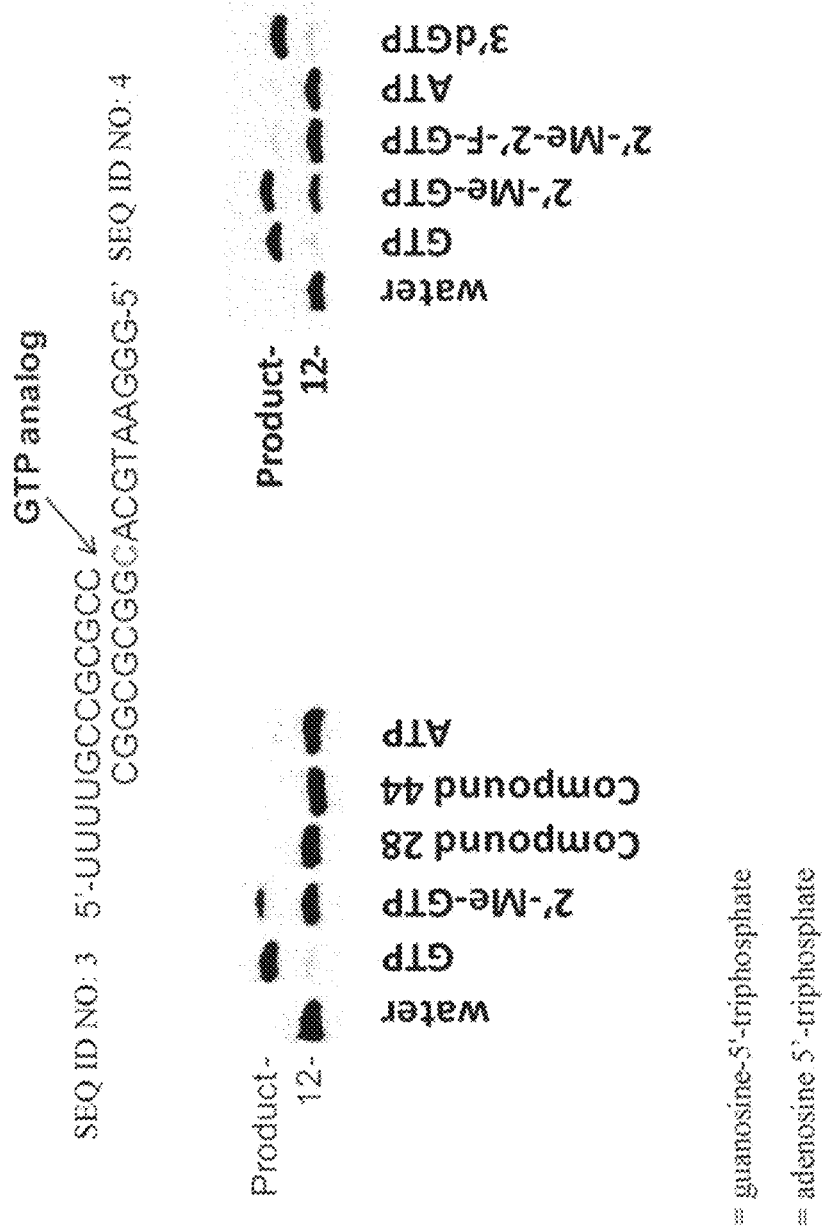
FIG. 11 shows the gels from the assessment of incorporation of several compounds with a guanine base by the human mitochondrial RNA polymerase.

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

As used herein, any "R" group(s) such as, without limitation, $R^1$, $R^2$, $R^3$, $R^4$, $R^{5A}$, $R^{5B}$, $R^{6A}$, $R^{6B}$, $R^{6C}$, $R^{6D}$, $R^{6E}$, $R^{6F}$, $R^{6G}$, $R^{6H}$, $R^{7A}$, $R^{7B}$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{A1}$, $R^{A2}$, $R^{A3}$ and $R^{A4}$ represent substituents that can be attached to the indicated atom. An R group may be substituted or unsubstituted. If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^aR^b$ group are indicated to be "taken together," it means that they are covalently bonded to one another to form a ring:

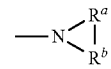

In addition, if two "R" groups are described as being "taken together" with the atom(s) to which they are attached to form a ring as an alternative, the R groups are not limited to the variables or substituents defined previously.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, aryl, heteroaryl, heterocyclyl, aryl(alkyl), heteroaryl (alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heterocyclyl group. That is, the alkyl, alkenyl, alkynyl, ring of the cycloalkyl, ring of the cycloalkenyl, ring of the aryl, ring of the heteroaryl or ring of the heterocyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. An alkenyl group may be unsubstituted or substituted.

As used herein, "alkynyl" refers to an alkyl group that contains in the straight or branched hydrocarbon chain one or more triple bonds. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl can contain 3 to 10 atoms in the ring(s) or 3 to 8 atoms in the ring(s). A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic, bicyclic and tricyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heteroalicyclic may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and 3,4-methylenedioxyphenyl).

As used herein, "aralkyl" and "aryl(alkyl)" refer to an aryl group connected, as a substituent, via a lower alkylene group. The lower alkylene and aryl group of an aryl(alkyl)

may be substituted or unsubstituted. Examples include but are not limited to benzyl, 2-phenylalkyl, 3-phenylalkyl and naphthylalkyl.

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, imidazolylalkyl and their benzo-fused analogs.

A "(heteroalicyclyl)alkyl" and "(heterocyclyl)alkyl" refer to a heterocyclic or a heteroalicyclylic group connected, as a substituent, via a lower alkylene group. The lower alkylene and heterocyclyl of a (heteroalicyclyl)alkyl may be substituted or unsubstituted. Examples include but are not limited tetrahydro-2H-pyran-4-yl)methyl, (piperidin-4-yl)ethyl, (piperidin-4-yl)propyl, (tetrahydro-2H-thiopyran-4-yl)methyl and (1,3-thiazinan-4-yl)methyl.

"Lower alkylene groups" are straight-chained —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—) and butylene (—$CH_2CH_2CH_2CH_2$—). A lower alkylene group can be substituted by replacing one or more hydrogen of the lower alkylene group with a substituent(s) listed under the definition of "substituted."

As used herein, "alkoxy" refers to the formula —OR wherein R is an alkyl, an alkenyl, an alkynyl, a cycloalkyl, a cycloalkenyl, aryl, heteroaryl, heterocyclyl, aryl(alkyl), (heteroaryl)alkyl or (heterocyclyl)alkyl is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen, alkyl, alkenyl, alkynyl, or aryl connected, as substituents, via a carbonyl group. Examples include formyl, acetyl, propanoyl, benzoyl and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to an —O-alkyl group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

A "sulfenyl" group refers to an "—SR" group in which R can be hydrogen, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "$SO_2R$" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, aryl, heteroaryl, heterocyclyl, aryl(alkyl), (heteroaryl)alkyl or (heterocyclyl)alkyl, as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "$X_3CSO_2$—" group wherein each X is a halogen.

A "trihalomethanesulfonamido" group refers to an "$X_3CS(O)_2N(R_A)$—" group wherein each X is a halogen, and $R_A$ is hydrogen, alkyl, alkenyl, alkynyl, cycloalkyl, cycloalkenyl, aryl, heteroaryl, heterocyclyl, aryl(alkyl), (heteroaryl)alkyl or (heterocyclyl)alkyl.

The term "amino" as used herein refers to a —$NH_2$ group.

As used herein, the term "hydroxy" refers to a —OH group.

A "cyano" group refers to a "—CN" group.

The term "azido" as used herein refers to a —$N_3$ group.

An "isocyanato" group refers to a "—NCO" group.

A "thiocyanato" group refers to a "—CNS" group.

An "isothiocyanato" group refers to an "—NCS" group.

A "mercapto" group refers to an "—SH" group.

A "carbonyl" group refers to a C=O group.

An "S-sulfonamido" group refers to a "—$SO_2N(R_AR_B)$" group in which $R_A$ and $R_B$ can be independently hydrogen, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. An S-sulfonamido may be substituted or unsubstituted.

An "N-sulfonamido" group refers to a "$RSO_2N(R_A)$—" group in which R and $R_A$ can be independently hydrogen, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. An N-sulfonamido may be substituted or unsubstituted.

An "O-carbamyl" group refers to a "—OC(=O)N($R_AR_B$)" group in which $R_A$ and $R_B$ can be independently hydrogen, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. An 0-carbamyl may be substituted or unsubstituted.

An "N-carbamyl" group refers to an "ROC(=O)N($R_A$)—" group in which R and $R_A$ can be independently hydrogen, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. An N-carbamyl may be substituted or unsubstituted.

An "O-thiocarbamyl" group refers to a "—OC(=S)—N($R_AR_B$)" group in which $R_A$ and $R_B$ can be independently hydrogen, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. An O-thiocarbamyl may be substituted or unsubstituted.

An "N-thiocarbamyl" group refers to an "ROC(=S)N($R_A$)—" group in which R and $R_A$ can be independently hydrogen, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. An N-thiocarbamyl may be substituted or unsubstituted.

A "C-amido" group refers to a "—C(=O)N($R_A R_B$)—" group in which $R_A$ and $R_B$ can be independently hydrogen, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. A C-amido may be substituted or unsubstituted.

An "N-amido" group refers to a "RC(=O)N($R_A$)—" group in which R and $R_A$ can be independently hydrogen, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. An N-amido may be substituted or unsubstituted.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "nucleoside" is used herein in its ordinary sense as understood by those skilled in the art, and refers to a compound composed of an optionally substituted pentose moiety or modified pentose moiety attached to a heterocyclic base or tautomer thereof via a N-glycosidic bond, such as attached via the 9-position of a purine-base or the 1-position of a pyrimidine-base. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers. In some instances, the nucleoside can be a nucleoside analog drug.

The term "nucleotide" is used herein in its ordinary sense as understood by those skilled in the art, and refers to a nucleoside having a phosphate ester bound to the pentose moiety, for example, at the 5'-position.

As used herein, the term "heterocyclic base" refers to an optionally substituted nitrogen-containing heterocyclyl that can be attached to an optionally substituted pentose moiety or modified pentose moiety. In some embodiments, the heterocyclic base can be selected from an optionally substituted purine-base, an optionally substituted pyrimidine-base and an optionally substituted triazole-base (for example, a 1,2,4-triazole). The term "purine-base" is used herein in its ordinary sense as understood by those skilled in the art, and includes its tautomers. Similarly, the term "pyrimidine-base" is used herein in its ordinary sense as understood by those skilled in the art, and includes its tautomers. A non-limiting list of optionally substituted purine-bases includes purine, adenine, guanine, hypoxanthine, xanthine, alloxanthine, 7-alkylguanine (e.g. 7-methylguanine), theobromine, caffeine, uric acid and isoguanine. Examples of pyrimidine-bases include, but are not limited to, cytosine, thymine, uracil, 5,6-dihydrouracil and 5-alkylcytosine (e.g., 5-methylcytosine). An example of an optionally substituted triazole-base is 1,2,4-triazole-3-carboxamide. Other non-limiting examples of heterocyclic bases include diaminopurine, 8-oxo-$N^6$-alkyladenine (e.g., 8-oxo-$N^6$-methyladenine), 7-deazaxanthine, 7-deazaguanine, 7-deazaadenine, $N^4,N^4$-ethanocytosin, $N^6,N^6$-ethano-2,6-diaminopurine, 5-halouracil (e.g., 5-fluorouracil and 5-bromouracil), pseudoisocytosine, isocytosine, isoguanine, and other heterocyclic bases described in U.S. Pat. Nos. 5,432,272 and 7,125,855, which are incorporated herein by reference for the limited purpose of disclosing additional heterocyclic bases. In some embodiments, a heterocyclic base can be optionally substituted with an amine or an enol protecting group(s).

The term "—N-linked amino acid" refers to an amino acid that is attached to the indicated moiety via a main-chain amino or mono-substituted amino group. When the amino acid is attached in an —N-linked amino acid, one of the hydrogens that is part of the main-chain amino or mono-substituted amino group is not present and the amino acid is attached via the nitrogen. N-linked amino acids can be substituted or unsubstituted.

The term "—N-linked amino acid ester derivative" refers to an amino acid in which a main-chain carboxylic acid group has been converted to an ester group. In some embodiments, the ester group has a formula selected from alkyl-O—C(=O)—, cycloalkyl-O—C(=O)—, aryl-O—C(=O)— and aryl(alkyl)-O—C(=O)—. A non-limiting list of ester groups include substituted and unsubstituted versions of the following: methyl-O—C(=O)—, ethyl-O—C(=O)—, n-propyl-O—C(=O)—, isopropyl-O—C(=O)—, n-butyl-O—C(=O)—, isobutyl-O—C(=O)—, tert-butyl-O—C(=O)—, neopentyl-O—C(=O)—, cyclopropyl-O—C(=O)—, cyclobutyl-O—C(=O)—, cyclopentyl-O—C(=O)—, cyclohexyl-O—C(=O)—, phenyl-O—C(=O)—, benzyl-O—C(=O)— and naphthyl-O—C(=O)—. N-linked amino acid ester derivatives can be substituted or unsubstituted.

The term "—O-linked amino acid" refers to an amino acid that is attached to the indicated moiety via the hydroxy from its main-chain carboxylic acid group. When the amino acid is attached in an —O-linked amino acid, the hydrogen that is part of the hydroxy from its main-chain carboxylic acid group is not present and the amino acid is attached via the oxygen. O-linked amino acids can be substituted or unsubstituted.

As used herein, the term "amino acid" refers to any amino acid (both standard and non-standard amino acids), including, but not limited to, α-amino acids, β-amino acids, γ-amino acids and δ-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine.

The terms "phosphorothioate" and "phosphothioate" refer to a compound of the general formula

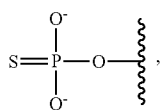

its protonated forms (for example,

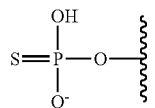

and

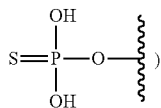

and its tautomers (such as

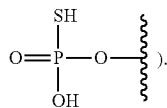

As used herein, the term "phosphate" is used in its ordinary sense as understood by those skilled in the art, and includes its protonated forms (for example,

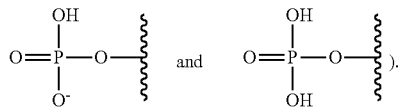 [SMILES: *OP(=O)([O-])O ; *OP(=O)(O)O]

As used herein, the terms "monophosphate," "diphosphate," and "triphosphate" are used in their ordinary sense as understood by those skilled in the art, and include protonated forms.

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis,* 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkyl-carbonyls and alkoxycarbonyls (e.g., t-butoxycarbonyl (BOC), acetyl, or isobutyryl); arylalkylcarbonyls and aryl-alkoxycarbonyls (e.g., benzyloxycarbonyl); substituted methyl ether (e.g. methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl or t-butyldiphenylsilyl); esters (e.g. benzoate ester); carbonates (e.g. methoxymethylcarbonate); sulfonates (e.g. tosylate or mesylate); acyclic ketal (e.g. dimethyl acetal); cyclic ketals (e.g., 1,3-dioxane, 1,3-dioxolanes and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4"-trimethoxytrityl (TMTr); and those described herein).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalene-sulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Likewise, it is understood that, in any compound described, all tautomeric forms are also intended to be included. For example all tautomers of a phosphate and a phosphorothioate groups are intended to be included. Examples of tautomers of a phosphorothioate include the following:

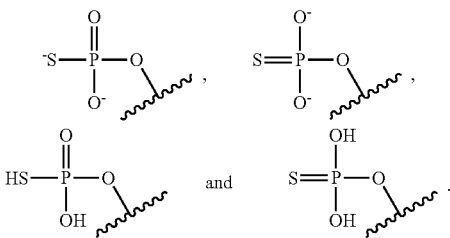

Furthermore, all tautomers of heterocyclic bases known in the art are intended to be included, including tautomers of natural and non-natural purine-bases and pyrimidine-bases.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Compounds

Some embodiments disclosed herein relate to a compound of Formula (I) or a pharmaceutically acceptable salt thereof:

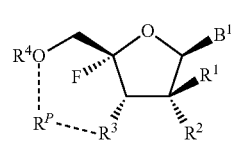

(I)

wherein: $B^1$ can be selected from an optionally substituted

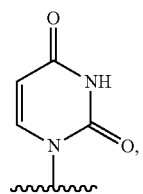

an optionally substituted

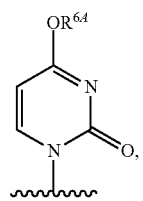

an optionally substituted

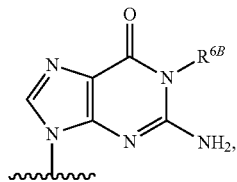

an optionally substituted

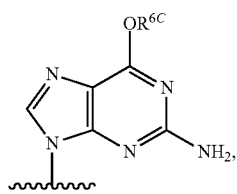

an optionally substituted

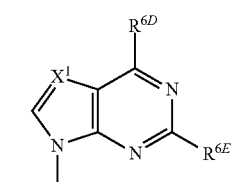

and an optionally substituted

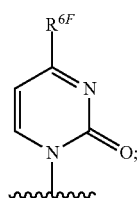

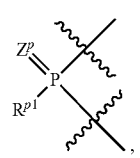

$R^1$ can be selected from an optionally substituted $C_{1-6}$ alkyl, an optionally substituted $C_{2-6}$ alkenyl, an optionally substituted $C_{2-6}$ alkynyl and an optionally substituted $C_{3-6}$ cycloalkyl; each -------- can be absent or a single bond, provided that both -------- are each absent or both -------- are each a single bond; when both -------- are each a single bond, then $R^2$ can be halo, $N_3$, —OR$^{7A}$ or —N(R$^{7B}$R$^{7C}$); $R^4$ can be absent; $R^3$ can be oxygen (O); and $R^P$ can be

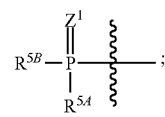

wherein $Z^p$ can be oxygen (O) or sulfur (S) and $R^{p1}$ can be selected from O⁻, OH, an —O-optionally substituted $C_{1-6}$ alkyl.

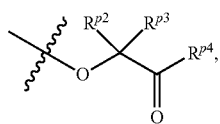

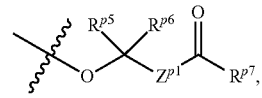

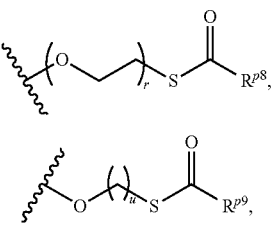

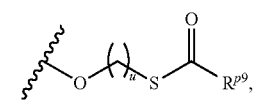

an optionally substituted N-linked amino acid and an optionally substituted N-linked amino acid ester derivative; when both -------- are each absent, then $R^P$ can be absent; $R^2$ can be halo, $N_3$, —OR$^{7A}$ or —N(R$^{7B}$R$^{7C}$); $R^3$ can be —OH or —OC(=O)R$^8$; or $R^2$ and $R^3$ can be each an oxygen atom which are linked together by a carbonyl group; and $R^4$ can be hydrogen or

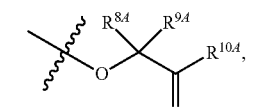

$R^{5A}$ can be selected from O⁻, OH, an optionally substituted N-linked amino acid, an optionally substituted N-linked amino acid ester derivative,

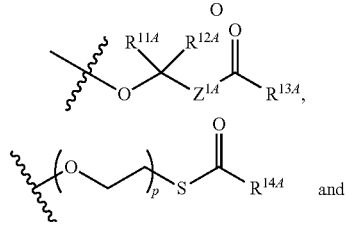

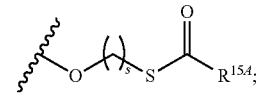

$R^{5B}$ can be selected from O⁻, OH, an —O-optionally substituted aryl, an —O-optionally substituted heteroaryl, an —O-optionally substituted heterocyclyl, an optionally substituted N-linked amino acid, an optionally substituted N-linked amino acid ester derivative,

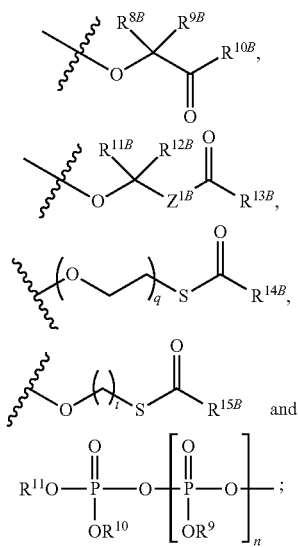

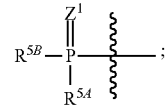

and $R^{5A}$ is $O^-$ or OH, then $R^{5B}$ is $O^-$, OH,

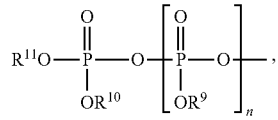

$R^{6A}$ can be an optionally substituted $C_{1-6}$ alkyl or an optionally substituted $C_{3-6}$ cycloalkyl; $R^{6B}$ and $R^{6C}$ can be independently selected from hydrogen, an unsubstituted $C_{1-6}$ alkyl, an unsubstituted $C_{3-6}$ alkenyl, an unsubstituted $C_{3-6}$ alkynyl and an unsubstituted $C_{3-6}$ cycloalkyl; $R^{6D}$ can be $NHR^{6G}$; $R^{6E}$ can be hydrogen, halogen or $NHR^{6H}$; $R^{6F}$ can be $NHR^{6I}$; $R^{6G}$ can be selected from hydrogen, an optionally substituted $C_{1-6}$ alkyl, an optionally substituted $C_{3-6}$ alkenyl, an optionally substituted $C_{3-6}$ cycloalkyl, —C(=O)$R^{A1}$ and —C(=O)O$R^{A2}$; $R^{6H}$ can be selected from hydrogen, an optionally substituted $C_{1-6}$ alkyl, an optionally substituted $C_{3-6}$ alkenyl, an optionally substituted $C_{3-6}$ cycloalkyl, —C(=O)$R^{A3}$ and —C(=O)O$R^{A4}$; $R^{6I}$ can be selected from hydrogen, an optionally substituted $C_{1-6}$ alkyl, an optionally substituted $C_{3-6}$ alkenyl, an optionally substituted $C_{3-6}$ cycloalkyl, —C(=O)$R^{A5}$ and —C(=O)O$R^{A6}$; $X^1$ can be N (nitrogen) or —C$R^{6J}$, $R^{6J}$ can be selected from hydrogen, halogen, an optionally substituted $C_{1-6}$ alkyl, an optionally substituted $C_{2-6}$ alkenyl and an optionally substituted $C_{2-6}$ alkynyl; $R^{A1}$, $R^{A2}$, $R^{A3}$, $R^{A4}$, $R^{A5}$ and $R^{A6}$ can be independently selected from $C_{1-6}$ alkyl, $C_{2-6}$ alkenyl, $C_{2-6}$ alkynyl, $C_{3-6}$ cycloalkyl, $C_{3-6}$ cycloalkenyl, $C_{6-10}$ aryl, heteroaryl, heterocyclyl, aryl($C_{1-6}$ alkyl), heteroaryl($C_{1-6}$ alkyl) and heterocyclyl($C_{1-6}$ alkyl); $R^{7A}$ can be hydrogen or —C(=O)$R^{12}$; and $R^{7C}$ can be independently hydrogen or an optionally substituted $C_{1-6}$ alkyl; $R^8$ and $R^{12}$ can be independently an optionally substituted $C_{1-6}$ alkyl or an optionally substituted $C_{3-6}$ cycloalkyl; $R^9$, $R^{10}$ and $R^{11}$ can be independently absent or hydrogen; $R^{8A}$, $R^{9A}$, $R^{11A}$, $R^{12A}$, $R^{8B}$, $R^{9B}$, $R^{11B}$, $R^{12B}$, $R^{p2}$, $R^{p3}$, $R^{p5}$ and $R^{p6}$ can be independently selected from hydrogen, an optionally substituted $C_{1-24}$ alkyl and an optionally substituted aryl; $R^{10A}$, $R^{10B}$, $R^{13A}$, $R^{13B}$, $R^{p4}$ and $R^{p7}$ can be independently selected from hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl and an optionally substituted —O-monocyclic heterocyclyl; $R^{14A}$, $R^{14B}$, $R^{15A}$, $R^{15B}$, $R^{p8}$ and $R^{p9}$ can be independently selected from hydrogen, an optionally substituted $C_{1-24}$ alkyl and an optionally substituted aryl; n can be 0 or 1; p, q, and r can be independently 1 or 2; s, t and u can be independently 3, 4 or 5; $Z^1$, $Z^{1A}$, $Z^{1B}$ and $Z^{p1}$ can be independently O (oxygen) or S (sulfur); and provided that when $R^4$ is an optionally substituted N-linked amino acid or an optionally substituted N-linked amino acid ester derivative.

The substituents attached to the 2'-carbon can vary. In some embodiments, $R^2$ can be halo. For example, $R^2$ can be fluoro or chloro. In other embodiments, $R^2$ can be $N_3$. In some embodiments, $R^2$ can be —OH. In other embodiments, $R^2$ can be $OR^{7A}$, wherein $R^{7A}$ can be —C(=O)$R^{12}$, and $R^{12}$ can be an optionally substituted $C_{1-6}$ alkyl. Suitable alkyl groups include, but are not limited to optionally substituted variants of the following: methyl, ethyl, n-propyl, isopropyl, n-butyl, isobutyl, tert-butyl, pentyl (branched and straight-chained) and hexyl (branched and straight-chained). In yet still other embodiments, $R^2$ can be $OR^{7A}$, wherein $R^{7A}$ can be —C(=O)$R^{12}$, and $R^{12}$ can be an optionally substituted $C_{3-6}$ cycloalkyl. Suitable cycloalkyl groups include, but are not limited to optionally substituted variants of the following: cyclopropyl, cyclobutyl, cyclopentyl and cyclohexyl. In some embodiment, $R^2$ can be —N($R^{7B}R^{7C}$), wherein $R^{7B}$ and $R^{7C}$ can be independently hydrogen or an optionally substituted $C_{1-6}$ alkyl. In some embodiments, $R^{7B}$ and $R^{7C}$ can be both hydrogen, such that $R^2$ can be —$NH_2$. In other embodiments, at least one of $R^{7B}$ and $R^{7C}$ can be an optionally substituted $C_{1-6}$ alkyl. In some embodiments, $R^{7B}$ and $R^{7C}$ can be both an optionally substituted $C_{1-6}$ alkyl. In some embodiments, $R^{7B}$ and $R^{7C}$ can be the same. In other embodiments, $R^{7B}$ and $R^{7C}$ can be different.

Various substituents can be attached to the 3'-carbon of the pentose ring. In some embodiments, $R^3$ can be —OH. In other embodiments, $R^3$ can be —OC(=O)$R^8$, wherein $R^8$ can be an optionally substituted $C_{1-6}$ alkyl such as those described herein. In still other embodiments, $R^3$ can be —OC(=O)$R^8$, wherein $R^8$ can be an optionally substituted $C_{3-6}$ cycloalkyl. Examples of suitable optionally substituted $C_{3-6}$ cycloalkyl groups are described herein.

In some embodiments, $R^2$ and $R^3$ can each be an oxygen atom and the oxygen atoms can be linked together by a carbonyl group. In other embodiments, $R^2$ and $R^3$ can be both —OH. In other embodiments, $R^2$ can be halo and $R^3$ can be —OH. In still other embodiments, $R^2$ can be halo and $R^3$ can be —OC(=O)$R^8$.

In some embodiments, $R^1$ can be an optionally substituted $C_{1-6}$ alkyl. In some embodiments, $R^1$ can be an unsubstituted $C_{1-6}$ alkyl. For example, $R^1$ can be unsubstituted methyl, unsubstituted ethyl, unsubstituted n-propyl, unsubstituted isopropyl, unsubstituted n-butyl, unsubstituted isobutyl, unsubstituted tert-butyl, unsubstituted pentyl (branched and straight-chained) or unsubstituted hexyl (branched and straight-chained). In some embodiments, $R^1$ can be a substituted $C_{1-6}$ alkyl. Suitable substitutions are described herein. As an example, $R^1$ can be a halo-substituted $C_{1-6}$ alkyl (such as —$CF_3$ or —$CH_2CH_2F$). In other embodiments, $R^1$ can be an optionally substituted $C_{2-6}$ alkenyl. Suitable alkenyl groups include, but are not limited to optionally substituted variants of the following: ethenyl, n-propenyl, isopropenyl, n-butenyl, isobutenyl, tert-butenyl, pentenyl (branched and straight-chained), hexenyl (branched and straight-chained), vinyl and allenyl. In still other embodiments, $R^1$ can be an optionally substituted $C_{2-6}$ alkynyl. In yet still other embodiments, $R^1$ can be an optionally substituted $C_{3-6}$ cycloalkyl, such as those described herein.

In some embodiments, both -------- can be each absent; $R^P$ can be absent; $R^2$ can be halo, $N_3$, —$OR^{7A}$ or —$N(R^{7B}R^{7C})$; $R^3$ can be —OH or —OC(=O)$R^8$; or $R^2$ and $R^3$ can be each an oxygen atom which are linked together by a carbonyl group; and $R^4$ can be hydrogen or

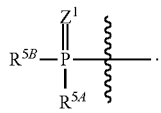

When both -------- are absent, Formula (I) can have the structure:

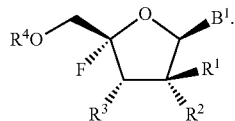

In some embodiments, $R^4$ can be hydrogen. In other embodiments, $R^4$ can be

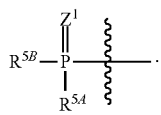

In some embodiments, the compound of Formula (I) can be a monophosphate. In other embodiments, the compound of Formula (I) can be a thiomonophosphate. In some embodiments, the compound of Formula (I) can be a diphosphate. In other embodiments, the compound of Formula (I) can be an alpha-thiodiphosphate. In some embodiments, the compound of Formula (I) can be a triphosphate. In other embodiments, the compound of Formula (I) can be an alpha-thiotriphosphate. In some embodiments, $R^4$ can be

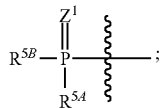

$R^{5A}$ can be O⁻ or OH; and $R^{5B}$ can be O⁻ or OH. In other embodiments, $R^4$ can be

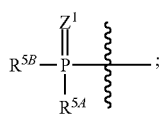

$R^{5A}$ can be O⁻ or OH; $R^{5B}$ can be

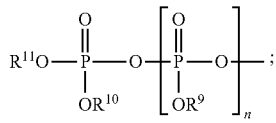

and n can be 0. In still other embodiments, $R^4$ can be

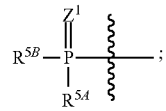

$R^{5A}$ can be O⁻ or OH; $R^{5B}$ can be

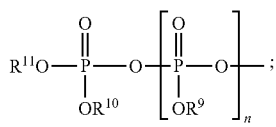

and n can be 1. The substituents attached to the phosphorus can vary. In some embodiments, a compound of Formula (I) can be a phosphoroamidate. In other embodiments, a compound of Formula (I) can be a thiophosphoroamidate. In still other embodiments, a compound of Formula (I) can be a phosphorbisamidate. In yet still other embodiments, a compound of Formula (I) can be a thiophosphorbisamidate.

In some embodiments, $R^{5A}$ can be an optionally substituted N-linked amino acid. Various amino acids are suitable, including those described herein. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. In other embodiments, $R^{5A}$ can be an optionally substituted N-linked amino acid ester derivative. Examples of N-linked amino acid ester derivatives include, but are not limited to, ester derivatives of any of the following amino acids: alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of N-linked amino acid ester derivatives include, but are not limited to, an ester derivative of any of the following amino acids: alpha-ethyl-glycine, alpha-propyl-glycine and beta-alanine. In some embodiments, the N-linked amino acid ester derivative can be a $C_{1-6}$ alkyl ester derivative, for example, an isopropyl ester of alanine. In other embodiments, the N-linked amino acid ester derivative can be a $C_{3-6}$ cycloalkyl ester derivative, such as a cyclohexyl ester of alanine.

In some embodiments, $R^{5A}$ can have the structure

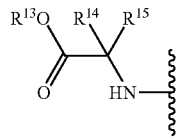

wherein $R^{13}$ can be selected from hydrogen, an optionally substituted $C_{1-6}$-alkyl, an optionally substituted $C_{3-6}$ cycloalkyl, an optionally substituted aryl, an optionally substituted aryl($C_{1-6}$ alkyl) and an optionally substituted haloalkyl; $R^{14}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{15}$ can be hydrogen or an optionally substituted $C_{1-4}$-alkyl; or $R^{14}$ and $R^{15}$ can be taken together to form an optionally substituted $C_{3-6}$ cycloalkyl.

When $R^{14}$ is substituted, $R^{14}$ can be substituted with one or more substituents selected from N-amido, mercapto, alkylthio, an optionally substituted aryl, hydroxy, an optionally substituted heteroaryl, O-carboxy and amino. In some embodiments, $R^{14}$ can be an unsubstituted $C_{1-6}$-alkyl, such as those described herein. In some embodiments, $R^{14}$ can be hydrogen. In other embodiments, $R^{14}$ can be methyl. In some embodiments, $R^{13}$ can be an optionally substituted $C_{1-6}$ alkyl. Examples of optionally substituted $C_{1-6}$-alkyls include optionally substituted variants of the following: methyl, ethyl, n-propyl, isopropyl, n-butyl, isobutyl, tert-butyl, pentyl (branched and straight-chained) and hexyl (branched and straight-chained). In some embodiments, $R^{13}$ can be methyl or isopropyl. In some embodiments, $R^{13}$ can be ethyl or neopentyl. In other embodiments, $R^{13}$ can be an optionally substituted $C_{3-6}$ cycloalkyl. Examples of optionally substituted $C_{3-6}$ cycloalkyl include optionally substituted variants of the following: cyclopropyl, cyclobutyl, cyclopentyl and cyclohexyl. In some embodiments, $R^{13}$ can be an optionally substituted cyclohexyl. In still other embodiments, $R^{13}$ can be an optionally substituted aryl, such as phenyl and naphthyl. In yet still other embodiments, $R^{13}$ can be an optionally substituted aryl($C_{1-6}$ alkyl). In some embodiments, $R^{13}$ can be an optionally substituted benzyl. In some embodiments, $R^{13}$ can be an optionally substituted $C_{1-6}$ haloalkyl, for example, $CF_3$. In some embodiments, $R^{15}$ can be hydrogen. In other embodiments, $R^{15}$ can be an optionally substituted $C_{1-4}$ alkyl, such as methyl, ethyl, n-propyl, isopropyl, n-butyl, isobutyl or tert-butyl. In some embodiments, $R^{15}$ can be methyl. In some embodiments, $R^{14}$ and $R^{15}$ can be taken together to form an optionally substituted $C_{3-6}$ cycloalkyl. Examples of optionally substituted $C_{3-6}$ cycloalkyl include optionally substituted variants of the following: cyclopropyl, cyclobutyl, cyclopentyl and cyclohexyl. Depending on the groups that are selected for $R^{14}$ and $R^{15}$, the carbon to which $R^{14}$ and $R^{15}$ are attached may be a chiral center. In some embodiment, the carbon to which $R^{14}$ and $R^{15}$ are attached may be a (R)-chiral center. In other embodiments, the carbon to which $R^{14}$ and $R^{15}$ are attached may be a (S)-chiral center.

Examples of suitable

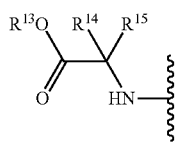

groups include the following:

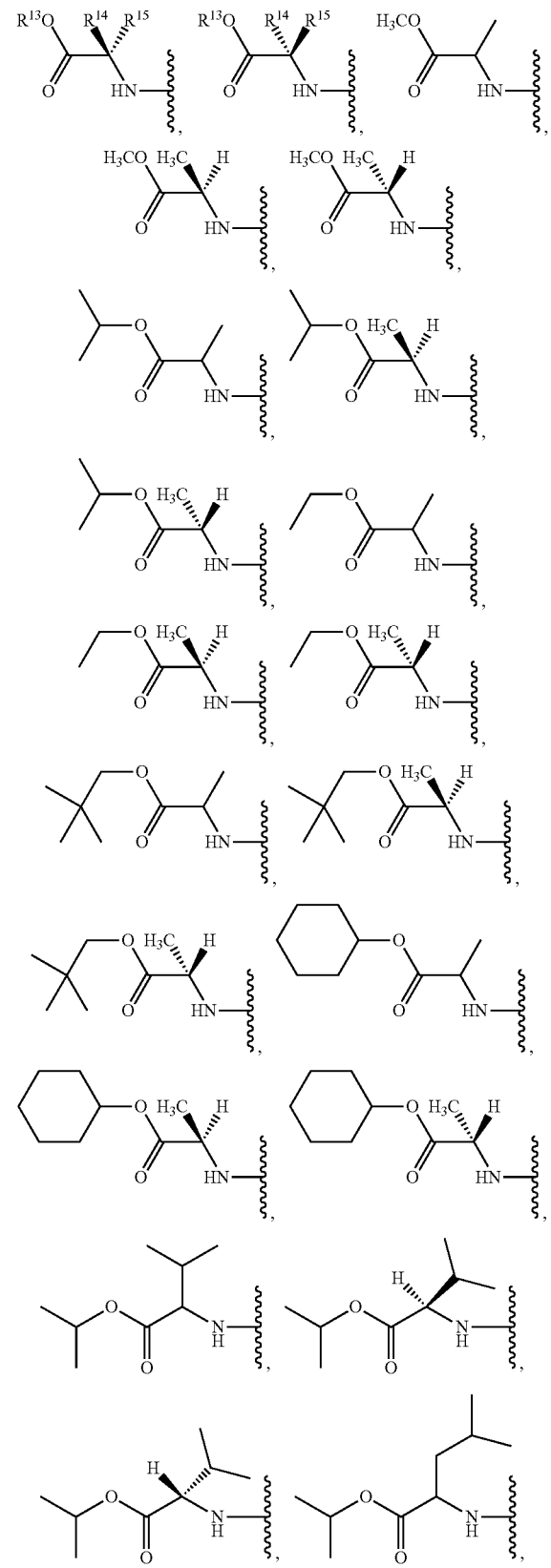

-continued

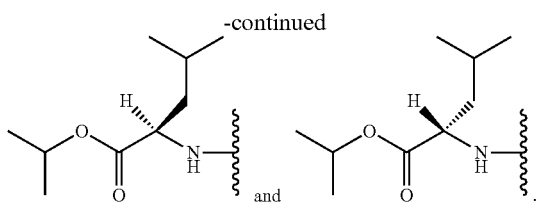

In some embodiments, $R^{5B}$ can be an —O-optionally substituted aryl. For example, $R^{5B}$ can be an —O-optionally substituted phenyl. When the phenyl is substituted, the ring can be substituted 1, 2, 3 or more than 3 times. Suitable mono-substituted phenyl groups include, ortho-substituted phenyl, meta-substituted phenyl and para-substituted phenyl. In other embodiments, $R^{5B}$ can be an —O-unsubstituted aryl. Alternatively, $R^{5B}$ can be an —O-optionally substituted naphthyl. In other embodiments, $R^{5B}$ can be an —O-optionally substituted heteroaryl. For example, $R^{5B}$ can be an —O-optionally substituted quinolinyl. In still other embodiments, $R^{5B}$ can be an —O-optionally substituted heterocyclyl.

In some embodiments, $R^{5B}$ is an optionally substituted N-linked amino acid, such as those described for $R^{5A}$. In other embodiments, $R^{5B}$ is an optionally substituted N-linked amino acid ester derivative, for example, those described herein. In some embodiments, $R^{5B}$ can have the structure

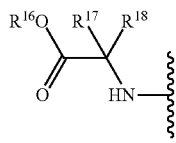

wherein $R^{16}$ can be selected from hydrogen, an optionally substituted $C_{1-6}$-alkyl, an optionally substituted $C_{3-6}$ cycloalkyl, an optionally substituted aryl, an optionally substituted aryl($C_{1-6}$ alkyl) and an optionally substituted haloalkyl; $R^{17}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{18}$ can be hydrogen or an optionally substituted $C_{1-4}$-alkyl; or $R^{17}$ and $R^{18}$ can be taken together to form an optionally substituted $C_{3-6}$ cycloalkyl.

When $R^{17}$ is substituted, $R^{17}$ can be substituted with one or more substituents selected from N-amido, mercapto, alkylthio, an optionally substituted aryl, hydroxy, an optionally substituted heteroaryl, O-carboxy and amino. In some embodiments, $R^{17}$ can be an unsubstituted $C_{1-6}$-alkyl, such as those described herein. In some embodiments, $R^{17}$ can be hydrogen. In other embodiments, $R^{17}$ can be methyl. In some embodiments, $R^{16}$ can be an optionally substituted $C_{1-6}$ alkyl. Examples of optionally substituted $C_{1-6}$-alkyls include optionally substituted variants of the following: methyl, ethyl, n-propyl, isopropyl, n-butyl, isobutyl, tert-butyl, pentyl (branched and straight-chained) and hexyl (branched and straight-chained). In some embodiments, $R^{16}$ can be methyl or isopropyl. In some embodiments, $R^{16}$ can be ethyl or neopentyl. In other embodiments, $R^{16}$ can be an optionally substituted $C_{3-6}$ cycloalkyl. Examples of optionally substituted $C_{3-6}$ cycloalkyl include optionally substituted variants of the following: cyclopropyl, cyclobutyl, cyclopentyl and cyclohexyl. In some embodiments, $R^{16}$ can be an optionally substituted cyclohexyl. In still other embodiments, $R^{16}$ can be an optionally substituted aryl, such as phenyl and naphthyl. In yet still other embodiments, $R^{16}$ can be an optionally substituted aryl($C_{1-6}$ alkyl). In some embodiments, $R^{16}$ can be an optionally substituted benzyl. In some embodiments, $R^{16}$ can be an optionally substituted $C_{1-6}$ haloalkyl, for example, $CF_3$. In some embodiments, $R^{18}$ can be hydrogen. In other embodiments, $R^{18}$ can be an optionally substituted $C_{1-4}$-alkyl, such as methyl, ethyl, n-propyl, isopropyl, n-butyl, isobutyl or tert-butyl. In some embodiments, $R^{18}$ can be methyl. In some embodiments, $R^{17}$ and $R^{18}$ can be taken together to form an optionally substituted $C_{3-6}$ cycloalkyl. Examples of optionally substituted $C_{3-6}$ cycloalkyl include optionally substituted variants of the following: cyclopropyl, cyclobutyl, cyclopentyl and cyclohexyl. Depending on the groups that are selected for $R^{17}$ and $R^{18}$, the carbon to which $R^{17}$ and $R^{18}$ are attached may be a chiral center. In some embodiment, the carbon to which $R^{17}$ and $R^{18}$ are attached may be a (R)-chiral center. In other embodiments, the carbon to which $R^{17}$ and $R^{18}$ are attached may be a (S)-chiral center.

Examples of suitable

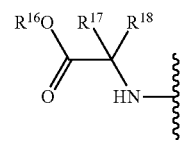

groups include the following:

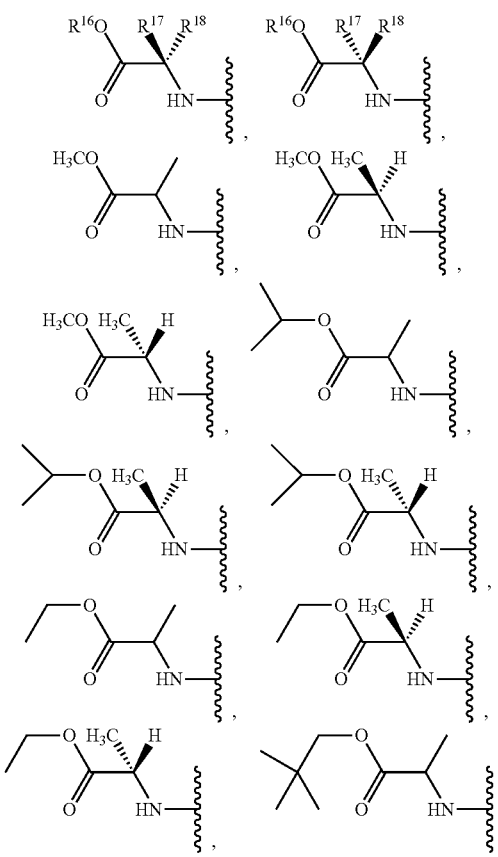

-continued

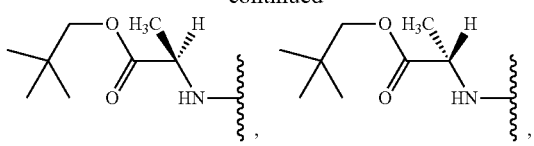

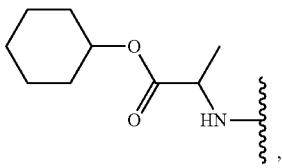

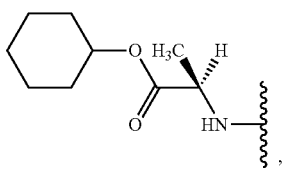

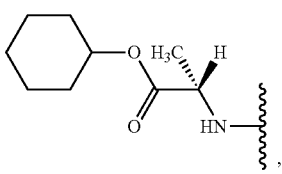

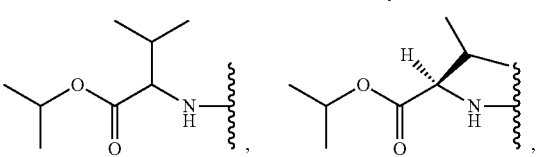

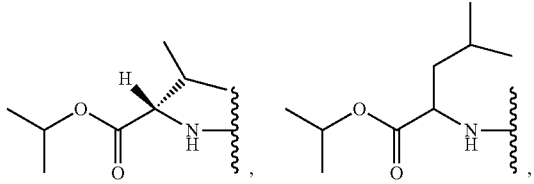

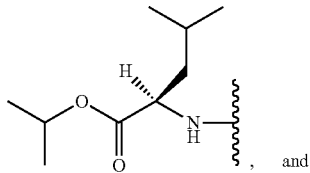, and

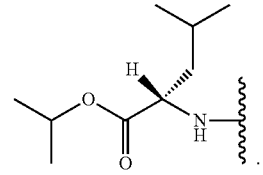.

In some embodiments, $R^{5A}$ can be an optionally substituted N-linked amino acid or an optionally substituted N-linked amino acid ester derivative and $R^{5B}$ can be an —O-optionally substituted aryl. In other embodiments, $R^{5A}$ can be an optionally substituted N-linked amino acid or an optionally substituted N-linked amino acid ester derivative and $R^{5B}$ can be an —O-optionally substituted heteroaryl. In some embodiments, $R^{5A}$ can be an optionally substituted N-linked amino acid or an optionally substituted N-linked amino acid ester derivative and $R^{5A}$ can be an optionally substituted N-linked amino acid or an optionally substituted N-linked amino acid ester derivative.

In some embodiments, $R^{5A}$ can be

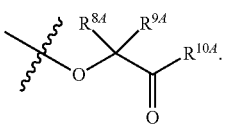

When $R^{5A}$ is

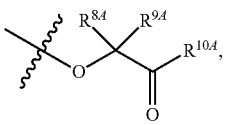

$R^{8A}$ and $R^{9A}$ can be independently selected from hydrogen, an optionally substituted $C_{1-24}$ alkyl and an optionally substituted aryl; and $R^{10A}$ can be selected from hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl and an optionally substituted —O-monocyclic heterocyclyl. In some embodiments, $R^{8A}$ and $R^{9A}$ can be hydrogen. In other embodiments, at least one of $R^{8A}$ and $R^{9A}$ can be an optionally substituted $C_{1-24}$ alkyl or an optionally substituted aryl. In some embodiments, $R^{10A}$ can be hydrogen. In other embodiments, $R^{10A}$ can be an optionally substituted $C_{1-24}$ alkyl. In some embodiments, $R^{10A}$ can be an unsubstituted $C_{1-4}$ alkyl. In still other embodiments, $R^{10A}$ can be an optionally substituted aryl. In yet still other embodiments, $R^{10A}$ can be —O—$C_{1-24}$ alkyl, an optionally substituted —O-aryl, an optionally substituted —O-heteroaryl or an optionally substituted —O-monocyclic heterocyclyl. In some embodiments, $R^{10A}$ can be an unsubstituted —O—$C_{1-4}$ alkyl.

In some embodiments, $R^{5B}$ can be

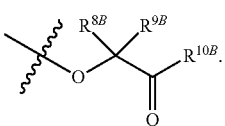

When $R^{5B}$ is

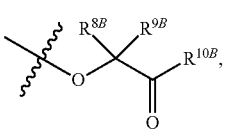

$R^{8B}$ and $R^{9B}$ can be independently selected from hydrogen, an optionally substituted $C_{1-24}$ alkyl and an optionally substituted aryl; and $R^{10B}$ can be selected from hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl and an optionally substituted —O-monocyclic heterocyclyl. In some embodiments, $R^{8B}$ and $R^{9B}$ can be hydrogen. In other embodiments, at least one of $R^{8B}$ and $R^{9B}$ can be an optionally substituted $C_{1-24}$ alkyl or an optionally substituted aryl. In some embodiments, $R^{10B}$ can be hydrogen. In other embodiments, $R^{10B}$ can be an optionally substituted $C_{1-24}$ alkyl. In some embodiments, $R^{10B}$ can be an unsubstituted $C_{1-4}$ alkyl. In still other embodiments, $R^{10B}$ can be an optionally substituted aryl. In yet still other embodiments, $R^{10B}$ can be —O—$C_{1-24}$ alkyl, an optionally substituted —O-aryl, an optionally substituted —O-heteroaryl or an optionally substituted —O-monocyclic heterocyclyl. In some embodiments, $R^{10B}$ can be an unsubstituted —O—$C_{1-4}$ alkyl. In some embodiments, $R^{5A}$ can be

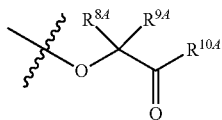

and $R^{5B}$ can be

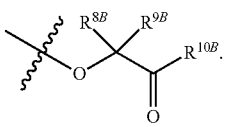

In some embodiments, $R^{5A}$ can be

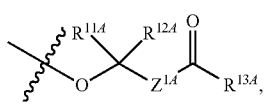

wherein $R^{11A}$ and $R^{12A}$ can be independently selected from hydrogen, an optionally substituted $C_{1-24}$ alkyl and an optionally substituted aryl; $R^{13A}$ can be independently selected from hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl and an optionally substituted —O-monocyclic heterocyclyl; and $Z^{1A}$ can be independently O (oxygen) or S (sulfur). In some embodiments, $R^{11A}$ and $R^{12A}$ can be hydrogen. In other embodiments, at least one of $R^{11A}$ and $R^{12A}$ can be an optionally substituted $C_{1-24}$ alkyl or an optionally substituted aryl. In some embodiments, $R^{13A}$ can be an optionally substituted $C_{1-24}$ alkyl. In some embodiments, $R^{13A}$ can be an unsubstituted $C_{1-4}$ alkyl. In other embodiments, $R^{13A}$ can be an optionally substituted aryl. In still other embodiments, $R^{13A}$ can be an optionally substituted —O—$C_{1-24}$ alkyl, an optionally substituted —O-aryl, an optionally substituted —O-heteroaryl or an optionally substituted —O-monocyclic heterocyclyl. In some embodiments, $R^{13A}$ can be an unsubstituted —O—$C_{1-4}$ alkyl. In some embodiments, $Z^{1A}$ can be O (oxygen). In other embodiments, $Z^{1A}$ can be or S (sulfur).

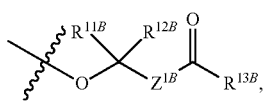

In some embodiments, $R^{5B}$ can be wherein $R^{11B}$ and $R^{12B}$ can be independently selected from hydrogen, an optionally substituted $C_{1-24}$ alkyl and an optionally substituted aryl; $R^{13B}$ can be independently selected from hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl and an optionally substituted —O-monocyclic heterocyclyl; and $Z^{1B}$ can be independently O (oxygen) or S (sulfur). In some embodiments, $R^{11B}$ and $R^{12B}$ can be hydrogen. In other embodiments, at least one of $R^{11B}$ and $R^{12B}$ can be an optionally substituted $C_{1-24}$ alkyl or an optionally substituted aryl. In some embodiments, $R^{13B}$ can be an optionally substituted $C_{1-24}$ alkyl. In some embodiments, $R^{13B}$ can be an unsubstituted $C_{1-4}$ alkyl. In other embodiments, $R^{13B}$ can be an optionally substituted aryl. In still other embodiments, $R^{13B}$ can be an optionally substituted —O—$C_{1-24}$ alkyl, an optionally substituted —O-aryl, an optionally substituted —O-heteroaryl or an optionally substituted —O-monocyclic heterocyclyl. In some embodiments, $R^{13B}$ can be an unsubstituted —O—$C_{1-4}$ alkyl. In some embodiments, $Z^{1B}$ can be O (oxygen). In other embodiments, $Z^{1B}$ can be or S (sulfur). In some embodiments, $R^{5A}$ can be

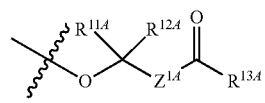

and $R^{5B}$ can be

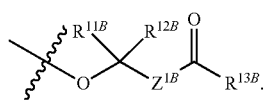

In some embodiments, $R^{5A}$ can be

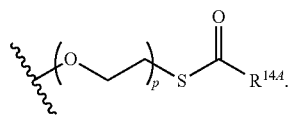

In some embodiments, $R^{14A}$ can be hydrogen. In other embodiments, $R^{14B}$ can be an optionally substituted $C_{1-24}$ alkyl. In still other embodiments, $R^{14A}$ can be an optionally substituted aryl. In some embodiments, $R^{14A}$ can be a $C_{1-6}$ alkyl, for example, methyl, ethyl, n-propyl, isopropyl, n-butyl, isobutyl, tert-butyl, pentyl (branched and straight-chained), and hexyl (branched and straight-chained). In some embodiments, p can be 1. In other embodiments, p can be 2.

In some embodiments, $R^{5B}$ can be

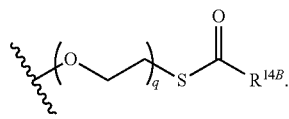

In some embodiments, $R^{14B}$ can be hydrogen. In other embodiments, $R^{14B}$ can be an optionally substituted $C_{1-24}$ alkyl. In still other embodiments, $R^{14B}$ can be an optionally substituted aryl. In some embodiments, $R^{14B}$ can be a $C_{1-6}$ alkyl, for example, methyl, ethyl, n-propyl, isopropyl, n-butyl, isobutyl, tert-butyl, pentyl (branched and straight-chained), and hexyl (branched and straight-chained). In some embodiments, q can be 1. In other embodiments, q can be 2. In some embodiments, $R^{5A}$ can be

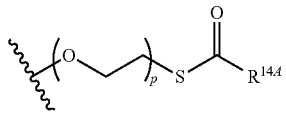

and $R^{5B}$ can be

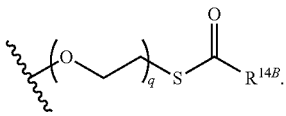

In some embodiments, $R^{5A}$ can be

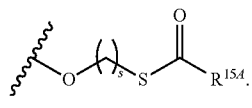

In some embodiments, $R^{15A}$ can be hydrogen. In other embodiments, $R^{15A}$ can be an optionally substituted $C_{1-24}$ alkyl. In still other embodiments, $R^{15A}$ can be an optionally substituted aryl, for example, an optionally substituted phenyl. In some embodiments, $R^{15A}$ can be an optionally substituted $C_{1-6}$ alkyl. In some embodiments, $R^{15A}$ can be an unsubstituted $C_{1-6}$ alkyl. In some embodiments, s can be 3. In other embodiments, s can be 4. In still other embodiments, s can be 5.

In some embodiments, $R^{5B}$ can be

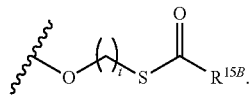

In some embodiments, $R^{15B}$ can be hydrogen. In other embodiments, $R^{15B}$ can be an optionally substituted $C_{1-24}$ alkyl. In still other embodiments, $R^{15B}$ can be an optionally substituted aryl, for example, an optionally substituted phenyl. In some embodiments, $R^{15B}$ can be an optionally substituted $C_{1-6}$ alkyl. In some embodiments, $R^{15B}$ can be an unsubstituted $C_{1-6}$ alkyl. In some embodiments, t can be 3. In other embodiments, t can be 4. In still other embodiments, t can be 5. In some embodiments, $R^{5A}$ can be

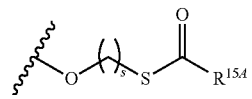

and $R^{5B}$ can be

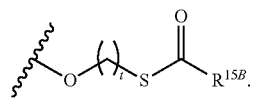

In some embodiments, $R^{5A}$ and/or $R^{5B}$ can be isopropyloxycarbonyloxymethoxy (POC) group. In some embodiments, $R^{5A}$ and/or $R^{5B}$ can be pivaloyloxymethoxy (POM) group. In some embodiments, $R^{5A}$ and $R^{5B}$ can be both a isopropyloxycarbonyloxymethoxy (POC) group, and form a bis(isopropyloxycarbonyloxymethoxy) (bis(POC)) prodrug. In other embodiments, $R^{5A}$ and $R^{5B}$ can be both a pivaloyloxymethoxy (POM) group, and form a bis(pivaloyloxymethoxy) (bis(POM)) prodrug. In still other embodiments, $R^{5A}$ and $R^{5B}$ can be both a S-acylthioethyl (SATE)-O— group and form a SATE ester prodrug. In some embodiments, $R^{5A}$ and $R^{5B}$ can be the same. In other embodiments, $R^{5A}$ and $R^{5B}$ can be different.

In some embodiments, both -------- can be each a single bond; $R^4$ can be absent; $R^3$ can be oxygen (O); and $R^P$ can be

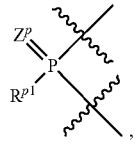

wherein $Z^P$ can be oxygen (O) or sulfur (S) and $R^{P1}$ can be selected from O⁻, OH, an —O-optionally substituted $C_{1-6}$ alkyl.

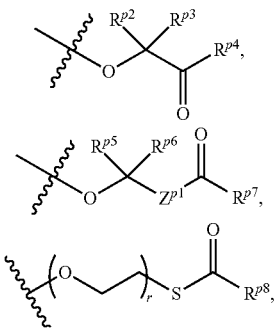

an optionally substituted N-linked amino acid and an optionally substituted N-linked amino acid ester derivative. When both -------- are each a single bond, Formula (I) can have the structure:

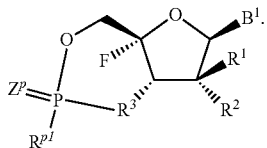

In some embodiments, $R^{P1}$ can be O⁻. In other embodiments, $R^{P1}$ can be OH. In other embodiments, $R^{P1}$ can be an —O-optionally substituted $C_{1-6}$ alkyl. For example, $R^{p1}$ can be a substituted or an unsubstituted version of the following: methoxy, ethoxy, n-propoxy, iso-propoxy, n-butoxy, iso-butoxy, tert-butoxy, pentoxy (branched or straight chained) and hexoxy (branched or straight chained).

In some embodiments, $R^{p1}$ can be

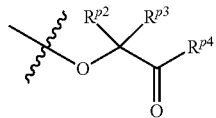

wherein $R^{p2}$ and $R^{p3}$ can be independently selected from hydrogen, an optionally substituted $C_{1-24}$ alkyl and an optionally substituted aryl; and $R^{p4}$ can be selected from hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl and an optionally substituted —O-monocyclic heterocyclyl. In some embodiments, $R^{p2}$ and $R^{p3}$ can be hydrogen. In other embodiments, at least one of $R^{p2}$ and $R^{p3}$ can be an optionally substituted $C_{1-24}$ alkyl or an optionally substituted aryl. In some embodiments, $R^{p4}$ can be an optionally substituted $C_{1-24}$ alkyl. In some embodiments, $R^{p4}$ can be an unsubstituted $C_{1-4}$ alkyl. In other embodiments, $R^{p4}$ can be an optionally substituted aryl. In still other embodiments, $R^{p4}$ can be an optionally substituted —O—$C_{1-24}$ alkyl, an optionally substituted —O-aryl, an optionally substituted —O-heteroaryl or an optionally substituted —O-monocyclic heterocyclyl. In some embodiments, $R^{p4}$ can be an unsubstituted —O—$C_{1-4}$ alkyl.

In some embodiments, $R^{p1}$ can be

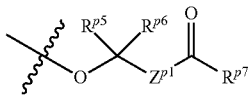

wherein $R^{p5}$ and $R^{p6}$ can be independently selected from hydrogen, an optionally substituted $C_{1-24}$ alkyl and an optionally substituted aryl; $R^{p7}$ can be independently selected from hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl and an optionally substituted —O-monocyclic heterocyclyl; and $Z^{p1}$ can be independently O (oxygen) or S (sulfur). In some embodiments, $R^{p5}$ and $R^{p6}$ can be hydrogen. In other embodiments, at least one of $R^{p5}$ and $R^{p6}$ can be an optionally substituted $C_{1-24}$ alkyl or an optionally substituted aryl. In some embodiments, $R^{p7}$ can be an optionally substituted $C_{1-24}$ alkyl. In some embodiments, $R^{p7}$ can be an unsubstituted $C_{1-4}$ alkyl. In other embodiments, $R^{p7}$ can be an optionally substituted aryl. In still other embodiments, $R^{p7}$ can be an optionally substituted —O—$C_{1-24}$ alkyl, an optionally substituted —O-aryl, an optionally substituted —O-heteroaryl or an optionally substituted —O-monocyclic heterocyclyl. In some embodiments, $R^7$ can be an unsubstituted —O—$C_{1-4}$ alkyl. In some embodiments, $Z^{p1}$ can be O (oxygen). In other embodiments, $Z^{p1}$ can be or S (sulfur). In some embodiments, $R^{p1}$ can be isopropyloxycarbonyloxymethyloxy (POC) group. In some embodiments, $R^{p1}$ can be pivaloyloxymethyloxy (POM) group.

In some embodiments, $R^{p1}$ can be

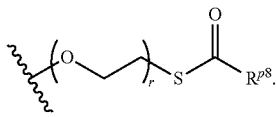

In some embodiments, $R^{p8}$ can be hydrogen. In other embodiments, $R^{p8}$ can be an optionally substituted $C_{1-24}$ alkyl. In still other embodiments, $R^{p8}$ can be an optionally substituted aryl. In some embodiments, $R^{p8}$ can be a $C_{1-6}$ alkyl, for example, methyl, ethyl, n-propyl, isopropyl, n-butyl, isobutyl, tert-butyl, pentyl (branched and straight-chained), and hexyl (branched and straight-chained). In some embodiments, r can be 1. In other embodiments, r can be 2.

In some embodiments, $R^{p1}$ can be

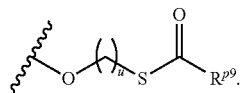

In some embodiments, $R^{p9}$ can be hydrogen. In other embodiments, $R^{p9}$ can be an optionally substituted $C_{1-24}$ alkyl. In still other embodiments, $R^{p9}$ can be an optionally substituted aryl, for example, an optionally substituted phenyl. In some embodiments, $R^{p9}$ can be an optionally substituted $C_{1-6}$ alkyl. In some embodiments, $R^{p9}$ can be an unsubstituted $C_{1-6}$ alkyl. In some embodiments, u can be 3. In other embodiments, u can be 4. In still other embodiments, u can be 5. In some embodiments, $R^{p1}$ can be a S-acylthioethyl (SATE) group and form a SATE ester prodrug.

In some embodiments, $R^{p1}$ can be an optionally substituted N-linked amino acid or an optionally substituted N-linked amino acid ester derivative. For example, $R^{p1}$ can be optionally substituted version of the following: alanine, asparagine, aspartate, cysteine, glutamate, glutamine, glycine, proline, serine, tyrosine, arginine, histidine, isoleucine, leucine, lysine, methionine, phenylalanine, threonine, tryptophan, valine and ester derivatives thereof. In some embodiments, $R^{p10}$ can be selected from N-alanine isopropyl ester, N-alanine cyclohexyl ester, N-alanine neopentyl ester, N-valine isopropyl ester and N-leucine isopropyl ester. In some embodiments, $R^{p10}$ can have the structure

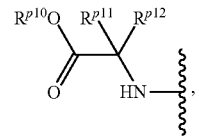

wherein $R^{p10}$ can be selected from hydrogen, an optionally substituted $C_{1-6}$-alkyl, an optionally substituted $C_{3-6}$ cycloalkyl, an optionally substituted aryl, an optionally substituted aryl($C_{1-6}$ alkyl) and an optionally substituted haloalkyl; $R^{p11}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{p12}$ can be hydrogen or an optionally substituted $C_{1-4}$-alkyl; or $R^{p11}$ and $R^{p12}$ can be taken together to form an optionally substituted $C_{3-6}$ cycloalkyl.

When $R^{p11}$ is substituted, $R^{p11}$ can be substituted with one or more substituents selected from N-amido, mercapto, alkylthio, an optionally substituted aryl, hydroxy, an optionally substituted heteroaryl, O-carboxy, and amino. In some embodiments, $R^{p11}$ can be an unsubstituted $C_{1-6}$-alkyl, such as those described herein. In some embodiments, $R^{p11}$ can be hydrogen. In other embodiments, $R^{p11}$ can be methyl. In some embodiments, $R^{p10}$ can be an optionally substituted $C_{1-6}$ alkyl. Examples of optionally substituted $C_{1-6}$-alkyls include optionally substituted variants of the following: methyl, ethyl, n-propyl, isopropyl, n-butyl, isobutyl, tert-butyl, pentyl (branched and straight-chained), and hexyl (branched and straight-chained). In some embodiments, $R^{p10}$ can be methyl or isopropyl. In some embodiments, $R^{p10}$ can be ethyl or neopentyl. In other embodiments, $R^{p10}$ can be an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. In some embodiments, $R^{p10}$ can be an optionally substituted cyclohexyl. In still other embodiments, $R^{p10}$ can be an optionally substituted aryl, such as phenyl and naphthyl. In yet still other embodiments, $R^{p10}$ can be an optionally substituted aryl ($C_{1-6}$ alkyl). In some embodiments, $R^{p10}$ can be an optionally substituted benzyl. In some embodiments, $R^{p10}$ can be an optionally substituted $C_{1-6}$ haloalkyl, for example, $CF_3$. In some embodiments, $R^{p12}$ can be hydrogen. In other embodiments, $R^{p12}$ can be an optionally substituted $C_{1-4}$-alkyl, such as methyl, ethyl, n-propyl, isopropyl, n-butyl, isobutyl and tert-butyl. In some embodiments, $R^{p12}$ can be methyl. In some embodiments, $R^{p11}$ and $R^{p12}$ can be taken together to form an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. Depending on the groups that are selected for $R^{p11}$ and $R^{p12}$, the carbon to which $R^{p11}$ and $R^{p12}$ are attached may be a chiral center. In some embodiment, the carbon to which $R^{p11}$ and $R^{p12}$ are attached may be a (R)-chiral center. In other embodiments, the carbon to which $R^{p11}$ and $R^{p12}$ are attached may be a (S)-chiral center.

Examples of suitable

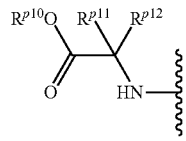

groups include the following:

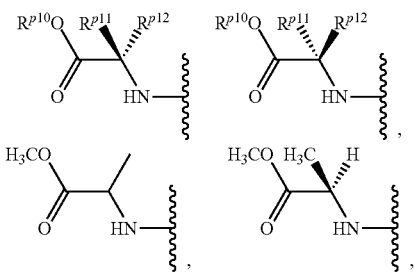

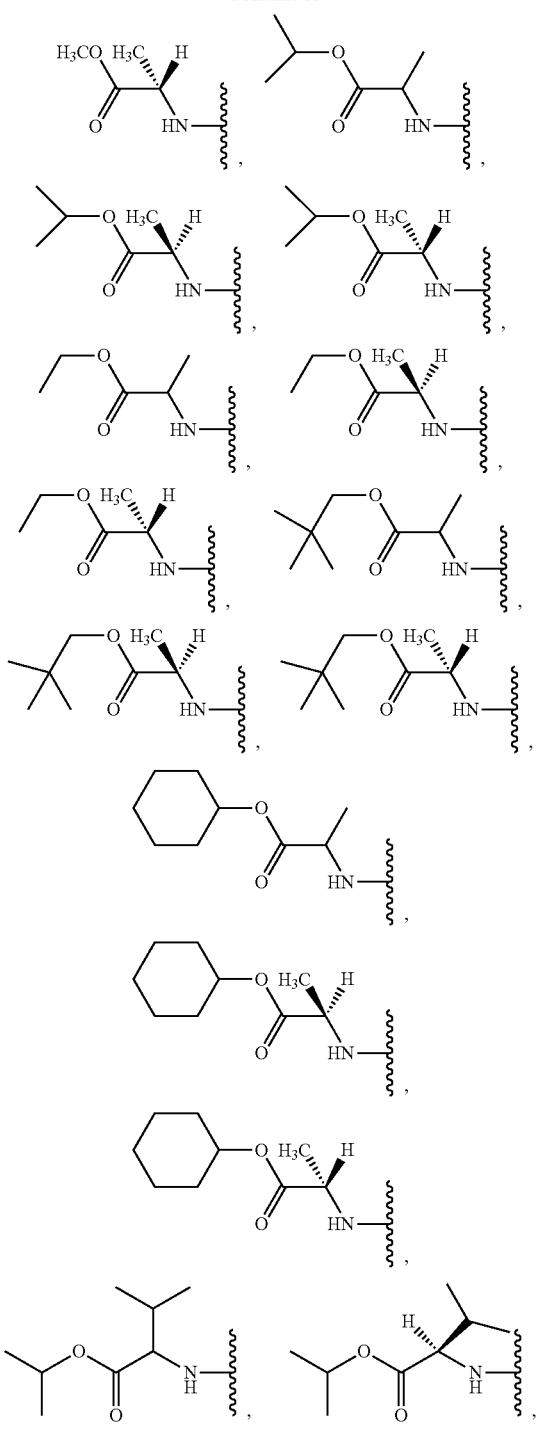

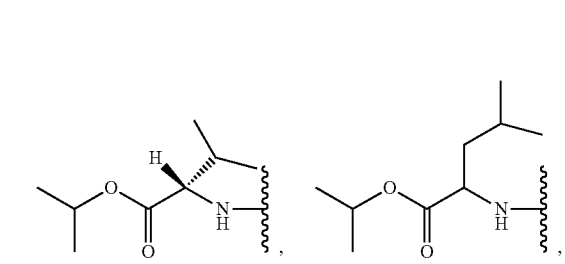

-continued

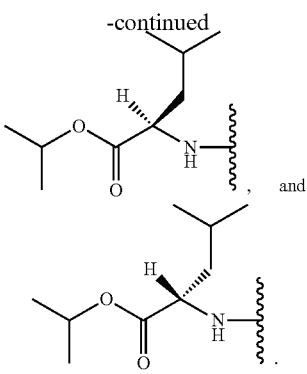
, and

The nucleobase can vary. In some embodiments, $B^1$ can be uracil. In some embodiments, $B^1$ can be an optionally substituted

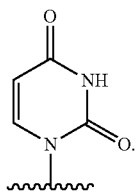 [SMILES: *n1ccc(=O)[nH]c1=O]

In some embodiments, $B^1$ can be unsubstituted

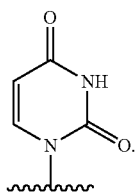 [SMILES: *n1ccc(=O)[nH]c1=O]

In other embodiments, $B^1$ can be an optionally substituted

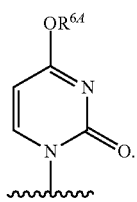

In some embodiments, $B^1$ can be unsubstituted

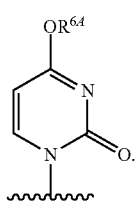

In some embodiments, $R^{6A}$ can be an optionally substituted $C_{1-6}$ alkyl. For example, $R^{6A}$ can be methyl, ethyl, n-propyl, isopropyl, n-butyl, isobutyl, tert-butyl, pentyl (branched and straight-chained) or hexyl (branched and straight-chained). In other embodiments, $R^{6A}$ can be an optionally substituted $C_{3-6}$ cycloalkyl, for example, optionally substituted variants of the following: cyclopropyl, cyclobutyl, cyclopentyl or cyclohexyl.

In some embodiments, $B^1$ can be guanine. In some embodiments, $B^1$ can be an optionally substituted

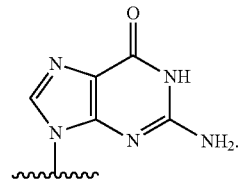 [SMILES: *n1cnc2c(=O)[nH]c(N)nc21]

In other embodiments, $B^1$ can be an optionally substituted

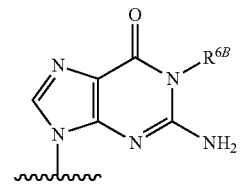

wherein $R^{6B}$ can be selected from hydrogen, an unsubstituted $C_{1-6}$ alkyl, an unsubstituted $C_{3-6}$ alkenyl, an unsubstituted $C_{3-6}$ alkynyl and an unsubstituted $C_{3-6}$ cycloalkyl. In some embodiments, $B^1$ can be unsubstituted

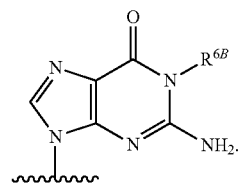

In some embodiments, $R^{6B}$ can be an unsubstituted $C_{1-6}$ alkyl. For example, $R^{6B}$ can be methyl, ethyl, n-propyl, isopropyl, n-butyl, isobutyl, tert-butyl, pentyl (branched and straight-chained) or hexyl (branched and straight-chained). In some embodiments, $R^{6B}$ can be an unsubstituted $C_{3-6}$ alkenyl. In other embodiments, $R^{6B}$ can be an unsubstituted $C_{3-6}$ alkynyl. In still other embodiments, $R^{6B}$ can be an unsubstituted $C_{3-6}$ cycloalkyl, for example, cyclopropyl, cyclobutyl, cyclopentyl or cyclohexyl.

In some embodiments, $B^1$ can be an optionally substituted

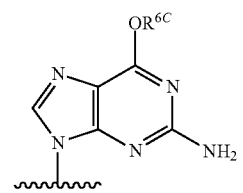

wherein $R^{6C}$ can be selected from hydrogen, an unsubstituted $C_{1-6}$ alkyl, an unsubstituted $C_{3-6}$ alkenyl, an unsubstituted $C_{3-6}$ alkynyl and an unsubstituted $C_{3-6}$ cycloalkyl. In some embodiments, $B^1$ can be unsubstituted

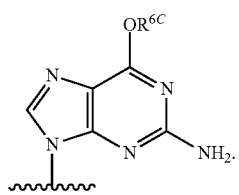

In some embodiments, $R^{6C}$ can be hydrogen. In some embodiments, $R^{6C}$ can be an unsubstituted $C_{1-6}$ alkyl. For example, $R^{6C}$ can be methyl, ethyl, n-propyl, isopropyl, n-butyl, isobutyl, tert-butyl, pentyl (branched and straight-chained) or hexyl (branched and straight-chained). In some embodiments, $R^{6C}$ can be an ethyl. In some embodiments, $R^{6C}$ can be an unsubstituted $C_{3-6}$ alkenyl. In other embodiments, $R^{6C}$ can be an unsubstituted $C_{3-6}$ alkynyl. In other embodiments, $R^{6C}$ can be an unsubstituted $C_{3-6}$ cycloalkyl, for example, cyclopropyl, cyclobutyl, cyclopentyl or cyclohexyl.

In some embodiments, $B^1$ can be adenine. In some embodiments, $B^1$ can be an optionally substituted

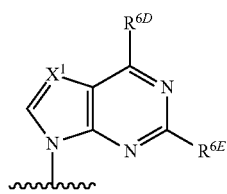

wherein $X^1$ can be N (nitrogen) or —$CR^{6J}$; $R^{6J}$ can be selected from hydrogen, halogen, an optionally substituted $C_{1-6}$ alkyl, an optionally substituted $C_{2-6}$ alkenyl and an optionally substituted $C_{2-6}$ alkynyl; $R^{6D}$ can be $NHR^{6G}$; $R^{6E}$ can be hydrogen, halogen or $NHR^{6H}$; $R^{6G}$ can be selected from hydrogen, an optionally substituted $C_{1-6}$ alkyl, an optionally substituted $C_{3-6}$ alkenyl, an optionally substituted $C_{3-6}$ cycloalkyl, —C(=O)$R^{A1}$ and —C(=O)$OR^{A2}$; $R^{6H}$ can be selected from hydrogen, an optionally substituted $C_{1-6}$ alkyl, an optionally substituted $C_{3-6}$ alkenyl, an optionally substituted $C_{3-6}$ cycloalkyl, —C(=O)$R^{A3}$ and —C(=O)$OR^{A4}$; $R^{A1}$, $R^{A2}$, $R^{A3}$ and $R^{A4}$ can be independently selected from $C_{1-6}$ alkyl, $C_{2-6}$ alkenyl, $C_{2-6}$ alkynyl, $C_{3-6}$ cycloalkyl, $C_{3-6}$ cycloalkenyl, $C_{6-10}$ aryl, heteroaryl, heterocyclyl, aryl($C_{1-6}$ alkyl), heteroaryl($C_{1-6}$ alkyl) and heterocyclyl($C_{1-6}$ alkyl). In some embodiments, $X^1$ can be N (nitrogen). In other embodiments, $X^1$ can be —$CR^{6I}$, wherein $CR^{6I}$ can be selected from hydrogen, halogen, an optionally substituted $C_{1-6}$ alkyl, an optionally substituted $C_{2-6}$ alkenyl and an optionally substituted $C_{2-6}$ alkynyl. In some embodiments, $X^1$ can be CH. In some embodiments, $R^{6D}$ and $R^{6E}$ can be both $NH_2$. In other embodiments, at least one of $R^{6D}$ and $R^{6E}$ can be $NH_2$. In some embodiments, $R^{6D}$ can be $NHR^{6G}$, wherein $R^{6G}$ can be an optionally substituted $C_{1-6}$ alkyl. In some embodiments, $R^{6E}$ can be hydrogen. In other embodiments, $R^{6E}$ can be halogen. In still other embodiments, $R^{6E}$ can be $NHR^{6H}$, wherein $R^{6H}$ can be an optionally substituted $C_{1-6}$ alkyl. In other embodiments, $R^{6D}$ can be $NHR^{6G}$, wherein $R^{6G}$ can be selected from an optionally substituted $C_{3-6}$ alkenyl, an optionally substituted $C_{3-6}$ cycloalkyl, —C(=O)$R^{A1}$ and —C(=O)$OR^{A2}$. In other embodiments, $R^{6E}$ can be $NHR^{6H}$, wherein $R^{6H}$ can be selected from an optionally substituted $C_{3-6}$ alkenyl, an optionally substituted $C_{3-6}$ cycloalkyl, —C(=O)$R^{A3}$ and —C(=O)$OR^{A4}$. In some embodiments, $R^{6D}$ and $R^{6E}$ can be the same. In other embodiments, $R^{6D}$ and $R^{6E}$ can be different.

In some embodiments, $B^1$ can be cytosine. In some embodiments, $B^1$ can be an optionally substituted

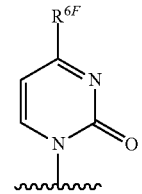

wherein $R^{6F}$ can be $NHR^{6I}$; $R^{6I}$ can be selected hydrogen, an optionally substituted $C_{1-6}$ alkyl, an optionally substituted $C_{3-6}$ alkenyl, an optionally substituted $C_{3-6}$ cycloalkyl, —C(=O)$R^{A5}$ and —C(=O)$OR^{A6}$; and $R^{A5}$ and $R^{A6}$ are independently selected from the group consisting of $C_{1-6}$ alkyl, $C_{2-6}$ alkenyl, $C_{2-6}$ alkynyl, $C_{3-6}$ cycloalkyl, $C_{3-6}$ cycloalkenyl, $C_{6-10}$ aryl, heteroaryl, heterocyclyl, aryl($C_{1-6}$ alkyl), heteroaryl($C_{1-6}$ alkyl) and heterocyclyl($C_{1-6}$ alkyl). In some embodiments, $R^{6F}$ can be $NH_2$. In other embodiments, $R^{6F}$ can be $NHR^{6I}$, wherein $R^{6I}$ can be an optionally substituted $C_{1-6}$ alkyl, an optionally substituted $C_{3-6}$ alkenyl or an optionally substituted $C_{3-6}$ cycloalkyl. In still other embodiments, $R^{6F}$ can be $NHR^{6I}$, wherein $R^{6I}$ can be —C(=O)$R^{A5}$ or —C(=O)$OR^{A6}$. When $R^{6I}$ is —C(=O)$R^{A5}$ or —C(=O)$OR^{A6}$, $R^{A5}$ and $R^{A6}$ can be $C_{1-6}$ alkyl, $C_{2-6}$ alkenyl or $C_{2-6}$ alkynyl. $R^{A5}$ and $R^{A6}$ can also be $C_{3-6}$ cycloalkyl, $C_{3-6}$ cycloalkenyl, $C_{6-10}$ aryl or heteroaryl, heterocyclyl. Additionally, $R^{A5}$ and $R^{A6}$ can be aryl($C_{1-6}$ alkyl), heteroaryl($C_{1-6}$ alkyl) or heterocyclyl($C_{1-6}$ alkyl).

In some embodiments, $Z^1$ can be O (oxygen). In other embodiments, $Z^1$ can be S (sulfur).

In some embodiments, $R^2$ is not halo. In some embodiments, $R^2$ is not fluoro. In some embodiments, $R^{5B}$ is not an —O-optionally substituted aryl. In some embodiments, $R^{5B}$ is not an —O-unsubstituted aryl. In some embodiments, $R^{5A}$ is not N-alanine isopropyl ester. In some embodiments, $R^1$ is not an optionally substituted $C_{1-6}$ alkyl. For example, le is not an unsubstituted $C_{1-6}$ alkyl, such as methyl. In some embodiments, $B^1$ is not an optionally substituted uracil, for example, a halo-substituted uracil. In some embodiment, when both -------- are each absent; $R^P$ is absent; $R^3$ is OH or —OC(=O)$R^8$; $R^2$ is F; and $R^1$ is methyl, ethyl or ethenyl; then $R^4$ cannot be selected from H and

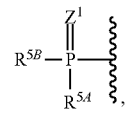

wherein $R^{5B}$ is an —O-unsubstituted aryl; $R^{5A}$ is

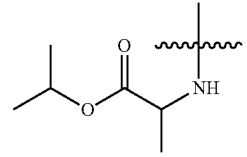 [SMILES: *NC(C)C(=O)OC(C)C]

and $Z^1$ is oxygen. In some embodiments, $R^2$ is not halo (such as fluoro) when $B^1$ is uracil. In some embodiments, a compound of Formula (I) is not a compound in WO 2013/092481 (filed Dec. 17, 2012).
Example structures of a compound of Formula (I) include the following:
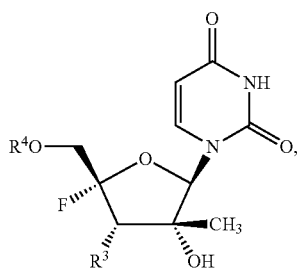
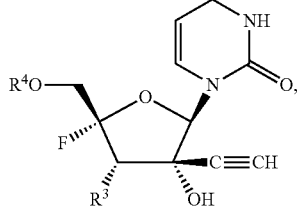
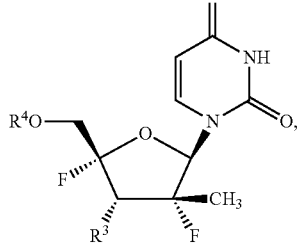
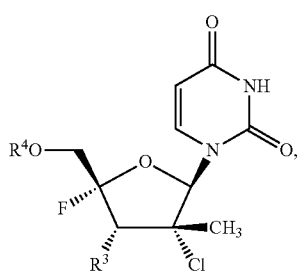
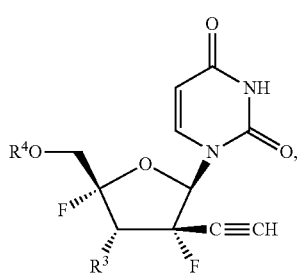
-continued

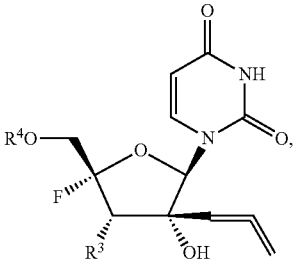
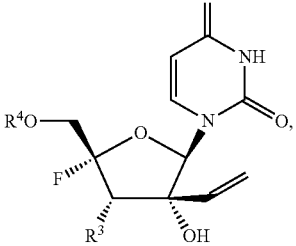
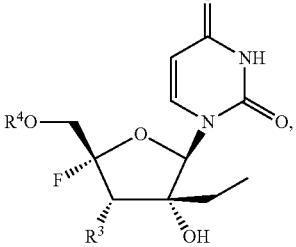
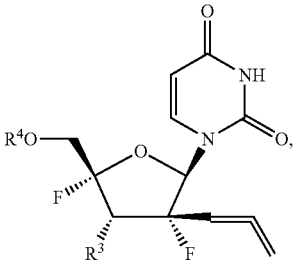
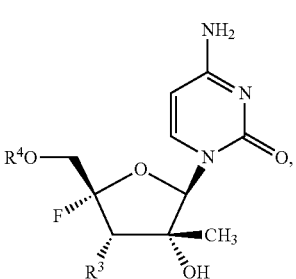

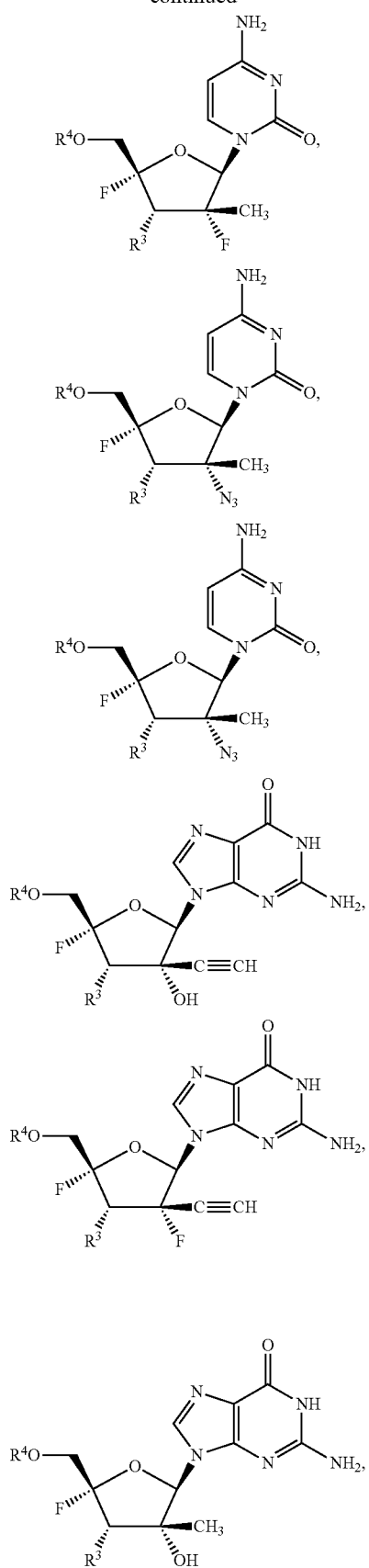
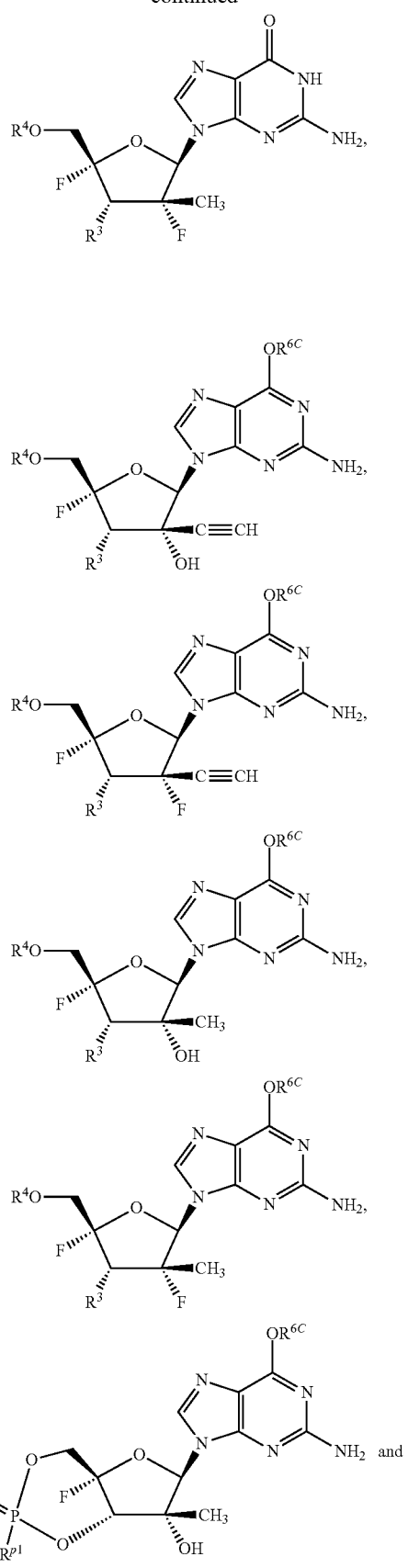

-continued

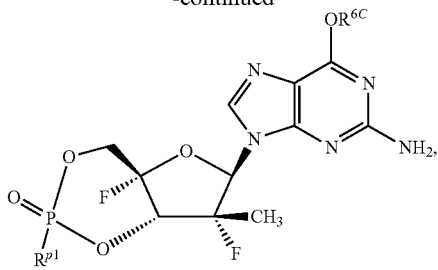

or a pharmaceutically acceptable salt of the foregoing. In some embodiments of this paragraph, $R^3$ can be OH. In some embodiments of this paragraph, $R^{6C}$ can be an unsubstituted $C_{1-6}$ alkyl, such as $CH_2CH_3$. In some embodiments of this paragraph, $R^{P1}$ can be —O-unsubstituted $C_{1-6}$ alkyl. In some embodiments, of this paragraph, $R^4$ can be H. In other embodiments, of this paragraph, $R^4$ can be a phosphoroamidate group. In still other embodiments, of this paragraph, $R^4$ can be a phosphate group (such as a mono-, di- or tri-phosphate). In yet still other embodiments, of this paragraph, $R^4$ can be a thiophosphoroamidate group. In some embodiments, of this paragraph, $R^4$ can be thiophosphate group (such as an alpha-thiomono-, alpha-thiodi- or alpha-thiotri-phosphate). In some embodiments of this paragraph, $R^{P1}$ can be —O-ethyl, —O-isopropyl or —O-isobutyl.

Examples of compounds of Formula (I) include the following:

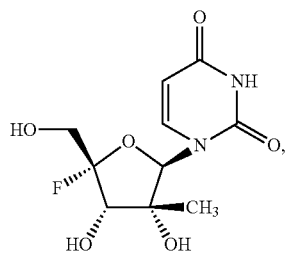

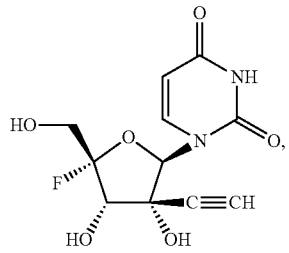

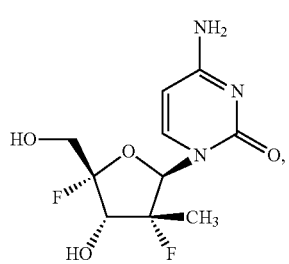

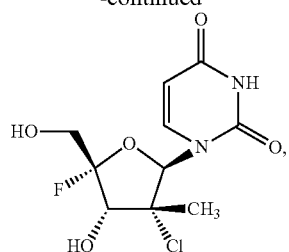

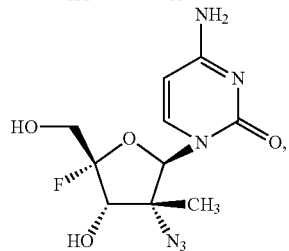

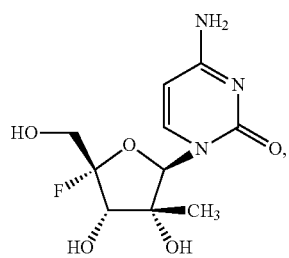

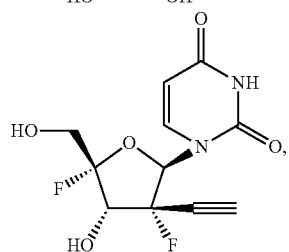

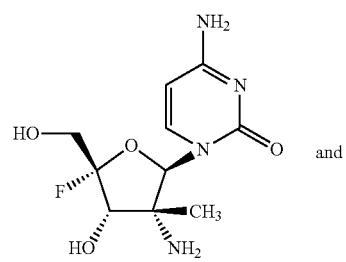

and

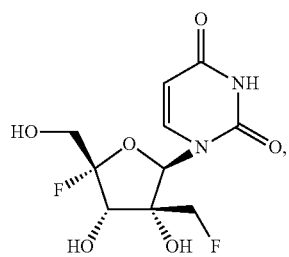

or a pharmaceutically acceptable salt of the foregoing.

Additional examples of compounds of Formula (I) include the following:
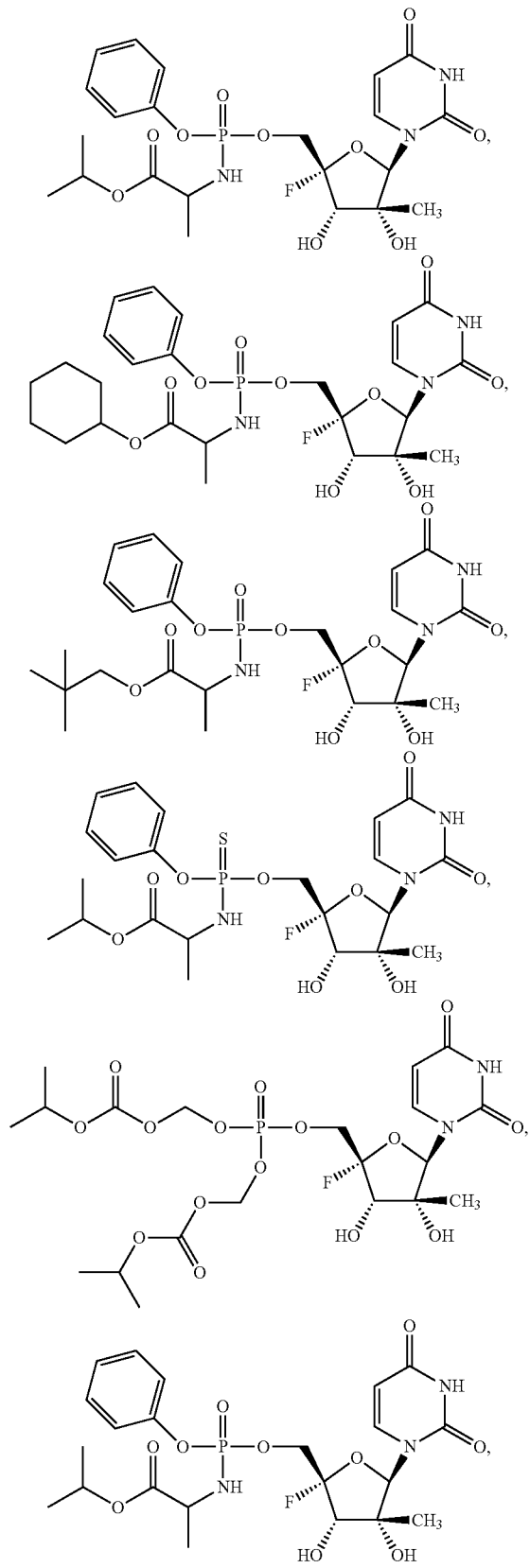
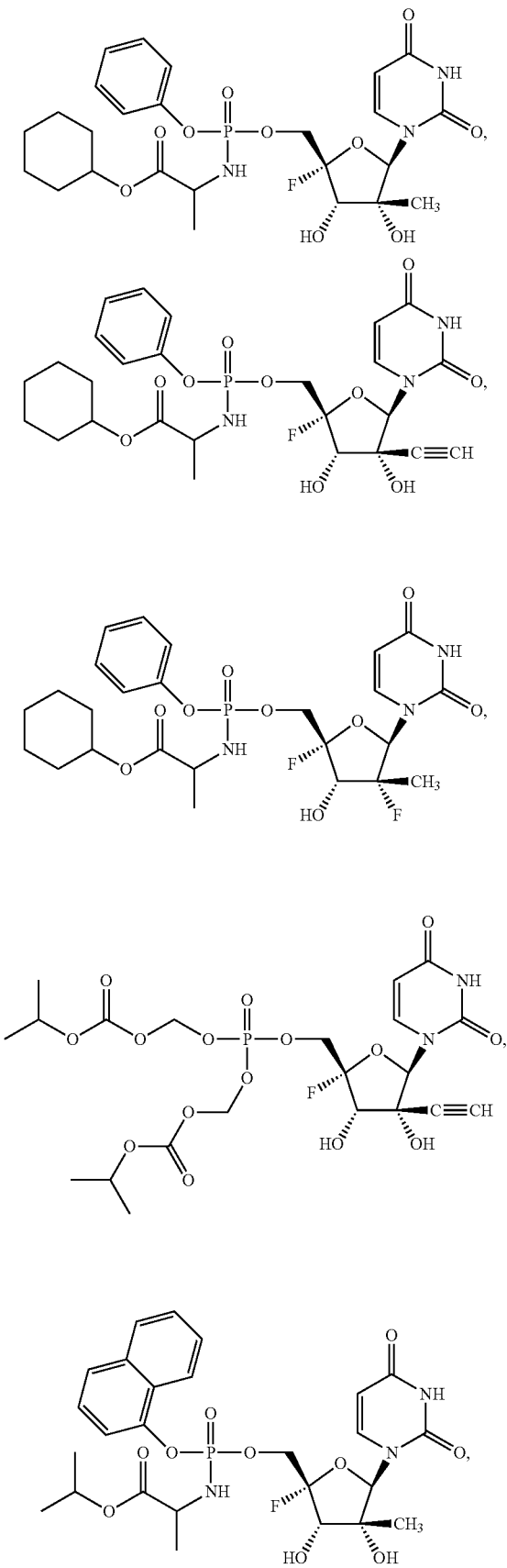

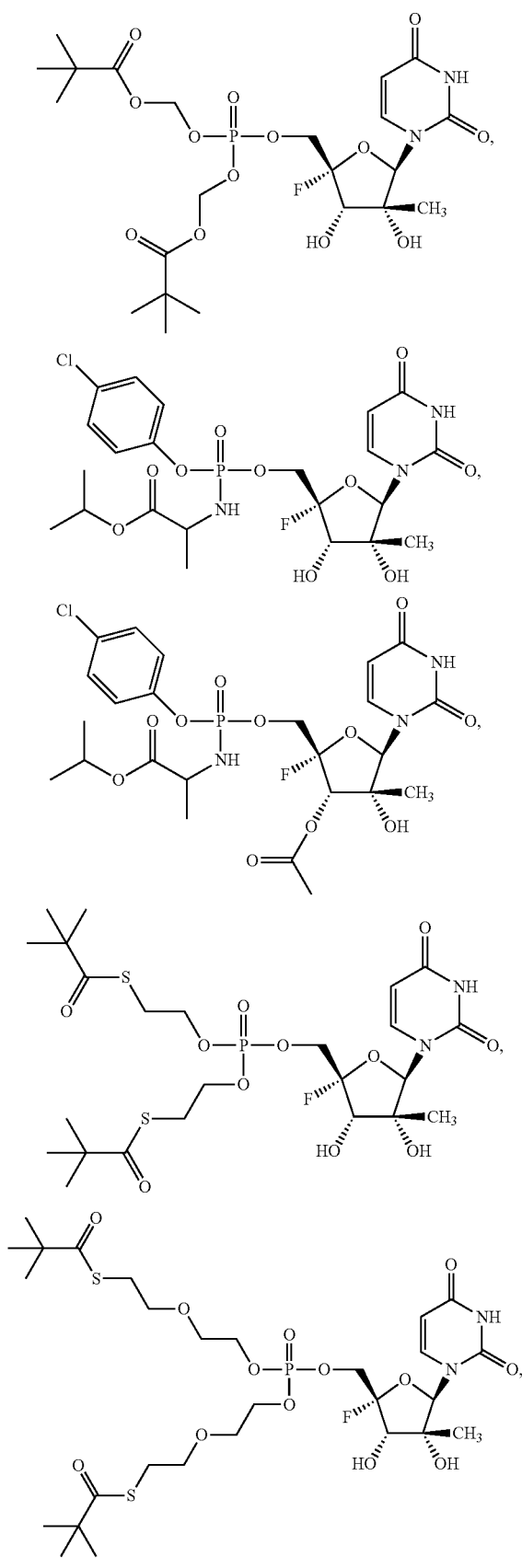
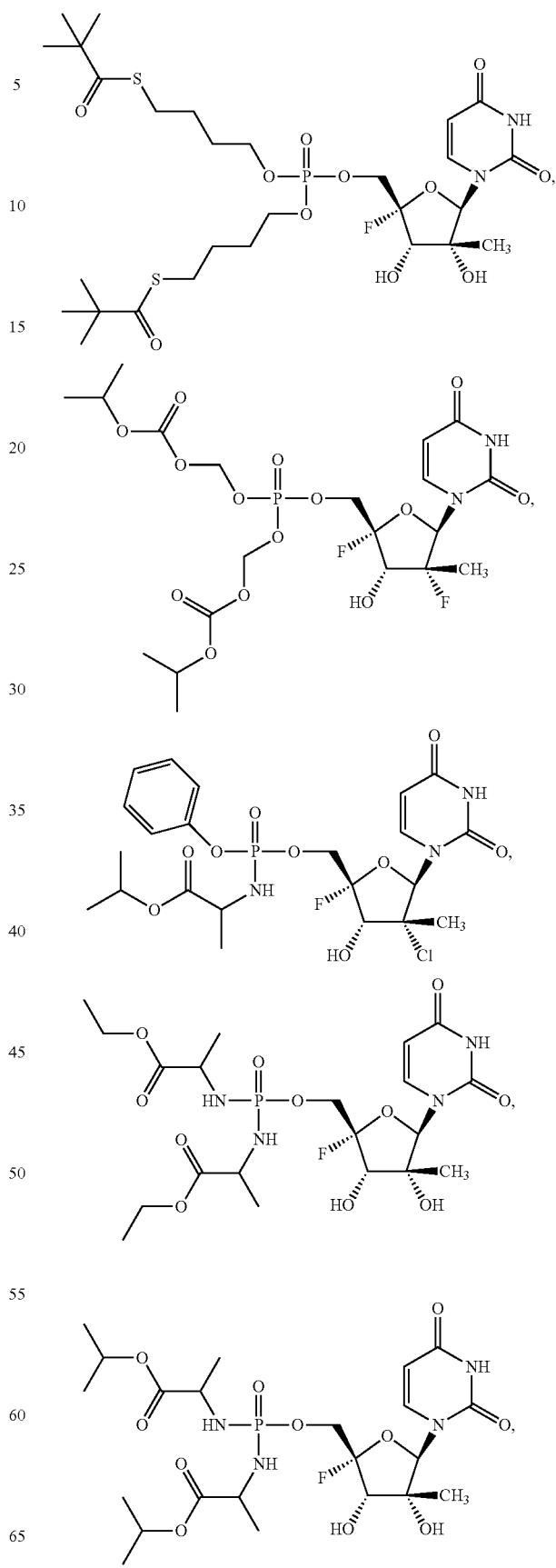

-continued
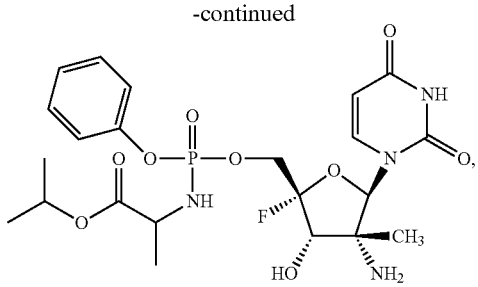
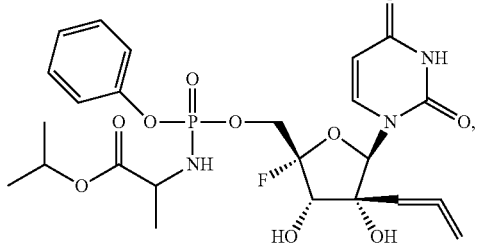
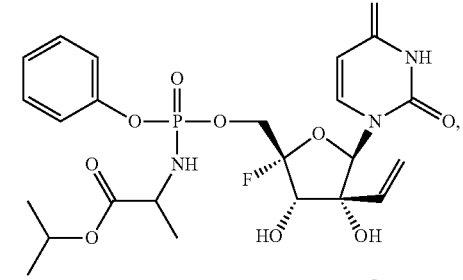
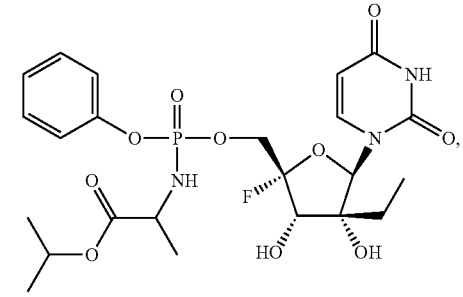
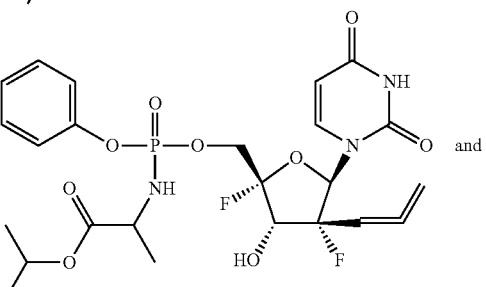
and
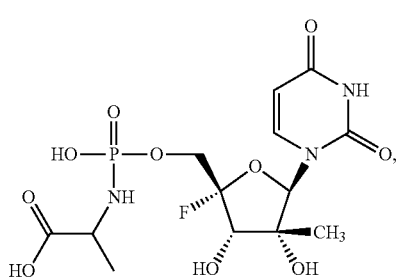
or a pharmaceutically acceptable salt of the foregoing.
Still further examples of compounds of Formula (I) include the following:
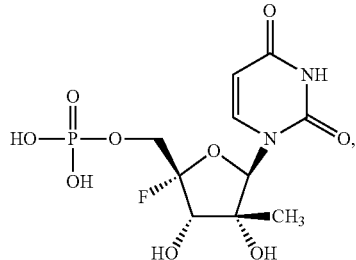
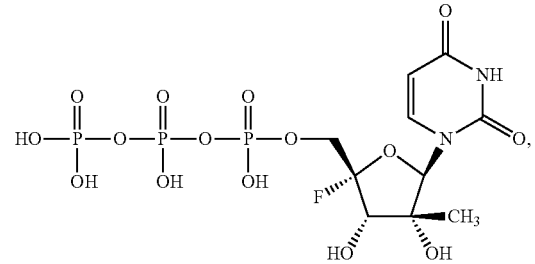
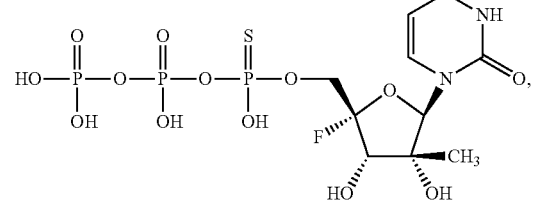
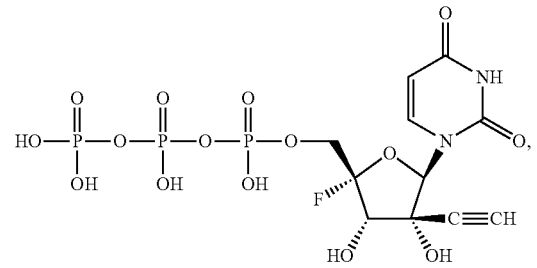
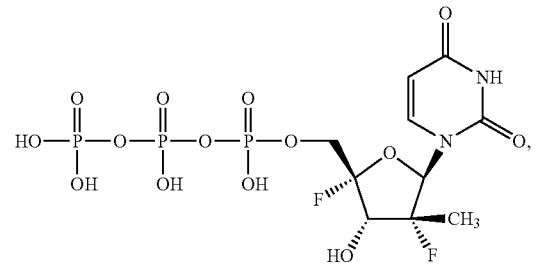

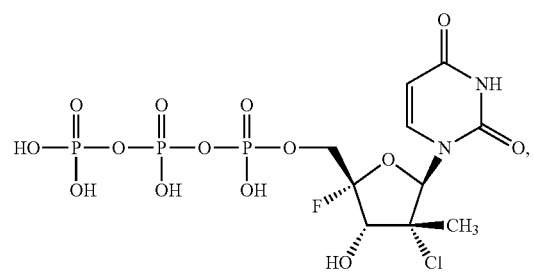
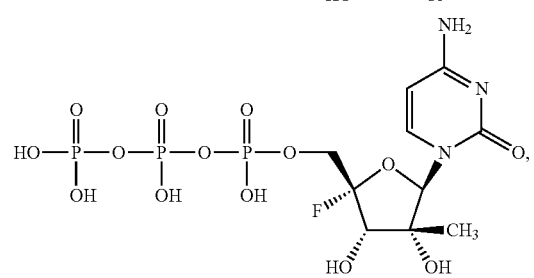
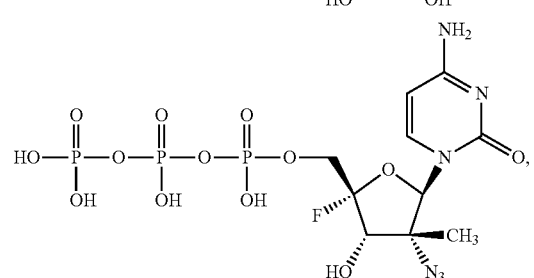
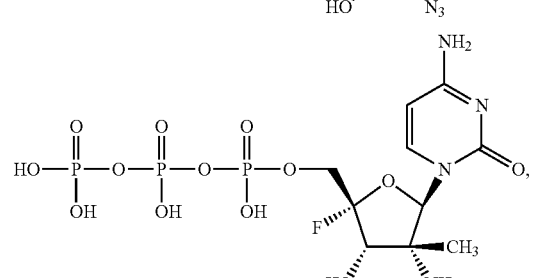
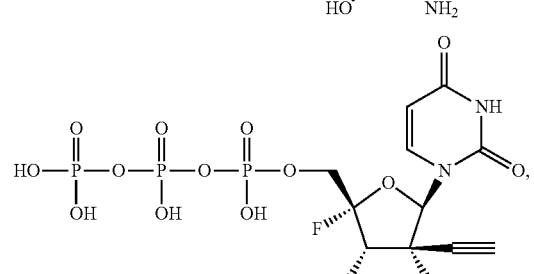
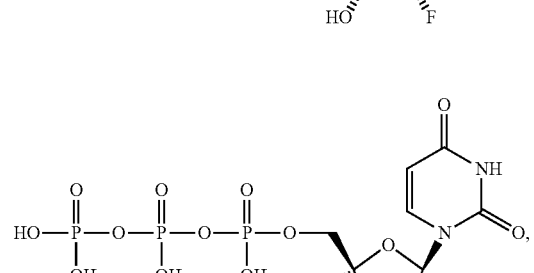
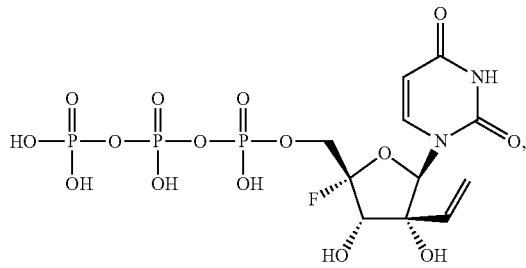
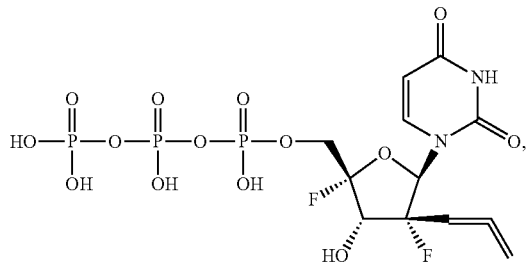
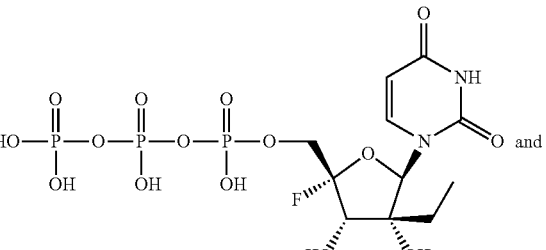
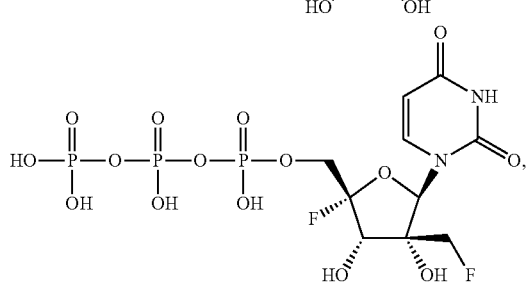
or a pharmaceutically acceptable salt of the foregoing.
Examples of compounds of Formula (I) include the following:
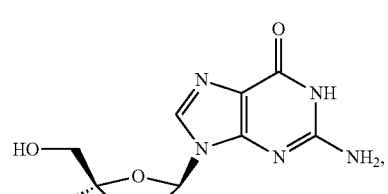
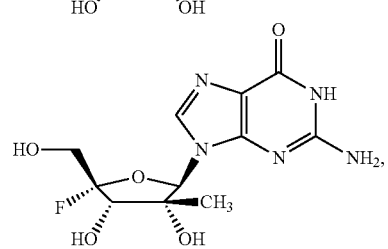

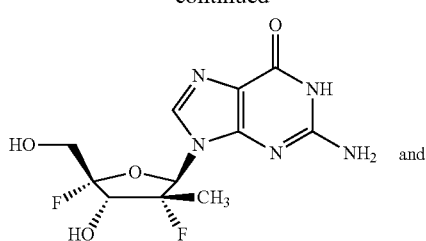
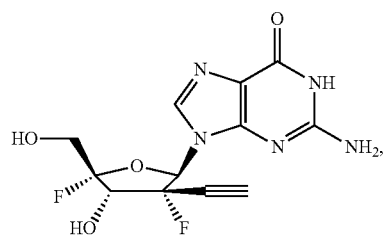
or a pharmaceutically acceptable salt of the foregoing.
Further examples of compounds of Formula (I) include the following:
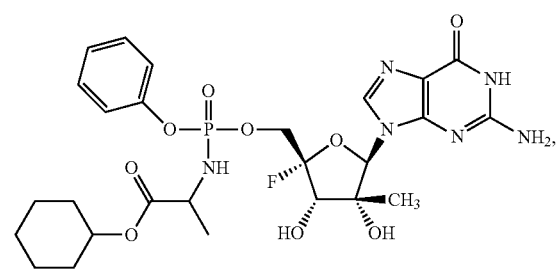
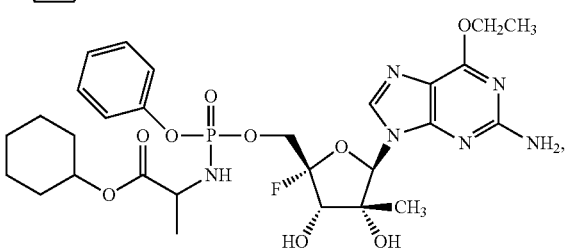
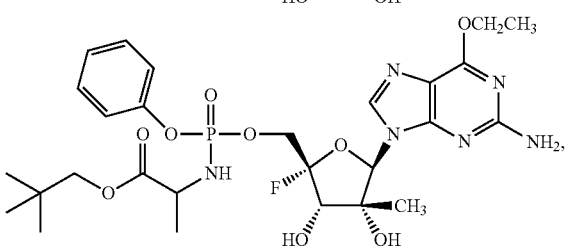
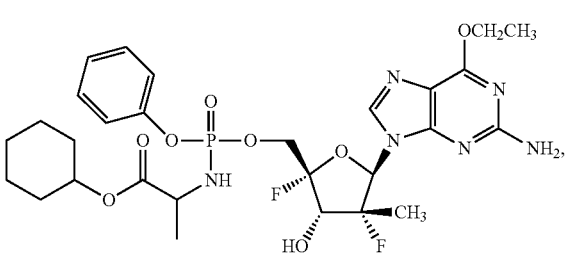
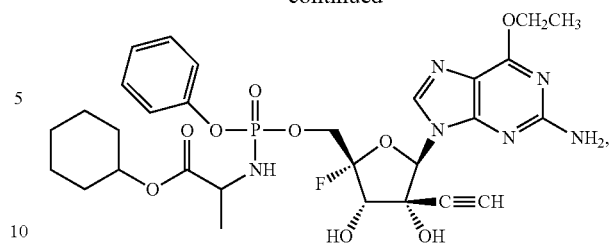
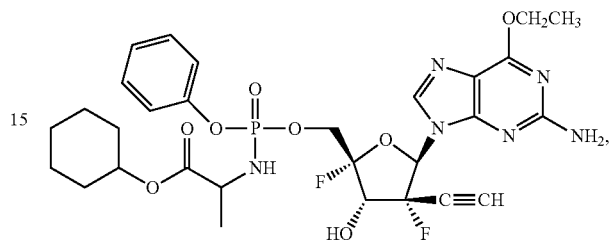
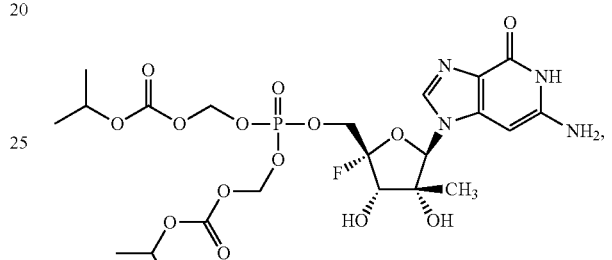
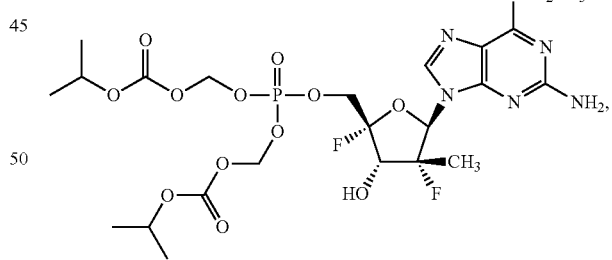
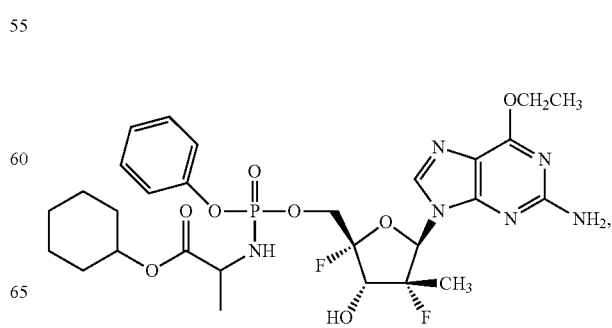

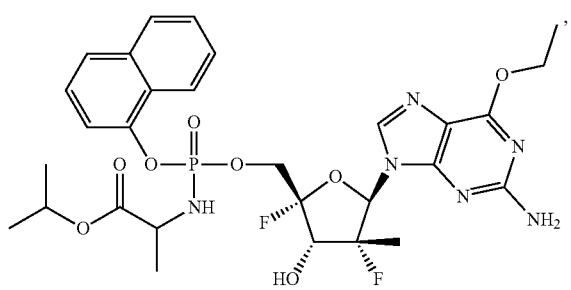
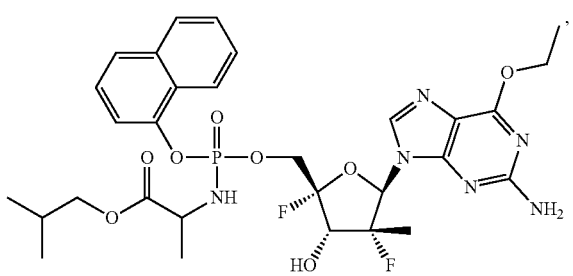
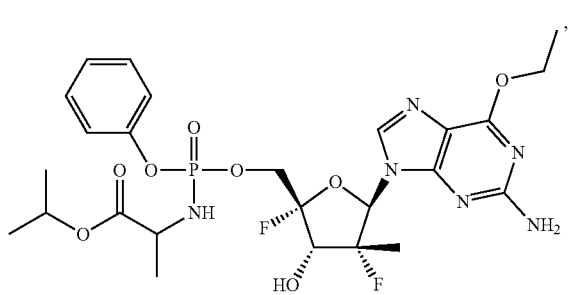
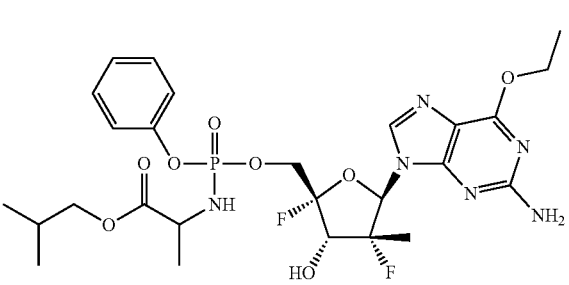
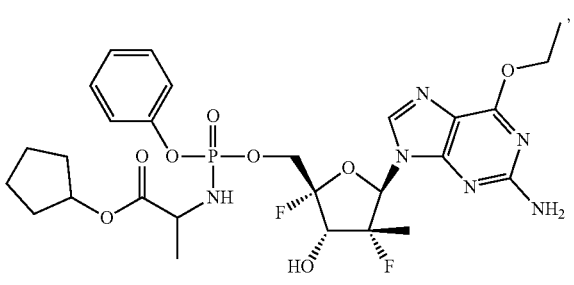
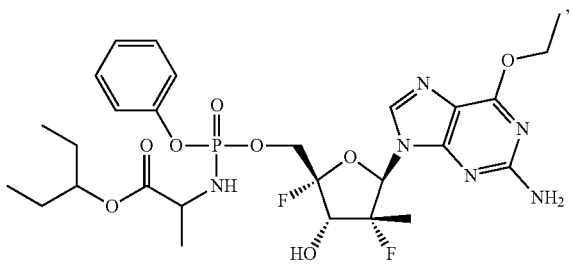
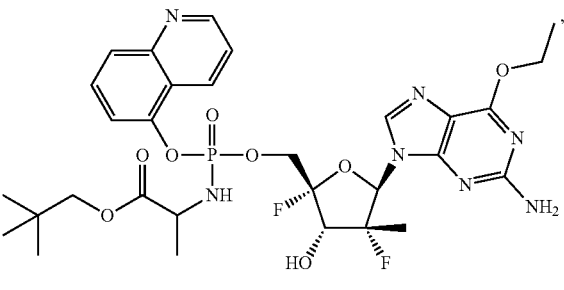
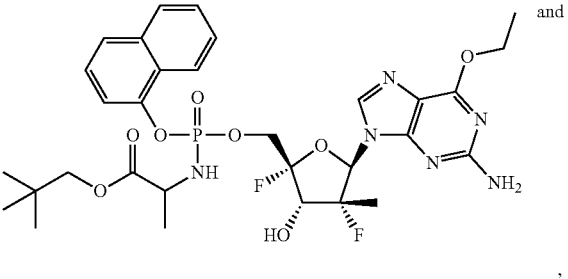
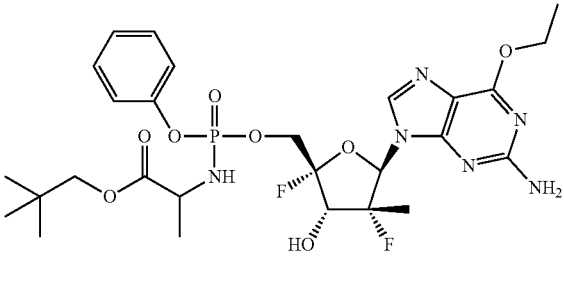
or a pharmaceutically acceptable salt of the foregoing.
Further examples of compounds of Formula (I) include the following:
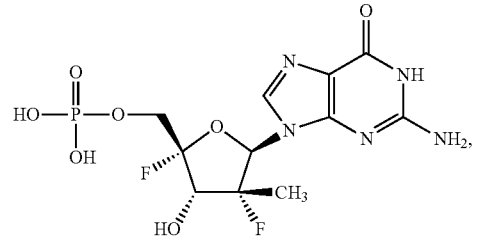
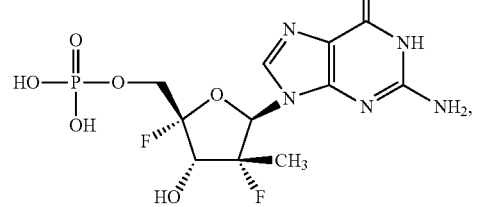

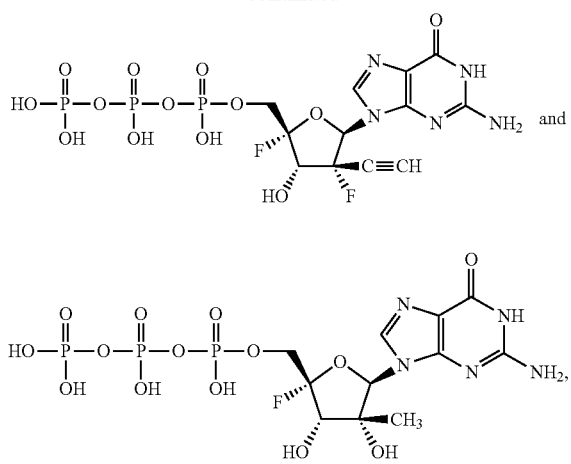
or a pharmaceutically acceptable salt of the foregoing.
Additional examples of compounds of Formula (I) include the following:
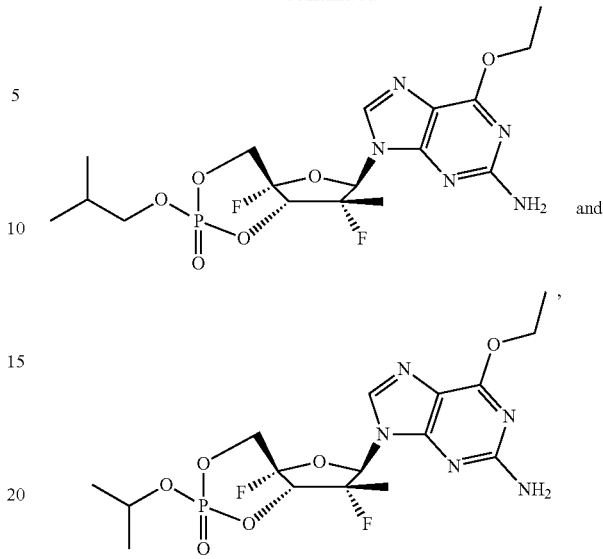
or a pharmaceutically acceptable salt of the foregoing.
In some embodiments, a compound of Formula (I) cannot be selected from:
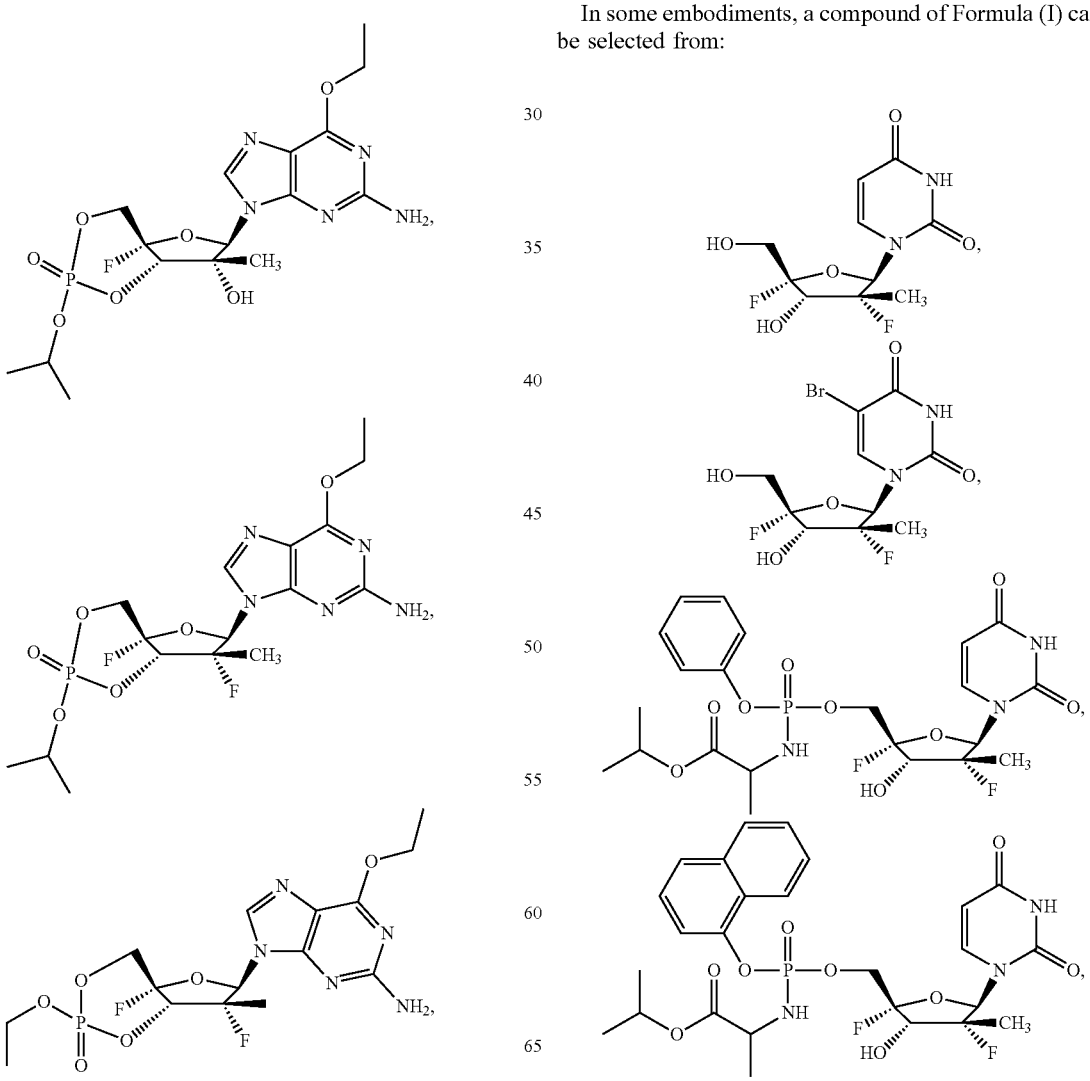

-continued

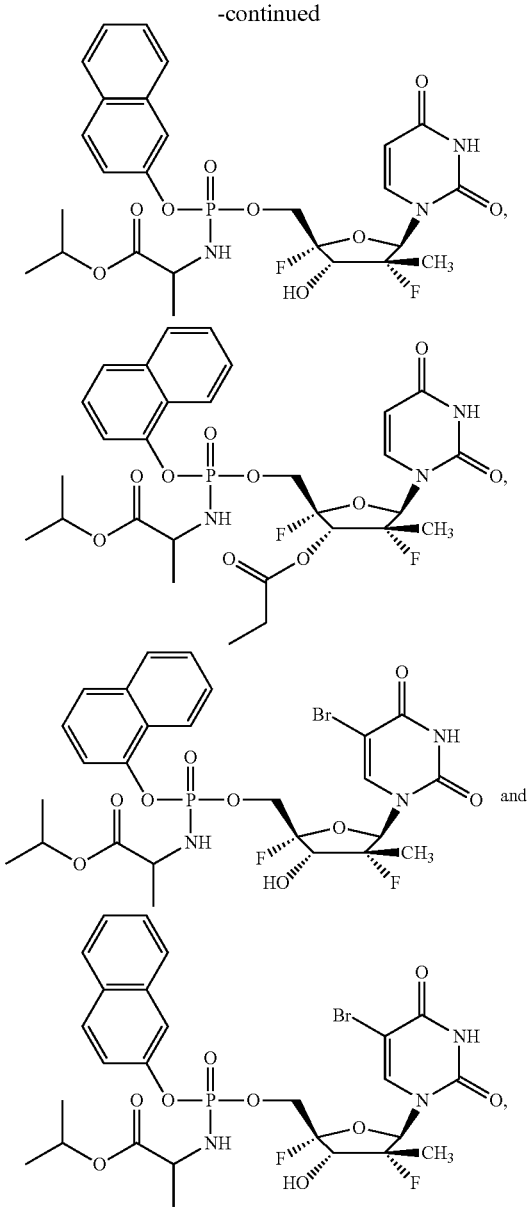

or a pharmaceutically acceptable salt of the foregoing.

As described herein, a compound of Formula (I), or a pharmaceutically acceptable salt thereof, can have $R^4$ being

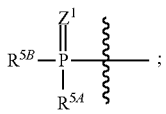

$R^{5A}$ being an optionally substituted N-linked amino acid or an optionally substituted N-linked amino acid ester derivative; and $R^{5B}$ being an —O-optionally substituted aryl, an —O-optionally substituted heteroaryl, an —O-optionally substituted heterocyclyl, an optionally substituted N-linked amino acid or an optionally substituted N-linked amino acid ester derivative. By neutralizing the charge on the phosphate or thiophosphate, penetration of the cell membrane may be facilitated as a result of the increased lipophilicity of the compound. Once absorbed and taken inside the cell, the groups attached to the phosphorus can be easily removed by esterases, proteases and/or other enzymes. In some embodiments, the groups attached to the phosphorus can be removed by simple hydrolysis. Inside the cell, the phosphate thus released may then be metabolized by cellular enzymes to the diphosphate or the active triphosphate. Likewise, the thio-phosphate may be metabolized to the alpha-thiodiphosphate or the alpha-thiotriphosphate. Furthermore, in some embodiments, varying the substituents on a compound described herein, such as compound of Formula (I), can help maintain the efficacy of such the compound by reducing undesirable effects, such as isomerization.

In some embodiments, the phosphorylation of a thio-monophosphate of a compound of Formula (I), or pharmaceutically acceptable salt thereof, can be stereoselective. For example, a thio-monophosphate of a compound of Formula (I) can be phosphorylated to give an alpha-thiodiphosphate and/or an alpha-thiotriphosphate compound that can be enriched in the (R) or (9 diastereomer with respect to the 5'-O-phosphorous atom. For example, one of the (R) and (9 configuration with respect to the 5'-O-phosphorous atom of the alpha-thiodiphosphate and/or the alpha-thiotriphosphate compound can be present in an amount >50%, ≥75%, ≥90%, ≥95% or ≥99% compared to the amount of the other of the (R) or (9 configuration with respect to the 5'-O-phosphorous atom. In some embodiments, phosphorylation of a compound of Formula (I), or pharmaceutically acceptable salt thereof, can result in the formation of a compound that has the (R)-configuration at the 5'-O-phosphorous atom. In some embodiments, phosphorylation of a compound of Formula (I), or pharmaceutically acceptable salt thereof, can result in formation of a compound that has the (9-configuration at the 5'-O-phosphorous atom.

In some embodiments, a compound of Formula (I), or a pharmaceutically acceptable salt thereof, can act as a chain terminator of HCV replication. For example, compounds of Formula (I) can contain a moiety at the 2'-carbon position such that once the compound is incorporated into an RNA chain of HCV no further elongation is observed to occur. For example, a compound of Formula (I) can contain a 2'-carbon modification wherein $R^1$ is a non-hydrogen group selected from an optionally substituted $C_{1-6}$ alkyl, an optionally substituted $C_{2-6}$ alkenyl, an optionally substituted $C_{2-6}$ alkynyl and an optionally substituted $C_{3-6}$ cycloalkyl.

In some embodiments, a compound of Formula (I), or a pharmaceutically acceptable salt thereof, can have increased metabolic and/or plasma stability. In some embodiments, a compound of Formula (I), or a pharmaceutically acceptable salt thereof, can be more resistant to hydrolysis and/or more resistant to enzymatic transformations. For example, a compound of Formula (I), or a pharmaceutically acceptable salt thereof, can have increased metabolic stability, increased plasma stability, can be more resistant to hydrolysis and/or can be more resistant to enzymatic transformations compared to a compound that is identical in structure but for having a hydrogen in place of the fluoro at the 4'-position.

In some embodiments, a compound of Formula (I), or a pharmaceutically acceptable salt thereof, can have improved properties. A non-limiting list of example properties include, but are not limited to, increased biological half-life, increased bioavailability, increase potency, a sustained in vivo response, increased dosing intervals, decreased dosing amounts, decreased cytotoxicity, reduction in required amounts for treating disease conditions, reduction in viral load, reduction in time to seroconversion (i.e., the virus becomes undetectable in patient serum), increased sustained viral response, a reduction of morbidity or mortality in clinical outcomes, increased subject compliance, decreased liver conditions (such as liver fibrosis, liver cirrhosis and/or liver cancer), and compatibility with other medications. In some embodiments, a compound of Formula (I), or a pharmaceutically acceptable salt thereof, can have a biological half-life of greater than 24 hours. In some embodiments, a compound of Formula (I), or a pharmaceutically acceptable salt thereof, can have a biological half-life greater than a compound that is identical in structure but for having a hydrogen in place of the fluoro at the 4'-position. In some embodiments, a compound of Formula (I), or a pharmaceutically acceptable salt thereof, can have more potent antiviral activity (for example, a lower $EC_{50}$ in an HCV replicon assay) as compared to the current standard of care. In some embodiments, a compound of Formula (I), or a pharmaceutically acceptable salt thereof, does not significantly inhibit mitochondrial function of the mitochondrial RNA polymerase. For example, a compound of Formula (I), or a pharmaceutically acceptable salt thereof, is incorporated in the human mitochondrial RNA polymerase less than 10% compared to the natural 5'-triphosphate nucleotide with the same $B^1$.

Additionally, in some embodiments, the presence of a thiophosphoroamidate, phosphoroamidate, thiophosphorbisamidate or phosphorbisamidate in a compound of Formula (I) can increase the stability of the compound by inhibiting its degradation. Also, in some embodiments, the presence of a thiophosphoroamidate, phosphoroamidate, thiophosphorbisamidate or phosphorbisamidate can make the compound more resistant to cleavage in vivo and provide sustained, extended efficacy. In some embodiments, a thiophosphoroamidate, phosphoroamidate, thiophosphorbisamidate or phosphorbisamidate can facilitate the penetration of the cell membrane by a compound of Formula (I) by making the compound more lipophilic. In some embodiments, a thiophosphoroamidate, phosphoroamidate, thiophosphorbisamidate or phosphorbisamidate can have improved oral bioavailability, improved aqueous stability and/or reduced risk of byproduct-related toxicity. In some embodiments, for comparison purposes, a compound of Formula (I) can be compared to a compound that is identical in structure but for having a hydrogen in place of the fluoro at the 4'-position.

Synthesis

Compounds of Formula (I) and those described herein may be prepared in various ways. General synthetic routes to the compound of Formula (I), and some examples of starting materials used to synthesize the compounds of Formula (I) are shown in Scheme 1 and 2, and described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Compounds of Formula (I) can be prepared using various methods known to those skilled in the art. Examples of methods are shown in Schemes 1 and 2. Suitable phosphorus containing precursors can be commercially obtained or prepared by synthetic methods known to those skilled in the art. Examples of general structures of phosphorus containing precursors are shown in Schemes 1 and 2, and include phosphorochloridates and thiophosphorochloridates. Suitable phosphorochloridates and thiophosphorochloridates are commercially available and/or can be synthetically prepared.

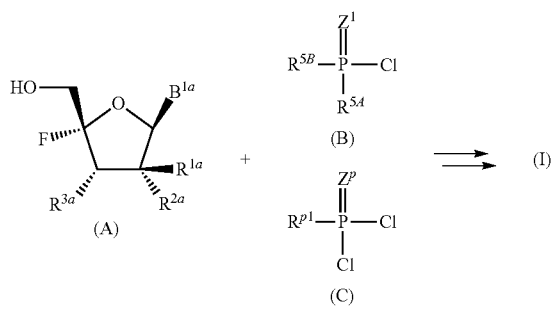

Scheme 1

One method for forming a compound of Formula (I) is shown in Scheme 1. In Scheme 1, $R^{1a}$, $R^{2a}$, $R^{3a}$ and $B^{1a}$ can be the same as $R^1$, $R^2$, $R^3$ and $B^1$ as described herein for Formula (I). In some embodiments, a compound of Formula (I) can be generated from a compound of Formula (A) and a compound of Formula (B) or a compound of Formula (A) and a compound of Formula (C) using an organometallic reagent, such as a Grignard reagent. Suitable Grignard reagents are known to those skilled in the art and include, but are not limited to, alkylmagnesium chlorides and alkylmagnesium bromides. In other embodiments, an appropriate base can be used to form a compound of Formula (I). Examples of suitable bases include, but are not limited to, an amine base, such as an alkylamine (including mono-, di- and tri-alkylamines (e.g., triethylamine)), optionally substituted pyridines (e.g. collidine) and optionally substituted imidazoles (e.g., N-methylimidazole)).

When compounds of Formula (I) has $Z^1$ being sulfur, the sulfur can be added in various manners. In some embodiments, the sulfur can be part of the phosphorus containing precursor, for example,

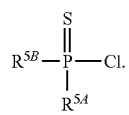

Alternatively, one of the oxygens attached to the phosphorus can be exchanged with a sulfur using a sulfurization reagent. Suitable sulfurization agents are known to those skilled in the art, and include, but are not limited to, elemental sulfur, Lawesson's reagent, cyclooctasulfur, 3H-1,2-Benzodithiole-3-one-1,1-dioxide (Beaucage's reagent), 3-((N,N-dimethylaminomethylidene)amino)-3H-1,2,4-dithiazole-5-thione (DDTT) and bis(3-triethoxysilyl)propyl-tetrasulfide (TEST).

Scheme 2

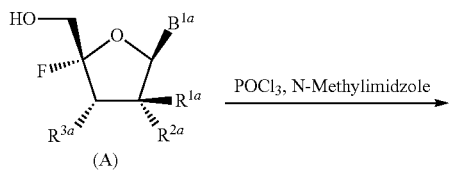

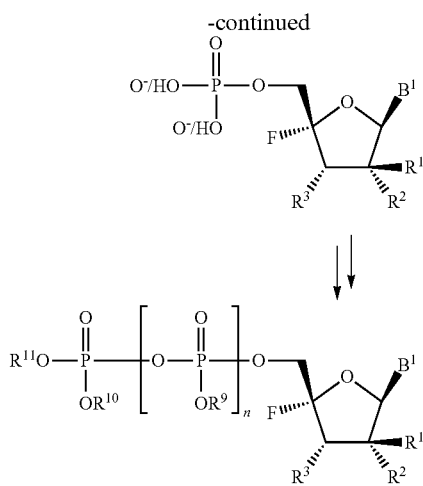

A phosphorus containing precursor can be coupled to the nucleoside, for example, a compound of Formula (A). Following the coupling of the phosphorus containing precursor, any leaving groups can be cleaved under suitable conditions, such as hydrolysis. In Scheme 2, $R^{1a}$, $R^{2a}$, $R^{3a}$ and $B^{1a}$ can be the same as $R^1$, $R^2$, $R^3$ and $B^1$ as described herein for Formula (I). Further phosphorus containing groups can be added using methods known to those skilled in the art, for example using a pyrophosphate. If desired, one or more bases can be used during the addition of each phosphorus-containing group. Examples of suitable bases are described herein.

As described herein, in some embodiments, $R^2$ and $R^3$ can be each an oxygen atom, wherein the oxygen atoms are linked together by a carbonyl groups. The —O—C(=O)—O-group can be formed using methods known to those skilled in the art. For example, a compound of Formula (I), wherein $R^2$ and $R^3$ are both hydroxy groups, can be treated with 1,1'-carbonyldiimidazole (CDI).

In some embodiments, $R^2$ and/or $R^3$ can be —OC(=O)$R^{12}$ and —OC(=O)$R^8$, respectively. The —OC(=O)$R^{12}$ and —OC(=O)$R^8$ groups can be formed at the 2'- and 3'-positions using various methods known to those skilled in the art. As an example, a compound of Formula (I), wherein $R^2$ and $R^3$ are both hydroxy groups, can be treated with an alkyl anhydride (e.g., acetic anhydride and propionic anhydride) or an alkyl acid chloride (e.g., acetylchloride). If desired, a catalyst can be used to facilitate the reaction. An example of suitable catalyst is 4-dimethylaminopyridine (DMAP). Alternatively, the —OC(=O)$R^{12}$ and —OC(=O)$R^8$ groups can be formed at the 2'- and 3'-positions by reacting an alkyl acid (e.g. acetic acid and propionic acid) in the presences of a carbodiimide or a coupling reagent. Examples of carbodiimides include, but are not limited to, N,N'-dicyclohexylcarbodiimide (DCC), N,N'-diisopropyl-carbodiimide (DIC) and 1-ethyl-3-(3-dimethylaminopropyl) carbodiimide (EDC).

To reduce the formation of side products, one or more the groups attached to the pentose ring can be protected with one or more suitable protecting groups. As an example, if $R^2$ and/or $R^3$ is/are hydroxy group(s), the hydroxy group(s) can be protected with suitable protecting groups, such as triarylmethyl and/or silyl groups. Examples of triarylmethyl groups include but are not limited to, trityl, monomethoxytrityl (MMTr), 4,4'-dimethoxytrityl (DMTr), 4,4',4''-trimethoxytrityl (TMTr). 4,4',4''-tris-(benzoyloxy) trityl (TBTr), 4,4',4''-tris (4,5-dichlorophthalimido) trityl (CPTr), 4,4',4''-tris (levulinyloxy) trityl (TLTr), p-anisyl-1-naphthylphenylmethyl, di-o-anisyl-1-naphthylmethyl, p-tolyldipheylmethyl, 3-(imidazolylmethyl)-4,4'-dimethoxytrityl, 9-phenylxanthen-9-yl (Pixyl), 9-(p-methoxyphenyl) xanthen-9-yl (Mox), 4-decyloxytrityl, 4-hexadecyloxytrityl, 4,4'-dioctadecyltrityl, 9-(4-octadecyloxyphenyl) xanthen-9-yl, 1,1'-bis-(4-methoxyphenyl)-1'-pyrenylmethyl, 4,4',4''-tris-(tert-butylphenyl) methyl (TTTr) and 4,4'-di-3,5-hexadienoxytrityl. Examples of suitable silyl groups are described herein and include trimethylsilyl (TMS), tert-butyldimethylsilyl (TBDMS), triisopropylsilyl (TIPS), tert-butyldiphenylsilyl (TBDPS), tri-iso-propylsilyloxymethyl and [2-(trimethylsilyl)ethoxy]methyl. Alternatively, $R^2$ and/or $R^3$ can be protected by a single achiral or chiral protecting group, for example, by forming an orthoester, a cyclic acetal or a cyclic ketal. Suitable orthoesters include methoxymethylene acetal, ethoxymethylene acetal, 2-oxacyclopentylidene orthoester, dimethoxymethylene orthoester, 1-methoxyethylidene orthoester, 1-ethoxyethylidene orthoester, methylidene orthoester, phthalide orthoester 1,2-dimethoxyethylidene orthoester, and alpha-methoxybenzylidene orthoester; suitable cyclic acetals include methylene acetal, ethylidene acetal, t-butylmethylidene acetal, 3-(benzyloxy) propyl acetal, benzylidene acetal, 3,4-dimethoxybenzylidene acetal and p-acetoxybenzylidene acetal; and suitable cyclic ketals include 1-t-butylethylidene ketal, 1-phenylethylidene ketal, isopropylidene ketal, cyclopentylidene ketal, cyclohexylidene ketal, cycloheptylidene ketal and 1-(4-methoxyphenyl)ethylidene ketal.

Pharmaceutical Compositions

Some embodiments described herein relates to a pharmaceutical composition, that can include an effective amount of one or more compounds described herein (e.g., a compound of Formula (I)), or a pharmaceutically acceptable salt thereof) and a pharmaceutically acceptable carrier, diluent, excipient or combination thereof. In some embodiments, the pharmaceutical composition can include a single diastereomer of a compound of Formula (I), or a pharmaceutically acceptable salt thereof, (for example, a single diastereomer is present in the pharmaceutical composition at a concentration of greater than 99% compared to the total concentration of the other diastereomers). In other embodiments, the pharmaceutical composition can include a mixture of diastereomers of a compound of Formula (I), or a pharmaceutically acceptable salt thereof. For example, the pharmaceutical composition can include a concentration of one diastereomer of >50%, ≥60%, ≥70%, ≥80%, ≥90%, ≥95%, or ≥98%, as compared to the total concentration of the other diastereomers. In some embodiments, the pharmaceutical composition includes a 1:1 mixture of two diastereomers of a compound of Formula (I), or a pharmaceutically acceptable salt thereof.

The term "pharmaceutical composition" refers to a mixture of one or more compounds disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid and salicylic acid. Pharmaceutical compositions will generally be tailored to the specific intended route of administration. A pharmaceutical composition is suitable for human and/or veterinary applications.

The term "physiologically acceptable" defines a carrier, diluent or excipient that does not abrogate the biological activity and properties of the compound.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes will be targeted to and taken up selectively by the organ.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

Methods of Use

Some embodiments disclosed herein relate to a method of treating and/or ameliorating a disease or condition that can include administering to a subject an effective amount of one or more compounds described herein, such as a compound of Formula (I), or a pharmaceutically acceptable salt thereof, or a pharmaceutical composition that includes a compound described herein, or a pharmaceutically acceptable salt thereof. Other embodiments disclosed herein relate to a method of treating and/or ameliorating a disease or condition that can include administering to a subject identified as suffering from the disease or condition an effective amount of one or more compounds described herein, such as a compound of Formula (I), or a pharmaceutically acceptable salt thereof, or a pharmaceutical composition that includes a compound described herein, or a pharmaceutically acceptable salt thereof.

Some embodiments disclosed herein relates to a method of ameliorating or treating a HCV infection that can include administering to a subject identified as suffering from a HCV infection an effective amount of one or more compounds described herein (for example, a compound of Formula (I)), or a pharmaceutical composition that includes one or more compounds described herein, or a pharmaceutically acceptable salt thereof. Other embodiments described herein relate to using one or more compounds described herein, or a pharmaceutically acceptable salt of a compound described herein, in the manufacture of a medicament for ameliorating and/or treating a HCV infection that can include administering to a subject identified as suffering from a HCV infection an effective amount of one or more compounds described herein. Still other embodiments described herein relate to one or more compounds described herein, or a pharmaceutically acceptable salt of a compound described herein, that can be used for ameliorating and/or treating a HCV infection by administering to a subject identified as suffering from a HCV infection an effective amount of one or more compounds described herein.

Some embodiments disclosed herein relate to methods of ameliorating and/or treating a HCV infection that can include contacting a cell infected with the hepatitis C virus with an effective amount of one or more compounds described herein, or a pharmaceutically acceptable salt of a compound described herein, or a pharmaceutical composition that includes one or more compounds described herein, or a pharmaceutically acceptable salt thereof. Other embodiments described herein relate to using one or more compounds described herein, or a pharmaceutically acceptable salt of a compound described herein, in the manufacture of a medicament for ameliorating and/or treating a HCV infection that can include contacting a cell infected with the hepatitis C virus with an effective amount of said compound(s). Still other embodiments described herein relate to one or more compounds described herein, or a pharmaceutically acceptable salt of a compound described herein, that can be used for ameliorating and/or treating a HCV infection by contacting a cell infected with the hepatitis C virus with an effective amount of said compound(s).

Some embodiments disclosed herein relate to methods of inhibiting replication of a hepatitis C virus that can include contacting a cell infected with the hepatitis C virus with an effective amount of one or more compounds described herein, or a pharmaceutically acceptable salt of a compound described herein, or a pharmaceutical composition that includes one or more compounds described herein, or a pharmaceutically acceptable salt thereof. Other embodiments described herein relate to using one or more compounds described herein, or a pharmaceutically acceptable salt of a compound described herein, in the manufacture of a medicament for inhibiting replication of a hepatitis C virus that can include contacting a cell infected with the hepatitis C virus with an effective amount of said compound(s). Still other embodiments described herein relate to a compound described herein, or a pharmaceutically acceptable salt of a compound described herein, that can be used for inhibiting replication of a hepatitis C virus by contacting a cell infected with the hepatitis C virus with an effective amount of said compound(s).

In some embodiments, the compound can be a compound of Formula (I), or a pharmaceutical acceptable salt thereof, wherein $R^4$ is hydrogen. In other embodiments, the compound can be a compound of Formula (I), wherein compound of Formula (I) is a mono, di, or triphosphate, or a pharmaceutically acceptable salt of the foregoing. In still other embodiments, the compound can be a compound of Formula (I), wherein compound of Formula (I) is a thiomonophosphate, alpha-thiodiphosphate, or alpha-thiotriphosphate, or a pharmaceutically acceptable salt of the foregoing. In yet still other embodiments, the compound can be a compound of Formula (I), wherein compound of Formula (I) is phosphoroamidate or phosphorbisamidate, or a pharmaceutically acceptable salt of the foregoing. In some embodiments, the compound can be a compound of Formula (I), wherein compound of Formula (I) is thiophosphoroamidate or thiophosphorbisamidate, or a pharmaceutically acceptable salt of the foregoing. In some embodiments, the compound of Formula (I), or a pharmaceutical acceptable salt thereof, that can be used to ameliorating and/or treating a viral infection (for example, a HCV infection) and/or inhibit replication of a virus (such as a HCV virus) can be any of the embodiments provided in any of the embodiments described in the "Compounds" section above.

HCV is an enveloped positive strand RNA virus in the Flaviviridae family. There are various nonstructural proteins of HCV, such as NS2, NS3, NS4, NS4A, NS4B, NS5A and NS5B. NS5B is believed to be an RNA-dependent RNA polymerase involved in the replication of HCV RNA.

Some embodiments described herein relate to a method of inhibiting NS5B polymerase activity that can include contacting a cell infected with hepatitis C virus with an effective amount of a compound of Formula (I), or a pharmaceutical acceptable salt thereof. Some embodiments described herein relate to a method of inhibiting NS5B polymerase activity that can include administering to a subject infected with hepatitis C virus an effective amount of a compound of Formula (I), or a pharmaceutical acceptable salt thereof. In some embodiments, a compound of Formula (I), or a pharmaceutically acceptable salt thereof, can inhibit a RNA dependent RNA polymerase, and thus, inhibit the replication of HCV RNA. In some embodiments, a compound of Formula (I), or a pharmaceutically acceptable salt thereof, can inhibit a HCV polymerase (for example, NS5B polymerase).

Some embodiments described herein relate to a method of treating a condition selected from liver fibrosis, liver cirrhosis and liver cancer in a subject suffering from one or more of the aforementioned liver conditions that can include administering to the subject an effective amount of a compound or a pharmaceutical composition described herein (for example, a compound of Formula (I), or a pharmaceutical acceptable salt thereof), wherein the liver condition is caused by a HCV infection. Some embodiments described herein relate to a method of increasing liver function in a subject having a HCV infection that can include administering to the subject an effective amount of a compound or a pharmaceutical composition described herein (for example, a compound of Formula (I), or a pharmaceutical acceptable salt thereof). Also contemplated is a method for reducing or eliminating further virus-caused liver damage in a subject having an HCV infection by administering to the subject an effective amount of a compound or a pharmaceutical composition described herein (for example, a compound of Formula (I), or a pharmaceutical acceptable salt thereof). In some embodiments, this method can include slowing or halting the progression of liver disease. In other embodiments, the course of the disease can be reversed, and stasis or improvement in liver function is contemplated. In some embodiments, liver fibrosis, liver cirrhosis and/or liver cancer can be treated; liver function can be increased; virus-caused liver damage can be reduced or eliminated; progression of liver disease can be slowed or halted; the course of the liver disease can be reversed and/or liver function can be improved or maintained by contacting a cell infected with hepatitis C virus with an effective amount of a compound described herein (for example, a compound of Formula (I), or a pharmaceutically acceptable salt thereof.)

There are a variety of genotypes of HCV, and a variety of subtypes within each genotype. For example, at present it is known that there are eleven (numbered 1 through 11) main genotypes of HCV, although others have classified the genotypes as 6 main genotypes. Each of these genotypes is further subdivided into subtypes (1a-1c; 2a-2c; 3a-3b; 4a-4e; 5a; 6a; 7a-7b; 8a-8b; 9a; 10a; and 11a). In some embodiments, an effective amount of a compound of Formula (I), or a pharmaceutical acceptable salt thereof, or a pharmaceutical composition that includes an effective amount of a compound of Formula (I), or a pharmaceutical acceptable salt thereof, can be effective to treat at least one genotype of HCV. In some embodiments, a compound described herein (for example, a compound of Formula (I), or a pharmaceutical acceptable salt thereof) can be effective to treat all 11 genotypes of HCV. In some embodiments, a compound described herein (for example, a compound of Formula (I), or a pharmaceutical acceptable salt thereof) can be effective to treat 3 or more, 5 or more, 7 or more, or 9 or more genotypes of HCV. In some embodiments, a compound of Formula (I), or a pharmaceutical acceptable salt thereof can be more effective against a larger number of HCV genotypes than the standard of care. In some embodiments, a compound of Formula (I), or a pharmaceutical acceptable salt thereof, can be more effective against a particular HCV genotype than the standard of care (such as genotype 1, 2, 3, 4, 5 and/or 6).

Various indicators for determining the effectiveness of a method for treating a HCV infection are known to those skilled in the art. Examples of suitable indicators include, but are not limited to, a reduction in viral load, a reduction in viral replication, a reduction in time to seroconversion (virus undetectable in patient serum), an increase in the rate of sustained viral response to therapy, a reduction of morbidity or mortality in clinical outcomes, a reduction in the rate of liver function decrease; stasis in liver function;

improvement in liver function; reduction in one or more markers of liver dysfunction, including alanine transaminase, aspartate transaminase, total bilirubin, conjugated bilirubin, gamma glutamyl transpeptidase and/or other indicator of disease response. Similarly, successful therapy with an effective amount of a compound or a pharmaceutical composition described herein (for example, a compound of Formula (I), or a pharmaceutical acceptable salt thereof) can reduce the incidence of liver cancer in HCV infected subjects.

In some embodiments, an effective amount of a compound of Formula (I), or a pharmaceutically acceptable salt thereof, is an amount that is effective to reduce HCV viral titers to undetectable levels, for example, to about 100 to about 500, to about 50 to about 100, to about 10 to about 50, or to about 15 to about 25 international units/mL serum. In some embodiments, an effective amount of a compound of Formula (I), or a pharmaceutically acceptable salt thereof, is an amount that is effective to reduce HCV viral load compared to the HCV viral load before administration of the compound of Formula (I), or a pharmaceutically acceptable salt thereof. For example, wherein the HCV viral load is measured before administration of the compound of Formula (I), or a pharmaceutically acceptable salt thereof, and again after completion of the treatment regime with the compound of Formula (I), or a pharmaceutically acceptable salt thereof (for example, 1 month after completion). In some embodiments, an effective amount of a compound of Formula (I), or a pharmaceutically acceptable salt thereof, can be an amount that is effective to reduce HCV viral load to lower than about 25 international units/mL serum. In some embodiments, an effective amount of a compound of Formula (I), or a pharmaceutically acceptable salt thereof, is an amount that is effective to achieve a reduction in HCV viral titer in the serum of the subject in the range of about 1.5-log to about a 2.5-log reduction, about a 3-log to about a 4-log reduction, or a greater than about 5-log reduction compared to the viral load before administration of the compound of Formula (I), or a pharmaceutically acceptable salt thereof. For example, the HCV viral load can be measured before administration of the compound of Formula (I), or a pharmaceutically acceptable salt thereof, and again after completion of the treatment regime with the compound of Formula (I), or a pharmaceutically acceptable salt thereof (for example, 1 month after completion).

In some embodiments, a compound of Formula (I), or a pharmaceutically acceptable salt thereof, can result in at least a 1, 2, 3, 4, 5, 10, 15, 20, 25, 50, 75, 100-fold or more reduction in the replication of the hepatitis C virus relative to pre-treatment levels in a subject, as determined after completion of the treatment regime (for example, 1 month after completion). In some embodiments, a compound of Formula (I), or a pharmaceutically acceptable salt thereof, can result in a reduction of the replication of the hepatitis C virus relative to pre-treatment levels in the range of about 2 to about 5 fold, about 10 to about 20 fold, about 15 to about 40 fold, or about 50 to about 100 fold. In some embodiments, a compound of Formula (I), or a pharmaceutically acceptable salt thereof, can result in a reduction of the hepatitis C virus replication in the range of 1 to 1.5 log, 1.5 log to 2 log, 2 log to 2.5 log, 2.5 to 3 log, 3 log to 3.5 log or 3.5 to 4 log more reduction of the hepatitis C virus replication compared to the reduction of the hepatitis C virus reduction achieved by pegylated interferon in combination with ribavirin, administered according to the standard of care, or may achieve the same reduction as that standard of care therapy in a shorter period of time, for example, in one month, two months, or three months, as compared to the reduction achieved after six months of standard of care therapy with ribavirin and pegylated interferon.

In some embodiments, an effective amount of a compound of Formula (I), or a pharmaceutically acceptable salt thereof, is an amount that is effective to achieve a sustained viral response, for example, non-detectable or substantially non-detectable HCV RNA (e.g., less than about 500, less than about 200, less than about 100, less than about 25, or less than about 15 international units per milliliter serum) is found in the subject's serum for a period of at least about one month, at least about two months, at least about three months, at least about four months, at least about five months, or at least about six months following cessation of therapy.

In some embodiments, an effective amount of a compound of Formula (I), or a pharmaceutically acceptable salt thereof, can reduce a level of a marker of liver fibrosis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the level of the marker in an untreated subject, or to a placebo-treated subject. Methods of measuring serum markers are known to those skilled in the art and include immunological-based methods, e.g., enzyme-linked immunosorbent assays (ELISA), radioimmunoassays, and the like, using antibody specific for a given serum marker. A non-limiting list of examples of markers includes measuring the levels of serum alanine aminotransferase (ALT), aspartate aminotransferase (AST), alkaline phosphatase (ALP), gamma-glutamyl transpeptidase (GGT) and total bilirubin (TBIL) using known methods. In general, an ALT level of less than about 45 IU/L (international units/liter), an AST in the range of 10-34 IU/L, ALP in the range of 44-147 IU/L, GGT in the range of 0-51 IU/L, TBIL in the range of 0.3-1.9 mg/dL is considered normal. In some embodiments, an effective amount of a compound of Formula (I), or a pharmaceutically acceptable salt thereof, can be an amount effective to reduce ALT, AST, ALP, GGT and/or TBIL levels to with what is considered a normal level.

Subjects who are clinically diagnosed with HCV infection include "naïve" subjects (e.g., subjects not previously treated for HCV, particularly those who have not previously received IFN-alpha-based and/or ribavirin-based therapy) and individuals who have failed prior treatment for HCV ("treatment failure" subjects). Treatment failure subjects include "non-responders" (i.e., subjects in whom the HCV titer was not significantly or sufficiently reduced by a previous treatment for HCV (≤0.5 log IU/mL), for example, a previous IFN-alpha monotherapy, a previous IFN-alpha and ribavirin combination therapy, or a previous pegylated IFN-alpha and ribavirin combination therapy); and "relapsers" (i.e., subjects who were previously treated for HCV, for example, who received a previous IFN-alpha monotherapy, a previous IFN-alpha and ribavirin combination therapy, or a previous pegylated IFN-alpha and ribavirin combination therapy, whose HCV titer decreased, and subsequently increased).

In some embodiments, a compound of Formula (I), or a pharmaceutically acceptable salt thereof, can be administered to a treatment failure subject suffering from HCV. In some embodiments, a compound of Formula (I), or a pharmaceutically acceptable salt thereof, can be administered to a non-responder subject suffering from HCV. In some embodiments, a compound of Formula (I), or a pharmaceutically acceptable salt thereof, can be administered to a relapsed subject suffering from HCV.

After a period of time, infectious agents can develop resistance to one or more therapeutic agents. The term "resistance" as used herein refers to a viral strain displaying a delayed, lessened and/or null response to a therapeutic agent(s). For example, after treatment with an antiviral agent, the viral load of a subject infected with a resistant virus may be reduced to a lesser degree compared to the amount in viral load reduction exhibited by a subject infected with a non-resistant strain. In some embodiments, a compound of Formula (I), or a pharmaceutically acceptable salt thereof, can be administered to a subject infected with an HCV strain that is resistant to one or more different anti-HCV agents (for example, an agent used in a conventional standard of care). In some embodiments, development of resistant HCV strains is delayed when a subject is treated with a compound of Formula (I), or a pharmaceutically acceptable salt thereof, compared to the development of HCV strains resistant to other HCV drugs (such as an agent used in a conventional standard of care).

In some embodiments, an effective amount of a compound of Formula (I), or a pharmaceutically acceptable salt thereof, can be administered to a subject for whom other anti-HCV medications are contraindicated. For example, administration of pegylated interferon alpha in combination with ribavirin is contraindicated in subjects with hemoglobinopathies (e.g., thalassemia major, sickle-cell anemia) and other subjects at risk from the hematologic side effects of current therapy. In some embodiments, a compound of Formula (I), or a pharmaceutically acceptable salt thereof, can be provided to a subject that is hypersensitive to interferon and/or ribavirin.

Some subjects being treated for HCV experience a viral load rebound. The term "viral load rebound" as used herein refers to a sustained ≥0.5 log IU/mL increase of viral load above nadir before the end of treatment, where nadir is a ≥0.5 log IU/mL decrease from baseline. In some embodiments, a compound of Formula (I), or a pharmaceutically acceptable salt thereof, can be administered to a subject experiencing viral load rebound, or can prevent such viral load rebound when used to treat the subject.

The standard of care for treating HCV has been associated with several side effects (adverse events). In some embodiments, a compound of Formula (I), or a pharmaceutically acceptable salt thereof, can decrease the number and/or severity of side effects that can be observed in HCV patients being treated with ribavirin and pegylated interferon according to the standard of care. Examples of side effects include, but are not limited to fever, malaise, tachycardia, chills, headache, arthralgias, myalgias, fatigue, apathy, loss of appetite, nausea, vomiting, cognitive changes, asthenia, drowsiness, lack of initiative, irritability, confusion, depression, severe depression, suicidal ideation, anemia, low white blood cell counts, and thinning of hair. In some embodiments, a compound of Formula (I), or a pharmaceutically acceptable salt thereof, can be provided to a subject that discontinued a HCV therapy because of one or more adverse effects or side effects associated with one or more other HCV agents (for example, an agent used in a conventional standard of care).

Table 1 provides some embodiments of the percentage improvement obtained using a compound of Formula (I), or a pharmaceutically acceptable salt thereof, as compared to the standard of care. Examples include the following: in some embodiments, a compound of Formula (I), or a pharmaceutically acceptable salt thereof, results in a percentage of non-responders that is 10% less than the percentage of non-responders receiving the standard of care; in some embodiments, a compound of Formula (I), or a pharmaceutically acceptable salt thereof, results in a number of side effects that is in the range of about 10% to about 30% less than compared to the number of side effects experienced by a subject receiving the standard of care; and in some embodiments, a compound of Formula (I), or a pharmaceutically acceptable salt thereof, results in a severity of a side effect (such as one of those described herein) that is 25% less than compared to the severity of the same side effect experienced by a subject receiving the standard of care. Methods of quantifying the severity of a side effect are known to those skilled in the art.

TABLE 1

| Percentage of non-responders | Percentage of relapsers | Percentage of resistance | Percentage of viral load rebound | Number of side effects | Severity of side effects |
| --- | --- | --- | --- | --- | --- |
| 10% less | 10% less | 10% less | 10% less | 10% less | 10% less |
| 25% less | 25% less | 25% less | 25% less | 25% less | 25% less |
| 40% less | 40% less | 40% less | 40% less | 40% less | 40% less |
| 50% less | 50% less | 50% less | 50% less | 50% less | 50% less |
| 60% less | 60% less | 60% less | 60% less | 60% less | 60% less |
| 70% less | 70% less | 70% less | 70% less | 70% less | 70% less |
| 80% less | 80% less | 80% less | 80% less | 80% less | 80% less |
| 90% less | 90% less | 90% less | 90% less | 90% less | 90% less |
| about 10% to about 30% less | about 10% to about 30% less | about 10% to about 30% less | about 10% to about 30% less | about 10% to about 30% less | about 10% to about 30% less |
| about 20% to about 50% less | about 20% to about 50% less | about 20% to about 50% less | about 20% to about 50% less | about 20% to about 50% less | about 20% to about 50% less |
| about 30% to about 70% less | about 30% to about 70% less | about 30% to about 70% less | about 30% to about 70% less | about 30% to about 70% less | about 30% to about 70% less |
| about 20% to about 80% less | about 20% to about 80% less | about 20% to about 80% less | about 20% to about 80% less | about 20% to about 80% less | about 20% to about 80% less |

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject is human.

As used herein, the terms "treating," "treatment," "therapeutic," or "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the patient's overall feeling of well-being or appearance.

The terms "therapeutically effective amount" and "effective amount" are used to indicate an amount of an active compound, or pharmaceutical agent, that elicits the biological or medicinal response indicated. For example, an effective amount of compound can be the amount needed to prevent, alleviate or ameliorate symptoms of disease or prolong the survival of the subject being treated This response may occur in a tissue, system, animal or human and includes alleviation of the signs or symptoms of the disease being treated. Determination of an effective amount is well within the capability of those skilled in the art, in view of the disclosure provided herein. The effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials and in vitro studies.

The dosage may range broadly, depending upon the desired effects and the therapeutic indication. Alternatively dosages may be based and calculated upon the surface area of the patient, as understood by those of skill in the art. Although the exact dosage will be determined on a drug-by-drug basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g. 5 to 200 mg. The dosage may be a single one or a series of two or more given in the course of one or more days, as is needed by the subject. In some embodiments, the compounds will be administered for a period of continuous therapy, for example for a week or more, or for months or years. In some embodiments, a compound of Formula (I), or a pharmaceutically acceptable salt thereof, can be administered less frequently compared to the frequency of administration of an agent within the standard of care. In some embodiments, a compound of Formula (I), or a pharmaceutically acceptable salt thereof, can be administered one time per day. For example, a compound of Formula (I), or a pharmaceutically acceptable salt thereof, can be administered one time per day to a subject suffering from a HCV infection. In some embodiments, the total time of the treatment regime with a compound of Formula (I), or a pharmaceutically acceptable salt thereof, can less compared to the total time of the treatment regime with the standard of care.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

Combination Therapies

In some embodiments, the compounds disclosed herein, such as a compound of Formula (I), or a pharmaceutically acceptable salt thereof, or a pharmaceutical composition that includes a compound described herein, or a pharmaceutically acceptable salt thereof, can be used in combination with one or more additional agent(s). Examples of additional agents that can be used in combination with a compound of Formula (I), or a pharmaceutically acceptable salt thereof, or a pharmaceutical composition that includes a compound of Formula (I), or a pharmaceutically acceptable salt thereof, include, but are not limited to, agents currently used in a conventional standard of care for treating HCV, HCV protease inhibitors, HCV polymerase inhibitors, NS5A inhibitors, other antiviral compounds, compounds of Formula (AA), (including pharmaceutically acceptable salts and pharmaceutical compositions that can include a compound of Formula (AA), or a pharmaceutically acceptable salt thereof), compounds of Formula (BB) (including pharmaceutically acceptable salts and pharmaceutical compositions that can include a compound of Formula (BB), or a pharmaceutically acceptable salt thereof), compounds of Formula (CC) (including pharmaceutically acceptable salts and pharmaceutical compositions that can include a compound of Formula (CC), or a pharmaceutically acceptable salt thereof), and/or combinations thereof. In some embodiments, a compound of Formula (I), or a pharmaceutically acceptable salt thereof, or a pharmaceutical composition that includes a compound of Formula (I), or a pharmaceutically acceptable salt thereof, can be used with one, two, three or more additional agents described herein. A non-limiting list of examples of combinations of a compound of Formula (I), or a pharmaceutically acceptable salt thereof, or a pharmaceutical composition that includes a compound of Formula (I), or a pharmaceutically acceptable salt thereof, is provided in Tables A, B, C, D and E.

In some embodiments, a compound of Formula (I), or a pharmaceutically acceptable salt thereof, or a pharmaceutical composition that includes a compound of Formula (I), or a pharmaceutically acceptable salt thereof, can be used in combination with an agent(s) currently used in a conventional standard of care therapy. For example, for the treatment of HCV, a compound disclosed herein can be used in combination with Pegylated interferon-alpha-2a (brand name PEGASYS®) and ribavirin, Pegylated interferon-alpha-2b (brand name PEG-INTRON®) and ribavirin, Pegylated interferon-alpha-2a, Pegylated interferon-alpha-2b, or ribavirin.

In some embodiments, a compound of Formula (I), or a pharmaceutically acceptable salt thereof, or a pharmaceutical composition that includes a compound of Formula (I), or a pharmaceutically acceptable salt thereof, can be substituted for an agent currently used in a conventional standard of care therapy. For example, for the treatment of HCV, a compound of Formula (I), or a pharmaceutically acceptable salt thereof, or a pharmaceutical composition that includes a compound of Formula (I), or a pharmaceutically acceptable salt thereof, can be used in place of ribavirin.

In some embodiments, a compound of Formula (I), or a pharmaceutically acceptable salt thereof, or a pharmaceutical composition that includes a compound of Formula (I), or a pharmaceutically acceptable salt thereof, can be used in combination with an interferon, such as a pegylated interferon. Examples of suitable interferons include, but are not limited to, Pegylated interferon-alpha-2a (brand name PEGASYS®), Pegylated interferon-alpha-2b (brand name PEG-INTRON®), interferon alfacon-1 (brand name INFERGEN®), pegylated interferon lambda and/or a combination thereof.

Figure 1:
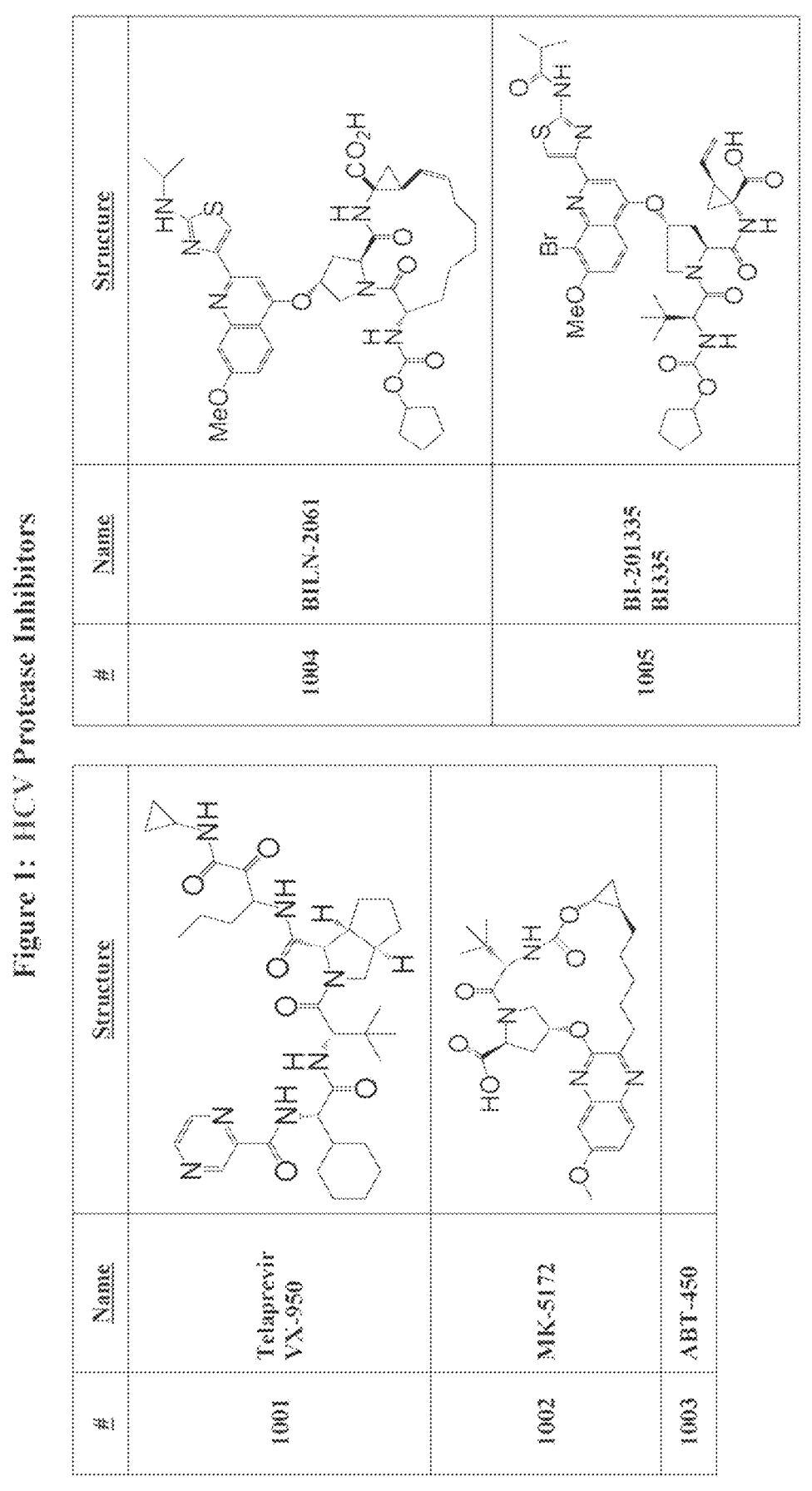

In some embodiments, a compound of Formula (I), or a pharmaceutically acceptable salt thereof, or a pharmaceutical composition that includes a compound of Formula (I), or a pharmaceutically acceptable salt thereof, can be used in combination with a HCV protease inhibitor. A non-limiting list of example HCV protease inhibitors include the following: VX-950 (TELAPREVIR®), MK-5172, ABT-450, BILN-2061, BI-201335, BMS-650032, SCH 503034 (BOCEPREVIR®), GS-9256, GS-9451, IDX-320, ACH-1625, ACH-2684, TMC-435, ITMN-191 (DANOPREVIR®) and/or a combination thereof. Additional HCV protease inhibitors suitable for use in combination with a compound of Formula (I), or a pharmaceutically acceptable salt thereof, or a pharmaceutical composition that includes a compound of Formula (I), or a pharmaceutically acceptable salt thereof, include VP-19744, PSI-879, VCH-759/VX-759, HCV-371, IDX-375, GL-60667, JTK-109, PSI-6130, R1479, R-1626, R-7182, MK-0608, INX-8014, INX-8018, A-848837, A-837093, BILB-1941, VCH-916, VCH-716, GSK-71185, GSK-625433, XTL-2125 and those disclosed in PCT Publication No. WO 2012/142085, which is hereby incorporated by reference for the limited purpose of its disclosure of HCV protease inhibitors, HCV polymerase inhibitors and NS5A inhibitors. A non-limiting list of example HCV protease inhibitors includes the compounds numbered 1001-1016 in FIG. 1.

In some embodiments, a compound of Formula (I), or a pharmaceutically acceptable salt thereof, or a pharmaceutical composition that includes a compound of Formula (I), or a pharmaceutically acceptable salt thereof, can be used in combination with a HCV polymerase inhibitor. In some embodiments, the HCV polymerase inhibitor can be a nucleoside inhibitor. In other embodiments, the HCV polymerase inhibitor can be a non-nucleoside inhibitor. Examples of suitable nucleoside inhibitors include, but are not limited to, RG7128, PSI-7851, PSI-7977, INX-189, PSI-352938, PSI-661, 4'-azidouridine (including known prodrugs of 4'-azidouridine), GS-6620, IDX-184, and TMC649128 and/or combinations thereof. A non-limiting list of example nucleoside inhibitors includes compounds numbered 2001-2012 in FIG. 2. Examples of suitable non-nucleoside inhibitors include, but are not limited to, ABT-333, ANA-598, VX-222, HCV-796, BI-207127, GS-9190, PF-00868554 (FILIBUVIR®), VX-497 and/or combinations thereof. A non-limiting list of example non-nucleoside inhibitors includes the compounds numbered 3001-3014 in FIG. 3. Further HCV polymerase inhibitors suitable for use in combination with a compound of Formula (I), or a pharmaceutically acceptable salt thereof, or a pharmaceutical composition that includes a compound of Formula (I), or a pharmaceutically acceptable salt thereof, include VX-500, VX-813, VBY-376, TMC-435350, EZ-058, EZ-063, GS-9132, ACH-1095, IDX-136, IDX-316, ITMN-8356, ITMN-8347, ITMN-8096, ITMN-7587, VX-985, and those disclosed in PCT Publication No. WO 2012/142085.

In some embodiments, a compound of Formula (I), or a pharmaceutically acceptable salt thereof, or a pharmaceutical composition that includes a compound of Formula (I), or a pharmaceutically acceptable salt thereof, can be used in combination with a NS5A inhibitor. Examples of NS5A inhibitors include BMS-790052, PPI-461, ACH-2928, GS-5885, BMS-824393 and/or combinations thereof. A non-limiting list of example NS5A inhibitors includes the compounds numbered 4001-4012 in FIG. 4. Additional NS5A inhibitors suitable for use in combination with a compound of Formula (I), or a pharmaceutically acceptable salt thereof, or a pharmaceutical composition that includes a compound of Formula (I), or a pharmaceutically acceptable salt thereof, include A-832, PPI-1301 and those disclosed in PCT Publication No. WO 2012/142085.

In some embodiments, a compound of Formula (I), or a pharmaceutically acceptable salt thereof, or a pharmaceutical composition that includes a compound of Formula (I), or a pharmaceutically acceptable salt thereof, can be used in combination with other antiviral compounds. Examples of other antiviral compounds include, but are not limited to, Debio-025, MIR-122, cyclosporin A and/or combinations thereof. A non-limiting list of example other antiviral compounds includes the compounds numbered 5001-5012 in FIG. 5.

In some embodiments, a compound of Formula (I), or a pharmaceutically acceptable salt thereof, or a pharmaceutical composition that includes a compound of Formula (I), or a pharmaceutically acceptable salt thereof, can be used in combination with a compound of Formula (AA), or a pharmaceutically acceptable salt thereof, or a pharmaceutical composition that includes a compound of Formula (AA), or a pharmaceutically acceptable salt thereof (see, U.S.

Publication No. 2013/0164261, published Jun. 27, 2013, the contents of which are incorporated by reference in its entirety):

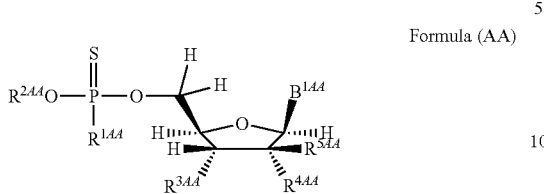

Formula (AA)

wherein: $B^{AA1}$ can be an optionally substituted heterocyclic base or an optionally substituted heterocyclic base with a protected amino group; $R^{AA1}$ can be selected from $O^-$, OH, an optionally substituted N-linked amino acid and an optionally substituted N-linked amino acid ester derivative; $R^{AA2}$ can be absent or selected from hydrogen, an optionally substituted aryl, an optionally substituted heteroaryl, an optionally substituted heterocyclyl and

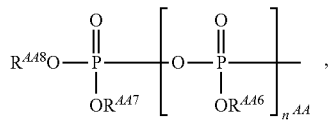

wherein $R^{AA6}$, $R^{AA7}$ and $R^{AA8}$ can be independently absent or hydrogen, and $n^{AA}$ can be 0 or 1; provided that when $R^{AA1}$ is $O^-$ or OH, then $R^{AA2}$ is absent, hydrogen or

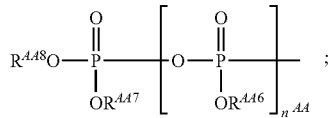

$R^{AA3}$ can be selected from hydrogen, halogen, $-OR^{AA9}$ and $-OC(=O)R^{AA10}$; $R^{AA4}$ can be selected from halogen, $-OR^{AA11}$ and $-OC(=O)R^{AA12}$; or $R^{AA3}$ and $R^{AA4}$ can be both an oxygen atom which are linked together by a carbonyl group; $R^{AA5}$ can be selected from an optionally substituted $C_{2-6}$ alkyl, an optionally substituted $C_{2-6}$ alkenyl, an optionally substituted $C_{2-6}$ alkynyl and an optionally substituted $C_{3-6}$ cycloalkyl; or $R^{AA4}$ and $R^{AA5}$ together can form $-(C_{1-6}$ alkyl$)-O-$ or $-O-(C_{1-6}$ alkyl$)-$; $R^{AA9}$ and $R^{AA11}$ can be independently hydrogen or an optionally substituted $C_{1-6}$ alkyl; and $R^{AA10}$ and $R^{AA12}$ can be independently an optionally substituted $C_{1-6}$ alkyl or an optionally substituted $C_{3-6}$ cycloalkyl. A non-limiting list of examples of compounds of Formula (AA) includes the compounds numbered 7000-7027 in FIG. 7.

In some embodiments, a compound of Formula (I), or a pharmaceutically acceptable salt thereof, or a pharmaceutical composition that includes a compound of Formula (I), or a pharmaceutically acceptable salt thereof, can be used in combination with a compound of Formula (BB), or a pharmaceutically acceptable salt thereof, or a pharmaceutical composition that includes a compound of Formula (BB), or a pharmaceutically acceptable salt thereof (see, U.S. Publication No. 2012/0165286, published Jun. 28, 2012, the contents of which are incorporated by reference in their entireties):

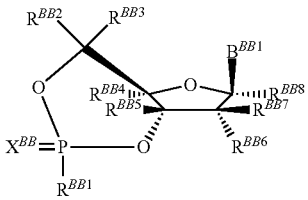

Formula (BB)

wherein $B^{BB1}$ can be an optionally substituted heterocyclic base or an optionally substituted heterocyclic base with a protected amino group; $X^{BB}$ can be O (oxygen) or S (sulfur); $R^{BB1}$ can be selected from $-Z^{BB}-R^{BB9}$, an optionally substituted N-linked amino acid and an optionally substituted N-linked amino acid ester derivative; $Z^{BB}$ can be selected from O (oxygen), S (sulfur) and $N(R^{BB10})$; $R^{BB2}$ and $R^{BB3}$ can be independently selected from hydrogen, an optionally substituted $C_{1-6}$ alkyl, an optionally substituted $C_{2-6}$ alkenyl, an optionally substituted $C_{2-6}$ alkynyl, an optionally substituted $C_{1-6}$ haloalkyl and an optionally substituted aryl($C_{1-6}$ alkyl); or $R^{BB2}$ and $R^{BB3}$ can be taken together to form a group selected from an optionally substituted $C_{3-6}$ cycloalkyl, an optionally substituted $C_{3-6}$ cycloalkenyl, an optionally substituted $C_{3-6}$ aryl and an optionally substituted $C_{3-6}$ heteroaryl; $R^{BB4}$ can be selected from hydrogen, halogen, azido, cyano, an optionally substituted $C_{1-6}$ alkyl, an optionally substituted $C_{2-6}$ alkenyl, an optionally substituted $C_{2-6}$ alkynyl and an optionally substituted allenyl; $R^{BB5}$ can be hydrogen or an optionally substituted $C_{1-6}$ alkyl; $R^{BB6}$ can be selected from hydrogen, halogen, azido, amino, cyano, an optionally substituted $C_{1-6}$ alkyl, $-OR^{BB11}$ and $-OC(=O)R^{BB12}$; $R^{BB7}$ can be selected from hydrogen, halogen, azido, cyano, an optionally substituted $C_{1-6}$ alkyl, $-OR^{BB13}$ and $-OC(=O)R^{BB14}$; $R^{BB8}$ can be selected from hydrogen, halogen, azido, cyano, an optionally substituted $C_{1-6}$ alkyl, $-OR^{BB15}$ and $-OC(=O)R^{BB16}$; $R^{BB9}$ can be selected from an optionally substituted alkyl, an optionally substituted alkenyl, an optionally substituted alkynyl, an optionally substituted cycloalkyl, an optionally substituted cycloalkenyl, an optionally substituted aryl, an optionally substituted heteroaryl, an optionally substituted heterocyclyl, an optionally substituted aryl($C_{1-6}$alkyl), an optionally substituted heteroaryl($C_{1-6}$alkyl) and an optionally substituted heterocyclyl ($C_{1-6}$alkyl); $R^{BB10}$ can be selected from hydrogen, an optionally substituted alkyl, an optionally substituted alkenyl, an optionally substituted alkynyl, an optionally substituted cycloalkyl, an optionally substituted cycloalkenyl, an optionally substituted aryl, an optionally substituted heteroaryl, an optionally substituted heterocyclyl, an optionally substituted aryl($C_{1-6}$alkyl), an optionally substituted heteroaryl($C_{1-6}$alkyl) and an optionally substituted heterocyclyl ($C_{1-6}$alkyl); $R^{BB11}$, $R^{BB13}$ and $R^{BB16}$ can be independently hydrogen or an optionally substituted $C_{1-6}$ alkyl; and $R^{BB12}$, $R^{BB14}$ and $R^{BB16}$ can be independently an optionally substituted $C_{1-6}$ alkyl or an optionally substituted $C_{3-6}$ cycloalkyl. In some embodiments, at least one of $R^{BB2}$ and $R^{BB3}$ is not hydrogen. A non-limiting list of example compounds of Formula (BB) includes the compound numbered 8000-8016 in FIG. 8.

In some embodiments, a compound of Formula (I), or a pharmaceutically acceptable salt thereof, or a pharmaceutical composition that includes a compound of Formula (I), or a pharmaceutically acceptable salt thereof, can be used in combination with a compound of Formula (CC), or a pharmaceutically acceptable salt thereof, or a pharmaceutical composition that includes a compound of Formula (CC), or a pharmaceutically acceptable salt thereof (see, U.S. Publication No. 2012/0071434, published Mar. 22, 2012, the contents of which are incorporated by reference in its entirety):

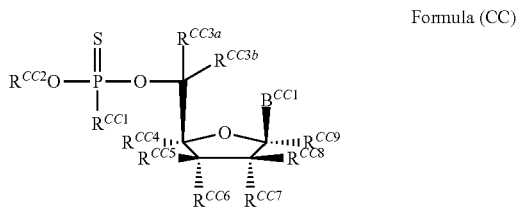

wherein $B^{CC1}$ can be an optionally substituted heterocyclic base or an optionally substituted heterocyclic base with a protected amino group; $R^{CC1}$ can be selected from O⁻, OH, an optionally substituted N-linked amino acid and an optionally substituted N-linked amino acid ester derivative; $R^{CC2}$ can be selected from an optionally substituted aryl, an optionally substituted heteroaryl, an optionally substituted heterocyclyl and

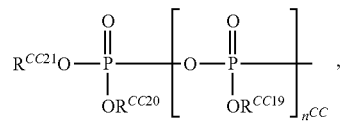

wherein $R^{CC19}$, $R^{CC20}$ and $R^{CC21}$ can be independently absent or hydrogen, and $n^{CC}$ can be 0 or 1; provided that when $R^{CC1}$ is O⁻ or OH, then $R^{CC2}$ is

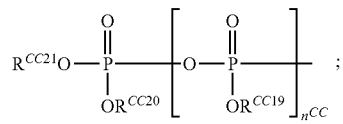

$R^{CC3a}$ and $R^{CC3b}$ can be independently selected from hydrogen, deuterium, an optionally substituted $C_{1-6}$ alkyl, an optionally substituted $C_{2-6}$ alkenyl, an optionally substituted $C_{2-6}$ alkynyl, an optionally substituted $C_{1-6}$ haloalkyl and aryl($C_{1-6}$ alkyl); or $R^{CC3a}$ and $R^{CC3b}$ can be taken together to form an optionally substituted $C_{3-6}$ cycloalkyl; $R^{CC4}$ can be selected from hydrogen, azido, an optionally substituted $C_{1-6}$ alkyl, an optionally substituted $C_{2-6}$ alkenyl and an optionally substituted $C_{2-6}$ alkynyl; $R^{CC5}$ can be selected from hydrogen, halogen, azido, cyano, an optionally substituted $C_{1-6}$ alkyl, —OC$^{CC10}$ and —OC(=O)$R^{CC11}$, $R^{CC6}$ can be selected from hydrogen, halogen, azido, cyano, an optionally substituted $C_{1-6}$ alkyl, —OR$^{CC12}$ and —OC(=O)$R^{CC13}$; $R^{CC7}$ can be selected from hydrogen, halogen, azido, cyano, an optionally substituted $C_{1-6}$ alkyl, —OR$^{CC14}$ and —OC(=O)$R^{CC15}$, or $R^{CC6}$ and $R^{CC7}$ can be both oxygen atoms and linked together by a carbonyl group; $R^{CC8}$ can be selected from hydrogen, halogen, azido, cyano, an optionally substituted $C_{1-6}$ alkyl, —OR$^{CC16}$ and —OC(=O)$R^{CC17}$; $R^{CC9}$ can be selected from hydrogen, azido, cyano, an optionally substituted $C_{1-6}$ alkyl and —OR$^{CC18}$; $R^{CC10}$; $R^{CC12}$; $R^{CC14}$; $R^{CC16}$ and $R^{CC18}$ can be independently selected from hydrogen and an optionally substituted $C_{1-6}$ alkyl; and $R^{CC11}$, $R^{CC13}$; $R^{CC15}$ and $R^{CC17}$ can be independently selected from an optionally substituted $C_{1-6}$ alkyl and an optionally substituted $C_{3-6}$ cycloalkyl. In some embodiments, when $R^{CC3a}$, $R^{CC3b}$, $R^{CC4}$, $R^{CC5}$, $R^{CC7}$, $R^{CC8}$ and $R^{CC9}$ are all hydrogen, then $R^{CC6}$ is not azido. In some embodiments, $R^{CC2}$ cannot be

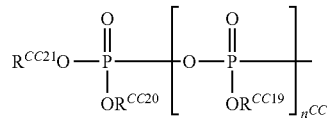

when $R^{CC3a}$ is hydrogen, $R^{CC3b}$ is hydrogen, $R^{CC4}$ is H, $R^{CC5}$ is OH or H, $R^{CC6}$ is hydrogen, OH, or —OC(=O)CH$_3$, $R^{CC7}$ is hydrogen, OH, OCH$_3$ or —OC(=O)CH$_3$, $R^{CC8}$ is hydrogen, OH or OCH$_3$, $R^{CC9}$ is H and $B^{CC1}$ is an optionally substituted adenine, an optionally substituted guanine, an optionally substituted uracil or an optionally substituted hypoxanthine. In some embodiments, $R^{CC2}$ cannot be

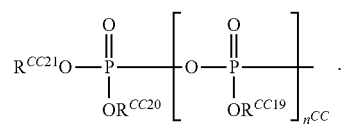

A non-limiting list of examples of compounds of Formula (CC) includes the compounds numbered 6000-6078 in FIG. 6.

Some embodiments described herein relate to a method of ameliorating or treating a HCV infection that can include contacting a cell infected with the HCV infection with an effective amount of a compound of Formula (I), or a pharmaceutically acceptable salt thereof, in combination with one or more agents selected from an interferon, ribavirin, a HCV protease inhibitor, a HCV polymerase inhibitor, a NS5A inhibitor, an antiviral compound, a compound of Formula (AA), a compound of Formula (BB) and a compound of Formula (CC), or a pharmaceutically acceptable salt of any of the aforementioned compounds.

Some embodiments described herein relate to a method of ameliorating or treating a HCV infection that can include administering to a subject suffering from the HCV infection an effective amount of a compound of Formula (I), or a pharmaceutically acceptable salt thereof, in combination with one or more agents selected from an interferon, ribavirin, a HCV protease inhibitor, a HCV polymerase inhibitor, a NS5A inhibitor, an antiviral compound, a compound of Formula (AA), a compound of Formula (BB) and a compound of Formula (CC), or a pharmaceutically acceptable salt of any of the aforementioned compounds.

Some embodiments described herein relate to a method of inhibiting the replication of a hepatitis C virus that can include contacting a cell infected with the hepatitis C virus with an effective amount of a compound of Formula (I), or a pharmaceutically acceptable salt thereof, in combination with one or more agents selected from an interferon, ribavirin, a HCV protease inhibitor, a HCV polymerase inhibitor, a NS5A inhibitor, an antiviral compound, a compound of Formula (AA), a compound of Formula (BB) and a compound of Formula (CC), or a pharmaceutically acceptable salt of any of the aforementioned compounds.

Some embodiments described herein relate to a method of inhibiting the replication of a hepatitis C virus that can include administering to a subject infected with the hepatitis C virus an effective amount of a compound of Formula (I), or a pharmaceutically acceptable salt thereof, in combination with one or more agents selected from an interferon, ribavirin, a HCV protease inhibitor, a HCV polymerase inhibitor, a NS5A inhibitor, an antiviral compound, a compound of Formula (AA), a compound of Formula (BB) and a compound of Formula (CC), or a pharmaceutically acceptable salt of any of the aforementioned compounds.

In some embodiments, a compound of Formula (I), or a pharmaceutically acceptable salt thereof, can be administered with one or more additional agent(s) together in a single pharmaceutical composition. In some embodiments, a compound of Formula (I), or a pharmaceutically acceptable salt the thereof, can be administered with one or more additional agent(s) as two or more separate pharmaceutical compositions. For example, a compound of Formula (I), or a pharmaceutically acceptable salt thereof, can be administered in one pharmaceutical composition, and at least one of the additional agents can be administered in a second pharmaceutical composition. If there are at least two additional agents, one or more of the additional agents can be in a first pharmaceutical composition that includes a compound of Formula (I), or a pharmaceutically acceptable salt thereof, and at least one of the other additional agent(s) can be in a second pharmaceutical composition.

The dosing amount(s) and dosing schedule(s) when using a compound of Formula (I), or a pharmaceutically acceptable salt thereof, or a pharmaceutical composition that includes a compound of Formula (I), or a pharmaceutically acceptable salt thereof, and one or more additional agents are within the knowledge of those skilled in the art. For example, when performing a conventional standard of care therapy using art-recognized dosing amounts and dosing schedules, a compound of Formula (I), or a pharmaceutically acceptable salt thereof, or a pharmaceutical composition that includes a compound of Formula (I), or a pharmaceutically acceptable salt thereof, can be administered in addition to that therapy, or in place of one of the agents of a combination therapy, using effective amounts and dosing protocols as described herein.

The order of administration of a compound of Formula (I), or a pharmaceutically acceptable salt thereof, with one or more additional agent(s) can vary. In some embodiments, a compound of Formula (I), or a pharmaceutically acceptable salt thereof, can be administered prior to all additional agents. In other embodiments, a compound of Formula (I), or a pharmaceutically acceptable salt thereof, can be administered prior to at least one additional agent. In still other embodiments, a compound of Formula (I), or a pharmaceutically acceptable salt thereof, can be administered concomitantly with one or more additional agent(s). In yet still other embodiments, a compound of Formula (I), or a pharmaceutically acceptable salt thereof, can be administered subsequent to the administration of at least one additional agent. In some embodiments, a compound of Formula (I), or a pharmaceutically acceptable salt thereof, can be administered subsequent to the administration of all additional agents.

In some embodiments, the combination of a compound of Formula (I), or a pharmaceutically acceptable salt thereof, in combination with one or more additional agent(s) in FIGS. 1-8 (including pharmaceutically acceptable salts and prodrugs thereof) can result in an additive effect. In some embodiments, the combination of a compound of Formula (I), or a pharmaceutically acceptable salt thereof, in combination with one or more additional agent(s) in FIGS. 1-8 (including pharmaceutically acceptable salts and prodrugs thereof) can result in a synergistic effect. In some embodiments, the combination of a compound of Formula (I), or a pharmaceutically acceptable salt thereof, in combination with one or more additional agent(s) in FIGS. 1-8 (including pharmaceutically acceptable salts and prodrugs thereof) can result in a strongly synergistic effect. In some embodiments, the combination of a compound of Formula (I), or a pharmaceutically acceptable salt thereof, in combination with one or more additional agent(s) in FIGS. 1-8 (including pharmaceutically acceptable salts and prodrugs thereof) is not antagonistic.

As used herein, the term "antagonistic" means that the activity of the combination of compounds is less compared to the sum of the activities of the compounds in combination when the activity of each compound is determined individually (i.e. as a single compound). As used herein, the term "synergistic effect" means that the activity of the combination of compounds is greater than the sum of the individual activities of the compounds in the combination when the activity of each compound is determined individually. As used herein, the term "additive effect" means that the activity of the combination of compounds is about equal to the sum of the individual activities of the compound in the combination when the activity of each compound is determined individually.

A potential advantage of utilizing a compound of Formula (I), or a pharmaceutically acceptable salt thereof, in combination with one or more additional agent(s) in FIGS. 1-8 (including pharmaceutically acceptable salts thereof) may be a reduction in the required amount(s) of one or more compounds of FIGS. 1-8 (including pharmaceutically acceptable salts thereof) that is effective in treating a disease condition disclosed herein (for example, HCV), as compared to the amount required to achieve same therapeutic result when one or more compounds of FIGS. 1-8 (including pharmaceutically acceptable salts thereof) are administered without a compound of Formula (I), or a pharmaceutically acceptable salt thereof. For example, the amount of a compound in FIGS. 1-8 (including a pharmaceutically acceptable salt thereof), can be less compared to the amount of the compound in FIGS. 1-8 (including a pharmaceutically acceptable salt thereof), needed to achieve the same viral load reduction when administered as a monotherapy. Another potential advantage of utilizing a compound of Formula (I), or a pharmaceutically acceptable salt thereof, in combination with one or more additional agent(s) in FIGS. 1-8 (including pharmaceutically acceptable salts thereof) is that the use of two or more compounds having different mechanism of actions can create a higher barrier to the development of resistant viral strains compared to the barrier when a compound is administered as monotherapy.

Additional advantages of utilizing a compound of Formula (I), or a pharmaceutically acceptable salt thereof, in combination with one or more additional agent(s) in FIGS. 1-8 (including pharmaceutically acceptable salts thereof) may include little to no cross resistance between a compound of Formula (I), or a pharmaceutically acceptable salt thereof, and one or more additional agent(s) in FIGS. 1-8 (including pharmaceutically acceptable salts thereof) thereof; different routes for elimination of a compound of Formula (I), or a pharmaceutically acceptable salt thereof, and one or more additional agent(s) in FIGS. 1-8 (including pharmaceutically acceptable salts thereof); little to no overlapping toxicities between a compound of Formula (I), or a pharmaceutically acceptable salt thereof, and one or more additional agent(s) in FIGS. 1-8 (including pharmaceutically acceptable salts thereof); little to no significant effects on cytochrome P450; little to no pharmacokinetic interactions between a compound of Formula (I), or a pharmaceutically acceptable salt thereof, and one or more additional agent(s) in FIGS. 1-8 (including pharmaceutically acceptable salts thereof); greater percentage of subjects achieving a sustained viral response compared to when a compound is administered as monotherapy and/or a decrease in treatment time to achieve a sustained viral response compared to when a compound is administered as monotherapy.

A non-limiting list of example combination of compounds of Formula (I), or a pharmaceutically acceptable salt thereof, or a pharmaceutical composition that includes a compound described herein, with one or more additional agent(s) are provided in Tables A, B, C, D and E. Each numbered X and Y compound in Tables A, B, C, D and E has a corresponding name and/or structure provided in FIGS. 1-8. The numbered compounds in Tables A, B, C, D and E includes pharmaceutically acceptable salts of the compounds and pharmaceutical compositions containing the compounds or a pharmaceutically acceptable salt thereof. For example, 1001 includes the compound corresponding to 1001, pharmaceutically acceptable salts thereof, and pharmaceutical compositions that include compound 1001 and/or a pharmaceutically acceptable salt thereof. The combinations exemplified in Tables A, B, C, D and E are designated by the formula X:Y, which represents a combination of a compound X with a compound Y. For example, the combination designated as 1001:9004 in Table A represents a combination of compound 1001 with compound 9004, including pharmaceutically acceptable salts of compound 1001 and/or 9004, and pharmaceutical compositions including compound 1001 and 9004 (including pharmaceutical compositions that include pharmaceutically acceptable salts of compound 1001 and/or compound 9004). Thus, the combination designated as 1001:9004 in Table A represents the combination of Telaprevir (compound 1001, as shown in FIG. 1) and

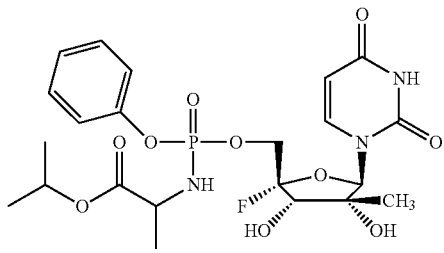 [SMILES: CC(C)OC(=O)C(C)NP(=O)(OC[C@@]1(F)O[C@@H](n2ccc(=O)[nH]c2=O)[C@](C)(O)[C@@H]1O)Oc1ccccc1]

(compound 9004, as shown in FIG. 9), including pharmaceutically acceptable salts of compound 1001 and/or 9004, and pharmaceutical compositions including compound 1001 and 9004 (including pharmaceutical compositions that include pharmaceutically acceptable salts of compound 1001 and/or compound 9004). Each of the combinations provided in Tables A, B, C, D and E can be used with one, two, three or more additional agents described herein. In some embodiments described herein, the combination of agents can be used to treat, ameliorate and/or inhibit a virus and/or a viral infection, wherein the virus can be HCV and the viral infection can be an HCV viral infection.

TABLE A

Example combinations of a compound X with a compound Y.

| X:Y | X:Y | X:Y | X:Y | X:Y | X:Y |
|---|---|---|---|---|---|
| 1001:9000 | 1001:9001 | 1001:9002 | 1001:9003 | 1001:9004 | 1001:9005 |
| 1002:9000 | 1002:9001 | 1002:9002 | 1002:9003 | 1002:9004 | 1002:9005 |
| 1003:9000 | 1003:9001 | 1003:9002 | 1003:9003 | 1003:9004 | 1003:9005 |
| 1004:9000 | 1004:9001 | 1004:9002 | 1004:9003 | 1004:9004 | 1004:9005 |
| 1005:9000 | 1005:9001 | 1005:9002 | 1005:9003 | 1005:9004 | 1005:9005 |
| 1006:9000 | 1006:9001 | 1006:9002 | 1006:9003 | 1006:9004 | 1006:9005 |
| 1007:9000 | 1007:9001 | 1007:9002 | 1007:9003 | 1007:9004 | 1007:9005 |
| 1008:9000 | 1008:9001 | 1008:9002 | 1008:9003 | 1008:9004 | 1008:9005 |
| 1009:9000 | 1009:9001 | 1009:9002 | 1009:9003 | 1009:9004 | 1009:9005 |
| 1010:9000 | 1010:9001 | 1010:9002 | 1010:9003 | 1010:9004 | 1010:9005 |
| 1011:9000 | 1011:9001 | 1011:9002 | 1011:9003 | 1011:9004 | 1011:9005 |
| 1012:9000 | 1012:9001 | 1012:9002 | 1012:9003 | 1012:9004 | 1012:9005 |
| 1013:9000 | 1013:9001 | 1013:9002 | 1013:9003 | 1013:9004 | 1013:9005 |
| 1014:9000 | 1014:9001 | 1014:9002 | 1014:9003 | 1014:9004 | 1014:9005 |
| 1015:9000 | 1015:9001 | 1015:9002 | 1015:9003 | 1015:9004 | 1015:9005 |
| 1016:9000 | 1016:9001 | 1016:9002 | 1016:9003 | 1016:9004 | 1016:9005 |
| 2001:9000 | 2001:9001 | 2001:9002 | 2001:9003 | 2001:9004 | 2001:9005 |
| 2002:9000 | 2002:9001 | 2002:9002 | 2002:9003 | 2002:9004 | 2002:9005 |
| 2003:9000 | 2003:9001 | 2003:9002 | 2003:9003 | 2003:9004 | 2003:9005 |
| 2004:9000 | 2004:9001 | 2004:9002 | 2004:9003 | 2004:9004 | 2004:9005 |
| 2005:9000 | 2005:9001 | 2005:9002 | 2005:9003 | 2005:9004 | 2005:9005 |
| 2006:9000 | 2006:9001 | 2006:9002 | 2006:9003 | 2006:9004 | 2006:9005 |
| 2007:9000 | 2007:9001 | 2007:9002 | 2007:9003 | 2007:9004 | 2007:9005 |
| 2008:9000 | 2008:9001 | 2008:9002 | 2008:9003 | 2008:9004 | 2008:9005 |
| 2009:9000 | 2009:9001 | 2009:9002 | 2009:9003 | 2009:9004 | 2009:9005 |
| 2010:9000 | 2010:9001 | 2010:9002 | 2010:9003 | 2010:9004 | 2010:9005 |
| 2011:9000 | 2011:9001 | 2011:9002 | 2011:9003 | 2011:9004 | 2011:9005 |
| 2012:9000 | 2012:9001 | 2012:9002 | 2012:9003 | 2012:9004 | 2012:9005 |

| X:Y | X:Y | X:Y | X:Y | X:Y | X:Y |
|---|---|---|---|---|---|
| 1001:9006 | 1001:9007 | 1001:9008 | 1001:9009 | 1001:9010 | 1001:9011 |
| 1002:9006 | 1002:9007 | 1002:9008 | 1002:9009 | 1002:9010 | 1002:9011 |
| 1003:9006 | 1003:9007 | 1003:9008 | 1003:9009 | 1003:9010 | 1003:9011 |
| 1004:9006 | 1004:9007 | 1004:9008 | 1004:9009 | 1004:9010 | 1004:9011 |
| 1005:9006 | 1005:9007 | 1005:9008 | 1005:9009 | 1005:9010 | 1005:9011 |
| 1006:9006 | 1006:9007 | 1006:9008 | 1006:9009 | 1006:9010 | 1006:9011 |
| 1007:9006 | 1007:9007 | 1007:9008 | 1007:9009 | 1007:9010 | 1007:9011 |
| 1008:9006 | 1008:9007 | 1008:9008 | 1008:9009 | 1008:9010 | 1008:9011 |
| 1009:9006 | 1009:9007 | 1009:9008 | 1009:9009 | 1009:9010 | 1009:9011 |
| 1010:9006 | 1010:9007 | 1010:9008 | 1010:9009 | 1010:9010 | 1010:9011 |
| 1011:9006 | 1011:9007 | 1011:9008 | 1011:9009 | 1011:9010 | 1011:9011 |
| 1012:9006 | 1012:9007 | 1012:9008 | 1012:9009 | 1012:9010 | 1012:9011 |
| 1013:9006 | 1013:9007 | 1013:9008 | 1013:9009 | 1013:9010 | 1013:9011 |
| 1014:9006 | 1014:9007 | 1014:9008 | 1014:9009 | 1014:9010 | 1014:9011 |
| 1015:9006 | 1015:9007 | 1015:9008 | 1015:9009 | 1015:9010 | 1015:9011 |
| 1016:9006 | 1016:9007 | 1016:9008 | 1016:9009 | 1016:9010 | 1016:9011 |
| 2001:9006 | 2001:9007 | 2001:9008 | 2001:9009 | 2001:9010 | 2001:9011 |
| 2002:9006 | 2002:9007 | 2002:9008 | 2002:9009 | 2002:9010 | 2002:9011 |
| 2003:9006 | 2003:9007 | 2003:9008 | 2003:9009 | 2003:9010 | 2003:9011 |
| 2004:9006 | 2004:9007 | 2004:9008 | 2004:9009 | 2004:9010 | 2004:9011 |
| 2005:9006 | 2005:9007 | 2005:9008 | 2005:9009 | 2005:9010 | 2005:9011 |
| 2006:9006 | 2006:9007 | 2006:9008 | 2006:9009 | 2006:9010 | 2006:9011 |
| 2007:9006 | 2007:9007 | 2007:9008 | 2007:9009 | 2007:9010 | 2007:9011 |
| 2008:9006 | 2008:9007 | 2008:9008 | 2008:9009 | 2008:9010 | 2008:9011 |
| 2009:9006 | 2009:9007 | 2009:9008 | 2009:9009 | 2009:9010 | 2009:9011 |
| 2010:9006 | 2010:9007 | 2010:9008 | 2010:9009 | 2010:9010 | 2010:9011 |
| 2011:9006 | 2011:9007 | 2011:9008 | 2011:9009 | 2011:9010 | 2011:9011 |
| 2012:9006 | 2012:9007 | 2012:9008 | 2012:9009 | 2012:9010 | 2012:9011 |

| X:Y | X:Y | X:Y | X:Y | X:Y | X:Y |
|---|---|---|---|---|---|
| 1001:9012 | 1001:9013 | 1001:9014 | 1001:9015 | 1001:9016 | 1001:9017 |
| 1002:9012 | 1002:9013 | 1002:9014 | 1002:9015 | 1002:9016 | 1002:9017 |
| 1003:9012 | 1003:9013 | 1003:9014 | 1003:9015 | 1003:9016 | 1003:9017 |
| 1004:9012 | 1004:9013 | 1004:9014 | 1004:9015 | 1004:9016 | 1004:9017 |
| 1005:9012 | 1005:9013 | 1005:9014 | 1005:9015 | 1005:9016 | 1005:9017 |
| 1006:9012 | 1006:9013 | 1006:9014 | 1006:9015 | 1006:9016 | 1006:9017 |
| 1007:9012 | 1007:9013 | 1007:9014 | 1007:9015 | 1007:9016 | 1007:9017 |
| 1008:9012 | 1008:9013 | 1008:9014 | 1008:9015 | 1008:9016 | 1008:9017 |
| 1009:9012 | 1009:9013 | 1009:9014 | 1009:9015 | 1009:9016 | 1009:9017 |
| 1010:9012 | 1010:9013 | 1010:9014 | 1010:9015 | 1010:9016 | 1010:9017 |
| 1011:9012 | 1011:9013 | 1011:9014 | 1011:9015 | 1011:9016 | 1011:9017 |
| 1012:9012 | 1012:9013 | 1012:9014 | 1012:9015 | 1012:9016 | 1012:9017 |
| 1013:9012 | 1013:9013 | 1013:9014 | 1013:9015 | 1013:9016 | 1013:9017 |
| 1014:9012 | 1014:9013 | 1014:9014 | 1014:9015 | 1014:9016 | 1014:9017 |

TABLE A-continued

Example combinations of a compound X with a compound Y.

| | | | | | |
|---|---|---|---|---|---|
| 1015:9012 | 1015:9013 | 1015:9014 | 1015:9015 | 1015:9016 | 1015:9017 |
| 1016:9012 | 1016:9013 | 1016:9014 | 1016:9015 | 1016:9016 | 1016:9017 |
| 2001:9012 | 2001:9013 | 2001:9014 | 2001:9015 | 2001:9016 | 2001:9017 |
| 2002:9012 | 2002:9013 | 2002:9014 | 2002:9015 | 2002:9016 | 2002:9017 |
| 2003:9012 | 2003:9013 | 2003:9014 | 2003:9015 | 2003:9016 | 2003:9017 |
| 2004:9012 | 2004:9013 | 2004:9014 | 2004:9015 | 2004:9016 | 2004:9017 |
| 2005:9012 | 2005:9013 | 2005:9014 | 2005:9015 | 2005:9016 | 2005:9017 |
| 2006:9012 | 2006:9013 | 2006:9014 | 2006:9015 | 2006:9016 | 2006:9017 |
| 2007:9012 | 2007:9013 | 2007:9014 | 2007:9015 | 2007:9016 | 2007:9017 |
| 2008:9012 | 2008:9013 | 2008:9014 | 2008:9015 | 2008:9016 | 2008:9017 |
| 2009:9012 | 2009:9013 | 2009:9014 | 2009:9015 | 2009:9016 | 2009:9017 |
| 2010:9012 | 2010:9013 | 2010:9014 | 2010:9015 | 2010:9016 | 2010:9017 |
| 2011:9012 | 2011:9013 | 2011:9014 | 2011:9015 | 2011:9016 | 2011:9017 |
| 2012:9012 | 2012:9013 | 2012:9014 | 2012:9015 | 2012:9016 | 2012:9017 |

| X:Y | X:Y | X:Y | X:Y | X:Y | X:Y |
|---|---|---|---|---|---|
| 1001:9018 | 1001:9019 | 1001:9020 | 1001:9021 | 1001:9022 | 1001:9023 |
| 1002:9018 | 1002:9019 | 1002:9020 | 1002:9021 | 1002:9022 | 1002:9023 |
| 1003:9018 | 1003:9019 | 1003:9020 | 1003:9021 | 1003:9022 | 1003:9023 |
| 1004:9018 | 1004:9019 | 1004:9020 | 1004:9021 | 1004:9022 | 1004:9023 |
| 1005:9018 | 1005:9019 | 1005:9020 | 1005:9021 | 1005:9022 | 1005:9023 |
| 1006:9018 | 1006:9019 | 1006:9020 | 1006:9021 | 1006:9022 | 1006:9023 |
| 1007:9018 | 1007:9019 | 1007:9020 | 1007:9021 | 1007:9022 | 1007:9023 |
| 1008:9018 | 1008:9019 | 1008:9020 | 1008:9021 | 1008:9022 | 1008:9023 |
| 1009:9018 | 1009:9019 | 1009:9020 | 1009:9021 | 1009:9022 | 1009:9023 |
| 1010:9018 | 1010:9019 | 1010:9020 | 1010:9021 | 1010:9022 | 1010:9023 |
| 1011:9018 | 1011:9019 | 1011:9020 | 1011:9021 | 1011:9022 | 1011:9023 |
| 1012:9018 | 1012:9019 | 1012:9020 | 1012:9021 | 1012:9022 | 1012:9023 |
| 1013:9018 | 1013:9019 | 1013:9020 | 1013:9021 | 1013:9022 | 1013:9023 |
| 1014:9018 | 1014:9019 | 1014:9020 | 1014:9021 | 1014:9022 | 1014:9023 |
| 1015:9018 | 1015:9019 | 1015:9020 | 1015:9021 | 1015:9022 | 1015:9023 |
| 1016:9018 | 1016:9019 | 1016:9020 | 1016:9021 | 1016:9022 | 1016:9023 |
| 2001:9018 | 2001:9019 | 2001:9020 | 2001:9021 | 2001:9022 | 2001:9023 |
| 2002:9018 | 2002:9019 | 2002:9020 | 2002:9021 | 2002:9022 | 2002:9023 |
| 2003:9018 | 2003:9019 | 2003:9020 | 2003:9021 | 2003:9022 | 2003:9023 |
| 2004:9018 | 2004:9019 | 2004:9020 | 2004:9021 | 2004:9022 | 2004:9023 |
| 2005:9018 | 2005:9019 | 2005:9020 | 2005:9021 | 2005:9022 | 2005:9023 |
| 2006:9018 | 2006:9019 | 2006:9020 | 2006:9021 | 2006:9022 | 2006:9023 |
| 2007:9018 | 2007:9019 | 2007:9020 | 2007:9021 | 2007:9022 | 2007:9023 |
| 2008:9018 | 2008:9019 | 2008:9020 | 2008:9021 | 2008:9022 | 2008:9023 |
| 2009:9018 | 2009:9019 | 2009:9020 | 2009:9021 | 2009:9022 | 2009:9023 |
| 2010:9018 | 2010:9019 | 2010:9020 | 2010:9021 | 2010:9022 | 2010:9023 |
| 2011:9018 | 2011:9019 | 2011:9020 | 2011:9021 | 2011:9022 | 2011:9023 |
| 2012:9018 | 2012:9019 | 2012:9020 | 2012:9021 | 2012:9022 | 2012:9023 |

| X:Y | X:Y | X:Y | X:Y | X:Y | X:Y |
|---|---|---|---|---|---|
| 1001:9024 | 1001:9025 | 1001:9026 | 1001:9027 | 1001:9028 | 1001:9029 |
| 1002:9024 | 1002:9025 | 1002:9026 | 1002:9027 | 1002:9028 | 1002:9029 |
| 1003:9024 | 1003:9025 | 1003:9026 | 1003:9027 | 1003:9028 | 1003:9029 |
| 1004:9024 | 1004:9025 | 1004:9026 | 1004:9027 | 1004:9028 | 1004:9029 |
| 1005:9024 | 1005:9025 | 1005:9026 | 1005:9027 | 1005:9028 | 1005:9029 |
| 1006:9024 | 1006:9025 | 1006:9026 | 1006:9027 | 1006:9028 | 1006:9029 |
| 1007:9024 | 1007:9025 | 1007:9026 | 1007:9027 | 1007:9028 | 1007:9029 |
| 1008:9024 | 1008:9025 | 1008:9026 | 1008:9027 | 1008:9028 | 1008:9029 |
| 1009:9024 | 1009:9025 | 1009:9026 | 1009:9027 | 1009:9028 | 1009:9029 |
| 1010:9024 | 1010:9025 | 1010:9026 | 1010:9027 | 1010:9028 | 1010:9029 |
| 1011:9024 | 1011:9025 | 1011:9026 | 1011:9027 | 1011:9028 | 1011:9029 |
| 1012:9024 | 1012:9025 | 1012:9026 | 1012:9027 | 1012:9028 | 1012:9029 |
| 1013:9024 | 1013:9025 | 1013:9026 | 1013:9027 | 1013:9028 | 1013:9029 |
| 1014:9024 | 1014:9025 | 1014:9026 | 1014:9027 | 1014:9028 | 1014:9029 |
| 1015:9024 | 1015:9025 | 1015:9026 | 1015:9027 | 1015:9028 | 1015:9029 |
| 1016:9024 | 1016:9025 | 1016:9026 | 1016:9027 | 1016:9028 | 1016:9029 |
| 2001:9024 | 2001:9025 | 2001:9026 | 2001:9027 | 2001:9028 | 2001:9029 |
| 2002:9024 | 2002:9025 | 2002:9026 | 2002:9027 | 2002:9028 | 2002:9029 |
| 2003:9024 | 2003:9025 | 2003:9026 | 2003:9027 | 2003:9028 | 2003:9029 |
| 2004:9024 | 2004:9025 | 2004:9026 | 2004:9027 | 2004:9028 | 2004:9029 |
| 2005:9024 | 2005:9025 | 2005:9026 | 2005:9027 | 2005:9028 | 2005:9029 |
| 2006:9024 | 2006:9025 | 2006:9026 | 2006:9027 | 2006:9028 | 2006:9029 |
| 2007:9024 | 2007:9025 | 2007:9026 | 2007:9027 | 2007:9028 | 2007:9029 |
| 2008:9024 | 2008:9025 | 2008:9026 | 2008:9027 | 2008:9028 | 2008:9029 |
| 2009:9024 | 2009:9025 | 2009:9026 | 2009:9027 | 2009:9028 | 2009:9029 |
| 2010:9024 | 2010:9025 | 2010:9026 | 2010:9027 | 2010:9028 | 2010:9029 |
| 2011:9024 | 2011:9025 | 2011:9026 | 2011:9027 | 2011:9028 | 2011:9029 |
| 2012:9024 | 2012:9025 | 2012:9026 | 2012:9027 | 2012:9028 | 2012:9029 |

| X:Y | X:Y | X:Y | X:Y | X:Y | X:Y |
|---|---|---|---|---|---|
| 1001:9030 | 1001:9031 | 1001:9032 | 1001:9033 | 1001:9034 | 1001:9035 |
| 1002:9030 | 1002:9031 | 1002:9032 | 1002:9033 | 1002:9034 | 1002:9035 |
| 1003:9030 | 1003:9031 | 1003:9032 | 1003:9033 | 1003:9034 | 1003:9035 |
| 1004:9030 | 1004:9031 | 1004:9032 | 1004:9033 | 1004:9034 | 1004:9035 |
| 1005:9030 | 1005:9031 | 1005:9032 | 1005:9033 | 1005:9034 | 1005:9035 |
| 1006:9030 | 1006:9031 | 1006:9032 | 1006:9033 | 1006:9034 | 1006:9035 |
| 1007:9030 | 1007:9031 | 1007:9032 | 1007:9033 | 1007:9034 | 1007:9035 |
| 1008:9030 | 1008:9031 | 1008:9032 | 1008:9033 | 1008:9034 | 1008:9035 |
| 1009:9030 | 1009:9031 | 1009:9032 | 1009:9033 | 1009:9034 | 1009:9035 |
| 1010:9030 | 1010:9031 | 1010:9032 | 1010:9033 | 1010:9034 | 1010:9035 |
| 1011:9030 | 1011:9031 | 1011:9032 | 1011:9033 | 1011:9034 | 1011:9035 |
| 1012:9030 | 1012:9031 | 1012:9032 | 1012:9033 | 1012:9034 | 1012:9035 |
| 1013:9030 | 1013:9031 | 1013:9032 | 1013:9033 | 1013:9034 | 1013:9035 |
| 1014:9030 | 1014:9031 | 1014:9032 | 1014:9033 | 1014:9034 | 1014:9035 |
| 1015:9030 | 1015:9031 | 1015:9032 | 1015:9033 | 1015:9034 | 1015:9035 |
| 1016:9030 | 1016:9031 | 1016:9032 | 1016:9033 | 1016:9034 | 1016:9035 |
| 2001:9030 | 2001:9031 | 2001:9032 | 2001:9033 | 2001:9034 | 2001:9035 |
| 2002:9030 | 2002:9031 | 2002:9032 | 2002:9033 | 2002:9034 | 2002:9035 |
| 2003:9030 | 2003:9031 | 2003:9032 | 2003:9033 | 2003:9034 | 2003:9035 |
| 2004:9030 | 2004:9031 | 2004:9032 | 2004:9033 | 2004:9034 | 2004:9035 |
| 2005:9030 | 2005:9031 | 2005:9032 | 2005:9033 | 2005:9034 | 2005:9035 |
| 2006:9030 | 2006:9031 | 2006:9032 | 2006:9033 | 2006:9034 | 2006:9035 |
| 2007:9030 | 2007:9031 | 2007:9032 | 2007:9033 | 2007:9034 | 2007:9035 |
| 2008:9030 | 2008:9031 | 2008:9032 | 2008:9033 | 2008:9034 | 2008:9035 |
| 2009:9030 | 2009:9031 | 2009:9032 | 2009:9033 | 2009:9034 | 2009:9035 |
| 2010:9030 | 2010:9031 | 2010:9032 | 2010:9033 | 2010:9034 | 2010:9035 |
| 2011:9030 | 2011:9031 | 2011:9032 | 2011:9033 | 2011:9034 | 2011:9035 |
| 2012:9030 | 2012:9031 | 2012:9032 | 2012:9033 | 2012:9034 | 2012:9035 |

| X:Y | X:Y | X:Y | X:Y | X:Y | X:Y |
|---|---|---|---|---|---|
| 1001:9036 | 1001:9037 | 1001:9038 | 1001:9039 | 1001:9040 | 1001:9041 |
| 1002:9036 | 1002:9037 | 1002:9038 | 1002:9039 | 1002:9040 | 1002:9041 |
| 1003:9036 | 1003:9037 | 1003:9038 | 1003:9039 | 1003:9040 | 1003:9041 |
| 1004:9036 | 1004:9037 | 1004:9038 | 1004:9039 | 1004:9040 | 1004:9041 |
| 1005:9036 | 1005:9037 | 1005:9038 | 1005:9039 | 1005:9040 | 1005:9041 |
| 1006:9036 | 1006:9037 | 1006:9038 | 1006:9039 | 1006:9040 | 1006:9041 |
| 1007:9036 | 1007:9037 | 1007:9038 | 1007:9039 | 1007:9040 | 1007:9041 |
| 1008:9036 | 1008:9037 | 1008:9038 | 1008:9039 | 1008:9040 | 1008:9041 |
| 1009:9036 | 1009:9037 | 1009:9038 | 1009:9039 | 1009:9040 | 1009:9041 |
| 1010:9036 | 1010:9037 | 1010:9038 | 1010:9039 | 1010:9040 | 1010:9041 |
| 1011:9036 | 1011:9037 | 1011:9038 | 1011:9039 | 1011:9040 | 1011:9041 |
| 1012:9036 | 1012:9037 | 1012:9038 | 1012:9039 | 1012:9040 | 1012:9041 |
| 1013:9036 | 1013:9037 | 1013:9038 | 1013:9039 | 1013:9040 | 1013:9041 |
| 1014:9036 | 1014:9037 | 1014:9038 | 1014:9039 | 1014:9040 | 1014:9041 |
| 1015:9036 | 1015:9037 | 1015:9038 | 1015:9039 | 1015:9040 | 1015:9041 |
| 1016:9036 | 1016:9037 | 1016:9038 | 1016:9039 | 1016:9040 | 1016:9041 |
| 2001:9036 | 2001:9037 | 2001:9038 | 2001:9039 | 2001:9040 | 2001:9041 |
| 2002:9036 | 2002:9037 | 2002:9038 | 2002:9039 | 2002:9040 | 2002:9041 |
| 2003:9036 | 2003:9037 | 2003:9038 | 2003:9039 | 2003:9040 | 2003:9041 |
| 2004:9036 | 2004:9037 | 2004:9038 | 2004:9039 | 2004:9040 | 2004:9041 |
| 2005:9036 | 2005:9037 | 2005:9038 | 2005:9039 | 2005:9040 | 2005:9041 |
| 2006:9036 | 2006:9037 | 2006:9038 | 2006:9039 | 2006:9040 | 2006:9041 |
| 2007:9036 | 2007:9037 | 2007:9038 | 2007:9039 | 2007:9040 | 2007:9041 |
| 2008:9036 | 2008:9037 | 2008:9038 | 2008:9039 | 2008:9040 | 2008:9041 |
| 2009:9036 | 2009:9037 | 2009:9038 | 2009:9039 | 2009:9040 | 2009:9041 |
| 2010:9036 | 2010:9037 | 2010:9038 | 2010:9039 | 2010:9040 | 2010:9041 |
| 2011:9036 | 2011:9037 | 2011:9038 | 2011:9039 | 2011:9040 | 2011:9041 |
| 2012:9036 | 2012:9037 | 2012:9038 | 2012:9039 | 2012:9040 | 2012:9041 |

| X:Y | X:Y | X:Y | X:Y | X:Y | X:Y |
|---|---|---|---|---|---|
| 1001:9042 | 1001:9043 | 1001:9044 | 1001:9045 | 1001:9046 | 1001:9047 |
| 1002:9042 | 1002:9043 | 1002:9044 | 1002:9045 | 1002:9046 | 1002:9047 |
| 1003:9042 | 1003:9043 | 1003:9044 | 1003:9045 | 1003:9046 | 1003:9047 |
| 1004:9042 | 1004:9043 | 1004:9044 | 1004:9045 | 1004:9046 | 1004:9047 |
| 1005:9042 | 1005:9043 | 1005:9044 | 1005:9045 | 1005:9046 | 1005:9047 |
| 1006:9042 | 1006:9043 | 1006:9044 | 1006:9045 | 1006:9046 | 1006:9047 |
| 1007:9042 | 1007:9043 | 1007:9044 | 1007:9045 | 1007:9046 | 1007:9047 |
| 1008:9042 | 1008:9043 | 1008:9044 | 1008:9045 | 1008:9046 | 1008:9047 |
| 1009:9042 | 1009:9043 | 1009:9044 | 1009:9045 | 1009:9046 | 1009:9047 |
| 1010:9042 | 1010:9043 | 1010:9044 | 1010:9045 | 1010:9046 | 1010:9047 |

TABLE A-continued

Example combinations of a compound X with a compound Y.

| | | | | | |
|---|---|---|---|---|---|
| 1011:9042 | 1011:9043 | 1011:9044 | 1011:9045 | 1011:9046 | 1011:9047 |
| 1012:9042 | 1012:9043 | 1012:9044 | 1012:9045 | 1012:9046 | 1012:9047 |
| 1013:9042 | 1013:9043 | 1013:9044 | 1013:9045 | 1013:9046 | 1013:9047 |
| 1014:9042 | 1014:9043 | 1014:9044 | 1014:9045 | 1014:9046 | 1014:9047 |
| 1015:9042 | 1015:9043 | 1015:9044 | 1015:9045 | 1015:9046 | 1015:9047 |
| 1016:9042 | 1016:9043 | 1016:9044 | 1016:9045 | 1016:9046 | 1016:9047 |
| 2001:9042 | 2001:9043 | 2001:9044 | 2001:9045 | 2001:9046 | 2001:9047 |
| 2002:9042 | 2002:9043 | 2002:9044 | 2002:9045 | 2002:9046 | 2002:9047 |
| 2003:9042 | 2003:9043 | 2003:9044 | 2003:9045 | 2003:9046 | 2003:9047 |
| 2004:9042 | 2004:9043 | 2004:9044 | 2004:9045 | 2004:9046 | 2004:9047 |
| 2005:9042 | 2005:9043 | 2005:9044 | 2005:9045 | 2005:9046 | 2005:9047 |
| 2006:9042 | 2006:9043 | 2006:9044 | 2006:9045 | 2006:9046 | 2006:9047 |
| 2007:9042 | 2007:9043 | 2007:9044 | 2007:9045 | 2007:9046 | 2007:9047 |
| 2008:9042 | 2008:9043 | 2008:9044 | 2008:9045 | 2008:9046 | 2008:9047 |
| 2009:9042 | 2009:9043 | 2009:9044 | 2009:9045 | 2009:9046 | 2009:9047 |
| 2010:9042 | 2010:9043 | 2010:9044 | 2010:9045 | 2010:9046 | 2010:9047 |
| 2011:9042 | 2011:9043 | 2011:9044 | 2011:9045 | 2011:9046 | 2011:9047 |
| 2012:9042 | 2012:9043 | 2012:9044 | 2012:9045 | 2012:9046 | 2012:9047 |

| X:Y | X:Y | X:Y | X:Y | X:Y | X:Y |
|---|---|---|---|---|---|
| 1001:9048 | 1001:9049 | 1001:9050 | 1001:9051 | 1001:9052 | 1001:9053 |
| 1002:9048 | 1002:9049 | 1002:9050 | 1002:9051 | 1002:9052 | 1002:9053 |
| 1003:9048 | 1003:9049 | 1003:9050 | 1003:9051 | 1003:9052 | 1003:9053 |
| 1004:9048 | 1004:9049 | 1004:9050 | 1004:9051 | 1004:9052 | 1004:9053 |
| 1005:9048 | 1005:9049 | 1005:9050 | 1005:9051 | 1005:9052 | 1005:9053 |
| 1006:9048 | 1006:9049 | 1006:9050 | 1006:9051 | 1006:9052 | 1006:9053 |
| 1007:9048 | 1007:9049 | 1007:9050 | 1007:9051 | 1007:9052 | 1007:9053 |
| 1008:9048 | 1008:9049 | 1008:9050 | 1008:9051 | 1008:9052 | 1008:9053 |
| 1009:9048 | 1009:9049 | 1009:9050 | 1009:9051 | 1009:9052 | 1009:9053 |
| 1010:9048 | 1010:9049 | 1010:9050 | 1010:9051 | 1010:9052 | 1010:9053 |
| 1011:9048 | 1011:9049 | 1011:9050 | 1011:9051 | 1011:9052 | 1011:9053 |
| 1012:9048 | 1012:9049 | 1012:9050 | 1012:9051 | 1012:9052 | 1012:9053 |
| 1013:9048 | 1013:9049 | 1013:9050 | 1013:9051 | 1013:9052 | 1013:9053 |
| 1014:9048 | 1014:9049 | 1014:9050 | 1014:9051 | 1014:9052 | 1014:9053 |
| 1015:9048 | 1015:9049 | 1015:9050 | 1015:9051 | 1015:9052 | 1015:9053 |
| 1016:9048 | 1016:9049 | 1016:9050 | 1016:9051 | 1016:9052 | 1016:9053 |
| 2001:9048 | 2001:9049 | 2001:9050 | 2001:9051 | 2001:9052 | 2001:9053 |
| 2002:9048 | 2002:9049 | 2002:9050 | 2002:9051 | 2002:9052 | 2002:9053 |
| 2003:9048 | 2003:9049 | 2003:9050 | 2003:9051 | 2003:9052 | 2003:9053 |
| 2004:9048 | 2004:9049 | 2004:9050 | 2004:9051 | 2004:9052 | 2004:9053 |
| 2005:9048 | 2005:9049 | 2005:9050 | 2005:9051 | 2005:9052 | 2005:9053 |
| 2006:9048 | 2006:9049 | 2006:9050 | 2006:9051 | 2006:9052 | 2006:9053 |
| 2007:9048 | 2007:9049 | 2007:9050 | 2007:9051 | 2007:9052 | 2007:9053 |
| 2008:9048 | 2008:9049 | 2008:9050 | 2008:9051 | 2008:9052 | 2008:9053 |
| 2009:9048 | 2009:9049 | 2009:9050 | 2009:9051 | 2009:9052 | 2009:9053 |
| 2010:9048 | 2010:9049 | 2010:9050 | 2010:9051 | 2010:9052 | 2010:9053 |
| 2011:9048 | 2011:9049 | 2011:9050 | 2011:9051 | 2011:9052 | 2011:9053 |
| 2012:9048 | 2012:9049 | 2012:9050 | 2012:9051 | 2012:9052 | 2012:9053 |

| X:Y | X:Y | X:Y | X:Y | X:Y | X:Y |
|---|---|---|---|---|---|
| 1001:9054 | 1001:9055 | 1001:9056 | 1001:9057 | 1001:9058 | 1001:9059 |
| 1002:9054 | 1002:9055 | 1002:9056 | 1002:9057 | 1002:9058 | 1002:9059 |
| 1003:9054 | 1003:9055 | 1003:9056 | 1003:9057 | 1003:9058 | 1003:9059 |
| 1004:9054 | 1004:9055 | 1004:9056 | 1004:9057 | 1004:9058 | 1004:9059 |
| 1005:9054 | 1005:9055 | 1005:9056 | 1005:9057 | 1005:9058 | 1005:9059 |
| 1006:9054 | 1006:9055 | 1006:9056 | 1006:9057 | 1006:9058 | 1006:9059 |
| 1007:9054 | 1007:9055 | 1007:9056 | 1007:9057 | 1007:9058 | 1007:9059 |
| 1008:9054 | 1008:9055 | 1008:9056 | 1008:9057 | 1008:9058 | 1008:9059 |
| 1009:9054 | 1009:9055 | 1009:9056 | 1009:9057 | 1009:9058 | 1009:9059 |
| 1010:9054 | 1010:9055 | 1010:9056 | 1010:9057 | 1010:9058 | 1010:9059 |
| 1011:9054 | 1011:9055 | 1011:9056 | 1011:9057 | 1011:9058 | 1011:9059 |
| 1012:9054 | 1012:9055 | 1012:9056 | 1012:9057 | 1012:9058 | 1012:9059 |
| 1013:9054 | 1013:9055 | 1013:9056 | 1013:9057 | 1013:9058 | 1013:9059 |
| 1014:9054 | 1014:9055 | 1014:9056 | 1014:9057 | 1014:9058 | 1014:9059 |
| 1015:9054 | 1015:9055 | 1015:9056 | 1015:9057 | 1015:9058 | 1015:9059 |
| 1016:9054 | 1016:9055 | 1016:9056 | 1016:9057 | 1016:9058 | 1016:9059 |
| 2001:9054 | 2001:9055 | 2001:9056 | 2001:9057 | 2001:9058 | 2001:9059 |
| 2002:9054 | 2002:9055 | 2002:9056 | 2002:9057 | 2002:9058 | 2002:9059 |
| 2003:9054 | 2003:9055 | 2003:9056 | 2003:9057 | 2003:9058 | 2003:9059 |
| 2004:9054 | 2004:9055 | 2004:9056 | 2004:9057 | 2004:9058 | 2004:9059 |
| 2005:9054 | 2005:9055 | 2005:9056 | 2005:9057 | 2005:9058 | 2005:9059 |
| 2006:9054 | 2006:9055 | 2006:9056 | 2006:9057 | 2006:9058 | 2006:9059 |
| 2007:9054 | 2007:9055 | 2007:9056 | 2007:9057 | 2007:9058 | 2007:9059 |
| 2008:9054 | 2008:9055 | 2008:9056 | 2008:9057 | 2008:9058 | 2008:9059 |
| 2009:9054 | 2009:9055 | 2009:9056 | 2009:9057 | 2009:9058 | 2009:9059 |
| 2010:9054 | 2010:9055 | 2010:9056 | 2010:9057 | 2010:9058 | 2010:9059 |
| 2011:9054 | 2011:9055 | 2011:9056 | 2011:9057 | 2011:9058 | 2011:9059 |
| 2012:9054 | 2012:9055 | 2012:9056 | 2012:9057 | 2012:9058 | 2012:9059 |

| X:Y | X:Y | X:Y | X:Y | X:Y | X:Y |
|---|---|---|---|---|---|
| 1001:9060 | 1001:9061 | 1001:9062 | 1001:9063 | 1001:9064 | 1001:9065 |
| 1002:9060 | 1002:9061 | 1002:9062 | 1002:9063 | 1002:9064 | 1002:9065 |
| 1003:9060 | 1003:9061 | 1003:9062 | 1003:9063 | 1003:9064 | 1003:9065 |
| 1004:9060 | 1004:9061 | 1004:9062 | 1004:9063 | 1004:9064 | 1004:9065 |
| 1005:9060 | 1005:9061 | 1005:9062 | 1005:9063 | 1005:9064 | 1005:9065 |
| 1006:9060 | 1006:9061 | 1006:9062 | 1006:9063 | 1006:9064 | 1006:9065 |
| 1007:9060 | 1007:9061 | 1007:9062 | 1007:9063 | 1007:9064 | 1007:9065 |
| 1008:9060 | 1008:9061 | 1008:9062 | 1008:9063 | 1008:9064 | 1008:9065 |
| 1009:9060 | 1009:9061 | 1009:9062 | 1009:9063 | 1009:9064 | 1009:9065 |
| 1010:9060 | 1010:9061 | 1010:9062 | 1010:9063 | 1010:9064 | 1010:9065 |
| 1011:9060 | 1011:9061 | 1011:9062 | 1011:9063 | 1011:9064 | 1011:9065 |
| 1012:9060 | 1012:9061 | 1012:9062 | 1012:9063 | 1012:9064 | 1012:9065 |
| 1013:9060 | 1013:9061 | 1013:9062 | 1013:9063 | 1013:9064 | 1013:9065 |
| 1014:9060 | 1014:9061 | 1014:9062 | 1014:9063 | 1014:9064 | 1014:9065 |
| 1015:9060 | 1015:9061 | 1015:9062 | 1015:9063 | 1015:9064 | 1015:9065 |
| 1016:9060 | 1016:9061 | 1016:9062 | 1016:9063 | 1016:9064 | 1016:9065 |
| 2001:9060 | 2001:9061 | 2001:9062 | 2001:9063 | 2001:9064 | 2001:9065 |
| 2002:9060 | 2002:9061 | 2002:9062 | 2002:9063 | 2002:9064 | 2002:9065 |
| 2003:9060 | 2003:9061 | 2003:9062 | 2003:9063 | 2003:9064 | 2003:9065 |
| 2004:9060 | 2004:9061 | 2004:9062 | 2004:9063 | 2004:9064 | 2004:9065 |
| 2005:9060 | 2005:9061 | 2005:9062 | 2005:9063 | 2005:9064 | 2005:9065 |
| 2006:9060 | 2006:9061 | 2006:9062 | 2006:9063 | 2006:9064 | 2006:9065 |
| 2007:9060 | 2007:9061 | 2007:9062 | 2007:9063 | 2007:9064 | 2007:9065 |
| 2008:9060 | 2008:9061 | 2008:9062 | 2008:9063 | 2008:9064 | 2008:9065 |
| 2009:9060 | 2009:9061 | 2009:9062 | 2009:9063 | 2009:9064 | 2009:9065 |
| 2010:9060 | 2010:9061 | 2010:9062 | 2010:9063 | 2010:9064 | 2010:9065 |
| 2011:9060 | 2011:9061 | 2011:9062 | 2011:9063 | 2011:9064 | 2011:9065 |
| 2012:9060 | 2012:9061 | 2012:9062 | 2012:9063 | 2012:9064 | 2012:9065 |

| X:Y | X:Y | X:Y | X:Y | X:Y | X:Y |
|---|---|---|---|---|---|
| 1001:9066 | 1001:9067 | 1001:9068 | 1001:9069 | 1001:9070 | 1001:9071 |
| 1002:9066 | 1002:9067 | 1002:9068 | 1002:9069 | 1002:9070 | 1002:9071 |
| 1003:9066 | 1003:9067 | 1003:9068 | 1003:9069 | 1003:9070 | 1003:9071 |
| 1004:9066 | 1004:9067 | 1004:9068 | 1004:9069 | 1004:9070 | 1004:9071 |
| 1005:9066 | 1005:9067 | 1005:9068 | 1005:9069 | 1005:9070 | 1005:9071 |
| 1006:9066 | 1006:9067 | 1006:9068 | 1006:9069 | 1006:9070 | 1006:9071 |
| 1007:9066 | 1007:9067 | 1007:9068 | 1007:9069 | 1007:9070 | 1007:9071 |
| 1008:9066 | 1008:9067 | 1008:9068 | 1008:9069 | 1008:9070 | 1008:9071 |
| 1009:9066 | 1009:9067 | 1009:9068 | 1009:9069 | 1009:9070 | 1009:9071 |
| 1010:9066 | 1010:9067 | 1010:9068 | 1010:9069 | 1010:9070 | 1010:9071 |
| 1011:9066 | 1011:9067 | 1011:9068 | 1011:9069 | 1011:9070 | 1011:9071 |
| 1012:9066 | 1012:9067 | 1012:9068 | 1012:9069 | 1012:9070 | 1012:9071 |
| 1013:9066 | 1013:9067 | 1013:9068 | 1013:9069 | 1013:9070 | 1013:9071 |
| 1014:9066 | 1014:9067 | 1014:9068 | 1014:9069 | 1014:9070 | 1014:9071 |
| 1015:9066 | 1015:9067 | 1015:9068 | 1015:9069 | 1015:9070 | 1015:9071 |
| 1016:9066 | 1016:9067 | 1016:9068 | 1016:9069 | 1016:9070 | 1016:9071 |
| 2001:9066 | 2001:9067 | 2001:9068 | 2001:9069 | 2001:9070 | 2001:9071 |
| 2002:9066 | 2002:9067 | 2002:9068 | 2002:9069 | 2002:9070 | 2002:9071 |
| 2003:9066 | 2003:9067 | 2003:9068 | 2003:9069 | 2003:9070 | 2003:9071 |
| 2004:9066 | 2004:9067 | 2004:9068 | 2004:9069 | 2004:9070 | 2004:9071 |
| 2005:9066 | 2005:9067 | 2005:9068 | 2005:9069 | 2005:9070 | 2005:9071 |
| 2006:9066 | 2006:9067 | 2006:9068 | 2006:9069 | 2006:9070 | 2006:9071 |
| 2007:9066 | 2007:9067 | 2007:9068 | 2007:9069 | 2007:9070 | 2007:9071 |
| 2008:9066 | 2008:9067 | 2008:9068 | 2008:9069 | 2008:9070 | 2008:9071 |
| 2009:9066 | 2009:9067 | 2009:9068 | 2009:9069 | 2009:9070 | 2009:9071 |
| 2010:9066 | 2010:9067 | 2010:9068 | 2010:9069 | 2010:9070 | 2010:9071 |
| 2011:9066 | 2011:9067 | 2011:9068 | 2011:9069 | 2011:9070 | 2011:9071 |
| 2012:9066 | 2012:9067 | 2012:9068 | 2012:9069 | 2012:9070 | 2012:9071 |

| X:Y | X:Y | X:Y | X:Y | X:Y | X:Y |
|---|---|---|---|---|---|
| 1001:9072 | 1001:9073 | 1001:9074 | 1001:9075 | 1001:9076 | 1001:9077 |
| 1002:9072 | 1002:9073 | 1002:9074 | 1002:9075 | 1002:9076 | 1002:9077 |
| 1003:9072 | 1003:9073 | 1003:9074 | 1003:9075 | 1003:9076 | 1003:9077 |
| 1004:9072 | 1004:9073 | 1004:9074 | 1004:9075 | 1004:9076 | 1004:9077 |
| 1005:9072 | 1005:9073 | 1005:9074 | 1005:9075 | 1005:9076 | 1005:9077 |
| 1006:9072 | 1006:9073 | 1006:9074 | 1006:9075 | 1006:9076 | 1006:9077 |
| 1007:9072 | 1007:9073 | 1007:9074 | 1007:9075 | 1007:9076 | 1007:9077 |
| 1008:9072 | 1008:9073 | 1008:9074 | 1008:9075 | 1008:9076 | 1008:9077 |
| 1009:9072 | 1009:9073 | 1009:9074 | 1009:9075 | 1009:9076 | 1009:9077 |
| 1010:9072 | 1010:9073 | 1010:9074 | 1010:9075 | 1010:9076 | 1010:9077 |
| 1011:9072 | 1011:9073 | 1011:9074 | 1011:9075 | 1011:9076 | 1011:9077 |

TABLE A-continued

Example combinations of a compound X with a compound Y.

| X:Y | X:Y | X:Y | X:Y | X:Y | X:Y |
|---|---|---|---|---|---|
| 1012:9072 | 1012:9073 | 1012:9074 | 1012:9075 | 1012:9076 | 1012:9077 |
| 1013:9072 | 1013:9073 | 1013:9074 | 1013:9075 | 1013:9076 | 1013:9077 |
| 1014:9072 | 1014:9073 | 1014:9074 | 1014:9075 | 1014:9076 | 1014:9077 |
| 1015:9072 | 1015:9073 | 1015:9074 | 1015:9075 | 1015:9076 | 1015:9077 |
| 1016:9072 | 1016:9073 | 1016:9074 | 1016:9075 | 1016:9076 | 1016:9077 |
| 2001:9072 | 2001:9073 | 2001:9074 | 2001:9075 | 2001:9076 | 2001:9077 |
| 2002:9072 | 2002:9073 | 2002:9074 | 2002:9075 | 2002:9076 | 2002:9077 |
| 2003:9072 | 2003:9073 | 2003:9074 | 2003:9075 | 2003:9076 | 2003:9077 |
| 2004:9072 | 2004:9073 | 2004:9074 | 2004:9075 | 2004:9076 | 2004:9077 |
| 2005:9072 | 2005:9073 | 2005:9074 | 2005:9075 | 2005:9076 | 2005:9077 |
| 2006:9072 | 2006:9073 | 2006:9074 | 2006:9075 | 2006:9076 | 2006:9077 |
| 2007:9072 | 2007:9073 | 2007:9074 | 2007:9075 | 2007:9076 | 2007:9077 |
| 2008:9072 | 2008:9073 | 2008:9074 | 2008:9075 | 2008:9076 | 2008:9077 |
| 2009:9072 | 2009:9073 | 2009:9074 | 2009:9075 | 2009:9076 | 2009:9077 |
| 2010:9072 | 2010:9073 | 2010:9074 | 2010:9075 | 2010:9076 | 2010:9077 |
| 2011:9072 | 2011:9073 | 2011:9074 | 2011:9075 | 2011:9076 | 2011:9077 |
| 2012:9072 | 2012:9073 | 2012:9074 | 2012:9075 | 2012:9076 | 2012:9077 |

| X:Y | X:Y | X:Y | X:Y | X:Y | X:Y |
|---|---|---|---|---|---|
| 1001:9078 | 1001:9079 | 1001:9080 | 1001:9081 | 1001:9082 | 1001:9083 |
| 1002:9078 | 1002:9079 | 1002:9080 | 1002:9081 | 1002:9082 | 1002:9083 |
| 1003:9078 | 1003:9079 | 1003:9080 | 1003:9081 | 1003:9082 | 1003:9083 |
| 1004:9078 | 1004:9079 | 1004:9080 | 1004:9081 | 1004:9082 | 1004:9083 |
| 1005:9078 | 1005:9079 | 1005:9080 | 1005:9081 | 1005:9082 | 1005:9083 |
| 1006:9078 | 1006:9079 | 1006:9080 | 1006:9081 | 1006:9082 | 1006:9083 |
| 1007:9078 | 1007:9079 | 1007:9080 | 1007:9081 | 1007:9082 | 1007:9083 |
| 1008:9078 | 1008:9079 | 1008:9080 | 1008:9081 | 1008:9082 | 1008:9083 |
| 1009:9078 | 1009:9079 | 1009:9080 | 1009:9081 | 1009:9082 | 1009:9083 |
| 1010:9078 | 1010:9079 | 1010:9080 | 1010:9081 | 1010:9082 | 1010:9083 |
| 1011:9078 | 1011:9079 | 1011:9080 | 1011:9081 | 1011:9082 | 1011:9083 |
| 1012:9078 | 1012:9079 | 1012:9080 | 1012:9081 | 1012:9082 | 1012:9083 |
| 1013:9078 | 1013:9079 | 1013:9080 | 1013:9081 | 1013:9082 | 1013:9083 |
| 1014:9078 | 1014:9079 | 1014:9080 | 1014:9081 | 1014:9082 | 1014:9083 |
| 1015:9078 | 1015:9079 | 1015:9080 | 1015:9081 | 1015:9082 | 1015:9083 |
| 1016:9078 | 1016:9079 | 1016:9080 | 1016:9081 | 1016:9082 | 1016:9083 |
| 2001:9078 | 2001:9079 | 2001:9080 | 2001:9081 | 2001:9082 | 2001:9083 |
| 2002:9078 | 2002:9079 | 2002:9080 | 2002:9081 | 2002:9082 | 2002:9083 |
| 2003:9078 | 2003:9079 | 2003:9080 | 2003:9081 | 2003:9082 | 2003:9083 |
| 2004:9078 | 2004:9079 | 2004:9080 | 2004:9081 | 2004:9082 | 2004:9083 |
| 2005:9078 | 2005:9079 | 2005:9080 | 2005:9081 | 2005:9082 | 2005:9083 |
| 2006:9078 | 2006:9079 | 2006:9080 | 2006:9081 | 2006:9082 | 2006:9083 |
| 2007:9078 | 2007:9079 | 2007:9080 | 2007:9081 | 2007:9082 | 2007:9083 |
| 2008:9078 | 2008:9079 | 2008:9080 | 2008:9081 | 2008:9082 | 2008:9083 |
| 2009:9078 | 2009:9079 | 2009:9080 | 2009:9081 | 2009:9082 | 2009:9083 |
| 2010:9078 | 2010:9079 | 2010:9080 | 2010:9081 | 2010:9082 | 2010:9083 |
| 2011:9078 | 2011:9079 | 2011:9080 | 2011:9081 | 2011:9082 | 2011:9083 |
| 2012:9078 | 2012:9079 | 2012:9080 | 2012:9081 | 2012:9082 | 2012:9083 |

| X:Y | X:Y | X:Y | X:Y | X:Y | X:Y |
|---|---|---|---|---|---|
| 1001:9084 | 1001:9085 | 1001:9086 | 1001:9087 | 1001:9088 | 1001:9089 |
| 1002:9084 | 1002:9085 | 1002:9086 | 1002:9087 | 1002:9088 | 1002:9089 |
| 1003:9084 | 1003:9085 | 1003:9086 | 1003:9087 | 1003:9088 | 1003:9089 |
| 1004:9084 | 1004:9085 | 1004:9086 | 1004:9087 | 1004:9088 | 1004:9089 |
| 1005:9084 | 1005:9085 | 1005:9086 | 1005:9087 | 1005:9088 | 1005:9089 |
| 1006:9084 | 1006:9085 | 1006:9086 | 1006:9087 | 1006:9088 | 1006:9089 |
| 1007:9084 | 1007:9085 | 1007:9086 | 1007:9087 | 1007:9088 | 1007:9089 |
| 1008:9084 | 1008:9085 | 1008:9086 | 1008:9087 | 1008:9088 | 1008:9089 |
| 1009:9084 | 1009:9085 | 1009:9086 | 1009:9087 | 1009:9088 | 1009:9089 |
| 1010:9084 | 1010:9085 | 1010:9086 | 1010:9087 | 1010:9088 | 1010:9089 |
| 1011:9084 | 1011:9085 | 1011:9086 | 1011:9087 | 1011:9088 | 1011:9089 |
| 1012:9084 | 1012:9085 | 1012:9086 | 1012:9087 | 1012:9088 | 1012:9089 |
| 1013:9084 | 1013:9085 | 1013:9086 | 1013:9087 | 1013:9088 | 1013:9089 |
| 1014:9084 | 1014:9085 | 1014:9086 | 1014:9087 | 1014:9088 | 1014:9089 |
| 1015:9084 | 1015:9085 | 1015:9086 | 1015:9087 | 1015:9088 | 1015:9089 |
| 1016:9084 | 1016:9085 | 1016:9086 | 1016:9087 | 1016:9088 | 1016:9089 |
| 2001:9084 | 2001:9085 | 2001:9086 | 2001:9087 | 2001:9088 | 2001:9089 |
| 2002:9084 | 2002:9085 | 2002:9086 | 2002:9087 | 2002:9088 | 2002:9089 |
| 2003:9084 | 2003:9085 | 2003:9086 | 2003:9087 | 2003:9088 | 2003:9089 |
| 2004:9084 | 2004:9085 | 2004:9086 | 2004:9087 | 2004:9088 | 2004:9089 |
| 2005:9084 | 2005:9085 | 2005:9086 | 2005:9087 | 2005:9088 | 2005:9089 |
| 2006:9084 | 2006:9085 | 2006:9086 | 2006:9087 | 2006:9088 | 2006:9089 |
| 2007:9084 | 2007:9085 | 2007:9086 | 2007:9087 | 2007:9088 | 2007:9089 |
| 2008:9084 | 2008:9085 | 2008:9086 | 2008:9087 | 2008:9088 | 2008:9089 |
| 2009:9084 | 2009:9085 | 2009:9086 | 2009:9087 | 2009:9088 | 2009:9089 |
| 2010:9084 | 2010:9085 | 2010:9086 | 2010:9087 | 2010:9088 | 2010:9089 |
| 2011:9084 | 2011:9085 | 2011:9086 | 2011:9087 | 2011:9088 | 2011:9089 |
| 2012:9084 | 2012:9085 | 2012:9086 | 2012:9087 | 2012:9088 | 2012:9089 |

| X:Y | X:Y | X:Y | X:Y | X:Y | X:Y |
|---|---|---|---|---|---|
| 1001:9090 | 1001:9091 | 1001:9092 | 1001:9093 | 1001:9094 | 1001:9095 |
| 1002:9090 | 1002:9091 | 1002:9092 | 1002:9093 | 1002:9094 | 1002:9095 |
| 1003:9090 | 1003:9091 | 1003:9092 | 1003:9093 | 1003:9094 | 1003:9095 |
| 1004:9090 | 1004:9091 | 1004:9092 | 1004:9093 | 1004:9094 | 1004:9095 |
| 1005:9090 | 1005:9091 | 1005:9092 | 1005:9093 | 1005:9094 | 1005:9095 |
| 1006:9090 | 1006:9091 | 1006:9092 | 1006:9093 | 1006:9094 | 1006:9095 |
| 1007:9090 | 1007:9091 | 1007:9092 | 1007:9093 | 1007:9094 | 1007:9095 |
| 1008:9090 | 1008:9091 | 1008:9092 | 1008:9093 | 1008:9094 | 1008:9095 |
| 1009:9090 | 1009:9091 | 1009:9092 | 1009:9093 | 1009:9094 | 1009:9095 |
| 1010:9090 | 1010:9091 | 1010:9092 | 1010:9093 | 1010:9094 | 1010:9095 |
| 1011:9090 | 1011:9091 | 1011:9092 | 1011:9093 | 1011:9094 | 1011:9095 |
| 1012:9090 | 1012:9091 | 1012:9092 | 1012:9093 | 1012:9094 | 1012:9095 |
| 1013:9090 | 1013:9091 | 1013:9092 | 1013:9093 | 1013:9094 | 1013:9095 |
| 1014:9090 | 1014:9091 | 1014:9092 | 1014:9093 | 1014:9094 | 1014:9095 |
| 1015:9090 | 1015:9091 | 1015:9092 | 1015:9093 | 1015:9094 | 1015:9095 |
| 1016:9090 | 1016:9091 | 1016:9092 | 1016:9093 | 1016:9094 | 1016:9095 |
| 2001:9090 | 2001:9091 | 2001:9092 | 2001:9093 | 2001:9094 | 2001:9095 |
| 2002:9090 | 2002:9091 | 2002:9092 | 2002:9093 | 2002:9094 | 2002:9095 |
| 2003:9090 | 2003:9091 | 2003:9092 | 2003:9093 | 2003:9094 | 2003:9095 |
| 2004:9090 | 2004:9091 | 2004:9092 | 2004:9093 | 2004:9094 | 2004:9095 |
| 2005:9090 | 2005:9091 | 2005:9092 | 2005:9093 | 2005:9094 | 2005:9095 |
| 2006:9090 | 2006:9091 | 2006:9092 | 2006:9093 | 2006:9094 | 2006:9095 |
| 2007:9090 | 2007:9091 | 2007:9092 | 2007:9093 | 2007:9094 | 2007:9095 |
| 2008:9090 | 2008:9091 | 2008:9092 | 2008:9093 | 2008:9094 | 2008:9095 |
| 2009:9090 | 2009:9091 | 2009:9092 | 2009:9093 | 2009:9094 | 2009:9095 |
| 2010:9090 | 2010:9091 | 2010:9092 | 2010:9093 | 2010:9094 | 2010:9095 |
| 2011:9090 | 2011:9091 | 2011:9092 | 2011:9093 | 2011:9094 | 2011:9095 |
| 2012:9090 | 2012:9091 | 2012:9092 | 2012:9093 | 2012:9094 | 2012:9095 |

| X:Y | X:Y | X:Y | X:Y | X:Y | X:Y |
|---|---|---|---|---|---|
| 1001:9096 | 1001:9097 | 1001:9098 | 1001:9099 | 1001:9100 | 1001:9101 |
| 1002:9096 | 1002:9097 | 1002:9098 | 1002:9099 | 1002:9100 | 1002:9101 |
| 1003:9096 | 1003:9097 | 1003:9098 | 1003:9099 | 1003:9100 | 1003:9101 |
| 1004:9096 | 1004:9097 | 1004:9098 | 1004:9099 | 1004:9100 | 1004:9101 |
| 1005:9096 | 1005:9097 | 1005:9098 | 1005:9099 | 1005:9100 | 1005:9101 |
| 1006:9096 | 1006:9097 | 1006:9098 | 1006:9099 | 1006:9100 | 1006:9101 |
| 1007:9096 | 1007:9097 | 1007:9098 | 1007:9099 | 1007:9100 | 1007:9101 |
| 1008:9096 | 1008:9097 | 1008:9098 | 1008:9099 | 1008:9100 | 1008:9101 |
| 1009:9096 | 1009:9097 | 1009:9098 | 1009:9099 | 1009:9100 | 1009:9101 |
| 1010:9096 | 1010:9097 | 1010:9098 | 1010:9099 | 1010:9100 | 1010:9101 |
| 1011:9096 | 1011:9097 | 1011:9098 | 1011:9099 | 1011:9100 | 1011:9101 |
| 1012:9096 | 1012:9097 | 1012:9098 | 1012:9099 | 1012:9100 | 1012:9101 |
| 1013:9096 | 1013:9097 | 1013:9098 | 1013:9099 | 1013:9100 | 1013:9101 |
| 1014:9096 | 1014:9097 | 1014:9098 | 1014:9099 | 1014:9100 | 1014:9101 |
| 1015:9096 | 1015:9097 | 1015:9098 | 1015:9099 | 1015:9100 | 1015:9101 |
| 1016:9096 | 1016:9097 | 1016:9098 | 1016:9099 | 1016:9100 | 1016:9101 |
| 2001:9096 | 2001:9097 | 2001:9098 | 2001:9099 | 2001:9100 | 2001:9101 |
| 2002:9096 | 2002:9097 | 2002:9098 | 2002:9099 | 2002:9100 | 2002:9101 |
| 2003:9096 | 2003:9097 | 2003:9098 | 2003:9099 | 2003:9100 | 2003:9101 |
| 2004:9096 | 2004:9097 | 2004:9098 | 2004:9099 | 2004:9100 | 2004:9101 |
| 2005:9096 | 2005:9097 | 2005:9098 | 2005:9099 | 2005:9100 | 2005:9101 |
| 2006:9096 | 2006:9097 | 2006:9098 | 2006:9099 | 2006:9100 | 2006:9101 |
| 2007:9096 | 2007:9097 | 2007:9098 | 2007:9099 | 2007:9100 | 2007:9101 |
| 2008:9096 | 2008:9097 | 2008:9098 | 2008:9099 | 2008:9100 | 2008:9101 |
| 2009:9096 | 2009:9097 | 2009:9098 | 2009:9099 | 2009:9100 | 2009:9101 |
| 2010:9096 | 2010:9097 | 2010:9098 | 2010:9099 | 2010:9100 | 2010:9101 |
| 2011:9096 | 2011:9097 | 2011:9098 | 2011:9099 | 2011:9100 | 2011:9101 |
| 2012:9096 | 2012:9097 | 2012:9098 | 2012:9099 | 2012:9100 | 2012:9101 |

| X:Y | X:Y | X:Y | X:Y | X:Y | X:Y |
|---|---|---|---|---|---|
| 1001:9102 | 1001:9103 | 1001:9104 | 1001:9105 | — | — |
| 1002:9102 | 1002:9103 | 1002:9104 | 1002:9105 | | |
| 1003:9102 | 1003:9103 | 1003:9104 | 1003:9105 | | |
| 1004:9102 | 1004:9103 | 1004:9104 | 1004:9105 | | |
| 1005:9102 | 1005:9103 | 1005:9104 | 1005:9105 | | |
| 1006:9102 | 1006:9103 | 1006:9104 | 1006:9105 | | |
| 1007:9102 | 1007:9103 | 1007:9104 | 1007:9105 | | |
| 1008:9102 | 1008:9103 | 1008:9104 | 1008:9105 | | |
| 1009:9102 | 1009:9103 | 1009:9104 | 1009:9105 | | |

TABLE A-continued

Example combinations of a compound X with a compound Y.

| | | | |
|---|---|---|---|
| 1010:9102 | 1010:9103 | 1010:9104 | 1010:9105 |
| 1011:9102 | 1011:9103 | 1011:9104 | 1011:9105 |
| 1012:9102 | 1012:9103 | 1012:9104 | 1012:9105 |
| 1013:9102 | 1013:9103 | 1013:9104 | 1013:9105 |
| 1014:9102 | 1014:9103 | 1014:9104 | 1014:9105 |
| 1015:9102 | 1015:9103 | 1015:9104 | 1015:9105 |
| 1016:9102 | 1016:9103 | 1016:9104 | 1016:9105 |
| 2001:9102 | 2001:9103 | 2001:9104 | 2001:9105 |
| 2002:9102 | 2002:9103 | 2002:9104 | 2002:9105 |
| 2003:9102 | 2003:9103 | 2003:9104 | 2003:9105 |
| 2004:9102 | 2004:9103 | 2004:9104 | 2004:9105 |
| 2005:9102 | 2005:9103 | 2005:9104 | 2005:9105 |
| 2006:9102 | 2006:9103 | 2006:9104 | 2006:9105 |
| 2007:9102 | 2007:9103 | 2007:9104 | 2007:9105 |
| 2008:9102 | 2008:9103 | 2008:9104 | 2008:9105 |
| 2009:9102 | 2009:9103 | 2009:9104 | 2009:9105 |
| 2010:9102 | 2010:9103 | 2010:9104 | 2010:9105 |
| 2011:9102 | 2011:9103 | 2011:9104 | 2011:9105 |
| 2012:9102 | 2012:9103 | 2012:9104 | 2012:9105 |

TABLE B

Example combinations of a compound X with a compound Y.

| X:Y | X:Y | X:Y | X:Y | X:Y | X:Y |
|---|---|---|---|---|---|
| 3001:9000 | 3001:9001 | 3001:9002 | 3001:9003 | 3001:9004 | 3001:9005 |
| 3002:9000 | 3002:9001 | 3002:9002 | 3002:9003 | 3002:9004 | 3002:9005 |
| 3003:9000 | 3003:9001 | 3003:9002 | 3003:9003 | 3003:9004 | 3003:9005 |
| 3004:9000 | 3004:9001 | 3004:9002 | 3004:9003 | 3004:9004 | 3004:9005 |
| 3005:9000 | 3005:9001 | 3005:9002 | 3005:9003 | 3005:9004 | 3005:9005 |
| 3006:9000 | 3006:9001 | 3006:9002 | 3006:9003 | 3006:9004 | 3006:9005 |
| 3007:9000 | 3007:9001 | 3007:9002 | 3007:9003 | 3007:9004 | 3007:9005 |
| 3008:9000 | 3008:9001 | 3008:9002 | 3008:9003 | 3008:9004 | 3008:9005 |
| 3009:9000 | 3009:9001 | 3009:9002 | 3009:9003 | 3009:9004 | 3009:9005 |
| 3010:9000 | 3010:9001 | 3010:9002 | 3010:9003 | 3010:9004 | 3010:9005 |
| 3011:9000 | 3011:9001 | 3011:9002 | 3011:9003 | 3011:9004 | 3011:9005 |
| 3012:9000 | 3012:9001 | 3012:9002 | 3012:9003 | 3012:9004 | 3012:9005 |
| 3013:9000 | 3013:9001 | 3013:9002 | 3013:9003 | 3013:9004 | 3013:9005 |
| 3014:9000 | 3014:9001 | 3014:9002 | 3014:9003 | 3014:9004 | 3014:9005 |
| 4001:9000 | 4001:9001 | 4001:9002 | 4001:9003 | 4001:9004 | 4001:9005 |
| 4002:9000 | 4002:9001 | 4002:9002 | 4002:9003 | 4002:9004 | 4002:9005 |
| 4003:9000 | 4003:9001 | 4003:9002 | 4003:9003 | 4003:9004 | 4003:9005 |
| 4004:9000 | 4004:9001 | 4004:9002 | 4004:9003 | 4004:9004 | 4004:9005 |
| 4005:9000 | 4005:9001 | 4005:9002 | 4005:9003 | 4005:9004 | 4005:9005 |
| 4006:9000 | 4006:9001 | 4006:9002 | 4006:9003 | 4006:9004 | 4006:9005 |
| 4007:9000 | 4007:9001 | 4007:9002 | 4007:9003 | 4007:9004 | 4007:9005 |
| 4008:9000 | 4008:9001 | 4008:9002 | 4008:9003 | 4008:9004 | 4008:9005 |
| 4009:9000 | 4009:9001 | 4009:9002 | 4009:9003 | 4009:9004 | 4009:9005 |
| 4010:9000 | 4010:9001 | 4010:9002 | 4010:9003 | 4010:9004 | 4010:9005 |
| 4011:9000 | 4011:9001 | 4011:9002 | 4011:9003 | 4011:9004 | 4011:9005 |
| 4012:9000 | 4012:9001 | 4012:9002 | 4012:9003 | 4012:9004 | 4012:9005 |
| 5001:9000 | 5001:9001 | 5001:9002 | 5001:9003 | 5001:9004 | 5001:9005 |
| 5002:9000 | 5002:9001 | 5002:9002 | 5002:9003 | 5002:9004 | 5002:9005 |
| 5003:9000 | 5003:9001 | 5003:9002 | 5003:9003 | 5003:9004 | 5003:9005 |
| 5004:9000 | 5004:9001 | 5004:9002 | 5004:9003 | 5004:9004 | 5004:9005 |
| 5005:9000 | 5005:9001 | 5005:9002 | 5005:9003 | 5005:9004 | 5005:9005 |
| 5006:9000 | 5006:9001 | 5006:9002 | 5006:9003 | 5006:9004 | 5006:9005 |
| 5007:9000 | 5007:9001 | 5007:9002 | 5007:9003 | 5007:9004 | 5007:9005 |
| 5008:9000 | 5008:9001 | 5008:9002 | 5008:9003 | 5008:9004 | 5008:9005 |
| 5009:9000 | 5009:9001 | 5009:9002 | 5009:9003 | 5009:9004 | 5009:9005 |
| 5010:9000 | 5010:9001 | 5010:9002 | 5010:9003 | 5010:9004 | 5010:9005 |
| 5011:9000 | 5011:9001 | 5011:9002 | 5011:9003 | 5011:9004 | 5011:9005 |
| 5012:9000 | 5012:9001 | 5012:9002 | 5012:9003 | 5012:9004 | 5012:9005 |

| X:Y | X:Y | X:Y | X:Y | X:Y | X:Y |
|---|---|---|---|---|---|
| 3001:9006 | 3001:9007 | 3001:9008 | 3001:9009 | 3001:9010 | 3001:9011 |
| 3002:9006 | 3002:9007 | 3002:9008 | 3002:9009 | 3002:9010 | 3002:9011 |
| 3003:9006 | 3003:9007 | 3003:9008 | 3003:9009 | 3003:9010 | 3003:9011 |
| 3004:9006 | 3004:9007 | 3004:9008 | 3004:9009 | 3004:9010 | 3004:9011 |
| 3005:9006 | 3005:9007 | 3005:9008 | 3005:9009 | 3005:9010 | 3005:9011 |
| 3006:9006 | 3006:9007 | 3006:9008 | 3006:9009 | 3006:9010 | 3006:9011 |
| 3007:9006 | 3007:9007 | 3007:9008 | 3007:9009 | 3007:9010 | 3007:9011 |
| 3008:9006 | 3008:9007 | 3008:9008 | 3008:9009 | 3008:9010 | 3008:9011 |

TABLE B-continued

Example combinations of a compound X with a compound Y.

| | | | | | |
|---|---|---|---|---|---|
| 3009:9006 | 3009:9007 | 3009:9008 | 3009:9009 | 3009:9010 | 3009:9011 |
| 3010:9006 | 3010:9007 | 3010:9008 | 3010:9009 | 3010:9010 | 3010:9011 |
| 3011:9006 | 3011:9007 | 3011:9008 | 3011:9009 | 3011:9010 | 3011:9011 |
| 3012:9006 | 3012:9007 | 3012:9008 | 3012:9009 | 3012:9010 | 3012:9011 |
| 3013:9006 | 3013:9007 | 3013:9008 | 3013:9009 | 3013:9010 | 3013:9011 |
| 3014:9006 | 3014:9007 | 3014:9008 | 3014:9009 | 3014:9010 | 3014:9011 |
| 4001:9006 | 4001:9007 | 4001:9008 | 4001:9009 | 4001:9010 | 4001:9011 |
| 4002:9006 | 4002:9007 | 4002:9008 | 4002:9009 | 4002:9010 | 4002:9011 |
| 4003:9006 | 4003:9007 | 4003:9008 | 4003:9009 | 4003:9010 | 4003:9011 |
| 4004:9006 | 4004:9007 | 4004:9008 | 4004:9009 | 4004:9010 | 4004:9011 |
| 4005:9006 | 4005:9007 | 4005:9008 | 4005:9009 | 4005:9010 | 4005:9011 |
| 4006:9006 | 4006:9007 | 4006:9008 | 4006:9009 | 4006:9010 | 4006:9011 |
| 4007:9006 | 4007:9007 | 4007:9008 | 4007:9009 | 4007:9010 | 4007:9011 |
| 4008:9006 | 4008:9007 | 4008:9008 | 4008:9009 | 4008:9010 | 4008:9011 |
| 4009:9006 | 4009:9007 | 4009:9008 | 4009:9009 | 4009:9010 | 4009:9011 |
| 4010:9006 | 4010:9007 | 4010:9008 | 4010:9009 | 4010:9010 | 4010:9011 |
| 4011:9006 | 4011:9007 | 4011:9008 | 4011:9009 | 4011:9010 | 4011:9011 |
| 4012:9006 | 4012:9007 | 4012:9008 | 4012:9009 | 4012:9010 | 4012:9011 |
| 5001:9006 | 5001:9007 | 5001:9008 | 5001:9009 | 5001:9010 | 5001:9011 |
| 5002:9006 | 5002:9007 | 5002:9008 | 5002:9009 | 5002:9010 | 5002:9011 |
| 5003:9006 | 5003:9007 | 5003:9008 | 5003:9009 | 5003:9010 | 5003:9011 |
| 5004:9006 | 5004:9007 | 5004:9008 | 5004:9009 | 5004:9010 | 5004:9011 |
| 5005:9006 | 5005:9007 | 5005:9008 | 5005:9009 | 5005:9010 | 5005:9011 |
| 5006:9006 | 5006:9007 | 5006:9008 | 5006:9009 | 5006:9010 | 5006:9011 |
| 5007:9006 | 5007:9007 | 5007:9008 | 5007:9009 | 5007:9010 | 5007:9011 |
| 5008:9006 | 5008:9007 | 5008:9008 | 5008:9009 | 5008:9010 | 5008:9011 |
| 5009:9006 | 5009:9007 | 5009:9008 | 5009:9009 | 5009:9010 | 5009:9011 |
| 5010:9006 | 5010:9007 | 5010:9008 | 5010:9009 | 5010:9010 | 5010:9011 |
| 5011:9006 | 5011:9007 | 5011:9008 | 5011:9009 | 5011:9010 | 5011:9011 |
| 5012:9006 | 5012:9007 | 5012:9008 | 5012:9009 | 5012:9010 | 5012:9011 |

| X:Y | X:Y | X:Y | X:Y | X:Y | X:Y |
|---|---|---|---|---|---|
| 3001:9012 | 3001:9013 | 3001:9014 | 3001:9015 | 3001:9016 | 3001:9017 |
| 3002:9012 | 3002:9013 | 3002:9014 | 3002:9015 | 3002:9016 | 3002:9017 |
| 3003:9012 | 3003:9013 | 3003:9014 | 3003:9015 | 3003:9016 | 3003:9017 |
| 3004:9012 | 3004:9013 | 3004:9014 | 3004:9015 | 3004:9016 | 3004:9017 |
| 3005:9012 | 3005:9013 | 3005:9014 | 3005:9015 | 3005:9016 | 3005:9017 |
| 3006:9012 | 3006:9013 | 3006:9014 | 3006:9015 | 3006:9016 | 3006:9017 |
| 3007:9012 | 3007:9013 | 3007:9014 | 3007:9015 | 3007:9016 | 3007:9017 |
| 3008:9012 | 3008:9013 | 3008:9014 | 3008:9015 | 3008:9016 | 3008:9017 |
| 3009:9012 | 3009:9013 | 3009:9014 | 3009:9015 | 3009:9016 | 3009:9017 |
| 3010:9012 | 3010:9013 | 3010:9014 | 3010:9015 | 3010:9016 | 3010:9017 |
| 3011:9012 | 3011:9013 | 3011:9014 | 3011:9015 | 3011:9016 | 3011:9017 |
| 3012:9012 | 3012:9013 | 3012:9014 | 3012:9015 | 3012:9016 | 3012:9017 |
| 3013:9012 | 3013:9013 | 3013:9014 | 3013:9015 | 3013:9016 | 3013:9017 |
| 3014:9012 | 3014:9013 | 3014:9014 | 3014:9015 | 3014:9016 | 3014:9017 |
| 4001:9012 | 4001:9013 | 4001:9014 | 4001:9015 | 4001:9016 | 4001:9017 |
| 4002:9012 | 4002:9013 | 4002:9014 | 4002:9015 | 4002:9016 | 4002:9017 |
| 4003:9012 | 4003:9013 | 4003:9014 | 4003:9015 | 4003:9016 | 4003:9017 |
| 4004:9012 | 4004:9013 | 4004:9014 | 4004:9015 | 4004:9016 | 4004:9017 |
| 4005:9012 | 4005:9013 | 4005:9014 | 4005:9015 | 4005:9016 | 4005:9017 |
| 4006:9012 | 4006:9013 | 4006:9014 | 4006:9015 | 4006:9016 | 4006:9017 |
| 4007:9012 | 4007:9013 | 4007:9014 | 4007:9015 | 4007:9016 | 4007:9017 |
| 4008:9012 | 4008:9013 | 4008:9014 | 4008:9015 | 4008:9016 | 4008:9017 |
| 4009:9012 | 4009:9013 | 4009:9014 | 4009:9015 | 4009:9016 | 4009:9017 |
| 4010:9012 | 4010:9013 | 4010:9014 | 4010:9015 | 4010:9016 | 4010:9017 |
| 4011:9012 | 4011:9013 | 4011:9014 | 4011:9015 | 4011:9016 | 4011:9017 |
| 4012:9012 | 4012:9013 | 4012:9014 | 4012:9015 | 4012:9016 | 4012:9017 |
| 5001:9012 | 5001:9013 | 5001:9014 | 5001:9015 | 5001:9016 | 5001:9017 |
| 5002:9012 | 5002:9013 | 5002:9014 | 5002:9015 | 5002:9016 | 5002:9017 |
| 5003:9012 | 5003:9013 | 5003:9014 | 5003:9015 | 5003:9016 | 5003:9017 |
| 5004:9012 | 5004:9013 | 5004:9014 | 5004:9015 | 5004:9016 | 5004:9017 |
| 5005:9012 | 5005:9013 | 5005:9014 | 5005:9015 | 5005:9016 | 5005:9017 |
| 5006:9012 | 5006:9013 | 5006:9014 | 5006:9015 | 5006:9016 | 5006:9017 |
| 5007:9012 | 5007:9013 | 5007:9014 | 5007:9015 | 5007:9016 | 5007:9017 |
| 5008:9012 | 5008:9013 | 5008:9014 | 5008:9015 | 5008:9016 | 5008:9017 |
| 5009:9012 | 5009:9013 | 5009:9014 | 5009:9015 | 5009:9016 | 5009:9017 |
| 5010:9012 | 5010:9013 | 5010:9014 | 5010:9015 | 5010:9016 | 5010:9017 |
| 5011:9012 | 5011:9013 | 5011:9014 | 5011:9015 | 5011:9016 | 5011:9017 |
| 5012:9012 | 5012:9013 | 5012:9014 | 5012:9015 | 5012:9016 | 5012:9017 |

| X:Y | X:Y | X:Y | X:Y | X:Y | X:Y |
|---|---|---|---|---|---|
| 3001:9018 | 3001:9019 | 3001:9020 | 3001:9021 | 3001:9022 | 3001:9023 |
| 3002:9018 | 3002:9019 | 3002:9020 | 3002:9021 | 3002:9022 | 3002:9023 |
| 3003:9018 | 3003:9019 | 3003:9020 | 3003:9021 | 3003:9022 | 3003:9023 |
| 3004:9018 | 3004:9019 | 3004:9020 | 3004:9021 | 3004:9022 | 3004:9023 |

TABLE B-continued

Example combinations of a compound X with a compound Y.

| | | | | | |
|---|---|---|---|---|---|
| 3005:9018 | 3005:9019 | 3005:9020 | 3005:9021 | 3005:9022 | 3005:9023 |
| 3006:9018 | 3006:9019 | 3006:9020 | 3006:9021 | 3006:9022 | 3006:9023 |
| 3007:9018 | 3007:9019 | 3007:9020 | 3007:9021 | 3007:9022 | 3007:9023 |
| 3008:9018 | 3008:9019 | 3008:9020 | 3008:9021 | 3008:9022 | 3008:9023 |
| 3009:9018 | 3009:9019 | 3009:9020 | 3009:9021 | 3009:9022 | 3009:9023 |
| 3010:9018 | 3010:9019 | 3010:9020 | 3010:9021 | 3010:9022 | 3010:9023 |
| 3011:9018 | 3011:9019 | 3011:9020 | 3011:9021 | 3011:9022 | 3011:9023 |
| 3012:9018 | 3012:9019 | 3012:9020 | 3012:9021 | 3012:9022 | 3012:9023 |
| 3013:9018 | 3013:9019 | 3013:9020 | 3013:9021 | 3013:9022 | 3013:9023 |
| 3014:9018 | 3014:9019 | 3014:9020 | 3014:9021 | 3014:9022 | 3014:9023 |
| 4001:9018 | 4001:9019 | 4001:9020 | 4001:9021 | 4001:9022 | 4001:9023 |
| 4002:9018 | 4002:9019 | 4002:9020 | 4002:9021 | 4002:9022 | 4002:9023 |
| 4003:9018 | 4003:9019 | 4003:9020 | 4003:9021 | 4003:9022 | 4003:9023 |
| 4004:9018 | 4004:9019 | 4004:9020 | 4004:9021 | 4004:9022 | 4004:9023 |
| 4005:9018 | 4005:9019 | 4005:9020 | 4005:9021 | 4005:9022 | 4005:9023 |
| 4006:9018 | 4006:9019 | 4006:9020 | 4006:9021 | 4006:9022 | 4006:9023 |
| 4007:9018 | 4007:9019 | 4007:9020 | 4007:9021 | 4007:9022 | 4007:9023 |
| 4008:9018 | 4008:9019 | 4008:9020 | 4008:9021 | 4008:9022 | 4008:9023 |
| 4009:9018 | 4009:9019 | 4009:9020 | 4009:9021 | 4009:9022 | 4009:9023 |
| 4010:9018 | 4010:9019 | 4010:9020 | 4010:9021 | 4010:9022 | 4010:9023 |
| 4011:9018 | 4011:9019 | 4011:9020 | 4011:9021 | 4011:9022 | 4011:9023 |
| 4012:9018 | 4012:9019 | 4012:9020 | 4012:9021 | 4012:9022 | 4012:9023 |
| 5001:9018 | 5001:9019 | 5001:9020 | 5001:9021 | 5001:9022 | 5001:9023 |
| 5002:9018 | 5002:9019 | 5002:9020 | 5002:9021 | 5002:9022 | 5002:9023 |
| 5003:9018 | 5003:9019 | 5003:9020 | 5003:9021 | 5003:9022 | 5003:9023 |
| 5004:9018 | 5004:9019 | 5004:9020 | 5004:9021 | 5004:9022 | 5004:9023 |
| 5005:9018 | 5005:9019 | 5005:9020 | 5005:9021 | 5005:9022 | 5005:9023 |
| 5006:9018 | 5006:9019 | 5006:9020 | 5006:9021 | 5006:9022 | 5006:9023 |
| 5007:9018 | 5007:9019 | 5007:9020 | 5007:9021 | 5007:9022 | 5007:9023 |
| 5008:9018 | 5008:9019 | 5008:9020 | 5008:9021 | 5008:9022 | 5008:9023 |
| 5009:9018 | 5009:9019 | 5009:9020 | 5009:9021 | 5009:9022 | 5009:9023 |
| 5010:9018 | 5010:9019 | 5010:9020 | 5010:9021 | 5010:9022 | 5010:9023 |
| 5011:9018 | 5011:9019 | 5011:9020 | 5011:9021 | 5011:9022 | 5011:9023 |
| 5012:9018 | 5012:9019 | 5012:9020 | 5012:9021 | 5012:9022 | 5012:9023 |

| X:Y | X:Y | X:Y | X:Y | X:Y | X:Y |
|---|---|---|---|---|---|
| 3001:9024 | 3001:9025 | 3001:9026 | 3001:9027 | 3001:9028 | 3001:9029 |
| 3002:9024 | 3002:9025 | 3002:9026 | 3002:9027 | 3002:9028 | 3002:9029 |
| 3003:9024 | 3003:9025 | 3003:9026 | 3003:9027 | 3003:9028 | 3003:9029 |
| 3004:9024 | 3004:9025 | 3004:9026 | 3004:9027 | 3004:9028 | 3004:9029 |
| 3005:9024 | 3005:9025 | 3005:9026 | 3005:9027 | 3005:9028 | 3005:9029 |
| 3006:9024 | 3006:9025 | 3006:9026 | 3006:9027 | 3006:9028 | 3006:9029 |
| 3007:9024 | 3007:9025 | 3007:9026 | 3007:9027 | 3007:9028 | 3007:9029 |
| 3008:9024 | 3008:9025 | 3008:9026 | 3008:9027 | 3008:9028 | 3008:9029 |
| 3009:9024 | 3009:9025 | 3009:9026 | 3009:9027 | 3009:9028 | 3009:9029 |
| 3010:9024 | 3010:9025 | 3010:9026 | 3010:9027 | 3010:9028 | 3010:9029 |
| 3011:9024 | 3011:9025 | 3011:9026 | 3011:9027 | 3011:9028 | 3011:9029 |
| 3012:9024 | 3012:9025 | 3012:9026 | 3012:9027 | 3012:9028 | 3012:9029 |
| 3013:9024 | 3013:9025 | 3013:9026 | 3013:9027 | 3013:9028 | 3013:9029 |
| 3014:9024 | 3014:9025 | 3014:9026 | 3014:9027 | 3014:9028 | 3014:9029 |
| 4001:9024 | 4001:9025 | 4001:9026 | 4001:9027 | 4001:9028 | 4001:9029 |
| 4002:9024 | 4002:9025 | 4002:9026 | 4002:9027 | 4002:9028 | 4002:9029 |
| 4003:9024 | 4003:9025 | 4003:9026 | 4003:9027 | 4003:9028 | 4003:9029 |
| 4004:9024 | 4004:9025 | 4004:9026 | 4004:9027 | 4004:9028 | 4004:9029 |
| 4005:9024 | 4005:9025 | 4005:9026 | 4005:9027 | 4005:9028 | 4005:9029 |
| 4006:9024 | 4006:9025 | 4006:9026 | 4006:9027 | 4006:9028 | 4006:9029 |
| 4007:9024 | 4007:9025 | 4007:9026 | 4007:9027 | 4007:9028 | 4007:9029 |
| 4008:9024 | 4008:9025 | 4008:9026 | 4008:9027 | 4008:9028 | 4008:9029 |
| 4009:9024 | 4009:9025 | 4009:9026 | 4009:9027 | 4009:9028 | 4009:9029 |
| 4010:9024 | 4010:9025 | 4010:9026 | 4010:9027 | 4010:9028 | 4010:9029 |
| 4011:9024 | 4011:9025 | 4011:9026 | 4011:9027 | 4011:9028 | 4011:9029 |
| 4012:9024 | 4012:9025 | 4012:9026 | 4012:9027 | 4012:9028 | 4012:9029 |
| 5001:9024 | 5001:9025 | 5001:9026 | 5001:9027 | 5001:9028 | 5001:9029 |
| 5002:9024 | 5002:9025 | 5002:9026 | 5002:9027 | 5002:9028 | 5002:9029 |
| 5003:9024 | 5003:9025 | 5003:9026 | 5003:9027 | 5003:9028 | 5003:9029 |
| 5004:9024 | 5004:9025 | 5004:9026 | 5004:9027 | 5004:9028 | 5004:9029 |
| 5005:9024 | 5005:9025 | 5005:9026 | 5005:9027 | 5005:9028 | 5005:9029 |
| 5006:9024 | 5006:9025 | 5006:9026 | 5006:9027 | 5006:9028 | 5006:9059 |
| 5007:9024 | 5007:9025 | 5007:9026 | 5007:9027 | 5007:9028 | 5007:9029 |
| 5008:9024 | 5008:9025 | 5008:9026 | 5008:9027 | 5008:9028 | 5008:9029 |
| 5009:9024 | 5009:9025 | 5009:9026 | 5009:9027 | 5009:9028 | 5009:9029 |
| 5010:9024 | 5010:9025 | 5010:9026 | 5010:9027 | 5010:9028 | 5010:9029 |
| 5011:9024 | 5011:9025 | 5011:9026 | 5011:9027 | 5011:9028 | 5011:9029 |
| 5012:9024 | 5012:9025 | 5012:9026 | 5012:9027 | 5012:9028 | 5012:9029 |

| X:Y | X:Y | X:Y | X:Y | X:Y | X:Y |
|---|---|---|---|---|---|
| 3001:9030 | 3001:9031 | 3001:9032 | 3001:9033 | 3001:9034 | 3001:9035 |
| 3002:9030 | 3002:9031 | 3002:9032 | 3002:9033 | 3002:9034 | 3002:9035 |
| 3003:9030 | 3003:9031 | 3003:9032 | 3003:9033 | 3003:9034 | 3003:9035 |
| 3004:9030 | 3004:9031 | 3004:9032 | 3004:9033 | 3004:9034 | 3004:9035 |
| 3005:9030 | 3005:9031 | 3005:9032 | 3005:9033 | 3005:9034 | 3005:9035 |
| 3006:9030 | 3006:9031 | 3006:9032 | 3006:9033 | 3006:9034 | 3006:9035 |
| 3007:9030 | 3007:9031 | 3007:9032 | 3007:9033 | 3007:9034 | 3007:9035 |
| 3008:9030 | 3008:9031 | 3008:9032 | 3008:9033 | 3008:9034 | 3008:9035 |
| 3009:9030 | 3009:9031 | 3009:9032 | 3009:9033 | 3009:9034 | 3009:9035 |
| 3010:9030 | 3010:9031 | 3010:9032 | 3010:9033 | 3010:9034 | 3010:9035 |
| 3011:9030 | 3011:9031 | 3011:9032 | 3011:9033 | 3011:9034 | 3011:9035 |
| 3012:9030 | 3012:9031 | 3012:9032 | 3012:9033 | 3012:9034 | 3012:9035 |
| 3013:9030 | 3013:9031 | 3013:9032 | 3013:9033 | 3013:9034 | 3013:9035 |
| 3014:9030 | 3014:9031 | 3014:9032 | 3014:9033 | 3014:9034 | 3014:9035 |
| 4001:9030 | 4001:9031 | 4001:9032 | 4001:9033 | 4001:9034 | 4001:9035 |
| 4002:9030 | 4002:9031 | 4002:9032 | 4002:9033 | 4002:9034 | 4002:9035 |
| 4003:9030 | 4003:9031 | 4003:9032 | 4003:9033 | 4003:9034 | 4003:9035 |
| 4004:9030 | 4004:9031 | 4004:9032 | 4004:9033 | 4004:9034 | 4004:9035 |
| 4005:9030 | 4005:9031 | 4005:9032 | 4005:9033 | 4005:9034 | 4005:9035 |
| 4006:9030 | 4006:9031 | 4006:9032 | 4006:9033 | 4006:9034 | 4006:9035 |
| 4007:9030 | 4007:9031 | 4007:9032 | 4007:9033 | 4007:9034 | 4007:9035 |
| 4008:9030 | 4008:9031 | 4008:9032 | 4008:9033 | 4008:9034 | 4008:9035 |
| 4009:9030 | 4009:9031 | 4009:9032 | 4009:9033 | 4009:9034 | 4009:9035 |
| 4010:9030 | 4010:9031 | 4010:9032 | 4010:9033 | 4010:9034 | 4010:9035 |
| 4011:9030 | 4011:9031 | 4011:9032 | 4011:9033 | 4011:9034 | 4011:9035 |
| 4012:9030 | 4012:9031 | 4012:9032 | 4012:9033 | 4012:9034 | 4012:9035 |
| 5001:9030 | 5001:9031 | 5001:9032 | 5001:9033 | 5001:9034 | 5001:9035 |
| 5002:9030 | 5002:9031 | 5002:9032 | 5002:9033 | 5002:9034 | 5002:9035 |
| 5003:9030 | 5003:9031 | 5003:9032 | 5003:9033 | 5003:9034 | 5003:9035 |
| 5004:9030 | 5004:9031 | 5004:9032 | 5004:9033 | 5004:9034 | 5004:9035 |
| 5005:9030 | 5005:9031 | 5005:9032 | 5005:9033 | 5005:9034 | 5005:9035 |
| 5006:9030 | 5006:9031 | 5006:9032 | 5006:9033 | 5006:9034 | 5006:9035 |
| 5007:9030 | 5007:9031 | 5007:9032 | 5007:9033 | 5007:9034 | 5007:9035 |
| 5008:9030 | 5008:9031 | 5008:9032 | 5008:9033 | 5008:9034 | 5008:9035 |
| 5009:9030 | 5009:9031 | 5009:9032 | 5009:9033 | 5009:9034 | 5009:9035 |
| 5010:9030 | 5010:9031 | 5010:9032 | 5010:9033 | 5010:9034 | 5010:9035 |
| 5011:9030 | 5011:9031 | 5011:9032 | 5011:9033 | 5011:9034 | 5011:9035 |
| 5012:9030 | 5012:9031 | 5012:9032 | 5012:9033 | 5012:9034 | 5012:9035 |

| X:Y | X:Y | X:Y | X:Y | X:Y | X:Y |
|---|---|---|---|---|---|
| 3001:9036 | 3001:9037 | 3001:9038 | 3001:9039 | 3001:9040 | 3001:9041 |
| 3002:9036 | 3002:9037 | 3002:9038 | 3002:9039 | 3002:9040 | 3002:9041 |
| 3003:9036 | 3003:9037 | 3003:9038 | 3003:9039 | 3003:9040 | 3003:9041 |
| 3004:9036 | 3004:9037 | 3004:9038 | 3004:9039 | 3004:9040 | 3004:9041 |
| 3005:9036 | 3005:9037 | 3005:9038 | 3005:9039 | 3005:9040 | 3005:9041 |
| 3006:9036 | 3006:9037 | 3006:9038 | 3006:9039 | 3006:9040 | 3006:9041 |
| 3007:9036 | 3007:9037 | 3007:9038 | 3007:9039 | 3007:9040 | 3007:9041 |
| 3008:9036 | 3008:9037 | 3008:9038 | 3008:9039 | 3008:9040 | 3008:9041 |
| 3009:9036 | 3009:9037 | 3009:9038 | 3009:9039 | 3009:9040 | 3009:9041 |
| 3010:9036 | 3010:9037 | 3010:9038 | 3010:9039 | 3010:9040 | 3010:9041 |
| 3011:9036 | 3011:9037 | 3011:9038 | 3011:9039 | 3011:9040 | 3011:9041 |
| 3012:9036 | 3012:9037 | 3012:9038 | 3012:9039 | 3012:9040 | 3012:9041 |
| 3013:9036 | 3013:9037 | 3013:9038 | 3013:9039 | 3013:9040 | 3013:9041 |
| 3014:9036 | 3014:9037 | 3014:9038 | 3014:9039 | 3014:9040 | 3014:9041 |
| 4001:9036 | 4001:9037 | 4001:9038 | 4001:9039 | 4001:9040 | 4001:9041 |
| 4002:9036 | 4002:9037 | 4002:9038 | 4002:9039 | 4002:9040 | 4002:9041 |
| 4003:9036 | 4003:9037 | 4003:9038 | 4003:9039 | 4003:9040 | 4003:9041 |
| 4004:9036 | 4004:9037 | 4004:9038 | 4004:9039 | 4004:9040 | 4004:9041 |
| 4005:9036 | 4005:9037 | 4005:9038 | 4005:9039 | 4005:9040 | 4005:9041 |
| 4006:9036 | 4006:9037 | 4006:9038 | 4006:9039 | 4006:9040 | 4006:9041 |
| 4007:9036 | 4007:9037 | 4007:9038 | 4007:9039 | 4007:9040 | 4007:9041 |
| 4008:9036 | 4008:9037 | 4008:9038 | 4008:9039 | 4008:9040 | 4008:9041 |
| 4009:9036 | 4009:9037 | 4009:9038 | 4009:9039 | 4009:9040 | 4009:9041 |
| 4010:9036 | 4010:9037 | 4010:9038 | 4010:9039 | 4010:9040 | 4010:9041 |
| 4011:9036 | 4011:9037 | 4011:9038 | 4011:9039 | 4011:9040 | 4011:9041 |
| 4012:9036 | 4012:9037 | 4012:9038 | 4012:9039 | 4012:9040 | 4012:9041 |
| 5001:9036 | 5001:9037 | 5001:9038 | 5001:9039 | 5001:9040 | 5001:9041 |
| 5002:9036 | 5002:9037 | 5002:9038 | 5002:9039 | 5002:9040 | 5002:9041 |
| 5003:9036 | 5003:9037 | 5003:9038 | 5003:9039 | 5003:9040 | 5003:9041 |
| 5004:9036 | 5004:9037 | 5004:9038 | 5004:9039 | 5004:9040 | 5004:9041 |
| 5005:9036 | 5005:9037 | 5005:9038 | 5005:9039 | 5005:9040 | 5005:9041 |
| 5006:9036 | 5006:9037 | 5006:9038 | 5006:9039 | 5006:9040 | 5006:9041 |

TABLE B-continued

Example combinations of a compound X with a compound Y.

| | | | | | |
|---|---|---|---|---|---|
| 5007:9036 | 5007:9037 | 5007:9038 | 5007:9039 | 5007:9040 | 5007:9041 |
| 5008:9036 | 5008:9037 | 5008:9038 | 5008:9039 | 5008:9040 | 5008:9041 |
| 5009:9036 | 5009:9037 | 5009:9038 | 5009:9039 | 5009:9040 | 5009:9041 |
| 5010:9036 | 5010:9037 | 5010:9038 | 5010:9039 | 5010:9040 | 5010:9041 |
| 5011:9036 | 5011:9037 | 5011:9038 | 5011:9039 | 5011:9040 | 5011:9041 |
| 5012:9036 | 5012:9037 | 5012:9038 | 5012:9039 | 5012:9040 | 5012:9041 |

| X:Y | X:Y | X:Y | X:Y | X:Y | X:Y |
|---|---|---|---|---|---|
| 3001:9042 | 3001:9043 | 3001:9044 | 3001:9045 | 3001:9046 | 3001:9047 |
| 3002:9042 | 3002:9043 | 3002:9044 | 3002:9045 | 3002:9046 | 3002:9047 |
| 3003:9042 | 3003:9043 | 3003:9044 | 3003:9045 | 3003:9046 | 3003:9047 |
| 3004:9042 | 3004:9043 | 3004:9044 | 3004:9045 | 3004:9046 | 3004:9047 |
| 3005:9042 | 3005:9043 | 3005:9044 | 3005:9045 | 3005:9046 | 3005:9047 |
| 3006:9042 | 3006:9043 | 3006:9044 | 3006:9045 | 3006:9046 | 3006:9047 |
| 3007:9042 | 3007:9043 | 3007:9044 | 3007:9045 | 3007:9046 | 3007:9047 |
| 3008:9042 | 3008:9043 | 3008:9044 | 3008:9045 | 3008:9046 | 3008:9047 |
| 3009:9042 | 3009:9043 | 3009:9044 | 3009:9045 | 3009:9046 | 3009:9047 |
| 3010:9042 | 3010:9043 | 3010:9044 | 3010:9045 | 3010:9046 | 3010:9047 |
| 3011:9042 | 3011:9043 | 3011:9044 | 3011:9045 | 3011:9046 | 3011:9047 |
| 3012:9042 | 3012:9043 | 3012:9044 | 3012:9045 | 3012:9046 | 3012:9047 |
| 3013:9042 | 3013:9043 | 3013:9044 | 3013:9045 | 3013:9046 | 3013:9047 |
| 3014:9042 | 3014:9043 | 3014:9044 | 3014:9045 | 3014:9046 | 3014:9047 |
| 4001:9042 | 4001:9043 | 4001:9044 | 4001:9045 | 4001:9046 | 4001:9047 |
| 4002:9042 | 4002:9043 | 4002:9044 | 4002:9045 | 4002:9046 | 4002:9047 |
| 4003:9042 | 4003:9043 | 4003:9044 | 4003:9045 | 4003:9046 | 4003:9047 |
| 4004:9042 | 4004:9043 | 4004:9044 | 4004:9045 | 4004:9046 | 4004:9047 |
| 4005:9042 | 4005:9043 | 4005:9044 | 4005:9045 | 4005:9046 | 4005:9047 |
| 4006:9042 | 4006:9043 | 4006:9044 | 4006:9045 | 4006:9046 | 4006:9047 |
| 4007:9042 | 4007:9043 | 4007:9044 | 4007:9045 | 4007:9046 | 4007:9047 |
| 4008:9042 | 4008:9043 | 4008:9044 | 4008:9045 | 4008:9046 | 4008:9047 |
| 4009:9042 | 4009:9043 | 4009:9044 | 4009:9045 | 4009:9046 | 4009:9047 |
| 4010:9042 | 4010:9043 | 4010:9044 | 4010:9045 | 4010:9046 | 4010:9047 |
| 4011:9042 | 4011:9043 | 4011:9044 | 4011:9045 | 4011:9046 | 4011:9047 |
| 4012:9042 | 4012:9043 | 4012:9044 | 4012:9045 | 4012:9046 | 4012:9047 |
| 5001:9042 | 5001:9043 | 5001:9044 | 5001:9045 | 5001:9046 | 5001:9047 |
| 5002:9042 | 5002:9043 | 5002:9044 | 5002:9045 | 5002:9046 | 5002:9047 |
| 5003:9042 | 5003:9043 | 5003:9044 | 5003:9045 | 5003:9046 | 5003:9047 |
| 5004:9042 | 5004:9043 | 5004:9044 | 5004:9045 | 5004:9046 | 5004:9047 |
| 5005:9042 | 5005:9043 | 5005:9044 | 5005:9045 | 5005:9046 | 5005:9047 |
| 5006:9042 | 5006:9043 | 5006:9044 | 5006:9045 | 5006:9046 | 5006:9047 |
| 5007:9042 | 5007:9043 | 5007:9044 | 5007:9045 | 5007:9046 | 5007:9047 |
| 5008:9042 | 5008:9043 | 5008:9044 | 5008:9045 | 5008:9046 | 5008:9047 |
| 5009:9042 | 5009:9043 | 5009:9044 | 5009:9045 | 5009:9046 | 5009:9047 |
| 5010:9042 | 5010:9043 | 5010:9044 | 5010:9045 | 5010:9046 | 5010:9047 |
| 5011:9042 | 5011:9043 | 5011:9044 | 5011:9045 | 5011:9046 | 5011:9047 |
| 5012:9042 | 5012:9043 | 5012:9044 | 5012:9045 | 5012:9046 | 5012:9047 |

| X:Y | X:Y | X:Y | X:Y | X:Y | X:Y |
|---|---|---|---|---|---|
| 3001:9048 | 3001:9049 | 3001:9050 | 3001:9051 | 3001:9052 | 3001:9053 |
| 3002:9048 | 3002:9049 | 3002:9050 | 3002:9051 | 3002:9052 | 3002:9053 |
| 3003:9048 | 3003:9049 | 3003:9050 | 3003:9051 | 3003:9052 | 3003:9053 |
| 3004:9048 | 3004:9049 | 3004:9050 | 3004:9051 | 3004:9052 | 3004:9053 |
| 3005:9048 | 3005:9049 | 3005:9050 | 3005:9051 | 3005:9052 | 3005:9053 |
| 3006:9048 | 3006:9049 | 3006:9050 | 3006:9051 | 3006:9052 | 3006:9053 |
| 3007:9048 | 3007:9049 | 3007:9050 | 3007:9051 | 3007:9052 | 3007:9053 |
| 3008:9048 | 3008:9049 | 3008:9050 | 3008:9051 | 3008:9052 | 3008:9053 |
| 3009:9048 | 3009:9049 | 3009:9050 | 3009:9051 | 3009:9052 | 3009:9053 |
| 3010:9048 | 3010:9049 | 3010:9050 | 3010:9051 | 3010:9052 | 3010:9053 |
| 3011:9048 | 3011:9049 | 3011:9050 | 3011:9051 | 3011:9052 | 3011:9053 |
| 3012:9048 | 3012:9049 | 3012:9050 | 3012:9051 | 3012:9052 | 3012:9053 |
| 3013:9048 | 3013:9049 | 3013:9050 | 3013:9051 | 3013:9052 | 3013:9053 |
| 3014:9048 | 3014:9049 | 3014:9050 | 3014:9051 | 3014:9052 | 3014:9053 |
| 4001:9048 | 4001:9049 | 4001:9050 | 4001:9051 | 4001:9052 | 4001:9053 |
| 4002:9048 | 4002:9049 | 4002:9050 | 4002:9051 | 4002:9052 | 4002:9053 |
| 4003:9048 | 4003:9049 | 4003:9050 | 4003:9051 | 4003:9052 | 4003:9053 |
| 4004:9048 | 4004:9049 | 4004:9050 | 4004:9051 | 4004:9052 | 4004:9053 |
| 4005:9048 | 4005:9049 | 4005:9050 | 4005:9051 | 4005:9052 | 4005:9053 |
| 4006:9048 | 4006:9049 | 4006:9050 | 4006:9051 | 4006:9052 | 4006:9053 |
| 4007:9048 | 4007:9049 | 4007:9050 | 4007:9051 | 4007:9052 | 4007:9053 |
| 4008:9048 | 4008:9049 | 4008:9050 | 4008:9051 | 4008:9052 | 4008:9053 |
| 4009:9048 | 4009:9049 | 4009:9050 | 4009:9051 | 4009:9052 | 4009:9053 |
| 4010:9048 | 4010:9049 | 4010:9050 | 4010:9051 | 4010:9052 | 4010:9053 |
| 4011:9048 | 4011:9049 | 4011:9050 | 4011:9051 | 4011:9052 | 4011:9053 |
| 4012:9048 | 4012:9049 | 4012:9050 | 4012:9051 | 4012:9052 | 4012:9053 |
| 5001:9048 | 5001:9049 | 5001:9050 | 5001:9051 | 5001:9052 | 5001:9053 |
| 5002:9048 | 5002:9049 | 5002:9050 | 5002:9051 | 5002:9052 | 5002:9053 |
| 5003:9048 | 5003:9049 | 5003:9050 | 5003:9051 | 5003:9052 | 5003:9053 |
| 5004:9048 | 5004:9049 | 5004:9050 | 5004:9051 | 5004:9052 | 5004:9053 |
| 5005:9048 | 5005:9049 | 5005:9050 | 5005:9051 | 5005:9052 | 5005:9053 |
| 5006:9048 | 5006:9049 | 5006:9050 | 5006:9051 | 5006:9052 | 5006:9053 |
| 5007:9048 | 5007:9049 | 5007:9050 | 5007:9051 | 5007:9052 | 5007:9053 |
| 5008:9048 | 5008:9049 | 5008:9050 | 5008:9051 | 5008:9052 | 5008:9053 |
| 5009:9048 | 5009:9049 | 5009:9050 | 5009:9051 | 5009:9052 | 5009:9053 |
| 5010:9048 | 5010:9049 | 5010:9050 | 5010:9051 | 5010:9052 | 5010:9053 |
| 5011:9048 | 5011:9049 | 5011:9050 | 5011:9051 | 5011:9052 | 5011:9053 |
| 5012:9048 | 5012:9049 | 5012:9050 | 5012:9051 | 5012:9051 | 5012:9053 |

| X:Y | X:Y | X:Y | X:Y | X:Y | X:Y |
|---|---|---|---|---|---|
| 3001:9054 | 3001:9055 | 3001:9056 | 3001:9057 | 3001:9058 | 3001:9059 |
| 3002:9054 | 3002:9055 | 3002:9056 | 3002:9057 | 3002:9058 | 3002:9059 |
| 3003:9054 | 3003:9055 | 3003:9056 | 3003:9057 | 3003:9058 | 3003:9059 |
| 3004:9054 | 3004:9055 | 3004:9056 | 3004:9057 | 3004:9058 | 3004:9059 |
| 3005:9054 | 3005:9055 | 3005:9056 | 3005:9057 | 3005:9058 | 3005:9059 |
| 3006:9054 | 3006:9055 | 3006:9056 | 3006:9057 | 3006:9058 | 3006:9059 |
| 3007:9054 | 3007:9055 | 3007:9056 | 3007:9057 | 3007:9058 | 3007:9059 |
| 3008:9054 | 3008:9055 | 3008:9056 | 3008:9057 | 3008:9058 | 3008:9059 |
| 3009:9054 | 3009:9055 | 3009:9056 | 3009:9057 | 3009:9058 | 3009:9059 |
| 3010:9054 | 3010:9055 | 3010:9056 | 3010:9057 | 3010:9058 | 3010:9059 |
| 3011:9054 | 3011:9055 | 3011:9056 | 3011:9057 | 3011:9058 | 3011:9059 |
| 3012:9054 | 3012:9055 | 3012:9056 | 3012:9057 | 3012:9058 | 3012:9059 |
| 3013:9054 | 3013:9055 | 3013:9056 | 3013:9057 | 3013:9058 | 3013:9059 |
| 3014:9054 | 3014:9055 | 3014:9056 | 3014:9057 | 3014:9058 | 3014:9059 |
| 4001:9054 | 4001:9055 | 4001:9056 | 4001:9057 | 4001:9058 | 4001:9059 |
| 4002:9054 | 4002:9055 | 4002:9056 | 4002:9057 | 4002:9058 | 4002:9059 |
| 4003:9054 | 4003:9055 | 4003:9056 | 4003:9057 | 4003:9058 | 4003:9059 |
| 4004:9054 | 4004:9055 | 4004:9056 | 4004:9057 | 4004:9058 | 4004:9059 |
| 4005:9054 | 4005:9055 | 4005:9056 | 4005:9057 | 4005:9058 | 4005:9059 |
| 4006:9054 | 4006:9055 | 4006:9056 | 4006:9057 | 4006:9058 | 4006:9059 |
| 4007:9054 | 4007:9055 | 4007:9056 | 4007:9057 | 4007:9058 | 4007:9059 |
| 4008:9054 | 4008:9055 | 4008:9056 | 4008:9057 | 4008:9058 | 4008:9059 |
| 4009:9054 | 4009:9055 | 4009:9056 | 4009:9057 | 4009:9058 | 4009:9059 |
| 4010:9054 | 4010:9055 | 4010:9056 | 4010:9057 | 4010:9058 | 4010:9059 |
| 4011:9054 | 4011:9055 | 4011:9056 | 4011:9057 | 4011:9058 | 4011:9059 |
| 4012:9054 | 4012:9055 | 4012:9056 | 4012:9057 | 4012:9058 | 4012:9059 |
| 5001:9054 | 5001:9055 | 5001:9056 | 5001:9057 | 5001:9058 | 5001:9059 |
| 5002:9054 | 5002:9055 | 5002:9056 | 5002:9057 | 5002:9058 | 5002:9059 |
| 5003:9054 | 5003:9055 | 5003:9056 | 5003:9057 | 5003:9058 | 5003:9059 |
| 5004:9054 | 5004:9055 | 5004:9056 | 5004:9057 | 5004:9058 | 5004:9059 |
| 5005:9054 | 5005:9055 | 5005:9056 | 5005:9057 | 5005:9058 | 5005:9059 |
| 5006:9054 | 5006:9055 | 5006:9056 | 5006:9057 | 5006:9058 | 5006:9059 |
| 5007:9054 | 5007:9055 | 5007:9056 | 5007:9057 | 5007:9058 | 5007:9059 |
| 5008:9054 | 5008:9055 | 5008:9056 | 5008:9057 | 5008:9058 | 5008:9059 |
| 2009:9054 | 5009:9055 | 5009:9056 | 5009:9057 | 5009:9058 | 5009:9059 |
| 5010:9054 | 5010:9055 | 5010:9056 | 5010:9057 | 5010:9058 | 5010:9059 |
| 5011:9054 | 5011:9055 | 5011:9056 | 5011:9057 | 5011:9058 | 5011:9059 |
| 5012:9054 | 5012:9055 | 5012:9056 | 5012:9057 | 5012:9058 | 5012:9059 |

| X:Y | X:Y | X:Y | X:Y | X:Y | X:Y |
|---|---|---|---|---|---|
| 3001:9060 | 3001:9061 | 3001:9062 | 3001:9063 | 3001:9064 | 3001:9065 |
| 3002:9060 | 3002:9061 | 3002:9062 | 3002:9063 | 3002:9064 | 3002:9065 |
| 3003:9060 | 3003:9061 | 3003:9062 | 3003:9063 | 3003:9064 | 3003:9065 |
| 3004:9060 | 3004:9061 | 3004:9062 | 3004:9063 | 3004:9064 | 3004:9065 |
| 3005:9060 | 3005:9061 | 3005:9062 | 3005:9063 | 3005:9064 | 3005:9065 |
| 3006:9060 | 3006:9061 | 3006:9062 | 3006:9063 | 3006:9064 | 3006:9065 |
| 3007:9060 | 3007:9061 | 3007:9062 | 3007:9063 | 3007:9064 | 3007:9065 |
| 3008:9060 | 3008:9061 | 3008:9062 | 3008:9063 | 3008:9064 | 3008:9065 |
| 3009:9060 | 3009:9061 | 3009:9062 | 3009:9063 | 3009:9064 | 3009:9065 |
| 3010:9060 | 3010:9061 | 3010:9062 | 3010:9063 | 3010:9064 | 3010:9065 |
| 3011:9060 | 3011:9061 | 3011:9062 | 3011:9063 | 3011:9064 | 3011:9065 |
| 3012:9060 | 3012:9061 | 3012:9062 | 3012:9063 | 3012:9064 | 3012:9065 |
| 3013:9060 | 3013:9061 | 3013:9062 | 3013:9063 | 3013:9064 | 3013:9065 |
| 3014:9060 | 3014:9061 | 3014:9062 | 3014:9063 | 3014:9064 | 3014:9065 |
| 4001:9060 | 4001:9061 | 4001:9062 | 4001:9063 | 4001:9064 | 4001:9065 |
| 4002:9060 | 4002:9061 | 4002:9062 | 4002:9063 | 4002:9064 | 4002:9065 |
| 4003:9060 | 4003:9061 | 4003:9062 | 4003:9063 | 4003:9064 | 4003:9065 |
| 4004:9060 | 4004:9061 | 4004:9062 | 4004:9063 | 4004:9064 | 4004:9065 |
| 4005:9060 | 4005:9061 | 4005:9062 | 4005:9063 | 4005:9064 | 4005:9065 |
| 4006:9060 | 4006:9061 | 4006:9062 | 4006:9063 | 4006:9064 | 4006:9065 |
| 4007:9060 | 4007:9061 | 4007:9062 | 4007:9063 | 4007:9064 | 4007:9065 |
| 4008:9060 | 4008:9061 | 4008:9062 | 4008:9063 | 4008:9064 | 4008:9065 |
| 4009:9060 | 4009:9061 | 4009:9062 | 4009:9063 | 4009:9064 | 4009:9065 |
| 4010:9060 | 4010:9061 | 4010:9062 | 4010:9063 | 4010:9064 | 4010:9065 |

TABLE B-continued

Example combinations of a compound X with a compound Y.

| | | | | | |
|---|---|---|---|---|---|
| 4011:9060 | 4011:9061 | 4011:9062 | 4011:9063 | 4011:9064 | 4011:9065 |
| 4012:9060 | 4012:9061 | 4012:9062 | 4012:9063 | 4012:9064 | 4012:9065 |
| 5001:9060 | 5001:9061 | 5001:9062 | 5001:9063 | 5001:9064 | 5001:9065 |
| 5002:9060 | 5002:9061 | 5002:9062 | 5002:9063 | 5002:9064 | 5002:9065 |
| 5003:9060 | 5003:9061 | 5003:9062 | 5003:9063 | 5003:9064 | 5003:9065 |
| 5004:9060 | 5004:9061 | 5004:9062 | 5004:9063 | 5004:9064 | 5004:9065 |
| 5005:9060 | 5005:9061 | 5005:9062 | 5005:9063 | 5005:9064 | 5005:9065 |
| 5006:9060 | 5006:9061 | 5006:9062 | 5006:9063 | 5006:9064 | 5006:9065 |
| 5007:9060 | 5007:9061 | 5007:9062 | 5007:9063 | 5007:9064 | 5007:9065 |
| 5008:9060 | 5008:9061 | 5008:9062 | 5008:9063 | 5008:9064 | 5008:9065 |
| 5009:9060 | 5009:9061 | 5009:9062 | 5009:9063 | 5009:9064 | 5009:9065 |
| 5010:9060 | 5010:9061 | 5010:9062 | 5010:9063 | 5010:9064 | 5010:9065 |
| 5011:9060 | 5011:9061 | 5011:9062 | 5011:9063 | 5011:9064 | 5011:9065 |
| 5012:9060 | 5012:9061 | 5012:9062 | 5012:9063 | 5012:9064 | 5012:9065 |

| X:Y | X:Y | X:Y | X:Y | X:Y | X:Y |
|---|---|---|---|---|---|
| 3001:9066 | 3001:9067 | 3001:9068 | 3001:9069 | 3001:9070 | 3001:9071 |
| 3002:9066 | 3002:9067 | 3002:9068 | 3002:9069 | 3002:9070 | 3002:9071 |
| 3003:9066 | 3003:9067 | 3003:9068 | 3003:9069 | 3003:9070 | 3003:9071 |
| 3004:9066 | 3004:9067 | 3004:9068 | 3004:9069 | 3004:9070 | 3004:9071 |
| 3005:9066 | 3005:9067 | 3005:9068 | 3005:9069 | 3005:9070 | 3005:9071 |
| 3006:9066 | 3006:9067 | 3006:9068 | 3006:9069 | 3006:9070 | 3006:9071 |
| 3007:9066 | 3007:9067 | 3007:9068 | 3007:9069 | 3007:9070 | 3007:9071 |
| 3008:9066 | 3008:9067 | 3008:9068 | 3008:9069 | 3008:9070 | 3008:9071 |
| 3009:9066 | 3009:9067 | 3009:9068 | 3009:9069 | 3009:9070 | 3009:9071 |
| 3010:9066 | 3010:9067 | 3010:9068 | 3010:9069 | 3010:9070 | 3010:9071 |
| 3011:9066 | 3011:9067 | 3011:9068 | 3011:9069 | 3011:9070 | 3011:9071 |
| 3012:9066 | 3012:9067 | 3012:9068 | 3012:9069 | 3012:9070 | 3012:9071 |
| 3013:9066 | 3013:9067 | 3013:9068 | 3013:9069 | 3013:9070 | 3013:9071 |
| 3014:9066 | 3014:9067 | 3014:9068 | 3014:9069 | 3014:9070 | 3014:9071 |
| 4001:9066 | 4001:9067 | 4001:9068 | 4001:9069 | 4001:9070 | 4001:9071 |
| 4002:9066 | 4002:9067 | 4002:9068 | 4002:9069 | 4002:9070 | 4002:9071 |
| 4003:9066 | 4003:9067 | 4003:9068 | 4003:9069 | 4003:9070 | 4003:9071 |
| 4004:9066 | 4004:9067 | 4004:9068 | 4004:9069 | 4004:9070 | 4004:9071 |
| 4005:9066 | 4005:9067 | 4005:9068 | 4005:9069 | 4005:9070 | 4005:9071 |
| 4006:9066 | 4006:9067 | 4006:9068 | 4006:9069 | 4006:9070 | 4006:9071 |
| 4007:9066 | 4007:9067 | 4007:9068 | 4007:9069 | 4007:9070 | 4007:9071 |
| 4008:9066 | 4008:9067 | 4008:9068 | 4008:9069 | 4008:9070 | 4008:9071 |
| 4009:9066 | 4009:9067 | 4009:9068 | 4009:9069 | 4009:9070 | 4009:9071 |
| 4010:9066 | 4010:9067 | 4010:9068 | 4010:9069 | 4010:9070 | 4010:9071 |
| 4011:9066 | 4011:9067 | 4011:9068 | 4011:9069 | 4011:9070 | 4011:9071 |
| 4012:9066 | 4012:9067 | 4012:9068 | 4012:9069 | 4012:9070 | 4012:9071 |
| 5001:9066 | 5001:9067 | 5001:9068 | 5001:9069 | 5001:9070 | 5001:9071 |
| 5002:9066 | 5002:9067 | 5002:9068 | 5002:9069 | 5002:9070 | 5002:9071 |
| 5003:9066 | 5003:9067 | 5003:9068 | 5003:9069 | 5003:9070 | 5003:9071 |
| 5004:9066 | 5004:9067 | 5004:9068 | 5004:9069 | 5003:9070 | 5003:9071 |
| 5005:9066 | 5005:9067 | 5005:9068 | 5005:9069 | 5005:9070 | 5005:9071 |
| 5006:9066 | 5006:9067 | 5006:9068 | 5006:9069 | 5006:9070 | 5006:9071 |
| 5007:9066 | 5007:9067 | 5007:9068 | 5007:9069 | 5007:9070 | 5007:9071 |
| 5008:9066 | 5008:9067 | 5008:9068 | 5008:9069 | 5008:9070 | 5008:9071 |
| 5009:9066 | 5009:9067 | 5009:9068 | 5009:9069 | 5009:9070 | 5009:9071 |
| 5010:9066 | 5010:9067 | 5010:9068 | 5010:9069 | 5010:9070 | 5010:9071 |
| 5011:9066 | 5011:9067 | 5011:9068 | 5011:9069 | 5011:9070 | 5011:9071 |
| 5012:9066 | 5012:9067 | 5012:9068 | 5012:9069 | 5012:9070 | 5012:9071 |

| X:Y | X:Y | X:Y | X:Y | X:Y | X:Y |
|---|---|---|---|---|---|
| 3001:9072 | 3001:9073 | 3001:9074 | 3001:9075 | 3001:9076 | 3001:9077 |
| 3002:9072 | 3002:9073 | 3002:9074 | 3002:9075 | 3002:9076 | 3002:9077 |
| 3003:9072 | 3003:9073 | 3003:9074 | 3003:9075 | 3003:9076 | 3003:9077 |
| 3004:9072 | 3004:9073 | 3004:9074 | 3004:9075 | 3004:9076 | 3004:9077 |
| 3005:9072 | 3005:9073 | 3005:9074 | 3005:9075 | 3005:9076 | 3005:9077 |
| 3006:9072 | 3006:9073 | 3006:9074 | 3006:9075 | 3006:9076 | 3006:9077 |
| 3007:9072 | 3007:9073 | 3007:9074 | 3007:9075 | 3007:9076 | 3007:9077 |
| 3008:9072 | 3008:9073 | 3008:9074 | 3008:9075 | 3008:9076 | 3008:9077 |
| 3009:9072 | 3009:9073 | 3009:9074 | 3009:9075 | 3009:9076 | 3009:9077 |
| 3010:9072 | 3010:9073 | 3010:9074 | 3010:9075 | 3010:9076 | 3010:9077 |
| 3011:9072 | 3011:9073 | 3011:9074 | 3011:9075 | 3011:9076 | 3011:9077 |
| 3012:9072 | 3012:9073 | 3012:9074 | 3012:9075 | 3012:9076 | 3012:9077 |
| 3013:9072 | 3013:9073 | 3013:9074 | 3013:9075 | 3013:9076 | 3013:9077 |
| 3014:9072 | 3014:9073 | 3014:9074 | 3014:9075 | 3014:9076 | 3014:9077 |
| 4001:9072 | 4001:9073 | 4001:9074 | 4001:9075 | 4001:9076 | 4001:9077 |
| 4002:9072 | 4002:9073 | 4002:9074 | 4002:9075 | 4002:9076 | 4002:9077 |
| 4003:9072 | 4003:9073 | 4003:9074 | 4003:9075 | 4003:9076 | 4003:9077 |
| 4004:9072 | 4004:9073 | 4004:9074 | 4004:9075 | 4004:9076 | 4004:9077 |
| 4005:9072 | 4005:9073 | 4005:9074 | 4005:9075 | 4005:9076 | 4005:9077 |
| 4006:9072 | 4006:9073 | 4006:9074 | 4006:9075 | 4006:9076 | 4006:9077 |
| 4007:9072 | 4007:9073 | 4007:9074 | 4007:9075 | 4007:9076 | 4007:9077 |
| 4008:9072 | 4008:9073 | 4008:9074 | 4008:9075 | 4008:9076 | 4008:9077 |
| 4009:9072 | 4009:9073 | 4009:9074 | 4009:9075 | 4009:9076 | 4009:9077 |
| 4010:9072 | 4010:9073 | 4010:9074 | 4010:9075 | 4010:9076 | 4010:9077 |
| 4011:9072 | 4011:9073 | 4011:9074 | 4011:9075 | 4011:9076 | 4011:9077 |
| 4012:9072 | 4012:9073 | 4012:9074 | 4012:9075 | 4012:9076 | 4012:9077 |
| 5001:9072 | 5001:9073 | 5001:9074 | 5001:9075 | 5001:9076 | 5001:9077 |
| 5002:9072 | 5002:9073 | 5002:9074 | 5002:9075 | 5002:9076 | 5002:9077 |
| 5003:9072 | 5003:9073 | 5003:9074 | 5003:9075 | 5003:9076 | 5003:9077 |
| 5004:9072 | 5004:9073 | 5004:9074 | 5004:9075 | 5004:9076 | 5004:9077 |
| 5005:9072 | 5005:9073 | 5005:9074 | 5005:9075 | 5005:9076 | 5005:9077 |
| 5006:9072 | 5006:9073 | 5006:9074 | 5006:9075 | 5006:9076 | 5006:9077 |
| 5007:9072 | 5007:9073 | 5007:9074 | 5007:9075 | 5007:9076 | 5007:9077 |
| 5008:9072 | 5008:9073 | 5008:9074 | 5008:9075 | 5008:9076 | 5008:9077 |
| 5009:9072 | 5009:9073 | 5009:9074 | 5009:9075 | 5009:9076 | 5009:9077 |
| 5010:9072 | 5010:9073 | 5010:9074 | 5010:9075 | 5010:9076 | 5010:9077 |
| 5011:9072 | 5011:9073 | 5011:9074 | 5011:9075 | 5011:9076 | 5011:9077 |
| 5012:9072 | 5012:9073 | 5012:9074 | 5012:9075 | 5012:9076 | 5012:9077 |

| X:Y | X:Y | X:Y | X:Y | X:Y | X:Y |
|---|---|---|---|---|---|
| 3001:9078 | 3001:9079 | 3001:9080 | 3001:9081 | 3001:9082 | 3001:9083 |
| 3002:9078 | 3002:9079 | 3002:9080 | 3002:9081 | 3002:9082 | 3002:9083 |
| 3003:9078 | 3003:9079 | 3003:9080 | 3003:9081 | 3003:9082 | 3003:9083 |
| 3004:9078 | 3004:9079 | 3004:9080 | 3004:9081 | 3004:9082 | 3004:9083 |
| 3005:9078 | 3005:9079 | 3005:9080 | 3005:9081 | 3005:9082 | 3005:9083 |
| 3006:9078 | 3006:9079 | 3006:9080 | 3006:9081 | 3006:9082 | 3006:9083 |
| 3007:9078 | 3007:9079 | 3007:9080 | 3007:9081 | 3007:9082 | 3007:9083 |
| 3008:9078 | 3008:9079 | 3008:9080 | 3008:9081 | 3008:9082 | 3008:9083 |
| 3009:9078 | 3009:9079 | 3009:9080 | 3009:9081 | 3009:9082 | 3009:9083 |
| 3010:9078 | 3010:9079 | 3010:9080 | 3010:9081 | 3010:9082 | 3010:9083 |
| 3011:9078 | 3011:9079 | 3011:9080 | 3011:9081 | 3011:9082 | 3011:9083 |
| 3012:9078 | 3012:9079 | 3012:9080 | 3012:9081 | 3012:9082 | 3012:9083 |
| 3013:9078 | 3013:9079 | 3013:9080 | 3013:9081 | 3013:9082 | 3013:9083 |
| 3014:9078 | 3014:9079 | 3014:9080 | 3014:9081 | 3014:9082 | 3014:9083 |
| 4001:9078 | 4001:9079 | 4001:9080 | 4001:9081 | 4001:9082 | 4001:9083 |
| 4002:9078 | 4002:9079 | 4002:9080 | 4002:9081 | 4002:9082 | 4002:9083 |
| 4003:9078 | 4003:9079 | 4003:9080 | 4003:9081 | 4003:9082 | 4003:9083 |
| 4004:9078 | 4004:9079 | 4004:9080 | 4004:9081 | 4004:9082 | 4004:9083 |
| 4005:9078 | 4005:9079 | 4005:9080 | 4005:9081 | 4005:9082 | 4005:9083 |
| 4006:9078 | 4006:9079 | 4006:9080 | 4006:9081 | 4006:9082 | 4006:9083 |
| 4007:9078 | 4007:9079 | 4007:9080 | 4007:9081 | 4007:9082 | 4007:9083 |
| 4008:9078 | 4008:9079 | 4008:9080 | 4008:9081 | 4008:9082 | 4008:9083 |
| 4009:9078 | 4009:9079 | 4009:9080 | 4009:9081 | 4009:9082 | 4009:9083 |
| 4010:9078 | 4010:9079 | 4010:9080 | 4010:9081 | 4010:9082 | 4010:9083 |
| 4011:9078 | 4011:9079 | 4011:9080 | 4011:9081 | 4011:9082 | 4011:9083 |
| 4012:9078 | 4012:9079 | 4012:9080 | 4012:9081 | 4012:9082 | 4012:9083 |
| 5001:9078 | 5001:9079 | 5001:9080 | 5001:9081 | 5001:9082 | 5001:9083 |
| 5002:9078 | 5002:9079 | 5002:9080 | 5002:9081 | 5002:9082 | 5002:9083 |
| 5003:9078 | 5003:9079 | 5003:9080 | 5003:9081 | 5003:9082 | 5003:9083 |
| 5004:9078 | 5004:9079 | 5004:9080 | 5004:9081 | 5004:9082 | 5004:9083 |
| 5005:9078 | 5005:9079 | 5005:9080 | 5005:9081 | 5005:9082 | 5005:9083 |
| 5006:9078 | 5006:9079 | 5006:9080 | 5006:9081 | 5006:9082 | 5006:9083 |
| 5007:9078 | 5007:9079 | 5007:9080 | 5007:9081 | 5007:9082 | 5007:9083 |
| 5008:9078 | 5008:9079 | 5008:9080 | 5008:9081 | 5008:9082 | 5008:9083 |
| 5009:9078 | 5009:9079 | 5009:9080 | 5009:9081 | 5009:9082 | 5009:9083 |
| 5010:9078 | 5010:9079 | 5010:9080 | 5010:9081 | 5010:9082 | 5010:9083 |
| 5011:9078 | 5011:9079 | 5011:9080 | 5011:9081 | 5011:9082 | 5011:9083 |
| 5012:9078 | 5012:9079 | 5012:9080 | 5012:9081 | 5012:9082 | 5012:9083 |

| X:Y | X:Y | X:Y | X:Y | X:Y | X:Y |
|---|---|---|---|---|---|
| 3001:9084 | 3001:9085 | 3001:9086 | 3001:9087 | 3001:9088 | 3001:9089 |
| 3002:9084 | 3002:9085 | 3002:9086 | 3002:9087 | 3002:9088 | 3002:9089 |
| 3003:9084 | 3003:9085 | 3003:9086 | 3003:9087 | 3003:9088 | 3003:9089 |
| 3004:9084 | 3004:9085 | 3004:9086 | 3004:9087 | 3004:9088 | 3004:9089 |
| 3005:9084 | 3005:9085 | 3005:9086 | 3005:9087 | 3005:9088 | 3005:9089 |
| 3006:9084 | 3006:9085 | 3006:9086 | 3006:9087 | 3006:9088 | 3006:9089 |
| 3007:9084 | 3007:9085 | 3007:9086 | 3007:9087 | 3007:9088 | 3007:9089 |
| 3008:9084 | 3008:9085 | 3008:9086 | 3008:9087 | 3008:9088 | 3008:9089 |
| 3009:9084 | 3009:9085 | 3009:9086 | 3009:9087 | 3009:9088 | 3009:9089 |
| 3010:9084 | 3010:9085 | 3010:9086 | 3010:9087 | 3010:9088 | 3010:9089 |
| 3011:9084 | 3011:9085 | 3011:9086 | 3011:9087 | 3011:9088 | 3011:9089 |
| 3012:9084 | 3012:9085 | 3012:9086 | 3012:9087 | 3012:9088 | 3012:9089 |
| 3013:9084 | 3013:9085 | 3013:9086 | 3013:9087 | 3013:9088 | 3013:9089 |
| 3014:9084 | 3014:9085 | 3014:9086 | 3014:9087 | 3014:9088 | 3014:9089 |
| 4001:9084 | 4001:9085 | 4001:9086 | 4001:9087 | 4001:9088 | 4001:9089 |
| 4002:9084 | 4002:9085 | 4002:9086 | 4002:9087 | 4002:9088 | 4002:9089 |

TABLE B-continued

Example combinations of a compound X with a compound Y.

| | | | | | |
|---|---|---|---|---|---|
| 4003:9084 | 4003:9085 | 4003:9086 | 4003:9087 | 4003:9088 | 4003:9089 |
| 4004:9084 | 4004:9085 | 4004:9086 | 4004:9087 | 4004:9088 | 4004:9089 |
| 4005:9084 | 4005:9085 | 4005:9086 | 4005:9087 | 4005:9088 | 4005:9089 |
| 4006:9084 | 4006:9085 | 4006:9086 | 4006:9087 | 4006:9088 | 4006:9089 |
| 4007:9084 | 4007:9085 | 4007:9086 | 4007:9087 | 4007:9088 | 4007:9089 |
| 4008:9084 | 4008:9085 | 4008:9086 | 4008:9087 | 4008:9088 | 4008:9089 |
| 4009:9084 | 4009:9085 | 4009:9086 | 4009:9087 | 4009:9088 | 4009:9089 |
| 4010:9084 | 4010:9085 | 4010:9086 | 4010:9087 | 4010:9088 | 4010:9089 |
| 4011:9084 | 4011:9085 | 4011:9086 | 4011:9087 | 4011:9088 | 4011:9089 |
| 4012:9084 | 4012:9085 | 4012:9086 | 4012:9087 | 4012:9088 | 4012:9089 |
| 5001:9084 | 5001:9085 | 5001:9086 | 5001:9087 | 5001:9088 | 5001:9089 |
| 5002:9084 | 5002:9085 | 5002:9086 | 5002:9087 | 5002:9088 | 5002:9089 |
| 5003:9084 | 5003:9085 | 5003:9086 | 5003:9087 | 5003:9088 | 5003:9089 |
| 5004:9084 | 5004:9085 | 5004:9086 | 5004:9087 | 5004:9088 | 5004:9089 |
| 5005:9084 | 5005:9085 | 5005:9086 | 5005:9087 | 5005:9088 | 5005:9089 |
| 5006:9084 | 5006:9085 | 5006:9086 | 5006:9087 | 5006:9088 | 5006:9089 |
| 5007:9084 | 5007:9085 | 5007:9086 | 5007:9087 | 5007:9088 | 5007:9089 |
| 5008:9084 | 5008:9085 | 5008:9086 | 5008:9087 | 5008:9088 | 5008:9089 |
| 5009:9084 | 5009:9085 | 5009:9086 | 5009:9087 | 5009:9088 | 5009:9089 |
| 5010:9084 | 5010:9085 | 5010:9086 | 5010:9087 | 5010:9088 | 5010:9089 |
| 5011:9084 | 5011:9085 | 5011:9086 | 5011:9087 | 5011:9088 | 5011:9089 |
| 5012:9084 | 5012:9085 | 5012:9086 | 5012:9087 | 5012:9088 | 5012:9089 |

| X:Y | X:Y | X:Y | X:Y | X:Y | X:Y |
|---|---|---|---|---|---|
| 3001:9090 | 3001:9091 | 3001:9092 | 3001:9093 | 3001:9094 | 3001:9095 |
| 3002:9090 | 3002:9091 | 3002:9092 | 3002:9093 | 3002:9094 | 3002:9095 |
| 3003:9090 | 3003:9091 | 3003:9092 | 3003:9093 | 3003:9094 | 3003:9095 |
| 3004:9090 | 3004:9091 | 3004:9092 | 3004:9093 | 3004:9094 | 3004:9095 |
| 3005:9090 | 3005:9091 | 3005:9092 | 3005:9093 | 3005:9094 | 3005:9095 |
| 3006:9090 | 3006:9091 | 3006:9092 | 3006:9093 | 3006:9094 | 3006:9095 |
| 3007:9090 | 3007:9091 | 3007:9092 | 3007:9093 | 3007:9094 | 3007:9095 |
| 3008:9090 | 3008:9091 | 3008:9092 | 3008:9093 | 3008:9094 | 3008:9095 |
| 3009:9090 | 3009:9091 | 3009:9092 | 3009:9093 | 3009:9094 | 3009:9095 |
| 3010:9090 | 3010:9091 | 3010:9092 | 3010:9093 | 3010:9094 | 3010:9095 |
| 3011:9090 | 3011:9091 | 3011:9092 | 3011:9093 | 3011:9094 | 3011:9095 |
| 3012:9090 | 3012:9091 | 3012:9092 | 3012:9093 | 3012:9094 | 3012:9095 |
| 3013:9090 | 3013:9091 | 3013:9092 | 3013:9093 | 3013:9094 | 3013:9095 |
| 3014:9090 | 3014:9091 | 3014:9092 | 3014:9093 | 3014:9094 | 3014:9095 |
| 4001:9090 | 4001:9091 | 4001:9092 | 4001:9093 | 4001:9094 | 4001:9095 |
| 4002:9090 | 4002:9091 | 4002:9092 | 4002:9093 | 4002:9094 | 4002:9095 |
| 4003:9090 | 4003:9091 | 4003:9092 | 4003:9093 | 4003:9094 | 4003:9095 |
| 4004:9090 | 4004:9091 | 4004:9092 | 4004:9093 | 4004:9094 | 4004:9095 |
| 4005:9090 | 4005:9091 | 4005:9092 | 4005:9093 | 4005:9094 | 4005:9095 |
| 4006:9090 | 4006:9091 | 4006:9092 | 4006:9093 | 4006:9094 | 4006:9095 |
| 4007:9090 | 4007:9091 | 4007:9092 | 4007:9093 | 4007:9094 | 4007:9095 |
| 4008:9090 | 4008:9091 | 4008:9092 | 4008:9093 | 4008:9094 | 4008:9095 |
| 4009:9090 | 4009:9091 | 4009:9092 | 4009:9093 | 4009:9094 | 4009:9095 |
| 4010:9090 | 4010:9091 | 4010:9092 | 4010:9093 | 4010:9094 | 4010:9095 |
| 4011:9090 | 4011:9091 | 4011:9092 | 4011:9093 | 4011:9094 | 4011:9095 |
| 4012:9090 | 4012:9091 | 4012:9092 | 4012:9093 | 4012:9094 | 4012:9095 |
| 5001:9090 | 5001:9091 | 5001:9092 | 5001:9093 | 5001:9094 | 5001:9095 |
| 5002:9090 | 5002:9091 | 5002:9092 | 5002:9093 | 5002:9094 | 5002:9095 |
| 5003:9090 | 5003:9091 | 5003:9092 | 5003:9093 | 5003:9094 | 5003:9095 |
| 5004:9090 | 5004:9091 | 5004:9092 | 5004:9093 | 5004:9094 | 5004:9095 |
| 5005:9090 | 5005:9091 | 5005:9092 | 5005:9093 | 5005:9094 | 5005:9095 |
| 5006:9090 | 5006:9091 | 5006:9092 | 5006:9093 | 5006:9094 | 5006:9095 |
| 5007:9090 | 5007:9091 | 5007:9092 | 5007:9093 | 5007:9094 | 5007:9095 |
| 5008:9090 | 5008:9091 | 5008:9092 | 5008:9093 | 5008:9094 | 5008:9095 |
| 5009:9090 | 5009:9091 | 5009:9092 | 5009:9093 | 5009:9094 | 5009:9095 |
| 5010:9090 | 5010:9091 | 5010:9092 | 5010:9093 | 5010:9094 | 5010:9095 |
| 5011:9090 | 5011:9091 | 5011:9092 | 5011:9093 | 5011:9094 | 5011:9095 |
| 5012:9090 | 5012:9091 | 5012:9092 | 5012:9093 | 5012:9094 | 5012:9095 |

| X:Y | X:Y | X:Y | X:Y | X:Y | X:Y |
|---|---|---|---|---|---|
| 3001:9096 | 3001:9097 | 3001:9098 | 3001:9099 | 3001:9100 | 3001:9101 |
| 3002:9096 | 3002:9097 | 3002:9098 | 3002:9099 | 3002:9100 | 3002:9101 |
| 3003:9096 | 3003:9097 | 3003:9098 | 3003:9099 | 3003:9100 | 3003:9101 |
| 3004:9096 | 3004:9097 | 3004:9098 | 3004:9099 | 3004:9100 | 3004:9101 |
| 3005:9096 | 3005:9097 | 3005:9098 | 3005:9099 | 3005:9100 | 3005:9101 |
| 3006:9096 | 3006:9097 | 3006:9098 | 3006:9099 | 3006:9100 | 3006:9101 |
| 3007:9096 | 3007:9097 | 3007:9098 | 3007:9099 | 3007:9100 | 3007:9101 |
| 3008:9096 | 3008:9097 | 3008:9098 | 3008:9099 | 3008:9100 | 3008:9101 |
| 3009:9096 | 3009:9097 | 3009:9098 | 3009:9099 | 3009:9100 | 3009:9101 |
| 3010:9096 | 3010:9097 | 3010:9098 | 3010:9099 | 3010:9100 | 3010:9101 |
| 3011:9096 | 3011:9097 | 3011:9098 | 3011:9099 | 3011:9100 | 3011:9101 |
| 3012:9096 | 3012:9097 | 3012:9098 | 3012:9099 | 3012:9100 | 3012:9101 |
| 3013:9096 | 3013:9097 | 3013:9098 | 3013:9099 | 3013:9100 | 3013:9101 |
| 3014:9096 | 3014:9097 | 3014:9098 | 3014:9099 | 3014:9100 | 3014:9101 |
| 4001:9096 | 4001:9097 | 4001:9098 | 4001:9099 | 4001:9100 | 4001:9101 |
| 4002:9096 | 4002:9097 | 4002:9098 | 4002:9099 | 4002:9100 | 4002:9101 |
| 4003:9096 | 4003:9097 | 4003:9098 | 4003:9099 | 4003:9100 | 4003:9101 |
| 4004:9096 | 4004:9097 | 4004:9098 | 4004:9099 | 4004:9100 | 4004:9101 |
| 4005:9096 | 4005:9097 | 4005:9098 | 4005:9099 | 4005:9100 | 4005:9101 |
| 4006:9096 | 4006:9097 | 4006:9098 | 4006:9099 | 4006:9100 | 4006:9101 |
| 4007:9096 | 4007:9097 | 4007:9098 | 4007:9099 | 4007:9100 | 4007:9101 |
| 4008:9096 | 4008:9097 | 4008:9098 | 4008:9099 | 4008:9100 | 4008:9101 |
| 4009:9096 | 4009:9097 | 4009:9098 | 4009:9099 | 4009:9100 | 4009:9101 |
| 4010:9096 | 4010:9097 | 4010:9098 | 4010:9099 | 4010:9100 | 4010:9101 |
| 4011:9096 | 4011:9097 | 4011:9098 | 4011:9099 | 4011:9100 | 4011:9101 |
| 4012:9096 | 4012:9097 | 4012:9098 | 4012:9099 | 4012:9100 | 4012:9101 |
| 5001:9096 | 5001:9097 | 5001:9098 | 5001:9099 | 5001:9100 | 5001:9101 |
| 5002:9096 | 5002:9097 | 5002:9098 | 5002:9099 | 5002:9100 | 5002:9101 |
| 5003:9096 | 5003:9097 | 5003:9098 | 5003:9099 | 5003:9100 | 5003:9101 |
| 5004:9096 | 5004:9097 | 5004:9098 | 5004:9099 | 5004:9100 | 5004:9101 |
| 5005:9096 | 5005:9097 | 5005:9098 | 5005:9099 | 5005:9100 | 5005:9101 |
| 5006:9096 | 5006:9097 | 5006:9098 | 5006:9099 | 5006:9100 | 5006:9101 |
| 5007:9096 | 5007:9097 | 5007:9098 | 5007:9099 | 5007:9100 | 5007:9101 |
| 5008:9096 | 5008:9097 | 5008:9098 | 5008:9099 | 5008:9100 | 5008:9101 |
| 5009:9096 | 5009:9097 | 5009:9098 | 5009:9099 | 5009:9100 | 5009:9101 |
| 5010:9096 | 5010:9097 | 5010:9098 | 5010:9099 | 5010:9100 | 5010:9101 |
| 5011:9096 | 5011:9097 | 5011:9098 | 5011:9099 | 5011:9100 | 5011:9101 |
| 5012:9096 | 5012:9097 | 5012:9098 | 5012:9099 | 5012:9100 | 5012:9101 |

| X:Y | X:Y | X:Y | X:Y | X:Y | X:Y |
|---|---|---|---|---|---|
| 3001:9102 | 3001:9103 | 3001:9104 | 3001:9105 | — | — |
| 3002:9102 | 3002:9103 | 3002:9104 | 3002:9105 | | |
| 3003:9102 | 3003:9103 | 3003:9104 | 3003:9105 | | |
| 3004:9102 | 3004:9103 | 3004:9104 | 3004:9105 | | |
| 3005:9102 | 3005:9103 | 3005:9104 | 3005:9105 | | |
| 3006:9102 | 3006:9103 | 3006:9104 | 3006:9105 | | |
| 3007:9102 | 3007:9103 | 3007:9104 | 3007:9105 | | |
| 3008:9102 | 3008:9103 | 3008:9104 | 3008:9105 | | |
| 3009:9102 | 3009:9103 | 3009:9104 | 3009:9105 | | |
| 3010:9102 | 3010:9103 | 3010:9104 | 3010:9105 | | |
| 3011:9102 | 3011:9103 | 3011:9104 | 3011:9105 | | |
| 3012:9102 | 3012:9103 | 3012:9104 | 3012:9105 | | |
| 3013:9102 | 3013:9103 | 3013:9104 | 3013:9105 | | |
| 3014:9102 | 3014:9103 | 3014:9104 | 3014:9105 | | |
| 4001:9102 | 4001:9103 | 4001:9104 | 4001:9105 | | |
| 4002:9102 | 4002:9103 | 4002:9104 | 4002:9105 | | |
| 4003:9102 | 4003:9103 | 4003:9104 | 4003:9105 | | |
| 4004:9102 | 4004:9103 | 4004:9104 | 4004:9105 | | |
| 4005:9102 | 4005:9103 | 4005:9104 | 4005:9105 | | |
| 4006:9102 | 4006:9103 | 4006:9104 | 4006:9105 | | |
| 4007:9102 | 4007:9103 | 4007:9104 | 4007:9105 | | |
| 4008:9102 | 4008:9103 | 4008:9104 | 4008:9105 | | |
| 4009:9102 | 4009:9103 | 4009:9104 | 4009:9105 | | |
| 4010:9102 | 4010:9103 | 4010:9104 | 4010:9105 | | |
| 4011:9102 | 4011:9103 | 4011:9104 | 4011:9105 | | |
| 4012:9102 | 4012:9103 | 4012:9104 | 4012:9105 | | |
| 5001:9102 | 5001:9103 | 5001:9104 | 5001:9105 | | |
| 5002:9102 | 5002:9103 | 5002:9104 | 5002:9105 | | |
| 5003:9102 | 5003:9103 | 5003:9104 | 5003:9105 | | |
| 5004:9102 | 5004:9103 | 5004:9104 | 5004:9105 | | |
| 5005:9102 | 5005:9103 | 5005:9104 | 5005:9105 | | |
| 5006:9102 | 5006:9103 | 5006:9104 | 5006:9105 | | |
| 5007:9102 | 5007:9103 | 5007:9104 | 5007:9105 | | |
| 5008:9102 | 5008:9103 | 5008:9104 | 5008:9105 | | |
| 5009:9102 | 5009:9103 | 5009:9104 | 5009:9105 | | |
| 5010:9102 | 5010:9103 | 5010:9104 | 5010:9105 | | |
| 5011:9102 | 5011:9103 | 5011:9104 | 5011:9105 | | |
| 5012:9102 | 5012:9103 | 5012:9104 | 5012:9105 | | |

TABLE C

Example combinations of a compound X with a compound Y.

| X:Y | X:Y | X:Y | X:Y | X:Y | X:Y |
|---|---|---|---|---|---|
| 9000:7000 | 9001:7000 | 9002:7000 | 9003:7000 | 9004:7000 | 9005:7000 |
| 9000:7001 | 9001:7001 | 9002:7001 | 9003:7001 | 9004:7001 | 9005:7001 |
| 9000:7002 | 9001:7002 | 9002:7002 | 9003:7002 | 9004:7002 | 9005:7002 |
| 9000:7003 | 9001:7003 | 9002:7003 | 9003:7003 | 9004:7003 | 9005:7003 |
| 9000:7004 | 9001:7004 | 9002:7004 | 9003:7004 | 9004:7004 | 9005:7004 |
| 9000:7005 | 9001:7005 | 9002:7005 | 9003:7005 | 9004:7005 | 9005:7005 |
| 9000:7006 | 9001:7006 | 9002:7006 | 9003:7006 | 9004:7006 | 9005:7006 |
| 9000:7007 | 9001:7007 | 9002:7007 | 9003:7007 | 9004:7007 | 9005:7007 |
| 9000:7008 | 9001:7008 | 9002:7008 | 9003:7008 | 9004:7008 | 9005:7008 |
| 9000:7009 | 9001:7009 | 9002:7009 | 9003:7009 | 9004:7009 | 9005:7009 |
| 9000:7010 | 9001:7010 | 9002:7010 | 9003:7010 | 9004:7010 | 9005:7010 |
| 9000:7011 | 9001:7011 | 9002:7011 | 9003:7011 | 9004:7011 | 9005:7011 |
| 9000:7012 | 9001:7012 | 9002:7012 | 9003:7012 | 9004:7012 | 9005:7012 |
| 9000:7013 | 9001:7013 | 9002:7013 | 9003:7013 | 9004:7013 | 9005:7013 |
| 9000:7014 | 9001:7014 | 9002:7014 | 9003:7014 | 9004:7014 | 9005:7014 |
| 9000:7015 | 9001:7015 | 9002:7015 | 9003:7015 | 9004:7015 | 9005:7015 |
| 9000:7016 | 9001:7016 | 9002:7016 | 9003:7016 | 9004:7016 | 9005:7016 |
| 9000:7017 | 9001:7017 | 9002:7017 | 9003:7017 | 9004:7017 | 9005:7017 |
| 9000:7018 | 9001:7018 | 9002:7018 | 9003:7018 | 9004:7018 | 9005:7018 |
| 9000:7019 | 9001:7019 | 9002:7019 | 9003:7019 | 9004:7019 | 9005:7019 |
| 9000:7020 | 9001:7020 | 9002:7020 | 9003:7020 | 9004:7020 | 9005:7020 |
| 9000:7021 | 9001:7021 | 9002:7021 | 9003:7021 | 9004:7021 | 9005:7021 |
| 9000:7022 | 9001:7022 | 9002:7022 | 9003:7022 | 9004:7022 | 9005:7022 |
| 9000:7023 | 9001:7023 | 9002:7023 | 9003:7023 | 9004:7023 | 9005:7023 |
| 9000:7024 | 9001:7024 | 9002:7024 | 9003:7024 | 9004:7024 | 9005:7024 |
| 9000:7025 | 9001:7025 | 9002:7025 | 9003:7025 | 9004:7025 | 9005:7025 |
| 9000:7026 | 9001:7026 | 9002:7026 | 9003:7026 | 9004:7026 | 9005:7026 |
| 9000:7027 | 9001:7027 | 9002:7027 | 9003:7027 | 9004:7027 | 9005:7027 |

| X:Y | X:Y | X:Y | X:Y | X:Y | X:Y |
|---|---|---|---|---|---|
| 9006:7000 | 9007:7000 | 9008:7000 | 9009:7000 | 9010:7000 | 9011:7000 |
| 9006:7001 | 9007:7001 | 9008:7001 | 9009:7001 | 9010:7001 | 9011:7001 |
| 9006:7002 | 9007:7002 | 9008:7002 | 9009:7002 | 9010:7002 | 9011:7002 |
| 9006:7003 | 9007:7003 | 9008:7003 | 9009:7003 | 9010:7003 | 9011:7003 |
| 9006:7004 | 9007:7004 | 9008:7004 | 9009:7004 | 9010:7004 | 9011:7004 |
| 9006:7005 | 9007:7005 | 9008:7005 | 9009:7005 | 9010:7005 | 9011:7005 |
| 9006:7006 | 9007:7006 | 9008:7006 | 9009:7006 | 9010:7006 | 9011:7006 |
| 9006:7007 | 9007:7007 | 9008:7007 | 9009:7007 | 9010:7007 | 9011:7007 |
| 9006:7008 | 9007:7008 | 9008:7008 | 9009:7008 | 9010:7008 | 9011:7008 |
| 9006:7009 | 9007:7009 | 9008:7009 | 9009:7009 | 9010:7009 | 9011:7009 |
| 9006:7010 | 9007:7010 | 9008:7010 | 9009:7010 | 9010:7010 | 9011:7010 |
| 9006:7011 | 9007:7011 | 9008:7011 | 9009:7011 | 9010:7011 | 9011:7011 |
| 9006:7012 | 9007:7012 | 9008:7012 | 9009:7012 | 9010:7012 | 9011:7012 |
| 9006:7013 | 9007:7013 | 9008:7013 | 9009:7013 | 9010:7013 | 9011:7013 |
| 9006:7014 | 9007:7014 | 9008:7014 | 9009:7014 | 9010:7014 | 9011:7014 |
| 9006:7015 | 9007:7015 | 9008:7015 | 9009:7015 | 9010:7015 | 9011:7015 |
| 9006:7016 | 9007:7016 | 9008:7016 | 9009:7016 | 9010:7016 | 9011:7016 |
| 9006:7017 | 9007:7017 | 9008:7017 | 9009:7017 | 9010:7017 | 9011:7017 |
| 9006:7018 | 9007:7018 | 9008:7018 | 9009:7018 | 9010:7018 | 9011:7018 |
| 9006:7019 | 9007:7019 | 9008:7019 | 9009:7019 | 9010:7019 | 9011:7019 |
| 9006:7020 | 9007:7020 | 9008:7020 | 9009:7020 | 9010:7020 | 9011:7020 |
| 9006:7021 | 9007:7021 | 9008:7021 | 9009:7021 | 9010:7021 | 9011:7021 |
| 9006:7022 | 9007:7022 | 9008:7022 | 9009:7022 | 9010:7022 | 9011:7022 |
| 9006:7023 | 9007:7023 | 9008:7023 | 9009:7023 | 9010:7023 | 9011:7023 |
| 9006:7024 | 9007:7024 | 9008:7024 | 9009:7024 | 9010:7024 | 9011:7024 |
| 9006:7025 | 9007:7025 | 9008:7025 | 9009:7025 | 9010:7025 | 9011:7025 |
| 9006:7026 | 9007:7026 | 9008:7026 | 9009:7026 | 9010:7026 | 9011:7026 |
| 9006:7027 | 9007:7027 | 9008:7027 | 9009:7027 | 9010:7027 | 9011:7027 |

| X:Y | X:Y | X:Y | X:Y | X:Y | X:Y |
|---|---|---|---|---|---|
| 9012:7000 | 9013:7000 | 9014:7000 | 9015:7000 | 9016:7000 | 9017:7000 |
| 9012:7001 | 9013:7001 | 9014:7001 | 9015:7001 | 9016:7001 | 9017:7001 |
| 9012:7002 | 9013:7002 | 9014:7002 | 9015:7002 | 9016:7002 | 9017:7002 |
| 9012:7003 | 9013:7003 | 9014:7003 | 9015:7003 | 9016:7003 | 9017:7003 |
| 9012:7004 | 9013:7004 | 9014:7004 | 9015:7004 | 9016:7004 | 9017:7004 |
| 9012:7005 | 9013:7005 | 9014:7005 | 9015:7005 | 9016:7005 | 9017:7005 |
| 9012:7006 | 9013:7006 | 9014:7006 | 9015:7006 | 9016:7006 | 9017:7006 |
| 9012:7007 | 9013:7007 | 9014:7007 | 9015:7007 | 9016:7007 | 9017:7007 |
| 9012:7008 | 9013:7008 | 9014:7008 | 9015:7008 | 9016:7008 | 9017:7008 |
| 9012:7009 | 9013:7009 | 9014:7009 | 9015:7009 | 9016:7009 | 9017:7009 |
| 9012:7010 | 9013:7010 | 9014:7010 | 9015:7010 | 9016:7010 | 9017:7010 |
| 9012:7011 | 9013:7011 | 9014:7011 | 9015:7011 | 9016:7011 | 9017:7011 |
| 9012:7012 | 9013:7012 | 9014:7012 | 9015:7012 | 9016:7012 | 9017:7012 |
| 9012:7013 | 9013:7013 | 9014:7013 | 9015:7013 | 9016:7013 | 9017:7013 |
| 9012:7014 | 9013:7014 | 9014:7014 | 9015:7014 | 9016:7014 | 9017:7014 |
| 9012:7015 | 9013:7015 | 9014:7015 | 9015:7015 | 9016:7015 | 9017:7015 |
| 9012:7016 | 9013:7016 | 9014:7016 | 9015:7016 | 9016:7016 | 9017:7016 |
| 9012:7017 | 9013:7017 | 9014:7017 | 9015:7017 | 9016:7017 | 9017:7017 |
| 9012:7018 | 9013:7018 | 9014:7018 | 9015:7018 | 9016:7018 | 9017:7018 |
| 9012:7019 | 9013:7019 | 9014:7019 | 9015:7019 | 9016:7019 | 9017:7019 |
| 9012:7020 | 9013:7020 | 9014:7020 | 9015:7020 | 9016:7020 | 9017:7020 |
| 9012:7021 | 9013:7021 | 9014:7021 | 9015:7021 | 9016:7021 | 9017:7021 |
| 9012:7022 | 9013:7022 | 9014:7022 | 9015:7022 | 9016:7022 | 9017:7022 |
| 9012:7023 | 9013:7023 | 9014:7023 | 9015:7023 | 9016:7023 | 9017:7023 |
| 9012:7024 | 9013:7024 | 9014:7024 | 9015:7024 | 9016:7024 | 9017:7024 |
| 9012:7025 | 9013:7025 | 9014:7025 | 9015:7025 | 9016:7025 | 9017:7025 |
| 9012:7026 | 9013:7026 | 9014:7026 | 9015:7026 | 9016:7026 | 9017:7026 |
| 9012:7027 | 9013:7027 | 9014:7027 | 9015:7027 | 9016:7027 | 9017:7027 |

| X:Y | X:Y | X:Y | X:Y | X:Y | X:Y |
|---|---|---|---|---|---|
| 9018:7000 | 9019:7000 | 9020:7000 | 9021:7000 | 9022:7000 | 9023:7000 |
| 9018:7001 | 9019:7001 | 9020:7001 | 9021:7001 | 9022:7001 | 9023:7001 |
| 9018:7002 | 9019:7002 | 9020:7002 | 9021:7002 | 9022:7002 | 9023:7002 |
| 9018:7003 | 9019:7003 | 9020:7003 | 9021:7003 | 9022:7003 | 9023:7003 |
| 9018:7004 | 9019:7004 | 9020:7004 | 9021:7004 | 9022:7004 | 9023:7004 |
| 9018:7005 | 9019:7005 | 9020:7005 | 9021:7005 | 9022:7005 | 9023:7005 |
| 9018:7006 | 9019:7006 | 9020:7006 | 9021:7006 | 9022:7006 | 9023:7006 |
| 9018:7007 | 9019:7007 | 9020:7007 | 9021:7007 | 9022:7007 | 9023:7007 |
| 9018:7008 | 9019:7008 | 9020:7008 | 9021:7008 | 9022:7008 | 9023:7008 |
| 9018:7009 | 9019:7009 | 9020:7009 | 9021:7009 | 9022:7009 | 9023:7009 |
| 9018:7010 | 9019:7010 | 9020:7010 | 9021:7010 | 9022:7010 | 9023:7010 |
| 9018:7011 | 9019:7011 | 9020:7011 | 9021:7011 | 9022:7011 | 9023:7011 |
| 9018:7012 | 9019:7012 | 9020:7012 | 9021:7012 | 9022:7012 | 9023:7012 |
| 9018:7013 | 9019:7013 | 9020:7013 | 9021:7013 | 9022:7013 | 9023:7013 |
| 9018:7014 | 9019:7014 | 9020:7014 | 9021:7014 | 9022:7014 | 9023:7014 |
| 9018:7015 | 9019:7015 | 9020:7015 | 9021:7015 | 9022:7015 | 9023:7015 |
| 9018:7016 | 9019:7016 | 9020:7016 | 9021:7016 | 9022:7016 | 9023:7016 |
| 9018:7017 | 9019:7017 | 9020:7017 | 9021:7017 | 9022:7017 | 9023:7017 |
| 9018:7018 | 9019:7018 | 9020:7018 | 9021:7018 | 9022:7018 | 9023:7018 |
| 9018:7019 | 9019:7019 | 9020:7019 | 9021:7019 | 9022:7019 | 9023:7019 |
| 9018:7020 | 9019:7020 | 9020:7020 | 9021:7020 | 9022:7020 | 9023:7020 |
| 9018:7021 | 9019:7021 | 9020:7021 | 9021:7021 | 9022:7021 | 9023:7021 |
| 9018:7022 | 9019:7022 | 9020:7022 | 9021:7022 | 9022:7022 | 9023:7022 |
| 9018:7023 | 9019:7023 | 9020:7023 | 9021:7023 | 9022:7023 | 9023:7023 |
| 9018:7024 | 9019:7024 | 9020:7024 | 9021:7024 | 9022:7024 | 9023:7024 |
| 9018:7025 | 9019:7025 | 9020:7025 | 9021:7025 | 9022:7025 | 9023:7025 |
| 9018:7026 | 9019:7026 | 9020:7026 | 9021:7026 | 9022:7026 | 9023:7026 |
| 9018:7027 | 9019:7027 | 9020:7027 | 9021:7027 | 9022:7027 | 9023:7027 |

| X:Y | X:Y | X:Y | X:Y | X:Y | X:Y |
|---|---|---|---|---|---|
| 9024:7000 | 9025:7000 | 9026:7000 | 9027:7000 | 9028:7000 | 9029:7000 |
| 9024:7001 | 9025:7001 | 9026:7001 | 9027:7001 | 9028:7001 | 9029:7001 |
| 9024:7002 | 9025:7002 | 9026:7002 | 9027:7002 | 9028:7002 | 9029:7002 |
| 9024:7003 | 9025:7003 | 9026:7003 | 9027:7003 | 9028:7003 | 9029:7003 |
| 9024:7004 | 9025:7004 | 9026:7004 | 9027:7004 | 9028:7004 | 9029:7004 |
| 9024:7005 | 9025:7005 | 9026:7005 | 9027:7005 | 9028:7005 | 9029:7005 |
| 9024:7006 | 9025:7006 | 9026:7006 | 9027:7006 | 9028:7006 | 9029:7006 |
| 9024:7007 | 9025:7007 | 9026:7007 | 9027:7007 | 9028:7007 | 9029:7007 |
| 9024:7008 | 9025:7008 | 9026:7008 | 9027:7008 | 9028:7008 | 9029:7008 |
| 9024:7009 | 9025:7009 | 9026:7009 | 9027:7009 | 9028:7009 | 9029:7009 |
| 9024:7010 | 9025:7010 | 9026:7010 | 9027:7010 | 9028:7010 | 9029:7010 |
| 9024:7011 | 9025:7011 | 9026:7011 | 9027:7011 | 9028:7011 | 9029:7011 |
| 9024:7012 | 9025:7012 | 9026:7012 | 9027:7012 | 9028:7012 | 9029:7012 |
| 9024:7013 | 9025:7013 | 9026:7013 | 9027:7013 | 9028:7013 | 9029:7013 |
| 9024:7014 | 9025:7014 | 9026:7014 | 9027:7014 | 9028:7014 | 9029:7014 |
| 9024:7015 | 9025:7015 | 9026:7015 | 9027:7015 | 9028:7015 | 9029:7015 |
| 9024:7016 | 9025:7016 | 9026:7016 | 9027:7016 | 9028:7016 | 9029:7016 |
| 9024:7017 | 9025:7017 | 9026:7017 | 9027:7017 | 9028:7017 | 9029:7017 |
| 9024:7018 | 9025:7018 | 9026:7018 | 9027:7018 | 9028:7018 | 9029:7018 |
| 9024:7019 | 9025:7019 | 9026:7019 | 9027:7019 | 9028:7019 | 9029:7019 |
| 9024:7020 | 9025:7020 | 9026:7020 | 9027:7020 | 9028:7020 | 9029:7020 |
| 9024:7021 | 9025:7021 | 9026:7021 | 9027:7021 | 9028:7021 | 9029:7021 |
| 9024:7022 | 9025:7022 | 9026:7022 | 9027:7022 | 9028:7022 | 9029:7022 |
| 9024:7023 | 9025:7023 | 9026:7023 | 9027:7023 | 9028:7023 | 9029:7023 |
| 9024:7024 | 9025:7024 | 9026:7024 | 9027:7024 | 9028:7024 | 9029:7024 |
| 9024:7025 | 9025:7025 | 9026:7025 | 9027:7025 | 9028:7025 | 9029:7025 |

TABLE C-continued

| X:Y | X:Y | X:Y | X:Y | X:Y | X:Y |
|---|---|---|---|---|---|
| 9024:7026 | 9025:7026 | 9026:7026 | 9027:7026 | 9028:7026 | 9029:7026 |
| 9024:7027 | 9025:7027 | 9026:7027 | 9027:7027 | 9028:7027 | 9029:7027 |

| X:Y | X:Y | X:Y | X:Y | X:Y | X:Y |
|---|---|---|---|---|---|
| 9030:7000 | 9031:7000 | 9032:7000 | 9033:7000 | 9034:7000 | 9035:7000 |
| 9030:7001 | 9031:7001 | 9032:7001 | 9033:7001 | 9034:7001 | 9035:7001 |
| 9030:7002 | 9031:7002 | 9032:7002 | 9033:7002 | 9034:7002 | 9035:7002 |
| 9030:7003 | 9031:7003 | 9032:7003 | 9033:7003 | 9034:7003 | 9035:7003 |
| 9030:7004 | 9031:7004 | 9032:7004 | 9033:7004 | 9034:7004 | 9035:7004 |
| 9030:7005 | 9031:7005 | 9032:7005 | 9033:7005 | 9034:7005 | 9035:7005 |
| 9030:7006 | 9031:7006 | 9032:7006 | 9033:7006 | 9034:7006 | 9035:7006 |
| 9030:7007 | 9031:7007 | 9032:7007 | 9033:7007 | 9034:7007 | 9035:7007 |
| 9030:7008 | 9031:7008 | 9032:7008 | 9033:7008 | 9034:7008 | 9035:7008 |
| 9030:7009 | 9031:7009 | 9032:7009 | 9033:7009 | 9034:7009 | 9035:7009 |
| 9030:7010 | 9031:7010 | 9032:7010 | 9033:7010 | 9034:7010 | 9035:7010 |
| 9030:7011 | 9031:7011 | 9032:7011 | 9033:7011 | 9034:7011 | 9035:7011 |
| 9030:7012 | 9031:7012 | 9032:7012 | 9033:7012 | 9034:7012 | 9035:7012 |
| 9030:7013 | 9031:7013 | 9032:7013 | 9033:7013 | 9034:7013 | 9035:7013 |
| 9030:7014 | 9031:7014 | 9032:7014 | 9033:7014 | 9034:7014 | 9035:7014 |
| 9030:7015 | 9031:7015 | 9032:7015 | 9033:7015 | 9034:7015 | 9035:7015 |
| 9030:7016 | 9031:7016 | 9032:7016 | 9033:7016 | 9034:7016 | 9035:7016 |
| 9030:7017 | 9031:7017 | 9032:7017 | 9033:7017 | 9034:7017 | 9035:7017 |
| 9030:7018 | 9031:7018 | 9032:7018 | 9033:7018 | 9034:7018 | 9035:7018 |
| 9030:7019 | 9031:7019 | 9032:7019 | 9033:7019 | 9034:7019 | 9035:7019 |
| 9030:7020 | 9031:7020 | 9032:7020 | 9033:7020 | 9034:7020 | 9035:7020 |
| 9030:7021 | 9031:7021 | 9032:7021 | 9033:7021 | 9034:7021 | 9035:7021 |
| 9030:7022 | 9031:7022 | 9032:7022 | 9033:7022 | 9034:7022 | 9035:7022 |
| 9030:7023 | 9031:7023 | 9032:7023 | 9033:7023 | 9034:7023 | 9035:7023 |
| 9030:7024 | 9031:7024 | 9032:7024 | 9033:7024 | 9034:7024 | 9035:7024 |
| 9030:7025 | 9031:7025 | 9032:7025 | 9033:7025 | 9034:7025 | 9035:7025 |
| 9030:7026 | 9031:7026 | 9032:7026 | 9033:7026 | 9034:7026 | 9035:7026 |
| 9030:7027 | 9031:7027 | 9032:7027 | 9033:7027 | 9034:7027 | 9035:7027 |

| X:Y | X:Y | X:Y | X:Y | X:Y | X:Y |
|---|---|---|---|---|---|
| 9036:7000 | 9037:7000 | 9038:7000 | 9039:7000 | 9040:7000 | 9041:7000 |
| 9036:7001 | 9037:7001 | 9038:7001 | 9039:7001 | 9040:7001 | 9041:7001 |
| 9036:7002 | 9037:7002 | 9038:7002 | 9039:7002 | 9040:7002 | 9041:7002 |
| 9036:7003 | 9037:7003 | 9038:7003 | 9039:7003 | 9040:7003 | 9041:7003 |
| 9036:7004 | 9037:7004 | 9038:7004 | 9039:7004 | 9040:7004 | 9041:7004 |
| 9036:7005 | 9037:7005 | 9038:7005 | 9039:7005 | 9040:7005 | 9041:7005 |
| 9036:7006 | 9037:7006 | 9038:7006 | 9039:7006 | 9040:7006 | 9041:7006 |
| 9036:7007 | 9037:7007 | 9038:7007 | 9039:7007 | 9040:7007 | 9041:7007 |
| 9036:7008 | 9037:7008 | 9038:7008 | 9039:7008 | 9040:7008 | 9041:7008 |
| 9036:7009 | 9037:7009 | 9038:7009 | 9039:7009 | 9040:7009 | 9041:7009 |
| 9036:7010 | 9037:7010 | 9038:7010 | 9039:7010 | 9040:7010 | 9041:7010 |
| 9036:7011 | 9037:7011 | 9038:7011 | 9039:7011 | 9040:7011 | 9041:7011 |
| 9036:7012 | 9037:7012 | 9038:7012 | 9039:7012 | 9040:7012 | 9041:7012 |
| 9036:7013 | 9037:7013 | 9038:7013 | 9039:7013 | 9040:7013 | 9041:7013 |
| 9036:7014 | 9037:7014 | 9038:7014 | 9039:7014 | 9040:7014 | 9041:7014 |
| 9036:7015 | 9037:7015 | 9038:7015 | 9039:7015 | 9040:7015 | 9041:7015 |
| 9036:7016 | 9037:7016 | 9038:7016 | 9039:7016 | 9040:7016 | 9041:7016 |
| 9036:7017 | 9037:7017 | 9038:7017 | 9039:7017 | 9040:7017 | 9041:7017 |
| 9036:7018 | 9037:7018 | 9038:7018 | 9039:7018 | 9040:7018 | 9041:7018 |
| 9036:7019 | 9037:7019 | 9038:7019 | 9039:7019 | 9040:7019 | 9041:7019 |
| 9036:7020 | 9037:7020 | 9038:7020 | 9039:7020 | 9040:7020 | 9041:7020 |
| 9036:7021 | 9037:7021 | 9038:7021 | 9039:7021 | 9040:7021 | 9041:7021 |
| 9036:7022 | 9037:7022 | 9038:7022 | 9039:7022 | 9040:7022 | 9041:7022 |
| 9036:7023 | 9037:7023 | 9038:7023 | 9039:7023 | 9040:7023 | 9041:7023 |
| 9036:7024 | 9037:7024 | 9038:7024 | 9039:7024 | 9040:7024 | 9041:7024 |
| 9036:7025 | 9037:7025 | 9038:7025 | 9039:7025 | 9040:7025 | 9041:7025 |
| 9036:7026 | 9037:7026 | 9038:7026 | 9039:7026 | 9040:7026 | 9041:7026 |
| 9036:7027 | 9037:7027 | 9038:7027 | 9039:7027 | 9040:7027 | 9041:7027 |

| X:Y | X:Y | X:Y | X:Y | X:Y | X:Y |
|---|---|---|---|---|---|
| 9042:7000 | 9043:7000 | 9044:7000 | 9045:7000 | 9046:7000 | 9047:7000 |
| 9042:7001 | 9043:7001 | 9044:7001 | 9045:7001 | 9046:7001 | 9047:7001 |
| 9042:7002 | 9043:7002 | 9044:7002 | 9045:7002 | 9046:7002 | 9047:7002 |
| 9042:7003 | 9043:7003 | 9044:7003 | 9045:7003 | 9046:7003 | 9047:7003 |
| 9042:7004 | 9043:7004 | 9044:7004 | 9045:7004 | 9046:7004 | 9047:7004 |
| 9042:7005 | 9043:7005 | 9044:7005 | 9045:7005 | 9046:7005 | 9047:7005 |
| 9042:7006 | 9043:7006 | 9044:7006 | 9045:7006 | 9046:7006 | 9047:7006 |
| 9042:7007 | 9043:7007 | 9044:7007 | 9045:7007 | 9046:7007 | 9047:7007 |
| 9042:7008 | 9043:7008 | 9044:7008 | 9045:7008 | 9046:7008 | 9047:7008 |
| 9042:7009 | 9043:7009 | 9044:7009 | 9045:7009 | 9046:7009 | 9047:7009 |
| 9042:7010 | 9043:7010 | 9044:7010 | 9045:7010 | 9046:7010 | 9047:7010 |
| 9042:7011 | 9043:7011 | 9044:7011 | 9045:7011 | 9046:7011 | 9047:7011 |
| 9042:7012 | 9043:7012 | 9044:7012 | 9045:7012 | 9046:7012 | 9047:7012 |
| 9042:7013 | 9043:7013 | 9044:7013 | 9045:7013 | 9046:7013 | 9047:7013 |
| 9042:7014 | 9043:7014 | 9044:7014 | 9045:7014 | 9046:7014 | 9047:7014 |
| 9042:7015 | 9043:7015 | 9044:7015 | 9045:7015 | 9046:7015 | 9047:7015 |
| 9042:7016 | 9043:7016 | 9044:7016 | 9045:7016 | 9046:7016 | 9047:7016 |
| 9042:7017 | 9043:7017 | 9044:7017 | 9045:7017 | 9046:7017 | 9047:7017 |
| 9042:7018 | 9043:7018 | 9044:7018 | 9045:7018 | 9046:7018 | 9047:7018 |
| 9042:7019 | 9043:7019 | 9044:7019 | 9045:7019 | 9046:7019 | 9047:7019 |
| 9042:7020 | 9043:7020 | 9044:7020 | 9045:7020 | 9046:7020 | 9047:7020 |
| 9042:7021 | 9043:7021 | 9044:7021 | 9045:7021 | 9046:7021 | 9047:7021 |
| 9042:7022 | 9043:7022 | 9044:7022 | 9045:7022 | 9046:7022 | 9047:7022 |
| 9042:7023 | 9043:7023 | 9044:7023 | 9045:7023 | 9046:7023 | 9047:7023 |
| 9042:7024 | 9043:7024 | 9044:7024 | 9045:7024 | 9046:7024 | 9047:7024 |
| 9042:7025 | 9043:7025 | 9044:7025 | 9045:7025 | 9046:7025 | 9047:7025 |
| 9042:7026 | 9043:7026 | 9044:7026 | 9045:7026 | 9046:7026 | 9047:7026 |
| 9042:7027 | 9043:7027 | 9044:7027 | 9045:7027 | 9046:7027 | 9047:7027 |

| X:Y | X:Y | X:Y | X:Y | X:Y | X:Y |
|---|---|---|---|---|---|
| 9048:7000 | 9049:7000 | 9050:7000 | 9051:7000 | 9052:7000 | 9053:7000 |
| 9048:7001 | 9049:7001 | 9050:7001 | 9051:7001 | 9052:7001 | 9053:7001 |
| 9048:7002 | 9049:7002 | 9050:7002 | 9051:7002 | 9052:7002 | 9053:7002 |
| 9048:7003 | 9049:7003 | 9050:7003 | 9051:7003 | 9052:7003 | 9053:7003 |
| 9048:7004 | 9049:7004 | 9050:7004 | 9051:7004 | 9052:7004 | 9053:7004 |
| 9048:7005 | 9049:7005 | 9050:7005 | 9051:7005 | 9052:7005 | 9053:7005 |
| 9048:7006 | 9049:7006 | 9050:7006 | 9051:7006 | 9052:7006 | 9053:7006 |
| 9048:7007 | 9049:7007 | 9050:7007 | 9051:7007 | 9052:7007 | 9053:7007 |
| 9048:7008 | 9049:7008 | 9050:7008 | 9051:7008 | 9052:7008 | 9053:7008 |
| 9048:7009 | 9049:7009 | 9050:7009 | 9051:7009 | 9052:7009 | 9053:7009 |
| 9048:7010 | 9049:7010 | 9050:7010 | 9051:7010 | 9052:7010 | 9053:7010 |
| 9048:7011 | 9049:7011 | 9050:7011 | 9051:7011 | 9052:7011 | 9053:7011 |
| 9048:7012 | 9049:7012 | 9050:7012 | 9051:7012 | 9052:7012 | 9053:7012 |
| 9048:7013 | 9049:7013 | 9050:7013 | 9051:7013 | 9052:7013 | 9053:7013 |
| 9048:7014 | 9049:7014 | 9050:7014 | 9051:7014 | 9052:7014 | 9053:7014 |
| 9048:7015 | 9049:7015 | 9050:7015 | 9051:7015 | 9052:7015 | 9053:7015 |
| 9048:7016 | 9049:7016 | 9050:7016 | 9051:7016 | 9052:7016 | 9053:7016 |
| 9048:7017 | 9049:7017 | 9050:7017 | 9051:7017 | 9052:7017 | 9053:7017 |
| 9048:7018 | 9049:7018 | 9050:7018 | 9051:7018 | 9052:7018 | 9053:7018 |
| 9048:7019 | 9049:7019 | 9050:7019 | 9051:7019 | 9052:7019 | 9053:7019 |
| 9048:7020 | 9049:7020 | 9050:7020 | 9051:7020 | 9052:7020 | 9053:7020 |
| 9048:7021 | 9049:7021 | 9050:7021 | 9051:7021 | 9052:7021 | 9053:7021 |
| 9048:7022 | 9049:7022 | 9050:7022 | 9051:7022 | 9052:7022 | 9053:7022 |
| 9048:7023 | 9049:7023 | 9050:7023 | 9051:7023 | 9052:7023 | 9053:7023 |
| 9048:7024 | 9049:7024 | 9050:7024 | 9051:7024 | 9052:7024 | 9053:7024 |
| 9048:7025 | 9049:7025 | 9050:7025 | 9051:7025 | 9052:7025 | 9053:7025 |
| 9048:7026 | 9049:7026 | 9050:7026 | 9051:7026 | 9052:7026 | 9053:7026 |
| 9048:7027 | 9049:7027 | 9050:7027 | 9051:7027 | 9052:7027 | 9053:7027 |

| X:Y | X:Y | X:Y | X:Y | X:Y | X:Y |
|---|---|---|---|---|---|
| 9054:7000 | 9055:7000 | 9056:7000 | 9057:7000 | 9058:7000 | 9059:7000 |
| 9054:7001 | 9055:7001 | 9056:7001 | 9057:7001 | 9058:7001 | 9059:7001 |
| 9054:7002 | 9055:7002 | 9056:7002 | 9057:7002 | 9058:7002 | 9059:7002 |
| 9054:7003 | 9055:7003 | 9056:7003 | 9057:7003 | 9058:7003 | 9059:7003 |
| 9054:7004 | 9055:7004 | 9056:7004 | 9057:7004 | 9058:7004 | 9059:7004 |
| 9054:7005 | 9055:7005 | 9056:7005 | 9057:7005 | 9058:7005 | 9059:7005 |
| 9054:7006 | 9055:7006 | 9056:7006 | 9057:7006 | 9058:7006 | 9059:7006 |
| 9054:7007 | 9055:7007 | 9056:7007 | 9057:7007 | 9058:7007 | 9059:7007 |
| 9054:7008 | 9055:7008 | 9056:7008 | 9057:7008 | 9058:7008 | 9059:7008 |
| 9054:7009 | 9055:7009 | 9056:7009 | 9057:7009 | 9058:7009 | 9059:7009 |
| 9054:7010 | 9055:7010 | 9056:7010 | 9057:7010 | 9058:7010 | 9059:7010 |
| 9054:7011 | 9055:7011 | 9056:7011 | 9057:7011 | 9058:7011 | 9059:7011 |
| 9054:7012 | 9055:7012 | 9056:7012 | 9057:7012 | 9058:7012 | 9059:7012 |
| 9054:7013 | 9055:7013 | 9056:7013 | 9057:7013 | 9058:7013 | 9059:7013 |
| 9054:7014 | 9055:7014 | 9056:7014 | 9057:7014 | 9058:7014 | 9059:7014 |
| 9054:7015 | 9055:7015 | 9056:7015 | 9057:7015 | 9058:7015 | 9059:7015 |
| 9054:7016 | 9055:7016 | 9056:7016 | 9057:7016 | 9058:7016 | 9059:7016 |
| 9054:7017 | 9055:7017 | 9056:7017 | 9057:7017 | 9058:7017 | 9059:7017 |
| 9054:7018 | 9055:7018 | 9056:7018 | 9057:7018 | 9058:7018 | 9059:7018 |
| 9054:7019 | 9055:7019 | 9056:7019 | 9057:7019 | 9058:7019 | 9059:7019 |
| 9054:7020 | 9055:7020 | 9056:7020 | 9057:7020 | 9058:7020 | 9059:7020 |
| 9054:7021 | 9055:7021 | 9056:7021 | 9057:7021 | 9058:7021 | 9059:7021 |
| 9054:7022 | 9055:7022 | 9056:7022 | 9057:7022 | 9058:7022 | 9059:7022 |
| 9054:7023 | 9055:7023 | 9056:7023 | 9057:7023 | 9058:7023 | 9059:7023 |
| 9054:7024 | 9055:7024 | 9056:7024 | 9057:7024 | 9058:7024 | 9059:7024 |

TABLE C-continued

| X:Y | X:Y | X:Y | X:Y | X:Y | X:Y |
|---|---|---|---|---|---|
| 9054:7025 | 9055:7025 | 9056:7025 | 9057:7025 | 9058:7025 | 9059:7025 |
| 9054:7026 | 9055:7026 | 9056:7026 | 9057:7026 | 9058:7026 | 9059:7026 |
| 9054:7027 | 9055:7027 | 9056:7027 | 9057:7027 | 9058:7027 | 9059:7027 |

| X:Y | X:Y | X:Y | X:Y | X:Y | X:Y |
|---|---|---|---|---|---|
| 9060:7000 | 9061:7000 | 9062:7000 | 9063:7000 | 9064:7000 | 9065:7000 |
| 9060:7001 | 9061:7001 | 9062:7001 | 9063:7001 | 9064:7001 | 9065:7001 |
| 9060:7002 | 9061:7002 | 9062:7002 | 9063:7002 | 9064:7002 | 9065:7002 |
| 9060:7003 | 9061:7003 | 9062:7003 | 9063:7003 | 9064:7003 | 9065:7003 |
| 9060:7004 | 9061:7004 | 9062:7004 | 9063:7004 | 9064:7004 | 9065:7004 |
| 9060:7005 | 9061:7005 | 9062:7005 | 9063:7005 | 9064:7005 | 9065:7005 |
| 9060:7006 | 9061:7006 | 9062:7006 | 9063:7006 | 9064:7006 | 9065:7006 |
| 9060:7007 | 9061:7007 | 9062:7007 | 9063:7007 | 9064:7007 | 9065:7007 |
| 9060:7008 | 9061:7008 | 9062:7008 | 9063:7008 | 9064:7008 | 9065:7008 |
| 9060:7009 | 9061:7009 | 9062:7009 | 9063:7009 | 9064:7009 | 9065:7009 |
| 9060:7010 | 9061:7010 | 9062:7010 | 9063:7010 | 9064:7010 | 9065:7010 |
| 9060:7011 | 9061:7011 | 9062:7011 | 9063:7011 | 9064:7011 | 9065:7011 |
| 9060:7012 | 9061:7012 | 9062:7012 | 9063:7012 | 9064:7012 | 9065:7012 |
| 9060:7013 | 9061:7013 | 9062:7013 | 9063:7013 | 9064:7013 | 9065:7013 |
| 9060:7014 | 9061:7014 | 9062:7014 | 9063:7014 | 9064:7014 | 9065:7014 |
| 9060:7015 | 9061:7015 | 9062:7015 | 9063:7015 | 9064:7015 | 9065:7015 |
| 9060:7016 | 9061:7016 | 9062:7016 | 9063:7016 | 9064:7016 | 9065:7016 |
| 9060:7017 | 9061:7017 | 9062:7017 | 9063:7017 | 9064:7017 | 9065:7017 |
| 9060:7018 | 9061:7018 | 9062:7018 | 9063:7018 | 9064:7018 | 9065:7018 |
| 9060:7019 | 9061:7019 | 9062:7019 | 9063:7019 | 9064:7019 | 9065:7019 |
| 9060:7020 | 9061:7020 | 9062:7020 | 9063:7020 | 9064:7020 | 9065:7020 |
| 9060:7021 | 9061:7021 | 9062:7021 | 9063:7021 | 9064:7021 | 9065:7021 |
| 9060:7022 | 9061:7022 | 9062:7022 | 9063:7022 | 9064:7022 | 9065:7022 |
| 9060:7023 | 9061:7023 | 9062:7023 | 9063:7023 | 9064:7023 | 9065:7023 |
| 9060:7024 | 9061:7024 | 9062:7024 | 9063:7024 | 9064:7024 | 9065:7024 |
| 9060:7025 | 9061:7025 | 9062:7025 | 9063:7025 | 9064:7025 | 9065:7025 |
| 9060:7026 | 9061:7026 | 9062:7026 | 9063:7026 | 9064:7026 | 9065:7026 |
| 9060:7027 | 9061:7027 | 9062:7027 | 9063:7027 | 9064:7027 | 9065:7027 |

| X:Y | X:Y | X:Y | X:Y | X:Y | X:Y |
|---|---|---|---|---|---|
| 9066:7000 | 9067:7000 | 9068:7000 | 9069:7000 | 9070:7000 | 9071:7000 |
| 9066:7001 | 9067:7001 | 9068:7001 | 9069:7001 | 9070:7001 | 9071:7001 |
| 9066:7002 | 9067:7002 | 9068:7002 | 9069:7002 | 9070:7002 | 9071:7002 |
| 9066:7003 | 9067:7003 | 9068:7003 | 9069:7003 | 9070:7003 | 9071:7003 |
| 9066:7004 | 9067:7004 | 9068:7004 | 9069:7004 | 9070:7004 | 9071:7004 |
| 9066:7005 | 9067:7005 | 9068:7005 | 9069:7005 | 9070:7005 | 9071:7005 |
| 9066:7006 | 9067:7006 | 9068:7006 | 9069:7006 | 9070:7006 | 9071:7006 |
| 9066:7007 | 9067:7007 | 9068:7007 | 9069:7007 | 9070:7007 | 9071:7007 |
| 9066:7008 | 9067:7008 | 9068:7008 | 9069:7008 | 9070:7008 | 9071:7008 |
| 9066:7009 | 9067:7009 | 9068:7009 | 9069:7009 | 9070:7009 | 9071:7009 |
| 9066:7010 | 9067:7010 | 9068:7010 | 9069:7010 | 9070:7010 | 9071:7010 |
| 9066:7011 | 9067:7011 | 9068:7011 | 9069:7011 | 9070:7011 | 9071:7011 |
| 9066:7012 | 9067:7012 | 9068:7012 | 9069:7012 | 9070:7012 | 9071:7012 |
| 9066:7013 | 9067:7013 | 9068:7013 | 9069:7013 | 9070:7013 | 9071:7013 |
| 9066:7014 | 9067:7014 | 9068:7014 | 9069:7014 | 9070:7014 | 9071:7014 |
| 9066:7015 | 9067:7015 | 9068:7015 | 9069:7015 | 9070:7015 | 9071:7015 |
| 9066:7016 | 9067:7016 | 9068:7016 | 9069:7016 | 9070:7016 | 9071:7016 |
| 9066:7017 | 9067:7017 | 9068:7017 | 9069:7017 | 9070:7017 | 9071:7017 |
| 9066:7018 | 9067:7018 | 9068:7018 | 9069:7018 | 9070:7018 | 9071:7018 |
| 9066:7019 | 9067:7019 | 9068:7019 | 9069:7019 | 9070:7019 | 9071:7019 |
| 9066:7020 | 9067:7020 | 9068:7020 | 9069:7020 | 9070:7020 | 9071:7020 |
| 9066:7021 | 9067:7021 | 9068:7021 | 9069:7021 | 9070:7021 | 9071:7021 |
| 9066:7022 | 9067:7022 | 9068:7022 | 9069:7022 | 9070:7022 | 9071:7022 |
| 9066:7023 | 9067:7023 | 9068:7023 | 9069:7023 | 9070:7023 | 9071:7023 |
| 9066:7024 | 9067:7024 | 9068:7024 | 9069:7024 | 9070:7024 | 9071:7024 |
| 9066:7025 | 9067:7025 | 9068:7025 | 9069:7025 | 9070:7025 | 9071:7025 |
| 9066:7026 | 9067:7026 | 9068:7026 | 9069:7026 | 9070:7026 | 9071:7026 |
| 9066:7027 | 9067:7027 | 9068:7027 | 9069:7027 | 9070:7027 | 9071:7027 |

| X:Y | X:Y | X:Y | X:Y | X:Y | X:Y |
|---|---|---|---|---|---|
| 9072:7000 | 9073:7000 | 9074:7000 | 9075:7000 | 9076:7000 | 9077:7000 |
| 9072:7001 | 9073:7001 | 9074:7001 | 9075:7001 | 9076:7001 | 9077:7001 |
| 9072:7002 | 9073:7002 | 9074:7002 | 9075:7002 | 9076:7002 | 9077:7002 |
| 9072:7003 | 9073:7003 | 9074:7003 | 9075:7003 | 9076:7003 | 9077:7003 |
| 9072:7004 | 9073:7004 | 9074:7004 | 9075:7004 | 9076:7004 | 9077:7004 |
| 9072:7005 | 9073:7005 | 9074:7005 | 9075:7005 | 9076:7005 | 9077:7005 |
| 9072:7006 | 9073:7006 | 9074:7006 | 9075:7006 | 9076:7006 | 9077:7006 |
| 9072:7007 | 9073:7007 | 9074:7007 | 9075:7007 | 9076:7007 | 9077:7007 |
| 9072:7008 | 9073:7008 | 9074:7008 | 9075:7008 | 9076:7008 | 9077:7008 |
| 9072:7009 | 9073:7009 | 9074:7009 | 9075:7009 | 9076:7009 | 9077:7009 |
| 9072:7010 | 9073:7010 | 9074:7010 | 9075:7010 | 9076:7010 | 9077:7010 |
| 9072:7011 | 9073:7011 | 9074:7011 | 9075:7011 | 9076:7011 | 9077:7011 |
| 9072:7012 | 9073:7012 | 9074:7012 | 9075:7012 | 9076:7012 | 9077:7012 |
| 9072:7013 | 9073:7013 | 9074:7013 | 9075:7013 | 9076:7013 | 9077:7013 |
| 9072:7014 | 9073:7014 | 9074:7014 | 9075:7014 | 9076:7014 | 9077:7014 |
| 9072:7015 | 9073:7015 | 9074:7015 | 9075:7015 | 9076:7015 | 9077:7015 |
| 9072:7016 | 9073:7016 | 9074:7016 | 9075:7016 | 9076:7016 | 9077:7016 |
| 9072:7017 | 9073:7017 | 9074:7017 | 9075:7017 | 9076:7017 | 9077:7017 |
| 9072:7018 | 9073:7018 | 9074:7018 | 9075:7018 | 9076:7018 | 9077:7018 |
| 9072:7019 | 9073:7019 | 9074:7019 | 9075:7019 | 9076:7019 | 9077:7019 |
| 9072:7020 | 9073:7020 | 9074:7020 | 9075:7020 | 9076:7020 | 9077:7020 |
| 9072:7021 | 9073:7021 | 9074:7021 | 9075:7021 | 9076:7021 | 9077:7021 |
| 9072:7022 | 9073:7022 | 9074:7022 | 9075:7022 | 9076:7022 | 9077:7022 |
| 9072:7023 | 9073:7023 | 9074:7023 | 9075:7023 | 9076:7023 | 9077:7023 |
| 9072:7024 | 9073:7024 | 9074:7024 | 9075:7024 | 9076:7024 | 9077:7024 |
| 9072:7025 | 9073:7025 | 9074:7025 | 9075:7025 | 9076:7025 | 9077:7025 |
| 9072:7026 | 9073:7026 | 9074:7026 | 9075:7026 | 9076:7026 | 9077:7026 |
| 9072:7027 | 9073:7027 | 9074:7027 | 9075:7027 | 9076:7027 | 9077:7027 |

| X:Y | X:Y | X:Y | X:Y | X:Y | X:Y |
|---|---|---|---|---|---|
| 9078:7000 | 9079:7000 | 9080:7000 | 9081:7000 | 9082:7000 | 9083:7000 |
| 9078:7001 | 9079:7001 | 9080:7001 | 9081:7001 | 9082:7001 | 9083:7001 |
| 9078:7002 | 9079:7002 | 9080:7002 | 9081:7002 | 9082:7002 | 9083:7002 |
| 9078:7003 | 9079:7003 | 9080:7003 | 9081:7003 | 9082:7003 | 9083:7003 |
| 9078:7004 | 9079:7004 | 9080:7004 | 9081:7004 | 9082:7004 | 9083:7004 |
| 9078:7005 | 9079:7005 | 9080:7005 | 9081:7005 | 9082:7005 | 9083:7005 |
| 9078:7006 | 9079:7006 | 9080:7006 | 9081:7006 | 9082:7006 | 9083:7006 |
| 9078:7007 | 9079:7007 | 9080:7007 | 9081:7007 | 9082:7007 | 9083:7007 |
| 9078:7008 | 9079:7008 | 9080:7008 | 9081:7008 | 9082:7008 | 9083:7008 |
| 9078:7009 | 9079:7009 | 9080:7009 | 9081:7009 | 9082:7009 | 9083:7009 |
| 9078:7010 | 9079:7010 | 9080:7010 | 9081:7010 | 9082:7010 | 9083:7010 |
| 9078:7011 | 9079:7011 | 9080:7011 | 9081:7011 | 9082:7011 | 9083:7011 |
| 9078:7012 | 9079:7012 | 9080:7012 | 9081:7012 | 9082:7012 | 9083:7012 |
| 9078:7013 | 9079:7013 | 9080:7013 | 9081:7013 | 9082:7013 | 9083:7013 |
| 9078:7014 | 9079:7014 | 9080:7014 | 9081:7014 | 9082:7014 | 9083:7014 |
| 9078:7015 | 9079:7015 | 9080:7015 | 9081:7015 | 9082:7015 | 9083:7015 |
| 9078:7016 | 9079:7016 | 9080:7016 | 9081:7016 | 9082:7016 | 9083:7016 |
| 9078:7017 | 9079:7017 | 9080:7017 | 9081:7017 | 9082:7017 | 9083:7017 |
| 9078:7018 | 9079:7018 | 9080:7018 | 9081:7018 | 9082:7018 | 9083:7018 |
| 9078:7019 | 9079:7019 | 9080:7019 | 9081:7019 | 9082:7019 | 9083:7019 |
| 9078:7020 | 9079:7020 | 9080:7020 | 9081:7020 | 9082:7020 | 9083:7020 |
| 9078:7021 | 9079:7021 | 9080:7021 | 9081:7021 | 9082:7021 | 9083:7021 |
| 9078:7022 | 9079:7022 | 9080:7022 | 9081:7022 | 9082:7022 | 9083:7022 |
| 9078:7023 | 9079:7023 | 9080:7023 | 9081:7023 | 9082:7023 | 9083:7023 |
| 9078:7024 | 9079:7024 | 9080:7024 | 9081:7024 | 9082:7024 | 9083:7024 |
| 9078:7025 | 9079:7025 | 9080:7025 | 9081:7025 | 9082:7025 | 9083:7025 |
| 9078:7026 | 9079:7026 | 9080:7026 | 9081:7026 | 9082:7026 | 9083:7026 |
| 9078:7027 | 9079:7027 | 9080:7027 | 9081:7027 | 9082:7027 | 9083:7027 |

| X:Y | X:Y | X:Y | X:Y | X:Y | X:Y |
|---|---|---|---|---|---|
| 9084:7000 | 9085:7000 | 9086:7000 | 9087:7000 | 9088:7000 | 9089:7000 |
| 9084:7001 | 9085:7001 | 9086:7001 | 9087:7001 | 9088:7001 | 9089:7001 |
| 9084:7002 | 9085:7002 | 9086:7002 | 9087:7002 | 9088:7002 | 9089:7002 |
| 9084:7003 | 9085:7003 | 9086:7003 | 9087:7003 | 9088:7003 | 9089:7003 |
| 9084:7004 | 9085:7004 | 9086:7004 | 9087:7004 | 9088:7004 | 9089:7004 |
| 9084:7005 | 9085:7005 | 9086:7005 | 9087:7005 | 9088:7005 | 9089:7005 |
| 9084:7006 | 9085:7006 | 9086:7006 | 9087:7006 | 9088:7006 | 9089:7006 |
| 9084:7007 | 9085:7007 | 9086:7007 | 9087:7007 | 9088:7007 | 9089:7007 |
| 9084:7008 | 9085:7008 | 9086:7008 | 9087:7008 | 9088:7008 | 9089:7008 |
| 9084:7009 | 9085:7009 | 9086:7009 | 9087:7009 | 9088:7009 | 9089:7009 |
| 9084:7010 | 9085:7010 | 9086:7010 | 9087:7010 | 9088:7010 | 9089:7010 |
| 9084:7011 | 9085:7011 | 9086:7011 | 9087:7011 | 9088:7011 | 9089:7011 |
| 9084:7012 | 9085:7012 | 9086:7012 | 9087:7012 | 9088:7012 | 9089:7012 |
| 9084:7013 | 9085:7013 | 9086:7013 | 9087:7013 | 9088:7013 | 9089:7013 |
| 9084:7014 | 9085:7014 | 9086:7014 | 9087:7014 | 9088:7014 | 9089:7014 |
| 9084:7015 | 9085:7015 | 9086:7015 | 9087:7015 | 9088:7015 | 9089:7015 |
| 9084:7016 | 9085:7016 | 9086:7016 | 9087:7016 | 9088:7016 | 9089:7016 |
| 9084:7017 | 9085:7017 | 9086:7017 | 9087:7017 | 9088:7017 | 9089:7017 |
| 9084:7018 | 9085:7018 | 9086:7018 | 9087:7018 | 9088:7018 | 9089:7018 |
| 9084:7019 | 9085:7019 | 9086:7019 | 9087:7019 | 9088:7019 | 9089:7019 |
| 9084:7020 | 9085:7020 | 9086:7020 | 9087:7020 | 9088:7020 | 9089:7020 |
| 9084:7021 | 9085:7021 | 9086:7021 | 9087:7021 | 9088:7021 | 9089:7021 |
| 9084:7022 | 9085:7022 | 9086:7022 | 9087:7022 | 9088:7022 | 9089:7022 |
| 9084:7023 | 9085:7023 | 9086:7023 | 9087:7023 | 9088:7023 | 9089:7023 |
| 9084:7024 | 9085:7024 | 9086:7024 | 9087:7024 | 9088:7024 | 9089:7024 |

TABLE C-continued

| X:Y | X:Y | X:Y | X:Y | X:Y | X:Y |
|---|---|---|---|---|---|
| 9084:7025 | 9085:7025 | 9086:7025 | 9087:7025 | 9088:7025 | 9089:7025 |
| 9084:7026 | 9085:7026 | 9086:7026 | 9087:7026 | 9088:7026 | 9089:7026 |
| 9084:7027 | 9085:7027 | 9086:7027 | 9087:7027 | 9088:7027 | 9089:7027 |

| X:Y | X:Y | X:Y | X:Y | X:Y | X:Y |
|---|---|---|---|---|---|
| 9090:7000 | 9091:7000 | 9092:7000 | 9093:7000 | 9094:7000 | 9095:7000 |
| 9090:7001 | 9091:7001 | 9092:7001 | 9093:7001 | 9094:7001 | 9095:7001 |
| 9090:7002 | 9091:7002 | 9092:7002 | 9093:7002 | 9094:7002 | 9095:7002 |
| 9090:7003 | 9091:7003 | 9092:7003 | 9093:7003 | 9094:7003 | 9095:7003 |
| 9090:7004 | 9091:7004 | 9092:7004 | 9093:7004 | 9094:7004 | 9095:7004 |
| 9090:7005 | 9091:7005 | 9092:7005 | 9093:7005 | 9094:7005 | 9095:7005 |
| 9090:7006 | 9091:7006 | 9092:7006 | 9093:7006 | 9094:7006 | 9095:7006 |
| 9090:7007 | 9091:7007 | 9092:7007 | 9093:7007 | 9094:7007 | 9095:7007 |
| 9090:7008 | 9091:7008 | 9092:7008 | 9093:7008 | 9094:7008 | 9095:7008 |
| 9090:7009 | 9091:7009 | 9092:7009 | 9093:7009 | 9094:7009 | 9095:7009 |
| 9090:7010 | 9091:7010 | 9092:7010 | 9093:7010 | 9094:7010 | 9095:7010 |
| 9090:7011 | 9091:7011 | 9092:7011 | 9093:7011 | 9094:7011 | 9095:7011 |
| 9090:7012 | 9091:7012 | 9092:7012 | 9093:7012 | 9094:7012 | 9095:7012 |
| 9090:7013 | 9091:7013 | 9092:7013 | 9093:7013 | 9094:7013 | 9095:7013 |
| 9090:7014 | 9091:7014 | 9092:7014 | 9093:7014 | 9094:7014 | 9095:7014 |
| 9090:7015 | 9091:7015 | 9092:7015 | 9093:7015 | 9094:7015 | 9095:7015 |
| 9090:7016 | 9091:7016 | 9092:7016 | 9093:7016 | 9094:7016 | 9095:7016 |
| 9090:7017 | 9091:7017 | 9092:7017 | 9093:7017 | 9094:7017 | 9095:7017 |
| 9090:7018 | 9091:7018 | 9092:7018 | 9093:7018 | 9094:7018 | 9095:7018 |
| 9090:7019 | 9091:7019 | 9092:7019 | 9093:7019 | 9094:7019 | 9095:7019 |
| 9090:7020 | 9091:7020 | 9092:7020 | 9093:7020 | 9094:7020 | 9095:7020 |
| 9090:7021 | 9091:7021 | 9092:7021 | 9093:7021 | 9094:7021 | 9095:7021 |
| 9090:7022 | 9091:7022 | 9092:7022 | 9093:7022 | 9094:7022 | 9095:7022 |
| 9090:7023 | 9091:7023 | 9092:7023 | 9093:7023 | 9094:7023 | 9095:7023 |
| 9090:7024 | 9091:7024 | 9092:7024 | 9093:7024 | 9094:7024 | 9095:7024 |
| 9090:7025 | 9091:7025 | 9092:7025 | 9093:7025 | 9094:7025 | 9095:7025 |
| 9090:7026 | 9091:7026 | 9092:7026 | 9093:7026 | 9094:7026 | 9095:7026 |
| 9090:7027 | 9091:7027 | 9092:7027 | 9093:7027 | 9094:7027 | 9095:7027 |

| X:Y | X:Y | X:Y | X:Y | X:Y | X:Y |
|---|---|---|---|---|---|
| 9096:7000 | 9097:7000 | 9098:7000 | 9099:7000 | 9100:7000 | 9101:7000 |
| 9096:7001 | 9097:7001 | 9098:7001 | 9099:7001 | 9100:7001 | 9101:7001 |
| 9096:7002 | 9097:7002 | 9098:7002 | 9099:7002 | 9100:7002 | 9101:7002 |
| 9096:7003 | 9097:7003 | 9098:7003 | 9099:7003 | 9100:7003 | 9101:7003 |
| 9096:7004 | 9097:7004 | 9098:7004 | 9099:7004 | 9100:7004 | 9101:7004 |
| 9096:7005 | 9097:7005 | 9098:7005 | 9099:7005 | 9100:7005 | 9101:7005 |
| 9096:7006 | 9097:7006 | 9098:7006 | 9099:7006 | 9100:7006 | 9101:7006 |
| 9096:7007 | 9097:7007 | 9098:7007 | 9099:7007 | 9100:7007 | 9101:7007 |
| 9096:7008 | 9097:7008 | 9098:7008 | 9099:7008 | 9100:7008 | 9101:7008 |
| 9096:7009 | 9097:7009 | 9098:7009 | 9099:7009 | 9100:7009 | 9101:7009 |
| 9096:7010 | 9097:7010 | 9098:7010 | 9099:7010 | 9100:7010 | 9101:7010 |
| 9096:7011 | 9097:7011 | 9098:7011 | 9099:7011 | 9100:7011 | 9101:7011 |
| 9096:7012 | 9097:7012 | 9098:7012 | 9099:7012 | 9100:7012 | 9101:7012 |
| 9096:7013 | 9097:7013 | 9098:7013 | 9099:7013 | 9100:7013 | 9101:7013 |
| 9096:7014 | 9097:7014 | 9098:7014 | 9099:7014 | 9100:7014 | 9101:7014 |
| 9096:7015 | 9097:7015 | 9098:7015 | 9099:7015 | 9100:7015 | 9101:7015 |
| 9096:7016 | 9097:7016 | 9098:7016 | 9099:7016 | 9100:7016 | 9101:7016 |
| 9096:7017 | 9097:7017 | 9098:7017 | 9099:7017 | 9100:7017 | 9101:7017 |
| 9096:7018 | 9097:7018 | 9098:7018 | 9099:7018 | 9100:7018 | 9101:7018 |
| 9096:7019 | 9097:7019 | 9098:7019 | 9099:7019 | 9100:7019 | 9101:7019 |
| 9096:7020 | 9097:7020 | 9098:7020 | 9099:7020 | 9100:7020 | 9101:7020 |
| 9096:7021 | 9097:7021 | 9098:7021 | 9099:7021 | 9100:7021 | 9101:7021 |
| 9096:7022 | 9097:7022 | 9098:7022 | 9099:7022 | 9100:7022 | 9101:7022 |
| 9096:7023 | 9097:7023 | 9098:7023 | 9099:7023 | 9100:7023 | 9101:7023 |
| 9096:7024 | 9097:7024 | 9098:7024 | 9099:7024 | 9100:7024 | 9101:7024 |
| 9096:7025 | 9097:7025 | 9098:7025 | 9099:7025 | 9100:7025 | 9101:7025 |
| 9096:7026 | 9097:7026 | 9098:7026 | 9099:7026 | 9100:7026 | 9101:7026 |
| 9096:7027 | 9097:7027 | 9098:7027 | 9099:7027 | 9100:7027 | 9101:7027 |

| X:Y | X:Y | X:Y | X:Y | X:Y | X:Y |
|---|---|---|---|---|---|
| 9102:7000 | 9103:7000 | 9104:7000 | 9105:7000 | — | — |
| 9102:7001 | 9103:7001 | 9104:7001 | 9105:7001 | | |
| 9102:7002 | 9103:7002 | 9104:7002 | 9105:7002 | | |
| 9102:7003 | 9103:7003 | 9104:7003 | 9105:7003 | | |
| 9102:7004 | 9103:7004 | 9104:7004 | 9105:7004 | | |
| 9102:7005 | 9103:7005 | 9104:7005 | 9105:7005 | | |
| 9102:7006 | 9103:7006 | 9104:7006 | 9105:7006 | | |
| 9102:7007 | 9103:7007 | 9104:7007 | 9105:7007 | | |
| 9102:7008 | 9103:7008 | 9104:7008 | 9105:7008 | | |
| 9102:7009 | 9103:7009 | 9104:7009 | 9105:7009 | | |
| 9102:7010 | 9103:7010 | 9104:7010 | 9105:7010 | | |
| 9102:7011 | 9103:7011 | 9104:7011 | 9105:7011 | | |
| 9102:7012 | 9103:7012 | 9104:7012 | 9105:7012 | | |
| 9102:7013 | 9103:7013 | 9104:7013 | 9105:7013 | | |
| 9102:7014 | 9103:7014 | 9104:7014 | 9105:7014 | | |
| 9102:7015 | 9103:7015 | 9104:7015 | 9105:7015 | | |
| 9102:7016 | 9103:7016 | 9104:7016 | 9105:7016 | | |
| 9102:7017 | 9103:7017 | 9104:7017 | 9105:7017 | | |
| 9102:7018 | 9103:7018 | 9104:7018 | 9105:7018 | | |
| 9102:7019 | 9103:7019 | 9104:7019 | 9105:7019 | | |
| 9102:7020 | 9103:7020 | 9104:7020 | 9105:7020 | | |
| 9102:7021 | 9103:7021 | 9104:7021 | 9105:7021 | | |
| 9102:7022 | 9103:7022 | 9104:7022 | 9105:7022 | | |
| 9102:7023 | 9103:7023 | 9104:7023 | 9105:7023 | | |
| 9102:7024 | 9103:7024 | 9104:7024 | 9105:7024 | | |
| 9102:7025 | 9103:7025 | 9104:7025 | 9105:7025 | | |
| 9102:7026 | 9103:7026 | 9104:7026 | 9105:7026 | | |
| 9102:7027 | 9103:7027 | 9104:7027 | 9105:7027 | | |

TABLE D

Example combinations of a compound X with a compound Y.

| X:Y | X:Y | X:Y | X:Y | X:Y | X:Y |
|---|---|---|---|---|---|
| 6000:9000 | 6040:9000 | 6000:9001 | 6040:9001 | 6000:9002 | 6040:9002 |
| 6001:9000 | 6041:9000 | 6001:9001 | 6041:9001 | 6001:9002 | 6041:9002 |
| 6002:9000 | 6042:9000 | 6002:9001 | 6042:9001 | 6002:9002 | 6042:9002 |
| 6003:9000 | 6043:9000 | 6003:9001 | 6043:9001 | 6003:9002 | 6043:9002 |
| 6004:9000 | 6044:9000 | 6004:9001 | 6044:9001 | 6004:9002 | 6044:9002 |
| 6005:9000 | 6045:9000 | 6005:9001 | 6045:9001 | 6005:9002 | 6045:9002 |
| 6006:9000 | 6046:9000 | 6006:9001 | 6046:9001 | 6006:9002 | 6046:9002 |
| 6007:9000 | 6047:9000 | 6007:9001 | 6047:9001 | 6007:9002 | 6047:9002 |
| 6008:9000 | 6048:9000 | 6008:9001 | 6048:9001 | 6008:9002 | 6048:9002 |
| 6009:9000 | 6049:9000 | 6009:9001 | 6049:9001 | 6009:9002 | 6049:9002 |
| 6010:9000 | 6050:9000 | 6010:9001 | 6050:9001 | 6010:9002 | 6050:9002 |
| 6011:9000 | 6051:9000 | 6011:9001 | 6051:9001 | 6011:9002 | 6051:9002 |
| 6012:9000 | 6052:9000 | 6012:9001 | 6052:9001 | 6012:9002 | 6052:9002 |
| 6013:9000 | 6053:9000 | 6013:9001 | 6053:9001 | 6013:9002 | 6053:9002 |
| 6014:9000 | 6054:9000 | 6014:9001 | 6054:9001 | 6014:9002 | 6054:9002 |
| 6015:9000 | 6055:9000 | 6015:9001 | 6055:9001 | 6015:9002 | 6055:9002 |
| 6016:9000 | 6056:9000 | 6016:9001 | 6056:9001 | 6016:9002 | 6056:9002 |
| 6017:9000 | 6057:9000 | 6017:9001 | 6057:9001 | 6017:9002 | 6057:9002 |
| 6018:9000 | 6058:9000 | 6018:9001 | 6058:9001 | 6018:9002 | 6058:9002 |
| 6019:9000 | 6059:9000 | 6019:9001 | 6059:9001 | 6019:9002 | 6059:9002 |
| 6020:9000 | 6060:9000 | 6020:9001 | 6060:9001 | 6020:9002 | 6060:9002 |
| 6021:9000 | 6061:9000 | 6021:9001 | 6061:9001 | 6021:9002 | 6061:9002 |
| 6022:9000 | 6062:9000 | 6022:9001 | 6062:9001 | 6022:9002 | 6062:9002 |
| 6023:9000 | 6063:9000 | 6023:9001 | 6063:9001 | 6023:9002 | 6063:9002 |
| 6024:9000 | 6064:9000 | 6024:9001 | 6064:9001 | 6024:9002 | 6064:9002 |
| 6025:9000 | 6065:9000 | 6025:9001 | 6065:9001 | 6025:9002 | 6065:9002 |
| 6026:9000 | 6066:9000 | 6026:9001 | 6066:9001 | 6026:9002 | 6066:9002 |
| 6027:9000 | 6067:9000 | 6027:9001 | 6067:9001 | 6027:9002 | 6067:9002 |
| 6028:9000 | 6068:9000 | 6028:9001 | 6068:9001 | 6028:9002 | 6068:9002 |
| 6029:9000 | 6069:9000 | 6029:9001 | 6069:9001 | 6029:9002 | 6069:9002 |
| 6030:9000 | 6070:9000 | 6030:9001 | 6070:9001 | 6030:9002 | 6070:9002 |
| 6031:9000 | 6071:9000 | 6031:9001 | 6071:9001 | 6031:9002 | 6071:9002 |
| 6032:9000 | 6072:9000 | 6032:9001 | 6072:9001 | 6032:9002 | 6072:9002 |
| 6033:9000 | 6073:9000 | 6033:9001 | 6073:9001 | 6033:9002 | 6073:9002 |
| 6034:9000 | 6074:9000 | 6034:9001 | 6074:9001 | 6034:9002 | 6074:9002 |
| 6035:9000 | 6075:9000 | 6035:9001 | 6075:9001 | 6035:9002 | 6075:9002 |
| 6036:9000 | 6076:9000 | 6036:9001 | 6076:9001 | 6036:9002 | 6076:9002 |
| 6037:9000 | 6077:9000 | 6037:9001 | 6077:9001 | 6037:9002 | 6077:9002 |
| 6038:9000 | 6078:9000 | 6038:9001 | 6078:9001 | 6038:9002 | 6078:9002 |
| 6039:9000 | | 6039:9001 | | 6039:9002 | |

| X:Y | X:Y | X:Y | X:Y | X:Y | X:Y |
|---|---|---|---|---|---|
| 6000:9003 | 6040:9003 | 6000:9004 | 6040:9004 | 6000:9005 | 6040:9005 |
| 6001:9003 | 6041:9003 | 6001:9004 | 6041:9004 | 6001:9005 | 6041:9005 |
| 6002:9003 | 6042:9003 | 6002:9004 | 6042:9004 | 6002:9005 | 6042:9005 |
| 6003:9003 | 6043:9003 | 6003:9004 | 6043:9004 | 6003:9005 | 6043:9005 |
| 6004:9003 | 6044:9003 | 6004:9004 | 6044:9004 | 6004:9005 | 6044:9005 |
| 6005:9003 | 6045:9003 | 6005:9004 | 6045:9004 | 6005:9005 | 6045:9005 |
| 6006:9003 | 6046:9003 | 6006:9004 | 6046:9004 | 6006:9005 | 6046:9005 |
| 6007:9003 | 6047:9003 | 6007:9004 | 6047:9004 | 6007:9005 | 6047:9005 |
| 6008:9003 | 6048:9003 | 6008:9004 | 6048:9004 | 6008:9005 | 6048:9005 |
| 6009:9003 | 6049:9003 | 6009:9004 | 6049:9004 | 6009:9005 | 6049:9005 |
| 6010:9003 | 6050:9003 | 6010:9004 | 6050:9004 | 6010:9005 | 6050:9005 |

TABLE D-continued

| | | | | | |
|---|---|---|---|---|---|
| 6011:9003 | 6051:9003 | 6011:9004 | 6051:9004 | 6011:9005 | 6051:9005 |
| 6012:9003 | 6052:9003 | 6012:9004 | 6052:9004 | 6012:9005 | 6052:9005 |
| 6013:9003 | 6053:9003 | 6013:9004 | 6053:9004 | 6013:9005 | 6053:9005 |
| 6014:9003 | 6054:9003 | 6014:9004 | 6054:9004 | 6014:9005 | 6054:9005 |
| 6015:9003 | 6055:9003 | 6015:9004 | 6055:9004 | 6015:9005 | 6055:9005 |
| 6016:9003 | 6056:9003 | 6016:9004 | 6056:9004 | 6016:9005 | 6056:9005 |
| 6017:9003 | 6057:9003 | 6017:9004 | 6057:9004 | 6017:9005 | 6057:9005 |
| 6018:9003 | 6058:9003 | 6018:9004 | 6058:9004 | 6018:9005 | 6058:9005 |
| 6019:9003 | 6059:9003 | 6019:9004 | 6059:9004 | 6019:9005 | 6059:9005 |
| 6020:9003 | 6060:9003 | 6020:9004 | 6060:9004 | 6020:9005 | 6060:9005 |
| 6021:9003 | 6061:9003 | 6021:9004 | 6061:9004 | 6021:9005 | 6061:9005 |
| 6022:9003 | 6062:9003 | 6022:9004 | 6062:9004 | 6022:9005 | 6062:9005 |
| 6023:9003 | 6063:9003 | 6023:9004 | 6063:9004 | 6023:9005 | 6063:9005 |
| 6024:9003 | 6064:9003 | 6024:9004 | 6064:9004 | 6024:9005 | 6064:9005 |
| 6025:9003 | 6065:9003 | 6025:9004 | 6065:9004 | 6025:9005 | 6065:9005 |
| 6026:9003 | 6066:9003 | 6026:9004 | 6066:9004 | 6026:9005 | 6066:9005 |
| 6027:9003 | 6067:9003 | 6027:9004 | 6067:9004 | 6027:9005 | 6067:9005 |
| 6028:9003 | 6068:9003 | 6028:9004 | 6068:9004 | 6028:9005 | 6068:9005 |
| 6029:9003 | 6069:9003 | 6029:9004 | 6069:9004 | 6029:9005 | 6069:9005 |
| 6030:9003 | 6070:9003 | 6030:9004 | 6070:9004 | 6030:9005 | 6070:9005 |
| 6031:9003 | 6071:9003 | 6031:9004 | 6071:9004 | 6031:9005 | 6071:9005 |
| 6032:9003 | 6072:9003 | 6032:9004 | 6072:9004 | 6032:9005 | 6072:9005 |
| 6033:9003 | 6073:9003 | 6033:9004 | 6073:9004 | 6033:9005 | 6073:9005 |
| 6034:9003 | 6074:9003 | 6034:9004 | 6074:9004 | 6034:9005 | 6074:9005 |
| 6035:9003 | 6075:9003 | 6035:9004 | 6075:9004 | 6035:9005 | 6075:9005 |
| 6036:9003 | 6076:9003 | 6036:9004 | 6076:9004 | 6036:9005 | 6076:9005 |
| 6037:9003 | 6077:9003 | 6037:9004 | 6077:9004 | 6037:9005 | 6077:9005 |
| 6038:9003 | 6078:9003 | 6038:9004 | 6078:9004 | 6038:9005 | 6078:9005 |
| 6039:9003 | | 6039:9004 | | 6039:9005 | |

| X:Y | X:Y | X:Y | X:Y | X:Y | X:Y |
|---|---|---|---|---|---|
| 6000:9006 | 6040:9006 | 6000:9007 | 6040:9007 | 6000:9008 | 6040:9008 |
| 6001:9006 | 6041:9006 | 6001:9007 | 6041:9007 | 6001:9008 | 6041:9008 |
| 6002:9006 | 6042:9006 | 6002:9007 | 6042:9007 | 6002:9008 | 6042:9008 |
| 6003:9006 | 6043:9006 | 6003:9007 | 6043:9007 | 6003:9008 | 6043:9008 |
| 6004:9006 | 6044:9006 | 6004:9007 | 6044:9007 | 6004:9008 | 6044:9008 |
| 6005:9006 | 6045:9006 | 6005:9007 | 6045:9007 | 6005:9008 | 6045:9008 |
| 6006:9006 | 6046:9006 | 6006:9007 | 6046:9007 | 6006:9008 | 6046:9008 |
| 6007:9006 | 6047:9006 | 6007:9007 | 6047:9007 | 6007:9008 | 6047:9008 |
| 6008:9006 | 6048:9006 | 6008:9007 | 6048:9007 | 6008:9008 | 6048:9008 |
| 6009:9006 | 6049:9006 | 6009:9007 | 6049:9007 | 6009:9008 | 6049:9008 |
| 6010:9006 | 6050:9006 | 6010:9007 | 6050:9007 | 6010:9008 | 6050:9008 |
| 6011:9006 | 6051:9006 | 6011:9007 | 6051:9007 | 6011:9008 | 6051:9008 |
| 6012:9006 | 6052:9006 | 6012:9007 | 6052:9007 | 6012:9008 | 6052:9008 |
| 6013:9006 | 6053:9006 | 6013:9007 | 6053:9007 | 6013:9008 | 6053:9008 |
| 6014:9006 | 6054:9006 | 6014:9007 | 6054:9007 | 6014:9008 | 6054:9008 |
| 6015:9006 | 6055:9006 | 6015:9007 | 6055:9007 | 6015:9008 | 6055:9008 |
| 6016:9006 | 6056:9006 | 6016:9007 | 6056:9007 | 6016:9008 | 6056:9008 |
| 6017:9006 | 6057:9006 | 6017:9007 | 6057:9007 | 6017:9008 | 6057:9008 |
| 6018:9006 | 6058:9006 | 6018:9007 | 6058:9007 | 6018:9008 | 6058:9008 |
| 6019:9006 | 6059:9006 | 6019:9007 | 6059:9007 | 6019:9008 | 6059:9008 |
| 6020:9006 | 6060:9006 | 6020:9007 | 6060:9007 | 6020:9008 | 6060:9008 |
| 6021:9006 | 6061:9006 | 6021:9007 | 6061:9007 | 6021:9008 | 6061:9008 |
| 6022:9006 | 6062:9006 | 6022:9007 | 6062:9007 | 6022:9008 | 6062:9008 |
| 6023:9006 | 6063:9006 | 6023:9007 | 6063:9007 | 6023:9008 | 6063:9008 |
| 6024:9006 | 6064:9006 | 6024:9007 | 6064:9007 | 6024:9008 | 6064:9008 |
| 6025:9006 | 6065:9006 | 6025:9007 | 6065:9007 | 6025:9008 | 6065:9008 |
| 6026:9006 | 6066:9006 | 6026:9007 | 6066:9007 | 6026:9008 | 6066:9008 |
| 6027:9006 | 6067:9006 | 6027:9007 | 6067:9007 | 6027:9008 | 6067:9008 |
| 6028:9006 | 6068:9006 | 6028:9007 | 6068:9007 | 6028:9008 | 6068:9008 |
| 6029:9006 | 6069:9006 | 6029:9007 | 6069:9007 | 6029:9008 | 6069:9008 |
| 6030:9006 | 6070:9006 | 6030:9007 | 6070:9007 | 6030:9008 | 6070:9008 |
| 6031:9006 | 6071:9006 | 6031:9007 | 6071:9007 | 6031:9008 | 6071:9008 |
| 6032:9006 | 6072:9006 | 6032:9007 | 6072:9007 | 6032:9008 | 6072:9008 |
| 6033:9006 | 6073:9006 | 6033:9007 | 6073:9007 | 6033:9008 | 6073:9008 |
| 6034:9006 | 6074:9006 | 6034:9007 | 6074:9007 | 6034:9008 | 6074:9008 |
| 6035:9006 | 6075:9006 | 6035:9007 | 6075:9007 | 6035:9008 | 6075:9008 |
| 6036:9006 | 6076:9006 | 6036:9007 | 6076:9007 | 6036:9008 | 6076:9008 |
| 6037:9006 | 6077:9006 | 6037:9007 | 6077:9007 | 6037:9008 | 6077:9008 |
| 6038:9006 | 6078:9006 | 6038:9007 | 6078:9007 | 6038:9008 | 6078:9008 |
| 6039:9006 | | 6039:9007 | | 6039:9008 | |

| X:Y | X:Y | X:Y | X:Y | X:Y | X:Y |
|---|---|---|---|---|---|
| 6000:9009 | 6040:9009 | 6000:9010 | 6040:9010 | 6000:9011 | 6040:9011 |
| 6001:9009 | 6041:9009 | 6001:9010 | 6041:9010 | 6001:9011 | 6041:9011 |
| 6002:9009 | 6042:9009 | 6002:9010 | 6042:9010 | 6002:9011 | 6042:9011 |
| 6003:9009 | 6043:9009 | 6003:9010 | 6043:9010 | 6003:9011 | 6043:9011 |
| 6004:9009 | 6044:9009 | 6004:9010 | 6044:9010 | 6004:9011 | 6044:9011 |
| 6005:9009 | 6045:9009 | 6005:9010 | 6045:9010 | 6005:9011 | 6045:9011 |
| 6006:9009 | 6046:9009 | 6006:9010 | 6046:9010 | 6006:9011 | 6046:9011 |
| 6007:9009 | 6047:9009 | 6007:9010 | 6047:9010 | 6007:9011 | 6047:9011 |
| 6008:9009 | 6048:9009 | 6008:9010 | 6048:9010 | 6008:9011 | 6048:9011 |
| 6009:9009 | 6049:9009 | 6009:9010 | 6049:9010 | 6009:9011 | 6049:9011 |
| 6010:9009 | 6050:9009 | 6010:9010 | 6050:9010 | 6010:9011 | 6050:9011 |
| 6011:9009 | 6051:9009 | 6011:9010 | 6051:9010 | 6011:9011 | 6051:9011 |
| 6012:9009 | 6052:9009 | 6012:9010 | 6052:9010 | 6012:9011 | 6052:9011 |
| 6013:9009 | 6053:9009 | 6013:9010 | 6053:9010 | 6013:9011 | 6053:9011 |
| 6014:9009 | 6054:9009 | 6014:9010 | 6054:9010 | 6014:9011 | 6054:9011 |
| 6015:9009 | 6055:9009 | 6015:9010 | 6055:9010 | 6015:9011 | 6055:9011 |
| 6016:9009 | 6056:9009 | 6016:9010 | 6056:9010 | 6016:9011 | 6056:9011 |
| 6017:9009 | 6057:9009 | 6017:9010 | 6057:9010 | 6017:9011 | 6057:9011 |
| 6018:9009 | 6058:9009 | 6018:9010 | 6058:9010 | 6018:9011 | 6058:9011 |
| 6019:9009 | 6059:9009 | 6019:9010 | 6059:9010 | 6019:9011 | 6059:9011 |
| 6020:9009 | 6060:9009 | 6020:9010 | 6060:9010 | 6020:9011 | 6060:9011 |
| 6021:9009 | 6061:9009 | 6021:9010 | 6061:9010 | 6021:9011 | 6061:9011 |
| 6022:9009 | 6062:9009 | 6022:9010 | 6062:9010 | 6022:9011 | 6062:9011 |
| 6023:9009 | 6063:9009 | 6023:9010 | 6063:9010 | 6023:9011 | 6063:9011 |
| 6024:9009 | 6064:9009 | 6024:9010 | 6064:9010 | 6024:9011 | 6064:9011 |
| 6025:9009 | 6065:9009 | 6025:9010 | 6065:9010 | 6025:9011 | 6065:9011 |
| 6026:9009 | 6066:9009 | 6026:9010 | 6066:9010 | 6026:9011 | 6066:9011 |
| 6027:9009 | 6067:9009 | 6027:9010 | 6067:9010 | 6027:9011 | 6067:9011 |
| 6028:9009 | 6068:9009 | 6028:9010 | 6068:9010 | 6028:9011 | 6068:9011 |
| 6029:9009 | 6069:9009 | 6029:9010 | 6069:9010 | 6029:9011 | 6069:9011 |
| 6030:9009 | 6070:9009 | 6030:9010 | 6070:9010 | 6030:9011 | 6070:9011 |
| 6031:9009 | 6071:9009 | 6031:9010 | 6071:9010 | 6031:9011 | 6071:9011 |
| 6032:9009 | 6072:9009 | 6032:9010 | 6072:9010 | 6032:9011 | 6072:9011 |
| 6033:9009 | 6073:9009 | 6033:9010 | 6073:9010 | 6033:9011 | 6073:9011 |
| 6034:9009 | 6074:9009 | 6034:9010 | 6074:9010 | 6034:9011 | 6074:9011 |
| 6035:9009 | 6075:9009 | 6035:9010 | 6075:9010 | 6035:9011 | 6075:9011 |
| 6036:9009 | 6076:9009 | 6036:9010 | 6076:9010 | 6036:9011 | 6076:9011 |
| 6037:9009 | 6077:9009 | 6037:9010 | 6077:9010 | 6037:9011 | 6077:9011 |
| 6038:9009 | 6078:9009 | 6038:9010 | 6078:9010 | 6038:9011 | 6078:9011 |
| 6039:9009 | | 6039:9010 | | 6039:9011 | |

| X:Y | X:Y | X:Y | X:Y | X:Y | X:Y |
|---|---|---|---|---|---|
| 6000:9012 | 6040:9012 | 6000:9013 | 6040:9013 | 6000:9014 | 6040:9014 |
| 6001:9012 | 6041:9012 | 6001:9013 | 6041:9013 | 6001:9014 | 6041:9014 |
| 6002:9012 | 6042:9012 | 6002:9013 | 6042:9013 | 6002:9014 | 6042:9014 |
| 6003:9012 | 6043:9012 | 6003:9013 | 6043:9013 | 6003:9014 | 6043:9014 |
| 6004:9012 | 6044:9012 | 6004:9013 | 6044:9013 | 6004:9014 | 6044:9014 |
| 6005:9012 | 6045:9012 | 6005:9013 | 6045:9013 | 6005:9014 | 6045:9014 |
| 6006:9012 | 6046:9012 | 6006:9013 | 6046:9013 | 6006:9014 | 6046:9014 |
| 6007:9012 | 6047:9012 | 6007:9013 | 6047:9013 | 6007:9014 | 6047:9014 |
| 6008:9012 | 6048:9012 | 6008:9013 | 6048:9013 | 6008:9014 | 6048:9014 |
| 6009:9012 | 6049:9012 | 6009:9013 | 6049:9013 | 6009:9014 | 6049:9014 |
| 6010:9012 | 6050:9012 | 6010:9013 | 6050:9013 | 6010:9014 | 6050:9014 |
| 6011:9012 | 6051:9012 | 6011:9013 | 6051:9013 | 6011:9014 | 6051:9014 |
| 6012:9012 | 6052:9012 | 6012:9013 | 6052:9013 | 6012:9014 | 6052:9014 |
| 6013:9012 | 6053:9012 | 6013:9013 | 6053:9013 | 6013:9014 | 6053:9014 |
| 6014:9012 | 6054:9012 | 6014:9013 | 6054:9013 | 6014:9014 | 6054:9014 |
| 6015:9012 | 6055:9012 | 6015:9013 | 6055:9013 | 6015:9014 | 6055:9014 |
| 6016:9012 | 6056:9012 | 6016:9013 | 6056:9013 | 6016:9014 | 6056:9014 |
| 6017:9012 | 6057:9012 | 6017:9013 | 6057:9013 | 6017:9014 | 6057:9014 |
| 6018:9012 | 6058:9012 | 6018:9013 | 6058:9013 | 6018:9014 | 6058:9014 |
| 6019:9012 | 6059:9012 | 6019:9013 | 6059:9013 | 6019:9014 | 6059:9014 |
| 6020:9012 | 6060:9012 | 6020:9013 | 6060:9013 | 6020:9014 | 6060:9014 |
| 6021:9012 | 6061:9012 | 6021:9013 | 6061:9013 | 6021:9014 | 6061:9014 |
| 6022:9012 | 6062:9012 | 6022:9013 | 6062:9013 | 6022:9014 | 6062:9014 |
| 6023:9012 | 6063:9012 | 6023:9013 | 6063:9013 | 6023:9014 | 6063:9014 |
| 6024:9012 | 6064:9012 | 6024:9013 | 6064:9013 | 6024:9014 | 6064:9014 |
| 6025:9012 | 6065:9012 | 6025:9013 | 6065:9013 | 6025:9014 | 6065:9014 |
| 6026:9012 | 6066:9012 | 6026:9013 | 6066:9013 | 6026:9014 | 6066:9014 |
| 6027:9012 | 6067:9012 | 6027:9013 | 6067:9013 | 6027:9014 | 6067:9014 |
| 6028:9012 | 6068:9012 | 6028:9013 | 6068:9013 | 6028:9014 | 6068:9014 |
| 6029:9012 | 6069:9012 | 6029:9013 | 6069:9013 | 6029:9014 | 6069:9014 |
| 6030:9012 | 6070:9012 | 6030:9013 | 6070:9013 | 6030:9014 | 6070:9014 |
| 6031:9012 | 6071:9012 | 6031:9013 | 6071:9013 | 6031:9014 | 6071:9014 |
| 6032:9012 | 6072:9012 | 6032:9013 | 6072:9013 | 6032:9014 | 6072:9014 |
| 6033:9012 | 6073:9012 | 6033:9013 | 6073:9013 | 6033:9014 | 6073:9014 |
| 6034:9012 | 6074:9012 | 6034:9013 | 6074:9013 | 6034:9014 | 6074:9014 |
| 6035:9012 | 6075:9012 | 6035:9013 | 6075:9013 | 6035:9014 | 6075:9014 |
| 6036:9012 | 6076:9012 | 6036:9013 | 6076:9013 | 6036:9014 | 6076:9014 |

TABLE D-continued

| X:Y | X:Y | X:Y | X:Y | X:Y | X:Y |
|---|---|---|---|---|---|
| 6037:9012 | 6077:9012 | 6037:9013 | 6077:9013 | 6037:9014 | 6077:9014 |
| 6038:9012 | 6078:9012 | 6038:9013 | 6078:9013 | 6038:9014 | 6078:9014 |
| 6039:9012 | | 6039:9013 | | 6039:9014 | |

| X:Y | X:Y | X:Y | X:Y | X:Y | X:Y |
|---|---|---|---|---|---|
| 6000:9015 | 6040:9015 | 6000:9016 | 6040:9016 | 6000:9017 | 6040:9017 |
| 6001:9015 | 6041:9015 | 6001:9016 | 6041:9016 | 6001:9017 | 6041:9017 |
| 6002:9015 | 6042:9015 | 6002:9016 | 6042:9016 | 6002:9017 | 6042:9017 |
| 6003:9015 | 6043:9015 | 6003:9016 | 6043:9016 | 6003:9017 | 6043:9017 |
| 6004:9015 | 6044:9015 | 6004:9016 | 6044:9016 | 6004:9017 | 6044:9017 |
| 6005:9015 | 6045:9015 | 6005:9016 | 6045:9016 | 6005:9017 | 6045:9017 |
| 6006:9015 | 6046:9015 | 6006:9016 | 6046:9016 | 6006:9017 | 6046:9017 |
| 6007:9015 | 6047:9015 | 6007:9016 | 6047:9016 | 6007:9017 | 6047:9017 |
| 6008:9015 | 6048:9015 | 6008:9016 | 6048:9016 | 6008:9017 | 6048:9017 |
| 6009:9015 | 6049:9015 | 6009:9016 | 6049:9016 | 6009:9017 | 6049:9017 |
| 6010:9015 | 6050:9015 | 6010:9016 | 6050:9016 | 6010:9017 | 6050:9017 |
| 6011:9015 | 6051:9015 | 6011:9016 | 6051:9016 | 6011:9017 | 6051:9017 |
| 6012:9015 | 6052:9015 | 6012:9016 | 6052:9016 | 6012:9017 | 6052:9017 |
| 6013:9015 | 6053:9015 | 6013:9016 | 6053:9016 | 6013:9017 | 6053:9017 |
| 6014:9015 | 6054:9015 | 6014:9016 | 6054:9016 | 6014:9017 | 6054:9017 |
| 6015:9015 | 6055:9015 | 6015:9016 | 6055:9016 | 6015:9017 | 6055:9017 |
| 6016:9015 | 6056:9015 | 6016:9016 | 6056:9016 | 6016:9017 | 6056:9017 |
| 6017:9015 | 6057:9015 | 6017:9016 | 6057:9016 | 6017:9017 | 6057:9017 |
| 6018:9015 | 6058:9015 | 6018:9016 | 6058:9016 | 6018:9017 | 6058:9017 |
| 6019:9015 | 6059:9015 | 6019:9016 | 6059:9016 | 6019:9017 | 6059:9017 |
| 6020:9015 | 6060:9015 | 6020:9016 | 6060:9016 | 6020:9017 | 6060:9017 |
| 6021:9015 | 6061:9015 | 6021:9016 | 6061:9016 | 6021:9017 | 6061:9017 |
| 6022:9015 | 6062:9015 | 6022:9016 | 6062:9016 | 6022:9017 | 6062:9017 |
| 6023:9015 | 6063:9015 | 6023:9016 | 6063:9016 | 6023:9017 | 6063:9017 |
| 6024:9015 | 6064:9015 | 6024:9016 | 6064:9016 | 6024:9017 | 6064:9017 |
| 6025:9015 | 6065:9015 | 6025:9016 | 6065:9016 | 6025:9017 | 6065:9017 |
| 6026:9015 | 6066:9015 | 6026:9016 | 6066:9016 | 6026:9017 | 6066:9017 |
| 6027:9015 | 6067:9015 | 6027:9016 | 6067:9016 | 6027:9017 | 6067:9017 |
| 6028:9015 | 6068:9015 | 6028:9016 | 6068:9016 | 6028:9017 | 6068:9017 |
| 6029:9015 | 6069:9015 | 6029:9016 | 6069:9016 | 6029:9017 | 6069:9017 |
| 6030:9015 | 6070:9015 | 6030:9016 | 6070:9016 | 6030:9017 | 6070:9017 |
| 6031:9015 | 6071:9015 | 6031:9016 | 6071:9016 | 6031:9017 | 6071:9017 |
| 6032:9015 | 6072:9015 | 6032:9016 | 6072:9016 | 6032:9017 | 6072:9017 |
| 6033:9015 | 6073:9015 | 6033:9016 | 6073:9016 | 6033:9017 | 6073:9017 |
| 6034:9015 | 6074:9015 | 6034:9016 | 6074:9016 | 6034:9017 | 6074:9017 |
| 6035:9015 | 6075:9015 | 6035:9016 | 6075:9016 | 6035:9017 | 6075:9017 |
| 6036:9015 | 6076:9015 | 6036:9016 | 6076:9016 | 6036:9017 | 6076:9017 |
| 6037:9015 | 6077:9015 | 6037:9016 | 6077:9016 | 6037:9017 | 6077:9017 |
| 6038:9015 | 6078:9015 | 6038:9016 | 6078:9016 | 6038:9017 | 6078:9017 |
| 6039:9015 | | 6039:9016 | | 6039:9017 | |

| X:Y | X:Y | X:Y | X:Y | X:Y | X:Y |
|---|---|---|---|---|---|
| 6000:9018 | 6040:9018 | 6000:9019 | 6040:9019 | 6000:9020 | 6040:9020 |
| 6001:9018 | 6041:9018 | 6001:9019 | 6041:9019 | 6001:9020 | 6041:9020 |
| 6002:9018 | 6042:9018 | 6002:9019 | 6042:9019 | 6002:9020 | 6042:9020 |
| 6003:9018 | 6043:9018 | 6003:9019 | 6043:9019 | 6003:9020 | 6043:9020 |
| 6004:9018 | 6044:9018 | 6004:9019 | 6044:9019 | 6004:9020 | 6044:9020 |
| 6005:9018 | 6045:9018 | 6005:9019 | 6045:9019 | 6005:9020 | 6045:9020 |
| 6006:9018 | 6046:9018 | 6006:9019 | 6046:9019 | 6006:9020 | 6046:9020 |
| 6007:9018 | 6047:9018 | 6007:9019 | 6047:9019 | 6007:9020 | 6047:9020 |
| 6008:9018 | 6048:9018 | 6008:9019 | 6048:9019 | 6008:9020 | 6048:9020 |
| 6009:9018 | 6049:9018 | 6009:9019 | 6049:9019 | 6009:9020 | 6049:9020 |
| 6010:9018 | 6050:9018 | 6010:9019 | 6050:9019 | 6010:9020 | 6050:9020 |
| 6011:9018 | 6051:9018 | 6011:9019 | 6051:9019 | 6011:9020 | 6051:9020 |
| 6012:9018 | 6052:9018 | 6012:9019 | 6052:9019 | 6012:9020 | 6052:9020 |
| 6013:9018 | 6053:9018 | 6013:9019 | 6053:9019 | 6013:9020 | 6053:9020 |
| 6014:9018 | 6054:9018 | 6014:9019 | 6054:9019 | 6014:9020 | 6054:9020 |
| 6015:9018 | 6055:9018 | 6015:9019 | 6055:9019 | 6015:9020 | 6055:9020 |
| 6016:9018 | 6056:9018 | 6016:9019 | 6056:9019 | 6016:9020 | 6056:9020 |
| 6017:9018 | 6057:9018 | 6017:9019 | 6057:9019 | 6017:9020 | 6057:9020 |
| 6018:9018 | 6058:9018 | 6018:9019 | 6058:9019 | 6018:9020 | 6058:9020 |
| 6019:9018 | 6059:9018 | 6019:9019 | 6059:9019 | 6019:9020 | 6059:9020 |
| 6020:9018 | 6060:9018 | 6020:9019 | 6060:9019 | 6020:9020 | 6060:9020 |
| 6021:9018 | 6061:9018 | 6021:9019 | 6061:9019 | 6021:9020 | 6061:9020 |
| 6022:9018 | 6062:9018 | 6022:9019 | 6062:9019 | 6022:9020 | 6062:9020 |
| 6023:9018 | 6063:9018 | 6023:9019 | 6063:9019 | 6023:9020 | 6063:9020 |
| 6024:9018 | 6064:9018 | 6024:9019 | 6064:9019 | 6024:9020 | 6064:9020 |
| 6025:9018 | 6065:9018 | 6025:9019 | 6065:9019 | 6025:9020 | 6065:9020 |
| 6026:9018 | 6066:9018 | 6026:9019 | 6066:9019 | 6026:9020 | 6066:9020 |
| 6027:9018 | 6067:9018 | 6027:9019 | 6067:9019 | 6027:9020 | 6067:9020 |
| 6028:9018 | 6068:9018 | 6028:9019 | 6068:9019 | 6028:9020 | 6068:9020 |
| 6029:9018 | 6069:9018 | 6029:9019 | 6069:9019 | 6029:9020 | 6069:9020 |
| 6030:9018 | 6070:9018 | 6030:9019 | 6070:9019 | 6030:9020 | 6070:9020 |
| 6031:9018 | 6071:9018 | 6031:9019 | 6071:9019 | 6031:9020 | 6071:9020 |
| 6032:9018 | 6072:9018 | 6032:9019 | 6072:9019 | 6032:9020 | 6072:9020 |
| 6033:9018 | 6073:9018 | 6033:9019 | 6073:9019 | 6033:9020 | 6073:9020 |
| 6034:9018 | 6074:9018 | 6034:9019 | 6074:9019 | 6034:9020 | 6074:9020 |
| 6035:9018 | 6075:9018 | 6035:9019 | 6075:9019 | 6035:9020 | 6075:9020 |
| 6036:9018 | 6076:9018 | 6036:9019 | 6076:9019 | 6036:9020 | 6076:9020 |
| 6037:9018 | 6077:9018 | 6037:9019 | 6077:9019 | 6037:9020 | 6077:9020 |
| 6038:9018 | 6078:9018 | 6038:9019 | 6078:9019 | 6038:9020 | 6078:9020 |
| 6039:9018 | | 6039:9019 | | 6039:9020 | |

| X:Y | X:Y | X:Y | X:Y | X:Y | X:Y |
|---|---|---|---|---|---|
| 6000:9021 | 6040:9021 | 6000:9022 | 6040:9022 | 6000:9023 | 6040:9023 |
| 6001:9021 | 6041:9021 | 6001:9022 | 6041:9022 | 6001:9023 | 6041:9023 |
| 6002:9021 | 6042:9021 | 6002:9022 | 6042:9022 | 6002:9023 | 6042:9023 |
| 6003:9021 | 6043:9021 | 6003:9022 | 6043:9022 | 6003:9023 | 6043:9023 |
| 6004:9021 | 6044:9021 | 6004:9022 | 6044:9022 | 6004:9023 | 6044:9023 |
| 6005:9021 | 6045:9021 | 6005:9022 | 6045:9022 | 6005:9023 | 6045:9023 |
| 6006:9021 | 6046:9021 | 6006:9022 | 6046:9022 | 6006:9023 | 6046:9023 |
| 6007:9021 | 6047:9021 | 6007:9022 | 6047:9022 | 6007:9023 | 6047:9023 |
| 6008:9021 | 6048:9021 | 6008:9022 | 6048:9022 | 6008:9023 | 6048:9023 |
| 6009:9021 | 6049:9021 | 6009:9022 | 6049:9022 | 6009:9023 | 6049:9023 |
| 6010:9021 | 6050:9021 | 6010:9022 | 6050:9022 | 6010:9023 | 6050:9023 |
| 6011:9021 | 6051:9021 | 6011:9022 | 6051:9022 | 6011:9023 | 6051:9023 |
| 6012:9021 | 6052:9021 | 6012:9022 | 6052:9022 | 6012:9023 | 6052:9023 |
| 6013:9021 | 6053:9021 | 6013:9022 | 6053:9022 | 6013:9023 | 6053:9023 |
| 6014:9021 | 6054:9021 | 6014:9022 | 6054:9022 | 6014:9023 | 6054:9023 |
| 6015:9021 | 6055:9021 | 6015:9022 | 6055:9022 | 6015:9023 | 6055:9023 |
| 6016:9021 | 6056:9021 | 6016:9022 | 6056:9022 | 6016:9023 | 6056:9023 |
| 6017:9021 | 6057:9021 | 6017:9022 | 6057:9022 | 6017:9023 | 6057:9023 |
| 6018:9021 | 6058:9021 | 6018:9022 | 6058:9022 | 6018:9023 | 6058:9023 |
| 6019:9021 | 6059:9021 | 6019:9022 | 6059:9022 | 6019:9023 | 6059:9023 |
| 6020:9021 | 6060:9021 | 6020:9022 | 6060:9022 | 6020:9023 | 6060:9023 |
| 6021:9021 | 6061:9021 | 6021:9022 | 6061:9022 | 6021:9023 | 6061:9023 |
| 6022:9021 | 6062:9021 | 6022:9022 | 6062:9022 | 6022:9023 | 6062:9023 |
| 6023:9021 | 6063:9021 | 6023:9022 | 6063:9022 | 6023:9023 | 6063:9023 |
| 6024:9021 | 6064:9021 | 6024:9022 | 6064:9022 | 6024:9023 | 6064:9023 |
| 6025:9021 | 6065:9021 | 6025:9022 | 6065:9022 | 6025:9023 | 6065:9023 |
| 6026:9021 | 6066:9021 | 6026:9022 | 6066:9022 | 6026:9023 | 6066:9023 |
| 6027:9021 | 6067:9021 | 6027:9022 | 6067:9022 | 6027:9023 | 6067:9023 |
| 6028:9021 | 6068:9021 | 6028:9022 | 6068:9022 | 6028:9023 | 6068:9023 |
| 6029:9021 | 6069:9021 | 6029:9022 | 6069:9022 | 6029:9023 | 6069:9023 |
| 6030:9021 | 6070:9021 | 6030:9022 | 6070:9022 | 6030:9023 | 6070:9023 |
| 6031:9021 | 6071:9021 | 6031:9022 | 6071:9022 | 6031:9023 | 6071:9023 |
| 6032:9021 | 6072:9021 | 6032:9022 | 6072:9022 | 6032:9023 | 6072:9023 |
| 6033:9021 | 6073:9021 | 6033:9022 | 6073:9022 | 6033:9023 | 6073:9023 |
| 6034:9021 | 6074:9021 | 6034:9022 | 6074:9022 | 6034:9023 | 6074:9023 |
| 6035:9021 | 6075:9021 | 6035:9022 | 6075:9022 | 6035:9023 | 6075:9023 |
| 6036:9021 | 6076:9021 | 6036:9022 | 6076:9022 | 6036:9023 | 6076:9023 |
| 6037:9021 | 6077:9021 | 6037:9022 | 6077:9022 | 6037:9023 | 6077:9023 |
| 6038:9021 | 6078:9021 | 6038:9022 | 6078:9022 | 6038:9023 | 6078:9023 |
| 6039:9021 | | 6039:9022 | | 6039:9023 | |

| X:Y | X:Y | X:Y | X:Y | X:Y | X:Y |
|---|---|---|---|---|---|
| 6000:9024 | 6040:9024 | 6000:9025 | 6040:9025 | 6000:9026 | 6040:9026 |
| 6001:9024 | 6041:9024 | 6001:9025 | 6041:9025 | 6001:9026 | 6041:9026 |
| 6002:9024 | 6042:9024 | 6002:9025 | 6042:9025 | 6002:9026 | 6042:9026 |
| 6003:9024 | 6043:9024 | 6003:9025 | 6043:9025 | 6003:9026 | 6043:9026 |
| 6004:9024 | 6044:9024 | 6004:9025 | 6044:9025 | 6004:9026 | 6044:9026 |
| 6005:9024 | 6045:9024 | 6005:9025 | 6045:9025 | 6005:9026 | 6045:9026 |
| 6006:9024 | 6046:9024 | 6006:9025 | 6046:9025 | 6006:9026 | 6046:9026 |
| 6007:9024 | 6047:9024 | 6007:9025 | 6047:9025 | 6007:9026 | 6047:9026 |
| 6008:9024 | 6048:9024 | 6008:9025 | 6048:9025 | 6008:9026 | 6048:9026 |
| 6009:9024 | 6049:9024 | 6009:9025 | 6049:9025 | 6009:9026 | 6049:9026 |
| 6010:9024 | 6050:9024 | 6010:9025 | 6050:9025 | 6010:9026 | 6050:9026 |
| 6011:9024 | 6051:9024 | 6011:9025 | 6051:9025 | 6011:9026 | 6051:9026 |
| 6012:9024 | 6052:9024 | 6012:9025 | 6052:9025 | 6012:9026 | 6052:9026 |
| 6013:9024 | 6053:9024 | 6013:9025 | 6053:9025 | 6013:9026 | 6053:9026 |
| 6014:9024 | 6054:9024 | 6014:9025 | 6054:9025 | 6014:9026 | 6054:9026 |
| 6015:9024 | 6055:9024 | 6015:9025 | 6055:9025 | 6015:9026 | 6055:9026 |
| 6016:9024 | 6056:9024 | 6016:9025 | 6056:9025 | 6016:9026 | 6056:9026 |
| 6017:9024 | 6057:9024 | 6017:9025 | 6057:9025 | 6017:9026 | 6057:9026 |
| 6018:9024 | 6058:9024 | 6018:9025 | 6058:9025 | 6018:9026 | 6058:9026 |
| 6019:9024 | 6059:9024 | 6019:9025 | 6059:9025 | 6019:9026 | 6059:9026 |
| 6020:9024 | 6060:9024 | 6020:9025 | 6060:9025 | 6020:9026 | 6060:9026 |
| 6021:9024 | 6061:9024 | 6021:9025 | 6061:9025 | 6021:9026 | 6061:9026 |
| 6022:9024 | 6062:9024 | 6022:9025 | 6062:9025 | 6022:9026 | 6062:9026 |
| 6023:9024 | 6063:9024 | 6023:9025 | 6063:9025 | 6023:9026 | 6063:9026 |
| 6024:9024 | 6064:9024 | 6024:9025 | 6064:9025 | 6024:9026 | 6064:9026 |

TABLE D-continued

| X:Y | X:Y | X:Y | X:Y | X:Y | X:Y |
|---|---|---|---|---|---|
| 6025:9024 | 6065:9024 | 6025:9025 | 6065:9025 | 6025:9026 | 6065:9026 |
| 6026:9024 | 6066:9024 | 6026:9025 | 6066:9025 | 6026:9026 | 6066:9026 |
| 6027:9024 | 6067:9024 | 6027:9025 | 6067:9025 | 6027:9026 | 6067:9026 |
| 6028:9024 | 6068:9024 | 6028:9025 | 6068:9025 | 6028:9026 | 6068:9026 |
| 6029:9024 | 6069:9024 | 6029:9025 | 6069:9025 | 6029:9026 | 6069:9026 |
| 6030:9024 | 6070:9024 | 6030:9025 | 6070:9025 | 6030:9026 | 6070:9026 |
| 6031:9024 | 6071:9024 | 6031:9025 | 6071:9025 | 6031:9026 | 6071:9026 |
| 6032:9024 | 6072:9024 | 6032:9025 | 6072:9025 | 6032:9026 | 6072:9026 |
| 6033:9024 | 6073:9024 | 6033:9025 | 6073:9025 | 6033:9026 | 6073:9026 |
| 6034:9024 | 6074:9024 | 6034:9025 | 6074:9025 | 6034:9026 | 6074:9026 |
| 6035:9024 | 6075:9024 | 6035:9025 | 6075:9025 | 6035:9026 | 6075:9026 |
| 6036:9024 | 6076:9024 | 6036:9025 | 6076:9025 | 6036:9026 | 6076:9026 |
| 6037:9024 | 6077:9024 | 6037:9025 | 6077:9025 | 6037:9026 | 6077:9026 |
| 6038:9024 | 6078:9024 | 6038:9025 | 6078:9025 | 6038:9026 | 6078:9026 |
| 6039:9024 | | 6039:9025 | | 6039:9026 | |

| X:Y | X:Y | X:Y | X:Y | X:Y | X:Y |
|---|---|---|---|---|---|
| 6000:9027 | 6040:9027 | 6000:9028 | 6040:9028 | 6000:9029 | 6040:9029 |
| 6001:9027 | 6041:9027 | 6001:9028 | 6041:9028 | 6001:9029 | 6041:9029 |
| 6002:9027 | 6042:9027 | 6002:9028 | 6042:9028 | 6002:9029 | 6042:9029 |
| 6003:9027 | 6043:9027 | 6003:9028 | 6043:9028 | 6003:9029 | 6043:9029 |
| 6004:9027 | 6044:9027 | 6004:9028 | 6044:9028 | 6004:9029 | 6044:9029 |
| 6005:9027 | 6045:9027 | 6005:9028 | 6045:9028 | 6005:9029 | 6045:9029 |
| 6006:9027 | 6046:9027 | 6006:9028 | 6046:9028 | 6006:9029 | 6046:9029 |
| 6007:9027 | 6047:9027 | 6007:9028 | 6047:9028 | 6007:9029 | 6047:9029 |
| 6008:9027 | 6048:9027 | 6008:9028 | 6048:9028 | 6008:9029 | 6048:9029 |
| 6009:9027 | 6049:9027 | 6009:9028 | 6049:9028 | 6009:9029 | 6049:9029 |
| 6010:9027 | 6050:9027 | 6010:9028 | 6050:9028 | 6010:9029 | 6050:9029 |
| 6011:9027 | 6051:9027 | 6011:9028 | 6051:9028 | 6011:9029 | 6051:9029 |
| 6012:9027 | 6052:9027 | 6012:9028 | 6052:9028 | 6012:9029 | 6052:9029 |
| 6013:9027 | 6053:9027 | 6013:9028 | 6053:9028 | 6013:9029 | 6053:9029 |
| 6014:9027 | 6054:9027 | 6014:9028 | 6054:9028 | 6014:9029 | 6054:9029 |
| 6015:9027 | 6055:9027 | 6015:9028 | 6055:9028 | 6015:9029 | 6055:9029 |
| 6016:9027 | 6056:9027 | 6016:9028 | 6056:9028 | 6016:9029 | 6056:9029 |
| 6017:9027 | 6057:9027 | 6017:9028 | 6057:9028 | 6017:9029 | 6057:9029 |
| 6018:9027 | 6058:9027 | 6018:9028 | 6058:9028 | 6018:9029 | 6058:9029 |
| 6019:9027 | 6059:9027 | 6019:9028 | 6059:9028 | 6019:9029 | 6059:9029 |
| 6020:9027 | 6060:9027 | 6020:9028 | 6060:9028 | 6020:9029 | 6060:9029 |
| 6021:9027 | 6061:9027 | 6021:9028 | 6061:9028 | 6021:9029 | 6061:9029 |
| 6022:9027 | 6062:9027 | 6022:9028 | 6062:9028 | 6022:9029 | 6062:9029 |
| 6023:9027 | 6063:9027 | 6023:9028 | 6063:9028 | 6023:9029 | 6063:9029 |
| 6024:9027 | 6064:9027 | 6024:9028 | 6064:9028 | 6024:9029 | 6064:9029 |
| 6025:9027 | 6065:9027 | 6025:9028 | 6065:9028 | 6025:9029 | 6065:9029 |
| 6026:9027 | 6066:9027 | 6026:9028 | 6066:9028 | 6026:9029 | 6066:9029 |
| 6027:9027 | 6067:9027 | 6027:9028 | 6067:9028 | 6027:9029 | 6067:9029 |
| 6028:9027 | 6068:9027 | 6028:9028 | 6068:9028 | 6028:9029 | 6068:9029 |
| 6029:9027 | 6069:9027 | 6029:9028 | 6069:9028 | 6029:9029 | 6069:9029 |
| 6030:9027 | 6070:9027 | 6030:9028 | 6070:9028 | 6030:9029 | 6070:9029 |
| 6031:9027 | 6071:9027 | 6031:9028 | 6071:9028 | 6031:9029 | 6071:9029 |
| 6032:9027 | 6072:9027 | 6032:9028 | 6072:9028 | 6032:9029 | 6072:9029 |
| 6033:9027 | 6073:9027 | 6033:9028 | 6073:9028 | 6033:9029 | 6073:9029 |
| 6034:9027 | 6074:9027 | 6034:9028 | 6074:9028 | 6034:9029 | 6074:9029 |
| 6035:9027 | 6075:9027 | 6035:9028 | 6075:9028 | 6035:9029 | 6075:9029 |
| 6036:9027 | 6076:9027 | 6036:9028 | 6076:9028 | 6036:9029 | 6076:9029 |
| 6037:9027 | 6077:9027 | 6037:9028 | 6077:9028 | 6037:9029 | 6077:9029 |
| 6038:9027 | 6078:9027 | 6038:9028 | 6078:9028 | 6038:9029 | 6078:9029 |
| 6039:9027 | | 6039:9028 | | 6039:9029 | |

| X:Y | X:Y | X:Y | X:Y | X:Y | X:Y |
|---|---|---|---|---|---|
| 6000:9030 | 6040:9030 | 6000:9031 | 6040:9031 | 6000:9032 | 6040:9032 |
| 6001:9030 | 6041:9030 | 6001:9031 | 6041:9031 | 6001:9032 | 6041:9032 |
| 6002:9030 | 6042:9030 | 6002:9031 | 6042:9031 | 6002:9032 | 6042:9032 |
| 6003:9030 | 6043:9030 | 6003:9031 | 6043:9031 | 6003:9032 | 6043:9032 |
| 6004:9030 | 6044:9030 | 6004:9031 | 6044:9031 | 6004:9032 | 6044:9032 |
| 6005:9030 | 6045:9030 | 6005:9031 | 6045:9031 | 6005:9032 | 6045:9032 |
| 6006:9030 | 6046:9030 | 6006:9031 | 6046:9031 | 6006:9032 | 6046:9032 |
| 6007:9030 | 6047:9030 | 6007:9031 | 6047:9031 | 6007:9032 | 6047:9032 |
| 6008:9030 | 6048:9030 | 6008:9031 | 6048:9031 | 6008:9032 | 6048:9032 |
| 6009:9030 | 6049:9030 | 6009:9031 | 6049:9031 | 6009:9032 | 6049:9032 |
| 6010:9030 | 6050:9030 | 6010:9031 | 6050:9031 | 6010:9032 | 6050:9032 |
| 6011:9030 | 6051:9030 | 6011:9031 | 6051:9031 | 6011:9032 | 6051:9032 |
| 6012:9030 | 6052:9030 | 6012:9031 | 6052:9031 | 6012:9032 | 6052:9032 |
| 6013:9030 | 6053:9030 | 6013:9031 | 6053:9031 | 6013:9032 | 6053:9032 |
| 6014:9030 | 6054:9030 | 6014:9031 | 6054:9031 | 6014:9032 | 6054:9032 |
| 6015:9030 | 6055:9030 | 6015:9031 | 6055:9031 | 6015:9032 | 6055:9032 |
| 6016:9030 | 6056:9030 | 6016:9031 | 6056:9031 | 6016:9032 | 6056:9032 |
| 6017:9030 | 6057:9030 | 6017:9031 | 6057:9031 | 6017:9032 | 6057:9032 |
| 6018:9030 | 6058:9030 | 6018:9031 | 6058:9031 | 6018:9032 | 6058:9032 |
| 6019:9030 | 6059:9030 | 6019:9031 | 6059:9031 | 6019:9032 | 6059:9032 |
| 6020:9030 | 6060:9030 | 6020:9031 | 6060:9031 | 6020:9032 | 6060:9032 |
| 6021:9030 | 6061:9030 | 6021:9031 | 6061:9031 | 6021:9032 | 6061:9032 |
| 6022:9030 | 6062:9030 | 6022:9031 | 6062:9031 | 6022:9032 | 6062:9032 |
| 6023:9030 | 6063:9030 | 6023:9031 | 6063:9031 | 6023:9032 | 6063:9032 |
| 6024:9030 | 6064:9030 | 6024:9031 | 6064:9031 | 6024:9032 | 6064:9032 |
| 6025:9030 | 6065:9030 | 6025:9031 | 6065:9031 | 6025:9032 | 6065:9032 |
| 6026:9030 | 6066:9030 | 6026:9031 | 6066:9031 | 6026:9032 | 6066:9032 |
| 6027:9030 | 6067:9030 | 6027:9031 | 6067:9031 | 6027:9032 | 6067:9032 |
| 6028:9030 | 6068:9030 | 6028:9031 | 6068:9031 | 6028:9032 | 6068:9032 |
| 6029:9030 | 6069:9030 | 6029:9031 | 6069:9031 | 6029:9032 | 6069:9032 |
| 6030:9030 | 6070:9030 | 6030:9031 | 6070:9031 | 6030:9032 | 6070:9032 |
| 6031:9030 | 6071:9030 | 6031:9031 | 6071:9031 | 6031:9032 | 6071:9032 |
| 6032:9030 | 6072:9030 | 6032:9031 | 6072:9031 | 6032:9032 | 6072:9032 |
| 6033:9030 | 6073:9030 | 6033:9031 | 6073:9031 | 6033:9032 | 6073:9032 |
| 6034:9030 | 6074:9030 | 6034:9031 | 6074:9031 | 6034:9032 | 6074:9032 |
| 6035:9030 | 6075:9030 | 6035:9031 | 6075:9031 | 6035:9032 | 6075:9032 |
| 6036:9030 | 6076:9030 | 6036:9031 | 6076:9031 | 6036:9032 | 6076:9032 |
| 6037:9030 | 6077:9030 | 6037:9031 | 6077:9031 | 6037:9032 | 6077:9032 |
| 6038:9030 | 6078:9030 | 6038:9031 | 6078:9031 | 6038:9032 | 6078:9032 |
| 6039:9030 | | 6039:9031 | | 6039:9032 | |

| X:Y | X:Y | X:Y | X:Y | X:Y | X:Y |
|---|---|---|---|---|---|
| 6000:9033 | 6040:9033 | 6000:9034 | 6040:9034 | 6000:9035 | 6040:9035 |
| 6001:9033 | 6041:9033 | 6001:9034 | 6041:9034 | 6001:9035 | 6041:9035 |
| 6002:9033 | 6042:9033 | 6002:9034 | 6042:9034 | 6002:9035 | 6042:9035 |
| 6003:9033 | 6043:9033 | 6003:9034 | 6043:9034 | 6003:9035 | 6043:9035 |
| 6004:9033 | 6044:9033 | 6004:9034 | 6044:9034 | 6004:9035 | 6044:9035 |
| 6005:9033 | 6045:9033 | 6005:9034 | 6045:9034 | 6005:9035 | 6045:9035 |
| 6006:9033 | 6046:9033 | 6006:9034 | 6046:9034 | 6006:9035 | 6046:9035 |
| 6007:9033 | 6047:9033 | 6007:9034 | 6047:9034 | 6007:9035 | 6047:9035 |
| 6008:9033 | 6048:9033 | 6008:9034 | 6048:9034 | 6008:9035 | 6048:9035 |
| 6009:9033 | 6049:9033 | 6009:9034 | 6049:9034 | 6009:9035 | 6049:9035 |
| 6010:9033 | 6050:9033 | 6010:9034 | 6050:9034 | 6010:9035 | 6050:9035 |
| 6011:9033 | 6051:9033 | 6011:9034 | 6051:9034 | 6011:9035 | 6051:9035 |
| 6012:9033 | 6052:9033 | 6012:9034 | 6052:9034 | 6012:9035 | 6052:9035 |
| 6013:9033 | 6053:9033 | 6013:9034 | 6053:9034 | 6013:9035 | 6053:9035 |
| 6014:9033 | 6054:9033 | 6014:9034 | 6054:9034 | 6014:9035 | 6054:9035 |
| 6015:9033 | 6055:9033 | 6015:9034 | 6055:9034 | 6015:9035 | 6055:9035 |
| 6016:9033 | 6056:9033 | 6016:9034 | 6056:9034 | 6016:9035 | 6056:9035 |
| 6017:9033 | 6057:9033 | 6017:9034 | 6057:9034 | 6017:9035 | 6057:9035 |
| 6018:9033 | 6058:9033 | 6018:9034 | 6058:9034 | 6018:9035 | 6058:9035 |
| 6019:9033 | 6059:9033 | 6019:9034 | 6059:9034 | 6019:9035 | 6059:9035 |
| 6020:9033 | 6060:9033 | 6020:9034 | 6060:9034 | 6020:9035 | 6060:9035 |
| 6021:9033 | 6061:9033 | 6021:9034 | 6061:9034 | 6021:9035 | 6061:9035 |
| 6022:9033 | 6062:9033 | 6022:9034 | 6062:9034 | 6022:9035 | 6062:9035 |
| 6023:9033 | 6063:9033 | 6023:9034 | 6063:9034 | 6023:9035 | 6063:9035 |
| 6024:9033 | 6064:9033 | 6024:9034 | 6064:9034 | 6024:9035 | 6064:9035 |
| 6025:9033 | 6065:9033 | 6025:9034 | 6065:9034 | 6025:9035 | 6065:9035 |
| 6026:9033 | 6066:9033 | 6026:9034 | 6066:9034 | 6026:9035 | 6066:9035 |
| 6027:9033 | 6067:9033 | 6027:9034 | 6067:9034 | 6027:9035 | 6067:9035 |
| 6028:9033 | 6068:9033 | 6028:9034 | 6068:9034 | 6028:9035 | 6068:9035 |
| 6029:9033 | 6069:9033 | 6029:9034 | 6069:9034 | 6029:9035 | 6069:9035 |
| 6030:9033 | 6070:9033 | 6030:9034 | 6070:9034 | 6030:9035 | 6070:9035 |
| 6031:9033 | 6071:9033 | 6031:9034 | 6071:9034 | 6031:9035 | 6071:9035 |
| 6032:9033 | 6072:9033 | 6032:9034 | 6072:9034 | 6032:9035 | 6072:9035 |
| 6033:9033 | 6073:9033 | 6033:9034 | 6073:9034 | 6033:9035 | 6073:9035 |
| 6034:9033 | 6074:9033 | 6034:9034 | 6074:9034 | 6034:9035 | 6074:9035 |
| 6035:9033 | 6075:9033 | 6035:9034 | 6075:9034 | 6035:9035 | 6075:9035 |
| 6036:9033 | 6076:9033 | 6036:9034 | 6076:9034 | 6036:9035 | 6076:9035 |
| 6037:9033 | 6077:9033 | 6037:9034 | 6077:9034 | 6037:9035 | 6077:9035 |
| 6038:9033 | 6078:9033 | 6038:9034 | 6078:9034 | 6038:9035 | 6078:9035 |
| 6039:9033 | | 6039:9034 | | 6039:9035 | |

| X:Y | X:Y | X:Y | X:Y | X:Y | X:Y |
|---|---|---|---|---|---|
| 6000:9036 | 6040:9036 | 6000:9037 | 6040:9037 | 6000:9038 | 6040:9038 |
| 6001:9036 | 6041:9036 | 6001:9037 | 6041:9037 | 6001:9038 | 6041:9038 |
| 6002:9036 | 6042:9036 | 6002:9037 | 6042:9037 | 6002:9038 | 6042:9038 |
| 6003:9036 | 6043:9036 | 6003:9037 | 6043:9037 | 6003:9038 | 6043:9038 |
| 6004:9036 | 6044:9036 | 6004:9037 | 6044:9037 | 6004:9038 | 6044:9038 |
| 6005:9036 | 6045:9036 | 6005:9037 | 6045:9037 | 6005:9038 | 6045:9038 |
| 6006:9036 | 6046:9036 | 6006:9037 | 6046:9037 | 6006:9038 | 6046:9038 |
| 6007:9036 | 6047:9036 | 6007:9037 | 6047:9037 | 6007:9038 | 6047:9038 |
| 6008:9036 | 6048:9036 | 6008:9037 | 6048:9037 | 6008:9038 | 6048:9038 |
| 6009:9036 | 6049:9036 | 6009:9037 | 6049:9037 | 6009:9038 | 6049:9038 |
| 6010:9036 | 6050:9036 | 6010:9037 | 6050:9037 | 6010:9038 | 6050:9038 |
| 6011:9036 | 6051:9036 | 6011:9037 | 6051:9037 | 6011:9038 | 6051:9038 |
| 6012:9036 | 6052:9036 | 6012:9037 | 6052:9037 | 6012:9038 | 6052:9038 |

TABLE D-continued

| X:Y | X:Y | X:Y | X:Y | X:Y | X:Y |
|---|---|---|---|---|---|
| 6013:9036 | 6053:9036 | 6013:9037 | 6053:9037 | 6013:9038 | 6053:9038 |
| 6014:9036 | 6054:9036 | 6014:9037 | 6054:9037 | 6014:9038 | 6054:9038 |
| 6015:9036 | 6055:9036 | 6015:9037 | 6055:9037 | 6015:9038 | 6055:9038 |
| 6016:9036 | 6056:9036 | 6016:9037 | 6056:9037 | 6016:9038 | 6056:9038 |
| 6017:9036 | 6057:9036 | 6017:9037 | 6057:9037 | 6017:9038 | 6057:9038 |
| 6018:9036 | 6058:9036 | 6018:9037 | 6058:9037 | 6018:9038 | 6058:9038 |
| 6019:9036 | 6059:9036 | 6019:9037 | 6059:9037 | 6019:9038 | 6059:9038 |
| 6020:9036 | 6060:9036 | 6020:9037 | 6060:9037 | 6020:9038 | 6060:9038 |
| 6021:9036 | 6061:9036 | 6021:9037 | 6061:9037 | 6021:9038 | 6061:9038 |
| 6022:9036 | 6062:9036 | 6022:9037 | 6062:9037 | 6022:9038 | 6062:9038 |
| 6023:9036 | 6063:9036 | 6023:9037 | 6063:9037 | 6023:9038 | 6063:9038 |
| 6024:9036 | 6064:9036 | 6024:9037 | 6064:9037 | 6024:9038 | 6064:9038 |
| 6025:9036 | 6065:9036 | 6025:9037 | 6065:9037 | 6025:9038 | 6065:9038 |
| 6026:9036 | 6066:9036 | 6026:9037 | 6066:9037 | 6026:9038 | 6066:9038 |
| 6027:9036 | 6067:9036 | 6027:9037 | 6067:9037 | 6027:9038 | 6067:9038 |
| 6028:9036 | 6068:9036 | 6028:9037 | 6068:9037 | 6028:9038 | 6068:9038 |
| 6029:9036 | 6069:9036 | 6029:9037 | 6069:9037 | 6029:9038 | 6069:9038 |
| 6030:9036 | 6070:9036 | 6030:9037 | 6070:9037 | 6030:9038 | 6070:9038 |
| 6031:9036 | 6071:9036 | 6031:9037 | 6071:9037 | 6031:9038 | 6071:9038 |
| 6032:9036 | 6072:9036 | 6032:9037 | 6072:9037 | 6032:9038 | 6072:9038 |
| 6033:9036 | 6073:9036 | 6033:9037 | 6073:9037 | 6033:9038 | 6073:9038 |
| 6034:9036 | 6074:9036 | 6034:9037 | 6074:9037 | 6034:9038 | 6074:9038 |
| 6035:9036 | 6075:9036 | 6035:9037 | 6075:9037 | 6035:9038 | 6075:9038 |
| 6036:9036 | 6076:9036 | 6036:9037 | 6076:9037 | 6036:9038 | 6076:9038 |
| 6037:9036 | 6077:9036 | 6037:9037 | 6077:9037 | 6037:9038 | 6077:9038 |
| 6038:9036 | 6078:9036 | 6038:9037 | 6078:9037 | 6038:9038 | 6078:9038 |
| 6039:9036 | | 6039:9037 | | 6039:9038 | |

| X:Y | X:Y | X:Y | X:Y | X:Y | X:Y |
|---|---|---|---|---|---|
| 6000:9039 | 6040:9039 | 6000:9040 | 6040:9040 | 6000:9041 | 6040:9041 |
| 6001:9039 | 6041:9039 | 6001:9040 | 6041:9040 | 6001:9041 | 6041:9041 |
| 6002:9039 | 6042:9039 | 6002:9040 | 6042:9040 | 6002:9041 | 6042:9041 |
| 6003:9039 | 6043:9039 | 6003:9040 | 6043:9040 | 6003:9041 | 6043:9041 |
| 6004:9039 | 6044:9039 | 6004:9040 | 6044:9040 | 6004:9041 | 6044:9041 |
| 6005:9039 | 6045:9039 | 6005:9040 | 6045:9040 | 6005:9041 | 6045:9041 |
| 6006:9039 | 6046:9039 | 6006:9040 | 6046:9040 | 6006:9041 | 6046:9041 |
| 6007:9039 | 6047:9039 | 6007:9040 | 6047:9040 | 6007:9041 | 6047:9041 |
| 6008:9039 | 6048:9039 | 6008:9040 | 6048:9040 | 6008:9041 | 6048:9041 |
| 6009:9039 | 6049:9039 | 6009:9040 | 6049:9040 | 6009:9041 | 6049:9041 |
| 6010:9039 | 6050:9039 | 6010:9040 | 6050:9040 | 6010:9041 | 6050:9041 |
| 6011:9039 | 6051:9039 | 6011:9040 | 6051:9040 | 6011:9041 | 6051:9041 |
| 6012:9039 | 6052:9039 | 6012:9040 | 6052:9040 | 6012:9041 | 6052:9041 |
| 6013:9039 | 6053:9039 | 6013:9040 | 6053:9040 | 6013:9041 | 6053:9041 |
| 6014:9039 | 6054:9039 | 6014:9040 | 6054:9040 | 6014:9041 | 6054:9041 |
| 6015:9039 | 6055:9039 | 6015:9040 | 6055:9040 | 6015:9041 | 6055:9041 |
| 6016:9039 | 6056:9039 | 6016:9040 | 6056:9040 | 6016:9041 | 6056:9041 |
| 6017:9039 | 6057:9039 | 6017:9040 | 6057:9040 | 6017:9041 | 6057:9041 |
| 6018:9039 | 6058:9039 | 6018:9040 | 6058:9040 | 6018:9041 | 6058:9041 |
| 6019:9039 | 6059:9039 | 6019:9040 | 6059:9040 | 6019:9041 | 6059:9041 |
| 6020:9039 | 6060:9039 | 6020:9040 | 6060:9040 | 6020:9041 | 6060:9041 |
| 6021:9039 | 6061:9039 | 6021:9040 | 6061:9040 | 6021:9041 | 6061:9041 |
| 6022:9039 | 6062:9039 | 6022:9040 | 6062:9040 | 6022:9041 | 6062:9041 |
| 6023:9039 | 6063:9039 | 6023:9040 | 6063:9040 | 6023:9041 | 6063:9041 |
| 6024:9039 | 6064:9039 | 6024:9040 | 6064:9040 | 6024:9041 | 6064:9041 |
| 6025:9039 | 6065:9039 | 6025:9040 | 6065:9040 | 6025:9041 | 6065:9041 |
| 6026:9039 | 6066:9039 | 6026:9040 | 6066:9040 | 6026:9041 | 6066:9041 |
| 6027:9039 | 6067:9039 | 6027:9040 | 6067:9040 | 6027:9041 | 6067:9041 |
| 6028:9039 | 6068:9039 | 6028:9040 | 6068:9040 | 6028:9041 | 6068:9041 |
| 6029:9039 | 6069:9039 | 6029:9040 | 6069:9040 | 6029:9041 | 6069:9041 |
| 6030:9039 | 6070:9039 | 6030:9040 | 6070:9040 | 6030:9041 | 6070:9041 |
| 6031:9039 | 6071:9039 | 6031:9040 | 6071:9040 | 6031:9041 | 6071:9041 |
| 6032:9039 | 6072:9039 | 6032:9040 | 6072:9040 | 6032:9041 | 6072:9041 |
| 6033:9039 | 6073:9039 | 6033:9040 | 6073:9040 | 6033:9041 | 6073:9041 |
| 6034:9039 | 6074:9039 | 6034:9040 | 6074:9040 | 6034:9041 | 6074:9041 |
| 6035:9039 | 6075:9039 | 6035:9040 | 6075:9040 | 6035:9041 | 6075:9041 |
| 6036:9039 | 6076:9039 | 6036:9040 | 6076:9040 | 6036:9041 | 6076:9041 |
| 6037:9039 | 6077:9039 | 6037:9040 | 6077:9040 | 6037:9041 | 6077:9041 |
| 6038:9039 | 6078:9039 | 6038:9040 | 6078:9040 | 6038:9041 | 6078:9041 |
| 6039:9039 | | 6039:9040 | | 6039:9041 | |

| X:Y | X:Y | X:Y | X:Y | X:Y | X:Y |
|---|---|---|---|---|---|
| 6000:9042 | 6040:9042 | 6000:9043 | 6040:9043 | 6000:9044 | 6040:9044 |
| 6001:9042 | 6041:9042 | 6001:9043 | 6041:9043 | 6001:9044 | 6041:9044 |
| 6002:9042 | 6042:9042 | 6002:9043 | 6042:9043 | 6002:9044 | 6042:9044 |
| 6003:9042 | 6043:9042 | 6003:9043 | 6043:9043 | 6003:9044 | 6043:9044 |
| 6004:9042 | 6044:9042 | 6004:9043 | 6044:9043 | 6004:9044 | 6044:9044 |
| 6005:9042 | 6045:9042 | 6005:9043 | 6045:9043 | 6005:9044 | 6045:9044 |
| 6006:9042 | 6046:9042 | 6006:9043 | 6046:9043 | 6006:9044 | 6046:9044 |
| 6007:9042 | 6047:9042 | 6007:9043 | 6047:9043 | 6007:9044 | 6047:9044 |
| 6008:9042 | 6048:9042 | 6008:9043 | 6048:9043 | 6008:9044 | 6048:9044 |
| 6009:9042 | 6049:9042 | 6009:9043 | 6049:9043 | 6009:9044 | 6049:9044 |
| 6010:9042 | 6050:9042 | 6010:9043 | 6050:9043 | 6010:9044 | 6050:9044 |
| 6011:9042 | 6051:9042 | 6011:9043 | 6051:9043 | 6011:9044 | 6051:9044 |
| 6012:9042 | 6052:9042 | 6012:9043 | 6052:9043 | 6012:9044 | 6052:9044 |
| 6013:9042 | 6053:9042 | 6013:9043 | 6053:9043 | 6013:9044 | 6053:9044 |
| 6014:9042 | 6054:9042 | 6014:9043 | 6054:9043 | 6014:9044 | 6054:9044 |
| 6015:9042 | 6055:9042 | 6015:9043 | 6055:9043 | 6015:9044 | 6055:9044 |
| 6016:9042 | 6056:9042 | 6016:9043 | 6056:9043 | 6016:9044 | 6056:9044 |
| 6017:9042 | 6057:9042 | 6017:9043 | 6057:9043 | 6017:9044 | 6057:9044 |
| 6018:9042 | 6058:9042 | 6018:9043 | 6058:9043 | 6018:9044 | 6058:9044 |
| 6019:9042 | 6059:9042 | 6019:9043 | 6059:9043 | 6019:9044 | 6059:9044 |
| 6020:9042 | 6060:9042 | 6020:9043 | 6060:9043 | 6020:9044 | 6060:9044 |
| 6021:9042 | 6061:9042 | 6021:9043 | 6061:9043 | 6021:9044 | 6061:9044 |
| 6022:9042 | 6062:9042 | 6022:9043 | 6062:9043 | 6022:9044 | 6062:9044 |
| 6023:9042 | 6063:9042 | 6023:9043 | 6063:9043 | 6023:9044 | 6063:9044 |
| 6024:9042 | 6064:9042 | 6024:9043 | 6064:9043 | 6024:9044 | 6064:9044 |
| 6025:9042 | 6065:9042 | 6025:9043 | 6065:9043 | 6025:9044 | 6065:9044 |
| 6026:9042 | 6066:9042 | 6026:9043 | 6066:9043 | 6026:9044 | 6066:9044 |
| 6027:9042 | 6067:9042 | 6027:9043 | 6067:9043 | 6027:9044 | 6067:9044 |
| 6028:9042 | 6068:9042 | 6028:9043 | 6068:9043 | 6028:9044 | 6068:9044 |
| 6029:9042 | 6069:9042 | 6029:9043 | 6069:9043 | 6029:9044 | 6069:9044 |
| 6030:9042 | 6070:9042 | 6030:9043 | 6070:9043 | 6030:9044 | 6070:9044 |
| 6031:9042 | 6071:9042 | 6031:9043 | 6071:9043 | 6031:9044 | 6071:9044 |
| 6032:9042 | 6072:9042 | 6032:9043 | 6072:9043 | 6032:9044 | 6072:9044 |
| 6033:9042 | 6073:9042 | 6033:9043 | 6073:9043 | 6033:9044 | 6073:9044 |
| 6034:9042 | 6074:9042 | 6034:9043 | 6074:9043 | 6034:9044 | 6074:9044 |
| 6035:9042 | 6075:9042 | 6035:9043 | 6075:9043 | 6035:9044 | 6075:9044 |
| 6036:9042 | 6076:9042 | 6036:9043 | 6076:9043 | 6036:9044 | 6076:9044 |
| 6037:9042 | 6077:9042 | 6037:9043 | 6077:9043 | 6037:9044 | 6077:9044 |
| 6038:9042 | 6078:9042 | 6038:9043 | 6078:9043 | 6038:9044 | 6078:9044 |
| 6039:9042 | | 6039:9043 | | 6039:9044 | |

| X:Y | X:Y | X:Y | X:Y | X:Y | X:Y |
|---|---|---|---|---|---|
| 6000:9045 | 6040:9045 | 6000:9046 | 6040:9046 | 6000:9047 | 6040:9047 |
| 6001:9045 | 6041:9045 | 6001:9046 | 6041:9046 | 6001:9047 | 6041:9047 |
| 6002:9045 | 6042:9045 | 6002:9046 | 6042:9046 | 6002:9047 | 6042:9047 |
| 6003:9045 | 6043:9045 | 6003:9046 | 6043:9046 | 6003:9047 | 6043:9047 |
| 6004:9045 | 6044:9045 | 6004:9046 | 6044:9046 | 6004:9047 | 6044:9047 |
| 6005:9045 | 6045:9045 | 6005:9046 | 6045:9046 | 6005:9047 | 6045:9047 |
| 6006:9045 | 6046:9045 | 6006:9046 | 6046:9046 | 6006:9047 | 6046:9047 |
| 6007:9045 | 6047:9045 | 6007:9046 | 6047:9046 | 6007:9047 | 6047:9047 |
| 6008:9045 | 6048:9045 | 6008:9046 | 6048:9046 | 6008:9047 | 6048:9047 |
| 6009:9045 | 6049:9045 | 6009:9046 | 6049:9046 | 6009:9047 | 6049:9047 |
| 6010:9045 | 6050:9045 | 6010:9046 | 6050:9046 | 6010:9047 | 6050:9047 |
| 6011:9045 | 6051:9045 | 6011:9046 | 6051:9046 | 6011:9047 | 6051:9047 |
| 6012:9045 | 6052:9045 | 6012:9046 | 6052:9046 | 6012:9047 | 6052:9047 |
| 6013:9045 | 6053:9045 | 6013:9046 | 6053:9046 | 6013:9047 | 6053:9047 |
| 6014:9045 | 6054:9045 | 6014:9046 | 6054:9046 | 6014:9047 | 6054:9047 |
| 6015:9045 | 6055:9045 | 6015:9046 | 6055:9046 | 6015:9047 | 6055:9047 |
| 6016:9045 | 6056:9045 | 6016:9046 | 6056:9046 | 6016:9047 | 6056:9047 |
| 6017:9045 | 6057:9045 | 6017:9046 | 6057:9046 | 6017:9047 | 6057:9047 |
| 6018:9045 | 6058:9045 | 6018:9046 | 6058:9046 | 6018:9047 | 6058:9047 |
| 6019:9045 | 6059:9045 | 6019:9046 | 6059:9046 | 6019:9047 | 6059:9047 |
| 6020:9045 | 6060:9045 | 6020:9046 | 6060:9046 | 6020:9047 | 6060:9047 |
| 6021:9045 | 6061:9045 | 6021:9046 | 6061:9046 | 6021:9047 | 6061:9047 |
| 6022:9045 | 6062:9045 | 6022:9046 | 6062:9046 | 6022:9047 | 6062:9047 |
| 6023:9045 | 6063:9045 | 6023:9046 | 6063:9046 | 6023:9047 | 6063:9047 |
| 6024:9045 | 6064:9045 | 6024:9046 | 6064:9046 | 6024:9047 | 6064:9047 |
| 6025:9045 | 6065:9045 | 6025:9046 | 6065:9046 | 6025:9047 | 6065:9047 |
| 6026:9045 | 6066:9045 | 6026:9046 | 6066:9046 | 6026:9047 | 6066:9047 |
| 6027:9045 | 6067:9045 | 6027:9046 | 6067:9046 | 6027:9047 | 6067:9047 |
| 6028:9045 | 6068:9045 | 6028:9046 | 6068:9046 | 6028:9047 | 6068:9047 |
| 6029:9045 | 6069:9045 | 6029:9046 | 6069:9046 | 6029:9047 | 6069:9047 |
| 6030:9045 | 6070:9045 | 6030:9046 | 6070:9046 | 6030:9047 | 6070:9047 |
| 6031:9045 | 6071:9045 | 6031:9046 | 6071:9046 | 6031:9047 | 6071:9047 |
| 6032:9045 | 6072:9045 | 6032:9046 | 6072:9046 | 6032:9047 | 6072:9047 |
| 6033:9045 | 6073:9045 | 6033:9046 | 6073:9046 | 6033:9047 | 6073:9047 |
| 6034:9045 | 6074:9045 | 6034:9046 | 6074:9046 | 6034:9047 | 6074:9047 |
| 6035:9045 | 6075:9045 | 6035:9046 | 6075:9046 | 6035:9047 | 6075:9047 |

TABLE D-continued

| | | | | | |
|---|---|---|---|---|---|
| 6036:9045 | 6076:9045 | 6036:9046 | 6076:9046 | 6036:9047 | 6076:9047 |
| 6037:9045 | 6077:9045 | 6037:9046 | 6077:9046 | 6037:9047 | 6077:9047 |
| 6038:9045 | 6078:9045 | 6038:9046 | 6078:9046 | 6038:9047 | 6078:9047 |
| 6039:9045 | | 6039:9046 | | 6039:9047 | |

| X:Y | X:Y | X:Y | X:Y | X:Y | X:Y |
|---|---|---|---|---|---|
| 6000:9048 | 6040:9048 | 6000:9049 | 6040:9049 | 6000:9050 | 6040:9050 |
| 6001:9048 | 6041:9048 | 6001:9049 | 6041:9049 | 6001:9050 | 6041:9050 |
| 6002:9048 | 6042:9048 | 6002:9049 | 6042:9049 | 6002:9050 | 6042:9050 |
| 6003:9048 | 6043:9048 | 6003:9049 | 6043:9049 | 6003:9050 | 6043:9050 |
| 6004:9048 | 6044:9048 | 6004:9049 | 6044:9049 | 6004:9050 | 6044:9050 |
| 6005:9048 | 6045:9048 | 6005:9049 | 6045:9049 | 6005:9050 | 6045:9050 |
| 6006:9048 | 6046:9048 | 6006:9049 | 6046:9049 | 6006:9050 | 6046:9050 |
| 6007:9048 | 6047:9048 | 6007:9049 | 6047:9049 | 6007:9050 | 6047:9050 |
| 6008:9048 | 6048:9048 | 6008:9049 | 6048:9049 | 6008:9050 | 6048:9050 |
| 6009:9048 | 6049:9048 | 6009:9049 | 6049:9049 | 6009:9050 | 6049:9050 |
| 6010:9048 | 6050:9048 | 6010:9049 | 6050:9049 | 6010:9050 | 6050:9050 |
| 6011:9048 | 6051:9048 | 6011:9049 | 6051:9049 | 6011:9050 | 6051:9050 |
| 6012:9048 | 6052:9048 | 6012:9049 | 6052:9049 | 6012:9050 | 6052:9050 |
| 6013:9048 | 6053:9048 | 6013:9049 | 6053:9049 | 6013:9050 | 6053:9050 |
| 6014:9048 | 6054:9048 | 6014:9049 | 6054:9049 | 6014:9050 | 6054:9050 |
| 6015:9048 | 6055:9048 | 6015:9049 | 6055:9049 | 6015:9050 | 6055:9050 |
| 6016:9048 | 6056:9048 | 6016:9049 | 6056:9049 | 6016:9050 | 6056:9050 |
| 6017:9048 | 6057:9048 | 6017:9049 | 6057:9049 | 6017:9050 | 6057:9050 |
| 6018:9048 | 6058:9048 | 6018:9049 | 6058:9049 | 6018:9050 | 6058:9050 |
| 6019:9048 | 6059:9048 | 6019:9049 | 6059:9049 | 6019:9050 | 6059:9050 |
| 6020:9048 | 6060:9048 | 6020:9049 | 6060:9049 | 6020:9050 | 6060:9050 |
| 6021:9048 | 6061:9048 | 6021:9049 | 6061:9049 | 6021:9050 | 6061:9050 |
| 6022:9048 | 6062:9048 | 6022:9049 | 6062:9049 | 6022:9050 | 6062:9050 |
| 6023:9048 | 6063:9048 | 6023:9049 | 6063:9049 | 6023:9050 | 6063:9050 |
| 6024:9048 | 6064:9048 | 6024:9049 | 6064:9049 | 6024:9050 | 6064:9050 |
| 6025:9048 | 6065:9048 | 6025:9049 | 6065:9049 | 6025:9050 | 6065:9050 |
| 6026:9048 | 6066:9048 | 6026:9049 | 6066:9049 | 6026:9050 | 6066:9050 |
| 6027:9048 | 6067:9048 | 6027:9049 | 6067:9049 | 6027:9050 | 6067:9050 |
| 6028:9048 | 6068:9048 | 6028:9049 | 6068:9049 | 6028:9050 | 6068:9050 |
| 6029:9048 | 6069:9048 | 6029:9049 | 6069:9049 | 6029:9050 | 6069:9050 |
| 6030:9048 | 6070:9048 | 6030:9049 | 6070:9049 | 6030:9050 | 6070:9050 |
| 6031:9048 | 6071:9048 | 6031:9049 | 6071:9049 | 6031:9050 | 6071:9050 |
| 6032:9048 | 6072:9048 | 6032:9049 | 6072:9049 | 6032:9050 | 6072:9050 |
| 6033:9048 | 6073:9048 | 6033:9049 | 6073:9049 | 6033:9050 | 6073:9050 |
| 6034:9048 | 6074:9048 | 6034:9049 | 6074:9049 | 6034:9050 | 6074:9050 |
| 6035:9048 | 6075:9048 | 6035:9049 | 6075:9049 | 6035:9050 | 6075:9050 |
| 6036:9048 | 6076:9048 | 6036:9049 | 6076:9049 | 6036:9050 | 6076:9050 |
| 6037:9048 | 6077:9048 | 6037:9049 | 6077:9049 | 6037:9050 | 6077:9050 |
| 6038:9048 | 6078:9048 | 6038:9049 | 6078:9049 | 6038:9050 | 6078:9050 |
| 6039:9048 | | 6039:9049 | | 6039:9050 | |

| X:Y | X:Y | X:Y | X:Y | X:Y | X:Y |
|---|---|---|---|---|---|
| 6000:9051 | 6040:9051 | 6000:9052 | 6040:9052 | 6000:9053 | 6040:9053 |
| 6001:9051 | 6041:9051 | 6001:9052 | 6041:9052 | 6001:9053 | 6041:9053 |
| 6002:9051 | 6042:9051 | 6002:9052 | 6042:9052 | 6002:9053 | 6042:9053 |
| 6003:9051 | 6043:9051 | 6003:9052 | 6043:9052 | 6003:9053 | 6043:9053 |
| 6004:9051 | 6044:9051 | 6004:9052 | 6044:9052 | 6004:9053 | 6044:9053 |
| 6005:9051 | 6045:9051 | 6005:9052 | 6045:9052 | 6005:9053 | 6045:9053 |
| 6006:9051 | 6046:9051 | 6006:9052 | 6046:9052 | 6006:9053 | 6046:9053 |
| 6007:9051 | 6047:9051 | 6007:9052 | 6047:9052 | 6007:9053 | 6047:9053 |
| 6008:9051 | 6048:9051 | 6008:9052 | 6048:9052 | 6008:9053 | 6048:9053 |
| 6009:9051 | 6049:9051 | 6009:9052 | 6049:9052 | 6009:9053 | 6049:9053 |
| 6010:9051 | 6050:9051 | 6010:9052 | 6050:9052 | 6010:9053 | 6050:9053 |
| 6011:9051 | 6051:9051 | 6011:9052 | 6051:9052 | 6011:9053 | 6051:9053 |
| 6012:9051 | 6052:9051 | 6012:9052 | 6052:9052 | 6012:9053 | 6052:9053 |
| 6013:9051 | 6053:9051 | 6013:9052 | 6053:9052 | 6013:9053 | 6053:9053 |
| 6014:9051 | 6054:9051 | 6014:9052 | 6054:9052 | 6014:9053 | 6054:9053 |
| 6015:9051 | 6055:9051 | 6015:9052 | 6055:9052 | 6015:9053 | 6055:9053 |
| 6016:9051 | 6056:9051 | 6016:9052 | 6056:9052 | 6016:9053 | 6056:9053 |
| 6017:9051 | 6057:9051 | 6017:9052 | 6057:9052 | 6017:9053 | 6057:9053 |
| 6018:9051 | 6058:9051 | 6018:9052 | 6058:9052 | 6018:9053 | 6058:9053 |
| 6019:9051 | 6059:9051 | 6019:9052 | 6059:9052 | 6019:9053 | 6059:9053 |
| 6020:9051 | 6060:9051 | 6020:9052 | 6060:9052 | 6020:9053 | 6060:9053 |
| 6021:9051 | 6061:9051 | 6021:9052 | 6061:9052 | 6021:9053 | 6061:9053 |
| 6022:9051 | 6062:9051 | 6022:9052 | 6062:9052 | 6022:9053 | 6062:9053 |
| 6023:9051 | 6063:9051 | 6023:9052 | 6063:9052 | 6023:9053 | 6063:9053 |
| 6024:9051 | 6064:9051 | 6024:9052 | 6064:9052 | 6024:9053 | 6064:9053 |
| 6025:9051 | 6065:9051 | 6025:9052 | 6065:9052 | 6025:9053 | 6065:9053 |
| 6026:9051 | 6066:9051 | 6026:9052 | 6066:9052 | 6026:9053 | 6066:9053 |
| 6027:9051 | 6067:9051 | 6027:9052 | 6067:9052 | 6027:9053 | 6067:9053 |
| 6028:9051 | 6068:9051 | 6028:9052 | 6068:9052 | 6028:9053 | 6068:9053 |
| 6029:9051 | 6069:9051 | 6029:9052 | 6069:9052 | 6029:9053 | 6069:9053 |
| 6030:9051 | 6070:9051 | 6030:9052 | 6070:9052 | 6030:9053 | 6070:9053 |
| 6031:9051 | 6071:9051 | 6031:9052 | 6071:9052 | 6031:9053 | 6071:9053 |
| 6032:9051 | 6072:9051 | 6032:9052 | 6072:9052 | 6032:9053 | 6072:9053 |
| 6033:9051 | 6073:9051 | 6033:9052 | 6073:9052 | 6033:9053 | 6073:9053 |
| 6034:9051 | 6074:9051 | 6034:9052 | 6074:9052 | 6034:9053 | 6074:9053 |
| 6035:9051 | 6075:9051 | 6035:9052 | 6075:9052 | 6035:9053 | 6075:9053 |
| 6036:9051 | 6076:9051 | 6036:9052 | 6076:9052 | 6036:9053 | 6076:9053 |
| 6037:9051 | 6077:9051 | 6037:9052 | 6077:9052 | 6037:9053 | 6077:9053 |
| 6038:9051 | 6078:9051 | 6038:9052 | 6078:9052 | 6038:9053 | 6078:9053 |
| 6039:9051 | | 6039:9052 | | 6039:9053 | |

| X:Y | X:Y | X:Y | X:Y | X:Y | X:Y |
|---|---|---|---|---|---|
| 6000:9054 | 6040:9054 | 6000:9055 | 6040:9055 | 6000:9056 | 6040:9056 |
| 6001:9054 | 6041:9054 | 6001:9055 | 6041:9055 | 6001:9056 | 6041:9056 |
| 6002:9054 | 6042:9054 | 6002:9055 | 6042:9055 | 6002:9056 | 6042:9056 |
| 6003:9054 | 6043:9054 | 6003:9055 | 6043:9055 | 6003:9056 | 6043:9056 |
| 6004:9054 | 6044:9054 | 6004:9055 | 6044:9055 | 6004:9056 | 6044:9056 |
| 6005:9054 | 6045:9054 | 6005:9055 | 6045:9055 | 6005:9056 | 6045:9056 |
| 6006:9054 | 6046:9054 | 6006:9055 | 6046:9055 | 6006:9056 | 6046:9056 |
| 6007:9054 | 6047:9054 | 6007:9055 | 6047:9055 | 6007:9056 | 6047:9056 |
| 6008:9054 | 6048:9054 | 6008:9055 | 6048:9055 | 6008:9056 | 6048:9056 |
| 6009:9054 | 6049:9054 | 6009:9055 | 6049:9055 | 6009:9056 | 6049:9056 |
| 6010:9054 | 6050:9054 | 6010:9055 | 6050:9055 | 6010:9056 | 6050:9056 |
| 6011:9054 | 6051:9054 | 6011:9055 | 6051:9055 | 6011:9056 | 6051:9056 |
| 6012:9054 | 6052:9054 | 6012:9055 | 6052:9055 | 6012:9056 | 6052:9056 |
| 6013:9054 | 6053:9054 | 6013:9055 | 6053:9055 | 6013:9056 | 6053:9056 |
| 6014:9054 | 6054:9054 | 6014:9055 | 6054:9055 | 6014:9056 | 6054:9056 |
| 6015:9054 | 6055:9054 | 6015:9055 | 6055:9055 | 6015:9056 | 6055:9056 |
| 6016:9054 | 6056:9054 | 6016:9055 | 6056:9055 | 6016:9056 | 6056:9056 |
| 6017:9054 | 6057:9054 | 6017:9055 | 6057:9055 | 6017:9056 | 6057:9056 |
| 6018:9054 | 6058:9054 | 6018:9055 | 6058:9055 | 6018:9056 | 6058:9056 |
| 6019:9054 | 6059:9054 | 6019:9055 | 6059:9055 | 6019:9056 | 6059:9056 |
| 6020:9054 | 6060:9054 | 6020:9055 | 6060:9055 | 6020:9056 | 6060:9056 |
| 6021:9054 | 6061:9054 | 6021:9055 | 6061:9055 | 6021:9056 | 6061:9056 |
| 6022:9054 | 6062:9054 | 6022:9055 | 6062:9055 | 6022:9056 | 6062:9056 |
| 6023:9054 | 6063:9054 | 6023:9055 | 6063:9055 | 6023:9056 | 6063:9056 |
| 6024:9054 | 6064:9054 | 6024:9055 | 6064:9055 | 6024:9056 | 6064:9056 |
| 6025:9054 | 6065:9054 | 6025:9055 | 6065:9055 | 6025:9056 | 6065:9056 |
| 6026:9054 | 6066:9054 | 6026:9055 | 6066:9055 | 6026:9056 | 6066:9056 |
| 6027:9054 | 6067:9054 | 6027:9055 | 6067:9055 | 6027:9056 | 6067:9056 |
| 6028:9054 | 6068:9054 | 6028:9055 | 6068:9055 | 6028:9056 | 6068:9056 |
| 6029:9054 | 6069:9054 | 6029:9055 | 6069:9055 | 6029:9056 | 6069:9056 |
| 6030:9054 | 6070:9054 | 6030:9055 | 6070:9055 | 6030:9056 | 6070:9056 |
| 6031:9054 | 6071:9054 | 6031:9055 | 6071:9055 | 6031:9056 | 6071:9056 |
| 6032:9054 | 6072:9054 | 6032:9055 | 6072:9055 | 6032:9056 | 6072:9056 |
| 6033:9054 | 6073:9054 | 6033:9055 | 6073:9055 | 6033:9056 | 6073:9056 |
| 6034:9054 | 6074:9054 | 6034:9055 | 6074:9055 | 6034:9056 | 6074:9056 |
| 6035:9054 | 6075:9054 | 6035:9055 | 6075:9055 | 6035:9056 | 6075:9056 |
| 6036:9054 | 6076:9054 | 6036:9055 | 6076:9055 | 6036:9056 | 6076:9056 |
| 6037:9054 | 6077:9054 | 6037:9055 | 6077:9055 | 6037:9056 | 6077:9056 |
| 6038:9054 | 6078:9054 | 6038:9055 | 6078:9055 | 6038:9056 | 6078:9056 |
| 6039:9054 | | 6039:9055 | | 6039:9056 | |

| X:Y | X:Y | X:Y | X:Y | X:Y | X:Y |
|---|---|---|---|---|---|
| 6000:9057 | 6040:9057 | 6000:9058 | 6040:9058 | 6000:9059 | 6040:9059 |
| 6001:9057 | 6041:9057 | 6001:9058 | 6041:9058 | 6001:9059 | 6041:9059 |
| 6002:9057 | 6042:9057 | 6002:9058 | 6042:9058 | 6002:9059 | 6042:9059 |
| 6003:9057 | 6043:9057 | 6003:9058 | 6043:9058 | 6003:9059 | 6043:9059 |
| 6004:9057 | 6044:9057 | 6004:9058 | 6044:9058 | 6004:9059 | 6044:9059 |
| 6005:9057 | 6045:9057 | 6005:9058 | 6045:9058 | 6005:9059 | 6045:9059 |
| 6006:9057 | 6046:9057 | 6006:9058 | 6046:9058 | 6006:9059 | 6046:9059 |
| 6007:9057 | 6047:9057 | 6007:9058 | 6047:9058 | 6007:9059 | 6047:9059 |
| 6008:9057 | 6048:9057 | 6008:9058 | 6048:9058 | 6008:9059 | 6048:9059 |
| 6009:9057 | 6049:9057 | 6009:9058 | 6049:9058 | 6009:9059 | 6049:9059 |
| 6010:9057 | 6050:9057 | 6010:9058 | 6050:9058 | 6010:9059 | 6050:9059 |
| 6011:9057 | 6051:9057 | 6011:9058 | 6051:9058 | 6011:9059 | 6051:9059 |
| 6012:9057 | 6052:9057 | 6012:9058 | 6052:9058 | 6012:9059 | 6052:9059 |
| 6013:9057 | 6053:9057 | 6013:9058 | 6053:9058 | 6013:9059 | 6053:9059 |
| 6014:9057 | 6054:9057 | 6014:9058 | 6054:9058 | 6014:9059 | 6054:9059 |
| 6015:9057 | 6055:9057 | 6015:9058 | 6055:9058 | 6015:9059 | 6055:9059 |
| 6016:9057 | 6056:9057 | 6016:9058 | 6056:9058 | 6016:9059 | 6056:9059 |
| 6017:9057 | 6057:9057 | 6017:9058 | 6057:9058 | 6017:9059 | 6057:9059 |
| 6018:9057 | 6058:9057 | 6018:9058 | 6058:9058 | 6018:9059 | 6058:9059 |
| 6019:9057 | 6059:9057 | 6019:9058 | 6059:9058 | 6019:9059 | 6059:9059 |
| 6020:9057 | 6060:9057 | 6020:9058 | 6060:9058 | 6020:9059 | 6060:9059 |
| 6021:9057 | 6061:9057 | 6021:9058 | 6061:9058 | 6021:9059 | 6061:9059 |
| 6022:9057 | 6062:9057 | 6022:9058 | 6062:9058 | 6022:9059 | 6062:9059 |
| 6023:9057 | 6063:9057 | 6023:9058 | 6063:9058 | 6023:9059 | 6063:9059 |

TABLE D-continued

| X:Y | X:Y | X:Y | X:Y | X:Y | X:Y |
|---|---|---|---|---|---|
| 6024:9057 | 6064:9057 | 6024:9058 | 6064:9058 | 6024:9059 | 6064:9059 |
| 6025:9057 | 6065:9057 | 6025:9058 | 6065:9058 | 6025:9059 | 6065:9059 |
| 6026:9057 | 6066:9057 | 6026:9058 | 6066:9058 | 6026:9059 | 6066:9059 |
| 6027:9057 | 6067:9057 | 6027:9058 | 6067:9058 | 6027:9059 | 6067:9059 |
| 6028:9057 | 6068:9057 | 6028:9058 | 6068:9058 | 6028:9059 | 6068:9059 |
| 6029:9057 | 6069:9057 | 6029:9058 | 6069:9058 | 6029:9059 | 6069:9059 |
| 6030:9057 | 6070:9057 | 6030:9058 | 6070:9058 | 6030:9059 | 6070:9059 |
| 6031:9057 | 6071:9057 | 6031:9058 | 6071:9058 | 6031:9059 | 6071:9059 |
| 6032:9057 | 6072:9057 | 6032:9058 | 6072:9058 | 6032:9059 | 6072:9059 |
| 6033:9057 | 6073:9057 | 6033:9058 | 6073:9058 | 6033:9059 | 6073:9059 |
| 6034:9057 | 6074:9057 | 6034:9058 | 6074:9058 | 6034:9059 | 6074:9059 |
| 6035:9057 | 6075:9057 | 6035:9058 | 6075:9058 | 6035:9059 | 6075:9059 |
| 6036:9057 | 6076:9057 | 6036:9058 | 6076:9058 | 6036:9059 | 6076:9059 |
| 6037:9057 | 6077:9057 | 6037:9058 | 6077:9058 | 6037:9059 | 6077:9059 |
| 6038:9057 | 6078:9057 | 6038:9058 | 6078:9058 | 6038:9059 | 6078:9059 |
| 6039:9057 | | 6039:9058 | | 6039:9059 | |

| X:Y | X:Y | X:Y | X:Y | X:Y | X:Y |
|---|---|---|---|---|---|
| 6000:9060 | 6040:9060 | 6000:9061 | 6040:9061 | 6000:9062 | 6040:9062 |
| 6001:9060 | 6041:9060 | 6001:9061 | 6041:9061 | 6001:9062 | 6041:9062 |
| 6002:9060 | 6042:9060 | 6002:9061 | 6042:9061 | 6002:9062 | 6042:9062 |
| 6003:9060 | 6043:9060 | 6003:9061 | 6043:9061 | 6003:9062 | 6043:9062 |
| 6004:9060 | 6044:9060 | 6004:9061 | 6044:9061 | 6004:9062 | 6044:9062 |
| 6005:9060 | 6045:9060 | 6005:9061 | 6045:9061 | 6005:9062 | 6045:9062 |
| 6006:9060 | 6046:9060 | 6006:9061 | 6046:9061 | 6006:9062 | 6046:9062 |
| 6007:9060 | 6047:9060 | 6007:9061 | 6047:9061 | 6007:9062 | 6047:9062 |
| 6008:9060 | 6048:9060 | 6008:9061 | 6048:9061 | 6008:9062 | 6048:9062 |
| 6009:9060 | 6049:9060 | 6009:9061 | 6049:9061 | 6009:9062 | 6049:9062 |
| 6010:9060 | 6050:9060 | 6010:9061 | 6050:9061 | 6010:9062 | 6050:9062 |
| 6011:9060 | 6051:9060 | 6011:9061 | 6051:9061 | 6011:9062 | 6051:9062 |
| 6012:9060 | 6052:9060 | 6012:9061 | 6052:9061 | 6012:9062 | 6052:9062 |
| 6013:9060 | 6053:9060 | 6013:9061 | 6053:9061 | 6013:9062 | 6053:9062 |
| 6014:9060 | 6054:9060 | 6014:9061 | 6054:9061 | 6014:9062 | 6054:9062 |
| 6015:9060 | 6055:9060 | 6015:9061 | 6055:9061 | 6015:9062 | 6055:9062 |
| 6016:9060 | 6056:9060 | 6016:9061 | 6056:9061 | 6016:9062 | 6056:9062 |
| 6017:9060 | 6057:9060 | 6017:9061 | 6057:9061 | 6017:9062 | 6057:9062 |
| 6018:9060 | 6058:9060 | 6018:9061 | 6058:9061 | 6018:9062 | 6058:9062 |
| 6019:9060 | 6059:9060 | 6019:9061 | 6059:9061 | 6019:9062 | 6059:9062 |
| 6020:9060 | 6060:9060 | 6020:9061 | 6060:9061 | 6020:9062 | 6060:9062 |
| 6021:9060 | 6061:9060 | 6021:9061 | 6061:9061 | 6021:9062 | 6061:9062 |
| 6022:9060 | 6062:9060 | 6022:9061 | 6062:9061 | 6022:9062 | 6062:9062 |
| 6023:9060 | 6063:9060 | 6023:9061 | 6063:9061 | 6023:9062 | 6063:9062 |
| 6024:9060 | 6064:9060 | 6024:9061 | 6064:9061 | 6024:9062 | 6064:9062 |
| 6025:9060 | 6065:9060 | 6025:9061 | 6065:9061 | 6025:9062 | 6065:9062 |
| 6026:9060 | 6066:9060 | 6026:9061 | 6066:9061 | 6026:9062 | 6066:9062 |
| 6027:9060 | 6067:9060 | 6027:9061 | 6067:9061 | 6027:9062 | 6067:9062 |
| 6028:9060 | 6068:9060 | 6028:9061 | 6068:9061 | 6028:9062 | 6068:9062 |
| 6029:9060 | 6069:9060 | 6029:9061 | 6069:9061 | 6029:9062 | 6069:9062 |
| 6030:9060 | 6070:9060 | 6030:9061 | 6070:9061 | 6030:9062 | 6070:9062 |
| 6031:9060 | 6071:9060 | 6031:9061 | 6071:9061 | 6031:9062 | 6071:9062 |
| 6032:9060 | 6072:9060 | 6032:9061 | 6072:9061 | 6032:9062 | 6072:9062 |
| 6033:9060 | 6073:9060 | 6033:9061 | 6073:9061 | 6033:9062 | 6073:9062 |
| 6034:9060 | 6074:9060 | 6034:9061 | 6074:9061 | 6034:9062 | 6074:9062 |
| 6035:9060 | 6075:9060 | 6035:9061 | 6075:9061 | 6035:9062 | 6075:9062 |
| 6036:9060 | 6076:9060 | 6036:9061 | 6076:9061 | 6036:9062 | 6076:9062 |
| 6037:9060 | 6077:9060 | 6037:9061 | 6077:9061 | 6037:9062 | 6077:9062 |
| 6038:9060 | 6078:9060 | 6038:9061 | 6078:9061 | 6038:9062 | 6078:9062 |
| 6039:9060 | | 6039:9061 | | 6039:9062 | |

| X:Y | X:Y | X:Y | X:Y | X:Y | X:Y |
|---|---|---|---|---|---|
| 6000:9063 | 6040:9063 | 6000:9064 | 6040:9064 | 6000:9065 | 6040:9065 |
| 6001:9063 | 6041:9063 | 6001:9064 | 6041:9064 | 6001:9065 | 6041:9065 |
| 6002:9063 | 6042:9063 | 6002:9064 | 6042:9064 | 6002:9065 | 6042:9065 |
| 6003:9063 | 6043:9063 | 6003:9064 | 6043:9064 | 6003:9065 | 6043:9065 |
| 6004:9063 | 6044:9063 | 6004:9064 | 6044:9064 | 6004:9065 | 6044:9065 |
| 6005:9063 | 6045:9063 | 6005:9064 | 6045:9064 | 6005:9065 | 6045:9065 |
| 6006:9063 | 6046:9063 | 6006:9064 | 6046:9064 | 6006:9065 | 6046:9065 |
| 6007:9063 | 6047:9063 | 6007:9064 | 6047:9064 | 6007:9065 | 6047:9065 |
| 6008:9063 | 6048:9063 | 6008:9064 | 6048:9064 | 6008:9065 | 6048:9065 |
| 6009:9063 | 6049:9063 | 6009:9064 | 6049:9064 | 6009:9065 | 6049:9065 |
| 6010:9063 | 6050:9063 | 6010:9064 | 6050:9064 | 6010:9065 | 6050:9065 |
| 6011:9063 | 6051:9063 | 6011:9064 | 6051:9064 | 6011:9065 | 6051:9065 |
| 6012:9063 | 6052:9063 | 6012:9064 | 6052:9064 | 6012:9065 | 6052:9065 |
| 6013:9063 | 6053:9063 | 6013:9064 | 6053:9064 | 6013:9065 | 6053:9065 |
| 6014:9063 | 6054:9063 | 6014:9064 | 6054:9064 | 6014:9065 | 6054:9065 |
| 6015:9063 | 6055:9063 | 6015:9064 | 6055:9064 | 6015:9065 | 6055:9065 |
| 6016:9063 | 6056:9063 | 6016:9064 | 6056:9064 | 6016:9065 | 6056:9065 |
| 6017:9063 | 6057:9063 | 6017:9064 | 6057:9064 | 6017:9065 | 6057:9065 |
| 6018:9063 | 6058:9063 | 6018:9064 | 6058:9064 | 6018:9065 | 6058:9065 |
| 6019:9063 | 6059:9063 | 6019:9064 | 6059:9064 | 6019:9065 | 6059:9065 |
| 6020:9063 | 6060:9063 | 6020:9064 | 6060:9064 | 6020:9065 | 6060:9065 |
| 6021:9063 | 6061:9063 | 6021:9064 | 6061:9064 | 6021:9065 | 6061:9065 |
| 6022:9063 | 6062:9063 | 6022:9064 | 6062:9064 | 6022:9065 | 6062:9065 |
| 6023:9063 | 6063:9063 | 6023:9064 | 6063:9064 | 6023:9065 | 6063:9065 |
| 6024:9063 | 6064:9063 | 6024:9064 | 6064:9064 | 6024:9065 | 6064:9065 |
| 6025:9063 | 6065:9063 | 6025:9064 | 6065:9064 | 6025:9065 | 6065:9065 |
| 6026:9063 | 6066:9063 | 6026:9064 | 6066:9064 | 6026:9065 | 6066:9065 |
| 6027:9063 | 6067:9063 | 6027:9064 | 6067:9064 | 6027:9065 | 6067:9065 |
| 6028:9063 | 6068:9063 | 6028:9064 | 6068:9064 | 6028:9065 | 6068:9065 |
| 6029:9063 | 6069:9063 | 6029:9064 | 6069:9064 | 6029:9065 | 6069:9065 |
| 6030:9063 | 6070:9063 | 6030:9064 | 6070:9064 | 6030:9065 | 6070:9065 |
| 6031:9063 | 6071:9063 | 6031:9064 | 6071:9064 | 6031:9065 | 6071:9065 |
| 6032:9063 | 6072:9063 | 6032:9064 | 6072:9064 | 6032:9065 | 6072:9065 |
| 6033:9063 | 6073:9063 | 6033:9064 | 6073:9064 | 6033:9065 | 6073:9065 |
| 6034:9063 | 6074:9063 | 6034:9064 | 6074:9064 | 6034:9065 | 6074:9065 |
| 6035:9063 | 6075:9063 | 6035:9064 | 6075:9064 | 6035:9065 | 6075:9065 |
| 6036:9063 | 6076:9063 | 6036:9064 | 6076:9064 | 6036:9065 | 6076:9065 |
| 6037:9063 | 6077:9063 | 6037:9064 | 6077:9064 | 6037:9065 | 6077:9065 |
| 6038:9063 | 6078:9063 | 6038:9064 | 6078:9064 | 6038:9065 | 6078:9065 |
| 6039:9063 | | 6039:9064 | | 6039:9065 | |

| X:Y | X:Y | X:Y | X:Y | X:Y | X:Y |
|---|---|---|---|---|---|
| 6000:9066 | 6040:9066 | 6000:9067 | 6040:9067 | 6000:9068 | 6040:9068 |
| 6001:9066 | 6041:9066 | 6001:9067 | 6041:9067 | 6001:9068 | 6041:9068 |
| 6002:9066 | 6042:9066 | 6002:9067 | 6042:9067 | 6002:9068 | 6042:9068 |
| 6003:9066 | 6043:9066 | 6003:9067 | 6043:9067 | 6003:9068 | 6043:9068 |
| 6004:9066 | 6044:9066 | 6004:9067 | 6044:9067 | 6004:9068 | 6044:9068 |
| 6005:9066 | 6045:9066 | 6005:9067 | 6045:9067 | 6005:9068 | 6045:9068 |
| 6006:9066 | 6046:9066 | 6006:9067 | 6046:9067 | 6006:9068 | 6046:9068 |
| 6007:9066 | 6047:9066 | 6007:9067 | 6047:9067 | 6007:9068 | 6047:9068 |
| 6008:9066 | 6048:9066 | 6008:9067 | 6048:9067 | 6008:9068 | 6048:9068 |
| 6009:9066 | 6049:9066 | 6009:9067 | 6049:9067 | 6009:9068 | 6049:9068 |
| 6010:9066 | 6050:9066 | 6010:9067 | 6050:9067 | 6010:9068 | 6050:9068 |
| 6011:9066 | 6051:9066 | 6011:9067 | 6051:9067 | 6011:9068 | 6051:9068 |
| 6012:9066 | 6052:9066 | 6012:9067 | 6052:9067 | 6012:9068 | 6052:9068 |
| 6013:9066 | 6053:9066 | 6013:9067 | 6053:9067 | 6013:9068 | 6053:9068 |
| 6014:9066 | 6054:9066 | 6014:9067 | 6054:9067 | 6014:9068 | 6054:9068 |
| 6015:9066 | 6055:9066 | 6015:9067 | 6055:9067 | 6015:9068 | 6055:9068 |
| 6016:9066 | 6056:9066 | 6016:9067 | 6056:9067 | 6016:9068 | 6056:9068 |
| 6017:9066 | 6057:9066 | 6017:9067 | 6057:9067 | 6017:9068 | 6057:9068 |
| 6018:9066 | 6058:9066 | 6018:9067 | 6058:9067 | 6018:9068 | 6058:9068 |
| 6019:9066 | 6059:9066 | 6019:9067 | 6059:9067 | 6019:9068 | 6059:9068 |
| 6020:9066 | 6060:9066 | 6020:9067 | 6060:9067 | 6020:9068 | 6060:9068 |
| 6021:9066 | 6061:9066 | 6021:9067 | 6061:9067 | 6021:9068 | 6061:9068 |
| 6022:9066 | 6062:9066 | 6022:9067 | 6062:9067 | 6022:9068 | 6062:9068 |
| 6023:9066 | 6063:9066 | 6023:9067 | 6063:9067 | 6023:9068 | 6063:9068 |
| 6024:9066 | 6064:9066 | 6024:9067 | 6064:9067 | 6024:9068 | 6064:9068 |
| 6025:9066 | 6065:9066 | 6025:9067 | 6065:9067 | 6025:9068 | 6065:9068 |
| 6026:9066 | 6066:9066 | 6026:9067 | 6066:9067 | 6026:9068 | 6066:9068 |
| 6027:9066 | 6067:9066 | 6027:9067 | 6067:9067 | 6027:9068 | 6067:9068 |
| 6028:9066 | 6068:9066 | 6028:9067 | 6068:9067 | 6028:9068 | 6068:9068 |
| 6029:9066 | 6069:9066 | 6029:9067 | 6069:9067 | 6029:9068 | 6069:9068 |
| 6030:9066 | 6070:9066 | 6030:9067 | 6070:9067 | 6030:9068 | 6070:9068 |
| 6031:9066 | 6071:9066 | 6031:9067 | 6071:9067 | 6031:9068 | 6071:9068 |
| 6032:9066 | 6072:9066 | 6032:9067 | 6072:9067 | 6032:9068 | 6072:9068 |
| 6033:9066 | 6073:9066 | 6033:9067 | 6073:9067 | 6033:9068 | 6073:9068 |
| 6034:9066 | 6074:9066 | 6034:9067 | 6074:9067 | 6034:9068 | 6074:9068 |
| 6035:9066 | 6075:9066 | 6035:9067 | 6075:9067 | 6035:9068 | 6075:9068 |
| 6036:9066 | 6076:9066 | 6036:9067 | 6076:9067 | 6036:9068 | 6076:9068 |
| 6037:9066 | 6077:9066 | 6037:9067 | 6077:9067 | 6037:9068 | 6077:9068 |
| 6038:9066 | 6078:9066 | 6038:9067 | 6078:9067 | 6038:9068 | 6078:9068 |
| 6039:9066 | | 6039:9067 | | 6039:9068 | |

| X:Y | X:Y | X:Y | X:Y | X:Y | X:Y |
|---|---|---|---|---|---|
| 6000:9069 | 6040:9069 | 6000:9070 | 6040:9070 | 6000:9071 | 6040:9071 |
| 6001:9069 | 6041:9069 | 6001:9070 | 6041:9070 | 6001:9071 | 6041:9071 |
| 6002:9069 | 6042:9069 | 6002:9070 | 6042:9070 | 6002:9071 | 6042:9071 |
| 6003:9069 | 6043:9069 | 6003:9070 | 6043:9070 | 6003:9071 | 6043:9071 |
| 6004:9069 | 6044:9069 | 6004:9070 | 6044:9070 | 6004:9071 | 6044:9071 |
| 6005:9069 | 6045:9069 | 6005:9070 | 6045:9070 | 6005:9071 | 6045:9071 |
| 6006:9069 | 6046:9069 | 6006:9070 | 6046:9070 | 6006:9071 | 6046:9071 |
| 6007:9069 | 6047:9069 | 6007:9070 | 6047:9070 | 6007:9071 | 6047:9071 |
| 6008:9069 | 6048:9069 | 6008:9070 | 6048:9070 | 6008:9071 | 6048:9071 |
| 6009:9069 | 6049:9069 | 6009:9070 | 6049:9070 | 6009:9071 | 6049:9071 |
| 6010:9069 | 6050:9069 | 6010:9070 | 6050:9070 | 6010:9071 | 6050:9071 |
| 6011:9069 | 6051:9069 | 6011:9070 | 6051:9070 | 6011:9071 | 6051:9071 |

TABLE D-continued

| | | | | | |
|---|---|---|---|---|---|
| 6012:9069 | 6052:9069 | 6012:9070 | 6052:9070 | 6012:9071 | 6052:9071 |
| 6013:9069 | 6053:9069 | 6013:9070 | 6053:9070 | 6013:9071 | 6053:9071 |
| 6014:9069 | 6054:9069 | 6014:9070 | 6054:9070 | 6014:9071 | 6054:9071 |
| 6015:9069 | 6055:9069 | 6015:9070 | 6055:9070 | 6015:9071 | 6055:9071 |
| 6016:9069 | 6056:9069 | 6016:9070 | 6056:9070 | 6016:9071 | 6056:9071 |
| 6017:9069 | 6057:9069 | 6017:9070 | 6057:9070 | 6017:9071 | 6057:9071 |
| 6018:9069 | 6058:9069 | 6018:9070 | 6058:9070 | 6018:9071 | 6058:9071 |
| 6019:9069 | 6059:9069 | 6019:9070 | 6059:9070 | 6019:9071 | 6059:9071 |
| 6020:9069 | 6060:9069 | 6020:9070 | 6060:9070 | 6020:9071 | 6060:9071 |
| 6021:9069 | 6061:9069 | 6021:9070 | 6061:9070 | 6021:9071 | 6061:9071 |
| 6022:9069 | 6062:9069 | 6022:9070 | 6062:9070 | 6022:9071 | 6062:9071 |
| 6023:9069 | 6063:9069 | 6023:9070 | 6063:9070 | 6023:9071 | 6063:9071 |
| 6024:9069 | 6064:9069 | 6024:9070 | 6064:9070 | 6024:9071 | 6064:9071 |
| 6025:9069 | 6065:9069 | 6025:9070 | 6065:9070 | 6025:9071 | 6065:9071 |
| 6026:9069 | 6066:9069 | 6026:9070 | 6066:9070 | 6026:9071 | 6066:9071 |
| 6027:9069 | 6067:9069 | 6027:9070 | 6067:9070 | 6027:9071 | 6067:9071 |
| 6028:9069 | 6068:9069 | 6028:9070 | 6068:9070 | 6028:9071 | 6068:9071 |
| 6029:9069 | 6069:9069 | 6029:9070 | 6069:9070 | 6029:9071 | 6069:9071 |
| 6030:9069 | 6070:9069 | 6030:9070 | 6070:9070 | 6030:9071 | 6070:9071 |
| 6031:9069 | 6071:9069 | 6031:9070 | 6071:9070 | 6031:9071 | 6071:9071 |
| 6032:9069 | 6072:9069 | 6032:9070 | 6072:9070 | 6032:9071 | 6072:9071 |
| 6033:9069 | 6073:9069 | 6033:9070 | 6073:9070 | 6033:9071 | 6073:9071 |
| 6034:9069 | 6074:9069 | 6034:9070 | 6074:9070 | 6034:9071 | 6074:9071 |
| 6035:9069 | 6075:9069 | 6035:9070 | 6075:9070 | 6035:9071 | 6075:9071 |
| 6036:9069 | 6076:9069 | 6036:9070 | 6076:9070 | 6036:9071 | 6076:9071 |
| 6037:9069 | 6077:9069 | 6037:9070 | 6077:9070 | 6037:9071 | 6077:9071 |
| 6038:9069 | 6078:9069 | 6038:9070 | 6078:9070 | 6038:9071 | 6078:9071 |
| 6039:9069 | | 6039:9070 | | 6039:9071 | |

| X:Y | X:Y | X:Y | X:Y | X:Y | X:Y |
|---|---|---|---|---|---|
| 6000:9072 | 6040:9072 | 6000:9073 | 6040:9073 | 6000:9074 | 6040:9074 |
| 6001:9072 | 6041:9072 | 6001:9073 | 6041:9073 | 6001:9074 | 6041:9074 |
| 6002:9072 | 6042:9072 | 6002:9073 | 6042:9073 | 6002:9074 | 6042:9074 |
| 6003:9072 | 6043:9072 | 6003:9073 | 6043:9073 | 6003:9074 | 6043:9074 |
| 6004:9072 | 6044:9072 | 6004:9073 | 6044:9073 | 6004:9074 | 6044:9074 |
| 6005:9072 | 6045:9072 | 6005:9073 | 6045:9073 | 6005:9074 | 6045:9074 |
| 6006:9072 | 6046:9072 | 6006:9073 | 6046:9073 | 6006:9074 | 6046:9074 |
| 6007:9072 | 6047:9072 | 6007:9073 | 6047:9073 | 6007:9074 | 6047:9074 |
| 6008:9072 | 6048:9072 | 6008:9073 | 6048:9073 | 6008:9074 | 6048:9074 |
| 6009:9072 | 6049:9072 | 6009:9073 | 6049:9073 | 6009:9074 | 6049:9074 |
| 6010:9072 | 6050:9072 | 6010:9073 | 6050:9073 | 6010:9074 | 6050:9074 |
| 6011:9072 | 6051:9072 | 6011:9073 | 6051:9073 | 6011:9074 | 6051:9074 |
| 6012:9072 | 6052:9072 | 6012:9073 | 6052:9073 | 6012:9074 | 6052:9074 |
| 6013:9072 | 6053:9072 | 6013:9073 | 6053:9073 | 6013:9074 | 6053:9074 |
| 6014:9072 | 6054:9072 | 6014:9073 | 6054:9073 | 6014:9074 | 6054:9074 |
| 6015:9072 | 6055:9072 | 6015:9073 | 6055:9073 | 6015:9074 | 6055:9074 |
| 6016:9072 | 6056:9072 | 6016:9073 | 6056:9073 | 6016:9074 | 6056:9074 |
| 6017:9072 | 6057:9072 | 6017:9073 | 6057:9073 | 6017:9074 | 6057:9074 |
| 6018:9072 | 6058:9072 | 6018:9073 | 6058:9073 | 6018:9074 | 6058:9074 |
| 6019:9072 | 6059:9072 | 6019:9073 | 6059:9073 | 6019:9074 | 6059:9074 |
| 6020:9072 | 6060:9072 | 6020:9073 | 6060:9073 | 6020:9074 | 6060:9074 |
| 6021:9072 | 6061:9072 | 6021:9073 | 6061:9073 | 6021:9074 | 6061:9074 |
| 6022:9072 | 6062:9072 | 6022:9073 | 6062:9073 | 6022:9074 | 6062:9074 |
| 6023:9072 | 6063:9072 | 6023:9073 | 6063:9073 | 6023:9074 | 6063:9074 |
| 6024:9072 | 6064:9072 | 6024:9073 | 6064:9073 | 6024:9074 | 6064:9074 |
| 6025:9072 | 6065:9072 | 6025:9073 | 6065:9073 | 6025:9074 | 6065:9074 |
| 6026:9072 | 6066:9072 | 6026:9073 | 6066:9073 | 6026:9074 | 6066:9074 |
| 6027:9072 | 6067:9072 | 6027:9073 | 6067:9073 | 6027:9074 | 6067:9074 |
| 6028:9072 | 6068:9072 | 6028:9073 | 6068:9073 | 6028:9074 | 6068:9074 |
| 6029:9072 | 6069:9072 | 6029:9073 | 6069:9073 | 6029:9074 | 6069:9074 |
| 6030:9072 | 6070:9072 | 6030:9073 | 6070:9073 | 6030:9074 | 6070:9074 |
| 6031:9072 | 6071:9072 | 6031:9073 | 6071:9073 | 6031:9074 | 6071:9074 |
| 6032:9072 | 6072:9072 | 6032:9073 | 6072:9073 | 6032:9074 | 6072:9074 |
| 6033:9072 | 6073:9072 | 6033:9073 | 6073:9073 | 6033:9074 | 6073:9074 |
| 6034:9072 | 6074:9072 | 6034:9073 | 6074:9073 | 6034:9074 | 6074:9074 |
| 6035:9072 | 6075:9072 | 6035:9073 | 6075:9073 | 6035:9074 | 6075:9074 |
| 6036:9072 | 6076:9072 | 6036:9073 | 6076:9073 | 6036:9074 | 6076:9074 |
| 6037:9072 | 6077:9072 | 6037:9073 | 6077:9073 | 6037:9074 | 6077:9074 |
| 6038:9072 | 6078:9072 | 6038:9073 | 6078:9073 | 6038:9074 | 6078:9074 |
| 6039:9072 | | 6039:9073 | | 6039:9074 | |

| X:Y | X:Y | X:Y | X:Y | X:Y | X:Y |
|---|---|---|---|---|---|
| 6000:9075 | 6040:9075 | 6000:9076 | 6040:9076 | 6000:9077 | 6040:9077 |
| 6001:9075 | 6041:9075 | 6001:9076 | 6041:9076 | 6001:9077 | 6041:9077 |
| 6002:9075 | 6042:9075 | 6002:9076 | 6042:9076 | 6002:9077 | 6042:9077 |
| 6003:9075 | 6043:9075 | 6003:9076 | 6043:9076 | 6003:9077 | 6043:9077 |
| 6004:9075 | 6044:9075 | 6004:9076 | 6044:9076 | 6004:9077 | 6044:9077 |
| 6005:9075 | 6045:9075 | 6005:9076 | 6045:9076 | 6005:9077 | 6045:9077 |
| 6006:9075 | 6046:9075 | 6006:9076 | 6046:9076 | 6006:9077 | 6046:9077 |
| 6007:9075 | 6047:9075 | 6007:9076 | 6047:9076 | 6007:9077 | 6047:9077 |
| 6008:9075 | 6048:9075 | 6008:9076 | 6048:9076 | 6008:9077 | 6048:9077 |
| 6009:9075 | 6049:9075 | 6009:9076 | 6049:9076 | 6009:9077 | 6049:9077 |
| 6010:9075 | 6050:9075 | 6010:9076 | 6050:9076 | 6010:9077 | 6050:9077 |
| 6011:9075 | 6051:9075 | 6011:9076 | 6051:9076 | 6011:9077 | 6051:9077 |
| 6012:9075 | 6052:9075 | 6012:9076 | 6052:9076 | 6012:9077 | 6052:9077 |
| 6013:9075 | 6053:9075 | 6013:9076 | 6053:9076 | 6013:9077 | 6053:9077 |
| 6014:9075 | 6054:9075 | 6014:9076 | 6054:9076 | 6014:9077 | 6054:9077 |
| 6015:9075 | 6055:9075 | 6015:9076 | 6055:9076 | 6015:9077 | 6055:9077 |
| 6016:9075 | 6056:9075 | 6016:9076 | 6056:9076 | 6016:9077 | 6056:9077 |
| 6017:9075 | 6057:9075 | 6017:9076 | 6057:9076 | 6017:9077 | 6057:9077 |
| 6018:9075 | 6058:9075 | 6018:9076 | 6058:9076 | 6018:9077 | 6058:9077 |
| 6019:9075 | 6059:9075 | 6019:9076 | 6059:9076 | 6019:9077 | 6059:9077 |
| 6020:9075 | 6060:9075 | 6020:9076 | 6060:9076 | 6020:9077 | 6060:9077 |
| 6021:9075 | 6061:9075 | 6021:9076 | 6061:9076 | 6021:9077 | 6061:9077 |
| 6022:9075 | 6062:9075 | 6022:9076 | 6062:9076 | 6022:9077 | 6062:9077 |
| 6023:9075 | 6063:9075 | 6023:9076 | 6063:9076 | 6023:9077 | 6063:9077 |
| 6024:9075 | 6064:9075 | 6024:9076 | 6064:9076 | 6024:9077 | 6064:9077 |
| 6025:9075 | 6065:9075 | 6025:9076 | 6065:9076 | 6025:9077 | 6065:9077 |
| 6026:9075 | 6066:9075 | 6026:9076 | 6066:9076 | 6026:9077 | 6066:9077 |
| 6027:9075 | 6067:9075 | 6027:9076 | 6067:9076 | 6027:9077 | 6067:9077 |
| 6028:9075 | 6068:9075 | 6028:9076 | 6068:9076 | 6028:9077 | 6068:9077 |
| 6029:9075 | 6069:9075 | 6029:9076 | 6069:9076 | 6029:9077 | 6069:9077 |
| 6030:9075 | 6070:9075 | 6030:9076 | 6070:9076 | 6030:9077 | 6070:9077 |
| 6031:9075 | 6071:9075 | 6031:9076 | 6071:9076 | 6031:9077 | 6071:9077 |
| 6032:9075 | 6072:9075 | 6032:9076 | 6072:9076 | 6032:9077 | 6072:9077 |
| 6033:9075 | 6073:9075 | 6033:9076 | 6073:9076 | 6033:9077 | 6073:9077 |
| 6034:9075 | 6074:9075 | 6034:9076 | 6074:9076 | 6034:9077 | 6074:9077 |
| 6035:9075 | 6075:9075 | 6035:9076 | 6075:9076 | 6035:9077 | 6075:9077 |
| 6036:9075 | 6076:9075 | 6036:9076 | 6076:9076 | 6036:9077 | 6076:9077 |
| 6037:9075 | 6077:9075 | 6037:9076 | 6077:9076 | 6037:9077 | 6077:9077 |
| 6038:9075 | 6078:9075 | 6038:9076 | 6078:9076 | 6038:9077 | 6078:9077 |
| 6039:9075 | | 6039:9076 | | 6039:9077 | |

| X:Y | X:Y | X:Y | X:Y | X:Y | X:Y |
|---|---|---|---|---|---|
| 6000:9078 | 6040:9078 | 6000:9079 | 6040:9079 | 6000:9080 | 6040:9080 |
| 6001:9078 | 6041:9078 | 6001:9079 | 6041:9079 | 6001:9080 | 6041:9080 |
| 6002:9078 | 6042:9078 | 6002:9079 | 6042:9079 | 6002:9080 | 6042:9080 |
| 6003:9078 | 6043:9078 | 6003:9079 | 6043:9079 | 6003:9080 | 6043:9080 |
| 6004:9078 | 6044:9078 | 6004:9079 | 6044:9079 | 6004:9080 | 6044:9080 |
| 6005:9078 | 6045:9078 | 6005:9079 | 6045:9079 | 6005:9080 | 6045:9080 |
| 6006:9078 | 6046:9078 | 6006:9079 | 6046:9079 | 6006:9080 | 6046:9080 |
| 6007:9078 | 6047:9078 | 6007:9079 | 6047:9079 | 6007:9080 | 6047:9080 |
| 6008:9078 | 6048:9078 | 6008:9079 | 6048:9079 | 6008:9080 | 6048:9080 |
| 6009:9078 | 6049:9078 | 6009:9079 | 6049:9079 | 6009:9080 | 6049:9080 |
| 6010:9078 | 6050:9078 | 6010:9079 | 6050:9079 | 6010:9080 | 6050:9080 |
| 6011:9078 | 6051:9078 | 6011:9079 | 6051:9079 | 6011:9080 | 6051:9080 |
| 6012:9078 | 6052:9078 | 6012:9079 | 6052:9079 | 6012:9080 | 6052:9080 |
| 6013:9078 | 6053:9078 | 6013:9079 | 6053:9079 | 6013:9080 | 6053:9080 |
| 6014:9078 | 6054:9078 | 6014:9079 | 6054:9079 | 6014:9080 | 6054:9080 |
| 6015:9078 | 6055:9078 | 6015:9079 | 6055:9079 | 6015:9080 | 6055:9080 |
| 6016:9078 | 6056:9078 | 6016:9079 | 6056:9079 | 6016:9080 | 6056:9080 |
| 6017:9078 | 6057:9078 | 6017:9079 | 6057:9079 | 6017:9080 | 6057:9080 |
| 6018:9078 | 6058:9078 | 6018:9079 | 6058:9079 | 6018:9080 | 6058:9080 |
| 6019:9078 | 6059:9078 | 6019:9079 | 6059:9079 | 6019:9080 | 6059:9080 |
| 6020:9078 | 6060:9078 | 6020:9079 | 6060:9079 | 6020:9080 | 6060:9080 |
| 6021:9078 | 6061:9078 | 6021:9079 | 6061:9079 | 6021:9080 | 6061:9080 |
| 6022:9078 | 6062:9078 | 6022:9079 | 6062:9079 | 6022:9080 | 6062:9080 |
| 6023:9078 | 6063:9078 | 6023:9079 | 6063:9079 | 6023:9080 | 6063:9080 |
| 6024:9078 | 6064:9078 | 6024:9079 | 6064:9079 | 6024:9080 | 6064:9080 |
| 6025:9078 | 6065:9078 | 6025:9079 | 6065:9079 | 6025:9080 | 6065:9080 |
| 6026:9078 | 6066:9078 | 6026:9079 | 6066:9079 | 6026:9080 | 6066:9080 |
| 6027:9078 | 6067:9078 | 6027:9079 | 6067:9079 | 6027:9080 | 6067:9080 |
| 6028:9078 | 6068:9078 | 6028:9079 | 6068:9079 | 6028:9080 | 6068:9080 |
| 6029:9078 | 6069:9078 | 6029:9079 | 6069:9079 | 6029:9080 | 6069:9080 |
| 6030:9078 | 6070:9078 | 6030:9079 | 6070:9079 | 6030:9080 | 6070:9080 |
| 6031:9078 | 6071:9078 | 6031:9079 | 6071:9079 | 6031:9080 | 6071:9080 |
| 6032:9078 | 6072:9078 | 6032:9079 | 6072:9079 | 6032:9080 | 6072:9080 |
| 6033:9078 | 6073:9078 | 6033:9079 | 6073:9079 | 6033:9080 | 6073:9080 |
| 6034:9078 | 6074:9078 | 6034:9079 | 6074:9079 | 6034:9080 | 6074:9080 |
| 6035:9078 | 6075:9078 | 6035:9079 | 6075:9079 | 6035:9080 | 6075:9080 |

TABLE D-continued

| X:Y | X:Y | X:Y | X:Y | X:Y | X:Y |
|---|---|---|---|---|---|
| 6036:9078 | 6076:9078 | 6036:9079 | 6076:9079 | 6036:9080 | 6076:9080 |
| 6037:9078 | 6077:9078 | 6037:9079 | 6077:9079 | 6037:9080 | 6077:9080 |
| 6038:9078 | 6078:9078 | 6038:9079 | 6078:9079 | 6038:9080 | 6078:9080 |
| 6039:9078 | | 6039:9079 | | 6039:9080 | |

| X:Y | X:Y | X:Y | X:Y | X:Y | X:Y |
|---|---|---|---|---|---|
| 6000:9081 | 6040:9081 | 6000:9082 | 6040:9082 | 6000:9083 | 6040:9083 |
| 6001:9081 | 6041:9081 | 6001:9082 | 6041:9082 | 6001:9083 | 6041:9083 |
| 6002:9081 | 6042:9081 | 6002:9082 | 6042:9082 | 6002:9083 | 6042:9083 |
| 6003:9081 | 6043:9081 | 6003:9082 | 6043:9082 | 6003:9083 | 6043:9083 |
| 6004:9081 | 6044:9081 | 6004:9082 | 6044:9082 | 6004:9083 | 6044:9083 |
| 6005:9081 | 6045:9081 | 6005:9082 | 6045:9082 | 6005:9083 | 6045:9083 |
| 6006:9081 | 6046:9081 | 6006:9082 | 6046:9082 | 6006:9083 | 6046:9083 |
| 6007:9081 | 6047:9081 | 6007:9082 | 6047:9082 | 6007:9083 | 6047:9083 |
| 6008:9081 | 6048:9081 | 6008:9082 | 6048:9082 | 6008:9083 | 6048:9083 |
| 6009:9081 | 6049:9081 | 6009:9082 | 6049:9082 | 6009:9083 | 6049:9083 |
| 6010:9081 | 6050:9081 | 6010:9082 | 6050:9082 | 6010:9083 | 6050:9083 |
| 6011:9081 | 6051:9081 | 6011:9082 | 6051:9082 | 6011:9083 | 6051:9083 |
| 6012:9081 | 6052:9081 | 6012:9082 | 6052:9082 | 6012:9083 | 6052:9083 |
| 6013:9081 | 6053:9081 | 6013:9082 | 6053:9082 | 6013:9083 | 6053:9083 |
| 6014:9081 | 6054:9081 | 6014:9082 | 6054:9082 | 6014:9083 | 6054:9083 |
| 6015:9081 | 6055:9081 | 6015:9082 | 6055:9082 | 6015:9083 | 6055:9083 |
| 6016:9081 | 6056:9081 | 6016:9082 | 6056:9082 | 6016:9083 | 6056:9083 |
| 6017:9081 | 6057:9081 | 6017:9082 | 6057:9082 | 6017:9083 | 6057:9083 |
| 6018:9081 | 6058:9081 | 6018:9082 | 6058:9082 | 6018:9083 | 6058:9083 |
| 6019:9081 | 6059:9081 | 6019:9082 | 6059:9082 | 6019:9083 | 6059:9083 |
| 6020:9081 | 6060:9081 | 6020:9082 | 6060:9082 | 6020:9083 | 6060:9083 |
| 6021:9081 | 6061:9081 | 6021:9082 | 6061:9082 | 6021:9083 | 6061:9083 |
| 6022:9081 | 6062:9081 | 6022:9082 | 6062:9082 | 6022:9083 | 6062:9083 |
| 6023:9081 | 6063:9081 | 6023:9082 | 6063:9082 | 6023:9083 | 6063:9083 |
| 6024:9081 | 6064:9081 | 6024:9082 | 6064:9082 | 6024:9083 | 6064:9083 |
| 6025:9081 | 6065:9081 | 6025:9082 | 6065:9082 | 6025:9083 | 6065:9083 |
| 6026:9081 | 6066:9081 | 6026:9082 | 6066:9082 | 6026:9083 | 6066:9083 |
| 6027:9081 | 6067:9081 | 6027:9082 | 6067:9082 | 6027:9083 | 6067:9083 |
| 6028:9081 | 6068:9081 | 6028:9082 | 6068:9082 | 6028:9083 | 6068:9083 |
| 6029:9081 | 6069:9081 | 6029:9082 | 6069:9082 | 6029:9083 | 6069:9083 |
| 6030:9081 | 6070:9081 | 6030:9082 | 6070:9082 | 6030:9083 | 6070:9083 |
| 6031:9081 | 6071:9081 | 6031:9082 | 6071:9082 | 6031:9083 | 6071:9083 |
| 6032:9081 | 6072:9081 | 6032:9082 | 6072:9082 | 6032:9083 | 6072:9083 |
| 6033:9081 | 6073:9081 | 6033:9082 | 6073:9082 | 6033:9083 | 6073:9083 |
| 6034:9081 | 6074:9081 | 6034:9082 | 6074:9082 | 6034:9083 | 6074:9083 |
| 6035:9081 | 6075:9081 | 6035:9082 | 6075:9082 | 6035:9083 | 6075:9083 |
| 6036:9081 | 6076:9081 | 6036:9082 | 6076:9082 | 6036:9083 | 6076:9083 |
| 6037:9081 | 6077:9081 | 6037:9082 | 6077:9082 | 6037:9083 | 6077:9083 |
| 6038:9081 | 6078:9081 | 6038:9082 | 6078:9082 | 6038:9083 | 6078:9083 |
| 6039:9081 | | 6039:9082 | | 6039:9083 | |

| X:Y | X:Y | X:Y | X:Y | X:Y | X:Y |
|---|---|---|---|---|---|
| 6000:9084 | 6040:9084 | 6000:9085 | 6040:9085 | 6000:9086 | 6040:9086 |
| 6001:9084 | 6041:9084 | 6001:9085 | 6041:9085 | 6001:9086 | 6041:9086 |
| 6002:9084 | 6042:9084 | 6002:9085 | 6042:9085 | 6002:9086 | 6042:9086 |
| 6003:9084 | 6043:9084 | 6003:9085 | 6043:9085 | 6003:9086 | 6043:9086 |
| 6004:9084 | 6044:9084 | 6004:9085 | 6044:9085 | 6004:9086 | 6044:9086 |
| 6005:9084 | 6045:9084 | 6005:9085 | 6045:9085 | 6005:9086 | 6045:9086 |
| 6006:9084 | 6046:9084 | 6006:9085 | 6046:9085 | 6006:9086 | 6046:9086 |
| 6007:9084 | 6047:9084 | 6007:9085 | 6047:9085 | 6007:9086 | 6047:9086 |
| 6008:9084 | 6048:9084 | 6008:9085 | 6048:9085 | 6008:9086 | 6048:9086 |
| 6009:9084 | 6049:9084 | 6009:9085 | 6049:9085 | 6009:9086 | 6049:9086 |
| 6010:9084 | 6050:9084 | 6010:9085 | 6050:9085 | 6010:9086 | 6050:9086 |
| 6011:9084 | 6051:9084 | 6011:9085 | 6051:9085 | 6011:9086 | 6051:9086 |
| 6012:9084 | 6052:9084 | 6012:9085 | 6052:9085 | 6012:9086 | 6052:9086 |
| 6013:9084 | 6053:9084 | 6013:9085 | 6053:9085 | 6013:9086 | 6053:9086 |
| 6014:9084 | 6054:9084 | 6014:9085 | 6054:9085 | 6014:9086 | 6054:9086 |
| 6015:9084 | 6055:9084 | 6015:9085 | 6055:9085 | 6015:9086 | 6055:9086 |
| 6016:9084 | 6056:9084 | 6016:9085 | 6056:9085 | 6016:9086 | 6056:9086 |
| 6017:9084 | 6057:9084 | 6017:9085 | 6057:9085 | 6017:9086 | 6057:9086 |
| 6018:9084 | 6058:9084 | 6018:9085 | 6058:9085 | 6018:9086 | 6058:9086 |
| 6019:9084 | 6059:9084 | 6019:9085 | 6059:9085 | 6019:9086 | 6059:9086 |
| 6020:9084 | 6060:9084 | 6020:9085 | 6060:9085 | 6020:9086 | 6060:9086 |
| 6021:9084 | 6061:9084 | 6021:9085 | 6061:9085 | 6021:9086 | 6061:9086 |
| 6022:9084 | 6062:9084 | 6022:9085 | 6062:9085 | 6022:9086 | 6062:9086 |
| 6023:9084 | 6063:9084 | 6023:9085 | 6063:9085 | 6023:9086 | 6063:9086 |
| 6024:9084 | 6064:9084 | 6024:9085 | 6064:9085 | 6024:9086 | 6064:9086 |
| 6025:9084 | 6065:9084 | 6025:9085 | 6065:9085 | 6025:9086 | 6065:9086 |
| 6026:9084 | 6066:9084 | 6026:9085 | 6066:9085 | 6026:9086 | 6066:9086 |
| 6027:9084 | 6067:9084 | 6027:9085 | 6067:9085 | 6027:9086 | 6067:9086 |
| 6028:9084 | 6068:9084 | 6028:9085 | 6068:9085 | 6028:9086 | 6068:9086 |
| 6029:9084 | 6069:9084 | 6029:9085 | 6069:9085 | 6029:9086 | 6069:9086 |
| 6030:9084 | 6070:9084 | 6030:9085 | 6070:9085 | 6030:9086 | 6070:9086 |
| 6031:9084 | 6071:9084 | 6031:9085 | 6071:9085 | 6031:9086 | 6071:9086 |
| 6032:9084 | 6072:9084 | 6032:9085 | 6072:9085 | 6032:9086 | 6072:9086 |
| 6033:9084 | 6073:9084 | 6033:9085 | 6073:9085 | 6033:9086 | 6073:9086 |
| 6034:9084 | 6074:9084 | 6034:9085 | 6074:9085 | 6034:9086 | 6074:9086 |
| 6035:9084 | 6075:9084 | 6035:9085 | 6075:9085 | 6035:9086 | 6075:9086 |
| 6036:9084 | 6076:9084 | 6036:9085 | 6076:9085 | 6036:9086 | 6076:9086 |
| 6037:9084 | 6077:9084 | 6037:9085 | 6077:9085 | 6037:9086 | 6077:9086 |
| 6038:9084 | 6078:9084 | 6038:9085 | 6078:9085 | 6038:9086 | 6078:9086 |
| 6039:9084 | | 6039:9085 | | 6039:9086 | |

| X:Y | X:Y | X:Y | X:Y | X:Y | X:Y |
|---|---|---|---|---|---|
| 6000:9087 | 6040:9087 | 6000:9088 | 6040:9088 | 6000:9089 | 6040:9089 |
| 6001:9087 | 6041:9087 | 6001:9088 | 6041:9088 | 6001:9089 | 6041:9089 |
| 6002:9087 | 6042:9087 | 6002:9088 | 6042:9088 | 6002:9089 | 6042:9089 |
| 6003:9087 | 6043:9087 | 6003:9088 | 6043:9088 | 6003:9089 | 6043:9089 |
| 6004:9087 | 6044:9087 | 6004:9088 | 6044:9088 | 6004:9089 | 6044:9089 |
| 6005:9087 | 6045:9087 | 6005:9088 | 6045:9088 | 6005:9089 | 6045:9089 |
| 6006:9087 | 6046:9087 | 6006:9088 | 6046:9088 | 6006:9089 | 6046:9089 |
| 6007:9087 | 6047:9087 | 6007:9088 | 6047:9088 | 6007:9089 | 6047:9089 |
| 6008:9087 | 6048:9087 | 6008:9088 | 6048:9088 | 6008:9089 | 6048:9089 |
| 6009:9087 | 6049:9087 | 6009:9088 | 6049:9088 | 6009:9089 | 6049:9089 |
| 6010:9087 | 6050:9087 | 6010:9088 | 6050:9088 | 6010:9089 | 6050:9089 |
| 6011:9087 | 6051:9087 | 6011:9088 | 6051:9088 | 6011:9089 | 6051:9089 |
| 6012:9087 | 6052:9087 | 6012:9088 | 6052:9088 | 6012:9089 | 6052:9089 |
| 6013:9087 | 6053:9087 | 6013:9088 | 6053:9088 | 6013:9089 | 6053:9089 |
| 6014:9087 | 6054:9087 | 6014:9088 | 6054:9088 | 6014:9089 | 6054:9089 |
| 6015:9087 | 6055:9087 | 6015:9088 | 6055:9088 | 6015:9089 | 6055:9089 |
| 6016:9087 | 6056:9087 | 6016:9088 | 6056:9088 | 6016:9089 | 6056:9089 |
| 6017:9087 | 6057:9087 | 6017:9088 | 6057:9088 | 6017:9089 | 6057:9089 |
| 6018:9087 | 6058:9087 | 6018:9088 | 6058:9088 | 6018:9089 | 6058:9089 |
| 6019:9087 | 6059:9087 | 6019:9088 | 6059:9088 | 6019:9089 | 6059:9089 |
| 6020:9087 | 6060:9087 | 6020:9088 | 6060:9088 | 6020:9089 | 6060:9089 |
| 6021:9087 | 6061:9087 | 6021:9088 | 6061:9088 | 6021:9089 | 6061:9089 |
| 6022:9087 | 6062:9087 | 6022:9088 | 6062:9088 | 6022:9089 | 6062:9089 |
| 6023:9087 | 6063:9087 | 6023:9088 | 6063:9088 | 6023:9089 | 6063:9089 |
| 6024:9087 | 6064:9087 | 6024:9088 | 6064:9088 | 6024:9089 | 6064:9089 |
| 6025:9087 | 6065:9087 | 6025:9088 | 6065:9088 | 6025:9089 | 6065:9089 |
| 6026:9087 | 6066:9087 | 6026:9088 | 6066:9088 | 6026:9089 | 6066:9089 |
| 6027:9087 | 6067:9087 | 6027:9088 | 6067:9088 | 6027:9089 | 6067:9089 |
| 6028:9087 | 6068:9087 | 6028:9088 | 6068:9088 | 6028:9089 | 6068:9089 |
| 6029:9087 | 6069:9087 | 6029:9088 | 6069:9088 | 6029:9089 | 6069:9089 |
| 6030:9087 | 6070:9087 | 6030:9088 | 6070:9088 | 6030:9089 | 6070:9089 |
| 6031:9087 | 6071:9087 | 6031:9088 | 6071:9088 | 6031:9089 | 6071:9089 |
| 6032:9087 | 6072:9087 | 6032:9088 | 6072:9088 | 6032:9089 | 6072:9089 |
| 6033:9087 | 6073:9087 | 6033:9088 | 6073:9088 | 6033:9089 | 6073:9089 |
| 6034:9087 | 6074:9087 | 6034:9088 | 6074:9088 | 6034:9089 | 6074:9089 |
| 6035:9087 | 6075:9087 | 6035:9088 | 6075:9088 | 6035:9089 | 6075:9089 |
| 6036:9087 | 6076:9087 | 6036:9088 | 6076:9088 | 6036:9089 | 6076:9089 |
| 6037:9087 | 6077:9087 | 6037:9088 | 6077:9088 | 6037:9089 | 6077:9089 |
| 6038:9087 | 6078:9087 | 6038:9088 | 6078:9088 | 6038:9089 | 6078:9089 |
| 6039:9087 | | 6039:9088 | | 6039:9089 | |

| X:Y | X:Y | X:Y | X:Y | X:Y | X:Y |
|---|---|---|---|---|---|
| 6000:9090 | 6040:9090 | 6000:9091 | 6040:9091 | 6000:9092 | 6040:9092 |
| 6001:9090 | 6041:9090 | 6001:9091 | 6041:9091 | 6001:9092 | 6041:9092 |
| 6002:9090 | 6042:9090 | 6002:9091 | 6042:9091 | 6002:9092 | 6042:9092 |
| 6003:9090 | 6043:9090 | 6003:9091 | 6043:9091 | 6003:9092 | 6043:9092 |
| 6004:9090 | 6044:9090 | 6004:9091 | 6044:9091 | 6004:9092 | 6044:9092 |
| 6005:9090 | 6045:9090 | 6005:9091 | 6045:9091 | 6005:9092 | 6045:9092 |
| 6006:9090 | 6046:9090 | 6006:9091 | 6046:9091 | 6006:9092 | 6046:9092 |
| 6007:9090 | 6047:9090 | 6007:9091 | 6047:9091 | 6007:9092 | 6047:9092 |
| 6008:9090 | 6048:9090 | 6008:9091 | 6048:9091 | 6008:9092 | 6048:9092 |
| 6009:9090 | 6049:9090 | 6009:9091 | 6049:9091 | 6009:9092 | 6049:9092 |
| 6010:9090 | 6050:9090 | 6010:9091 | 6050:9091 | 6010:9092 | 6050:9092 |
| 6011:9090 | 6051:9090 | 6011:9091 | 6051:9091 | 6011:9092 | 6051:9092 |
| 6012:9090 | 6052:9090 | 6012:9091 | 6052:9091 | 6012:9092 | 6052:9092 |
| 6013:9090 | 6053:9090 | 6013:9091 | 6053:9091 | 6013:9092 | 6053:9092 |
| 6014:9090 | 6054:9090 | 6014:9091 | 6054:9091 | 6014:9092 | 6054:9092 |
| 6015:9090 | 6055:9090 | 6015:9091 | 6055:9091 | 6015:9092 | 6055:9092 |
| 6016:9090 | 6056:9090 | 6016:9091 | 6056:9091 | 6016:9092 | 6056:9092 |
| 6017:9090 | 6057:9090 | 6017:9091 | 6057:9091 | 6017:9092 | 6057:9092 |
| 6018:9090 | 6058:9090 | 6018:9091 | 6058:9091 | 6018:9092 | 6058:9092 |
| 6019:9090 | 6059:9090 | 6019:9091 | 6059:9091 | 6019:9092 | 6059:9092 |
| 6020:9090 | 6060:9090 | 6020:9091 | 6060:9091 | 6020:9092 | 6060:9092 |
| 6021:9090 | 6061:9090 | 6021:9091 | 6061:9091 | 6021:9092 | 6061:9092 |
| 6022:9090 | 6062:9090 | 6022:9091 | 6062:9091 | 6022:9092 | 6062:9092 |
| 6023:9090 | 6063:9090 | 6023:9091 | 6063:9091 | 6023:9092 | 6063:9092 |

TABLE D-continued

| X:Y | X:Y | X:Y | X:Y | X:Y | X:Y |
|---|---|---|---|---|---|
| 6024:9090 | 6064:9090 | 6024:9091 | 6064:9091 | 6024:9092 | 6064:9092 |
| 6025:9090 | 6065:9090 | 6025:9091 | 6065:9091 | 6025:9092 | 6065:9092 |
| 6026:9090 | 6066:9090 | 6026:9091 | 6066:9091 | 6026:9092 | 6066:9092 |
| 6027:9090 | 6067:9090 | 6027:9091 | 6067:9091 | 6027:9092 | 6067:9092 |
| 6028:9090 | 6068:9090 | 6028:9091 | 6068:9091 | 6028:9092 | 6068:9092 |
| 6029:9090 | 6069:9090 | 6029:9091 | 6069:9091 | 6029:9092 | 6069:9092 |
| 6030:9090 | 6070:9090 | 6030:9091 | 6070:9091 | 6030:9092 | 6070:9092 |
| 6031:9090 | 6071:9090 | 6031:9091 | 6071:9091 | 6031:9092 | 6071:9092 |
| 6032:9090 | 6072:9090 | 6032:9091 | 6072:9091 | 6032:9092 | 6072:9092 |
| 6033:9090 | 6073:9090 | 6033:9091 | 6073:9091 | 6033:9092 | 6073:9092 |
| 6034:9090 | 6074:9090 | 6034:9091 | 6074:9091 | 6034:9092 | 6074:9092 |
| 6035:9090 | 6075:9090 | 6035:9091 | 6075:9091 | 6035:9092 | 6075:9092 |
| 6036:9090 | 6076:9090 | 6036:9091 | 6076:9091 | 6036:9092 | 6076:9092 |
| 6037:9090 | 6077:9090 | 6037:9091 | 6077:9091 | 6037:9092 | 6077:9092 |
| 6038:9090 | 6078:9090 | 6038:9091 | 6078:9091 | 6038:9092 | 6078:9092 |
| 6039:9090 | | 6039:9091 | | 6039:9092 | |

| X:Y | X:Y | X:Y | X:Y | X:Y | X:Y |
|---|---|---|---|---|---|
| 6000:9093 | 6040:9093 | 6000:9094 | 6040:9094 | 6000:9095 | 6040:9095 |
| 6001:9093 | 6041:9093 | 6001:9094 | 6041:9094 | 6001:9095 | 6041:9095 |
| 6002:9093 | 6042:9093 | 6002:9094 | 6042:9094 | 6002:9095 | 6042:9095 |
| 6003:9093 | 6043:9093 | 6003:9094 | 6043:9094 | 6003:9095 | 6043:9095 |
| 6004:9093 | 6044:9093 | 6004:9094 | 6044:9094 | 6004:9095 | 6044:9095 |
| 6005:9093 | 6045:9093 | 6005:9094 | 6045:9094 | 6005:9095 | 6045:9095 |
| 6006:9093 | 6046:9093 | 6006:9094 | 6046:9094 | 6006:9095 | 6046:9095 |
| 6007:9093 | 6047:9093 | 6007:9094 | 6047:9094 | 6007:9095 | 6047:9095 |
| 6008:9093 | 6048:9093 | 6008:9094 | 6048:9094 | 6008:9095 | 6048:9095 |
| 6009:9093 | 6049:9093 | 6009:9094 | 6049:9094 | 6009:9095 | 6049:9095 |
| 6010:9093 | 6050:9093 | 6010:9094 | 6050:9094 | 6010:9095 | 6050:9095 |
| 6011:9093 | 6051:9093 | 6011:9094 | 6051:9094 | 6011:9095 | 6051:9095 |
| 6012:9093 | 6052:9093 | 6012:9094 | 6052:9094 | 6012:9095 | 6052:9095 |
| 6013:9093 | 6053:9093 | 6013:9094 | 6053:9094 | 6013:9095 | 6053:9095 |
| 6014:9093 | 6054:9093 | 6014:9094 | 6054:9094 | 6014:9095 | 6054:9095 |
| 6015:9093 | 6055:9093 | 6015:9094 | 6055:9094 | 6015:9095 | 6055:9095 |
| 6016:9093 | 6056:9093 | 6016:9094 | 6056:9094 | 6016:9095 | 6056:9095 |
| 6017:9093 | 6057:9093 | 6017:9094 | 6057:9094 | 6017:9095 | 6057:9095 |
| 6018:9093 | 6058:9093 | 6018:9094 | 6058:9094 | 6018:9095 | 6058:9095 |
| 6019:9093 | 6059:9093 | 6019:9094 | 6059:9094 | 6019:9095 | 6059:9095 |
| 6020:9093 | 6060:9093 | 6020:9094 | 6060:9094 | 6020:9095 | 6060:9095 |
| 6021:9093 | 6061:9093 | 6021:9094 | 6061:9094 | 6021:9095 | 6061:9095 |
| 6022:9093 | 6062:9093 | 6022:9094 | 6062:9094 | 6022:9095 | 6062:9095 |
| 6023:9093 | 6063:9093 | 6023:9094 | 6063:9094 | 6023:9095 | 6063:9095 |
| 6024:9093 | 6064:9093 | 6024:9094 | 6064:9094 | 6024:9095 | 6064:9095 |
| 6025:9093 | 6065:9093 | 6025:9094 | 6065:9094 | 6025:9095 | 6065:9095 |
| 6026:9093 | 6066:9093 | 6026:9094 | 6066:9094 | 6026:9095 | 6066:9095 |
| 6027:9093 | 6067:9093 | 6027:9094 | 6067:9094 | 6027:9095 | 6067:9095 |
| 6028:9093 | 6068:9093 | 6028:9094 | 6068:9094 | 6028:9095 | 6068:9095 |
| 6029:9093 | 6069:9093 | 6029:9094 | 6069:9094 | 6029:9095 | 6069:9095 |
| 6030:9093 | 6070:9093 | 6030:9094 | 6070:9094 | 6030:9095 | 6070:9095 |
| 6031:9093 | 6071:9093 | 6031:9094 | 6071:9094 | 6031:9095 | 6071:9095 |
| 6032:9093 | 6072:9093 | 6032:9094 | 6072:9094 | 6032:9095 | 6072:9095 |
| 6033:9093 | 6073:9093 | 6033:9094 | 6073:9094 | 6033:9095 | 6073:9095 |
| 6034:9093 | 6074:9093 | 6034:9094 | 6074:9094 | 6034:9095 | 6074:9095 |
| 6035:9093 | 6075:9093 | 6035:9094 | 6075:9094 | 6035:9095 | 6075:9095 |
| 6036:9093 | 6076:9093 | 6036:9094 | 6076:9094 | 6036:9095 | 6076:9095 |
| 6037:9093 | 6077:9093 | 6037:9094 | 6077:9094 | 6037:9095 | 6077:9095 |
| 6038:9093 | 6078:9093 | 6038:9094 | 6078:9094 | 6038:9095 | 6078:9095 |
| 6039:9093 | | 6039:9094 | | 6039:9095 | |

| X:Y | X:Y | X:Y | X:Y | X:Y | X:Y |
|---|---|---|---|---|---|
| 6000:9096 | 6040:9096 | 6000:9097 | 6040:9097 | 6000:9098 | 6040:9098 |
| 6001:9096 | 6041:9096 | 6001:9097 | 6041:9097 | 6001:9098 | 6041:9098 |
| 6002:9096 | 6042:9096 | 6002:9097 | 6042:9097 | 6002:9098 | 6042:9098 |
| 6003:9096 | 6043:9096 | 6003:9097 | 6043:9097 | 6003:9098 | 6043:9098 |
| 6004:9096 | 6044:9096 | 6004:9097 | 6044:9097 | 6004:9098 | 6044:9098 |
| 6005:9096 | 6045:9096 | 6005:9097 | 6045:9097 | 6005:9098 | 6045:9098 |
| 6006:9096 | 6046:9096 | 6006:9097 | 6046:9097 | 6006:9098 | 6046:9098 |
| 6007:9096 | 6047:9096 | 6007:9097 | 6047:9097 | 6007:9098 | 6047:9098 |
| 6008:9096 | 6048:9096 | 6008:9097 | 6048:9097 | 6008:9098 | 6048:9098 |
| 6009:9096 | 6049:9096 | 6009:9097 | 6049:9097 | 6009:9098 | 6049:9098 |
| 6010:9096 | 6050:9096 | 6010:9097 | 6050:9097 | 6010:9098 | 6050:9098 |
| 6011:9096 | 6051:9096 | 6011:9097 | 6051:9097 | 6011:9098 | 6051:9098 |
| 6012:9096 | 6052:9096 | 6012:9097 | 6052:9097 | 6012:9098 | 6052:9098 |
| 6013:9096 | 6053:9096 | 6013:9097 | 6053:9097 | 6013:9098 | 6053:9098 |
| 6014:9096 | 6054:9096 | 6014:9097 | 6054:9097 | 6014:9098 | 6054:9098 |
| 6015:9096 | 6055:9096 | 6015:9097 | 6055:9097 | 6015:9098 | 6055:9098 |
| 6016:9096 | 6056:9096 | 6016:9097 | 6056:9097 | 6016:9098 | 6056:9098 |
| 6017:9096 | 6057:9096 | 6017:9097 | 6057:9097 | 6017:9098 | 6057:9098 |
| 6018:9096 | 6058:9096 | 6018:9097 | 6058:9097 | 6018:9098 | 6058:9098 |
| 6019:9096 | 6059:9096 | 6019:9097 | 6059:9097 | 6019:9098 | 6059:9098 |
| 6020:9096 | 6060:9096 | 6020:9097 | 6060:9097 | 6020:9098 | 6060:9098 |
| 6021:9096 | 6061:9096 | 6021:9097 | 6061:9097 | 6021:9098 | 6061:9098 |
| 6022:9096 | 6062:9096 | 6022:9097 | 6062:9097 | 6022:9098 | 6062:9098 |
| 6023:9096 | 6063:9096 | 6023:9097 | 6063:9097 | 6023:9098 | 6063:9098 |
| 6024:9096 | 6064:9096 | 6024:9097 | 6064:9097 | 6024:9098 | 6064:9098 |
| 6025:9096 | 6065:9096 | 6025:9097 | 6065:9097 | 6025:9098 | 6065:9098 |
| 6026:9096 | 6066:9096 | 6026:9097 | 6066:9097 | 6026:9098 | 6066:9098 |
| 6027:9096 | 6067:9096 | 6027:9097 | 6067:9097 | 6027:9098 | 6067:9098 |
| 6028:9096 | 6068:9096 | 6028:9097 | 6068:9097 | 6028:9098 | 6068:9098 |
| 6029:9096 | 6069:9096 | 6029:9097 | 6069:9097 | 6029:9098 | 6069:9098 |
| 6030:9096 | 6070:9096 | 6030:9097 | 6070:9097 | 6030:9098 | 6070:9098 |
| 6031:9096 | 6071:9096 | 6031:9097 | 6071:9097 | 6031:9098 | 6071:9098 |
| 6032:9096 | 6072:9096 | 6032:9097 | 6072:9097 | 6032:9098 | 6072:9098 |
| 6033:9096 | 6073:9096 | 6033:9097 | 6073:9097 | 6033:9098 | 6073:9098 |
| 6034:9096 | 6074:9096 | 6034:9097 | 6074:9097 | 6034:9098 | 6074:9098 |
| 6035:9096 | 6075:9096 | 6035:9097 | 6075:9097 | 6035:9098 | 6075:9098 |
| 6036:9096 | 6076:9096 | 6036:9097 | 6076:9097 | 6036:9098 | 6076:9098 |
| 6037:9096 | 6077:9096 | 6037:9097 | 6077:9097 | 6037:9098 | 6077:9098 |
| 6038:9096 | 6078:9096 | 6038:9097 | 6078:9097 | 6038:9098 | 6078:9098 |
| 6039:9096 | | 6039:9097 | | 6039:9098 | |

| X:Y | X:Y | X:Y | X:Y | X:Y | X:Y |
|---|---|---|---|---|---|
| 6000:9099 | 6040:9099 | 6000:9100 | 6040:9100 | 6000:9101 | 6040:9101 |
| 6001:9099 | 6041:9099 | 6001:9100 | 6041:9100 | 6001:9101 | 6041:9101 |
| 6002:9099 | 6042:9099 | 6002:9100 | 6042:9100 | 6002:9101 | 6042:9101 |
| 6003:9099 | 6043:9099 | 6003:9100 | 6043:9100 | 6003:9101 | 6043:9101 |
| 6004:9099 | 6044:9099 | 6004:9100 | 6044:9100 | 6004:9101 | 6044:9101 |
| 6005:9099 | 6045:9099 | 6005:9100 | 6045:9100 | 6005:9101 | 6045:9101 |
| 6006:9099 | 6046:9099 | 6006:9100 | 6046:9100 | 6006:9101 | 6046:9101 |
| 6007:9099 | 6047:9099 | 6007:9100 | 6047:9100 | 6007:9101 | 6047:9101 |
| 6008:9099 | 6048:9099 | 6008:9100 | 6048:9100 | 6008:9101 | 6048:9101 |
| 6009:9099 | 6049:9099 | 6009:9100 | 6049:9100 | 6009:9101 | 6049:9101 |
| 6010:9099 | 6050:9099 | 6010:9100 | 6050:9100 | 6010:9101 | 6050:9101 |
| 6011:9099 | 6051:9099 | 6011:9100 | 6051:9100 | 6011:9101 | 6051:9101 |
| 6012:9099 | 6052:9099 | 6012:9100 | 6052:9100 | 6012:9101 | 6052:9101 |
| 6013:9099 | 6053:9099 | 6013:9100 | 6053:9100 | 6013:9101 | 6053:9101 |
| 6014:9099 | 6054:9099 | 6014:9100 | 6054:9100 | 6014:9101 | 6054:9101 |
| 6015:9099 | 6055:9099 | 6015:9100 | 6055:9100 | 6015:9101 | 6055:9101 |
| 6016:9099 | 6056:9099 | 6016:9100 | 6056:9100 | 6016:9101 | 6056:9101 |
| 6017:9099 | 6057:9099 | 6017:9100 | 6057:9100 | 6017:9101 | 6057:9101 |
| 6018:9099 | 6058:9099 | 6018:9100 | 6058:9100 | 6018:9101 | 6058:9101 |
| 6019:9099 | 6059:9099 | 6019:9100 | 6059:9100 | 6019:9101 | 6059:9101 |
| 6020:9099 | 6060:9099 | 6020:9100 | 6060:9100 | 6020:9101 | 6060:9101 |
| 6021:9099 | 6061:9099 | 6021:9100 | 6061:9100 | 6021:9101 | 6061:9101 |
| 6022:9099 | 6062:9099 | 6022:9100 | 6062:9100 | 6022:9101 | 6062:9101 |
| 6023:9099 | 6063:9099 | 6023:9100 | 6063:9100 | 6023:9101 | 6063:9101 |
| 6024:9099 | 6064:9099 | 6024:9100 | 6064:9100 | 6024:9101 | 6064:9101 |
| 6025:9099 | 6065:9099 | 6025:9100 | 6065:9100 | 6025:9101 | 6065:9101 |
| 6026:9099 | 6066:9099 | 6026:9100 | 6066:9100 | 6026:9101 | 6066:9101 |
| 6027:9099 | 6067:9099 | 6027:9100 | 6067:9100 | 6027:9101 | 6067:9101 |
| 6028:9099 | 6068:9099 | 6028:9100 | 6068:9100 | 6028:9101 | 6068:9101 |
| 6029:9099 | 6069:9099 | 6029:9100 | 6069:9100 | 6029:9101 | 6069:9101 |
| 6030:9099 | 6070:9099 | 6030:9100 | 6070:9100 | 6030:9101 | 6070:9101 |
| 6031:9099 | 6071:9099 | 6031:9100 | 6071:9100 | 6031:9101 | 6071:9101 |
| 6032:9099 | 6072:9099 | 6032:9100 | 6072:9100 | 6032:9101 | 6072:9101 |
| 6033:9099 | 6073:9099 | 6033:9100 | 6073:9100 | 6033:9101 | 6073:9101 |
| 6034:9099 | 6074:9099 | 6034:9100 | 6074:9100 | 6034:9101 | 6074:9101 |
| 6035:9099 | 6075:9099 | 6035:9100 | 6075:9100 | 6035:9101 | 6075:9101 |
| 6036:9099 | 6076:9099 | 6036:9100 | 6076:9100 | 6036:9101 | 6076:9101 |
| 6037:9099 | 6077:9099 | 6037:9100 | 6077:9100 | 6037:9101 | 6077:9101 |
| 6038:9099 | 6078:9099 | 6038:9100 | 6078:9100 | 6038:9101 | 6078:9101 |
| 6039:9099 | | 6039:9100 | | 6039:9101 | |

| X:Y | X:Y | X:Y | X:Y | X:Y | X:Y |
|---|---|---|---|---|---|
| 6000:9102 | 6040:9102 | 6000:9103 | 6040:9103 | 6000:9104 | 6040:9104 |
| 6001:9102 | 6041:9102 | 6001:9103 | 6041:9103 | 6001:9104 | 6041:9104 |
| 6002:9102 | 6042:9102 | 6002:9103 | 6042:9103 | 6002:9104 | 6042:9104 |
| 6003:9102 | 6043:9102 | 6003:9103 | 6043:9103 | 6003:9104 | 6043:9104 |
| 6004:9102 | 6044:9102 | 6004:9103 | 6044:9103 | 6004:9104 | 6044:9104 |
| 6005:9102 | 6045:9102 | 6005:9103 | 6045:9103 | 6005:9104 | 6045:9104 |
| 6006:9102 | 6046:9102 | 6006:9103 | 6046:9103 | 6006:9104 | 6046:9104 |
| 6007:9102 | 6047:9102 | 6007:9103 | 6047:9103 | 6007:9104 | 6047:9104 |
| 6008:9102 | 6048:9102 | 6008:9103 | 6048:9103 | 6008:9104 | 6048:9104 |
| 6009:9102 | 6049:9102 | 6009:9103 | 6049:9103 | 6009:9104 | 6049:9104 |
| 6010:9102 | 6050:9102 | 6010:9103 | 6050:9103 | 6010:9104 | 6050:9104 |
| 6011:9102 | 6051:9102 | 6011:9103 | 6051:9103 | 6011:9104 | 6051:9104 |

TABLE D-continued

| | | | | | |
|---|---|---|---|---|---|
| 6012:9102 | 6052:9102 | 6012:9103 | 6052:9103 | 6012:9104 | 6052:9104 |
| 6013:9102 | 6053:9102 | 6013:9103 | 6053:9103 | 6013:9104 | 6053:9104 |
| 6014:9102 | 6054:9102 | 6014:9103 | 6054:9103 | 6014:9104 | 6054:9104 |
| 6015:9102 | 6055:9102 | 6015:9103 | 6055:9103 | 6015:9104 | 6055:9104 |
| 6016:9102 | 6056:9102 | 6016:9103 | 6056:9103 | 6016:9104 | 6056:9104 |
| 6017:9102 | 6057:9102 | 6017:9103 | 6057:9103 | 6017:9104 | 6057:9104 |
| 6018:9102 | 6058:9102 | 6018:9103 | 6058:9103 | 6018:9104 | 6058:9104 |
| 6019:9102 | 6059:9102 | 6019:9103 | 6059:9103 | 6019:9104 | 6059:9104 |
| 6020:9102 | 6060:9102 | 6020:9103 | 6060:9103 | 6020:9104 | 6060:9104 |
| 6021:9102 | 6061:9102 | 6021:9103 | 6061:9103 | 6021:9104 | 6061:9104 |
| 6022:9102 | 6062:9102 | 6022:9103 | 6062:9103 | 6022:9104 | 6062:9104 |
| 6023:9102 | 6063:9102 | 6023:9103 | 6063:9103 | 6023:9104 | 6063:9104 |
| 6024:9102 | 6064:9102 | 6024:9103 | 6064:9103 | 6024:9104 | 6064:9104 |
| 6025:9102 | 6065:9102 | 6025:9103 | 6065:9103 | 6025:9104 | 6065:9104 |
| 6026:9102 | 6066:9102 | 6026:9103 | 6066:9103 | 6026:9104 | 6066:9104 |
| 6027:9102 | 6067:9102 | 6027:9103 | 6067:9103 | 6027:9104 | 6067:9104 |
| 6028:9102 | 6068:9102 | 6028:9103 | 6068:9103 | 6028:9104 | 6068:9104 |
| 6029:9102 | 6069:9102 | 6029:9103 | 6069:9103 | 6029:9104 | 6069:9104 |
| 6030:9102 | 6070:9102 | 6030:9103 | 6070:9103 | 6030:9104 | 6070:9104 |
| 6031:9102 | 6071:9102 | 6031:9103 | 6071:9103 | 6031:9104 | 6071:9104 |
| 6032:9102 | 6072:9102 | 6032:9103 | 6072:9103 | 6032:9104 | 6072:9104 |
| 6033:9102 | 6073:9102 | 6033:9103 | 6073:9103 | 6033:9104 | 6073:9104 |
| 6034:9102 | 6074:9102 | 6034:9103 | 6074:9103 | 6034:9104 | 6074:9104 |
| 6035:9102 | 6075:9102 | 6035:9103 | 6075:9103 | 6035:9104 | 6075:9104 |
| 6036:9102 | 6076:9102 | 6036:9103 | 6076:9103 | 6036:9104 | 6076:9104 |
| 6037:9102 | 6077:9102 | 6037:9103 | 6077:9103 | 6037:9104 | 6077:9104 |
| 6038:9102 | 6078:9102 | 6038:9103 | 6078:9103 | 6038:9104 | 6078:9104 |
| 6039:9102 | | 6039:9103 | | 6039:9104 | |

| X:Y | X:Y | X:Y | X:Y | X:Y | X:Y |
|---|---|---|---|---|---|
| 6000:9105 | 6040:9105 | — | — | — | — |
| 6001:9105 | 6041:9105 | | | | |
| 6002:9105 | 6042:9105 | | | | |
| 6003:9105 | 6043:9105 | | | | |
| 6004:9105 | 6044:9105 | | | | |
| 6005:9105 | 6045:9105 | | | | |
| 6006:9105 | 6046:9105 | | | | |
| 6007:9105 | 6047:9105 | | | | |
| 6008:9105 | 6048:9105 | | | | |
| 6009:9105 | 6049:9105 | | | | |
| 6010:9105 | 6050:9105 | | | | |
| 6011:9105 | 6051:9105 | | | | |
| 6012:9105 | 6052:9105 | | | | |
| 6013:9105 | 6053:9105 | | | | |
| 6014:9105 | 6054:9105 | | | | |
| 6015:9105 | 6055:9105 | | | | |
| 6016:9105 | 6056:9105 | | | | |
| 6017:9105 | 6057:9105 | | | | |
| 6018:9105 | 6058:9105 | | | | |
| 6019:9105 | 6059:9105 | | | | |
| 6020:9105 | 6060:9105 | | | | |
| 6021:9105 | 6061:9105 | | | | |
| 6022:9105 | 6062:9105 | | | | |
| 6023:9105 | 6063:9105 | | | | |
| 6024:9105 | 6064:9105 | | | | |
| 6025:9105 | 6065:9105 | | | | |
| 6026:9105 | 6066:9105 | | | | |
| 6027:9105 | 6067:9105 | | | | |
| 6028:9105 | 6068:9105 | | | | |
| 6029:9105 | 6069:9105 | | | | |
| 6030:9105 | 6070:9105 | | | | |
| 6031:9105 | 6071:9105 | | | | |
| 6032:9105 | 6072:9105 | | | | |
| 6033:9105 | 6073:9105 | | | | |
| 6034:9105 | 6074:9105 | | | | |
| 6035:9105 | 6075:9105 | | | | |
| 6036:9105 | 6076:9105 | | | | |
| 6037:9105 | 6077:9105 | | | | |
| 6038:9105 | 6078:9105 | | | | |
| 6039:9105 | | | | | |

TABLE E

Example combinations of a compound X with a compound Y.

| X:Y | X:Y | X:Y | X:Y | X:Y | X:Y |
|---|---|---|---|---|---|
| 8000:9000 | 8000:9001 | 8000:9002 | 8000:9003 | 8000:9004 | 8000:9005 |
| 8001:9000 | 8001:9001 | 8001:9002 | 8001:9003 | 8001:9004 | 8001:9005 |
| 8002:9000 | 8002:9001 | 8002:9002 | 8002:9003 | 8002:9004 | 8002:9005 |
| 8003:9000 | 8003:9001 | 8003:9002 | 8003:9003 | 8003:9004 | 8003:9005 |
| 8004:9000 | 8004:9001 | 8004:9002 | 8004:9003 | 8004:9004 | 8004:9005 |
| 8005:9000 | 8005:9001 | 8005:9002 | 8005:9003 | 8005:9004 | 8005:9005 |
| 8006:9000 | 8006:9001 | 8006:9002 | 8006:9003 | 8006:9004 | 8006:9005 |
| 8007:9000 | 8007:9001 | 8007:9002 | 8007:9003 | 8007:9004 | 8007:9005 |
| 8008:9000 | 8008:9001 | 8008:9002 | 8008:9003 | 8008:9004 | 8008:9005 |
| 8009:9000 | 8009:9001 | 8009:9002 | 8009:9003 | 8009:9004 | 8009:9005 |
| 8010:9000 | 8010:9001 | 8010:9002 | 8010:9003 | 8010:9004 | 8010:9005 |
| 8011:9000 | 8011:9001 | 8011:9002 | 8011:9003 | 8011:9004 | 8011:9005 |
| 8012:9000 | 8012:9001 | 8012:9002 | 8012:9003 | 8012:9004 | 8012:9005 |
| 8013:9000 | 8013:9001 | 8013:9002 | 8013:9003 | 8013:9004 | 8013:9005 |
| 8014:9000 | 8014:9001 | 8014:9002 | 8014:9003 | 8014:9004 | 8014:9005 |
| 8015:9000 | 8015:9001 | 8015:9002 | 8015:9003 | 8015:9004 | 8015:9005 |
| 8016:9000 | 8016:9001 | 8016:9002 | 8016:9003 | 8016:9004 | 8016:9005 |
| 8000:9006 | 8000:9007 | 8000:9008 | 8000:9009 | 8000:9010 | 8000:9011 |
| 8001:9006 | 8001:9007 | 8001:9008 | 8001:9009 | 8001:9010 | 8001:9011 |
| 8002:9006 | 8002:9007 | 8002:9008 | 8002:9009 | 8002:9010 | 8002:9011 |
| 8003:9006 | 8003:9007 | 8003:9008 | 8003:9009 | 8003:9010 | 8003:9011 |
| 8004:9006 | 8004:9007 | 8004:9008 | 8004:9009 | 8004:9010 | 8004:9011 |
| 8005:9006 | 8005:9007 | 8005:9008 | 8005:9009 | 8005:9010 | 8005:9011 |
| 8006:9006 | 8006:9007 | 8006:9008 | 8006:9009 | 8006:9010 | 8006:9011 |
| 8007:9006 | 8007:9007 | 8007:9008 | 8007:9009 | 8007:9010 | 8007:9011 |
| 8008:9006 | 8008:9007 | 8008:9008 | 8008:9009 | 8008:9010 | 8008:9011 |
| 8009:9006 | 8009:9007 | 8009:9008 | 8009:9009 | 8009:9010 | 8009:9011 |
| 8010:9006 | 8010:9007 | 8010:9008 | 8010:9009 | 8010:9010 | 8010:9011 |
| 8011:9006 | 8011:9007 | 8011:9008 | 8011:9009 | 8011:9010 | 8011:9011 |
| 8012:9006 | 8012:9007 | 8012:9008 | 8012:9009 | 8012:9010 | 8012:9011 |
| 8013:9006 | 8013:9007 | 8013:9008 | 8013:9009 | 8013:9010 | 8013:9011 |
| 8014:9006 | 8014:9007 | 8014:9008 | 8014:9009 | 8014:9010 | 8014:9011 |
| 8015:9006 | 8015:9007 | 8015:9008 | 8015:9009 | 8015:9010 | 8015:9011 |
| 8016:9006 | 8016:9007 | 8016:9008 | 8016:9009 | 8016:9010 | 8016:9011 |

| X:Y | X:Y | X:Y | X:Y | X:Y | X:Y |
|---|---|---|---|---|---|
| 8000:9012 | 8000:9013 | 8000:9014 | 8000:9015 | 8000:9016 | 8000:9017 |
| 8001:9012 | 8001:9013 | 8001:9014 | 8001:9015 | 8001:9016 | 8001:9017 |
| 8002:9012 | 8002:9013 | 8002:9014 | 8002:9015 | 8002:9016 | 8002:9017 |
| 8003:9012 | 8003:9013 | 8003:9014 | 8003:9015 | 8003:9016 | 8003:9017 |
| 8004:9012 | 8004:9013 | 8004:9014 | 8004:9015 | 8004:9016 | 8004:9017 |
| 8005:9012 | 8005:9013 | 8005:9014 | 8005:9015 | 8005:9016 | 8005:9017 |
| 8006:9012 | 8006:9013 | 8006:9014 | 8006:9015 | 8006:9016 | 8006:9017 |
| 8007:9012 | 8007:9013 | 8007:9014 | 8007:9015 | 8007:9016 | 8007:9017 |
| 8008:9012 | 8008:9013 | 8008:9014 | 8008:9015 | 8008:9016 | 8008:9017 |
| 8009:9012 | 8009:9013 | 8009:9014 | 8009:9015 | 8009:9016 | 8009:9017 |
| 8010:9012 | 8010:9013 | 8010:9014 | 8010:9015 | 8010:9016 | 8010:9017 |
| 8011:9012 | 8011:9013 | 8011:9014 | 8011:9015 | 8011:9016 | 8011:9017 |
| 8012:9012 | 8012:9013 | 8012:9014 | 8012:9015 | 8012:9016 | 8012:9017 |
| 8013:9012 | 8013:9013 | 8013:9014 | 8013:9015 | 8013:9016 | 8013:9017 |
| 8014:9012 | 8014:9013 | 8014:9014 | 8014:9015 | 8014:9016 | 8014:9017 |
| 8015:9012 | 8015:9013 | 8015:9014 | 8015:9015 | 8015:9016 | 8015:9017 |
| 8016:9012 | 8016:9013 | 8016:9014 | 8016:9015 | 8016:9016 | 8016:9017 |
| 8000:9018 | 8000:9019 | 8000:9020 | 8000:9021 | 8000:9022 | 8000:9023 |
| 8001:9018 | 8001:9019 | 8001:9020 | 8001:9021 | 8001:9022 | 8001:9023 |
| 8002:9018 | 8002:9019 | 8002:9020 | 8002:9021 | 8002:9022 | 8002:9023 |
| 8003:9018 | 8003:9019 | 8003:9020 | 8003:9021 | 8003:9022 | 8003:9023 |
| 8004:9018 | 8004:9019 | 8004:9020 | 8004:9021 | 8004:9022 | 8004:9023 |
| 8005:9018 | 8005:9019 | 8005:9020 | 8005:9021 | 8005:9022 | 8005:9023 |
| 8006:9018 | 8006:9019 | 8006:9020 | 8006:9021 | 8006:9022 | 8006:9023 |
| 8007:9018 | 8007:9019 | 8007:9020 | 8007:9021 | 8007:9022 | 8007:9023 |
| 8008:9018 | 8008:9019 | 8008:9020 | 8008:9021 | 8008:9022 | 8008:9023 |
| 8009:9018 | 8009:9019 | 8009:9020 | 8009:9021 | 8009:9022 | 8009:9023 |
| 8010:9018 | 8010:9019 | 8010:9020 | 8010:9021 | 8010:9022 | 8010:9023 |
| 8011:9018 | 8011:9019 | 8011:9020 | 8011:9021 | 8011:9022 | 8011:9023 |
| 8012:9018 | 8012:9019 | 8012:9020 | 8012:9021 | 8012:9022 | 8012:9023 |
| 8013:9018 | 8013:9019 | 8013:9020 | 8013:9021 | 8013:9022 | 8013:9023 |
| 8014:9018 | 8014:9019 | 8014:9020 | 8014:9021 | 8014:9022 | 8014:9023 |
| 8015:9018 | 8015:9019 | 8015:9020 | 8015:9021 | 8015:9022 | 8015:9023 |
| 8016:9018 | 8016:9019 | 8016:9020 | 8016:9021 | 8016:9022 | 8016:9023 |

| X:Y | X:Y | X:Y | X:Y | X:Y | X:Y |
|---|---|---|---|---|---|
| 8000:9024 | 8000:9025 | 8000:9026 | 8000:9027 | 8000:9028 | 8000:9029 |
| 8001:9024 | 8001:9025 | 8001:9026 | 8001:9027 | 8001:9028 | 8001:9029 |

TABLE E-continued

Example combinations of a compound X with a compound Y.

| X:Y | X:Y | X:Y | X:Y | X:Y | X:Y |
|---|---|---|---|---|---|
| 8002:9024 | 8002:9025 | 8002:9026 | 8002:9027 | 8002:9028 | 8002:9029 |
| 8003:9024 | 8003:9025 | 8003:9026 | 8003:9027 | 8003:9028 | 8003:9029 |
| 8004:9024 | 8004:9025 | 8004:9026 | 8004:9027 | 8004:9028 | 8004:9029 |
| 8005:9024 | 8005:9025 | 8005:9026 | 8005:9027 | 8005:9028 | 8005:9029 |
| 8006:9024 | 8006:9025 | 8006:9026 | 8006:9027 | 8006:9028 | 8006:9029 |
| 8007:9024 | 8007:9025 | 8007:9026 | 8007:9027 | 8007:9028 | 8007:9029 |
| 8008:9024 | 8008:9025 | 8008:9026 | 8008:9027 | 8008:9028 | 8008:9029 |
| 8009:9024 | 8009:9025 | 8009:9026 | 8009:9027 | 8009:9028 | 8009:9029 |
| 8010:9024 | 8010:9025 | 8010:9026 | 8010:9027 | 8010:9028 | 8010:9029 |
| 8011:9024 | 8011:9025 | 8011:9026 | 8011:9027 | 8011:9028 | 8011:9029 |
| 8012:9024 | 8012:9025 | 8012:9026 | 8012:9027 | 8012:9028 | 8012:9029 |
| 8013:9024 | 8013:9025 | 8013:9026 | 8013:9027 | 8013:9028 | 8013:9029 |
| 8014:9024 | 8014:9025 | 8014:9026 | 8014:9027 | 8014:9028 | 8014:9029 |
| 8015:9024 | 8015:9025 | 8015:9026 | 8015:9027 | 8015:9028 | 8015:9029 |
| 8016:9024 | 8016:9025 | 8016:9026 | 8016:9027 | 8016:9028 | 8016:9029 |
| 8000:9030 | 8000:9031 | 8000:9032 | 8000:9033 | 8000:9034 | 8000:9035 |
| 8001:9030 | 8001:9031 | 8001:9032 | 8001:9033 | 8001:9034 | 8001:9035 |
| 8002:9030 | 8002:9031 | 8002:9032 | 8002:9033 | 8002:9034 | 8002:9035 |
| 8003:9030 | 8003:9031 | 8003:9032 | 8003:9033 | 8003:9034 | 8003:9035 |
| 8004:9030 | 8004:9031 | 8004:9032 | 8004:9033 | 8004:9034 | 8004:9035 |
| 8005:9030 | 8005:9031 | 8005:9032 | 8005:9033 | 8005:9034 | 8005:9035 |
| 8006:9030 | 8006:9031 | 8006:9032 | 8006:9033 | 8006:9034 | 8006:9035 |
| 8007:9030 | 8007:9031 | 8007:9032 | 8007:9033 | 8007:9034 | 8007:9035 |
| 8008:9030 | 8008:9031 | 8008:9032 | 8008:9033 | 8008:9034 | 8008:9035 |
| 8009:9030 | 8009:9031 | 8009:9032 | 8009:9033 | 8009:9034 | 8009:9035 |
| 8010:9030 | 8010:9031 | 8010:9032 | 8010:9033 | 8010:9034 | 8010:9035 |
| 8011:9030 | 8011:9031 | 8011:9032 | 8011:9033 | 8011:9034 | 8011:9035 |
| 8012:9030 | 8012:9031 | 8012:9032 | 8012:9033 | 8012:9034 | 8012:9035 |
| 8013:9030 | 8013:9031 | 8013:9032 | 8013:9033 | 8013:9034 | 8013:9035 |
| 8014:9030 | 8014:9031 | 8014:9032 | 8014:9033 | 8014:9034 | 8014:9035 |
| 8015:9030 | 8015:9031 | 8015:9032 | 8015:9033 | 8015:9034 | 8015:9035 |
| 8016:9030 | 8016:9031 | 8016:9032 | 8016:9033 | 8016:9034 | 8016:9035 |

| X:Y | X:Y | X:Y | X:Y | X:Y | X:Y |
|---|---|---|---|---|---|
| 8000:9036 | 8000:9037 | 8000:9038 | 8000:9039 | 8000:9040 | 8000:9041 |
| 8001:9036 | 8001:9037 | 8001:9038 | 8001:9039 | 8001:9040 | 8001:9041 |
| 8002:9036 | 8002:9037 | 8002:9038 | 8002:9039 | 8002:9040 | 8002:9041 |
| 8003:9036 | 8003:9037 | 8003:9038 | 8003:9039 | 8003:9040 | 8003:9041 |
| 8004:9036 | 8004:9037 | 8004:9038 | 8004:9039 | 8004:9040 | 8004:9041 |
| 8005:9036 | 8005:9037 | 8005:9038 | 8005:9039 | 8005:9040 | 8005:9041 |
| 8006:9036 | 8006:9037 | 8006:9038 | 8006:9039 | 8006:9040 | 8006:9041 |
| 8007:9036 | 8007:9037 | 8007:9038 | 8007:9039 | 8007:9040 | 8007:9041 |
| 8008:9036 | 8008:9037 | 8008:9038 | 8008:9039 | 8008:9040 | 8008:9041 |
| 8009:9036 | 8009:9037 | 8009:9038 | 8009:9039 | 8009:9040 | 8009:9041 |
| 8010:9036 | 8010:9037 | 8010:9038 | 8010:9039 | 8010:9040 | 8010:9041 |
| 8011:9036 | 8011:9037 | 8011:9038 | 8011:9039 | 8011:9040 | 8011:9041 |
| 8012:9036 | 8012:9037 | 8012:9038 | 8012:9039 | 8012:9040 | 8012:9041 |
| 8013:9036 | 8013:9037 | 8013:9038 | 8013:9039 | 8013:9040 | 8013:9041 |
| 8014:9036 | 8014:9037 | 8014:9038 | 8014:9039 | 8014:9040 | 8014:9041 |
| 8015:9036 | 8015:9037 | 8015:9038 | 8015:9039 | 8015:9040 | 8015:9041 |
| 8016:9036 | 8016:9037 | 8016:9038 | 8016:9039 | 8016:9040 | 8016:9041 |
| 8000:9042 | 8000:9043 | 8000:9044 | 8000:9045 | 8000:9046 | 8000:9047 |
| 8001:9042 | 8001:9043 | 8001:9044 | 8001:9045 | 8001:9046 | 8001:9047 |
| 8002:9042 | 8002:9043 | 8002:9044 | 8002:9045 | 8002:9046 | 8002:9047 |
| 8003:9042 | 8003:9043 | 8003:9044 | 8003:9045 | 8003:9046 | 8003:9047 |
| 8004:9042 | 8004:9043 | 8004:9044 | 8004:9045 | 8004:9046 | 8004:9047 |
| 8005:9042 | 8005:9043 | 8005:9044 | 8005:9045 | 8005:9046 | 8005:9047 |
| 8006:9042 | 8006:9043 | 8006:9044 | 8006:9045 | 8006:9046 | 8006:9047 |
| 8007:9042 | 8007:9043 | 8007:9044 | 8007:9045 | 8007:9046 | 8007:9047 |
| 8008:9042 | 8008:9043 | 8008:9044 | 8008:9045 | 8008:9046 | 8008:9047 |
| 8009:9042 | 8009:9043 | 8009:9044 | 8009:9045 | 8009:9046 | 8009:9047 |
| 8010:9042 | 8010:9043 | 8010:9044 | 8010:9045 | 8010:9046 | 8010:9047 |
| 8011:9042 | 8011:9043 | 8011:9044 | 8011:9045 | 8011:9046 | 8011:9047 |
| 8012:9042 | 8012:9043 | 8012:9044 | 8012:9045 | 8012:9046 | 8012:9047 |
| 8013:9042 | 8013:9043 | 8013:9044 | 8013:9045 | 8013:9046 | 8013:9047 |
| 8014:9042 | 8014:9043 | 8014:9044 | 8014:9045 | 8014:9046 | 8014:9047 |
| 8015:9042 | 8015:9043 | 8015:9044 | 8015:9045 | 8015:9046 | 8015:9047 |
| 8016:9042 | 8016:9043 | 8016:9044 | 8016:9045 | 8016:9046 | 8016:9047 |

| X:Y | X:Y | X:Y | X:Y | X:Y | X:Y |
|---|---|---|---|---|---|
| 8000:9048 | 8000:9049 | 8000:9050 | 8000:9051 | 8000:9052 | 8000:9053 |
| 8001:9048 | 8001:9049 | 8001:9050 | 8001:9051 | 8001:9052 | 8001:9053 |
| 8002:9048 | 8002:9049 | 8002:9050 | 8002:9051 | 8002:9052 | 8002:9053 |
| 8003:9048 | 8003:9049 | 8003:9050 | 8003:9051 | 8003:9052 | 8003:9053 |
| 8004:9048 | 8004:9049 | 8004:9050 | 8004:9051 | 8004:9052 | 8004:9053 |
| 8005:9048 | 8005:9049 | 8005:9050 | 8005:9051 | 8005:9052 | 8005:9053 |
| 8006:9048 | 8006:9049 | 8006:9050 | 8006:9051 | 8006:9052 | 8006:9053 |
| 8007:9048 | 8007:9049 | 8007:9050 | 8007:9051 | 8007:9052 | 8007:9053 |
| 8008:9048 | 8008:9049 | 8008:9050 | 8008:9051 | 8008:9052 | 8008:9053 |
| 8009:9048 | 8009:9049 | 8009:9050 | 8009:9051 | 8009:9052 | 8009:9053 |
| 8010:9048 | 8010:9049 | 8010:9050 | 8010:9051 | 8010:9052 | 8010:9053 |
| 8011:9048 | 8011:9049 | 8011:9050 | 8011:9051 | 8011:9052 | 8011:9053 |
| 8012:9048 | 8012:9049 | 8012:9050 | 8012:9051 | 8012:9052 | 8012:9053 |
| 8013:9048 | 8013:9049 | 8013:9050 | 8013:9051 | 8013:9052 | 8013:9053 |
| 8014:9048 | 8014:9049 | 8014:9050 | 8014:9051 | 8014:9052 | 8014:9053 |
| 8015:9048 | 8015:9049 | 8015:9050 | 8015:9051 | 8015:9052 | 8015:9053 |
| 8016:9048 | 8016:9049 | 8016:9050 | 8016:9051 | 8016:9052 | 8016:9053 |
| 8000:9054 | 8000:9055 | 8000:9056 | 8000:9057 | 8000:9058 | 8000:9059 |
| 8001:9054 | 8001:9055 | 8001:9056 | 8001:9057 | 8001:9058 | 8001:9059 |
| 8002:9054 | 8002:9055 | 8002:9056 | 8002:9057 | 8002:9058 | 8002:9059 |
| 8003:9054 | 8003:9055 | 8003:9056 | 8003:9057 | 8003:9058 | 8003:9059 |
| 8004:9054 | 8004:9055 | 8004:9056 | 8004:9057 | 8004:9058 | 8004:9059 |
| 8005:9054 | 8005:9055 | 8005:9056 | 8005:9057 | 8005:9058 | 8005:9059 |
| 8006:9054 | 8006:9055 | 8006:9056 | 8006:9057 | 8006:9058 | 8006:9059 |
| 8007:9054 | 8007:9055 | 8007:9056 | 8007:9057 | 8007:9058 | 8007:9059 |
| 8008:9054 | 8008:9055 | 8008:9056 | 8008:9057 | 8008:9058 | 8008:9059 |
| 8009:9054 | 8009:9055 | 8009:9056 | 8009:9057 | 8009:9058 | 8009:9059 |
| 8010:9054 | 8010:9055 | 8010:9056 | 8010:9057 | 8010:9058 | 8010:9059 |
| 8011:9054 | 8011:9055 | 8011:9056 | 8011:9057 | 8011:9058 | 8011:9059 |
| 8012:9054 | 8012:9055 | 8012:9056 | 8012:9057 | 8012:9058 | 8012:9059 |
| 8013:9054 | 8013:9055 | 8013:9056 | 8013:9057 | 8013:9058 | 8013:9059 |
| 8014:9054 | 8014:9055 | 8014:9056 | 8014:9057 | 8014:9058 | 8014:9059 |
| 8015:9054 | 8015:9055 | 8015:9056 | 8015:9057 | 8015:9058 | 8015:9059 |
| 8016:9054 | 8016:9055 | 8016:9056 | 8016:9057 | 8016:9058 | 8016:9059 |

| X:Y | X:Y | X:Y | X:Y | X:Y | X:Y |
|---|---|---|---|---|---|
| 8000:9060 | 8000:9061 | 8000:9062 | 8000:9063 | 8000:9064 | 8000:9065 |
| 8001:9060 | 8001:9061 | 8001:9062 | 8001:9063 | 8001:9064 | 8001:9065 |
| 8002:9060 | 8002:9061 | 8002:9062 | 8002:9063 | 8002:9064 | 8002:9065 |
| 8003:9060 | 8003:9061 | 8003:9062 | 8003:9063 | 8003:9064 | 8003:9065 |
| 8004:9060 | 8004:9061 | 8004:9062 | 8004:9063 | 8004:9064 | 8004:9065 |
| 8005:9060 | 8005:9061 | 8005:9062 | 8005:9063 | 8005:9064 | 8005:9065 |
| 8006:9060 | 8006:9061 | 8006:9062 | 8006:9063 | 8006:9064 | 8006:9065 |
| 8007:9060 | 8007:9061 | 8007:9062 | 8007:9063 | 8007:9064 | 8007:9065 |
| 8008:9060 | 8008:9061 | 8008:9062 | 8008:9063 | 8008:9064 | 8008:9065 |
| 8009:9060 | 8009:9061 | 8009:9062 | 8009:9063 | 8009:9064 | 8009:9065 |
| 8010:9060 | 8010:9061 | 8010:9062 | 8010:9063 | 8010:9064 | 8010:9065 |
| 8011:9060 | 8011:9061 | 8011:9062 | 8011 :9063 | 8011:9064 | 8011:9065 |
| 8012:9060 | 8012:9061 | 8012:9062 | 8012:9063 | 8012:9064 | 8012:9065 |
| 8013:9060 | 8013:9061 | 8013:9062 | 8013:9063 | 8013:9064 | 8013:9065 |
| 8014:9060 | 8014:9061 | 8014:9062 | 8014:9063 | 8014:9064 | 8014:9065 |
| 8015:9060 | 8015:9061 | 8015:9062 | 8015:9063 | 8015:9064 | 8015:9065 |
| 8016:9060 | 8016:9061 | 8016:9062 | 8016:9063 | 8016:9064 | 8016:9065 |
| 8000:9066 | 8000:9067 | 8000:9068 | 8000:9069 | 8000:9070 | 8000:9071 |
| 8001:9066 | 8001:9067 | 8001:9068 | 8001:9069 | 8001:9070 | 8001:9071 |
| 8002:9066 | 8002:9067 | 8002:9068 | 8002:9069 | 8002:9070 | 8002:9071 |
| 8003:9066 | 8003:9067 | 8003:9068 | 8003:9069 | 8003:9070 | 8003:9071 |
| 8004:9066 | 8004:9067 | 8004:9068 | 8004:9069 | 8004:9070 | 8004:9071 |
| 8005:9066 | 8005:9067 | 8005:9068 | 8005:9069 | 8005:9070 | 8005:9071 |
| 8006:9066 | 8006:9067 | 8006:9068 | 8006:9069 | 8006:9070 | 8006:9071 |
| 8007:9066 | 8007:9067 | 8007:9068 | 8007:9069 | 8007:9070 | 8007:9071 |
| 8008:9066 | 8008:9067 | 8008:9068 | 8008:9069 | 8008:9070 | 8008:9071 |
| 8009:9066 | 8009:9067 | 8009:9068 | 8009:9069 | 8009:9070 | 8009:9071 |
| 8010:9066 | 8010:9067 | 8010:9068 | 8010:9069 | 8010:9070 | 8010:9071 |
| 8011:9066 | 8011:9067 | 8011:9068 | 8011:9069 | 8011:9070 | 8011:9071 |
| 8012:9066 | 8012:9067 | 8012:9068 | 8012:9069 | 8012:9070 | 8012:9071 |
| 8013:9066 | 8013:9067 | 8013:9068 | 8013:9069 | 8013:9070 | 8013:9071 |
| 8014:9066 | 8014:9067 | 8014:9068 | 8014:9069 | 8014:9070 | 8014:9071 |
| 8015:9066 | 8015:9067 | 8015:9068 | 8015:9069 | 8015:9070 | 8015:9071 |
| 8016:9066 | 8016:9067 | 8016:9068 | 8016:9069 | 8016:9070 | 8016:9071 |

| X:Y | X:Y | X:Y | X:Y | X:Y | X:Y |
|---|---|---|---|---|---|
| 8000:9072 | 8000:9073 | 8000:9074 | 8000:9075 | 8000:9076 | 8000:9077 |
| 8001:9072 | 8001:9073 | 8001:9074 | 8001:9075 | 8001:9076 | 8001:9077 |
| 8002:9072 | 8002:9073 | 8002:9074 | 8002:9075 | 8002:9076 | 8002:9077 |
| 8003:9072 | 8003:9073 | 8003:9074 | 8003:9075 | 8003:9076 | 8003:9077 |
| 8004:9072 | 8004:9073 | 8004:9074 | 8004:9075 | 8004:9076 | 8004:9077 |
| 8005:9072 | 8005:9073 | 8005:9074 | 8005:9075 | 8005:9076 | 8005:9077 |
| 8006:9072 | 8006:9073 | 8006:9074 | 8006:9075 | 8006:9076 | 8006:9077 |
| 8007:9072 | 8007:9073 | 8007:9074 | 8007:9075 | 8007:9076 | 8007:9077 |
| 8008:9072 | 8008:9073 | 8008:9074 | 8008:9075 | 8008:9076 | 8008:9077 |
| 8009:9072 | 8009:9073 | 8009:9074 | 8009:9075 | 8009:9076 | 8009:9077 |

TABLE E-continued
Example combinations of a compound X with a compound Y.
| | | | | | |
|---|---|---|---|---|---|
| 8010:9072 | 8010:9073 | 8010:9074 | 8010:9075 | 8010:9076 | 8010:9077 |
| 8011:9072 | 8011:9073 | 8011:9074 | 8011:9075 | 8011:9076 | 8011:9077 |
| 8012:9072 | 8012:9073 | 8012:9074 | 8012:9075 | 8012:9076 | 8012:9077 |
| 8013:9072 | 8013:9073 | 8013:9074 | 8013:9075 | 8013:9076 | 8013:9077 |
| 8014:9072 | 8014:9073 | 8014:9074 | 8014:9075 | 8014:9076 | 8014:9077 |
| 8015:9072 | 8015:9073 | 8015:9074 | 8015:9075 | 8015:9076 | 8015:9077 |
| 8016:9072 | 8016:9073 | 8016:9074 | 8016:9075 | 8016:9076 | 8016:9077 |
| 8000:9078 | 8000:9079 | 8000:9080 | 8000:9081 | 8000:9082 | 8000:9083 |
| 8001:9078 | 8001:9079 | 8001:9080 | 8001:9081 | 8001:9082 | 8001:9083 |
| 8002:9078 | 8002:9079 | 8002:9080 | 8002:9081 | 8002:9082 | 8002:9083 |
| 8003:9078 | 8003:9079 | 8003:9080 | 8003:9081 | 8003:9082 | 8003:9083 |
| 8004:9078 | 8004:9079 | 8004:9080 | 8004:9081 | 8004:9082 | 8004:9083 |
| 8005:9078 | 8005:9079 | 8005:9080 | 8005:9081 | 8005:9082 | 8005:9083 |
| 8006:9078 | 8006:9079 | 8006:9080 | 8006:9081 | 8006:9082 | 8006:9083 |
| 8007:9078 | 8007:9079 | 8007:9080 | 8007:9081 | 8007:9082 | 8007:9083 |
| 8008:9078 | 8008:9079 | 8008:9080 | 8008:9081 | 8008:9082 | 8008:9083 |
| 8009:9078 | 8009:9079 | 8009:9080 | 8009:9081 | 8009:9082 | 8009:9083 |
| 8010:9078 | 8010:9079 | 8010:9080 | 8010:9081 | 8010:9082 | 8010:9083 |
| 8011:9078 | 8011:9079 | 8011:9080 | 8011:9081 | 8011:9082 | 8011:9083 |
| 8012:9078 | 8012:9079 | 8012:9080 | 8012:9081 | 8012:9082 | 8012:9083 |
| 8013:9078 | 8013:9079 | 8013:9080 | 8013:9081 | 8013:9082 | 8013:9083 |
| 8014:9078 | 8014:9079 | 8014:9080 | 8014:9081 | 8014:9082 | 8014:9083 |
| 8015:9078 | 8015:9079 | 8015:9080 | 8015:9081 | 8015:9082 | 8015:9083 |
| 8016:9078 | 8016:9079 | 8016:9080 | 8016:9081 | 8016:9082 | 8016:9083 |
| X:Y | X:Y | X:Y | X:Y | X:Y | X:Y |
|---|---|---|---|---|---|
| 8000:9084 | 8000:9085 | 8000:9086 | 8000:9087 | 8000:9088 | 8000:9089 |
| 8001:9084 | 8001:9085 | 8001:9086 | 8001:9087 | 8001:9088 | 8001:9089 |
| 8002:9084 | 8002:9085 | 8002:9086 | 8002:9087 | 8002:9088 | 8002:9089 |
| 8003:9084 | 8003:9085 | 8003:9086 | 8003:9087 | 8003:9088 | 8003:9089 |
| 8004:9084 | 8004:9085 | 8004:9086 | 8004:9087 | 8004:9088 | 8004:9089 |
| 8005:9084 | 8005:9085 | 8005:9086 | 8005:9087 | 8005:9088 | 8005:9089 |
| 8006:9084 | 8006:9085 | 8006:9086 | 8006:9087 | 8006:9088 | 8006:9089 |
| 8007:9084 | 8007:9085 | 8007:9086 | 8007:9087 | 8007:9088 | 8007:9089 |
| 8008:9084 | 8008:9085 | 8008:9086 | 8008:9087 | 8008:9088 | 8008:9089 |
| 8009:9084 | 8009:9085 | 8009:9086 | 8009:9087 | 8009:9088 | 8009:9089 |
| 8010:9084 | 8010:9085 | 8010:9086 | 8010:9087 | 8010:9088 | 8010:9089 |
| 8011:9084 | 8011:9085 | 8011:9086 | 8011:9087 | 8011:9088 | 8011:9089 |
| 8012:9084 | 8012:9085 | 8012:9086 | 8012:9087 | 8012:9088 | 8012:9089 |
| 8013:9084 | 8013:9085 | 8013:9086 | 8013:9087 | 8013:9088 | 8013:9089 |
| 8014:9084 | 8014:9085 | 8014:9086 | 8014:9087 | 8014:9088 | 8014:9089 |
| 8015:9084 | 8015:9085 | 8015:9086 | 8015:9087 | 8015:9088 | 8015:9089 |
| 8016:9084 | 8016:9085 | 8016:9086 | 8016:9087 | 8016:9088 | 8016:9089 |
| 8000:9090 | 8000:9091 | 8000:9092 | 8000:9093 | 8000:9094 | 8000:9095 |
| 8002:9090 | 8002:9091 | 8002:9092 | 8002:9093 | 8002:9094 | 8002:9095 |
| 8003:9090 | 8003:9091 | 8003:9092 | 8003:9093 | 8003:9094 | 8003:9095 |
| 8004:9090 | 8004:9091 | 8004:9092 | 8004:9093 | 8004:9094 | 8004:9095 |
| 8005:9090 | 8005:9091 | 8005:9092 | 8005:9093 | 8005:9094 | 8005:9095 |
| 8006:9090 | 8006:9091 | 8006:9092 | 8006:9093 | 8006:9094 | 8006:9095 |
| 8007:9090 | 8007:9091 | 8007:9092 | 8007:9093 | 8007:9094 | 8007:9095 |
| 8008:9090 | 8008:9091 | 8008:9092 | 8008:9093 | 8008:9094 | 8008:9095 |
| 8009:9090 | 8009:9091 | 8009:9092 | 8009:9093 | 8009 :9094 | 8009:9095 |
| 8010:9090 | 8010:9091 | 8010:9092 | 8010:9093 | 8010:9094 | 8010:9095 |
| 8011:9090 | 8011:9091 | 8011:9092 | 8011:9093 | 8011:9094 | 8011:9095 |
| 8012:9090 | 8012:9091 | 8012:9092 | 8012:9093 | 8012:9094 | 8012:9095 |
| 8013:9090 | 8013:9091 | 8013:9092 | 8013:9093 | 8013:9094 | 8013:9095 |
| 8014:9090 | 8014:9091 | 8014:9092 | 8014:9093 | 8014:9094 | 8014:9095 |
| 8015:9090 | 8015:9091 | 8015:9092 | 8015:9093 | 8015:9094 | 8015:9095 |
| 8016:9090 | 8016:9091 | 8016:9092 | 8016:9093 | 8016:9094 | 8016:9095 |
| X:Y | X:Y | X:Y | X:Y | X:Y | X:Y |
|---|---|---|---|---|---|
| 8000:9096 | 8000:9097 | 8000:9098 | 8000:9099 | 8000:9100 | 8000:9101 |
| 8001:9096 | 8001:9097 | 8001:9098 | 8001:9099 | 8001:9100 | 8001:9101 |
| 8002:9096 | 8002:9097 | 8002:9098 | 8002:9099 | 8002:9100 | 8002:9101 |
| 8003:9096 | 8003:9097 | 8003:9098 | 8003:9099 | 8003:9100 | 8003:9101 |
| 8004:9096 | 8004:9097 | 8004:9098 | 8004:9099 | 8004:9100 | 8004:9101 |
| 8005:9096 | 8005:9097 | 8005:9098 | 8005:9099 | 8005:9100 | 8005:9101 |
| 8006:9096 | 8006:9097 | 8006:9098 | 8006:9099 | 8006:9100 | 8006:9101 |
| 8007:9096 | 8007:9097 | 8007:9098 | 8007:9099 | 8007:9100 | 8007:9101 |
| 8008:9096 | 8008:9097 | 8008:9098 | 8008:9099 | 8008:9100 | 8008:9101 |
| 8009:9096 | 8009:9097 | 8009:9098 | 8009:9099 | 8009:9100 | 8009:9101 |
| 8010:9096 | 8010:9097 | 8010:9098 | 8010:9099 | 8010:9100 | 8010:9101 |
| 8011:9096 | 8011:9097 | 8011:9098 | 8011:9099 | 8011:9100 | 8011:9101 |
| 8012:9096 | 8012:9097 | 8012:9098 | 8012:9099 | 8012:9100 | 8012:9101 |
| 8013:9096 | 8013:9097 | 8013:9098 | 8013:9099 | 8013:9100 | 8013:9101 |
| 8014:9096 | 8014:9097 | 8014:9098 | 8014:9099 | 8014:9100 | 8014:9101 |
| 8015:9096 | 8015:9097 | 8015:9098 | 8015:9099 | 8015:9100 | 8015:9101 |
| 8016:9096 | 8016:9097 | 8016:9098 | 8016:9099 | 8016:9100 | 8016:9101 |
| 8000:9102 | 8000:9103 | 8000:9104 | 8000:9105 | — | — |
| 8001:9102 | 8001:9103 | 8001:9104 | 8001:9105 | | |
| 8002:9102 | 8002:9103 | 8002:9104 | 8002:9105 | | |
| 8003:9102 | 8003:9103 | 8003:9104 | 8003:9105 | | |
| 8004:9102 | 8004:9103 | 8004:9104 | 8004:9105 | | |
| 8005:9102 | 8005:9103 | 8005:9104 | 8005:9105 | | |
| 8006:9102 | 8006:9103 | 8006:9104 | 8006:9105 | | |
| 8007:9102 | 8007:9103 | 8007:9104 | 8007:9105 | | |
| 8008:9102 | 8008:9103 | 8008:9104 | 8008:9105 | | |
| 8009:9102 | 8009:9103 | 8009:9104 | 8009:9105 | | |
| 8010:9102 | 8010:9103 | 8010:9104 | 8010:9105 | | |
| 8011:9102 | 8011:9103 | 8011:9104 | 8011:9105 | | |
| 8012:9102 | 8012:9103 | 8012:9104 | 8012:9105 | | |
| 8013:9102 | 8013:9103 | 8013:9104 | 8013:9105 | | |
| 8014:9102 | 8014:9103 | 8014:9104 | 8014:9105 | | |
| 8015:9102 | 8015:9103 | 8015:9104 | 8015:9105 | | |
| 8016:9102 | 8016:9103 | 8016:9104 | 8016:9105 | | |
EXAMPLES
Additional embodiments are disclosed in further detail in the following examples, which are not in any way intended to limit the scope of the claims.
Example 1
2'-C-Methyl-4'-Fluorouridine 1
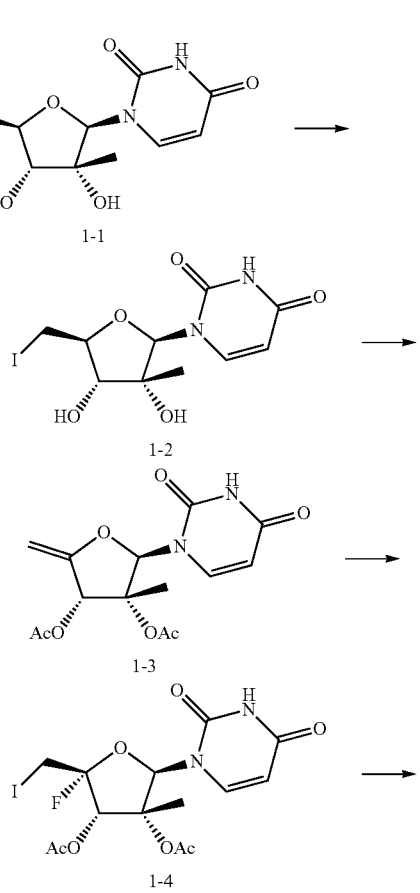

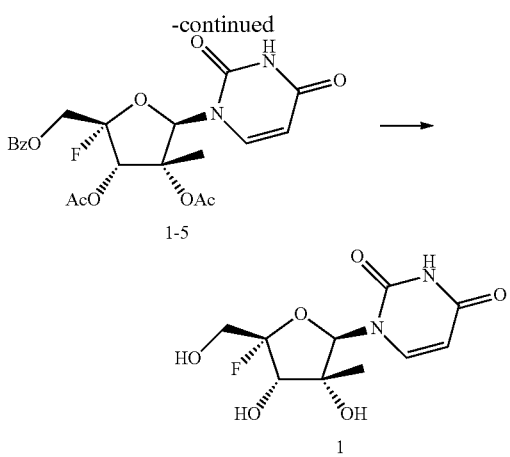

1-5

1

To a stirred suspension of 1-1 (20 g, 77.5 mmol), PPh$_3$ (30 g, 114.5 mmol), imidazole (10 g, 147 mmol) and pyridine (90 mL) in anhydrous THF (300 mL) was added a solution of I$_2$ (25 g, 98.4 mmol) in THF (100 mL) dropwise at 0° C. The mixture was warmed to room temperature (R.T.) and stirred at R.T. for 10 h. The reaction was quenched by MeOH (100 mL). The solvent was removed, and the residue was re-dissolved in a mixture ethyl acetate (EA) and THF (2 L, 10:1). The organic phase was washed with saturated Na$_2$S$_2$O$_3$ aq., and the aqueous phase was extracted with a mixture of EA and THF (2 L, 10:1). The organic layer was combined and concentrated to give a residue, which was purified on a silica gel column (0-10% MeOH in DCM) to give 1-2 (22.5 g, 78.9%) as a white solid. $^1$H NMR: (DMSO-d$_6$, 400 MHz) δ 11.42 (s, 1H), 7.59 (d, J=8.4 Hz, 1H), 5.82 (s, 1H), 5.63 (d, J=8.0 Hz, 1H), 5.50 (s, 1H), 5.23 (s, 1H), 3.77-3.79 (m, 1H), 3.40-3.62 (m, 3H), 0.97 (s, 3H).

To a stirred solution of 1-2 (24.3 g, 66.03 mmol) in anhydrous MeOH (240 mL) was added NaOMe (10.69 g, 198.09 mmol) at R.T. under N$_2$. The mixture was refluxed for 3 h. The solvent was removed, and the residue was re-dissolved in anhydrous pyridine (200 mL). To the mixture was added Ac$_2$O (84.9 g, 833.3 mmol) at 0° C. The mixture was warmed to 60° C. and stirred for 10 h. The solvent was removed, and the residue was diluted with DCM, washed with saturated NaHCO$_3$ and brine. The organic layer was concentrated and purified on a silica gel column (10-50% EA in PE) to give 1-3 (15 g, 70.1%) as a white solid. $^1$H NMR: (CDCl$_3$, 400 MHz) δ 8.82 (s, 1H), 7.23 (d, J=2.0 Hz, 1H), 6.54 (s, 1H), 5.85 (s, 1H), 5.77 (dd, J=8.0, 2.0 Hz, 1H), 4.69 (d, J=2.4 Hz, 1H), 4.58 (d, J=2.8 Hz, 1H), 2.07 (d, J=5.2 Hz, 6H), 1.45 (s, 3H).

To an ice-cooled solution of 1-3 (15 g, 46.29 mmol) in anhydrous DCM (300 mL) was added AgF (29.39 g, 231.4 mmol). I$_2$ (23.51 g, 92.58 mmol) in anhydrous DCM (1.0 L) was added dropwise to the solution. The reaction mixture was stirred at R.T. for 5 h. The reaction was quenched with saturated Na$_2$S$_2$O$_3$ and NaHCO$_3$, and extracted with DCM. The organic layer was separated, dried and evaporated to dryness. The residue was purified on a silica gel column (10-30% EA in PE) to give 1-4 (9.5 g, 43.6%) as a white solid. $^1$H NMR: (Methanol-d$_4$, 400 MHz) δ 7.52 (d, J=8.0 Hz, 1H), 6.21 (s, 1H), 5.80 (d, J=17.2 Hz, 1H), 5.73 (d, J=8.0 Hz, 1H), 3.58 (s, 1H), 3.54 (d, J=6.8 Hz, 1H), 2.17 (s, 3H), 2.09 (s, 3H), 1.58 (s, 3H).

To a solution of 1-4 (7.0 g, 14.89 mmol) in anhydrous DMF (400 mL) were added NaOBz (21.44 g, 148.9 mmol) and 15-crown-5 (32.75 g, 148.9 mmol). The reaction mixture was stirred at 130° C. for 6 h. The solvent was removed, diluted with EA and washed with water and brine. The organic layer was evaporated and purified on a silica gel column (10-30% EA in PE) to give 1-5 (2.8 g, 40.5%). $^1$H NMR: (CDCl$_3$, 400 MHz) δ 8.84 (s, 1H), 8.04-8.06 (m, 2H), 7.59 (t, J=7.2 Hz, 1H), 7.44-7.47 (m, 2H), 7.21-7.26 (m, 1H), 6.21 (s, 1H), 5.85 (d, J=18 Hz, 1H), 5.67 (d, J=8.0 Hz, 1H), 4.59-4.72 (m, 2H), 2.14 (s, 6H), 1.64 (d, J=6.0 Hz, 3H). ESI-MS: m/z 444.9 [M−F+H]$^+$.

A mixture of 1-5 (4.0 g; 8.6 mmol) and liquid ammonia was kept overnight at R. T. in a high-pressure stainless-steel vessel. Ammonia was then evaporated, and the residue purified on silica (50 g column) with a CH$_2$Cl$_2$/MeOH solvent mixture (4-12% gradient) to yield compound 1 as a colorless foam (2.0 g; 84% yield). ESI-MS: m/z 275.1 [M−H]$^-$.

Example 2

Compound 2

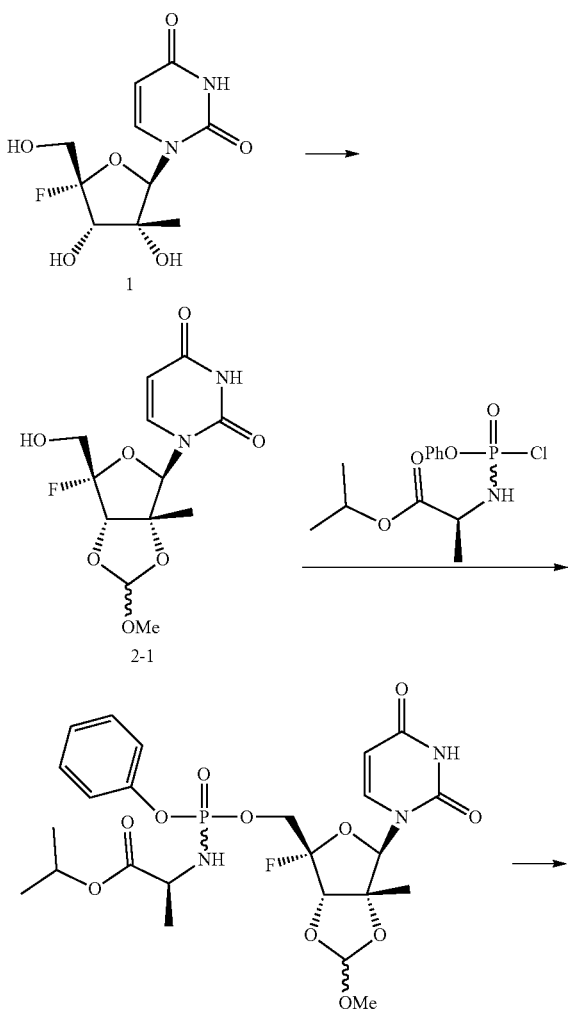

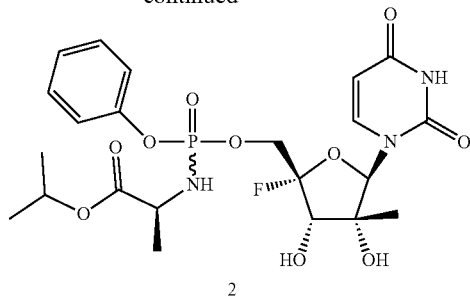

2

To a solution of 1 (1.2 g; 4.3 mmol) in dioxane (30 mL) were added p-toluenesulphonic acid monohydrate (820 mg; 1 eq.) and trimethyl orthoformate (14 mL; 30 eq.). The mixture was stirred overnight at R.T. The mixture was then neutralized with methanolic ammonia and the solvent evaporated. Purification on silica gel column with $CH_2Cl_2$-MeOH solvent system (4-10% gradient) yielded 2-1 (1.18 g, 87%).

To an ice cold solution of 2-1 (0.91 g; 2.9 mmol) in anhydrous THF (20 mL) was added iso-propylmagnesium chloride (2.1 mL; 2 M in THF). The mixture was stirred at 0° C. for 20 mins. A solution of phosphorochloridate reagent (2.2 g; 2.5 eq.) in THF (2 mL) was added dropwise. The mixture was stirred overnight at R.T. The reaction was quenched with saturated aq. $NH_4Cl$ solution and stirred at R.T. for 10 mins. The mixture was then diluted with water and $CH_2Cl_2$, and the two layers were separated. The organic layer was washed with water, half saturated aq. $NaHCO_3$ and brine, and dried with $Na_2SO_4$. The evaporated residue was purified on silica gel column with $CH_2Cl_2$-iPrOH solvent system (4-10% gradient) to yield Rp/Sp-mixture of 2-2 (1.59 g; 93%).

A mixture of 2-2 (1.45 g; 2.45 mmol) and 80% aq. HCOOH (7 mL) was stirred at R.T. for 1.5 h. The solvent was evaporated and coevaporated with toluene. The obtained residue was dissolved in MeOH, treated with $Et_3N$ (3 drops) and the solvent was evaporated. Purification on silica gel column with $CH_2Cl_2$-MeOH solvent system (4-10% gradient) yielded Rp/Sp-mixture of compound 2 (950 mg; 70%). $^{31}$P-NMR (DMSO-$d_6$): δ 3.52, 3.47. MS: m/z=544 [M−1]$^-$.

Example 3

Compound 3

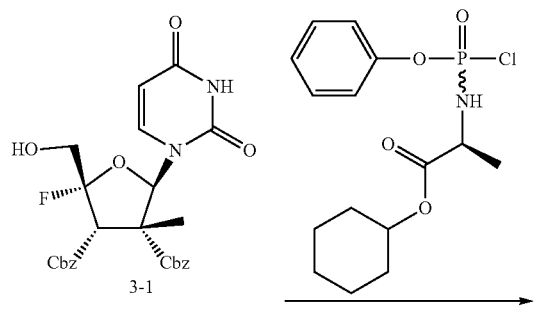

3-1

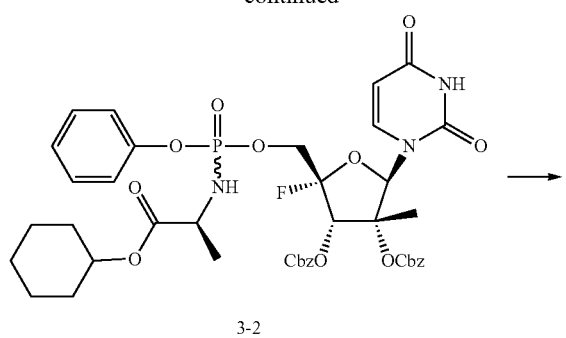

3-2

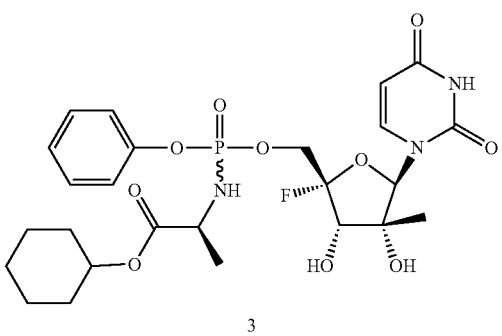

3

To an ice cold solution of 3-1 (80 mg; 015 mmol) in anhydrous THF (2 mL) was added isopropylmagnesium chloride (0.22 mL; 2 M in THF). The mixture was stirred at 0° C. for 20 mins. A solution of the phosphorochloridate reagent (0.16 g; 0.45 mmol) in THF (0.5 mL) was added dropwise. The mixture was stirred overnight at R.T. The reaction was quenched with saturated aq. $NH_4Cl$ solution and stirred at R.T. for 10 mins. The mixture was diluted with water and $CH_2Cl_2$, and the two layers were separated. The organic layer was washed with water, half saturated aq. $NaHCO_3$ and brine, and dried with $Na_2SO_4$. The evaporated residue was purified on silica gel column with $CH_2Cl_2$-MeOH solvent system (2-10% gradient) to yield Rp/Sp-mixture of 3-2 (102 mg; 80%).

A mixture of 3-2 (100 mg; 0.12 mmol) in EtOH (3 mL) and 10% Pd/C (10 mg) was stirred under the H2 atmosphere for 1.5 h. The mixture was filtered through a Celite pad, evaporated and purified on silica gel column with $CH_2Cl_2$-MeOH solvent system (4-10% gradient) to yield Rp/Sp-mixture of compound 3 (52 mg, 74%). $^{31}$P-NMR (DMSO-$d_6$): δ 3.51, 3.48. MS: m/z=584 [M−1]$^-$.

Example 4

Compounds 4 and 6

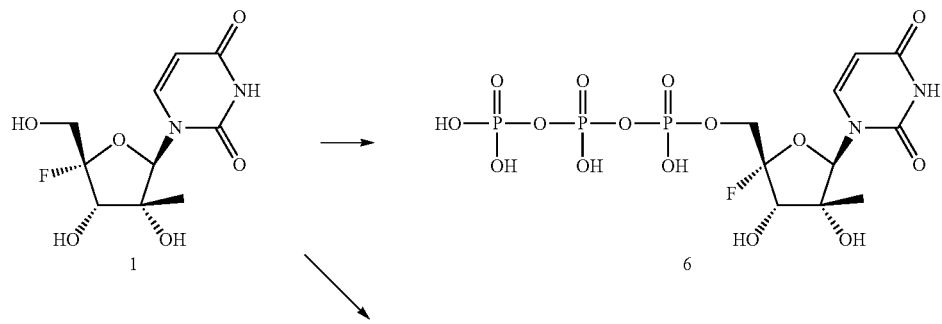

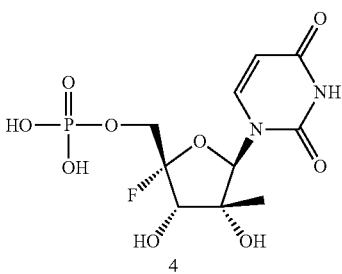

Dry 1 (14 mg, 0.05 mmol) was dissolved in the mixture of PO(OMe)$_3$ (0.750 mL) and pyridine (0.5 mL). The mixture was evaporated in vacuum for 15 mins at bath temperature 42° C., and then cooled down to R.T. N-Methylimidazole (0.009 mL, 0.11 mmol) was added followed by POCl$_3$ (0.009 mL, 0.1 mmol). The mixture was kept at R.T. for 45 mins. Tributylamine (0.065 mL, 0.3 mmol) and N-tetrabutyl ammonium salt of pyrophosphate (100 mg) was added. About 1 mL of dry DMF was added to get a homogeneous solution. In 1 h, the reaction was quenched with 2M ammonium acetate buffer (1 mL, pH=7.5), diluted water (10 mL) and loaded on a column HiLoad 16/10 with Q Sepharose High Performance. The separation was done in linear gradient of NaCl from 0 to 1N in 50 mM TRIS-buffer (pH7.5). The fractions eluted at 60% buffer B contained Compound 4 and at 80% buffer B contained Compound 6. The corresponding fractions were concentrated, and the residue purified by RP HPLC on Synergy 4 micron Hydro-RP column (Phenominex). A linear gradient of methanol from 0 to 30% in 50 mM triethylammonium acetate buffer (pH 7.5) was used for elution. The corresponding fractions were combined, concentrated and lyophilized 3 times to remove excess of buffer. Compound 4: $^{31}$P-NMR (D$_2$O): −3.76 (s); MS: m/z 355.3 [M−H]$^-$. Compound 6: $^{31}$P-NMR (D$_2$O): −9.28 (d, 1H, Pα), −12.31 (d, 1H, Pγ), −22.95 (t, 1H, Pβ); MS: m/z 515.0 [M−1]$^-$.

Example 5

Compound 5

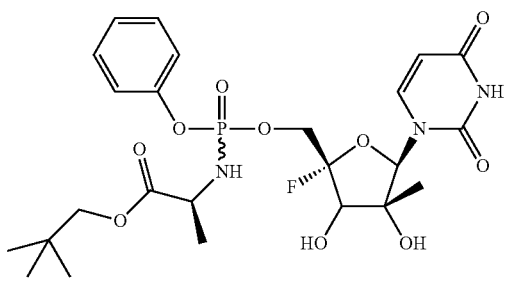 [SMILES: C[C@H](NP(=O)(OC[C@@]1(F)O[C@@H](n2ccc(=O)[nH]c2=O)[C@](C)(O)C1O)Oc1ccccc1)C(=O)OCC(C)(C)C]

Compound 5 was synthesized as described for 2 on 0.1 mmol scale and with neopentyl ester of phosphorochloridate reagent. Yield was 36 mg (63%). $^{31}$P-NMR (CDCl$_3$): δ 2.57 (s), 2.43 (s). MS: 572.6 [M−1]$^-$.

Example 6

Compound 7

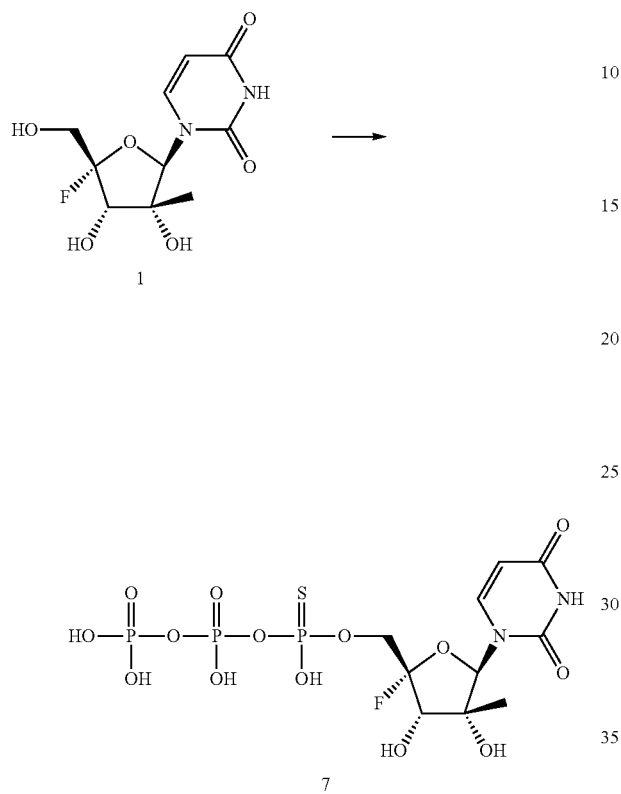

Dry 1 (14 mg, 0.05 mmol) was dissolved in the mixture of PO(OMe)$_3$ (0.750 mL) and pyridine (0.5 mL). The mixture was evaporated in vacuum for 15 mins at bath temperature 42° C., and then cooled down to R.T. N-Methylimidazole (0.009 mL, 0.11 mmol) was added followed by PSCl$_3$ (0.01 mL, 0.1 mmol). The mixture was kept at R.T. for 1 h. Tributylamine (0.065 mL, 0.3 mmol) and N-tetrabutyl ammonium salt of pyrophosphate (200 mg) was added. About 1 mL of dry DMF was added to get a homogeneous solution. In 2 h, the reaction was quenched with 2M ammonium acetate buffer (1 mL, pH=7.5), diluted with water (10 mL) and loaded on a column HiLoad 16/10 with Q Sepharose High Performance. Separation was done in linear gradient of NaCl from 0 to 1N in 50 mM TRIS-buffer (pH7.5). The fractions eluted at 80% buffer B contained 7 (compounds 7a and 7b). The corresponding fractions were concentrated, and the residue purified by RP HPLC on Synergy 4 micron Hydro-RP column (Phenominex). A linear gradient of methanol from 0 to 20% in 50 mM triethylammonium acetate buffer (pH 7.5) was used for elution. Two peaks were collected. The corresponding fractions were combined, concentrated and lyophilized 3 times to remove excess of buffer. Peak 1 (more polar): $^{31}$P-NMR (D$_2$O): +42.68 (d, 1H, Pα), −9.05 (d, 1H, Pγ), −22.95 (t, 1H, Pβ); MS 530.90 [M−1]$^-$. Peak 2 (less polar): $^{31}$P-NMR (D$_2$O): +42.78 (d, 1H, Pα), −10.12 (bs, 1H, Pγ), −23.94 (t, 1H, Pβ); and MS 530.90 [M−1]$^-$.

Example 7

Compound 23

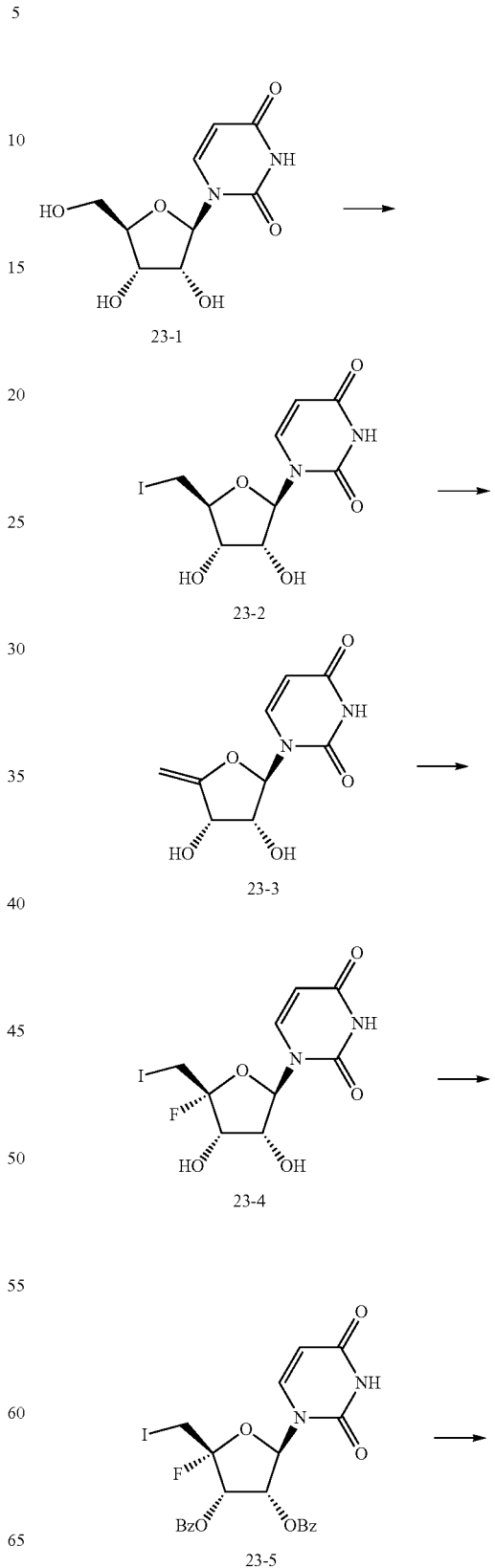

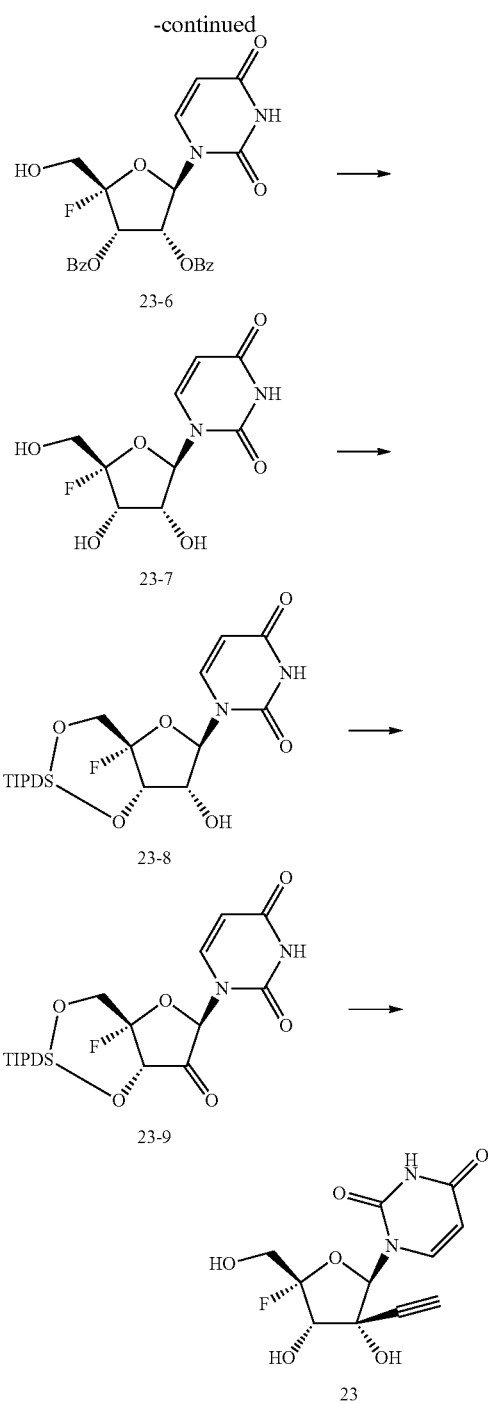

To a stirred suspension of 23-1 (20.0 g, 81.3 mmol), imidazole (15.9 g, 234.0 mmol), PPh$_3$ (53.5 g, 203.3 mmol) and pyridine (90 mL) in anhydrous THF (100 mL) was added a solution of I$_2$ (41.3 g, 162.6 mmol) in THF (150 mL) dropwise at 0° C. The mixture was slowly warmed to R.T. and stirred for 14 h. The reaction was quenched with sat. aq. Na$_2$S$_2$O$_3$ (150 mL) and extracted with THF/EA (1/1) (100 mL×3). The organic layer was dried over Na$_2$SO$_4$, and concentrated at a low pressure. The residue was recrystallized from EtOH to afford pure 23-2 (23 g, 79%) as a white solid.

To a stirred solution of 23-2 (23 g, 65 mmol) in anhydrous MeOH (200 mL) was added NaOCH$_3$ (10.5 g, 195 mmol) in MeOH (50 mL) at R.T. The mixture was stirred at 60° C. for 3 h, and quenched with dry ice. A solid precipitated and removed by filtration. The filtrate was concentrated at a low pressure. The residue was purified on column silica gel column (MeOH in DCM from 1% to 10%) to provide 23-3 (13.1 g, 92.5%) as a white foam solid.

To a stirred solution of 23-3 (12.0 g, 53 mmol) in anhydrous CH$_3$CN was added TEA.3HF (8.5 g, 53 mmol) and NIS (10.2 g, 63.6 mmol) at 0° C. The mixture was stirred for 30 mins, and slowly warmed to R.T. The mixture was stirred for another 30 mins. The solid was removed by filtration, and washed with DCM to give 23-4 (14 g, 73%) as a yellow solid. ESI-MS: m/z 373.0 [M+H]$^+$.

To a stirred solution of 23-4 (12.0 g, 32 mmol) and DMAP (1.2 g, 9.6 mmol) in pyridine (100 mL) was added Bz$_2$O (21.7 g, 96 mmol) at R.T. The mixture was stirred at 50° C. for 16 h. The resulting solution was quenched with water, and concentrated to dryness at low pressure. The crude was purified on silica gel column (50% EA in PE) to give 23-5 (15 g, 81%) as a white solid. ESI-TOF-MS: m/z 581.0 [M+H]$^+$.

Tetra-butylammonium hydroxide (288 mL as 54-56% aqueous solution, 576 mmol) was adjusted to pH-4 by adding TFA (48 mL). The resulting solution was treated with a solution of 23-5 (14 g, 24 mmol) in DCM (200 mL). m-Cloroperbenzoic acid (30 g, 60-70%, 120 mmol) was added portion wise with vigorous stirring, and the mixture was stirred overnight. The organic layer was separated and washed with brine. The resulting solution was dried over magnesium sulfate and concentrated under reduced pressure. The residue was purified by column chromatography to give 23-6 (7.5 g, 68%)

Compound 23-6 (5.0 g, 10.6 mmol) was treated with 7N NH$_3$.MeOH (100 mL), and the mixture was stirred for 5 h. The mixture was then concentrated to dryness at low pressure. The residue was washed with DCM, and the solid was filtered to give 23-7 (2.1 g, 75%) as a white foam. ESI-MS: m/z 263.0 [M+H]$^+$.

To a solution of 23-7 (2.1 g, 8.0 mmol) in pyridine was added TIDPSCl (2.5 g, 8.0 mmol) dropwise at 0° C., and stirred for 12 h. at R.T. The solution was quenched with water, and concentrated to dryness at low pressure. The crude was purified by column chromatography (EA in PE from 10% to 50%) to give pure 23-8 (1.6 g, 40%) as a white foam.

A solution of 23-8 (1.5 g, 3.0 mmol) and IBX (1.69 g, 6.0 mmol) in anhydrous CH$_3$CN (10 mL) was stirred at 80° C. for 3 h. The mixture was cooled down to R.T. and filtered. The filtrate was concentrated to dryness at low pressure. The residue was purified by column chromatography (EA in PE from 2% to 50%) to give pure 23-9 (1.2 g, 80%) as a white foam. ESI-MS: m/z 503.0 [M+H]$^+$ Compound 23-9 (500 mg, 1 mmol) was dissolved in dry THF (8 mL). Ethynyl magnesium bromide (8 mL of 0.5M solution in cyclohexane) was added at R.T. After 30 mins, additional ethynyl magnesium bromide (8 mL) was added. The mixture was left for 30 mins, and then quenched with sat. solution of ammonium chloride. The product was extracted with EA. The organic extracts were washed with brine, dried, and concentrated. The residue was purified by flash chromatography on silica gel in EA to remove the dark color. The yellow compound was dissolved in THF (3 mL) and treated with TBAF (1 mL, 2M solution in THF) for 30 mins. The solvent was evaporated, and the residue was subjected to silica gel chromatography on a Biotage cartridge (25 g). EA saturated with water was used for isocratic elution. Each fractions were analyzed by TLC in DCM- MeOH (9:1 v/v). Fractions containing only the isomer with a high Rf were concentrated to give pure compound 23 (110 mg). MS: 285.1 [M−1]⁻.

Example 8

Compound 22

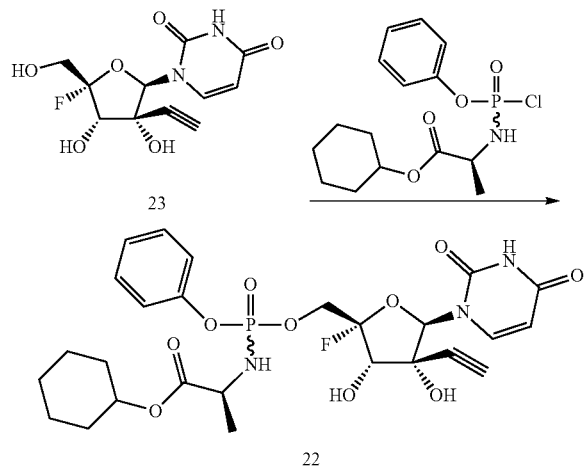

Compound 23 (57 mg, 0.2 mmol) was dissolved in CH₃CN (2 mL), containing N-methylimidazole (40 uL). The phosphorochloridate (207 mg, 0.6 mmol) was added, and the mixture was kept overnight at 40° C. The mixture was distributed between water and EA. The organic layer was separated, washed with brine, dried and evaporated. The product was isolated by silica gel chromatography in gradient of methanol in DCM from 0% to 15%. Compound 22 was obtained (46 mg, 39%). MS: m/z 593.9 [M−1]⁻.

Example 9

Compound 51

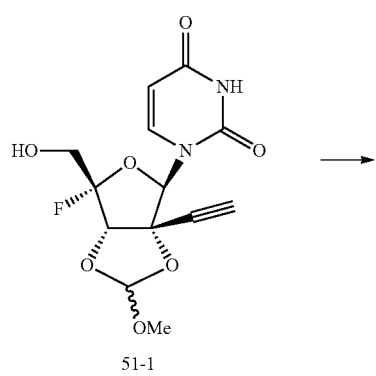

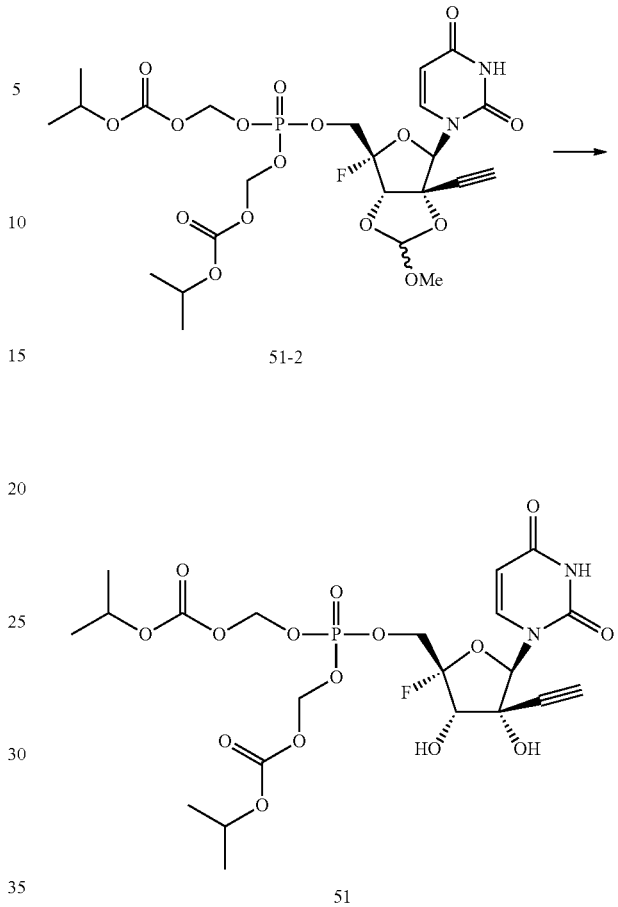

To a solution of triethylammonium bis(isopropyloxycarbonyloxymethyl)phosphate (0.74 mmol) in THF was added 51-1 (0.16 gg; 0.49 mmol). The mixture evaporated and rendered anhydrous by coevaporating with pyridine follow by toluene. The residue was dissolved in anhydrous THF and cooled in an ice-bath. Diisopropylethyl amine (0.34 mL) was added, followed by BOP—Cl (250 mg) and 3-nitro-1, 2,4-triazole (112 mg) in THF (5 mL). The mixture was stirred at 0° C. for 90 mins, diluted with EtOAc, washed with sat. aq. NaHCO₃ and brine, and dried (Na₂SO₄). The residue was purified on silica column with 3-10% i-PrOH in DCM to give 51-2 (0.2 g, 64%).

A solution of 51-2 (0.20 g; 0.31 mmol) in 80% aq. HCOOH was stirred at R.T. for 2 h, and then concentrated. The residue was coevaporated with toluene and then with MeOH containing a small amount of Et₃N (2 drops). Purification on silica gel (10 g column) with CH₂Cl₂/MeOH (4-10% gradient) was followed by RP-HPLC purification in 5 runs on a Synergi Hydro RP column 250×30 mm (Phenomenex P/N 00G-4375-UO-AX) using H₂O and ACN both 50 mM TEAA. The Gradient was 25-75% ACN in 20 mins at 24 mL/mins, 254 nM detection. The compound eluted at 16.0 minutes; and the pure fractions were pooled and lyophilized. TEAA was removed by dissolving the compound in DMSO (2 mL) and using the same column and same gradient, using only H₂O and ACN. Pure fractions were pooled and lyophilized to give compound 51 (18 mg). MS: m/z=1197 [2M+1]⁺.

Example 10
Compound 8
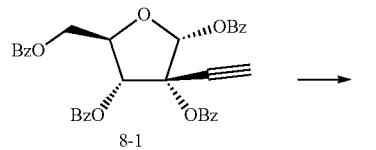
8-1
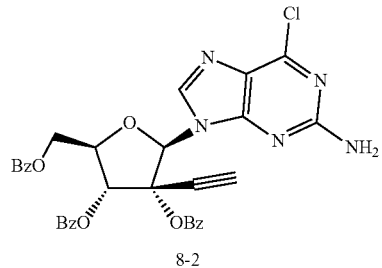
8-2
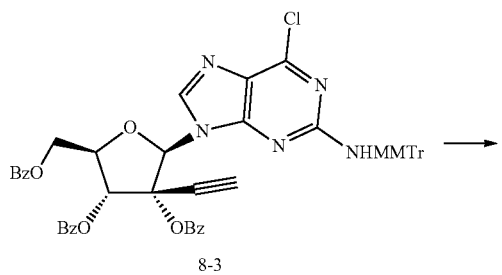
8-3
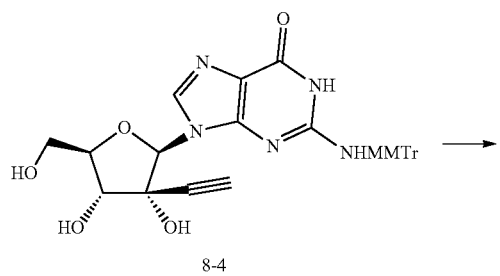
8-4
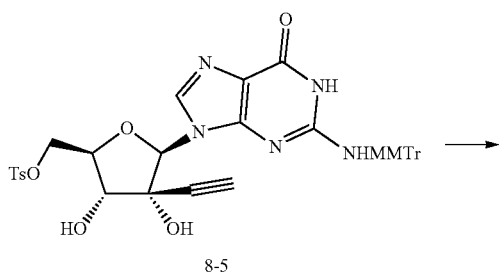
8-5
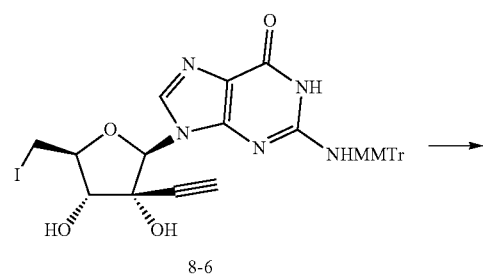
8-6
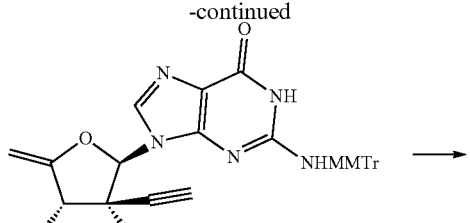
8-7
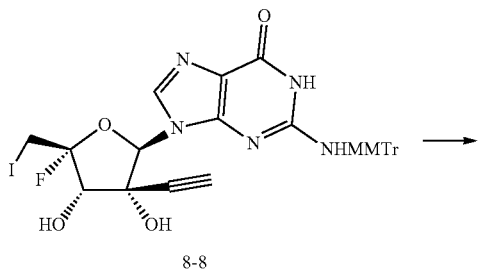
8-8
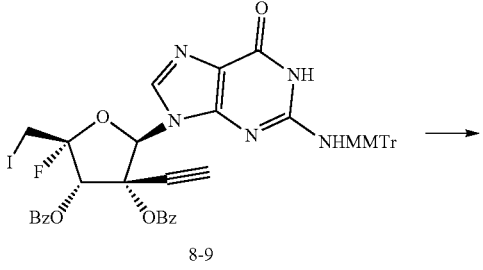
8-9
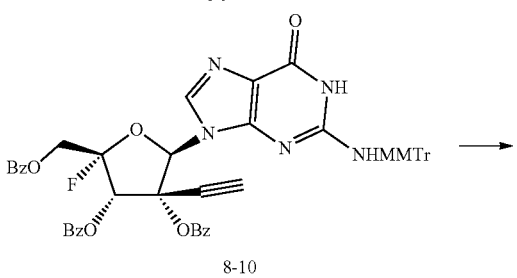
8-10
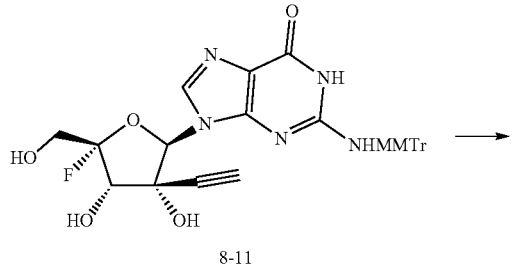
8-11
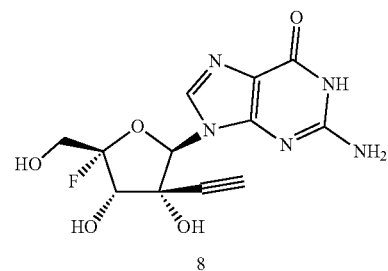
8
Compound 8-1 (5.0 g, 8.5 mmol) and 2-amino-6-chloropurine (3.0 g, 17.7 mmol) were co-concentrated with anhydrous toluene for 3 times. To a stirred suspension of the above mixtures in anhydrous MeCN (50 mL) was added DBU (7.5 g, 49 mmol) at 0° C. The mixture was stirred at 0° C. for 15 mins, and then TMSOTf (15 g, 67.6 mmol) was added dropwise at 0° C. The mixture was stirred at 0° C. for 15 mins. The mixture was heated at 70° C. overnight. The mixture was cooled to R.T., and diluted with EA (100 mL). The solution was washed with sat. NaHCO$_3$ solution and brine. The organic layer was dried over Na$_2$SO$_4$ and concentrated at low pressure. The residue was purified by column on silica gel (PE/EA: from 15/1 to 3/1) to give 8-2 (2.5 g, 46.3%) as a white foam.

To a solution of 8-2 (10 g, 15.7 mmol), AgNO$_3$ (8.0 g, 47 mmol) and collidine (10 mL) in anhydrous DCM (20 mL) was added MMTrCl (14.5 g, 47 mmol) in small portions under N$_2$. The mixture was stirred at R.T. overnight. The mixture was filtered, and the filtrate was washed with sat. aq. NaHCO$_3$ and brine. The organic layer was dried over anhydrous Na$_2$SO$_4$, and concentrated at low pressure. The residue was purified by silica gel column (PE/ME=20/1 to 8/1) to give 8-3 (10 g, 70%) as a yellow solid.

To a solution of 3-hydroxy-propionitrile (3.51 g, 49.4 mmol) in anhydrous THF (100 mL) was added NaH (2.8 g, 70 mmol) at 0° C., and the mixture was stirred at R.T. for 30 mins. A solution of 8-3 (8.5 g, 9.35 mmol) in anhydrous THF (100 mL) at 0° C. was added, and the mixture was stirred at R.T. overnight. The reaction was quenched with water, and extracted with EA (100 mL). The organic layer was dried over anhydrous Na$_2$SO$_4$, and concentrated at low pressure. The residue was purified by silica gel column (DCM/MeOH=100/1 to 20/1) to give 8-4 (4.5 g, 83%) as a white solid.

Compound 8-4 (1.5 g, 2.6 mmol) was co-concentrated with anhydrous pyridine 3 times. To an ice-cooled solution of 8-4 in anhydrous pyridine (30 mL) was added TsCl (1.086 g, 5.7 mmol), and the mixture was stirred at 0° C. for 1 h. The reaction was quenched with water, and extracted with EA (80 mL). The organic layer was dried over anhydrous Na$_2$SO$_4$, and concentrated at low pressure. The residue was purified by silica gel column (DCM/MeOH=100/1 to 15/1) to give 8-5 (1.4 g, 73%) as a white solid.

To a solution of 8-5 (4.22 g, 5.7 mmol) in acetone (60 mL) was added NaI (3.45 g, 23 mmol), and the mixture was refluxed overnight. The reaction was quenched with sat. aq. Na$_2$S$_2$O$_3$ and extracted with EA (100 mL). The organic layer was dried over anhydrous Na$_2$SO$_4$, and concentrated at low pressure. The residue was purified by silica gel column (DCM/MeOH=100/1 to 15/1) to give 8-6 (4 g, 73%) as a white solid.

To a solution of 8-6 (4.0 g, 5.8 mmol) in anhydrous THF (60 mL) was added DBU (3.67 g, 24 mmol), and the mixture was stirred at 60° C. overnight. The mixture was diluted with EA (80 mL), and the solution was washed with brine. The organic layer was dried over anhydrous Na$_2$SO$_4$, and concentrated at low pressure. The residue was purified by silica gel column (DCM/MeOH=100/1 to 20/1) to give 8-7 (2 g, 61%) as a white solid.

To an ice-cooled solution of 8-7 (500 mg, 0.89 mmol) in anhydrous DCM (20 mL) was added AgF (618 mg, 4.9 mmol) and a solution of I$_2$ (500 mg, 1.97 mmol) in anhydrous DCM (20 mL). The mixture was stirred at R.T. for 3 h. The reaction was quenched with sat Na$_2$S$_2$O$_3$ and NaHCO$_3$ aqueous, and the mixture was extracted with DCM (50 mL). The organic layer was separated, dried over anhydrous Na$_2$SO$_4$, and concentrated to give the crude 8-8 (250 mg) as a yellow solid.

To a solution of crude 8-8 (900 mg, 1.28 mmol) in anhydrous DCM (50 mL) was added DMAP (1.0 g, 8.2 mmol) and BzCl (795 mg, 5.66 mmol). The mixture was stirred at R.T. overnight. The mixture was washed with sat. aq. NaHCO$_3$ and brine. The organic layer was dried over anhydrous Na$_2$SO$_4$, and concentrated at low pressure. The residue was purified by prep-TLC (DCM/MeOH=15:1) to give 8-9 (300 mg, 26%) as a white solid.

To a solution of crude 8-9 (750 mg, 0.82 mmol) in anhydrous HMPA (20 mL) was added NaOBz (1.2 g, 8.3 mmol) and 15-crown-5 (1.8 g, 8.3 mmol). The mixture was stirred at 60° C. for 2 d. The mixture was diluted with EA, and the solution was washed with brine. The organic layer was dried over anhydrous Na$_2$SO$_4$, and concentrated at low pressure. The residue was purified by prep-TLC (PE/EA=1:1) to give crude 8-10 (550 mg, 73%) as a white solid.

The crude 8-10 (550 mg, 0.6 mmol) was dissolved in NH$_3$/MeOH (7N, 50 mL). The mixture was stirred at R.T. overnight. The mixture was concentrated, and the residue was purified by silica gel column (DCM/MeOH from 100/1 to 20/1) to give 8-11 (62 mg, 17%) as a white solid. ESI-MS: m/z 598.0 [M+H]$^+$ A solution of 8-11 (12 mg) in 80% formic acid (0.5 mL) stood at R.T. for 3.5 h and then was concentrated. The residue was co-evaporated with MeOH/toluene 4 times in a vial, and triturated with EtOAc at 40° C. The EtOAc solution removed with pippet. The trituration step was repeated several times, and the remaining solid was dissolved in MeOH. The solution was concentrated and dried to give compound 8 as off white solid (4.7 mg). ESI-MS: m/z 326.6 [M+H]$^+$.

Example 11

Compounds 34 and 35

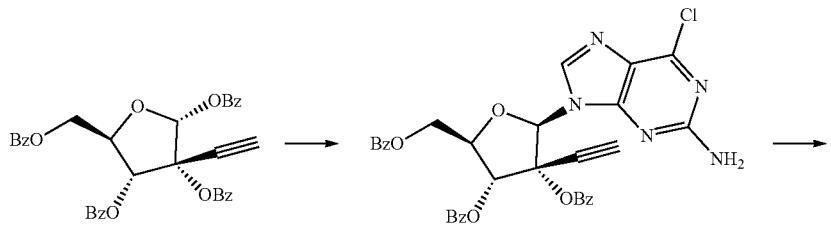

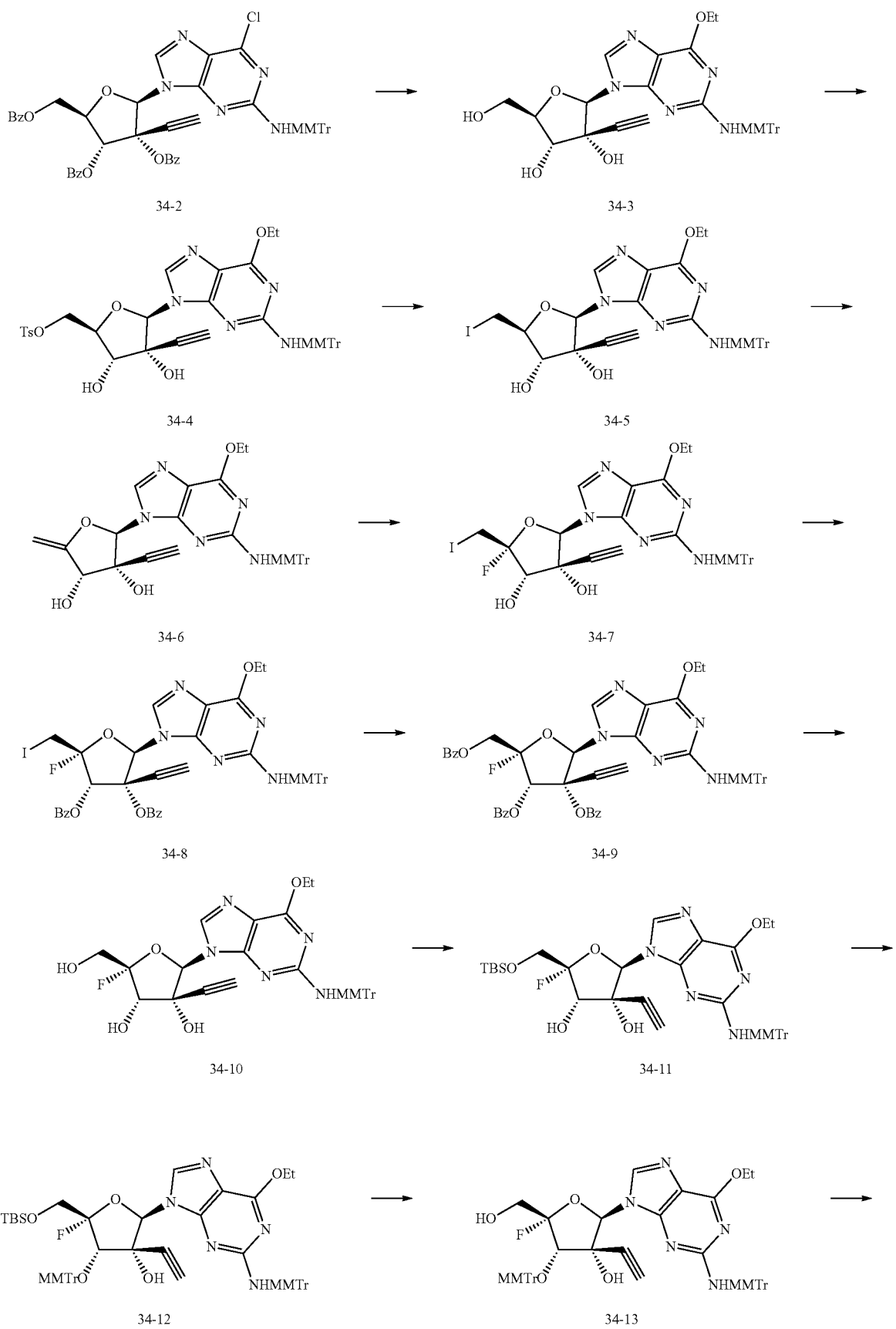

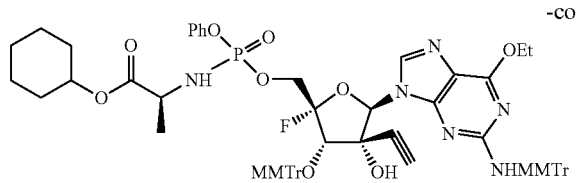

34-14

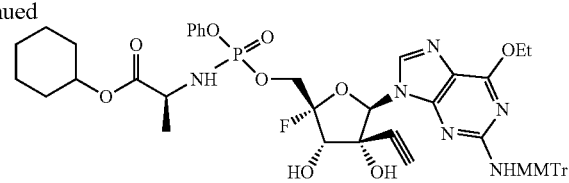

34-15

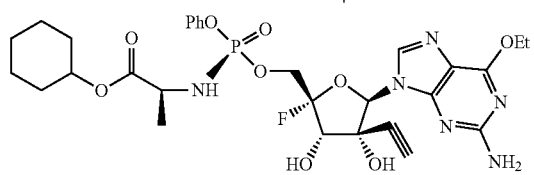

34

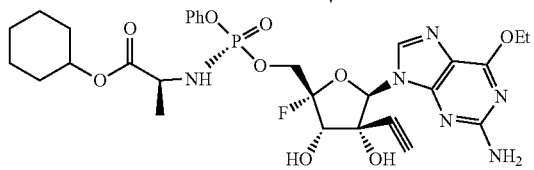

35

To a stirred suspension of 8-1 (50 g, 84.8 mmol) and 2-amino-6-chloropurine (28.6 g, 169.2 mmol) in anhydrous MeCN (500 mL) was added DBU (77.8 g, 508 mmol) at 0° C. The mixture was stirred at 0° C. for 30 mins, and TMSOTf (150.5 g, 678 mmol) was added dropwise at 0° C. The mixture was stirred at R.T. for 20 mins until a clear solution was formed. The mixture was stirred at 90-110° C. overnight. The mixture was cooled to R.T., and diluted with EA. The solution was washed with sat. NaHCO$_3$ solution and brine. The organic layer was dried over Na$_2$SO$_4$ and then concentrated at low pressure. The residue was purified by silica gel column (PE/EA=2/1) to give 34-1 (30 g, 55.5%) as a white solid.

To a solution of 34-1 (30 g, 47.1 mmol) in anhydrous DCM (300 mL) was added collidine (30 mL), AgNO$_3$ (24 g, 141.4 mmol) and MMTrCl (43.6 g, 141.4 mmol). The mixture was stirred at R.T. overnight. The mixture was filtered, and the filtrate was washed with water and brine. The organic layer was dried over anhydrous Na$_2$SO$_4$, and concentrated at low pressure. The residue was purified by silica gel column (PE/EA=4/1) to give 34-2 (35 g, 82%) as a white solid.

To a stirred solution of 34-2 (35 g, 38.5 mmol) in anhydrous EtOH (150 mL) was added a solution of EtONa in EtOH (2N, 150 mL). The mixture was stirred at R.T. overnight, and then concentrated at low pressure. The residue was dissolved in EA (200 mL) and the solution was washed with water and brine. The organic layer was dried over Na$_2$SO$_4$, and concentrated at low pressure. The residue was purified by silica gel column (DCM/MeOH=100/2) to give 34-3 (19 g, 81%) as a white solid.

Compound 34-3 (19 g, 31.3 mmol) was co-concentrated with anhydrous pyridine for 3 times. To an ice-cooled solution of 34-3 in anhydrous pyridine (120 mL) was added a solution of TsCl (6.6 g, 34.6 mmol) in pyridine (40 mL) dropwise at 0° C. The mixture was stirred at 0° C. for 16 h. The mixture was quenched with water, and the reaction mixture was concentrated. The residue was re-dissolved in EA (200 mL). The solution was washed with sat. aq. NaHCO$_3$ and brine. The organic layer was dried over anhydrous Na$_2$SO$_4$ and filtered, and the filtrate was concentrated. The residue was purified by silica gel column (DCM/MeOH=100/1) to give 34-4 (16 g, 67%) as a yellow solid.

To a solution of 34-4 (15 g, 19.7 mmol) in acetone (100 mL) was added NaI (30 g, 197 mmol). The mixture was refluxed overnight, and then concentrated at low pressure. The residue was purified by silica gel column (DCM/MeOH=100/1) to give 34-5 (9 g, 63.7%) as a white solid.

To a solution of 34-5 (8 g, 11.2 mmol) in anhydrous THF (60 mL) was added DBU (5.12 g, 33.5 mmol), and the mixture was heated at 60° C. overnight. The mixture was diluted with EA, and washed with water and brine. The organic layer was dried over anhydrous Na$_2$SO$_4$ and filtered, and the filtrate was concentrated. The residue was purified by silica gel column (PE/acetone=4/1) to give 34-6 (5.7 g, 86%) as a white solid. $^1$H-NMR (CD$_3$OH, 400 MHz) δ=8.18 (s, 1H), 7.17-7.33 (m, 12H), 6.80 (d, J=8.8 Hz, 2H), 5.98 (s, 1H), 5.40 (d, J=8.6 Hz, 1H), 3.87 (m, 5H), 3.75 (s, 3H), 2.69 (s, 1H), 1.05 (s, 3H).

To an ice-cooled solution of 34-6 (4.44 g, 7.5 mmol) in anhydrous MeCN (45 mL) was added TEA.3HF (1.23 g, 7.6 mmol) and NIS (2.16 g, 9.5 mmol). The mixture was stirred at R.T. for 2-3 h. The reaction was quenched with sat. Na$_2$SO$_3$ and NaHCO$_3$ solution. The mixture was extracted with EA (3×100 mL). The organic layer was separated, dried over anhydrous Na$_2$SO$_4$ and concentrated at low pressure. The residue was purified by silica gel column (DCM/acetone=100/2) to give 34-7 (4.4 g, 79.8%) as a white solid.

To a solution of 34-7 (5.36 g, 7.3 mmol) in anhydrous DCM (50 mL) was added DMAP (3.6 g, 29.8 mmol) and BzCl (3.1 g, 22.1 mmol) at 0° C. The mixture was stirred at R.T. overnight. The mixture was washed with sat. aq. NaHCO$_3$ and brine. The organic layer was concentrated, and the residue was purified by silica gel column (PE/EA=5/1) to give 34-8 (5.6 g, 81.3%) as a white solid.

To a solution of 34-8 (5.0 g, 5.3 mmol) in anhydrous DMF (150 mL) was added NaOBz (7.64 g, 53 mmol) and 15-crown-5 (14 g, 68 mmol). The mixture was stirred at 90-100° C. for 48 h. The mixture was diluted with EA, and washed with water and brine. The organic layer was concentrated, and the residue was purified by silica gel column (PE/EA=5/1) to give 34-9 (3.9 g, 78.5%) as a white solid.

Compound 34-9 in NH$_3$ in MeOH (7N, 60 mL) was stirred at R.T. for 18 h. The mixture was concentrated at low pressure. The residue was purified by silica gel column (DCM/acetone=50/1) to give 34-10 (500 mg, 74.7%) as a white solid. ESI-MS: m/z 626.3 [M+H]+.

To a solution of 34-10 (350 mg, 0.56 mmol) in anhydrous pyridine (4 mL) was added imidazole (50 mg, 0.72 mmol) and TBSCl (108 mg, 0.72 mmol) at 0 to 5° C., and stirred at R.T. for 15 h. The reaction was quenched with absolute EtOH (0.5 mL). The solution was concentrated to dryness under reduced pressure. The residue was dissolved in EA (150 mL), and washed with water, sat. NaHCO3 and brine. The combined organic layers were dried over Na2SO4, filtered and evaporated at low pressure. The residue was purified by silica gel column (10-30% EA in hexanes) to give 34-11 (338 mg, 81.8%) as a white solid.

To a solution of compound 34-11 (328 mg, 0.44 mmol), AgNO3 (226 mg, 1.33 mmol) and collidine (0.59 mL, 4.84 mmol) in anhydrous DCM (4 mL) was added MMTrCl (410 mg, 1.33 mmol) under N2. The mixture was stirred at R.T. overnight under N2, and monitored by TLC to completion. The mixture was filtered through pre-packed Celite filter, and the filtrate was washed with water, 50% aqueous citric acid, and brine. The organic layer was separated, dried over anhydrous Na2SO4, filtered and concentrated at low pressure. The residue was purified by silica gel column (EA in hexanes from 0% to 30%) to give 34-12 (337 mg).

To a solution of 34-12 (337 mg, 0.33 mmol) in anhydrous THF (4 mL) was added 1.0 M solution of TBAF (0.66 ML, 0.66 mmol) at 0 to 5° C. The reaction was slowly warmed to R.T., and stirred for 1 h. The mixture was quenched with silica gel, and filtered. The solvents were evaporated to give the crude product, which was purified by silica gel column (EA in hexanes from 0% to 50%) to give 34-13 (188 mg).

To a stirred solution of 34-13 (180 mg, 0.16 mmol) in anhydrous CH3CN (2.5 mL) was added N-methylimidazole (132 μL, 1.6 mmol) at 0-5° C. (ice/water bath) followed by solution of phenyl (cyclohexanoxy-L-alaninyl) phosphorochloridate (207 mg, 0.6 mmol, dissolved in 2 mL of CH3CN). The solution was stirred at R.T. for 2.5 h, and the mixture was diluted with EA followed by addition of water (15 mL). The solution was washed H2O, 50% aqueous citric acid solution and brine. The organic layer was separated, dried over anhydrous MgSO4 and filtered. The filtrate was concentrated in vacuum to give a residue, which was purified on silica gel with 0 to 40% EA/hexanes to give 34-14 (75.8 mg) and 34-15 (108 mg) as a slower eluting isomer.

Compound 34-14 (76 mg, 0.063 mmol) was dissolved in anhydrous CH3CN (0.5 mL), and 4N HCl in dioxane (47 μL) was added at 0 to 5° C. (ice/water bath). The mixture was stirred at R.T. for 40 mins, and anhydrous EtOH (200 μL) was added. The solvents were evaporated at R.T. and co-evaporated with toluene 3 times. The residue was dissolved in 50% CH3CN/H2O, purified on a reverse-phase HPLC (C18) using acetonitrile and water, and lyophilized to give compound 34 (26.6 mg). ESI-LCMS: m/z=663.3 [M+H]+.

Compound 34-15 (108 mg, 0.089 mmol) was dissolved in anhydrous CH3CN (0.7 mL), and 4N HCl in dioxane (67 μL) was added at 0 to 5° C. (ice/water bath). The mixture was stirred at R.T. for 60 mins, and anhydrous EtOH (200 μL) was added. The solvents were evaporated at R.T. and co-evaporated with toluene 3 times. The residue was dissolved in 50% CH3CN/H2O, purified on a reverse-phase HPLC (C18) using acetonitrile and water, and lyophilized to give compound 35 (40.3 mg). ESI-LCMS: m/z=663.2 [M+H]+.

Example 12

Compound 25

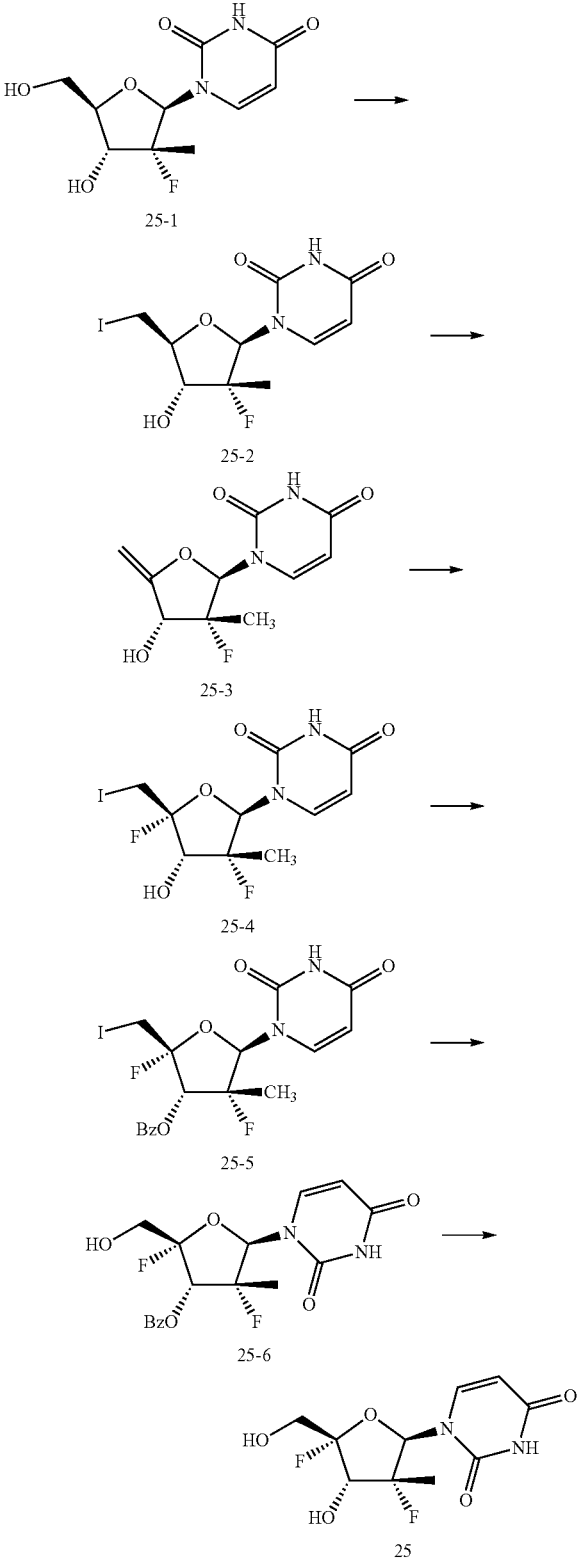

To a solution of 25-1 (260 mg, 1 mmol), PPh₃ (780 mg, 3 mmol) and pyridine (0.5 mL) in anhydrous THF (8 mL) were added I₂ (504 mg, 2 mmol) at R.T., and the mixture was stirred at R.T. for 12 h. The mixture was diluted with EtOAc and washed with 1M HCl solution. The organic layer was dried over Na₂SO₄, filtered and concentrated at low pressure. The residue was purified by silica gel column (5% MeOH in DCM) to give 25-2 (190 mg, 85%) as a white solid.

To a solution of 25-2 (190 mg, 0.52 mmol) in THF (4 mL) was added DBU (760 mg, 5 mmol) at R.T., and the mixture was heated at 50° C. overnight. The mixture was diluted with EtOAc, and washed with water. The organic layer was dried over anhydrous Na₂SO₄ and concentrated at low pressure. The residue was purified by silica gel column (30% EA in PE) to give 25-3 (75 mg, 52%) as a white solid.

To a solution of 25-3 (200 mg, 0.82 mmol) in MeCN (anhydrous, 4 mL) was added NIS (337 mg, 1.5 mmol) and TEA.3HF (213 mg, 1.25 mmol) at R.T., and the mixture was stirred at R.T. for 7 h. The reaction was quenched with sat. Na₂SO₃ solution and sat. aq. NaHCO₃ solution. The mixture was extracted with EA. The organic layer was separated, dried over anhydrous Na₂SO₄, and concentrated at low pressure. The residue was purified by silica gel column (20% EA in PE) to give 25-4 (300 mg, 62%) as a white solid.

To a solution of 25-4 (194 mg, 0.5 mmol) in pyridine (5 mL) was added BzCl (92 mg, 0.55 mmol) at 0° C. The mixture was stirred at R.T. for 5 h, and the reaction was quenched with water. The mixture was concentrated at low pressure, and the residue was purified by silica gel column (20% EA in PE) to give 25-5 (397 mg, 81%) as a white solid.

To a solution of 25-5 (1.05 g, 2.13 mmol) in DCM (12 mL) was added a mixture of TFA (0.5 mL) and Bu₄NOH (1 mL), followed by addition of m-CPBA (1.3 g, 6 mmol) at R.T. The mixture was stirred at R.T. for 5 h. The mixture was washed with sat. Na₂SO₃ solution and aq. NaHCO₃ solution. The organic layer was dried over anhydrous Na₂SO₄, and concentrated at low pressure. The residue was purified by silica gel column (30% EA in PE) to give 25-6 (450 mg, 63%) as a white solid.

Compound 25-6 (250 mg, 0.65 mmol) was dissolved in NH₃/MeOH (5 mL). The mixture was stirred at R.T. for 5 h, and then concentrated at low pressure. The residue was purified by silica gel column (5% MeOH in DCM) to give compound 25 (120 mg, 66%) as a white powder. ESI-MS: m/z 279.0 [M+H]⁺.

Example 13

Compound 31

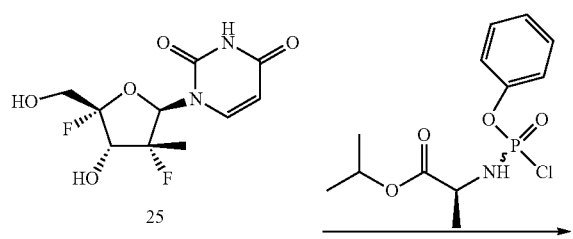

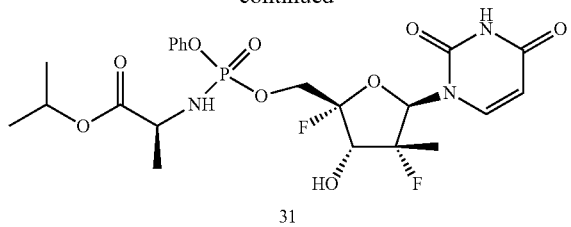

31

To a stirred solution of compound 25 (100 mg, 0.36 mmol) in anhydrous THF (3.0 mL) was added N-methylimidazole (236 µL, 2.87 mmol) at 0° C. (dry ice/acetone bath) followed by a solution of the phosphorochloridate (329 mg, 1.08 mmol, dissolved in 2 mL of THF). The solution was stirred at 0° C. for 1 h, the reaction temperature was raised up-to 10° C. during the next 1 h, and the solution was left at 10° C. for the next 4 h. The mixture was cooled to 0 to 5° C., diluted with EA, and water was added (15 mL). The solution was washed H₂O, 50% aqueous citric acid solution and brine. The organic layer was separated, dried over anhydrous MgSO₄ and filtered. The filtrate was concentrated in vacuum to give a residue, which dissolved in 25% CH₃CN/H₂O. The residue was purified on a reverse-phase HPLC (C18) using acetonitrile and water, followed by lyophilization to give a mixture of two isomers of compound 31 (17.5 mg). MS: m/z 546.05 [M–H]⁻.

Example 14

Compound 27

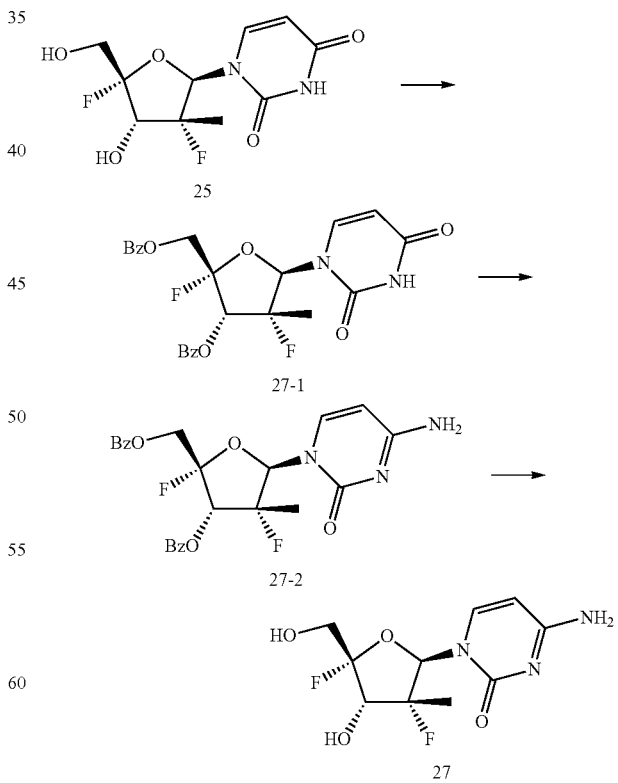

To a solution of compound 25 (139 mg, 0.5 mmol) in pyridine (5 mL) was added BzCl (92 mg, 0.55 mmol) at 0°

C. The mixture was stirred at R.T. for 5 h, diluted with EtOAc and washed with 1N HCl solution. The organic layer was dried over anhydrous Na₂SO₄, and concentrated at low pressure. The residue was purified by silica gel column (20% EA in PE) to give 27-1 (274 mg, 79%) as a white solid.

To a solution of 27-1 (490 mg, 1 mmol), DMAP (244 mg, 2 mmol) and TEA (205 mg, 2.1 mmol) in MeCN (10 mL) were added TPSCl (604 mg, 2 mmol) at 0° C. The mixture was stirred at R.T. for 2 h., and then NH₄OH aq. was added at R.T. The mixture was stirred for 0.5 h, diluted with EtOAc and washed with sat. aq. NaHCO₃ and brine. The organic layer was dried over anhydrous Na₂SO₄, and concentrated at low pressure. The residue was purified by silica gel column (30% EA in PE) to give 27-2 (250 mg, 41%) as a white solid.

Compound 27-2 (250 mg, 0.51 mmol) was dissolved in NH₃/MeOH (15 mL). The mixture was stirred at R.T. for 5 h. and then concentrated at low pressure. The residue was purified by silica gel column (5% DCM in DCM) to give compound 27 (95 mg, 66%) as a white powder. ESI-MS: m/z 278.1 [M+H]⁺.

Example 15

Compound 29

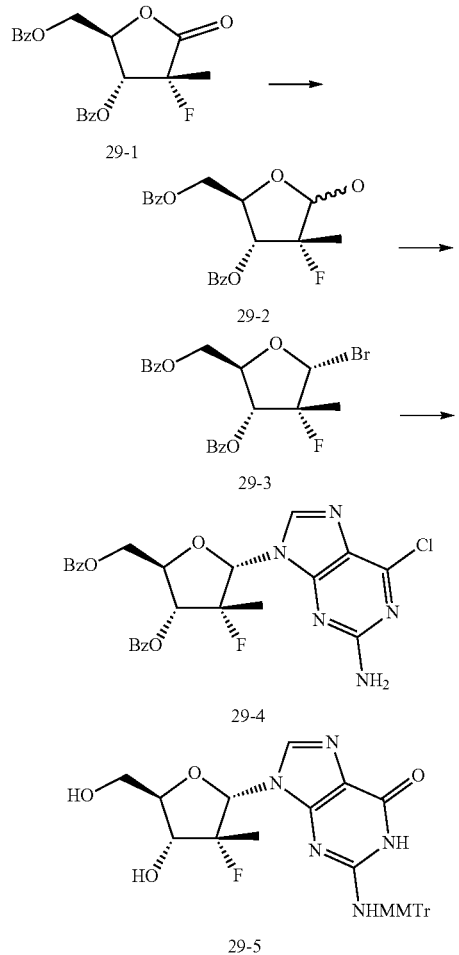

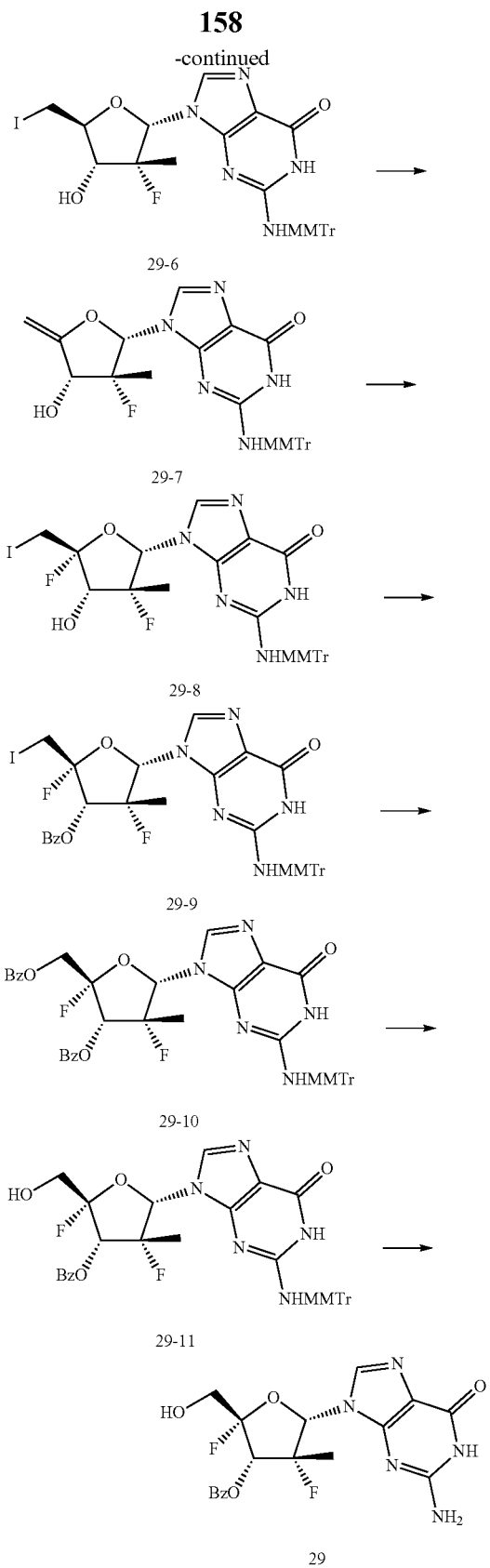

To a solution of compound 29-1 (30 g, 0.08 mol) in anhydrous THF (300 mL) was added a solution of lithium tri-tert-butoxyaluminohydride (120 mL, 0.12 mol) dropwise at −78° C. under N₂. The mixture was stirred at −20° C. for 1 h. The reaction was quenched with sat. aq. NH₄Cl and then filtered. The filtrate was extracted with EA (3×300 mL). The organic layer was dried over anhydrous Na₂SO₄, and concentrated at low pressure. The residue was purified by silica gel column (10% EA in PE) to give 29-2 (26 g, 86%) as a colorless oil.

To a stirred solution of PPh₃ (37.7 g, 0.144 mol) in DCM (100 mL) was added compound 29-2 (27 g, 0.072 mol) at −20° C. under N₂. After the mixture was stirred at R.T. for 15 mins, CBr₄ (42 g, 0.129 mol) was added while maintaining the reaction temperature between −25 and −20° C. under N₂. The mixture was then stirred below −17° C. for 20 mins. Silica gel was added into the solution, and then purified by flash silica gel column separation to give the crude oil product. The crude was purified by silica gel column (EA in PE from 2% to 20%) to give 29-3 (α-isomer, 17 g, 55%) as a colorless oil.

A mixture of 6-C₁-guanine (11.6 g, 68.8 mmol) and t-BuOK (8.2 g, 73 mmol) in t-BuOH (200 mL) and MeCN (150 mL) was stirred at 35° C. for 30 mins, and then 29-3 (10 g, 22.9 mmol) in MeCN 100 mL) was added at R.T. The mixture was heated at 50° C. overnight. The reaction was quenched with a solution of NH₄Cl (5 g) in water (40 mL), and the mixture was filtered. The filtrate was evaporated at low pressure. The residue was purified by silica gel column (20% EA in PE) to give 29-4 (6 g, 42%) as a yellow solid.

To a solution of 29-4 (12.5 g, 23.8 mol) in DCM (50 mL) was added AgNO₃ (8.1 g, 47.6 mmol), collidine (5.77 g, 47.6 mmol) and MMTrCl (11 g, 35.7 mmol). The mixture was stirred at R.T. overnight. The reaction was quenched with MeOH (5 mL), filtered and concentrated at low pressure. The residue was purified by silica gel column (5% MeOH in DCM) to give the intermediate (16 g, 86%) as a yellow solid. To a solution of HOCH₂CH₂CN (4.7 g, 66 mmol) in THF (200 mL) was added NaH (3.7 g, 92 mmol) at 0° C. The mixture was stirred at R.T. for 30 mins. A solution of the intermediate (10.5 g, 13 mmol) in THF (50 mL) was added, and the reaction mixture was stirred at R.T. for 12 h. The reaction was quenched with MeOH (2 mL), diluted with EA (100 mL), and washed with brine. The organic layer was dried over anhydrous Na₂SO₄, and concentrated at low pressure. The residue was purified by silica gel column (5% MeOH in DCM) to give 29-5 (5.8 g, 77%) as a yellow solid.

To a solution of PPh₃ (7.0 g, 26.6 mmol) in anhydrous pyridine (100 mL) was added I₂ (6.3 g, 24.9 mmol), and stirred at R.T. for 30 mins. The mixture was treated with a solution of 29-5 (9.5 g, 16.6 mmol) in pyridine (40 mL). The mixture was stirred at R.T. overnight. The reaction was quenched with sat. Na₂S₂O₃ solution, and the mixture was extracted with EA. The organic layer was washed with brine, dried over anhydrous Na₂SO₄, and concentrated at low pressure. The residue was purified by silica gel column (30% EA in PE) to give 29-6 (7 g, 66%) as a yellow solid.

To a solution of 29-6 (7.5 g, 11 mmol) in dry THF (50 mL) was added DBU (5.4 g, 33 mmol), and the mixture was heated to reflux for 4 h. The mixture was diluted with EA (3×100 mL), and washed with brine. The organic layer was dried over anhydrous Na₂SO₄, and concentrated at low pressure. The residue was purified by silica gel column (30% EA in PE) to give 29-7 (4.0 g, 67%) as a white solid.

To an ice-cooled solution of 29-7 (3.0 g, 5.4 mmol) in anhydrous MeCN (20 mL) was added TEA.3HF (0.65 g, 4.1 mmol) and NIS (1.53 g, 6.78 mmol) at R.T., and the reaction mixture was stirred at R.T. for 2 h. The mixture was diluted with EA (50 mL) and washed with sat. Na₂S₂O₃ solution and NaHCO₃aq. The organic layer was dried over anhydrous Na₂SO₄, and concentrated to dryness at low pressure. The residue was purified by prep-HPLC (0.1% HCOOH in water and MeCN) to separate the two isomers (about 1:1). NOE showed the polar one was 29-8 (0.6 g, 16%) as a white solid.

To a solution of 29-8 (0.7 g, 1 mmol) in dry pyridine (10 mL) was added BzCl (147 mg, 1.05 mmol) at 0° C. The mixture was stirred at R.T. for 3 h. The mixture was then diluted with EA, and washed with sat. NaHCO₃aq. and brine. The organic layer was dried over Na₂SO₄, and evaporated at low pressure. The residue was purified by silica gel column (20% EA in PE) to give 29-9 (0.65 g, 81%) as a white solid.

To a solution of 29-9 (0.65 g, 0.8 mmol) in dry DMF (40 mL) was added NaOBz (1.15 g, 8 mmol) and 15-crown-5 (1.77 g, 8 mmol). The mixture was stirred at 100° C. for 48 h. The solvent was evaporated at low pressure, and the residue was dissolved in EA (30 mL), and washed with water and brine. The organic layer was dried over Na₂SO₄ and concentrated at low pressure. The residue was purified by silica gel column (20% EA in PE) to give 29-10 (500 mg, 78%) as a white solid.

Compound 29-10 (400 mg, 0.5 mmol) in NH₃/MeOH (7N, 100 mL) was stirred at R.T. for 18 h. The mixture was concentrated at low pressure, and the residue was purified by silica gel column (5% MeOH in DCM) to give 29-11 (220 mg, 63%) as a white solid. ESI-MS: m/z 590.3 [M+H]⁺.

Compound 29-11 (59 mg, 0.1 mmol) was dissolved in 50% TFA in methanol (10 mL), and the mixture was kept at R.T. for 2 h. The solvent was evaporated and co-evaporated with a methanol/toluene mixture to remove traces of the acid. The residue was suspended in CH₃CN (1 mL) and centrifuged. The precipitate was washed with CH₃CN (1 mL) and dried. Compound 29 was obtained as a colorless solid (21 mg, 65%. MS: m/z 316.2 [M−1]⁻.

Example 16

Compounds 42 and 43

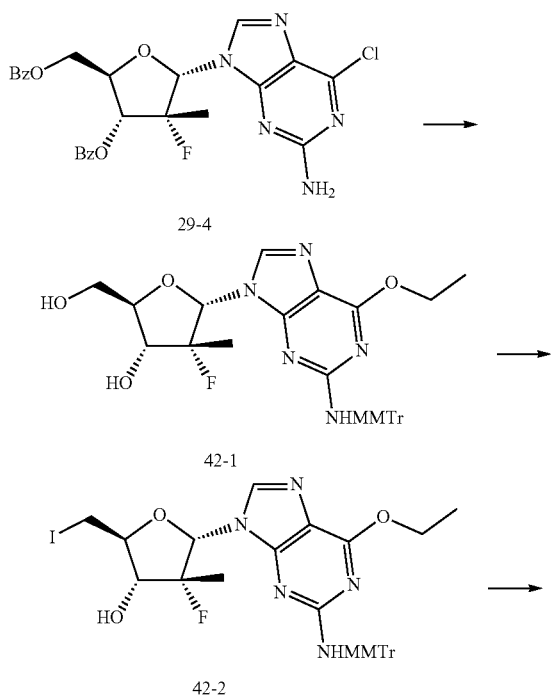

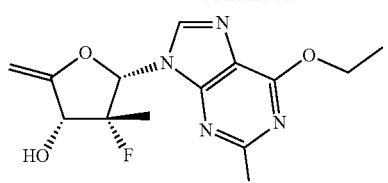

42-3

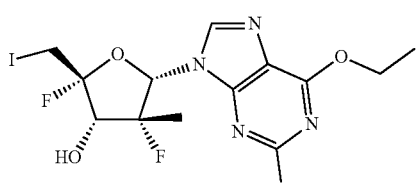

42-4

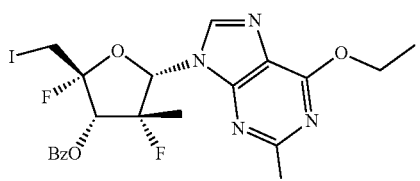

42-5

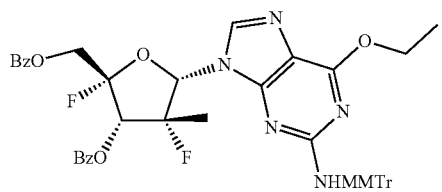

42-6

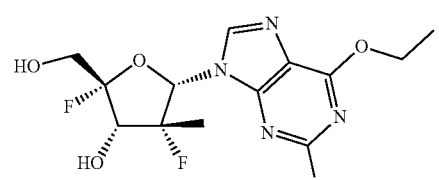

42-7

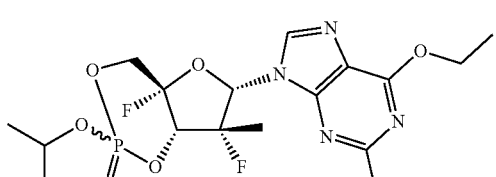

42-a and 42-b

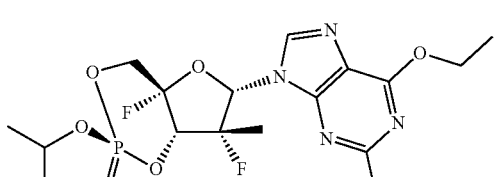

42

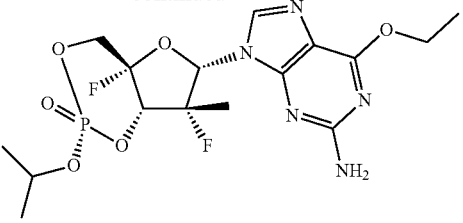

43

A freshly prepared EtONa in dry EtOH (2N, 150 mL) was added to a solution of 29-4 (13.67 g, 17.15 mmol) in EtOH (50 mL) at 0° C. The mixture was stirred at R.T. for 1 h, and then concentrated at low pressure. The residue was purified by silica gel column (5% MeOH in DCM) to give 42-1 (10 g, 98%) as a yellow solid.

To a solution of $PPh_3$ (2.73 g, 10.4 mol) in anhydrous pyridine (60 mL) was added $I_2$ (2.48 g, 9.76 mmol) at R.T., and the reaction mixture was stirred R.T. for 30 mins. A solution of 42-1 (3.9 g, 6.51 mmol) in pyridine (10 mL) was added. The mixture was stirred at R.T. overnight. The reaction was quenched with sat. $Na_2S_2O_3$ solution and $NaHCO_3$ aq., and then extracted with EA (100 mL). The organic layer was dried over anhydrous $Na_2SO_4$, and evaporated at low pressure. The residue was purified by silica gel column (2% MeOH in DCM) to give 42-2 (3.0 g, 75%) as a yellowed solid.

To a solution of 42-2 in dry THF (300 mL) was added DBU (14.0 g, 91.8 mmol), and the mixture was heated to reflux for 3 h. The mixture was concentrated at low pressure. The residue was dissolved in EA (100 mL), and washed with brine. The organic layer was dried over anhydrous $Na_2SO_4$, and evaporated at low pressure. The residue was purified by silica gel column (20% EA in PE) to give 42-3 (0.6 g, 37.5%) as a white solid.

To an ice-cooled solution of 42-3 (2.0 g, 3.44 mmol) in anhydrous MeCN (20 mL) was added NIS (0.975 g, 4.3 mmol) and TEA.3HF (0.82 g, 5.16 mmol) at 0° C. The mixture was stirred at R.T. for 2 h. The reaction was quenched with sat. $Na_2SO_3$ and $NaHCO_3$ aqueous solution, and then concentrated at low pressure. The residue was dissolved in EA (50 mL), washed with brine, dried over anhydrous $Na_2SO_4$, and evaporated at low pressure. The residue was purified by silica gel column (20% EA in PE) to give 42-4 (1.5 g, 60%) as a white solid.

To a solution of 42-4 (1 g, 1.37 mmol) in dry pyridine (100 mL) was added BzCl (0.23 g, 1.65 mmol) at 0° C. The reaction was stirred for 30 mins and checked by LCMS. The mixture was concentrated at low pressure, and the residue was dissolved in EA (50 mL). The solution was washed with brine. The organic layer was dried over $MgSO_4$, and evaporated at low pressure. The residue was purified by silica gel column chromatography (10% EA in PE) to give 42-5 (0.9 g, 78%) as a white solid.

To a solution of 42-5 (2 g, 2.4 mmol) in dry DMF (40 mL) was added NaOBz (3.46 g, 24 mmol) and 15-crown-5 (4.5 mL). The mixture was stirred at 95° C. for 72 h. The mixture was then diluted with EA (100 mL), and washed with water and brine. The organic phase was dried over $MgSO_4$, and concentrated at low pressure. The residue was purified by silica gel column (15% EA in PE) to give 42-6 (1.5 g, 75%) as a white solid.

Compound 42-6 (1.35 g, 1.64 mmol) in $NH_3$/MeOH (150 mL) was stirred at R.T. for 18 h. The mixture was concentrated at low pressure, and the residue was purified by silica gel column (5% MeOH in DCM) to give 42-7 (0.9 g, 90%) as a white solid. ESI-MS: m/z 618.3 [M+H]⁺.

To a solution of 42-7 (99 mg, 0.16 mmol) in DCM (1.0 mL), triethylamine (92.7 µL, 0.64 mmol) was added at R.T. The mixture was cooled to 0 to 5° C. (ice/water bath), and freshly prepared and distilled isopropyl phosphorodichloridate (36.6 µL, 0.2 mmol, prepared according to a procedure, Reddy et al. J. Org. Chem. 2011, 76 (10), 3782-3790) was added to the mixture. The mixture was stirred 0 to 5° C. (ice/water bath) for 15 mins, followed by addition of N-methylimidazole (26.3 µL, 0.32 mmol). The mixture was then stirred for 1 h at 0 to 5° C. TLC showed absence of 42-7. EA (100 mL) was added, followed by water. The organic layer was washed $H_2O$, saturated aqueous $NH_4Cl$ solution and brine. The organic layer was separated, dried over anhydrous $MgSO_4$ and filtered. The filtrate was concentrated in vacuum to give a residue, which was purified on silica gel with 0 to 10% iPrOH/DCM to give a mixture of 42-a and 42-b (61.5 mg).

A mixture of 42-a and 42-b (61.5 mg, 0.085 mmol) was dissolved in anhydrous $CH_3CN$ (0.5 mL), and 4N HCl in dioxane (64 µL) was added at 0 to 5° C. (ice/water bath). The mixture was stirred at R.T. for 40 mins, and anhydrous EtOH (200 µL) was added. The solvents were evaporated at R.T. and co-evaporated with toluene 3 times. The residue was dissolved in 50% $CH_3CN/H_2O$, was purified on a reverse-phase HPLC (C18) using acetonitrile and water, followed by lyophilization to give compound 42 (1.8 mg) and compound 43 (14.5 mg).

Compound 42: $^1$H NMR (CD$_3$OD-d$_4$, 400 MHz) δ 8.0 (s, 1H), 6.69 (d, J=16.0 Hz, 1H), 5.9-5.6 (br s, 1H), 4.94-4.85 (m, 1H), 4.68-4.52 (m, 3H), 1.49-1.3 (m, 12H); $^{19}$F NMR (CD$_3$OD-d$_4$) δ −122.8 (s), −160.06 (s); $^{31}$P NMR (CD$_3$OD-d$_4$) δ −7.97 (s). ESI-LCMS: m/z=450.1 [M+H]⁺; Compound 43: $^1$H NMR (CD$_3$OD-d$_4$, 400 MHz) δ 7.96 (s, 1H), 6.68 (s, 1H), 6.69 (d, J=16.8 Hz, 1H), 6.28-6.1 (br s, 1H), 4.81-4.5 (m, 4H), 1.45-1.39 (m, 12H); $^{31}$P NMR (CD$_3$OD-d$_4$) δ −5.84 (s). ESI-LCMS: m/z=450.0 [M+H]⁺.

Example 17

Compounds 32 and 33

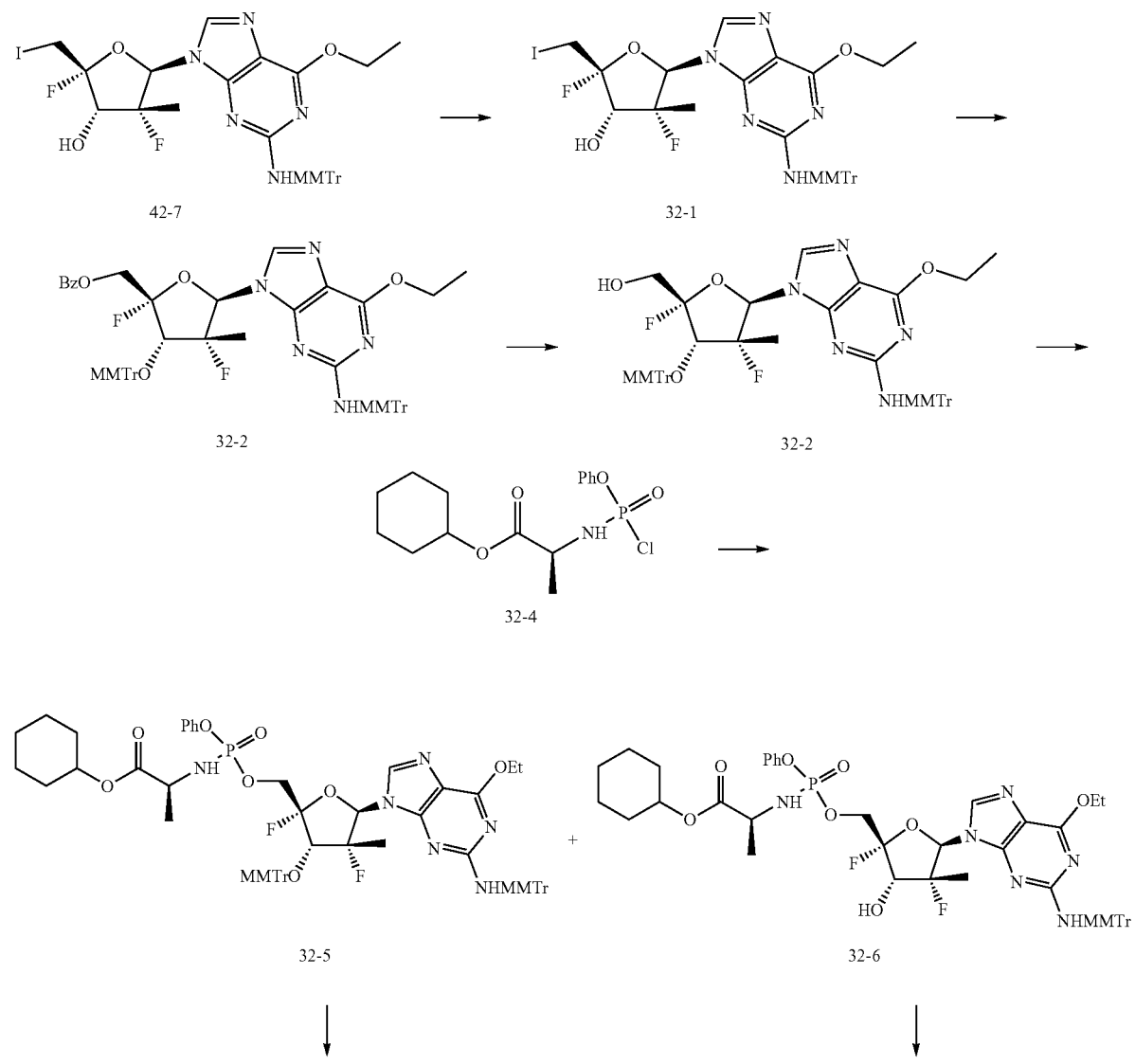

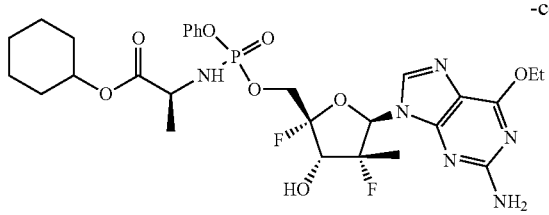

32

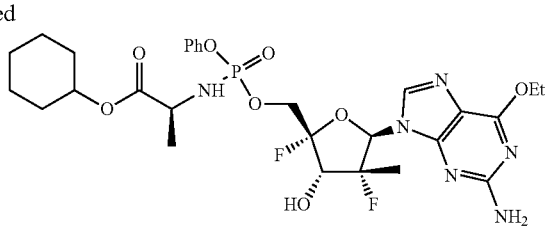

33

To a solution of 42-7 (0.47 g, 0.65 mol) in DCM (3 mL) was added AgNO₃ (0.22 g, 1.29 mmol), collidine (0.15 g, 1.29 mmol) and MMTrCl (0.3 g, 0.974 mmol) at 0° C. The mixture was stirred at R.T. overnight. The mixture was filtered, and the filter was washed with sat. aq. NaHCO₃ solution and brine. The organic layer was separated, dried over anhydrous Na₂SO₄ and concentrated at low pressure. The residue was purified by silica gel column to give 32-1 (0.55, 85%) as a white solid.

To a solution of 32-1 (0.5 g, 0.5 mmol) in dry DMF (10 mL) was added NaOBz (0.72 g, 5 mmol) and 15-crown-5 (0.9 mL). The mixture was stirred at 95° C. for 72 h. The mixture was diluted with EA, and washed with water and brine. The organic phase was dried over MgSO₄ and concentrated at low pressure. The residue was purified by silica gel column (10% EA in PE) to give 32-2 (0.3 g, 60%) as a white solid.

Compound 32-2 (0.3 g, 0.3 mmol) in NH₃/MeOH (30 mL) was stirred at R.T. for 18 h. The mixture was concentrated at low pressure, and the residue was purified by silica gel column (20% EA in PE) to give 32-3 (145 mg, 56%) as a white solid. ESI-LCMS: m/z 890.5 [M+H]⁺.

To a stirred solution of 32-3 (161 mg, 0.16 mmol) in anhydrous CH₃CN (2.0 mL) was added N-methylimidazole (118 µL, 2.87 mmol) at 0 to 5° C. (ice/water bath) followed by solution of 32-4 (186 mg, 0.54 mmol, dissolved in 2 mL of CH₃CN). The solution was stirred at 0 to 5° C. for 4 h. The mixture was diluted with EA, and water was added (15 mL). The solution was washed H₂O, 50% aqueous citric acid solution and brine. The organic layer was separated, dried over anhydrous MgSO₄ and filtered. The filtrate was concentrated in vacuum to give a residue, which was purified on silica gel with 0 to 40% EA/hexanes to give as 32-5 (82.6 mg) as the faster eluting isomer and 32-6 (106 mg) as the slower eluting isomer.

Compound 32-5 (82.6 mg, 0.07 mmol) was dissolved in anhydrous CH₃CN (0.5 mL), and 4N HCl in dioxane (35 µL) was added at 0 to 5° C. The mixture was stirred at R.T. for 1 h, and anhydrous EtOH (100 µL) was added. The solvents were evaporated at R.T. and co-evaporated with toluene 3 times. The residue was dissolved in 50% CH₃CN/H₂O, and purified on a reverse-phase HPLC (C18) using acetonitrile and water, followed by lyophilization to give compound 32 (19.4 mg). ¹H NMR (CD₃OD-d₄, 400 MHz) δ 7.9 (s, 1H), 7.32-7.28 (t, J=8.0 Hz, 2H), 7.2-7.12 (m, 3H), 6.43 (d, J=17.6 Hz, 1H), 4.70-4.63 (m, 2H), 4.55-4.4 (m, 3H), 3.94-3.9 (m, 1H), 1.79-1.67 (m, 4H), 1.53-1.49 (m, 1H), 1.45-1.22 (m, 15H); ³¹P NMR (CD₃OD-d₄) δ 4.06 (s); ESI-LCMS: m/z=655.2 [M+H]⁺, 653.15 [M−H]⁻.

Compound 32-6 (100 mg, 0.083 mmol) was dissolved in anhydrous CH₃CN (0.5 mL), and 4N HCl in dioxane (50 µL) was added at 0 to 5° C. Following the procedure for obtaining compound 32, compound 33 (31.8 mg) was obtained. ¹H NMR (CD₃OD-d₄, 400 MHz) δ 7.93 (s, 1H), 7.33-7.29 (m, 2H), 7.24-7.14 (m, 3H), 6.41 (d, J=17.6 Hz, 1H), 4.70-4.60 (m, 2H), 4.54-4.49 (m, 2H), 4.44-4.39 (m, 1H), 3.92-3.89 (m, 1H), 1.77-1.66 (m, 4H), 1.54-1.24 (m, 16H); ³¹P NMR (CD₃OD-d₄) δ 3.91 (s); ESI-LCMS: m/z=655.2 [M+H]⁺, 653.1 [M−H]⁻.

Example 18

Compound 53

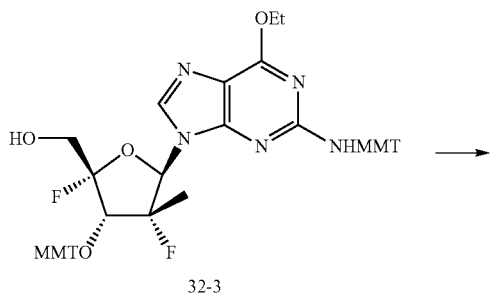

32-3

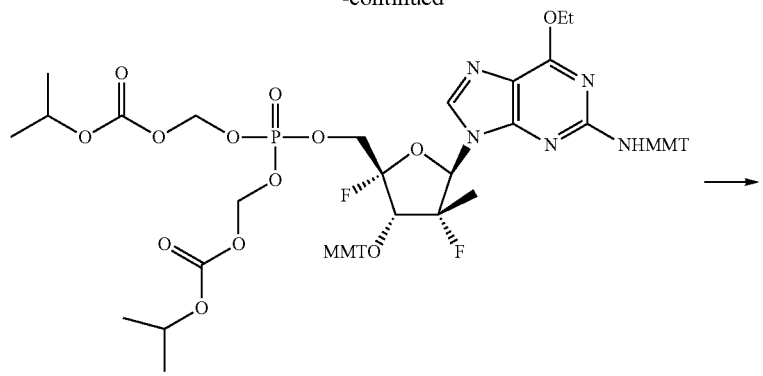

53-1

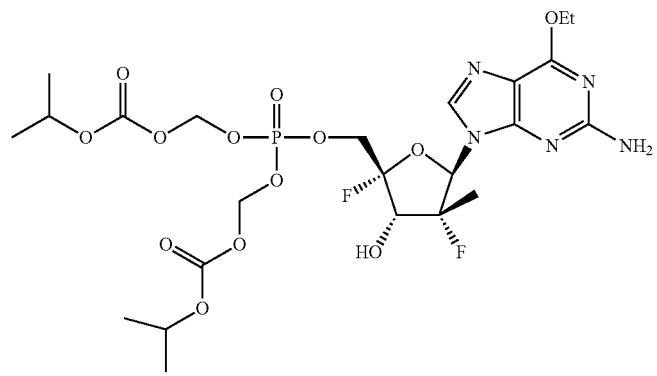

53

Compound 53-1 (70 mg, 58%) was prepared from 32-3 (90 mg; 0.1 mmol) and triethylammonium bis(isopropyloxy-carbonyloxymethyl)phosphate (0.2 mmol) with DIPEA (87 μL), BopCl (44 mg), and 3-nitro-1,2,4-triazole (29 mg) in THF (2 mL) according to a method described for compound 51-2. Purification was done with hexanes/EtOAc solvent system, 20-80% gradient.

Compound 53 (25 mg, 64%) was prepared from 53-1 (70 mg) in acetonitrile (0.6 mL) and 4 N HCl/dioxane (50 μL) according to a method described for compound 51. MS: m/z=658 [M+1]$^+$.

Example 19

Compounds 40 and 41

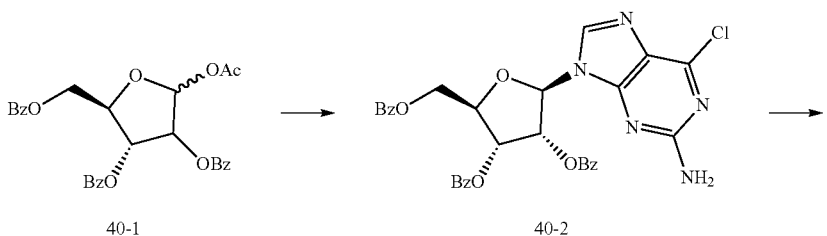

40-1      40-2

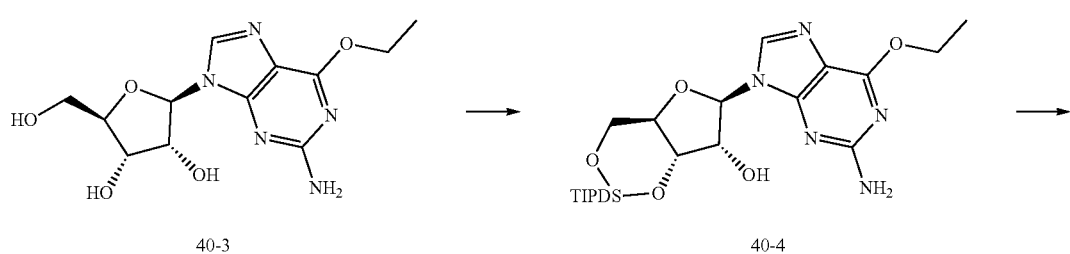

40-3      40-4

-continued
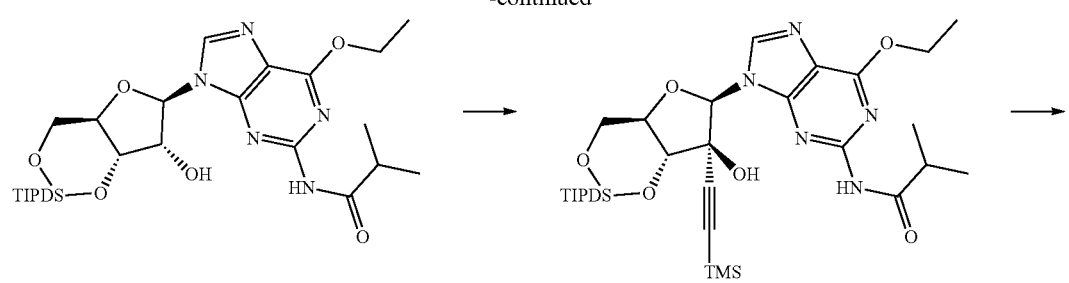
40-5 → 40-6
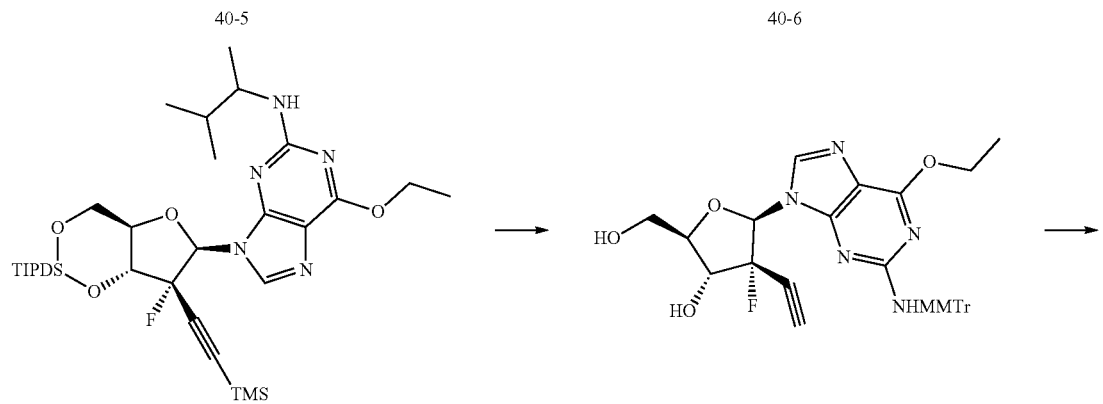
40-7 → 40-8
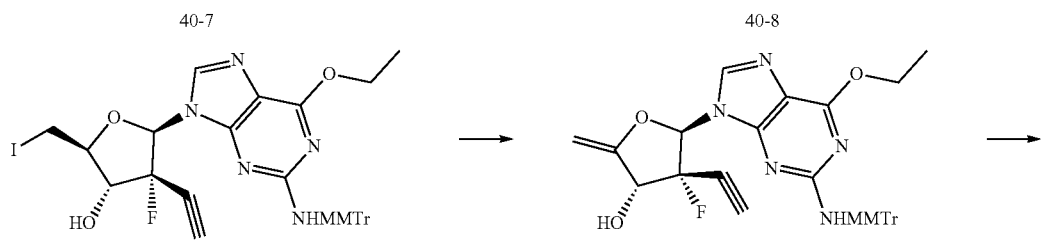
40-9 → 40-10
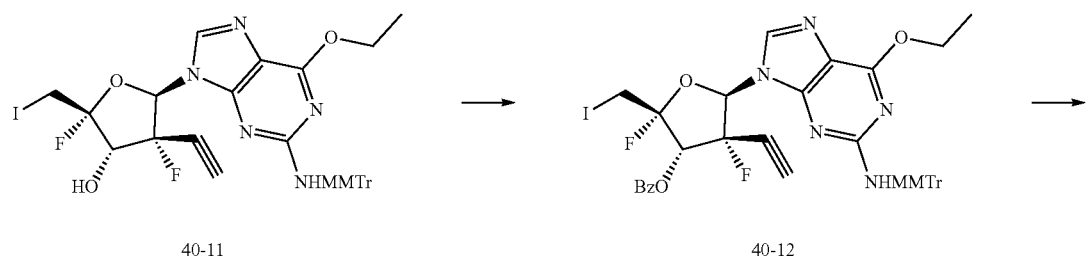
40-11 → 40-12
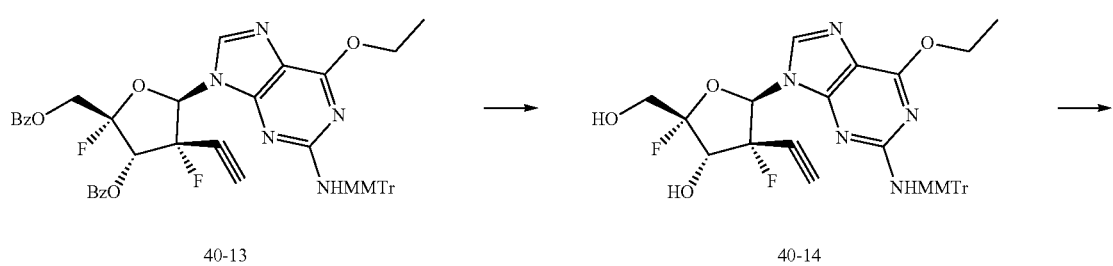
40-13 → 40-14

-continued

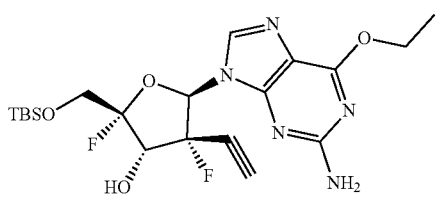

40-15

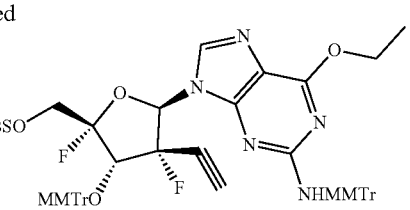

40-16

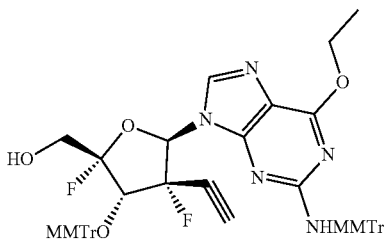

40-17

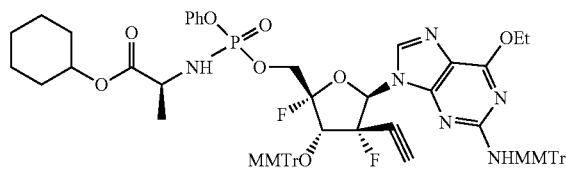

40-18

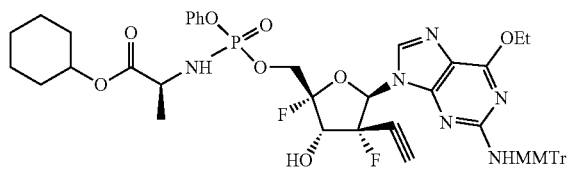

40-19

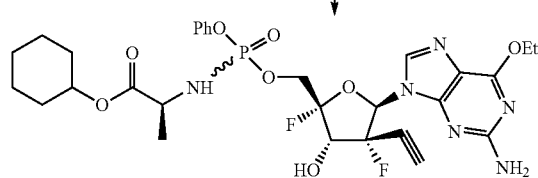

40

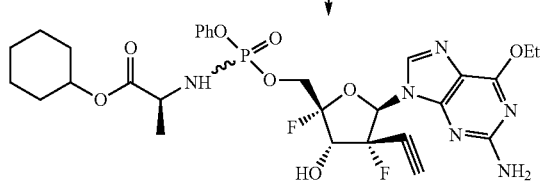

41

To a mixture of pre-silylated 6-$C_1$-guanine (using HMDS and $(NH_4)_2SO_4$) (25.2 g, 150 mmol) in DCE (300 mL) was added 40-1 (50 g, 100 mmol) and TMSOTf (33.3 g, 150 mmol) at 0° C. The mixture was stirred at 70° C. for 16 h, and then concentrated at low pressure. The residue was re-dissolved in EA, and washed with sat. aq. $NaHCO_3$ and brine. The organic layer was dried over anhydrous $Na_2SO_4$, and concentrated at low pressure. The residue was purified on silica gel column (PE/EA=2/1) to give pure 40-2 (45 g, 73%) as a white solid.

To a solution of 40-2 (45 g, 73.4 mmol) in EtOH (73 mL) was added with EtONa (1N in EtOH, 360 mL). The mixture was stirred at R.T. for 16 h. The mixture was then concentrated to give a residue, which was purified by silica gel column (DCM/MeOH=10/1) to give pure 40-3 (19 g, 83%) as a white solid.

To a solution of 40-3 (19 g, 61.1 mmol) in pyridine (120 mL) was added with $TIPDSCl_2$ (19.2 g, 61 mmol) dropwise at 0° C. The mixture was stirred at R.T. for 16 h, and then concentrated at low pressure. The residue was re-dissolved in EA, and washed with sat. aq. $NaHCO_3$. The organic layer was dried over anhydrous $Na_2SO_4$, and concentrated at low pressure. The residue was purified by silica gel column (DCM/MeOH=20/1) to give pure 40-4 (22 g, 65%) as a white solid.

To a solution of 40-4 (22 g, 39.8 mmol) in DMF/pyridine (5/1, 100 mL) was added TMSCl (12.9 g, 119 mmol) dropwise at 0° C. The mixture was stirred at R.T. for 1 h and then treated with isobutyryl chloride (5.4 g, 50 mmol). The mixture was stirred at R.T. for 3 h and then quenched by $NH_4OH$. The mixture was concentrated at low pressure. The residue was dissolved in EA (200 mL). The solution was washed with sat. aq. $NaHCO_3$, and then the organic layer was dried and concentrated at low pressure. The residue was purified by silica gel column (DCM/MeOH=50/1) to give pure 40-5 (15 g, 60%) as a white solid.

To a solution of 40-5 (15 g, 24.1 mmol) in DCM (100 mL) was added PDC (13.5 g, 26 mmol) and $Ac_2O$ (9.8 g, 96 mmol) at 0° C. The mixture was stirred at R.T. for 16 h. The reaction was quenched by sat. aq. $NaHCO_3$, and then extracted with EA. The organic layer was dried over anhydrous $Na_2SO_4$, and concentrated at low pressure. The residue was dissolved in anhydrous THF (100 mL). To a solution of TMSCCH (12 g, 112 mmol) in THF (200 mL)

was added n-BuLi (2.5 N, 44 mL) at −78° C. The mixture was stirred at −78° C. for 15 mins and 0° C. for 15 mins. The mixture was treated with a solution of crude ketone in THF at −78° C. and stirred at −30° C. for 2 h. The reaction was quenched by sat. aq. NH$_4$Cl, and then extracted by EA. The combined organic layer was dried over anhydrous Na$_2$SO$_4$, and concentrated at low pressure. The residue was purified by silica gel column (PE/EA=10/1) to give pure 40-6 (3.1 g, 18%) as a white solid.

To a solution of 40-6 (7 g, 7.5 mmol) and pyridine (1.4 g, 17 mmol) in DCM (35 mL) was added with DAST (5.6 g, 35 mmol) at −78° C. The mixture was stirred at −78° C. for 3 h. The reaction was quenched by sat. aq. NaHCO$_3$, and then extracted with EA. The combined organic layer was dried over anhydrous, and concentrated at low pressure. The residue was purified by silica gel column (PE/EA=10/1) to give pure 40-7 (3.1 g, 18%) as a white solid.

Compound 40-7 (4.1 g, 5.7 mmol) in sat. NH$_3$/MeOH (100 mL) was stirred at R.T. for 16 h, and concentrated at low pressure. The residue was re-dissolved in anhydrous DCM (300 mL), and was treated with AgNO$_3$ (27.0 g, 160 mmol), collidine (22 mL) and MMTrCl (23.0 g, 75.9 mmol) in small portions under N$_2$. The mixture was stirred at R.T. for 16 h. The mixture was filtered, and the filtrate was washed with sat. NaHCO$_3$ solution and brine. The organic layer was separated, dried over anhydrous Na$_2$SO$_4$, and concentrated at low pressure. The residue was purified by silica gel column (PE/EA=10/1) to give the pure intermediate. The intermediate was dissolved in a solution of TBAF/THF (1N, 20 mL). The mixture was stirred at R.T. for 2 h and then concentrated at low pressure. The residue was purified by silica gel column (DCM/MeOH=50/1) to give pure 40-8 (3.0 g, 86%) as a white solid.

To a solution of 40-8 (3.0 g, 4.9 mmol) in THF (50 mL) was added imidazole (840 mg, 12 mmol), PPh$_3$ (3.2 g, 12 mmol), and I$_2$ (2.4 g, 9.2 mmol) at 0° C. The mixture was stirred at R.T. for 16 h. The reaction was quenched by sat. aq. Na$_2$S$_2$O$_3$, and then extracted with EA. The combined organic layer was dried over anhydrous Na$_2$SO$_4$, and concentrated at low pressure. The residue was purified by silica gel column (PE/EA=2/1) to give crude 40-9 (4.2 g, >100%, containing TPPO) as a white solid.

To a solution of crude 40-9 in anhydrous THF (30 mL) was added DBU (2.7 g, 18 mmol), and heated to 80° C. The mixture was stirred for 1 h and checked by LCMS. The mixture was quenched by water, and extracted with EA. The organic layer was dried over anhydrous Na$_2$SO$_4$ and filtered, and the filtrate was concentrated at low pressure. The residue was purified by silica gel column (PE/EA=2/1) to give 40-10 (2.0 g, 69%) as a white solid.

To an ice-cooled solution of 40-10 (2.0 g, 3.38 mmol) in anhydrous MeCN (15 mL) was added NIS (777 mg, 3.5 mmol) and NEt$_3$.3HF (536 g, 3.3 mmol) at 0° C. The mixture was stirred at R.T. for 16 h and checked by LCMS. After completion, the mixture was quenched by sat. Na$_2$SO$_3$ and sat. NaHCO$_3$ solution, and extracted with EA. The organic layer was separated, dried over anhydrous Na$_2$SO$_4$ and concentrated at low pressure. The residue was purified by silica gel column chromatography (PE/EA=10/1 to 3/1) to give 40-11 (2.1 g, 84.0%) as a white solid.

To a solution of crude 40-11 (2.1 g, 2.85 mmol) in anhydrous DCM (100 mL) was added DMAP (490 mg, 4 mmol), and BzCl (580 mg, 4 mmol) at 0° C. The mixture was stirred overnight and checked by LCMS. The reaction was washed with sat. NaHCO$_3$ solution. The organic layer was dried over anhydrous Na$_2$SO$_4$, and concentrated at low pressure. The residue was purified by silica gel column chromatography (PE/EA=8/1 to 3/1) to give 40-12 (2.0 g, 83.4%) as a white solid.

To a solution of 40-12 (2.0 g, 2.4 mmol) in anhydrous DMF (60 mL) was added NaOBz (3.3 g, 23.0 mmol) and 15-crown-5 (5.11 g, 23 mmol). The mixture was stirred at 110° C. for 36 h. The reaction was quenched by water, and the mixture was extracted with EA. The organic layer was dried over anhydrous Na$_2$SO$_4$, and concentrated at low pressure. The residue was purified by silica gel column (PE/EA=5/1 to 3/1) to give 40-13 (830 mg, 42.0%) as a white solid. ESI-MS: m/z 836.11 [M+H]$^+$.

A solution of 40-13 (831 mg, 1.0 mmol) in anhydrous n-butylamine (4 mL) was stirred at R.T. for 3 h under N$_2$ atmosphere. The reaction was monitored by TLC. The solvent was evaporated in vacuo, and the residue was purified by silica gel column (MeOH in DCM from 0% to 10%) to give the crude product, which as re-purified using silica gel column to give 40-14 as a light pink solid (563 mg).

To a solution of 40-14 (560 mg, 0.89 mmol) in anhydrous pyridine (5 mL) was added imidazole (78.6 mg, 1.16 mmol) and TBSCl (202 mg, 1.34 mmol) at 0 to 5° C. The mixture was stirred at R.T. for 15 h. The reaction was quenched by adding absolute EtOH (0.3 mL). The solution was concentrated to dryness under reduced pressure, and co-evaporated with toluene 3 times. The residue was dissolved in EA (150 mL), and washed with water, sat. NaHCO$_3$, and brine. The combined organic layer was dried over Na$_2$SO$_4$, filtered and evaporated at low pressure. The residue was purified by silica gel column (0-20% EA in hexanes) to give 40-15 (303 mg) as a white solid.

To a solution of 40-15 (303 mg, 0.41 mmol), AgNO$_3$ (208 mg, 1.23 mmol) and collidine (0.55 mL, 4.51 mmol) in anhydrous DCM (4 mL) was added MMTrCl (378 mg, 1.3 mmol) under N$_2$. The mixture was stirred at R.T. overnight under N$_2$, and monitored by TLC. The mixture was filtered through pre-packed celite filter, and the filtrate was washed with water and, 50% aqueous citric acid, and brine. The organic layer was separated, dried over anhydrous Na$_2$SO$_4$, filtered and concentrated at low pressure. The residue was purified by silica gel column (EA in hexanes from 0% to 30%) to give 40-16 (374 mg, 90%).

To a solution of 40-16 (374 mg, 0.37 mmol) in anhydrous THF (4 mL) was added 1.0 M solution of TBAF (0.74 mL, 0.74 mmol) at 0 to 5° C. The mixture was stirred at R.T. for 1 h. The mixture was quenched with silica gel, and filtered. The solvents were evaporated to give the crude product, which was purified by silica gel column (EA in hexanes from 0% to 50%) to give 40-17 (265 mg).

To a stirred solution of 40-17 (187.5 mg, 0.16 mmol) in anhydrous CH$_3$CN (2.5 mL) was added N-methylimidazole (136 μL, 1.66 mmol) at 0-5° C. (ice/water bath) followed by solution of phenyl (cyclohexanoxy-L-alaninyl) phosphorochloridate (214 mg, 0.62 mmol, dissolved in 0.5 mL of CH$_3$CN). The solution was stirred at R.T. for 3 h, and then diluted with EA followed by the addition of water (15 mL). The solution was washed with H$_2$O, 50% aqueous citric acid solution and brine. The organic layer was separated, dried over anhydrous MgSO$_4$ and filtered. The filtrate was concentrated in vacuum to give a residue, which was purified on silica gel with 0 to 40% EA/hexanes to give (single isomers) of 40-18 (108 mg) Elution of the latter fraction gave (single isomers) of 40-19 (120 mg) as glassy solid.

Compound 40-18 (108 mg, 0.089 mmol) was dissolved in_anhydrous CH$_3$CN (0.5 mL), and 4N HCl in dioxane (67 μL) was added at 0 to 5° C. (ice/water bath). The mixture was stirred at R.T. for 40 mins, and anhydrous EtOH (200 μL) was added. The solvents were evaporated at R.T. and co-evaporated with toluene 3 times. The residue was dissolved in 50% $CH_3CN/H_2O$, was purified on a reverse-phase HPLC (C18) using acetonitrile and water, followed by lyophilization to give compound 40 (26.6 mg) as a white foam. $^1$H NMR ($CD_3OD$-$d_4$, 400 MHz) δ 7.89 (s, 1H), 7.33-7.29 (m, 2H), 7.20-7.13 (m, 3H), 7.17 (m, 1H), 6.62 (d, J=15.6 Hz, 1H), 5.39 (t, J=25.2 Hz, 1H), 4.75-4.42 (m, 6H), 3.92 (t, J=8.8 Hz, 1H), 3.24 (d, J=5.6 Hz, 1H), 1.76-1.51 (m, 5H), 1.45-1.25 (m, 12H); $^{31}$P NMR ($CD_3OD$-$d_4$) δ 4.04 (s); ESI-LCMS: m/z=665.2 [M+H]$^+$.

Compound 41 (44.4 mg, single isomer) was obtained according to the procedure described for compound 40 using 40-19. $^1$H NMR ($CD_3OD$-$d_4$, 400 MHz) δ 7.93 (s, 1H), 7.32 (t, J=8.0 Hz, 1H), 7.24 (d, J=7.6 Hz, 2H), 7.16 (t, J=7.6 Hz, 1H), 6.61 (d, J=16.0 Hz, 1H), 4.68-4.60 (m, 2H), 4.54-4.39 (m, 3H), 3.93-3.89 (m, 1H), 3.24 (d, J=5.6 Hz, 1H), 1.75-1.5 (m, 5H), 1.48-1.23 (m, 12H); $^{19}$F NMR ($CD_3OD$-$d_4$) δ −122.95 (s), −155.84-155.99 (m); $^{31}$P NMR ($CD_3OD$-$d_4$) δ 3.94 (s); ESI-LCMS: m/z=665.15 [M+H]$^+$.

Example 20

Compound 49

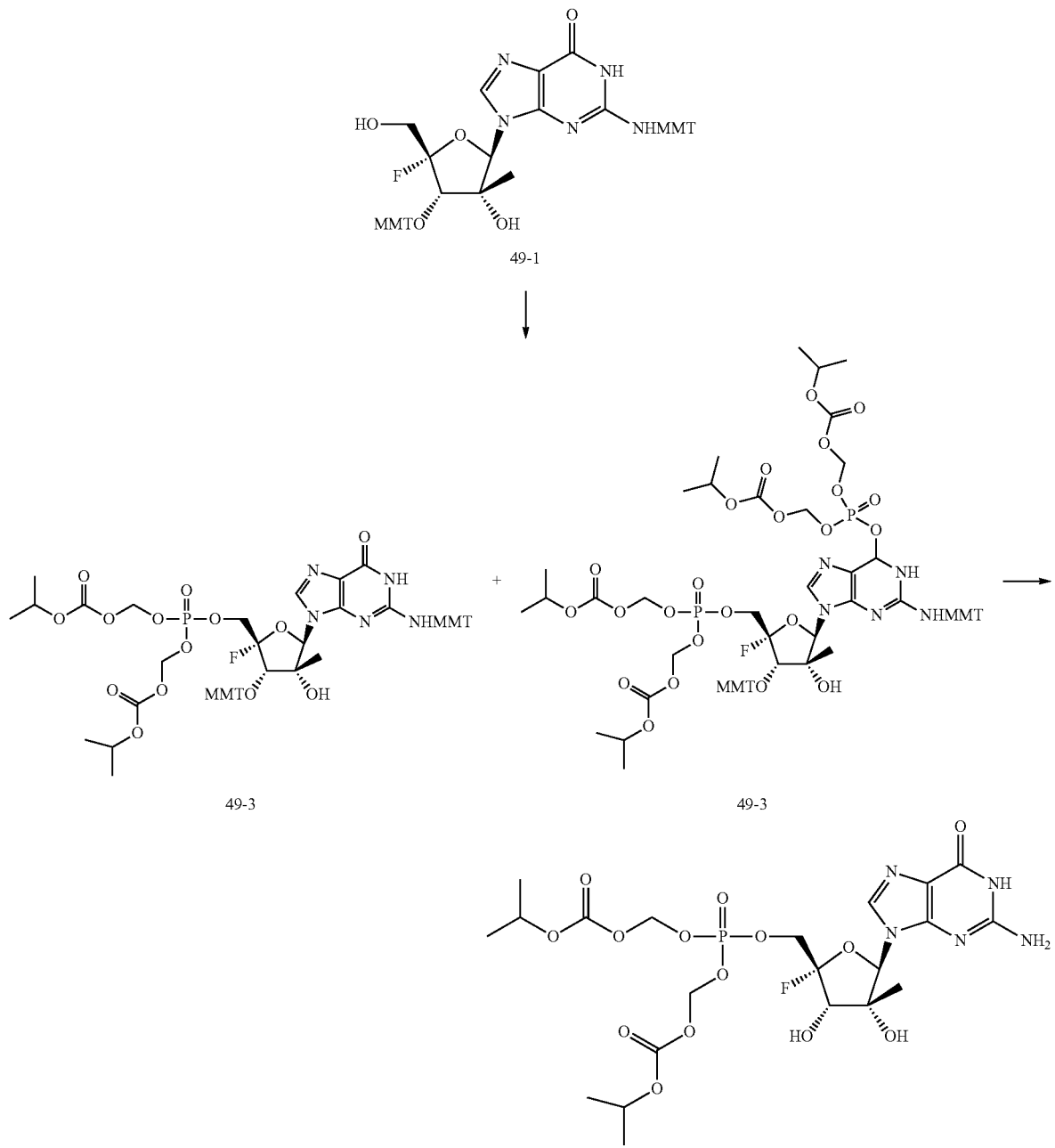

To a solution of triethylammonium bis(isopropyloxycarbonyloxymethyl)phosphate (0.33 mmol, prepared from 110 mg of bis(POC)phosphate and 46 µL of Et$_3$N) in THF was added 49-1 (91 mg, 0.11 mmol). The mixture evaporated and rendered anhydrous by co-evaporating with pyridine follow by toluene. The residue was dissolved in anhydrous THF (1.5 mL) and cooled in an ice-bath. Diisopropylethyl amine (0.19 mL, 10 eq.) was added, followed by BOP—Cl (0.14 g, 5 eq.), and 3-nitro-1,2,4-triazole (63 mg, 5 eq.). The mixture was stirred 0° C. for 90 mins, diluted with EtOAc (30 mL), washed with sat. aq. NaHCO$_3$, brine, and dried (Na$_2$SO$_4$). The residue was purified on silica (10 g column) with CH$_2$Cl$_2$/i-PrOH solvent system (2-10% gradient) to obtain 49-2 (13 mg, 10%) and 49-3 (95 mg, 58%).

A solution of 49-2 and 49-3 (13 mg and 95 mg, respectively) in 80% aq. HCOOH (3 mL) was stirred at R. T. for 3 h, then evaporated and co-evaporated with toluene. The residue was purified on silica (10 g column) with CH$_2$Cl$_2$/MeOH (4-10% gradient) to obtain compound 49 in (42 mg, 94%) yield. MS: m/z=628 [M+1]$^+$.

Example 21

Compound 52

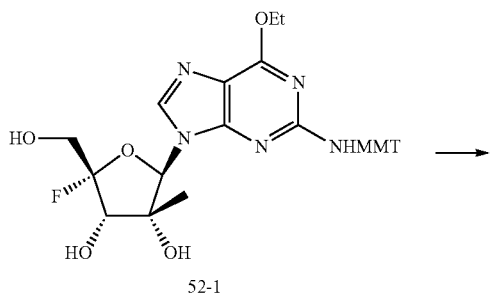

52-1

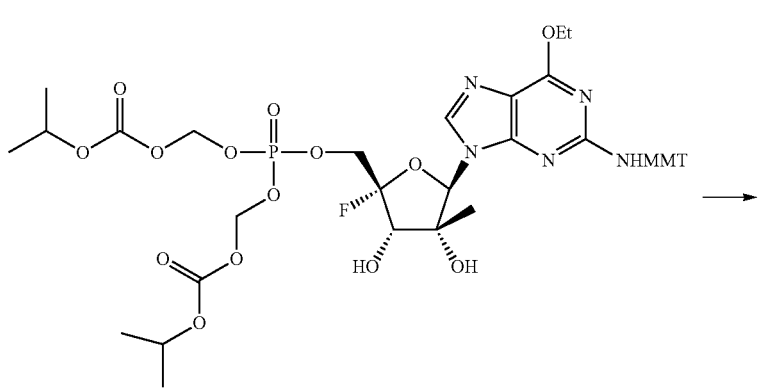

52-2

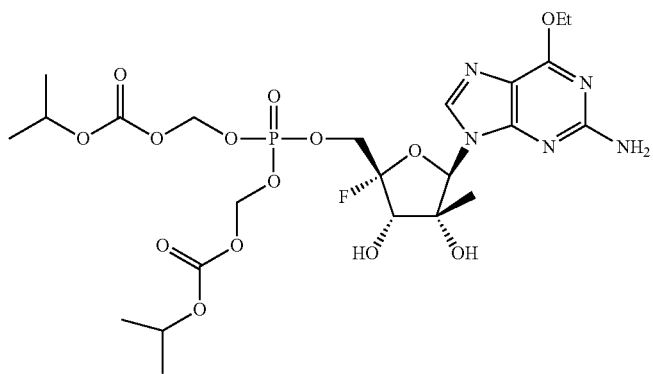

52

Compound 52-2 (158 mg, 50%) was from 52-1 (0.21 g; 0.35 mmol) and triethylammonium bis(isopropyloxycarbonyloxymethyl)phosphate (0.54 mmol) with DIPEA (0.18 mL), BopCl (178 mg), and 3-nitro-1,2,4-triazole (80 mg) in THF (4 mL).

A solution of 52-2 (158 mg) in acetonitrile (1 mL) and HCl (4 N/dioxane; 85 μL) was stirred at R.T. for 30 mins. The reaction was quenched with MeOH and concentrated. The residue was purified on silica gel (10 g column) with $CH_2Cl_2$/i-PrOH (3-10% gradient) to give compound 52 (85 mg, 76%). MS: m/z=656 [M+1]$^+$.

Example 22

Compound 11 trated and purified on silica gel (10 g column) with $CH_2Cl_2$/MeOH (4-11% gradient) to give 11-2 (100 mg, 90%).

Compound 11-2 was rendered anhydrous by co-evaporating with pyridine, followed by toluene. To a solution of 11-2 (24 mg, 0.04 mmol), and N-methylimidazole (17 μL, 5 eq.) in acetonitrile (1 mL) was added the phosphorochloridate (50 mg, 3.5 eq.) in 2 portions in 6 h intervals. The mixture was stirred at R.T. for 1 d and evaporated. Purification on silica (10 g column) with $CH_2Cl_2$/MeOH (4-12% gradient) yielded 11-3 (10 mg, 28%).

A solution of 11-3 (9 mg, 0.01 mmol) in 80% formic acid was stirred 3 h at R.T. The mixture was evaporated and purified on silica (10 g column) with $CH_2Cl_2$/MeOH (5-15% gradient) to give compound 11 (3 mg, 50%). MS: m/z=624 [M−1]$^-$.

Example 23

Compound 14

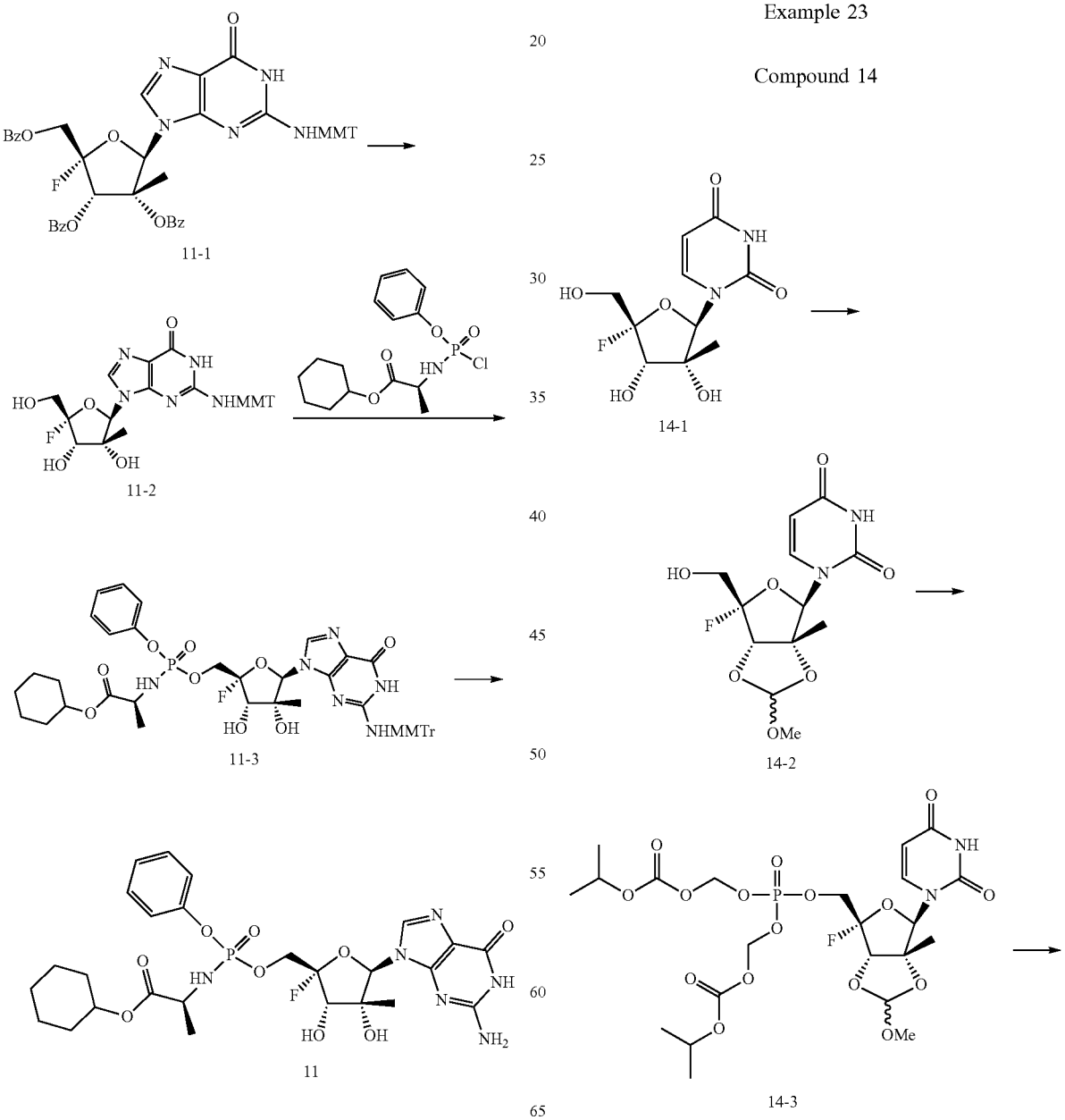

A mixture of 11-1 (170 mg, 0.19 mmol) and methanolic ammonia (7 N; 3 mL) was stirred at R.T. for 8 h, concen- -continued

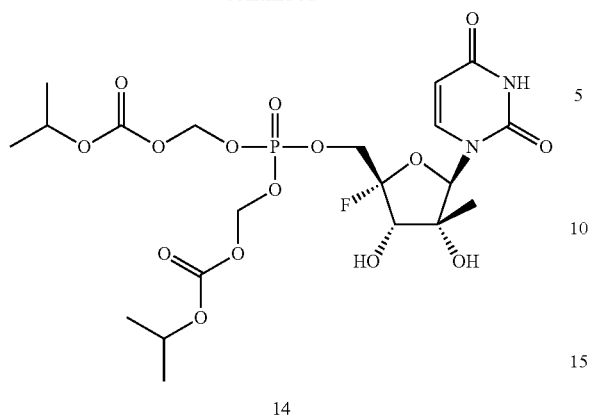

14

A mixture of 14-1 (1.2 g, 4.3 mmol), PTSA monohydrate (0.82 g, 1 eq.), and trimethyl orthoformate (14 mL, 30 eq.) in dioxane (30 mL) was stirred overnight at R.T. The reaction was neutralized with 7 N $NH_3$/MeOH and a white solid removed by filtration. The residue was dissolved in THF (10 mL) and treated with 80% aq. AcOH (5 mL). The mixture was kept at R.T. for 45 mins and then evaporated. The residue was purified on silica gel (25 g column) with $CH_2Cl_2$/MeOH (4-10% gradient) to give 14-2 (1.18 g, 87%).

Compound 14-3 (137 mg, 75%) was prepared from 14-2 (93 mg, 0.29 mmol) and triethylammonium bis(isopropyloxycarbonyloxymethyl)phosphate (0.44 mmol) with DIPEA (0.2 mL), BopCl (147 mg), and 3-nitro-1,2,4-triazole (66 mg) in THF (3 mL). Purification was done with $CH_2Cl_2$/i-PrOH solvent system (3-10% gradient).

A solution of 14-3 (137 mg) in 80% aq. HCOOH was stirred at R.T. for 2 h, and then concentrated. The residue was co-evaporated with toluene and then MeOH containing a small amount of a small amount of $Et_3N$ (2 drops). Purification on silica (25 g column) with $CH_2Cl_2$/MeOH (4-10% gradient) gave compound 14 (100 mg, 77%). MS: m/z=1175 [2M−1]⁻.

Example 24

Compound 16

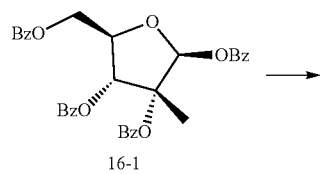

16-1

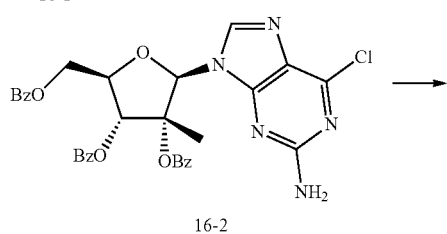

16-2

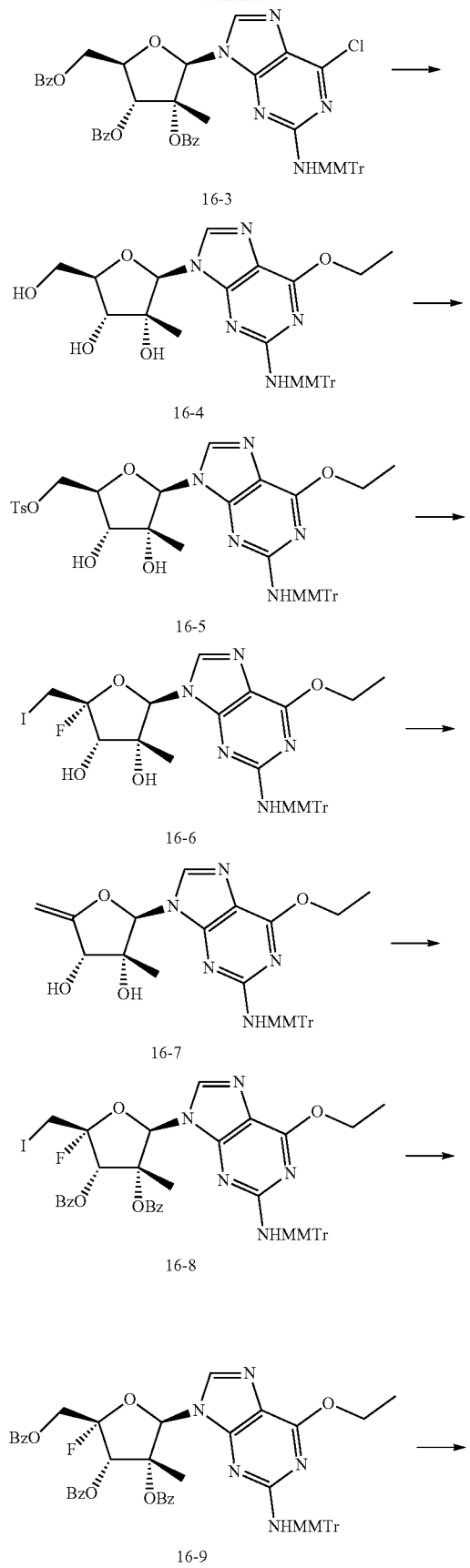

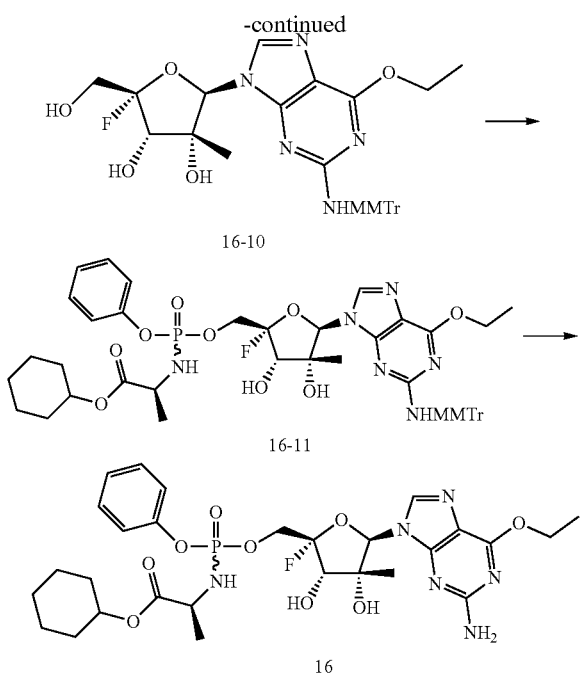

Compound 16-1 (50 g, 86.0 mmol) and 6-Cl-guanine (16.1 g, 98.2 mmol) were co-evaporated with anhydrous toluene 3 times. To a solution of 10-1 in MeCN (200 mL) was added DBU (39.5 g, 258.0 mmol) at 0° C. The mixture was stirred at 0° C. for 30 mins, and then TMSOTf (95.5 g, 430.0 mmol) was added dropwise at 0° C. The mixture was stirred at 0° C. for 30 mins. The mixture was heated to 70° C., and stirred overnight. The solution was cooled to R.T. and diluted with EA (100 mL). The solution was washed with sat. NaHCO$_3$ solution and brine. The organic layer was dried over Na$_2$SO$_4$, and concentrated at low pressure. The residue was purified by column on silica gel (EA in PE from 10% to 40%) to give 16-2 (48.0 g, yield: 88.7%) as a yellow foam. ESI-MS: m/z 628 [M+H]$^+$.

To a solution of 16-2 (48.0 g, 76.4 mol), AgNO$_3$ (50.0 g, 294.1 mmol) and collidine (40 mL) in anhydrous DCM (200 mL) was added MMTrCl (46.0 g, 149.2 mmol) in small portions under N$_2$. The mixture was stirred at R.T. for 3 h under N$_2$. The reaction was monitored by TLC. The mixture was filtered, and the filter was washed with sat. NaHCO$_3$ solution and brine. The organic layer was dried over anhydrous Na$_2$SO$_4$, and concentrated at low pressure. The residue was purified by silica gel column (EA in PE from 5% to 50%) to the give crude 16-3 (68 g, 98%). ESI-MS: m/z 900.1 [M+H]$^+$.

Sodium (8.7 g, 378.0 mmol) was dissolved in dry EtOH (100 mL) at 0° C., and slowly warmed to R.T. Compound 16-3 (68.0 g, 75.6 mmol) was treated with freshly prepared NaOEt solution, and stirred overnight at R.T. The reaction was monitored by TLC, and the mixture was concentrated at low pressure. The mixture was diluted with H$_2$O (100 mL), and extracted with EA (3×100 mL). The organic layer was dried over anhydrous Na$_2$SO$_4$, and evaporated at low pressure. The residue was purified by silica gel column chromatography (MeOH in DCM from 1% to 5%) to give 16-4 (34.0 g, 75.2%) as a yellow solid. ESI-MS: m/z 598 [M+H]$^+$.

Compound 16-4 (32.0 g, 53.5 mmol) was co-evaporated with anhydrous pyridine 3 times. To an ice-cooled solution of 16-4 in anhydrous pyridine (100 mL) was added TsCl (11.2 g, 58.9 mmol) in pyridine (50 mL) dropwise at 0° C. The mixture was stirred for 18 h. at 0° C. The reaction was checked by LCMS (about 70% was the desired product). The reaction was quenched with H$_2$O, and the solution was concentrated at low pressure. The residue was dissolved in EA (100 mL), and washed with sat. NaHCO$_3$ solution. The organic layer was dried over anhydrous Na$_2$SO$_4$, and evaporated at low pressure. The residue was purified by silica gel column chromatography (MeOH in DCM from 1% to 5%) to give crude 16-5 (25.0 g, 62.2%) as a yellow solid. ESI-MS: m/z 752 [M+H]$^+$.

To a solution of 16-5 (23.0 g, 30.6 mmol) in acetone (150 mL) was added NaI (45.9 g, 306.0 mmol) and TBAI (2.0 g), and refluxed overnight. The reaction was monitored by LCMS. After the reaction was complete, the mixture was concentrated at low pressure. The residue was dissolved in EA (100 mL), washed with brine, and dried over anhydrous Na$_2$SO$_4$. The organic solution was evaporated at low pressure. The residue was purified by silica gel column chromatography (DCM:MeOH=100:1 to 20:1) to give the crude product. To a solution of the crude product in dry THF (200 mL) was added DBU (14.0 g, 91.8 mmol), and heated to 60° C. The mixture was stirred overnight, and checked by LCMS. The reaction was quenched with sat. NaHCO$_3$, and the solution was extracted with EA (100 mL). The organic layer was dried over anhydrous Na$_2$SO$_4$, and evaporated at low pressure. The residue was purified by silica gel column chromatography (MeOH in DCM from 1% to 5%) to give 16-6 (12.0 g, 67.4%) as a yellow solid. ESI-MS: m/z 580 [M+H]$^+$.

To an ice-cooled solution of 16-6 (8.0 g, 13.8 mmol) in dry MeCN (100 mL) was added NIS (3.9 g, 17.2 mmol) and TEA.3HF (3.3 g, 20.7 mmol) at 0° C. The mixture was stirred at R.T. for 18 h and checked by LCMS. After the reaction was complete, the reaction was quenched with sat Na$_2$SO$_3$ and sat. NaHCO$_3$ solution. The solution was extracted with EA. The organic layer was dried over anhydrous Na$_2$SO$_4$, and evaporated at low pressure. The residue was purified by silica gel column chromatography (EA in PE from 10% to 50%) to give 16-7 (7.2 g, 72.0%) as a solid. ESI-MS: m/z 726 [M+H]$^+$.

To a solution of crude 16-7 (7.2 g, 9.9 mmol) in dry DCM (100 mL) was added DMAP (3.6 g, 29.8 mmol), and BzCl (2.8 g, 19.8 mmol) at 0° C. The mixture was stirred overnight, and checked by LCMS. The mixture was washed with sat. NaHCO$_3$ solution. The organic layer was dried over anhydrous Na$_2$SO$_4$, and evaporated at low pressure. The residue was purified by silica gel column chromatography (EA in PE from 10% to 30%) to give 16-8 (8.0 g, 86.4%) as a solid. ESI-MS: m/z 934 [M+H]$^+$.

To a solution of 16-8 (7.5 g, 8.0 mmol) in dry DMF (100 mL) was added NaOBz (11.5 g, 80.0 mmol) and 15-crown-5 (15.6 mL). The mixture was stirred for 36 h. at 90° C. The mixture was diluted with H$_2$O (100 mL), and extracted with EA (3×150 mL). The organic layer was dried over anhydrous Na$_2$SO$_4$, and evaporated at low pressure. The residue was purified by silica gel column chromatography (EA in PE from 10% to 30%) to give crude 16-9 (6.0 g, 80.0%) as a solid. ESI-MS: m/z 928 [M+H]$^+$.

Compound 16-9 (4.0 g, 4.3 mmol) was co-evaporated with anhydrous toluene 3 times, and treated with NH$_3$/MeOH (50 mL, 4N) at R.T. The mixture was stirred for 18 h at R.T. The reaction was monitored by LCMS, and the mixture was concentrated at low pressure. The residue was purified by silica gel column chromatography (EA in PE from 30% to 50%) to give 16-10 (1.9 g, 71.7%) as a solid. ESI-MS: m/z 616 [M+H]$^+$.

Compound 16-10 (300.0 mg, 0.49 mmol) was co-evaporated with anhydrous toluene 3 times, and was dissolved in MeCN (2 mL). The mixture was treated with NMI (120.5 mg, 1.47 mmol) and the phosphorochloridate reagent (338.1 mg, 0.98 mmol) in MeCN (1 mL) at 0° C. The mixture was stirred for 18 h at R.T. The reaction was monitored by LCMS. The mixture was diluted with 10% NaHCO₃ solution, and extracted with EA. The residue was purified by silica gel column chromatography (EA in PE from 30% to 50%) to give 16-11 (240 mg, 53.3%) as a solid. ESI-MS: m/z 925 [M+H]⁺.

Compound 16-11 (240.0 mg, 0.26 mmol) was treated with 80% AcOH (10 mL), and the mixture was stirred for 18 h at R.T. The reaction was monitored by LCMS. The mixture was concentrated at low pressure. The residue was purified by silica gel column chromatography (MeOH in DCM from 1% to 3%) to give compound 16 (87.6 mg, 51.7%) as a solid. ESI-MS: m/z 653 [M+H]⁺.

Example 25

Compound 30

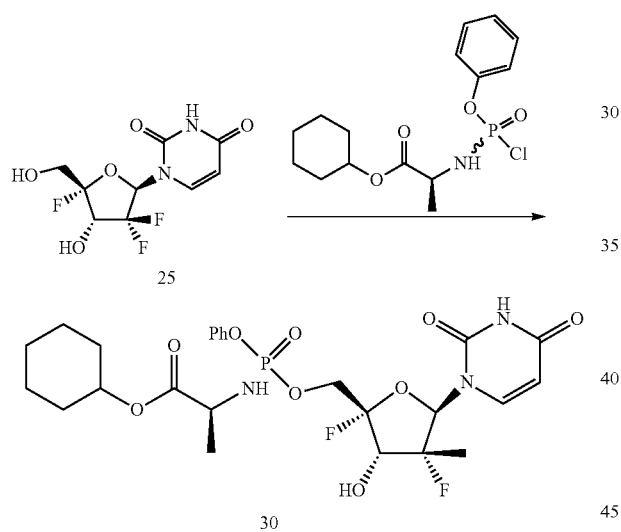

To a stirred solution of compound 25 (60 mg, 0.22 mmol) in anhydrous THF (2.0 mL) was added N-methylimidazole (0.142 mL, 1.73 mmol) at 0° C. (dry ice/acetone bath) followed by solution of phenyl (cyclohexanoxy-L-alaninyl) phosphorochloridate (235 mg, 0.68 mmol, dissolved in THF (2 mL). The resulting solution was stirred at 0° C. for 1 h, and the temperature was raised up-to 10° C. over the next 1 h. The reaction left at 10° C. for 3 h. The mixture was cooled to 0 to 5° C., diluted with EA, and water (5 mL) was added. The solution was washed with H₂O and brine. The organic layer was separated, dried over anhydrous Na₂SO₄ and filtered. The filtrate was concentrated in vacuum to give a residue, which dissolved in 25% CH₃CN/H₂O. The compound was purified on a reverse-phase HPLC (C18) using acetonitrile and water, followed by lyophilization gave a white foam. The produce was re-dissolved in EtOAc, washed with 50% aqueous citric acid solution, dried over anhydrous MgSO₄ and filtered. The filtrate was concentrated in vacuum, and lyophilized to give two isomers (Rp/Sp) of compound 30 (6.3 mg). MS: m/z 586.05 [1\441]⁻.

Example 26

Compound 17

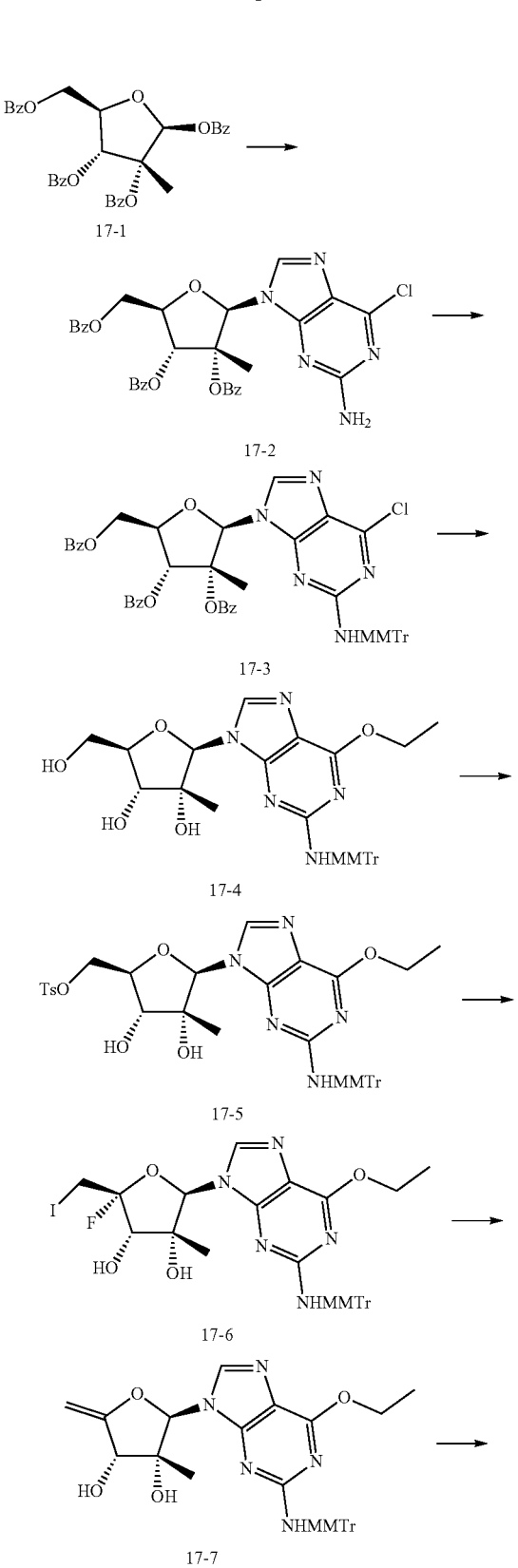

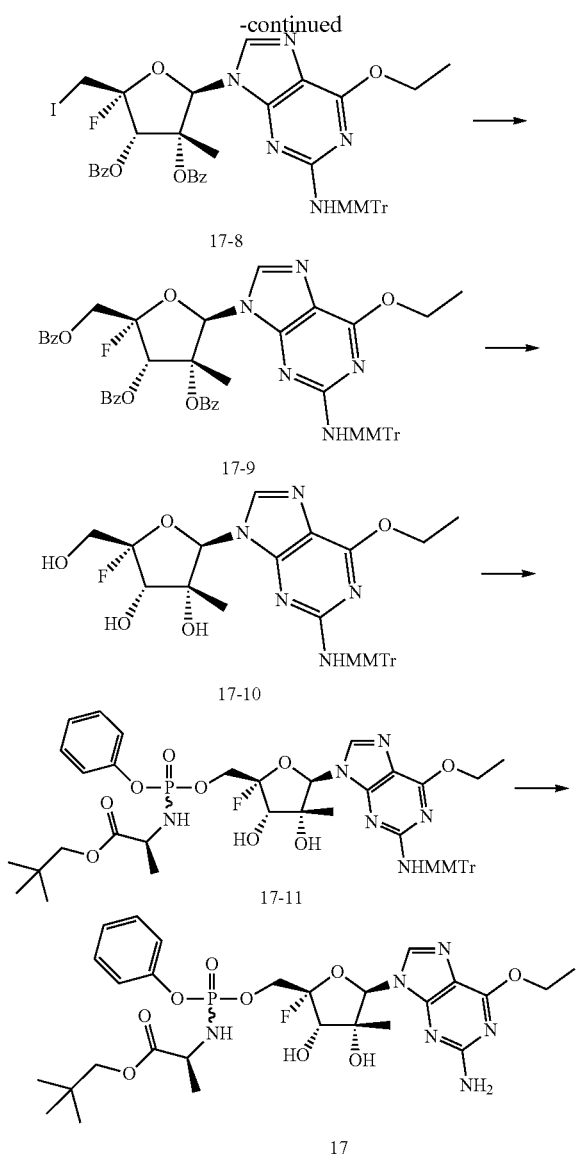

Compound 17-1 (50 g, 86.0 mmol) and 6-C₁-guanine (16.1 g, 98.2 mmol) were co-evaporated with anhydrous toluene 3 times. To a solution of 17-1 (50 g, 86.0 mmol) and 6-C₁-guanine (16.1 g, 98.2 mmol) in MeCN (200 mL) was added DBU (39.5 g, 258.0 mmol) at 0° C. The mixture was stirred at 0° C. for 30 mins, and TMSOTf (95.5 g, 430.0 mmol) was added dropwise at 0° C. The mixture was stirred at 0° C. for 30 mins until a clear solution was observed. The mixture was heated to 70° C., and stirred overnight. The solution was cooled to R.T., and diluted with EA (100 mL). The solution was washed with sat. NaHCO₃ solution and brine. The organic layer was dried over Na₂SO₄, and concentrated at low pressure. The residue was purified by column on silica gel (EA in PE from 10% to 40%) to give 17-2 (48.0 g, 88.7%) as a yellow foam. ESI-MS: m/z 628 [M+H]⁺.

To a solution of 17-2 (48.0 g, 76.4 mol), AgNO₃ (50.0 g, 294.1 mmol) and collidine (40 mL) in anhydrous DCM (200 mL) was added MMTrCl (46.0 g, 149.2 mmol) in small portions under N₂. The mixture was stirred at R.T. for 3 h under N₂. Completion of the reaction was determined by TLC. After filtration, the filtrate was washed with sat. NaHCO₃ solution and brine. The organic layer was dried over anhydrous Na₂SO₄, and concentrated at low pressure. The residue was purified by silica gel column (EA in PE from 5% to 50%) to the give crude 17-3 (68 g, 98%). ESI-MS: m/z 900.1 [M+H]⁺.

Sodium (8.7 g, 378.0 mmol) was dissolved in dry EtOH (100 mL) at 0° C., and slowly warmed to R.T. Compound 17-3 (68.0 g, 75.6 mmol) was treated with freshly prepared NaOEt solution, and stirred overnight at R.T. Completion of the reaction was determined by TLC and LCMS. The mixture was concentrated at a low pressure, diluted with H₂O (100 mL), and extracted with EA (3×100 mL). The organic layer was dried over anhydrous Na₂SO₄, and evaporated at low pressure. The residue was purified by silica gel column chromatography (MeOH in DCM from 1% to 5%) to give 17-4 (34.0 g, 75.2%) as a yellow solid. ESI-MS: m/z 598 [M+H]⁺.

Compound 17-4 (32.0 g, 53.5 mmol) was co-evaporated with anhydrous pyridine 3 times. To an ice-cooled solution of 17-4 (32.0 g, 53.5 mmol) in anhydrous pyridine (100 mL) was added a solution of TsCl (11.2 g, 58.9 mmol) in pyridine (50 mL) dropwise at 0° C. The mixture was stirred for 18 h. at 0° C. The reaction was monitored by LCMS, and quenched with H₂O. The solution was concentrated at low pressure, and the residue was dissolved in EA (100 mL), and washed with sat. NaHCO₃ solution. The organic layer was dried over anhydrous Na₂SO₄, and evaporated at a low pressure. The residue was purified by silica gel column chromatography (MeOH in DCM from 1% to 5%) to give crude 17-5 (25.0 g, 62.2%) as a yellow solid. ESI-MS: m/z 752 [M+H]⁺.

To a solution of 17-5 (23.0 g, 30.6 mmol) in acetone (150 mL) was added NaI (45.9 g, 306.0 mmol) and TBAI (2.0 g), and the mixture was refluxed overnight. Completion of the reaction was determined by LCMS. The mixture was concentrated at low pressure, and the residue was dissolved in EA (100 mL). The solution was washed with brine, and dried over anhydrous Na₂SO₄. The organic solution was evaporated at low pressure, and the residue was purified by silica gel column chromatography (DCM:MeOH=100:1 to 20:1) to give a crude product. To a solution of the crude product in dry THF (200 mL) was added DBU (14.0 g, 91.8 mmol), and the mixture was heated to 60° C. and stirred overnight. The reaction was monitored by LCMS. The reaction was quenched with sat. NaHCO₃ solution, and the solution was extracted with EA (100 mL). The organic layer was dried over anhydrous Na₂SO₄, and evaporated at low pressure. The residue was purified by silica gel column chromatography (MeOH in DCM from 1% to 5%) to give 17-6 (12.0 g, 67.4%) as a yellow solid. ESI-MS: m/z 580 [M+H]⁺.

To an ice-cooled solution of 17-6 (8.0 g, 13.8 mmol) in anhydrous MeCN (100 mL) was added NIS (3.9 g, 17.2 mmol) and TEA.3HF (3.3 g, 20.7 mmol) at 0° C. The mixture was stirred at R.T. for 18 h, and the reaction was checked by LCMS. After the reaction was completed, the reaction was quenched with sat. Na₂SO₃ solution and sat. NaHCO₃ solution. The solution was extracted with EA (3×100 mL). The organic layer was dried over anhydrous Na₂SO₄, and evaporated at low pressure. The residue was purified by silica gel column chromatography (EA in PE from 10% to 50%) to give 17-7 (7.2 g, 72.0%) as a solid. ESI-MS: m/z 726 [M+H]⁺.

To a solution of 17-7 (7.2 g, 9.9 mmol) in dry DCM (100 mL) was added DMAP (3.6 g, 29.8 mmol), and BzCl (2.8 g, 19.8 mmol) at 0° C. The mixture was stirred overnight, and checked by LCMS. The mixture was washed with sat.

NaHCO$_3$ solution. The organic layer was dried over anhydrous Na$_2$SO$_4$, and evaporated at low pressure. The residue was purified by silica gel column chromatography (EA in PE from 10% to 30%) to give 17-8 (8.0 g, 86.4%) as a solid. ESI-MS: m/z 934 [M+H]$^+$.

To a solution of 17-8 (7.5 g, 8.0 mmol) in dry DMF (100 mL) was added NaOBz (11.5 g, 80.0 mmol) and 15-crown-5 (15.6 mL). The mixture was stirred for 36 h. at 90° C. The mixture was diluted with H$_2$O (100 mL), and extracted with EA (3×150 mL). The organic layer was dried over anhydrous Na$_2$SO$_4$, and evaporated at low pressure. The residue was purified by silica gel column chromatography (EA in PE from 10% to 30%) to give crude 17-9 (6.0 g, 80.0%) as a solid. ESI-MS: m/z 928 [M+H]$^+$.

Compound 17-9 (4.0 g, 4.3 mmol) was co-evaporated with anhydrous toluene 3 times, and treated with NH$_3$/MeOH (50 mL, 4N) at R.T. The mixture was stirred for 18 h. at R.T. Completion of the reaction was determined by LCMS. The mixture was concentrated at low pressure, and the residue was purified by silica gel column chromatography (EA in PE from 30% to 50%) to give product 17-10 (1.9 g, 71.7%) as a solid. ESI-MS: m/z 616 [M+H]$^+$.

Compound 17-10 (300.0 mg, 0.49 mmol) was co-evaporated with anhydrous toluene 3 times, and was dissolved in MeCN (2 mL). The mixture was treated with NMI (120.5 mg, 1.47 mmol) and the phosphorochloridate reagent (326.3 mg, 0.98 mmol) in MeCN (1 mL) at 0° C. The mixture was stirred for 18 h at R.T. and monitored by LCMS. The mixture was diluted with 10% NaHCO$_3$ solution, and extracted with EA (3×30 mL). The residue was purified by silica gel column chromatography (EA in PE from 30% to 50%) to give 17-11 (210 mg, 47.5%) as a solid. ESI-MS: m/z 913.0 [M+H]$^+$.

Compound 17-11 (210 mg, 0.26 mmol) was treated with 80% of AcOH (15 mL), and the mixture was stirred for 18 h at R.T. Completion of the reaction was determined by LCMS. The mixture was concentrated at low pressure, and the residue was purified by silica gel column chromatography (MeOH in DCM from 1% to 3%) to give compound 17 (71.8 mg, 48.7%) as a solid. ESI-MS: m/z 641.3 [M+H]$^+$.

Example 27

Compounds 9, 12, 15, 26, 28, 38, 44, 46, 50, 63, 64, 69 and 76

Compounds 9, 12, 15, 26, 28, 38, 44, 46, 50, 63, 64, 69 and 76 were prepared in a manner similar to method for preparing compound 6. After the addition of POCl$_3$, the mixture was kept at R.T. for 20-40 mins. The reaction was controlled by LCMS and monitored by the appearance of corresponding nucleoside 5'-monophosphate. After completion of the reaction, tetrabutylammonium salt of pyrophosphate (150 mg) was added, followed by DMF (0.5 mL) to get a homogeneous solution. After 1.5 h at ambient temperature, the reaction was diluted with water (10 mL). The triphosphate (eluted at 75-80% B) were obtained as described for compound 6.

| Structure | MS [M − 1]$^-$ | $^{31}$P NMR P($\alpha$) | P($\beta$) | P($\gamma$) |
|---|---|---|---|---|
| 28 | 556.2 | −10.92 −11.03(d) | — 23.18(t) | −11.86 −11.89(d) |
| 38 | 516.1 | −7.49 −7.61(d) | — 22.42(t) | −12.17 −12.30(d) |
| 9 | 554.0 | −10.94 −11.06(d) | — 23.25(t) | −11.85 −11.97(d) |

-continued

| Structure | MS [M − 1]⁻ | ³¹P NMR P(α) | P(β) | P(γ) |
|---|---|---|---|---|
| 12 | 525.2 | −8.53(bs) | −22.61 (bs) | −12.17 −12.29(d) |
| 15 | 564.4 | −11.05 (bs) | −23.25 (bs) | −11.96 −12.08(d) |
| 44 | 566.0 | −10.92 −11.04(d) | — 23.18(t) | −11.93 −1(d) |
| 46 | 533.3 | −10.89 −11.01(d) | — 23.31(t) | −12.49 −1(d) |
| 50 | 513.8 | −8.66(bs) | — 22.80(t) | −12.17 −12.29(d) |

-continued
| Structure | MS [M − 1]− | 31P NMR | | |
|---|---|---|---|---|
| | | P(α) | P(β) | P(γ) |
| 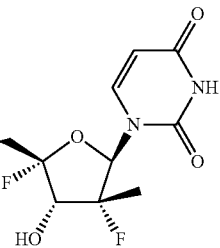 26 | 517.7 | −13.73 −13.60(d) | — 25.98(t) | −15.18 −15.06(d) |
| 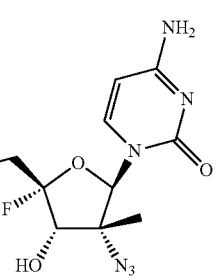 63 | 539.5 | −7.42(br.s) | — 22.57(t) | −12.23 −12.34(d) |
| 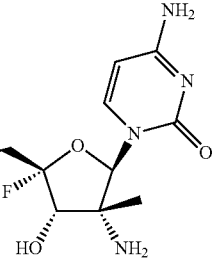 64 | 513.1 | −6.36 −6.49(d) | — 22.49(t) | −12.20 −12.33(d) |
| 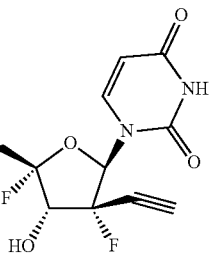 69 | 526.8 | −10.96 −11.08(d) | — 23.33(t) | −12.41 −12.53(d) |
| 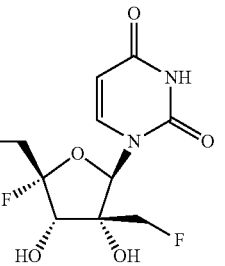 76 | 533.4 | −10.78 (br.s) | — 23.22(t) | −12.24 −12.36(d) |

The following compounds can also be prepared using a method similar to the method described in Example 27:
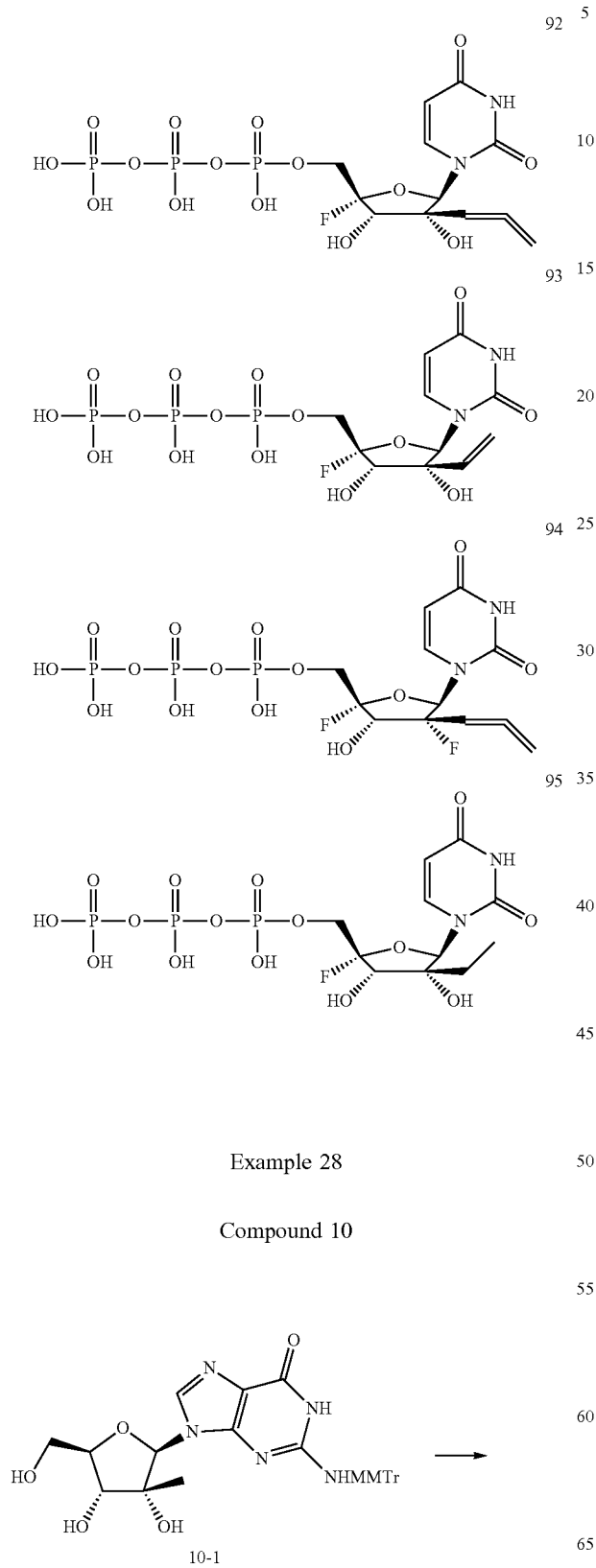
Example 28
Compound 10
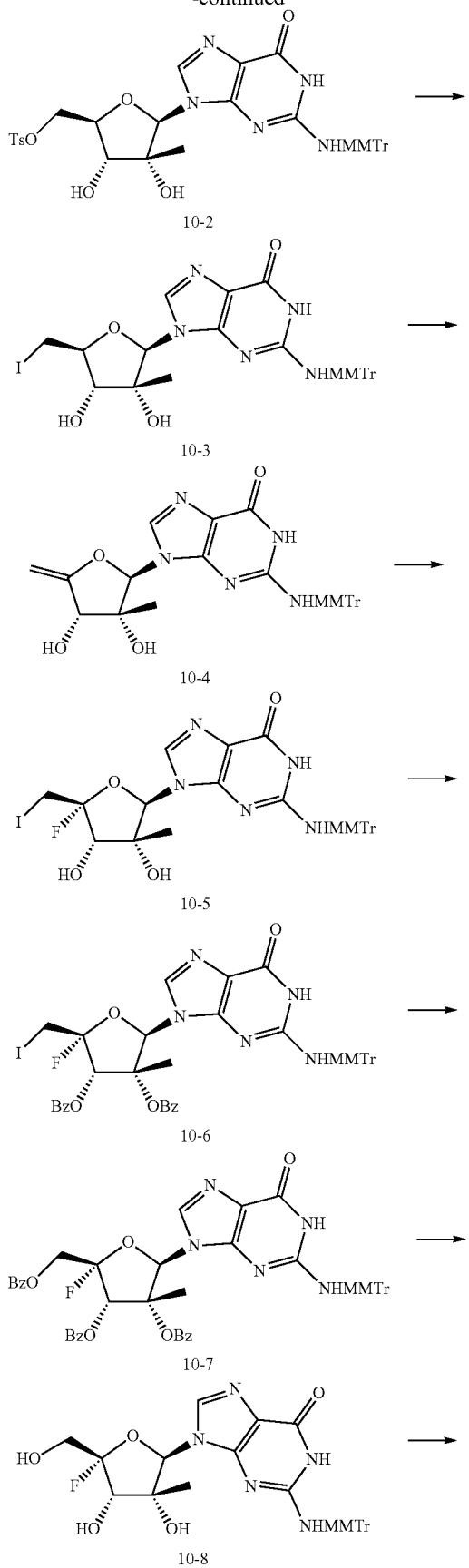

-continued

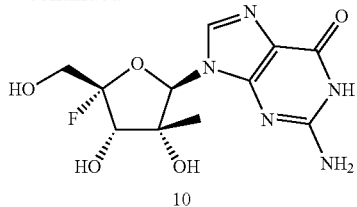

10

Compound 10-1 (5 g, 8.79 mmol) was co-evaporated with anhydrous pyridine. To an ice-cooled solution of 10-1 in anhydrous pyridine (15 mL) was added TsCl (3.43 g, 17.58 mmol), and stirred for 1 h at 0° C. The reaction was checked by LCMS and TLC. The reaction was quenched with H$_2$O, and extracted with EA. The organic phase was dried over anhydrous Na$_2$SO$_4$, and evaporated at low pressure. Compound 10-2 (6.35 g, 100%) was used for next step directly.

To a solution of 10-2 (31.77 g, 43.94 mmol) in acetone (300 mL) was added NaI (65.86 g, 439.4 mmol), and heated to reflux overnight. The reaction was checked by LCMS. The reaction was quenched with sat. Na$_2$S$_2$O$_3$ solution, and extracted with EA. The organic layer was dried over anhydrous Na$_2$SO$_4$, and evaporated at low pressure. The residue was purified by silica gel column chromatography (MeOH in DCM from 1% to 6%) to give 10-3 (11.5 g, 38%) as a white solid.

To a solution of 10-3 (11.5 g, 16.94 mmol) in dry THF (120 mL) was added DBU (12.87 g, 84.68 mmol), and heated to 60° C. The reaction was stirred overnight and checked by LCMS. The reaction was quenched with sat. NaHCO$_3$ solution, and extracted with EA. The organic phase was dried over anhydrous Na$_2$SO$_4$, and evaporated at low pressure. The residue was purified by silica gel column chromatography (MeOH in DCM from 1% to 5%) to give 10-4 (5.5 g, 54%) as a white solid.

To an ice-cooled solution of 10-4 (500 mg, 0.90 mmol) in dry DCM (20 ml) was added AgF (618 mg, 4.9 mmol) and a solution of I$_2$ (500 mg, 1.97 mmol) in dry DCM (20 mL). The reaction was stirred for 3 h., and checked by LCMS. The reaction was quenched with sat Na$_2$S$_2$O$_3$ solution and sat. NaHCO$_3$ solution, and the mixture was extracted with DCM. The organic layer was dried by anhydrous Na$_2$SO$_4$, and evaporated at low pressure to give crude 10-5 (420 mg, 66%).

To a solution of crude 10-5 (250 mg, 0.36 mmol) in dry DCM (8 mL) was added DMAP (0.28 g, 2.33 mmol), TEA (145 mg, 1.44 mmol) and BzCl (230 mg, 1.62 mmol) in a solution of DCM (2 mL). The reaction was stirred overnight, and checked by LCMS. The mixture was washed with sat. NaHCO$_3$ solution and brine. The organic layer was evaporated at low pressure. The residue was purified by prep-TLC to give crude 10-6 (150 mg, 46%).

To a solution of crude 10-6 (650 mg, 0.72 mmol) in dry HMPA (20 mL) was added NaOBz (1.03 g, 7.2 mmol) and 15-crown-5 (1.59 g, 7.2 mmol). The reaction was stirred for 2 d at 60° C. The mixture was diluted with H$_2$O, and extracted with EA. The organic layer was evaporated at low pressure. The residue was purified by prep-TLC to give 10-7 (210 mg, 32.4%). ESI-MS: m/z: 900.4 [M+H]$^+$.

A mixture of 10-7 (25 mg) and BuNH$_2$ (0.8 mL) was stirred overnight at R.T. The mixture was evaporated and purified on silica gel (10 g column) with CH$_2$Cl$_2$/MeOH (4-15% gradient) to yield 10-8 (15 mg, 91%).

A mixture of 10-8 (15 mg, 0.02 mmol) in ACN (0.25 mL) and 4 N HCL/dioxane (19 uL) was stirred at R.T. for 45 mins. The mixture was diluted with MeOH and evaporated. The crude residue was treated with MeCN, and the solid was filtered to yield compound 10 (7 mg). MS: m/z=314 [M−1]$^−$.

Example 29

Compounds 36 and 37

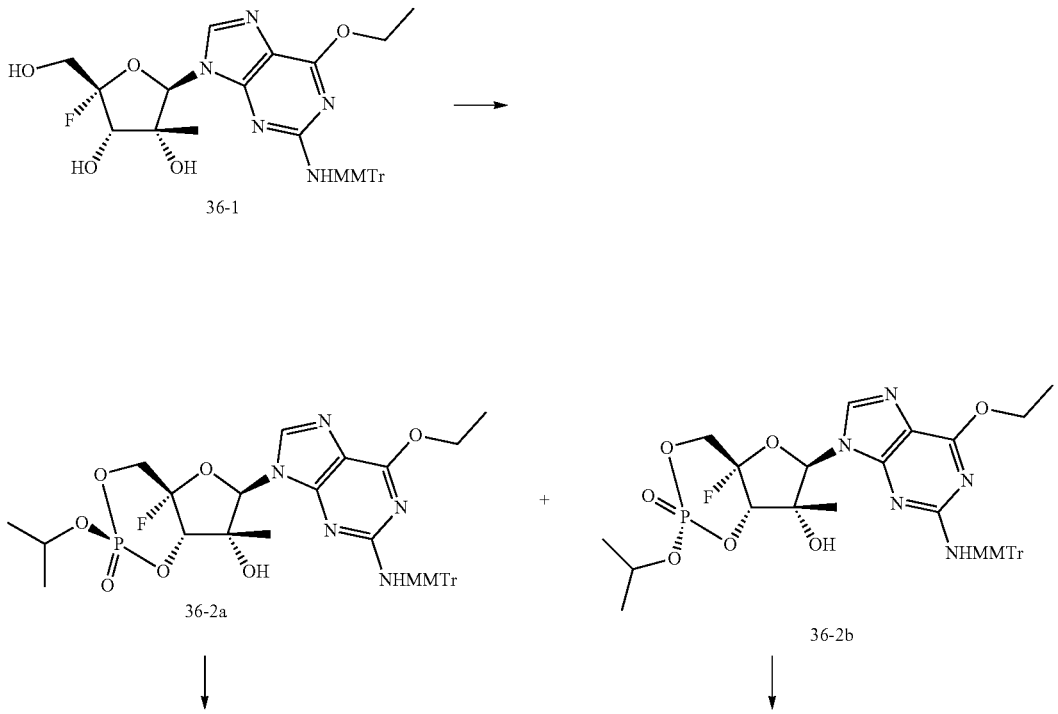

-continued

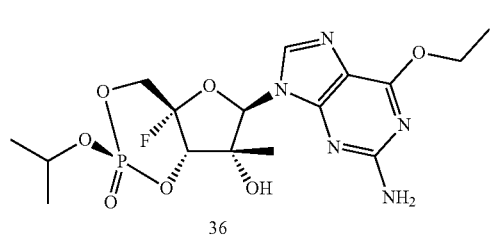

36

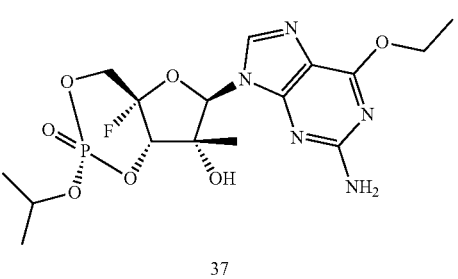

37

To a solution of 36-1 (150 mg, 0.24 mmol) in DCM (2.0 mL), triethylamine (141 μL, 2.0 mmol) was added at R.T. The mixture was cooled to 0 to 5° C. (ice/water bath), and freshly prepared and distilled isopropyl phosphorodichloridate (45 μL, 0.26 mmol, prepared according to a procedure, Reddy et al. J. Org. Chem. 2011, 76 (10), 3782-3790) was added. The mixture was stirred at 0 to 5° C. (ice/water bath) for 15 mins, followed by N-methylimidazole (40 μL, 0.49 mmol). The mixture was stirred for 1 h at 0 to 5° C. TLC showed the absence of starting material 36-1. EA (100 mL) was added, followed by water. The organic layer was washed with H$_2$O, sat. aq. NH$_4$Cl solution and brine. The organic layer was separated, dried over anhydrous MgSO$_4$ and filtered. The filtrate was concentrated in vacuum to give a residue, which was purified on silica gel with 0 to 10% iPrOH/DCM to give 36-2a (16.9 mg, faster eluting isomer) and 36-2b (72.7 mg, slower eluting isomer).

Compounds 36-2a and 36-2b were deprotected using a procedure described herein. Compound 36 (7.3 mg, single isomers from 36-2a (16.5 mg, 0.0235 mmol)) and compound 37 (29.0 mg. single isomers from 36-2b (72.7 mg, 0.1 mmol)) were obtained.

Compound 36: $^1$H NMR (CD$_3$OD-d$_4$, 400 MHz) δ 7.94 (s, 1H), 6.32 (s, 1H), 6.00-5.9 (br s, 1H), 4.9-4.487 (m, 1H), 4.83-4.77 (m, 1H), 4.65-4.50 (m, 3H), 1.45-1.39 (s, 9H), 1.2 (s, 3H); $^{19}$F NMR (CD$_3$OD-d$_4$) δ −120.3 (s); $^{31}$P NMR (CD$_3$OD-d$_4$) δ −5.19 (s); ESI-LCMS: m/z=448.05 [M+H]$^+$.
Compound 37: $^1$H NMR (CD$_3$OD-d$_4$, 400 MHz) δ 7.98 (s, 1H), 6.34 (s, 1H), 5.78-5.64 (br s, 1H), 4.95-4.48 (m, 2H), 4.62-4.52 (m, 3H), 1.48-1.42 (s, 9H), 1.1 (s, 3H); $^{19}$F NMR (CD$_3$OD-d$_4$) δ −121.3 (s); $^{31}$P NMR (CD$_3$OD-d$_4$) δ −7.38 (s); ESI-LCMS: m/z=448.05 [M+H]$^+$.

Example 30

Compound 48

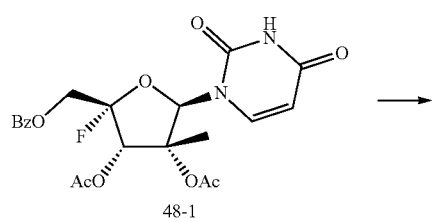

48-1

-continued 48-2

48

To a solution of 48-1 (600 mg, 1.29 mmol) in anhydrous CH$_3$CN (4 mL) was added DMAP (315 mg, 2.59 mmol), TEA (391 mg, 3.87 mmol) and TPSCl (782 mg, 2.58 mmol). The mixture was stirred for 3 h. under N$_2$. A solution of NH$_3$ in THF (2 mL) was added, and stirred for 1 h. The reaction was quenched with sat. NH$_4$Cl solution, and extracted with EA. The organic layer was dried over anhydrous Na$_2$SO$_4$, and concentrated to dryness at low pressure. The residue was purified by column chromatography to provide 48-2 (370 mg, 62%) as a white foam solid.

Compound 48-2 (370 mg, 1.48 mmol) in methanolic ammonium was stirred at R.T. for 4 h. The solution was concentrated to dryness to give compound 48 (200 mg, 91%) as a white solid. ESI-MS: m/z 275.9 [M+H]$^+$.

Example 31

Compounds 18 and 19

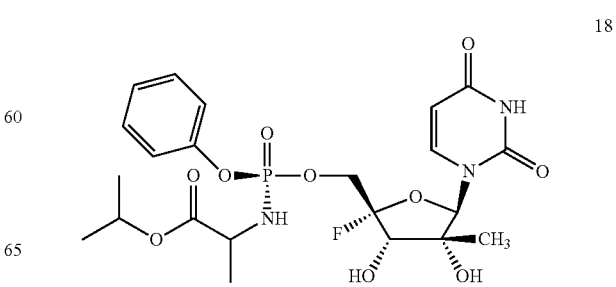

18

-continued

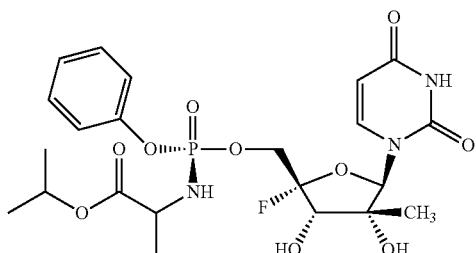

19

The diastereomers of compound 2 were separated by RP-HPLC. A gradient of 10-43% ACN in H$_2$O over 26 mins on a Synergi Hydro RP 30×250 m 4u particle column (Phenomenex PN 00G-4375-UO-AX) eluted compound 19 (29.5 mins) and compound 18 (30.1 mins). Pure fractions were lyophilized to produce a white powder. Compound 19: $^{31}$P-NMR (DMSO-d$_6$) 3.448 ppm; MS: m/z: 544 [M−1]$^-$; Compound 18: $^{31}$P-NMR (DMSO-d$_6$) 3.538 ppm; MS: m/z: 544 [M−1]$^-$.

Example 32

Compounds 20 and 21

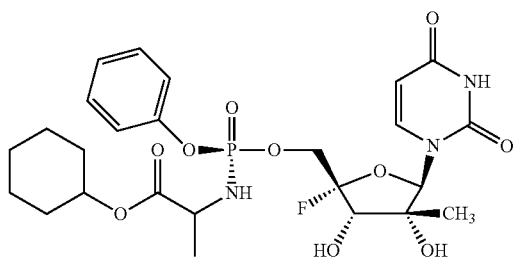

20

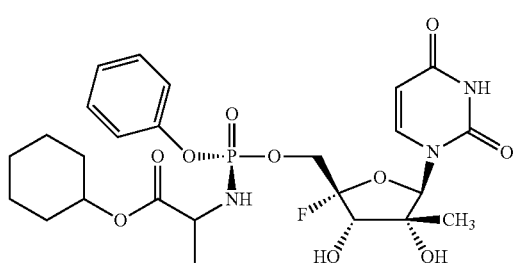

21

The diastereomers of compound 3 were separated by RP-HPLC. A gradient of 25-52% ACN in H$_2$O over 26 mins on a Synergi Hydro RP 30×250 m 4u particle column (Phenomenex PN 00G-4375-UO-AX) eluted compound 21 (24.8 mins) and compound 20 (25.3 mins). Pure fractions were lyophilized to produce a white powder. Compound 21: $^{31}$P-NMR (DMSO-d$_6$) 3.492 ppm; MS: m/z: 584 [M−1]$^-$. Compound 20: $^{31}$P-NMR (DMSO-d$_6$) 3.528 ppm; MS: m/z: 584 [M−1]$^-$.

Example 33

Compound 13

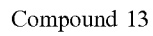

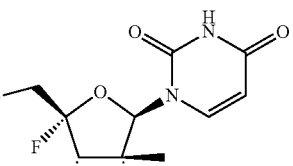

2-1

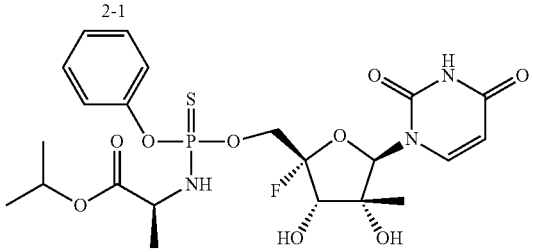

13

Compound 2-1 (32 mg, 0.1 mmol) was dissolved in dry THF (3 mL) and 2M solution of isopropylmagnesium bromide in THF (0.1 mL) was added at 0° C. The reaction was left for 1 h at R.T., and phenyl(isopropyl-L-alaninyl) thiophosphorochloridate was added (0.3 mmol). The mixture was left overnight at R.T. LSMS analysis showed about 20% of unreacted starting material. The same amount of Grignard reagent and thiophosphorochloridate were added, and the mixture was heated at 37° C. for 4 h. The reaction was quenched with NH$_4$Cl. The product was extracted with EA, washed with brine, dried over Na$_2$SO$_4$, and evaporated. The resulting oil was dissolved in 80% formic acid (4 mL) and in 1 h evaporated. Compound 13 was purified by RP HPLC in gradient of methanol in water from 30% to 95% on Synergy 4u Hydro-RP column (Phenominex) yielding a colorless solid. Compound 13 (7 mg, yield 12.5%). MS: m/z: 560.0 [M−1]$^-$.

Example 34

Compound 39, Bis-lithium Salt

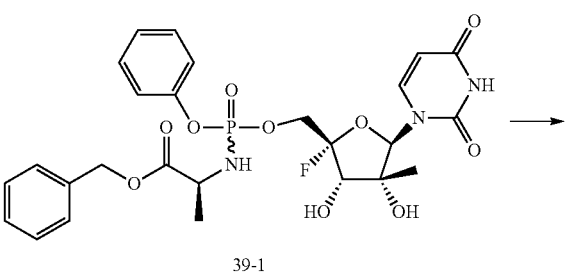

39-1

203
-continued

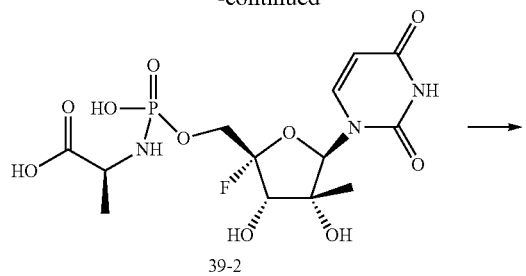
39-2

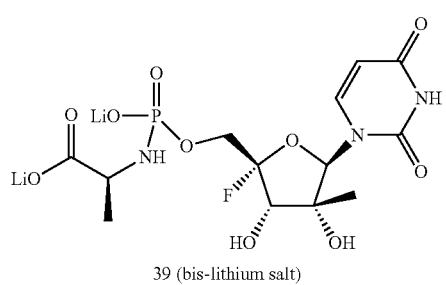
39 (bis-lithium salt)

Compound 39-1 was synthesized using a procedure similar for preparing compound 2 using alanine benzyl ester hydrochloride. LCMS: m/z 592 [M−1]⁻.

To a solution of 39-1 (1.1 g, 1.85 mmol) in dioxane (15 mL) and water (3 mL) was added aqueous triethylammonium acetate (2M, 2 mL, 4 mmol) followed by Pd—C (10%, 100 mg). The mixture was hydrogenated (balloon) for 2 h, and monitored by HPLC. The catalyst was filtered off, and the filtrate was concentrated to dryness. The residue was suspended in 3% solution of lithium perchlorate in acetone (25 mL). The solid was isolated by filtration, rinsed with acetone and dried under vacuum to give compound 39 (bis-lithium salt) (731 mg, 90%). LCMS: m/z 426 [M−1]⁻.

Example 35

Compound 55

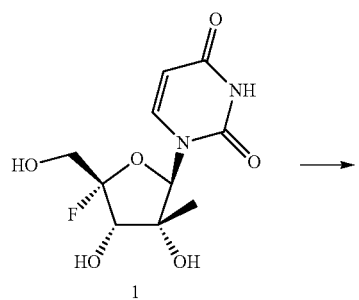
1

204
-continued

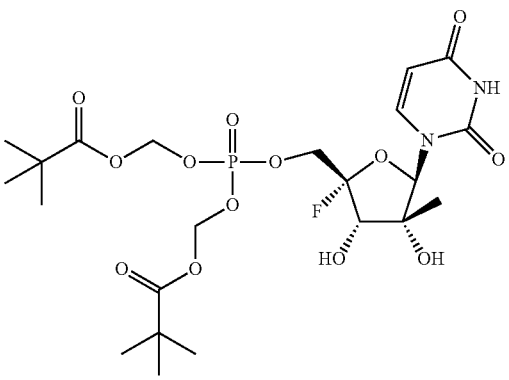
55

Compound 1 (40 mg, 0.14 mmol) and triethylammonium bis(pivaloyloxymethyl)phosphate (0.21 mmol, prepared from 80 mg of bis(pivaloyloxymethyl)phosphate and 30 μL of Et₃N) were rendered anhydrous by coevaporating with pyridine, followed by toluene. The evaporated residue was dissolved in anhydrous THF (2 mL) and cooled in an ice-bath. Diisopropylethyl amine (73 μL, 3 eq.), BopCl (71 mg, 2 eq.), and 3-nitro-1,2,4-triazole (32 mg, 2 eq.) were added. The mixture was stirred at 0° C. for 90 mins. The mixture was then diluted with EtOAc, washed with sat. aq. NaHCO₃ and brine, and dried (Na₂SO₄). Purification on silica gel column with CH₂Cl₂/i-PrOH solvent system (4-10% gradient) followed by RP-HPLC purification (A: water, B: MeCN) yielded compound 55 (13 mg, 16%). MS: m/z=1167 [2M−1].

Example 36

Compound 45

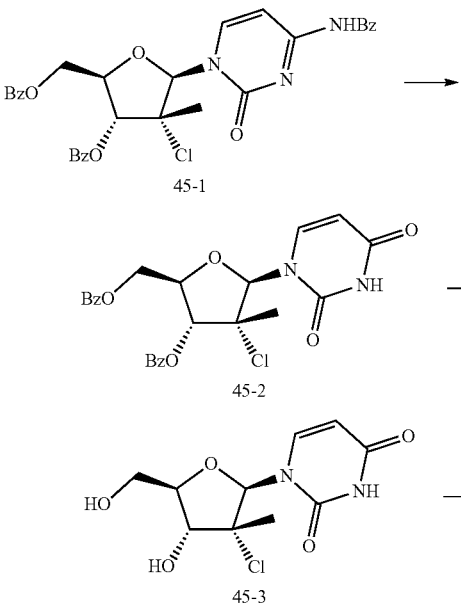

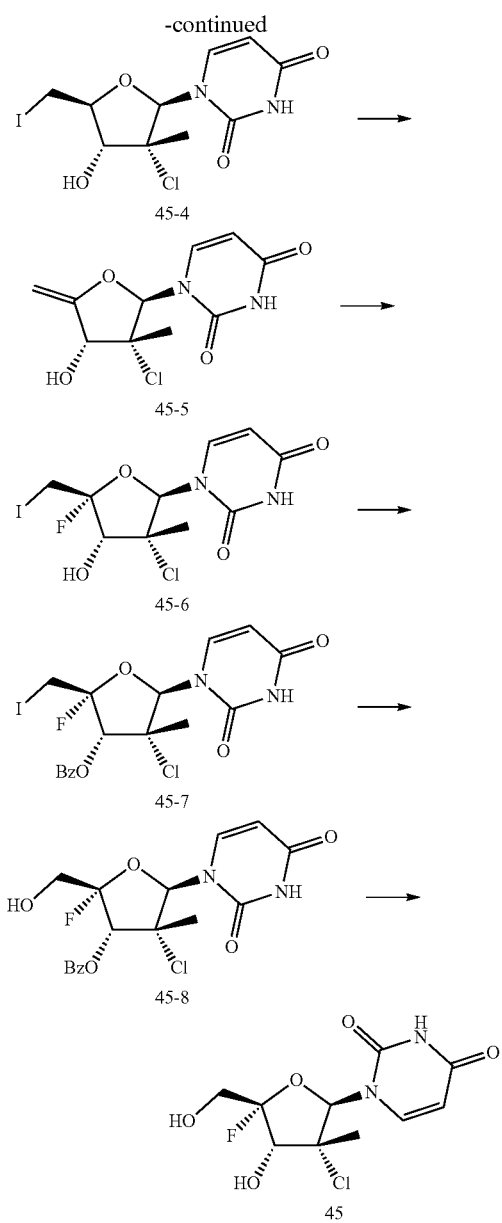

Compound 45-1 (15.0 g, 25.55 mmol) was treated with 90% HOAc (150 mL) at R.T. The mixture was stirred at 110° C. for 12 h, and then concentrated at a low pressure. The residue was dissolved in DCM, and the solution was washed with brine. The organic phase was dried over anhydrous Na$_2$SO$_4$, and then concentrated at a low pressure. The residue was purified by column chromatography (5% MeOH in DCM) to give 45-2 (11.0 g, 88.9%) as a white solid.

Compound 45-2 (12.0 g, 24.79 mmol) was treated with NH$_3$ in MeOH (200 mL, 7 M) at R.T. The solution was stirred at R.T. for 12 h, and then concentrated at a low pressure. The residue was purified by column chromatography (10% MeOH in DCM) to give 45-3 (6.5 g, 95.0%) as a white solid.

To a stirred suspension of 45-3 (4.3 g, 15.58 mmol), PPh$_3$ (8.16 g, 31.15 mmol), imidazole (2.11 g, 31.15 mmol) and pyridine (15 mL) in anhydrous THF (45 mL) was added a solution of I$_2$ (7.91 g, 31.15 mmol) in THF (100 mL) dropwise at 0° C. The mixture was slowly warmed to R.T. and stirred overnight. The mixture was quenched with MeOH (100 mL). The solvent was removed at a low pressure, and the residue was re-dissolved in a mixture of EA and THF (0.2 L, 10:1). The organic phase was washed with sat. Na$_2$S$_2$O$_3$ aq. (2×). The aqueous phase was extracted with a mixture of EA and THF (0.2 L, 10:1, 2×). The concentrated organic phase was dried over anhydrous Na$_2$SO$_4$. The residue was purified on a silica gel column (0-10% MeOH in DCM) to afford 45-4 (5.1 g, 85.0%) as a white solid.

Compound 45-4 (800 mg, 2.07 mmol) was dissolved in a mixture of DBU (4 mL) and THF (4 mL) at R.T. under N$_2$. The solution was stirred at R.T. for 1 h. The mixture was neutralized with HOAc, and extracted with a mixture of EA and THF (10:1, 40 mL). The organic phase was washed with brine, and dried over anhydrous Na$_2$SO$_4$. The concentrated organic phase was purified by column chromatography (0-10% MeOH in DCM) to give 45-5 (240 mg, 44.9%) as a white solid.

To an ice-cooled solution of 45-5 (1.20 g, 4.65 mmol) in anhydrous MeCN (12 mL) was added NIS (1.57 g, 6.97 mmol) and TEA.3HF (1.12 g, 6.97 mmol) under N$_2$. The mixture was stirred at R.T. for 5 h. The reaction was quenched with sat. NaHCO$_3$ solution, and extracted with EA (3×100 mL). The organic phase was dried over anhydrous Na$_2$SO$_4$, and evaporated to dryness at low pressure. The residue was purified on a silica gel column (0-5% MeOH in DCM) to give 45-6 (0.91 g, 48.6%) as a white solid.

To a stirred solution of 45-6 (1.2 g, 2.97 mmol) in anhydrous DCM (12 mL) was added BzCl (0.83 g, 5.94 mmol), TEA (0.6 g, 5.94 mmol) and DMAP (0.72 g, 5.94 mmol) successively at R.T. The mixture was stirred at R.T. for 12 h. The reaction was quenched with water, and extracted with EA (3×60 mL). The organic phase was concentrated at low pressure. The residue was purified by column chromatography (0-5% MeOH in DCM) to give 45-7 (1.2 g, 66.2%) as a white solid.

Tetra-butyl ammonium hydroxide (25.78 mL, 51.78 mmol) was neutralized with TFA (4.3 mL) to pH=4, and the solution was added to a solution of 45-7 (1.09 g, 2.14 mmol) in DCM (30 mL). m-CPBA (1.85 g, 10.74 mmol) was added portion-wise under vigorous stirring, and the mixture was stirred for 12 h. The mixture was diluted with EA (100 mL), and washed with sat. sodium bicarbonate. The organic phase was concentrated at low pressure. The residue was purified by column chromatography (50% EA in PE) to give 45-8 (350 mg, 41.1%) as a white solid.

Compound 45-8 (280 mg, 0.704 mmol) was treated with NH$_3$ in MeOH (10 mL, 7 M) at R.T. The mixture was stirred at R.T. for 2 h. The mixture was concentrated at a low pressure. The residue was purified by column chromatography (0-10% MeOH in DCM) to give compound 45 (110 mg, 53.1%) as a white solid. ESI-LCMS: m/z 295.1 [M+H]$^+$.

Example 37

Compound 54

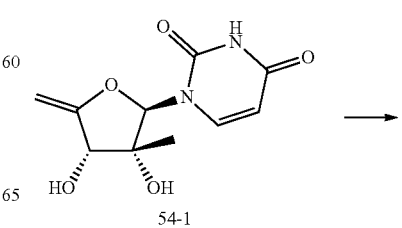

54-1

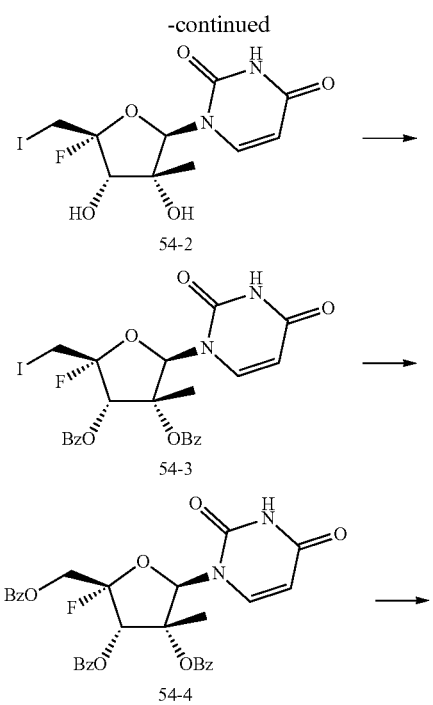

54-2

54-3

54-4

54-5

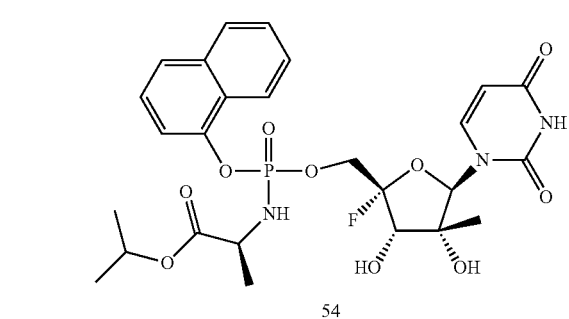

54

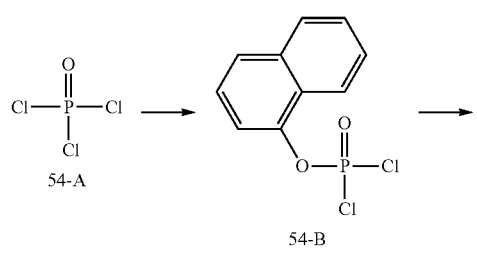

54-A

54-B

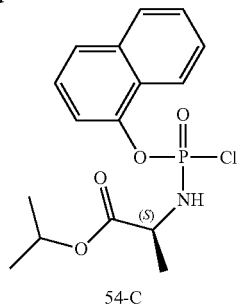

54-C

To an ice-cooled solution of 54-1 (10 g, 42 mmol) in anhydrous MeCN (200 mL) was added TEA.3HF (10 g, 62.5 mmol) and NIS (28 g, 126 mmol). The mixture was stirred at R.T. for 1.5 h, and monitored by LCMS. After the reaction was completed, the mixture was concentrated at a low pressure. The residue was purified by silica gel column chromatography (15% MeCN in DCM) to give 54-2 (12 g, 74%) as a yellow solid.

To a solution of 54-2 (22 g, 57 mmol) in anhydrous DCM (200 mL) was added DMAP (21 g, 171 mmol) and BzCl (17.6 g, 125 mol). The mixture was stirred for 5 h at R.T., and monitored by LCMS. The solution was washed with sat. $NaHCO_3$ solution, brine and extracted with EA. The organic phase was dried over anhydrous $Na_2SO_4$ and filtered. The filtrate was concentrated at low pressure. The residue was purified by silica gel column chromatography (20% EA in PE) to give 54-3 (30 g, 88%) as a white foam.

To a solution of 54-3 (6.5 g, 11 mmol) in anhydrous DMF (270 mL) was added NaOBz (15.8 g, 110 mmol) and 15-crown-5 (29 g, 132 mmol). The mixture was stirred at 95° C. for 48 h. The precipitate was removed by filtration, and the organic solvent was removed at low pressure. The residue was dissolved in EA (200 mL), and the solution was washed with sat. $NaHCO_3$ solution, and brine. The organic layer was dried over anhydrous $Na_2SO_4$ and filtered. The filtrate was concentrated at low pressure. The residue was purified by silica gel column chromatography (20% EA in PE) to give 54-4 (3 g crude, 46.1%) as an oil.

Compound 54-4 (3 g, crude) was treated with $NH_3$ in MeOH (120 mL, 7 M). The mixture was stirred for 3 h and monitored by TLC. The solution was concentrated at low pressure. The residue was purified by silica gel column chromatography (10% isopropanol in DCM) to give 54-5 (1.0 g, 67%) as a white solid. $^1$H-NMR (CD$_3$OD, 400 MHz) δ=1.19 (s, 3H), 3.76-3.82 (m, 2H), 4.02 (d, J=19.8 Hz, 1H), 5.70 (d, J=8.07 Hz, 1H), 6.27 (s, 1H), 7.89 (d, J=8.07 Hz, 1H).

Compound 54-5 (100 mg, 0.36 mmol) was co-evaporated with toluene 3 times. To a stirred solution of 54-5 (100 mg, 0.36 mmol) in a mixture of MeCN (1.0 mL) and NMI (295 mg, 3.6 mmol) was added a solution of 54-C (255.6 mg, 0.72 mmol, preparation described below) in MeCN (0.5 mL) at 0° C. The mixture was stirred at R.T. overnight. The reaction was quenched with water, and diluted with EA (20 mL). The organic layer was washed with water and brine. The organic layer was dried over anhydrous $Na_2SO_4$. The organic phase was concentrated at low pressure. The residue was purified on a silica gel column (5% i-PrOH in DCM) to give the crude product. The product was purified by prep-HPLC (0.1% HCOOH in water and MeCN) to give compound 54 (46.7 mg, 23.3%) as a white solid. ESI-LCMS: m/z 618 [M+Na]$^+$.

To a stirred solution of 54-A (2.0 g, 13.16 mmol) and naphthalen-1-ol (1.89 g, 13.16 mmol) in anhydrous DCM (100 mL) was added a solution of TEA (1.33 g, 13.16 mmol) in DCM (20 mL) dropwise at −78° C. After addition, the mixture was gradually warmed to R.T., and stirred for 2 h. The solution was cooled to −78° C., and (S)-isopropyl 2-aminopropanoate hydrochloride (2.20 g, 13.16 mmol) in DCM (20 mL) was added, followed by TEA (2.66 g, 26.29 mmol) in DCM (20 mL) dropwise. The mixture was gradually warmed to R.T., and stirred for 2 h. The organic solvent was removed at low pressure. The residue was dissolved in methyl-butyl ether. The precipitate was filtered, and the filtrate was concentrated at low pressure. The residue was purified on a silica gel column (anhydrous DCM) to give 54-C (1.0 g, 24.8%) as a colorless oil.

Example 38

Compounds 56 and 57

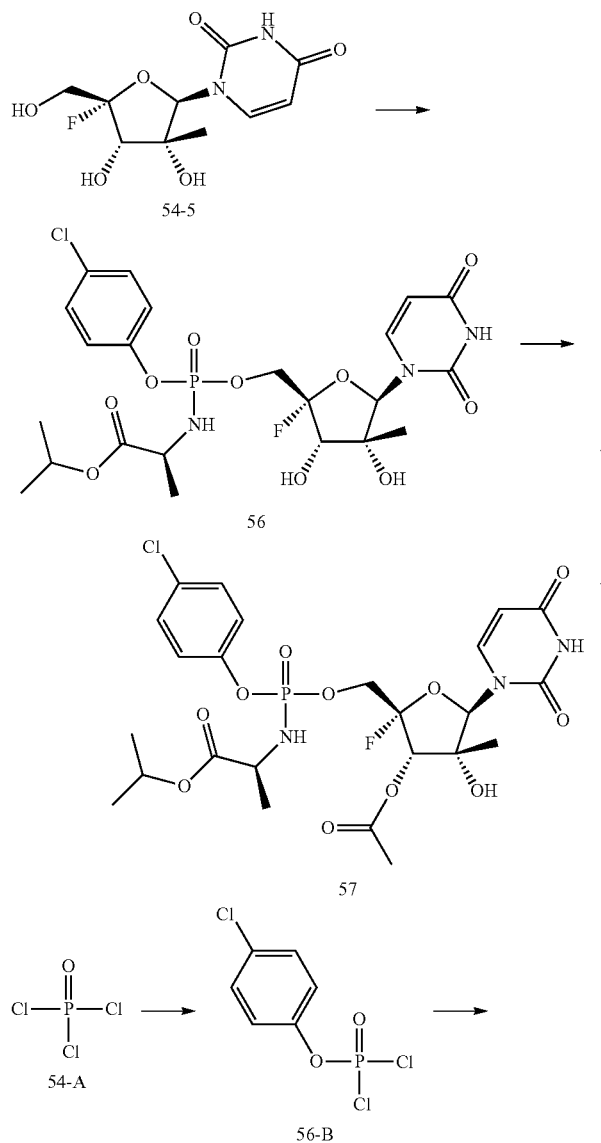

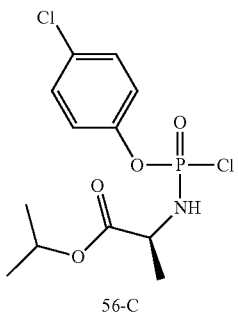

To a solution of 54-5 (300 mg, 1.08 mmol) and NMI (892 mg, 10 mmol) in anhydrous MeCN (4 mL) was added a solution of 57-C (736 mg, 2.17 mmol, preparation described below) in anhydrous MeCN (1 mL) dropwise at 0° C. The mixture was stirred at R.T. overnight. The reaction was quenched with water, and diluted with EA (30 mL). The organic layer was washed with water and brine. The organic phase was dried over anhydrous Na$_2$SO$_4$ and concentrated at low pressure. The residue was purified by a silica gel column (iPrOH in DCM from 1% to 5%) to give crude compound 56 (276 mg, crude). Crude compound 56 (96 mg) was purified by prep-HPLC (0.1% HCOOH in water and MeCN) to give pure compound 56 (46 mg, 47.9%) as a white solid. ESI-LCMS: m/z 560 [M−F]$^+$.

To a solution of compound 56 (180 mg, 0.31 mmol) in anhydrous pyridine (6 mL) was added acetic anhydride (158 mg, 1.54 mmol) dropwise at 0° C. The mixture was stirred at R.T. overnight. The solution was quenched with water and concentrated at a low pressure. The residue was dissolved in EA (10 mL), and washed with brine. The organic layer was dried over anhydrous Na$_2$SO$_4$. The organic phase was concentrated at low pressure. The residue was purified by silica gel column (i-PrOH in DCM from 1% to 3%) to give crude compound 57 (172 mg). Crude compound 57 was purified by prep-HPLC (0.1% HCOOH in water and MeCN) to give pure compound 57 (46 mg, 23.8%) as a white solid. ESI-LCMS: m/z 602.3 [M-F]$^+$.

Compound 56-C (1.02 g, 23%, a colorless oil) was prepared using a procedure similar to the preparation of 54-C using 54-A (2.00 g, 13.16 mmol) and 4-chlorophenol (1.68 g, 13.16 mmol).

Example 39

Compound 61

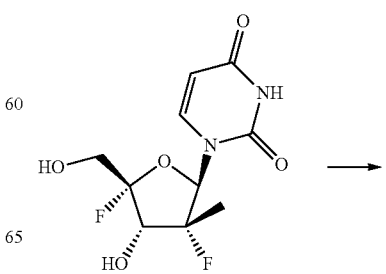

-continued

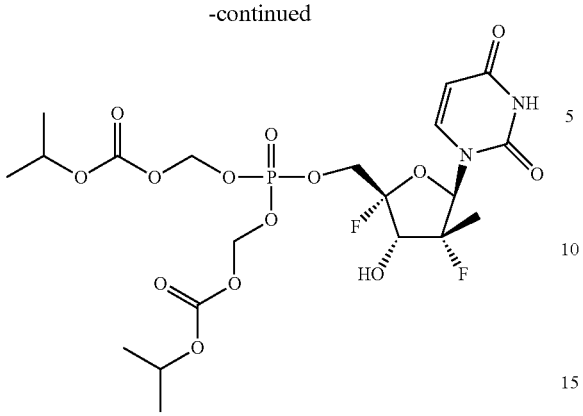

Compound 25 (109 mg, 0.39 mmol) and triethylammonium bis(isopropyloxycarbonyloxymethyl)phosphate (0.6 mmol, prepared from 195 mg of bis(isopropyloxycarbonyloxymethyl)phosphate and 85 µL of Et₃N) were rendered anhydrous by coevaporating with pyridine, followed by toluene. The residue was dissolved in anhydrous THF (3 mL) and cooled in an ice-bath. Diisopropylethyl amine (0.2 mL, 3 eq.), BopCl (190 mg, 2 eq.), and 3-nitro-1,2,4-triazole (81 mg, 2 eq.) were added, and the mixture was stirred at 0° C. for 90 mins. The mixture was diluted with EtOAc, washed with sat. aq. NaHCO₃ and brine, and dried (Na₂SO₄). Purification on silica gel column with CH₂Cl₂/i-PrOH (4-10% gradient) followed by RP-HPLC purification (A: 0.1% HCOOH in water, B: 0.1% HCOOH in MeCN) yielded compound 61 (28 mg, 12%). $^1$H-NMR (CDCl₃): δ 7.24 (d, 1H), 6.6 (br, 1H), 5.84 (d, 1H), 5.65-5.73 (m, 4H), 4.94 (m, 2H), 4.38 (m, 2H), 4.1 (b, 1H), 2.88 (d, 1H), 1.47 (d, 3H), 1.33 (m, 12H).

Example 40

Compound 74

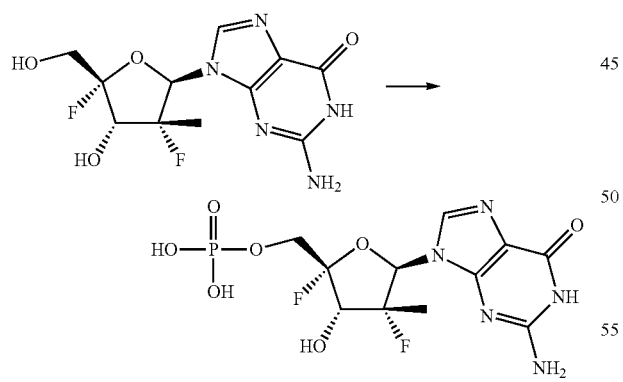

Dry nucleoside (0.05 mmol) was dissolved in a mixture of PO(OMe)₃ (0.7 mL) and pyridine (0.3 mL). The mixture was evaporated in vacuum for 15 mins. at 42° C., then cooled to R.T. N-Methylimidazole (0.009 mL, 0.11 mmol) was added followed by POCl₃ (0.009 mL, 0.11 mmol). The mixture was kept at R.T. for 20-40 mins and monitored for the formation of compound 74 by LCMS. The reaction was quenched with water and isolated by RP HPLC on Synergy 4 micron Hydro-RP column (Phenominex). A linear gradient of methanol from 0 to 30% in 50 mM triethylammonium acetate buffer (pH 7.5) was used for elution. The corresponding fractions were combined, concentrated and lyophilized 3 times to remove excess of buffer. MS: m/z 396.5 [M−1]⁻.

Example 41

Compound 68

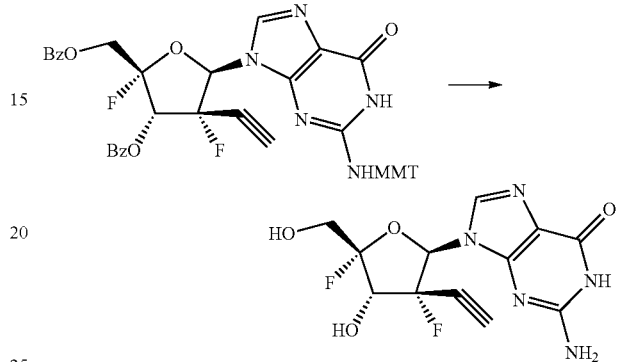

The nucleoside (140 mg, 0.42 mmol) was dissolved in n-butylamine (0.5 mL). The mixture was kept for 2 h at R.T., and the amine was then evaporated. The residue was dissolved in EtOAc, and the organic layer was washed twice with 10% citric acid, dried over Na₂SO₄, and evaporated. The residue purified by column chromatography on silica gel in linear gradient of methanol in DCM from 0% to 12% over 10 column volumes. The fractions containing the product were concentrated and treated with 80% HCOOH for 1 h at R.T. The mixture was evaporated to dryness, and suspended in CH₃CN. The precipitate was separated, washed with CH₃CN (1 mL) and dried to yield compound 68 (27 mg, 50%). MS: m/z 326.5 [M−1]⁻.

Example 42

Compound 62

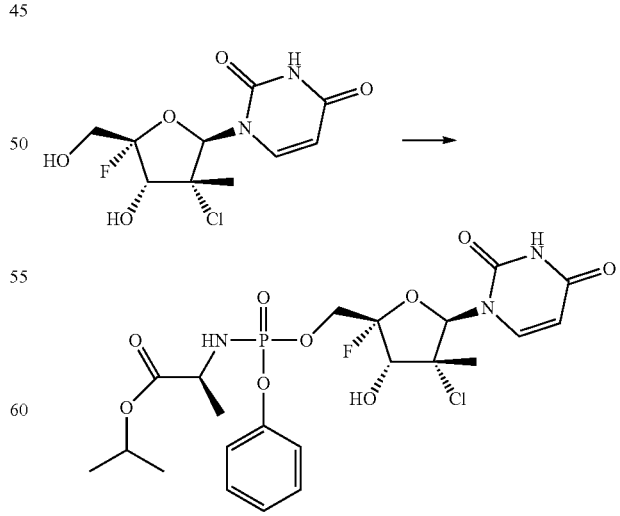

Compound 45 (30 mg, 0.1 mmol) was dissolved in a mixture of CH₃CN (2 mL) and N-methylimidazole (200 uL). Phosphorochloridate (100 mg, 0.3 mmol) was added, and the mixture was kept for 5 d at R.T. The mixture was distributed between water and EA. The organic layer was separated, washed with brine, dried and evaporated. The phosphoroamidate was isolated by silica gel chromatography in a gradient of methanol in DCM from 3% to 10%. The corresponding fractions were concentrated and re-purified by RP HPLC on Synergy 4 micron Hydro-RP column (Phenominex). A linear gradient of methanol in DCM from 3% to 95% containing 0.1% formic acid was used for elution. Compound 62 was obtained as a mixture Rp and Rs isomers (9 mg, 16%). MS: m/z 562.1[M−1]−.

Example 43

Compound 72

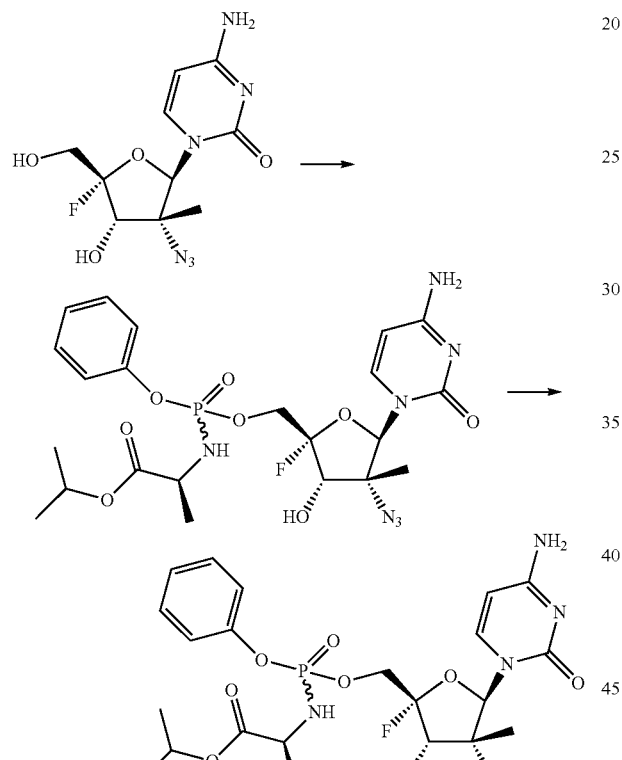

Compound 47 (30 mg, 0.1 mmol) was dissolved in a mixture of $CH_3CN$ (2 mL) and N-methylimidazole (200 uL). Phosphorochloridate (100 mg, 0.3 mmol) was added, and the mixture was kept overnight at 40° C. The temperature was increased to 65° C. and heated for 1 h. The mixture was distributed between water and EA. The organic layer was separated, washed with brine, dried and evaporated. The azido-phosphoramidate was purified by RP HPLC on Synergy 4 micron Hydro-RP column (Phenominex). A linear gradient of methanol from 30% to 100% in 50 mM triethylammonium acetate buffer (pH 7.5) was used for elution. The azido-phosphoramidate (8 mg) was dissolved in pyridine/$Et_3N$ (3 mL, 8:1 v/v) and cooled to 0° C. H25 gas was bubbled through the solution for 10 min, and the reaction was kept for 1 h at R.T. The solvents were evaporated, and the residue isolated by RP HPLC. The corresponding fractions were combined, concentrated and lyophilized 3 times to remove excess of buffer, to provide compound 72 (1.2 mg) as mixture Rp and Rs isomers. MS: m/z 544.1 [M+1]+.

Example 44

Compound 65

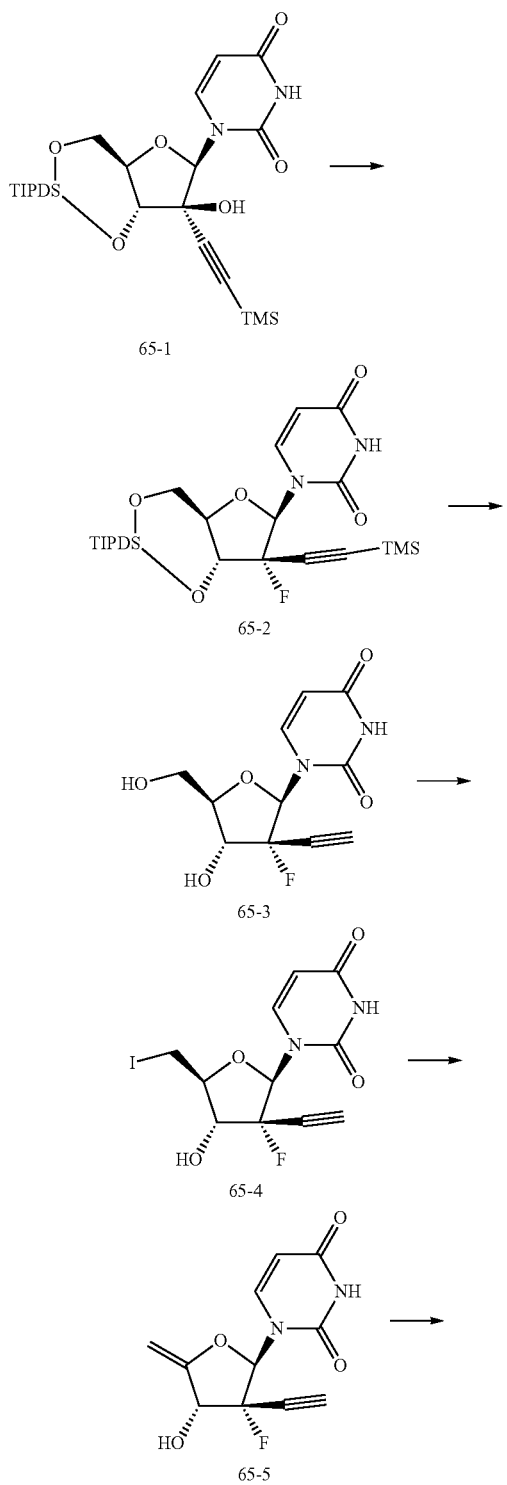

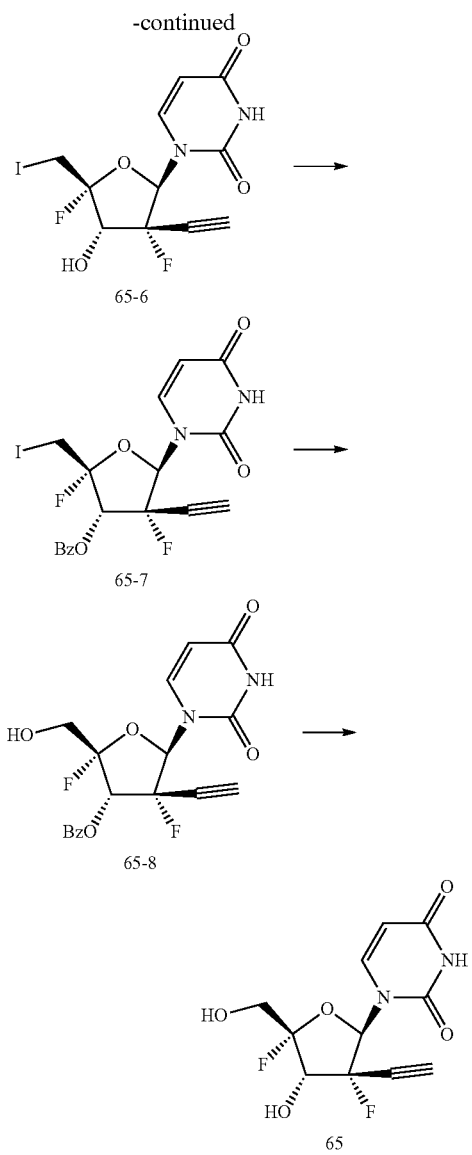

65-6

65-7

65-8

65

To a solution of 65-1 (23.0 g, 39.5 mmol) in anhydrous toluene (200 mL) was added DAST (31.9 g, 198 mmol) dropwise at −78° C., and the solution was stirred at −78° C. for 3 h. The mixture was quenched with sat. NaHCO$_3$, extracted with EA (2×200 mL) and dried over with anhydrous Na$_2$SO$_4$. The solution was concentrated to dryness under low pressure. The residue was purified on a silica gel column (50% EA in PE) to give 65-2 (16.5 g, 71%) as a yellow foam.

A mixture of 65-2 (16.0 g, 27.4 mmol) and NH$_4$F (3.0 g, 82.2 mmol) in methanol (100 mL) was stirred at 70° C. for 12 h. The reaction was cooled, and the salt was removed by filtration. The filtrate was concentrated to dryness at low pressure. The residue was purified on a silica gel column (3% MeOH in DCM) to give 65-3 (5.1 g, 69.0%) as a white foam.

To a stirred suspension of 65-3 (4.1 g, 15.2 mmol), PPh$_3$ (8.0 g, 30.4 mmol), imidazole (2.1 g, 30.4 mmol) and pyridine (18.2 mL) in anhydrous THF (40 mL) was added dropwise a solution of I$_2$ (5.8 g, 22.8 mmol) in THF (20 mL) at 0° C. The mixture was stirred at R.T. for 12 h. The reaction was quenched with MeOH (100 mL), and the solvent was removed under reduced pressure. The residue was purified on a silica gel column (4% MeOH in DCM) to give pure 65-4 (4.4 g, 77%) as a white solid. ESI-MS: m/z 381.1 [M+1]$^+$.

To a stirred solution of 65-4 (2.5 g, 0.7 mmol) in anhydrous THF (3 mL) was added DBU (2.1 g, 14 mmol) at R.T., and the mixture was stirred at R.T. for 1 h. The reaction was quenched with HOAc, and diluted with 2-Me-tetrahydrofuran. The solution was washed with brine, dried over with anhydrous Na$_2$SO$_4$ and concentrated to dryness at low pressure. The residue was purified on a silica gel column (MeOH 5% in DCM) to give 65-5 (1.1 g, 68.9%) as a white foam.

To a stirred solution of 65-5 (800 mg, 3.17 mmol) in anhydrous CH$_3$CN (10 mL) was added TEA.3HF (510 mg, 3.17 mmol) and NIS (785 mg, 3.49 mmol) at 0° C. The mixture was stirred for 30 mins, gradually warmed to R.T., and stirred for 1 h. The mixture was quenched with sat. NaHCO$_3$ solution and Na$_2$S$_2$O$_3$ solution, and extracted with EA (2×20 mL). The organic layer was dried over with anhydrous Na$_2$SO$_4$, and concentrated to dryness at low pressure. The residue was purified on a silica gel column to give pure 65-6 (695 mg, 57.9%) as a yellow solid.

To a stirred solution of 65-6 (650 mg, 1.63 mmol) in pyridine (3 mL) was added BzCl (507 mg, 3.59 mmol) at 0° C., and stirred at R.T. for 12 h. The mixture was quenched with water, and concentrated to dryness under reducing pressure. The residue was purified on a silica gel column (EA 50% in PE) to yield 65-7 (550 mg, 67%) as a white foam.

Tetra-butylammonium hydroxide (9 mL as 54-56% aqueous solution, 72 mmol) was neutralized with TFA to pH-4 (1.5 mL), and the mixture was added to a solution of 65-7 (375 mg, 0.75 mmol) in DCM (9 mL). m-Chloroperbenzoic acid (924 mg, 60-70%, 3.75 mmol) was added in portions with vigorous stirring, and the mixture was stirred overnight. The mixture was washed with brine, dried over magnesium sulfate and concentrated under reduced pressure. The residue was purified by column chromatography (EA 50% in PE) to give 65-8 (230 mg, 78.8%) as a white foam. ESI-MS: m/z 393.1 [M+1]$^+$.

Compound 65-8 (120 mg, 0.24 mmol) was treated with 7N NH$_3$.MeOH (20 mL), and stirred for 5 h. The mixture was concentrated to dryness at low pressure. The residue was purified on a silica gel column (propan-2-ol 15% in DCM) to yield compound 65 (53 mg, 60.2%) as a white solid. ESI-MS: m/z 288.8 [M+1]$^+$.

Example 45

Compound 70

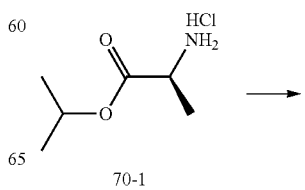

70-1

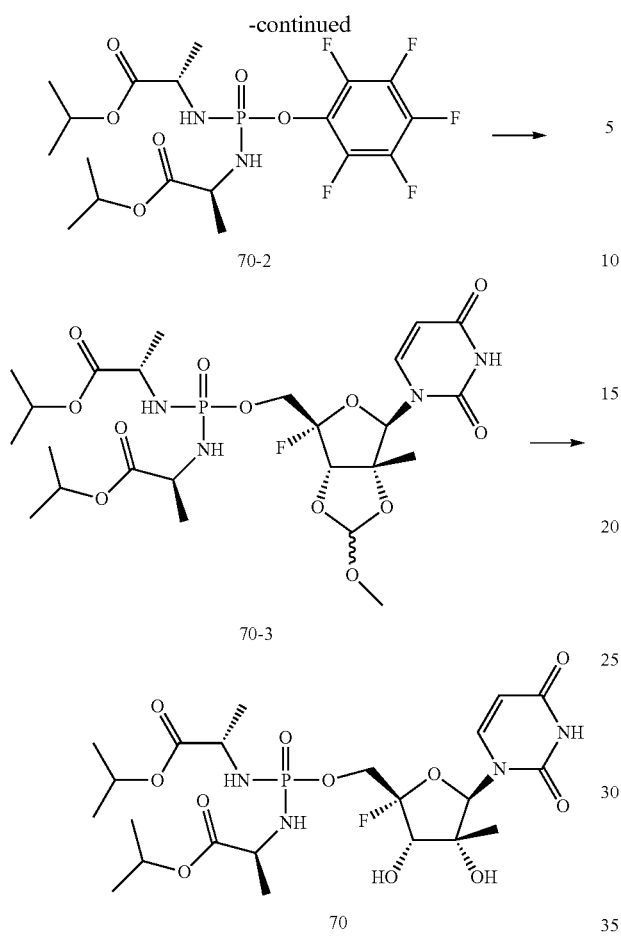

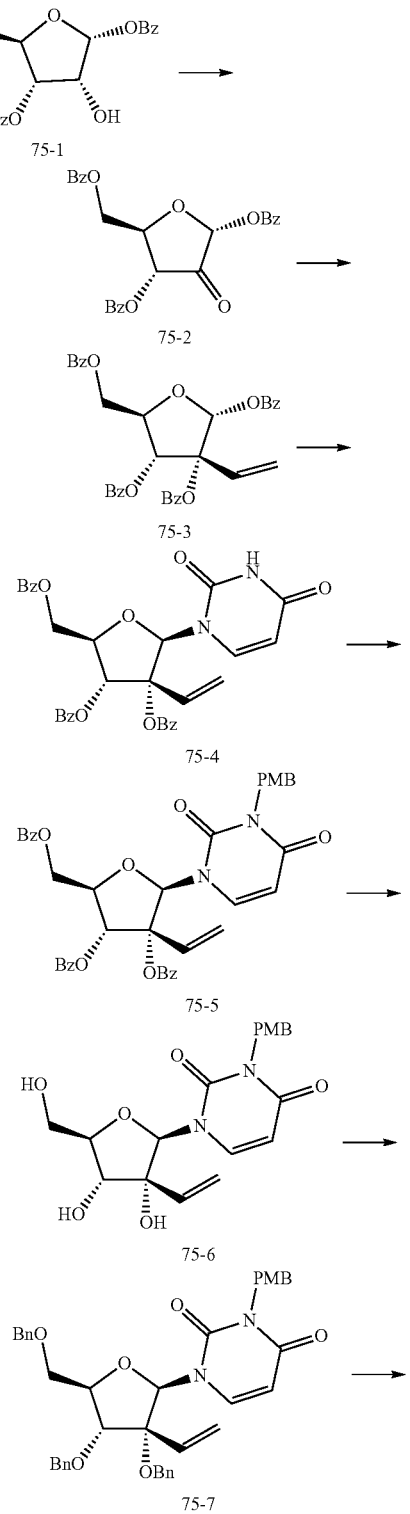

Example 46

Compound 75

To a solution of 70-1 (3.0 g, 18.0 mmol) and POCl$_3$ (1.35 g, 9.0 mmol) in DCM (80 mL) was added TEA (3.6 g, 36.0 mmol) in DCM (20 mL) dropwise at 0° C. The mixture was stirred at 0° C. for 2 h. A solution of pentafluorophenol (1.65 g, 9.0 mmol) and TEA (0.9 g, 9.0 mmol) in DCM (20 mL) was added dropwise at 0° C., and the mixture was stirred at 0° C. for 15 h. After the reaction was completed, the mixture was concentrated under reduced pressure. The residue was washed by TBME and filtered. The filtrate was concentrated under reduced pressure, and the residue was purified by silica gel chromatography (20% EA in PE) to give 70-2 (2.7 g, 62.7%) as a white solid. ESI-MS: m/z 491.1 [M+1]$^+$.

To a stirred solution of 1-((3aR,4R,6S,6aS)-6-fluoro-6-(hydroxymethyl)-2-methoxy-3a-methyltetrahydrofuro[3,4-d][1,3]dioxol-4-yl)pyrimidine-2,4(1H,3H)-dione (150 mg, 0.47 mmol) in anhydrous THF (2 mL) was added a solution of t-BuMgCl (0.46 mL, 1M in THF) dropwise at 0° C. The mixture was stirred at R.T. for 40 mins, and re-cooled to 0° C. A solution of 70-2 (462 mg, 0.94 mmol) was added, and the mixture was stirred at R.T. for 4 h. The mixture was quenched with H$_2$O, and extracted with EA. The organic layer was dried over Na$_2$SO$_4$ and concentrated under reducing pressure. The residue was purified on a silica gel column (50% EA in PE) to give 70-3 as a white foam (230 mg, 78%).

Compound 70-3 (230 mg, 0.37 mmol) was dissolved in 80% HCOOH aqueous solution (20 mL), and the mixture was stirred at R.T. for 24 h. The solvent was removed at low pressure. The residue was purified on a silica gel column to give the crude product, which was purified by RP HPLC (HCOOH system) to give compound 70 as a mixture of two P-isomers (75 mg, 33%). ESI-TOF-MS: m/z 583.0 [M+H]$^+$.

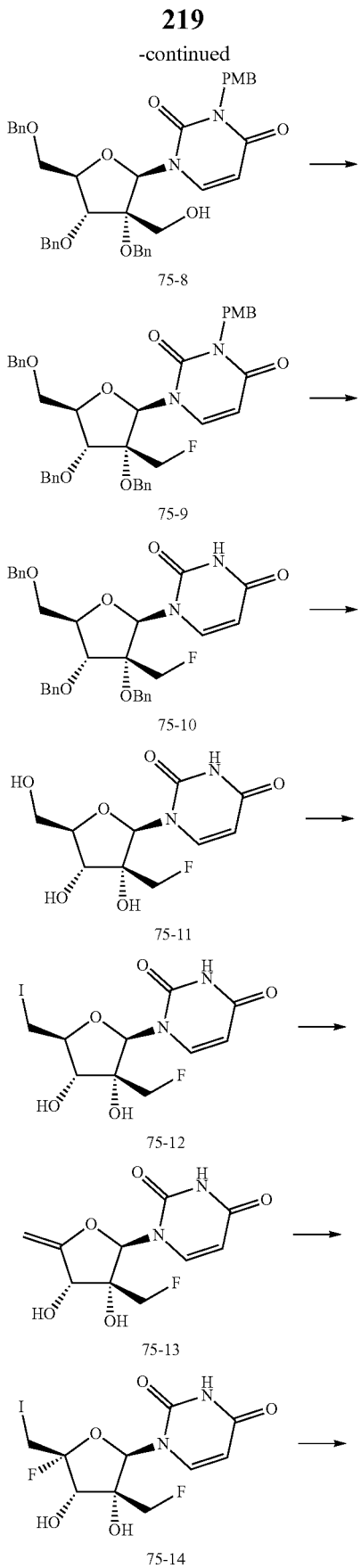

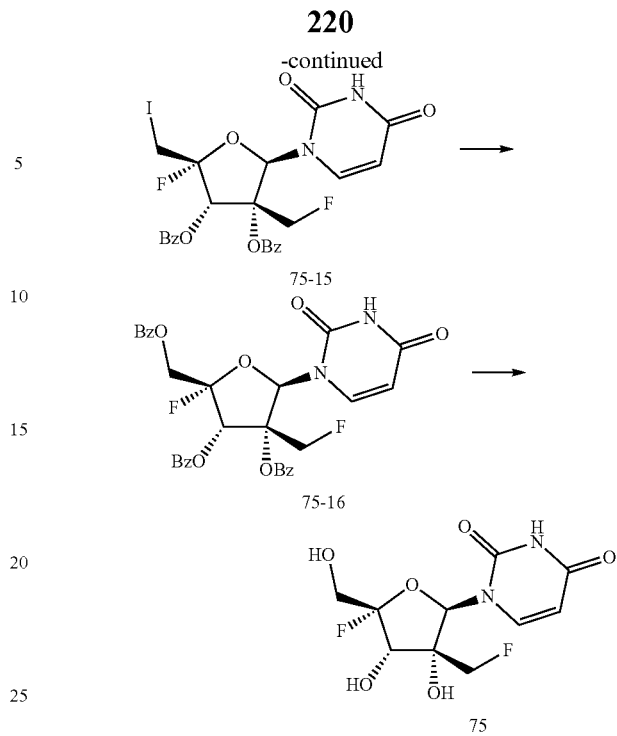

To a solution of 75-1 (120 g, 0.26 mol) in CH$_3$CN (2.0 L) was added IBX (109 g, 0.39 mol), and refluxed for 12 h. The reaction was monitored by TLC and LCMS. After cooling to R.T., the mixture was filtered, and the filtrate was concentrated at low pressure. The crude product was used directly for the next step.

Compound 75-2 (130 g, 0.26 mol) was co-evaporated with anhydrous toluene three times to remove H$_2$O. To a solution of 75-2 in THF (300 mL) was added dropwise vinyl magnesium bromide (700 mL, 0.78 mol, 1N in THF) over 30 min at −78° C. The mixture was stirred for about 1 h at R.T. After the starting material was consumed, the mixture was poured into a sat. NH$_4$Cl solution. The organic layer was washed with brine, dried with anhydrous Na$_2$SO$_4$ and filtered. The solution was concentrated at low pressure to get the crude product. To a solution of this crude product (170 g, 0.346 mol) in anhydrous CH$_2$Cl$_2$ was added TEA (105 g, 1.04 mol) and DMAP (84 g, 0.69 mol). Benzoyl chloride (146 g, 1.04 mol) was added slowly at R.T. for 12 h. The mixture was diluted with CH$_2$Cl$_2$ and then washed with sat. aq. NaHCO$_3$. The combined aq. phase was extracted with DCM (100 mL), and the combined organic phase was dried with Na$_2$SO$_4$. After filtration, the solution was evaporated to dryness under reduced pressure, and the residue was purified by column chromatography to give 75-3 (107 g, 52%).

Uracil (44.8 g, 0.4 mol) (co-evaporated with toluene twice) and NOBSA (81.4 g, 0.4 mol) were dissolved in CH$_3$CN (500 mL). The mixture was refluxed for 1.5 h and then slowly cooled to R.T. The mixture was treated with 75-3 (59 g, 0.1 mol) and TMSOTf (155 g, 0.7 mol), and then warmed to 60-70° C. for 12 h. The mixture was neutralized with a sat. NaHCO$_3$ solution, and extracted with EA (3×1000 mL). The solution was dried over anhydrous MgSO$_4$, and evaporated at low pressure. The residue was purified using a silica gel column to give pure 75-4 (40 g, 69%) as a white solid.

To a solution of 75-4 (50 g, 0.086 mol) in DMF was added PMBCl (16 g, 0.1 mol) and K$_2$CO$_3$ (17.8 g, 0.13 mol) at 0° C., and the mixture was stirred at R.T. for 12 h. The mixture was quenched with water (100 mL), and extracted with EA (3×200 mL). The organic phase was concentrated at low pressure to give crude 75-5 (65 g) which was used in the next step without further purification.

To a solution of crude 75-5 (65 g, 0.086 mol) in MeOH/DCM (4/1) (200 mL) was added NaOMe (16.8 g, 0.3 mol), and the mixture was stirred at R.T. for 2.5 h. The reaction was quenched with dry ice, and then concentrated at low pressure. The residue was dissolved in EA (200 mL) and washed with brine. The organic layer was concentrated at low pressure, and the residue was purified using a silica gel column using 1% MeOH in $CH_2Cl_2$ to give 75-6 as a yellow foam (25 g, 75%).

To a solution of 75-6 (25.5 g, 0.065 mol) in DMF was added NaH (10.5 g, 0.26 mol) slowly at 0° C., and the mixture was stirred for 30 mins. BnBr (36.3 g, 0.21 mol) was added, and the mixture was stirred at R.T. for 12 h. The reaction was quenched with sat. $NH_4Cl$ (aq.), and then extracted with EA (3×100 mL). The solution was dried over anhydrous $MgSO_4$, and evaporated at low pressure. The residue was purified by a silica gel column using 10% EA in PE to give 75-7 (20 g, 46%) as a white solid.

To a solution of 75-7 (20 g, 0.03 mol) and NMMO (7 g, 0.06 mol) in $THF:H_2O$ (5:1) (100 mL) was added $OsO_4$ (2.6 g, 0.01 mol) at R.T., and the mixture was stirred at R.T. for 24 h. The mixture was quenched with a sat. $Na_2S_2O_3$ solution, and extracted with EA (3×100 mL). The organic layer was washed with brine, and dried over anhydrous $MgSO_4$. The solution was evaporated at low pressure to give the crude compound, which was used in the next step without further purification.

To a solution of the crude diol (0.03 mol) in $MeOH:H_2O:THF$ (170 mL:30 mL:50 mL) was added $NaIO_4$ (9.6 g, 0.045 mol), and the mixture was stirred at R.T. for 2 h. After filtration, the filtrate was used directly in the next step. This solution was treated with $NaBH_4$ (1.8 g, 0.048 mol) at 0° C., and the mixture was stirred at R.T. for 30 mins. The mixture was quenched with MeOH, and evaporated at low pressure. The residue was dissolved in EA (100 mL), and washed with brine. The solution was evaporated at low pressure, and the residue was purified by a silica gel column using 20% EA in EA to give 75-8 (12 g, 61% over three steps).

To a solution of 75-8 (14 g, 21 mmol) and DMAP (5.1 g, 42 mmol) in DCM (100 mL) was added MsCl (3.1 g, 27 mmol) at 0° C., and the mixture was stirred at R.T. for 40 mins. The reaction was quenched with sat. $NaHCO_3$ (aq.), and washed with HCl (0.2 N) solution. The organic phase was dried over anhydrous $MgSO_4$, and evaporated at low pressure. The residue was purified by a silica gel column using 5% EA in PE to give mysolate product (14 g, 90%). The MsO-product (41 g, 55 mmol) was treated with TBAF (1 N in THF, 500 mL), and the mixture was stirred at 70-80° C. for 3 d. The mixture was concentrated at low pressure, and the residue was dissolved in EA (200 mL). The solution was washed with brine, dried over anhydrous $MgSO_4$ and evaporated at low pressure. The residue was purified by chromatography using 10% EA in PE to give 75-9 (9.9 g, 27%).

To a solution of 75-9 (6.3 g, 9.45 mmol) in $CH_3CN:H_2O$ (3:1, 36 mL:12 mL) was added CAN (15.5 g, 28.3 mmol), and the mixture was stirred at R.T. overnight. The mixture was extracted with EA (3×50 mL). The solution was dried over anhydrous $MgSO_4$, and evaporated at low pressure. The residue was purified by chromatography using 20% EA in PE to give 75-10 (3.6 g, 71%) as a white solid.

To a solution of 75-10 (2.4 g, 4.4 mmol) in anhydrous DCM (10 mL) was added slowly $BCl_3$ (1 N, 30 mL $CH_2Cl_2$) at −70° C., and the mixture was stirred for 2 h. at −70° C. The mixture was quenched with the slow addition of MeOH at −70° C., and the mixture was concentrated at low pressure. The residue was purified by chromatography using 50% EA in PE to give 75-11 (1.2 g, 86%) as a white solid. ESI-MS: m/z 277.1 $[M+H]^+$.

To a solution of $PPh_3$ (3.37 g, 12.8 mmol) in pyridine (15 mL) was added $I_2$ (3.06 g, 12 mmol) at 0° C., and the mixture was stirred at R.T. for 30-40 mins. The mixture was cooled to 0° C., and then treated with 75-11 (2.2 g, 8 mmol) in Py. (5 mL). The mixture was stirred at R.T. under $N_2$ for 12 h. The mixture was quenched with sat. $Na_2S_2O_3$ (aq.) and extracted with $CH_2Cl_2$ (3×50 mL). The organic phase was dried over anhydrous $MgSO_4$, and then concentrated at low pressure. The residue was purified by chromatography using 1-2% MeOH in $CH_2Cl_2$ to yield 75-12 (1.8 g, 58%) as a white solid.

To a solution of 75-12 (1.35 g, 3.5 mmol) in $THF:CH_3CN$ (10 mL:5 mL) was added DBU (1.06 g, 7 mmol), and the mixture was stirred at 60-70° C. for 2 h. The mixture was concentrated at low pressure, and the residue was dissolved in EA (20 mL). The solution was washed with 10% HCl solution and brine. The organic phase was dried over anhydrous $MgSO_4$ and concentrated at low pressure. The residue was purified by chromatography using 30% EA in PE to give 75-13 (0.5 g, 55%).

To a solution of 75-13 (670 mg, 2.6 mmol) in $CH_3CN$ (6 mL) was added NIS (730 mg, 3.25 mmol) and 3HF.TEA (335 mg, 2.1 mmol) at 0° C., and the mixture was stirred at R.T. for 2 h. The mixture was quenched with sat. $NaHCO_3$ (aq.) and $Na_2S_2O_3$ (aq.) solution. The mixture was extracted with EA (3×20 mL), dried over anhydrous $MgSO_4$ and concentrated at low pressure. The residue was purified by chromatography using 1-2% MeOH in $CH_2Cl_2$ to give 75-14 (1.2 g, 80%).

To a solution of 75-14 (1.0 g, 2.47 mmol), DMAP (0.75 g, 6.2 mmol) and TEA (0.75 g, 7.42 mmol) in DCM (10 mL) was added BzCl (1.15 g, 8.16 mmol) in DCM (1 mL) at 0° C., and the mixture was stirred at R.T. for 12 h. The mixture was diluted with $CH_2Cl_2$ (10 mL), and then washed with HCl (0.1 N, 20 mL) solution and brine. The organic phase was dried over anhydrous $MgSO_4$, and concentrated at low pressure. The residue was purified by chromatography using 20% EA in PE to afford 75-15 (850 mg, purity-80%).

To a solution of 75-15 (600 mg, 1 mmol) in DMF (25 mL) was added BzONa (1.45 g, 10 mmol), 15-crown-5 (2.2 g, 10 mmol), and the mixture was stirred at 90-100° C. for 24 h. The mixture was concentrated at low pressure, and the residue was dissolved in EA (20 mL), and washed with brine. The organic phase was dried over anhydrous $MgSO_4$, and then concentrated at low pressure. The residue was purified by chromatography using 15% EA in PE to give 75-16 (275 mg, 37%) as a light yellow foam.

Compound 75-16 (250 mg, 0.41 mmol) was treated with $NH_3$.MeOH (7 N, 5 mL), and the mixture stirred at R.T. for 15 h. The mixture was concentrated at low pressure, and the residue was purified by prep-HPLC to give compound 75 (33 mg, 25%) as a white solid. ESI-MS: m/z 295.1 $[M+H]^+$.

Example 47
Compound 73
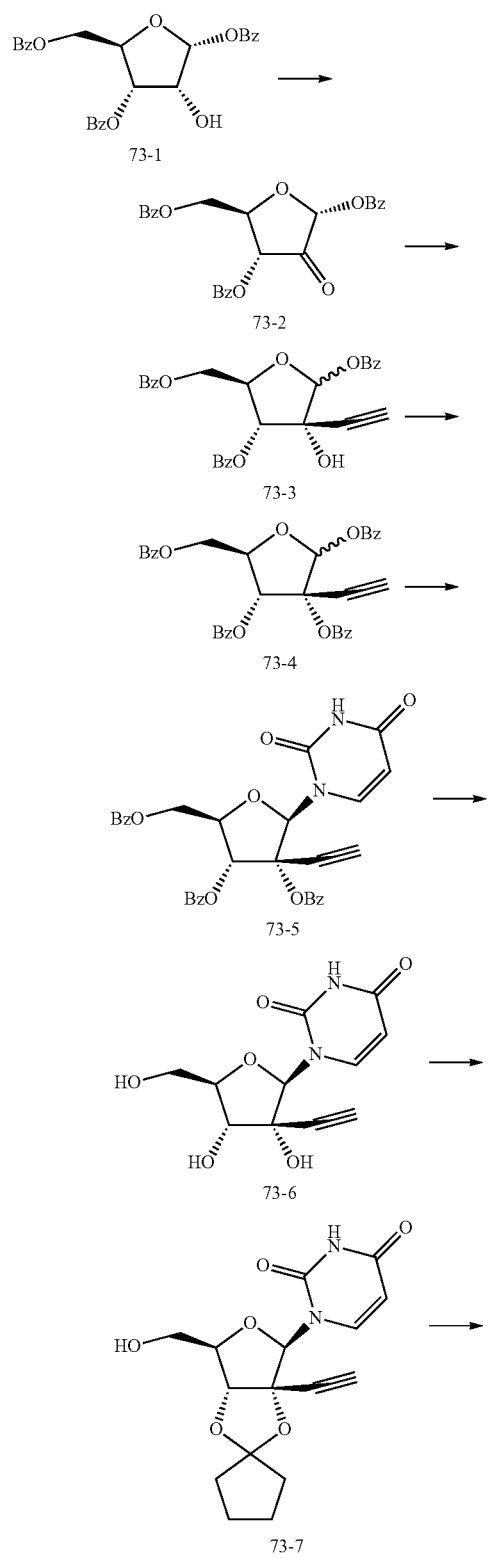
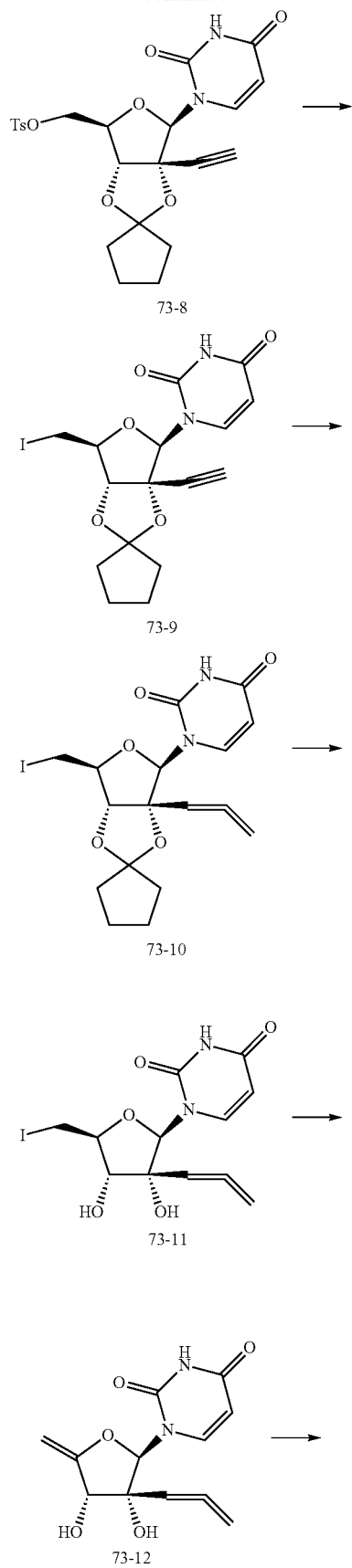

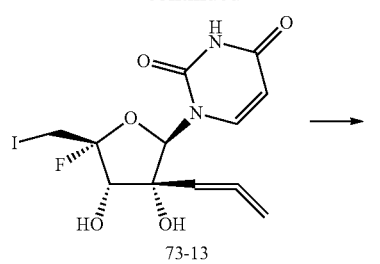
73-13

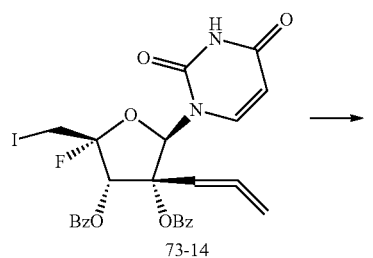
73-14

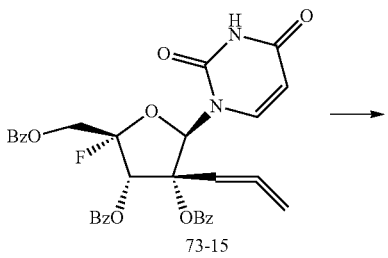
73-15

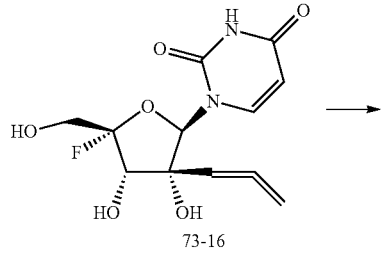
73-16

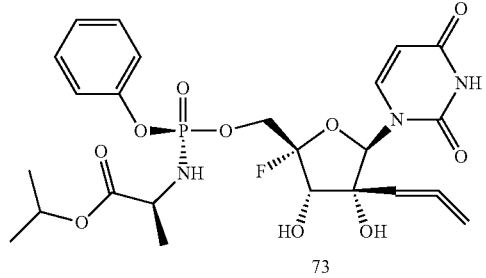
73

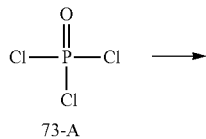
73-A

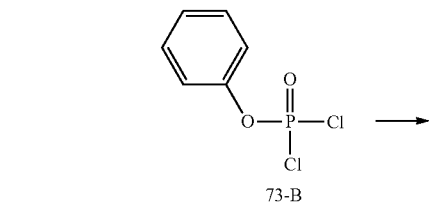
73-B

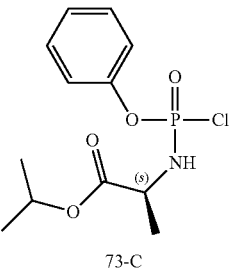
73-C

To a solution of IBX (133.33 g, 476 mmol) in dry $CH_3CN$ (2 L) was added 73-1 (100.0 g, 216 mol) at R.T. The mixture was refluxed and stirred for 12 h. The mixture was filtered, and the filtrate was concentrated at low pressure to give 73-2 as a yellow oil (90.0 g, 90.4%).

Compound 73-2 (50.0 g, 108.70 mmol) was coevaporated with anhydrous toluene twice to remove $H_2O$. Ethynyl magnesium bromide, (800 mL, 400.0 mmol) was added dropwise into a solution of 73-2 in THF (500 mL) over 20 mins at −78° C. The mixture was stirred for about 10 mins at −78° C. When the starting material was consumed, the ice-acetone cooling bath was removed. The mixture was quenched with a sat. $NH_4Cl$ solution with stirring, and then warmed to R.T. The mixture was extracted with EA, filtered through Celite and washed with brine. The combined organic phase was dried over anhydrous $Na_2SO_4$, filtered and concentrated at low pressure to give crude 73-3 as a deep yellow oil (48.0 g, yield: 90.8%).

Compound 73-3 (200.0 g, 411.52 mmol) was dissolved in anhydrous $CH_2Cl_2$ (2000 mL) and then DMAP (100.41 g, 823.05 mmol) and $Et_3N$ (124.94 g, 1.23 mol) were added at R.T. The mixture was treated with benzoyl chloride (173.46 g, 1.23 mol) at 0° C. After stirring for 12 h at R.T., the reaction was quenched with $H_2O$. The combined aq. phase was extracted with DCM. The combined organic phase was dried over anhydrous $Na_2SO_4$, filtered and evaporated to dryness under reduced pressure to give a black oil. The oil was purified by column chromatography using 7%-20% EA in PE as the eluent to give a yellow oil. The residue triturated with $CH_3OH$ and filtered. The filter cake was concentrated in vacuo to give 73-4 as a white solid (30.0 g, 36.4%).

Uracil (34.17 g, 305.08 mmol) were coevaporated with anhydrous toluene twice to remove $H_2O$. To a stirred suspension of uracil in anhydrous MeCN (150 mL) was added N,O-BSA (123.86 g, 610.17 mmol) at R.T. The mixture was refluxed for 1.5 h and then cooled to R.T. Compound 73-4 (90 g, 152.54 mmol, which were coevaporated with anhydrous toluene twice to remove $H_2O$) was added. TMSOTf (237.05 g, 1.07 mol) was then added at R.T. The mixture was heated to 70° C., and then stirred overnight and then monitored by LCMS. The mixture was cooled to R.T., and quenched with a sat. $NaHCO_3$ solution. The solution was extracted with EA. The organic layer was dried over $Na_2SO_4$, and then concentrated at low pressure. The residue was purified using a silica gel column eluted with 10%-50% EA in PE to give 73-5 as a white solid (45 g, 50.9%).

Compound 73-5 (50 g, 86.21 mmol) was treated with $NH_3$ in MeOH (1 L) at R.T., and then stirred for 48 h. The mixture was concentrated at low pressure, and the residue was purified by column chromatography (10% MeOH in DCM) to give 73-6 (12.6 g, 54.55%) as a white solid.

To a solution of cyclopentanone (100 g, 1.189 mmol) and trimethyl orthoformate (150 mL) in MeOH (600 mL) was added $TsOH·H_2O$ (1.13 g, 5.9 mmol), and the mixture was stirred at R.T. for 30 mins. The reaction was quenched with NaOMe (0.32 g, 5.9 mmol) and $H_2O$, and the solution was extracted by n-hexane. The organic layer was dried over anhydrous $Na_2SO_4$, and then concentrated at low pressure. The cyclopentyl dimethoxy acetal and 73-6 (20 g, 74.63 mmol) was dissolved in DCE (200 mL), and then treated with $TsOH.H_2O$ (0.71 g, 3.73 mmol). The mixture was stirred at 50° C. for 12 h, and then concentrated at low pressure. The residue was purified by silica gel column chromatography (1-10% MeOH in DCM) to give 73-7 (15.4 g, 61.8%) as a white solid.

Compound 73-7 (20.0 g, 0.06 mol) was coevaporated with anhydrous pyridine three times to remove $H_2O$. To an ice-cold solution of 73-7 in anhydrous pyridine (100 ml) was added TsCl (22.8 g, 0.12 mol) at 0° C., and the mixture was stirred overnight and monitored by LCMS and TLC. The reaction was quenched with $H_2O$ and extracted with EA. The organic phase was dried over anhydrous $NaSO_4$ and evaporated at low pressure. The residue was purified by silica gel column chromatography (DCM:MeOH=100:1 to 15:1) to give 78-8 (20.0 g, 69.0%) as a white solid.

To a solution of 73-8 (20.0 g, 0.04 mol) in acetone (200 ml) was added NaI (31.0 g, 0.2 mol) and heated to reflux overnight and monitored by LCMS. The mixture was quenched with a sat. $Na_2S_2O_3$ solution, and extracted with EA. The organic phase was dried over anhydrous $Na_2SO_4$ and evaporated at low pressure. The residue was purified by silica gel column chromatography (DCM:MeOH=100:1 to 15:1) to give 73-9 (15.0 g, 83.3%) as a white solid.

To 73-9 (30.0 g, 0.068 mol) in dioxane (60 mL) in sealed tube was added CuBr (4.9 g, 0.034 mol), i-$Pr_2NH$ (13.6 g, 0.135 mol) and $(CH_2O)_n$ (5.1 g, 0.17 mol) under $N_2$. The mixture was heated at reflux for 16 h. The mixture was diluted with EtOAc, and washed with a sat. $NH_4Cl$ solution and brine. The solution was dried over anhydrous $MgSO_4$, and concentrated under reduced pressure. The residue was purified by column chromatography (DCM:MeOH=100:1 to 15:1) to give 73-10 (10.0 g, 32.3%) as a white solid.

Compound 73-10 (10 g, 21.83 mmol) was treated with HCOOH (80%) in $H_2O$ at R.T. The solution was stirred at 60° C. for 2 h, and then concentrated at a low pressure. The residue was purified by column chromatography (1%-10% MeOH in DCM) to give 73-11 (5.1 g, 58.55%) as a white solid.

Compound 73-11 (5 g, 12.79 mmol) was dissolved in anhydrous MeOH (100 mL) and treated with NaOMe (4.83 g, 89.5 mmol) at R.T. The solution was stirred at 60° C. for 36 h. The mixture was quenched with $CO_2$ and then concentrated at low pressure. The residue was purified by column chromatography (0-10% MeOH in DCM) to give 73-12 (2.3 g, 68.05%) as a yellow solid. $^1$H-NMR ($CDCl_3$, 400 MHz) δ=7.29 (d, J=8 Hz 1H), 6.10 (s, 1H), 5.71 (d, J=8.0 Hz 1H), 5.18 (t, J=6.4 Hz, 1H), 4.79-4.84 (m, 1H), 4.61 (d, J=8.0 Hz, 2H), 4.39 (s, 1H), 3.45 (s, 1H).

To an ice-cold solution of 73-12 (1.5 g, 5.68 mmol) in anhydrous MeCN (15 mL) was added NIS (1.66 g, 7.39 mmol) and TEA.3HF (0.73 g, 4.55 mmol) under $N_2$. The mixture was stirred at R.T. for 1 h. The reaction was quenched with sat. $NaHCO_3$ and sat. $Na_2SO_3$ solution, and extracted with EA (3×100 mL). The organic phase was dried over anhydrous $Na_2SO_4$, and evaporated to dryness at low pressure. The residue was purified on a silica gel column (0-5% MeOH in DCM) to give 73-13 (1.08 g, 46.2%) as a yellow solid.

To a stirred solution of 73-13 (1 g, 2.44 mmol) in anhydrous DCM (10 mL) was added DMAP (0.60 g, 4.88 mmol) and $Et_3N$ (0.74 g, 7.32 mmol) at R.T. The mixture was treated with benzoyl chloride (0.79 g, 5.61 mmol) at 0° C. and then stirred at R.T. for 3 h. The reaction was quenched with water, and extracted with EA (3×60 mL). The organic phase was concentrated at low pressure, and the residue was purified by column chromatography (0-10% MeOH in DCM) to give 73-14 (0.9 g, 59.6%) as a white solid.

$Bu_4NOH$ (55% in $H_2O$, 13.74 mL) was treated with TFA (to adjust pH=3-4). The mixture was cooled to R.T. To a solution of 73-14 (0.9 g, 1.46 mmol) in DCM (9 mL) was added m-CPBA (80%, 1.57 g, 7.28 mmol) at R.T. The mixture was stirred at 25° C. for 48 h. The mixture was washed with sat. aq. $NaHCO_3$. The organic layer was passed through an anhydrous $Al_2O_3$ column, and the solution was concentrated at low pressure. The residue was purified by a silica gel column (30% EA in PE) to give 73-15 (0.26 g, 35.1%) as a yellow solid.

Compound 73-15 (0.25 g, 0.49 mmol) was dissolved in $NH_3$/MeOH (5 mL, 7 M), and the mixture was stirred at R.T. for 24 h under $N_2$. The mixture was concentrated at low pressure at R.T., and the residue was purified by a silica gel column (5% MeOH in DCM) to give 73-16 (100 g, 67.75%) as a white solid. $^1$H-NMR ($CD_3OD$, 400 MHz) δ=7.83 (d, J=8 Hz 1H), 6.29 (s, 1H), 5.67 (d, J=6.0 Hz 1H), 5.12 (t, J=6.8 Hz, 1H), 4.99-5.01 (m, 1H), 4.38 (d, J=19.6 Hz 1H), 3.74-3.81 (m, 2H), 3.35 (s, 1H).

Compound 73-16 (100 mg, 0.33 mmol) was co-evaporated with toluene three times to remove $H_2O$. To a stirred solution of 73-16 (100 mg, 0.33 mmol) in a mixture of MeCN (1.0 mL) and NMI (271 mg, 3.3 mmol) was added a solution of 73-C (216.5 mg, 0.66 mmol) in MeCN (0.5 mL) at 0° C. The mixture was stirred at R.T. overnight and then reaction was quenched with water. The mixture was diluted with EA (20 mL), and the organic layer was washed with water and brine, and dried over anhydrous $Na_2SO_4$. The organic phase was concentrated at low pressure, and the residue was purified on a silica gel column (5% i-PrOH in DCM) to give the crude product. The crude product was purified by prep-HPLC (0.1% HCOOH in water and MeCN) to give compound 73 (35.6 mg, 19.0%) as a white solid. ESI-LCMS: m/z 592 [M+Na]$^+$.

To a stirred solution of 73-A (2.0 g, 13.16 mmol) and phenol (1.22 g, 13.16 mmol) in anhydrous DCM (100 mL) was added a solution of TEA (1.33 g, 13.16 mmol) in DCM (20 mL) dropwise at −78° C. The mixture was warmed gradually to R.T., and then stirred for 2 h. The solution was re-cooled to −78° C., and (S)-isopropyl 2-aminopropanoate hydrochloride (2.20 g, 13.16 mmol) in DCM (20 mL) was added, followed by the dropwise addition of TEA (2.66 g, 26.29 mmol) in DCM (20 mL). The mixture was warmed gradually to R.T., and then stirred for 2 h. The organic solvent was removed at low pressure, and the residue was dissolved in methyl-butyl ether. The precipitate was filtered, and the filtrate was concentrated at low pressure. The residue was purified on a silica gel column (anhydrous DCM) to give 73-C (0.9 g, 22.3%) as a colorless oil.

Example 48
Compound 66
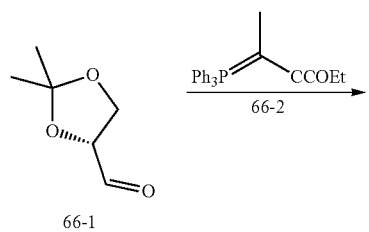
66-1
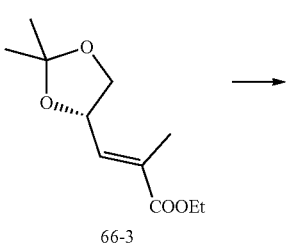
66-3
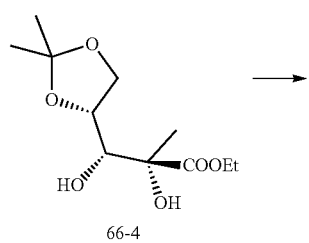
66-4
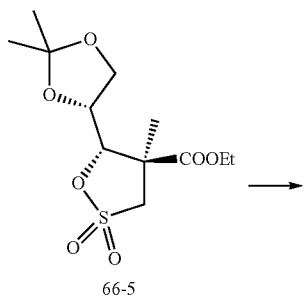
66-5
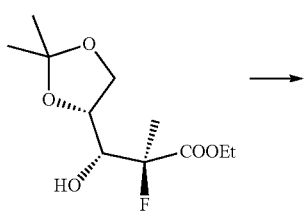
66-6
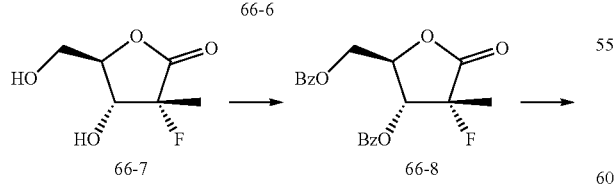
66-7  66-8
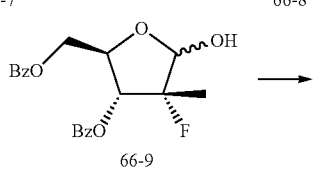
66-9
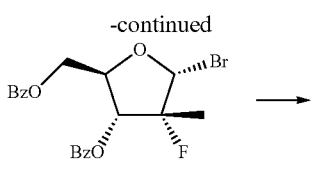
66-10
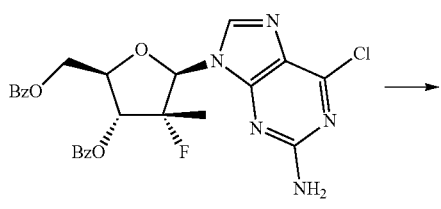
66-11
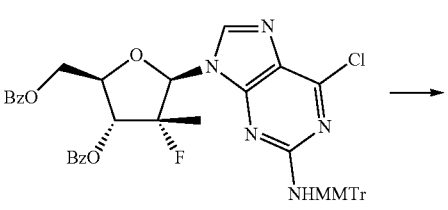
66-12
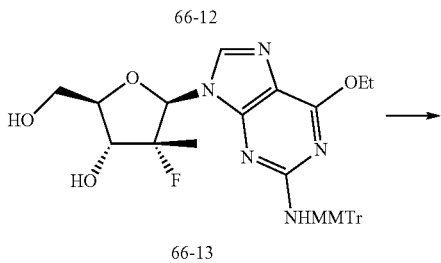
66-13
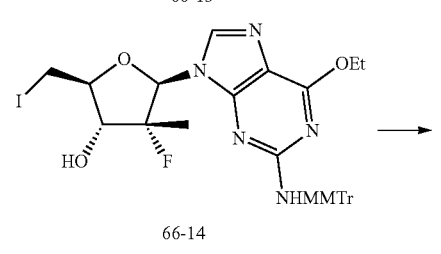
66-14
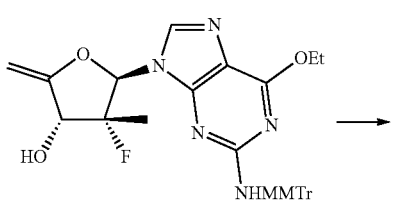
66-15
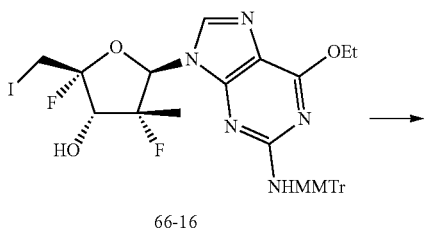
66-16

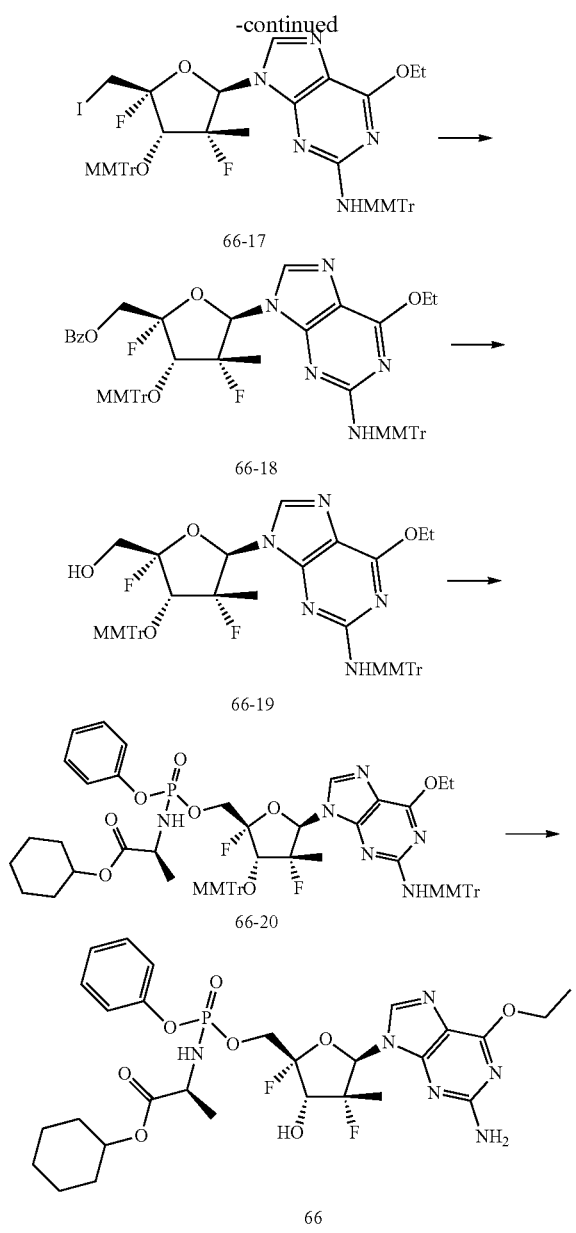

66-17

66-18

66-19

66-20

66

Compound 66-2 (2648 g, 7.3 mol) was dissolved in anhydrous dichloromethane (10 L), and the solution was cooled to −40° C. with stirring under $N_2$. Compound 66-1 (1 kg, 7.69 mol) was dissolved in anhydrous $CH_2Cl_2$ (3 L) and added to the solution of 66-2 over 30 mins at −40° C. The stirred mixture was allowed to warm to R.T. overnight. The mixture was concentrated under reduced pressure to dryness, and the residue was suspended in TMBE (6 L). The suspension was filtered to remove $Ph_3PO$, and the filtrate was concentrated under reduced pressure to afford crude 66-3 (1230 g, 78.6%). $^1$H NMR (400 Hz) ($CDCl_3$): δ 6.65 (dt, J=7.6 Hz, 1H), 4.82 (dd, J=14.8, 7.6 Hz, 1H), 4.20-4.10 (m, 3H), 3.59 (t, J=8.0 Hz, 1H), 1.86 (d, J=1.2 Hz, 3H), 1.41 (s, 3H), 1.37 (s, 3H), 1.26 (t, J=6.8 Hz, 3H).

Crude 66-3 (1230 g, 5.74 mol) was dissolved in acetone (30 L) at 0-5° C. $KMnO_4$ (1107 g, 5.17 mol) was added in one portion. After being stirred at 0-5° C. for 5 h, the reaction was quenched with sat. aq. sodium sulfite (20 L). After 30 mins, a colorless suspension was formed. The solid was removed by filtration and washed with EA (6 L). The filtrate was extracted with EA (3×2 L). The combined extracts were dried over $Na_2SO_4$, filtered, and concentrated under reduced pressure to give a white solid residue. The residue was dissolved in EA, and PE was added to give a precipitate. The solid was collected by filtration and recrystallization was 3 times to give 66-4 (770 g, 53.6%) as a white solid.

To a stirred solution of 66-4 (770 g, 3.1 mol) in anhydrous DCM (5 L) and triethylamine (1.1 L, 8.05 mol) at 0° C. was added slowly sulfuryl chloride (300 mL, 3.6 mmol). The mixture was stirred at R. T. for 2 h, diluted with DCM (3 L), and washed with sat. $NaHCO_3$aq. and brine. The organic phase was dried over anhydrous $Na_2SO_4$, filtered, and concentrated under reduced pressure. The residue was purified by a silica gel column using PE:EA=1:0 to 10:1 as the eluent to give 66-5 (490 g, 50.6%) as an oil.

Tetraethylammonium fluoride hydrate (650 g, 3.7 mol) was added into a solution of 66-5 (490 g, 1.6 mol) in anhydrous dioxane (3 L), and the mixture was heated to 120° C. for 16 h. The mixture was then cooled to ambient temperature. 2,2-Dimethoxypropane (3 L) was added followed by conc. aq hydrochloric acid (200 mL). The mixture was stirred for 3 h at ambient temperature. The solvent was concentrated to ⅓ of the original volume, and then diluted with EA (3 L). The mixture was washed with cold sat. aq. sodium bicarbonate and brine. The combined aqueous layer was back-extracted with EA (1 L). The combined organic layer was dried over anhydrous $Na_2SO_4$, filtered, and concentrated at low pressure to give crude 66-6 (220 g, 70.8%).

Crude 66-6 (220 g, 0.89 mol) was dissolved in ethanol (2 L) and conc. aq. HCl (60 mL). The solution was stirred at ambient temperature for 48 h. and then concentrated under reduced pressure followed by co-evaporations with toluene 3 times to give 66-7 as a pale yellow solid (110 g).

Compound 66-7 (110 g) was dissolved in anhydrous pyridine (1 L). Benzoyl chloride (200 mL, 1.67 mol) was added slowly at 0-5° C. The mixture was stirred at ambient temperature for 45 mins. The reaction was quenched with ice and MeOH to form a precipitate. After filtration, the filtrate was washed with MeOH to give 66-8 (200 g, 61.2%) as a white solid.

To a solution of 66-8 (100 g, 269 mmol) in anhydrous THF (1000 ml) was added dropwise a solution of lithium tri-tert-butoxyaluminohydride (400 ml, 1M, 0.4 mol) at −78° C. under $N_2$ for 30 mins. The solution was stirred at −20° C. for 1 h, and TLC (PE:EA=3:1) showed that the reaction was complete. The mixture was quenched with sat.$NH_4Cl$, and diluted with EA. After filtration, the filtrate was extracted with EA. The combined layers were dried over $Na_2SO_4$, and concentrated at low pressure. The residue was purified by a silica column gel (PE:EA=20:1) to give 66-9 (100 g, 100%) as a colorless oil.

To a stirred solution of $PPh_3$ (140 g, 382 mol) in $CH_2Cl_2$ (1000 ml) was added 66-9 (100 g, 269 mmol) at −20° C. under $N_2$. After stirring for 15 mins, $CBr_4$ (177 g, 382 mol) was added dropwise while maintaining the temperature between −25 and −20° C. under $N_2$. The mixture was stirred below −17° C. for 20 mins. Silica gel was added to the mixture. The mixture was filtered through cold silica column gel and washed with PE:EA (50:1 to 4:1). The combined filtrates were concentrated under reduced pressure at R.T. to give the crude oil product. The residue was purified by a silica column gel a second time (PE:EA=50:1 to 4:1) to give 66-10 (α-isomer, 64 g, yield: 55%) as a colorless oil.

A mixture of 6-chloro-guanine (55.8 g, 316.5 mol) and t-BuOK (39.5 g, 352.7 mmol) in t-BuOH (500 mL) and MeCN (280 mL) was stirred for 30 mins. Compound 66-10 (48 g, 105.5 mmol) was added at R.T., and the mixture was heated to 50° C. and stirred overnight. The reaction was monitored by TLC (PE:EA=2:1). The mixture was quenched with solid $NH_4Cl$. After stirring for 1 h, the mixture was filtered and washed with MeCN. The filtrate was evaporated at low pressure, and the residue was purified by a silica gel column to give 66-11 (33 g, 57%).

To a solution of 66-11 (49 g, 93.1 mol) in $CH_2Cl_2$ (200 mL) was added $AgNO_3$ (31.7 g, 186 mmol), collidine (22.5 g, 186 mmol) and MMTrCl (43 g, 140 mmol) in small portions under $N_2$ at 0° C. The mixture was stirred at R.T., and monitored by TLC (PE:EA=4:1). After filtration, the organic phase was washed with $NaHCO_3$ aqueous and brine. The organic layer was dried over anhydrous $Na_2SO_4$ and concentrated at low pressure. The residue was purified by a silica gel column (PE:ME=20:1 to 1:1) to give 66-12 (70 g, 94.2%).

Sodium (10.1 g, 439 mmol) was dissolved in dry EtOH (600 mL) at 70° C. and then cooled to 0° C. To a solution of 66-12 (70 g, 87.7 mmol) was added a freshly prepared NaOEt solution in portions at 0° C., and the mixture was stirred for 1 h. at R.T. After TLC and LCMS showed the reaction was completed, the reaction was quenched with carbon dioxide. The mixture was evaporated at low pressure, and the residue was purified using silica gel column chromatography (DCM:MeOH=100:1 to 20:1) to give 66-13 (50 g, yield 5%) as a yellow solid.

A mixture of $PPh_3$ (35 g, 133.5 mol) and $I_2$ (31.75 g, 125 mmol) in anhydrous pyridine (600 mL) was stirred for 30 mins, and then a solution of 66-13 (50 g, 83.3 mmol) in pyridine (100 mL) was added at 0° C. The mixture was stirred overnight at R.T. and monitored by TLC (DCM:MeOH=50:1). The reaction was quenched with a sat. $NaHCO_3$ solution, and extracted with DCM (3×50 mL). The organic phase was dried over anhydrous $MgSO_4$, and evaporated at low pressure. The residue was purified using silica gel column chromatography (DCM:MeOH=200:1 to 50:1) to give 66-14 (50 g, 84.7%).

To a solution of 66-14 (37 g, 52.1 mmol) in dry THF (400 mL) was added DBU (16 g, 105 mmol). The mixture was heated to reflux and stirred for 3 h. The reaction was monitored by LCMS. The reaction was quenched with a sat. $NaHCO_3$ solution, and extracted with EA. The combined organic layers were dried over anhydrous $Na_2SO_4$, and evaporated at low pressure. The residue was purified using silica gel column chromatography (PE:EA=10:1 to 5:1) to give 66-15 (25 g, 61.1%) as a white solid.

To an ice-cold solution of 66-15 (26 g, 44.6 mmol) in dry MeCN (300 mL) was added NIS (12.68 g, 56 mmol) and $NEt_3$.3HF (10.6 g, 67 mmol) at 0° C. The reaction was stirred at R.T. for 2 h. and monitored by LCMS. After the reaction was completed, the reaction was quenched with a sat $Na_2SO_3$ and sat. $NaHCO_3$ solution, and extracted with EA. The organic layer was separated, dried over anhydrous $Na_2SO_4$, and evaporated at low pressure. The residue was purified using silica gel column chromatography (PE:EA=8:1 to 1:1) to give 66-16 (21 g, 64.4%) as a white solid.

To a solution of 66-16 (21 g, 28.8 mol) in $CH_2Cl_2$ (150 mL) was added $AgNO_3$ (9.8 g, 59.6 mmol) and collidine (7 g, 59.8 mmol) and MMTrCl (13.1 g, 42.5 mmol) in small portions under $N_2$ at 0° C. The mixture was stirred at R.T., and the reaction was monitored by TLC (PE:EA=2:1). After filtration, the solution was washed with sat. aq. $NaHCO_3$ and brine. The organic layer was separated, dried over anhydrous $Na_2SO_4$ and concentrated at low pressure. The residue was purified by a silica gel column to give 66-17 (25 g, yield 86.5%).

To a solution of 66-17 (22 g, 22 mmol) in dry DMF (500 mL) was added NaOBz (31.9 g, 220 mmol) and 15-crown-5 (48.4 g, 220 mmol), and the mixture was stirred for 72 h. at 95° C. The mixture was diluted with EA, washed with water and brine, and dried over $MgSO_4$. The organic layer was evaporated at low pressure, and the residue was purified using a silica gel column chromatography to give 66-18 (15 g, 68.8%) as a white solid.

Compound 66-18 (15.2 g, 15.3 mmol) was co-evaporated with anhydrous toluene 3 times to remove $H_2O$. The compound was treated with $NH_3$ in MeOH (7 N, 200 mL) at R.T. The mixture was stirred for 18 h at R.T., and the reaction was monitored by LCMS. The residue was concentrated at low pressure, and purified using silica gel column chromatography to give 66-19 (11 g, 81%) as a white solid.

To a stirred solution of 66-20 (14 g, 15.73 mmol) in anhydrous $CH_3CN$ (150 mL) was added N-methylimidazole (23.5 g, 283.9 mmol) at 0 to 5° C. (ice/water bath) followed by a solution of phenyl(cyclohexanoxy-L-alaninyl)phosphorochloridate (16.33 g, 47.2 mmol, dissolved in 50 mL of $CH_3CN$). The solution was stirred at 0 to 5° C. for 12 h and then diluted with EA. The solution was washed 50% aqueous citric acid solution and brine. The organic layer was separated, dried over anhydrous $MgSO_4$ and filtered. The filtrate was concentrated at low pressure, and the residue was purified on silica gel with PE:EA=5:1 as the eluent to give 66-20 (17.62 g, 93.4%) as a white solid.

Compound 66-20 (17.62 g, 14.7 mmol) was dissolved in 80% AcOH (200 mL), and the mixture was stirred overnight at R.T. After removal of the solvents, the reside was purified on silica gel using PE:EA=2:1 to eluent to give the crude product, which was purified on via reverse-phase HPLC using acetonitrile and water to give compound 66 (5.25 g, yield 66%) as a white solid. ESI-LCMS: m/z 655 $[M+H]^+$.

Example 49

Compound 67

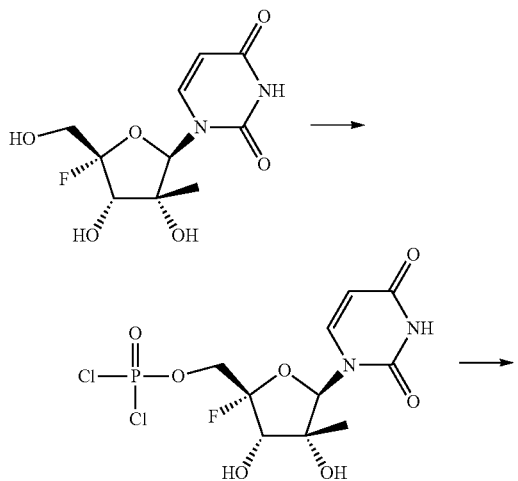

-continued

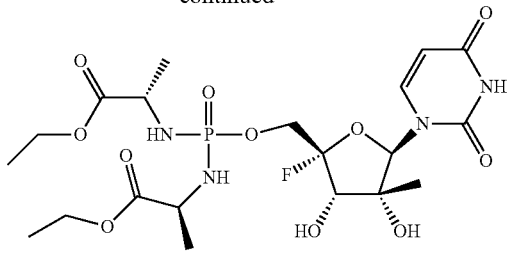

To a solution of the nucleoside (300 mg, 1.09 mmol) and proton-sponge (467 mg, 2.18 mmol) in anhydrous CH₃CN (5 mL) at 0° C. under N₂ was added dropwise a solution of phosphorus oxychloride (330 mg, 2.18 mmol) in anhydrous CH₃CN (1 mL). The mixture was stirred at 0° C. for 30 mins, and the hydrogen chloride salt of (S)-ethyl 2-aminopropanoate (998 mg, 6.52 mmol) and triethylamine (1.5 mL, 10.87 mmol) at 0° C. were added. The mixture was stirred overnight at 30° C. The reaction was quenched with water, and extracted with EA (3×20 mL). The organic layer was concentrated at low pressure, and the residue was purified by reverse phase HPLC to give compound 67 (20 mg, 3%) as a white solid. ESI-LCMS: m/z 535 [M-F]⁺.

Example 50

Compound 59

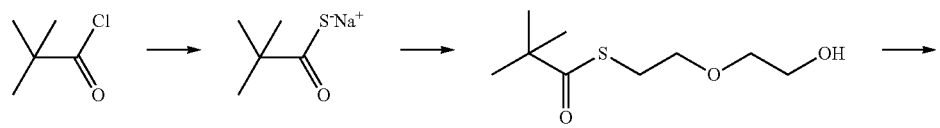

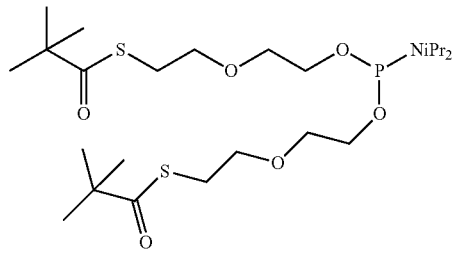

59-4

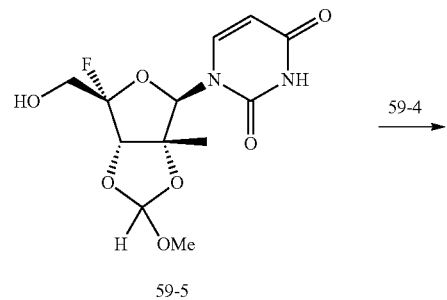

59-5

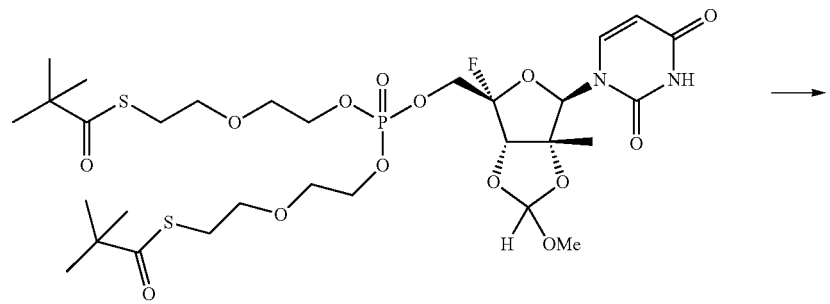

59-6

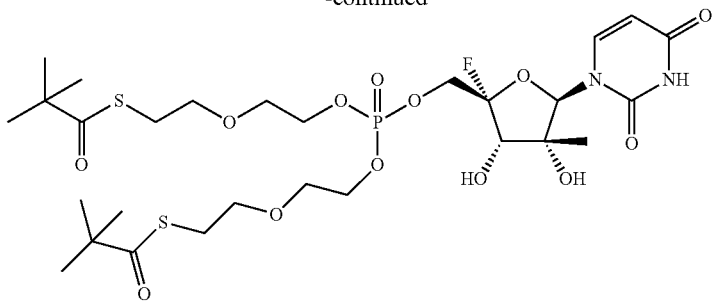

59

To a solution of sodium hydrosulfide (4.26 g, 76.0 mmol) in EtOH (100 mL) was added t-butyryl chloride (76.2 mmol; 9.35 mL) dropwise at 0° C., and the mixture was stirred at R.T. for 1 h. A solution of 2-(2-chloroethoxy)ethanol (57 mmol; 6.0 mL) and TEA (21 mL, 120 mmol) was added, and the mixture was heated at reflux for 60 h. The mixture was filtered, and then concentrated to a small volume. The residue was dissolved in EA, and then washed with water, sat. aq. NaHCO$_3$ and brine. The organic phase was dried over Na$_2$SO$_4$, filtered and concentrated in vacuo. The crude product (10.0 g) was isolated and 5 grams were purified by silica gel flash column chromatography using a gradient of 0 to 100% EA in hexane to give 59-3 (4.5 g, 22 mmol) as a clear, colorless oil. $^1$H-NMR (CDCl$_3$): 3.70-3.74 (m, 2H), 3.5-3.65 (m, 4H), 3.1 (t, 2H), 1.25 (s, 9H).

A solution 59-3 (4.5 g; 21.8 mmol) and triethylamine (6.7 mL, 87.2 mmol) in tetrahydrofuran (50 mL) was added dropwise over 1 h to a stirred solution of N,N-diisopropylphosphorodichloridite (2.0 mL, 10.9 mmol) in THF (50 mL) under argon at −78° C. The mixture was stirred at R.T. for 2 h, and then diluted with EA (200 mL). The mixture was washed with sat. aq. NaCl and dried over Na$_2$SO$_4$. After filtration, the filtrate was evaporated under reduced pressure to give a pale yellow oil. Purification by flash column chromatography using a gradient of EA (0-5%) in hexane containing 5% triethylamine afforded 59-4 (2.5 g, 4.25 mmol) as a clear, colorless oil. $^1$H-NMR (CDCl$_3$): 3.70-3.82 (m, 4H), 3.57-3.65 (m, 10H), 3.1 (t, 4H), 1.25 (s, 18H), 1.17 (t, 12H); $^{31}$P-NMR (CDCl$_3$): 148.0 ppm.

Compound 59-5 (285 mg, 0.9 mmol) and DCI (175 mg, 1.5 mmol) were coevaporated twice with ACN and then dissolved in ACN (5 mL). Compound 59-4 (790 mg, 1.35 mmol) in ACN (4 mL) was added, and the reaction was monitored by TLC. After 15 mins, tert-butylhydroperoxide (0.5 mL of 5.5M solution in decane) was added, and the mixture was stirred for 10 mins. The mixture was diluted with EA (25 mL), washed with sat. aq. NaHCO$_3$ and sat. aq. NaCl solution, dried over Na$_2$SO$_4$, filtered and concentrated. Purification by flash column chromatography using a gradient of EA (0-100%) in hexane afforded 59-6 (0.17 g, 0.22 mmol) as a white solid. Compound 59-6 was dissolved in 80% aq. HCOOH (5 mL). After 30 mins at R.T., the solvent was removed and coevaporated twice with toluene. The residue was dissolved in methanol (10 mL) and TEA (0.2 mL) was added. After 2 mins at R.T., the solvent was removed in vacuo. Purification by flash column chromatography using a gradient of methanol (0-15%) in DCM afforded compound 59 (90 mg). $^1$H-NMR (CDCl$_3$): 7.40 (d, 1H), 6.1 (s, 1H), 5.83 (d, 1H), 4.3 (t, 2H), 4.1-4.2 (m, 6H), 3.70-3.82 (m, 4H), 3.57-3.65 (m, 4H), 3.1 (t, 4H) 1.61 (s, 8H), 1.3 (s, 3H), 1.23 (s, 18H). $^{31}$P-NMR (CDCl$_3$): −1.55 ppm.

Example 51

Compound 60

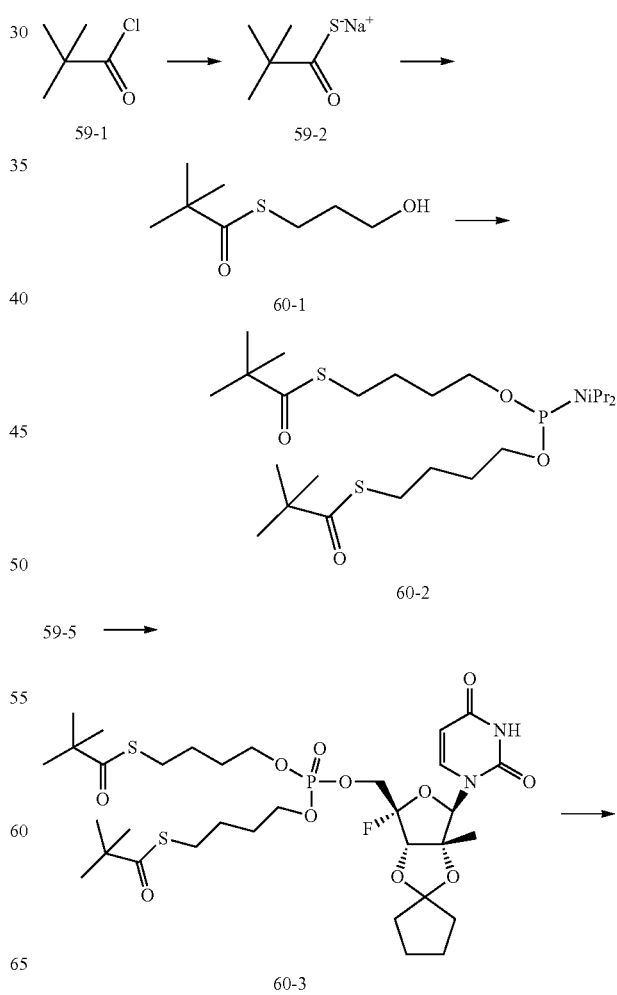

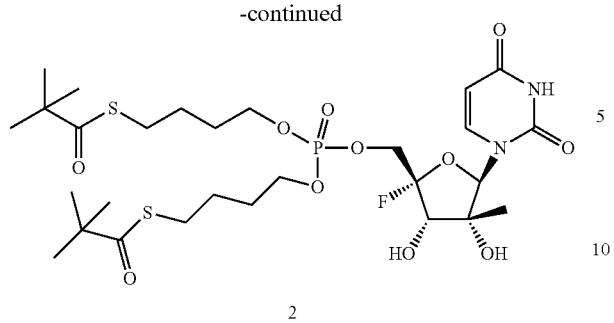

2

Compound 60-1 (6.0 g, 31.6 mmol) was prepared using a similar procedure to the one used to prepared 59-3 using 4-chlorobutanol. Compound 60-1 was obtained as a clear, colorless oil. $^1$H-NMR (CDCl$_3$): 3.67 (s, 2H), 2.86 (m, 2H), 1.65 (m, 4H), 1.25 (s, 9H).

Compound 60-2 (2.14 g, 4.0 mmol) was prepared using a similar procedure to the one used to prepared 59-4. Compound 60-2 was obtained as a clear, colorless oil. $^1$H-NMR (CDCl$_3$): 3.67 (m, 6H), 2.86 (t, 4H), 1.65 (m, 8H), 1.25 (s, 18H), 1.17 (t, 12H). $^{31}$P-NMR (CDCl$_3$): 143.7 ppm.

Compound 60-3 (0.23 g, 0.22 mmol) was prepared using a similar procedure to the one used to prepared 59-6 using 59-5 and 60-2. Compound 60-3 was obtained as a white solid. Using a similar procedure to the one used to prepared compound 59, 60-3 was used to prepare compound 60 (170 mg). $^1$H-NMR (CDCl$_3$): 7.40 (d, 1H), 6.1 (s, 1H), 5.83 (d, 1H), 4.3 (t, 2H), 4.1-4.2 (m, 6H), 2.8 (t, 4H), 1.78 (m, 4H), 1.69 (s, 8H), 1.3 (s, 3H), 1.23 (s, 18H). $^{31}$P-NMR (CDCl$_3$): −1.56 ppm.

Example 52

Compound 58

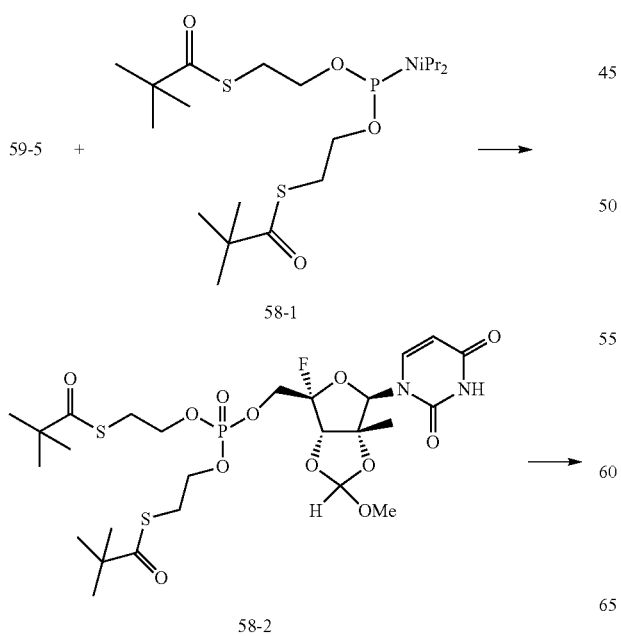

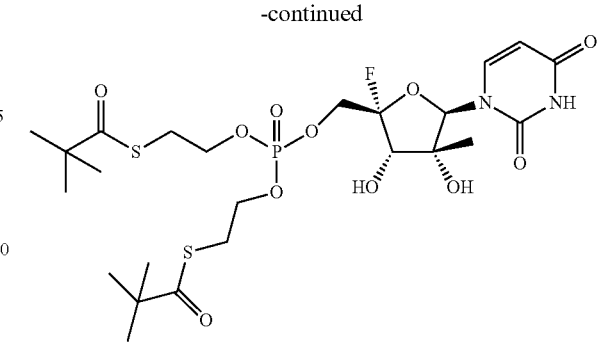

58

Compound 58-1 was prepared according to the procedure described in Lefebre et al. J. Med. Chem. (1995) 38:3941-3950, which is hereby incorporated by reference for the limited purpose of its description of the preparation of 58-1.

Compound 58-2 (0.33 g, 0.5 mmol) was prepared using a similar procedure to the one used to prepared 59-6 using 59-5 and 58-1. Compound 58-2 was obtained as a white solid. Using a similar procedure to the one used to prepared compound 59, 58-2 was used to prepare compound 58 (130 mg). $^1$H-NMR (CDCl$_3$): 7.40 (d, 1H), 6.1 (s, 1H), 5.83 (d, 1H), 4.3 (t, 2H), 4.1-4.2 (m, 6H), 3.2 (t, 4H), 1.69 (s, 4H), 1.3 (s, 3H), 1.23 (s, 18H); $^{31}$P-NMR (CDCl$_3$): −2.4 ppm.

Example 53

Compound 47

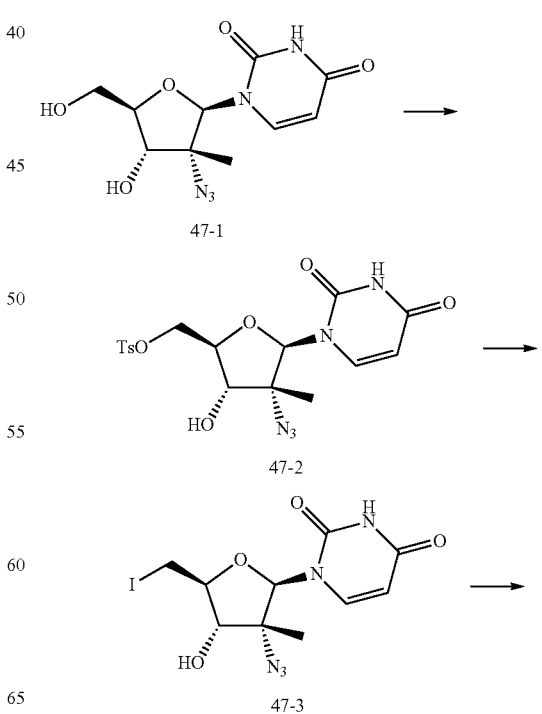

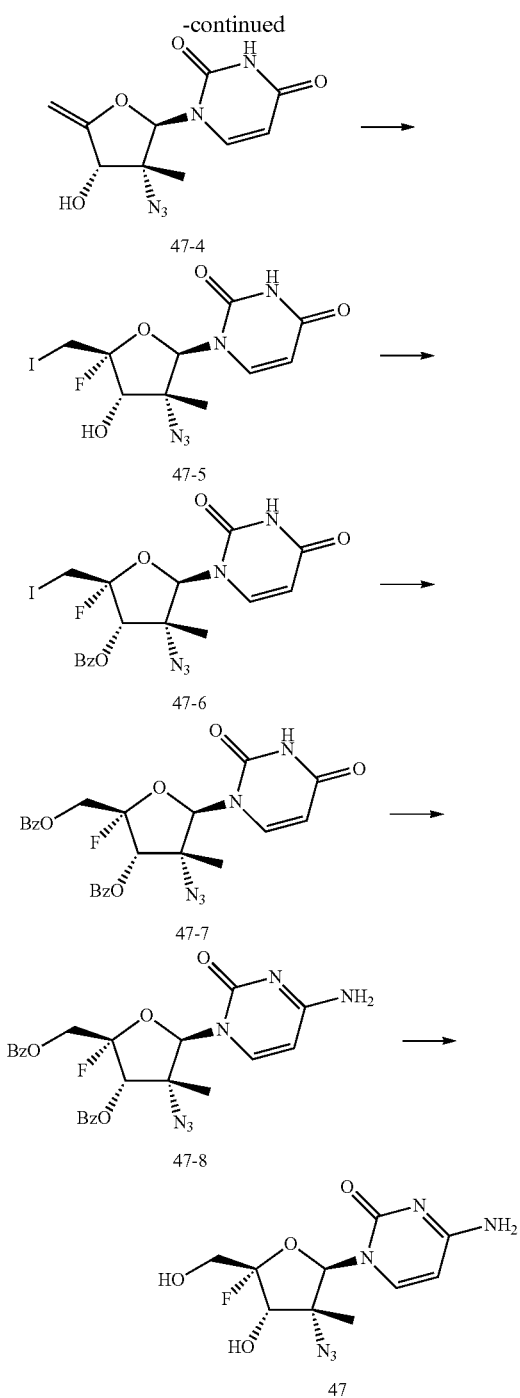

Compound 47-1 (1.0 g, 3.53 mmol) was coevaporated with anhydrous pyridine 3 times to remove $H_2O$. To an ice-cold solution of 47-1 in anhydrous pyridine (9 mL) was added TsCl (808 mg, 4.24 mmol) in pyridine (3 mL) drop-wise at 0° C., and the mixture was stirred for 18 h. at 0° C. The reaction was monitored by LCMS, and then quenched with $H_2O$. After concentration at low pressure, the residue was dissolved in EA (50 mL). The solution was washed with sat. $NaHCO_3$ solution and brine. The organic layer was dried over anhydrous $Na_2SO_4$ and filtered. The filtrate was evaporated at low pressure, and the residue was purified by silica gel column chromatography (1% MeOH in DCM) to give 47-2 (980 mg, 63%) as a white solid.

To a solution of 47-2 (980 mg, 2.24 mmol) in acetone (10 mL) was added NaI (1.01 g, 6.73 mmol), and the mixture was heated to reflux overnight. The reaction was monitored by LCMS. After the reaction was completed, the mixture was concentrated at low pressure. The residue was dissolved in EA (50 mL). The solution was washed with brine, and dried over anhydrous $Na_2SO_4$. The solution was evaporated at low pressure, and the residue was purified by silica gel column chromatography (1% MeOH in DCM) to give 47-3 (700 mg, 79%) as a solid.

To a solution of 47-3 (700 mg, 1.78 mmol) in dry THF (9 mL) was added DBU (817 mg, 5.34 mmol), and the mixture was heated to 60° C. The mixture was stirred overnight, and monitored by LCMS. The reaction was quenched with sat. $NaHCO_3$ and extracted with EA (3×50 mL). The organic phase was dried over anhydrous $Na_2SO_4$, and filtered. The filtrate was evaporated at low pressure, and the residue was purified by silica gel column chromatography (1% MeOH in DCM) to give 47-4 (250 mg, 53%) as a white solid.

To an ice-clod solution of 47-4 (250 mg, 0.94 mmol) in dry MeCN (5 mL) was added $NEt_3.3HF$ (151 mg, 0.94 mmol) and NIS (255 mg, 1.13 mmol). The mixture was stirred at R.T., for 3 h., and checked by LCMS. The reaction was quenched with sat $Na_2S_2O_3$ and sat. $NaHCO_3$ solution, and extracted with EA (3×50 mL). The organic layer was separated, dried over anhydrous $Na_2SO_4$, and evaporated at low pressure. The residue was purified by silica gel column chromatography (2% acetone in DCM) to give 47-5 (170 mg, 44%).

To a solution of 47-5 (270 mg, 0.65 mmol) in dry DCM (4 mL) was added DMAP (158.6 mg, 1.3 mmol), and BzCl (137 mg, 0.98 mmol). The mixture was stirred for 4-5 h. at R.T., and checked by LCMS. The mixture was diluted with $CH_2Cl_2$, and washed with sat. $NaHCO_3$ solution and brine. The organic layer was evaporated at low pressure, and the residue was purified by silica gel column chromatography (20% EA in PE) to give 47-6 (290 mg, 86%) as a solid.

To a solution of 47-6 (900 mg, 1.74 mmol) in dry DMF (45 mL) was added NaOBz (2.5 g, 17.4 mmol) and 15-crown-5 (4.5 g, 20.9 mmol). The mixture was stirred for 48 h at 90-100° C. The mixture was diluted with EA (100 mL), and washed with brine. The organic layer was evaporated at low pressure, and the residue was purified by silica gel column chromatography (20% EA in PE) to give 47-7 (500 mg, 56%) as a solid.

To a solution of 47-7 (500 mg, 0.98 mmol) in anhydrous $CH_3CN$ (5 mL) was added TPSCl (741 mg, 2.45 mmol), DMAP (299.6 mg, 2.45 mmol) and $NEt_3$ (248 mg, 2.45 mmol) at R.T., and the mixture was stirred overnight. The mixture was then treated with $NH_3$ in THF (5 mL) and then stirred for another 30 mins. The mixture was diluted with EA (100 mL). The solution was washed with 0.5% AcOH solution. The organic solvent was dried over anhydrous $MgSO_4$, and concentrated at low pressure. The crude product was purified by silica gel column chromatography (2% Acetone in DCM) to give 47-8 (257 mg, 51.6%) as a white solid. ESI-MS: m/z 509 $[M+H]^+$.

Compound 47-8 (80 mg, 0.16 mmol) was dissolved in n-butylamine (3 mL). The mixture was kept overnight at R.T. and evaporated. The residue was crystallized from methanol to give compound 47 (30 mg). The mother liquor was purified by RP HPLC on Synergy 4 micron Hydro-RP column (Phenomiex). A linear gradient of methanol from 0 to 30% in 50 mM triethylammonium acetate buffer (pH 7.5) was used for elution. The corresponding fractions were combined, concentrated and lyophilized 3 times to remove excess of buffer to yield additional compound 47 (13 mg). Compound 47 (total yield 43 mg, 73%). MS: m/z 299.7 [M–1]⁻.

Example 54

Compound 83

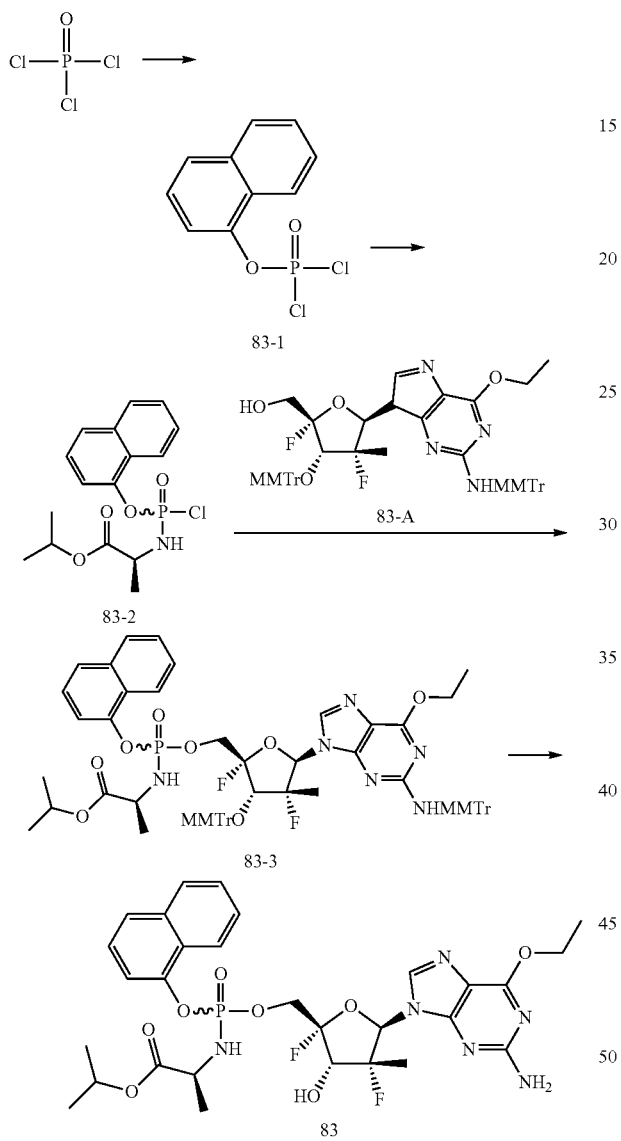

To a stirred solution of POCl$_3$ (2.0 g, 13 mmol) in anhydrous DCM (10 mL) was added 1-naphthol (1.88 g, 13 mmol) at –70° C., and TEA (1.31 g, 13 mmol) in DCM (3 mL) dropwise at –70° C. The mixture was gradually warmed to R.T. and stirred for 1 h. Crude 83-1 was obtained.

To a stirred solution of (S)-isopropyl 2-aminopropanoate hydrochloride (2.17 g, 13 mmol) in DCM (10 mL) was added crude 83-1 at –70° C. TEA (2.63 g, 26 mmol) was added to the stirred solution dropwise at –70° C. The mixture was gradually warmed to R.T. and stirred for 2 h. The reaction was monitored by LCMS and quenched with n-propylamine. The mixture was concentrated at low pressure, and the residue was purified by a silica gel column (PE:MTBE=5:1-1:1) to give pure 83-2 (1.6 g, 35%).

To a solution of 83-(A) (300 mg, 0.337 mmol) and NMI (276 mg, 3.37 mmol) in anhydrous CH$_3$CN (4 mL) was added 83-2 (240 mg, 0.674 mol, in DCM (5 mL)) at 0° C. The mixture was stirred at R.T. for 10 h. The reaction was monitored by LCMS. The reaction was quenched with water, and extracted with CH$_2$Cl$_2$ (3×20 mL). The organic phase was dried over anhydrous MgSO$_4$, and concentrated at low pressure. The residue was purified by sil-gel (PE: EA=5:1-2:1) to give 83-3 (380 mg, 93%).

Compound 83-3 (380 mg, 0.314 mmol) was dissolved in CH$_3$COOH (80%, 8 mL), and stirred at 40-50° C. for 2.5 h. The reaction was monitored by LCMS. The mixture was concentrated at low pressure, and the residue was purified by chromatography (PE:EA=1:1~EA) to give crude compound 83. The crude product was purified by prep-HPLC (neutral system, NH$_4$HCO$_3$) to give pure compound 83 (70 mg, 80%) as a white solid. ESI-MS: m/z 665.1 [M+H]⁺.

Example 55

Compound 79

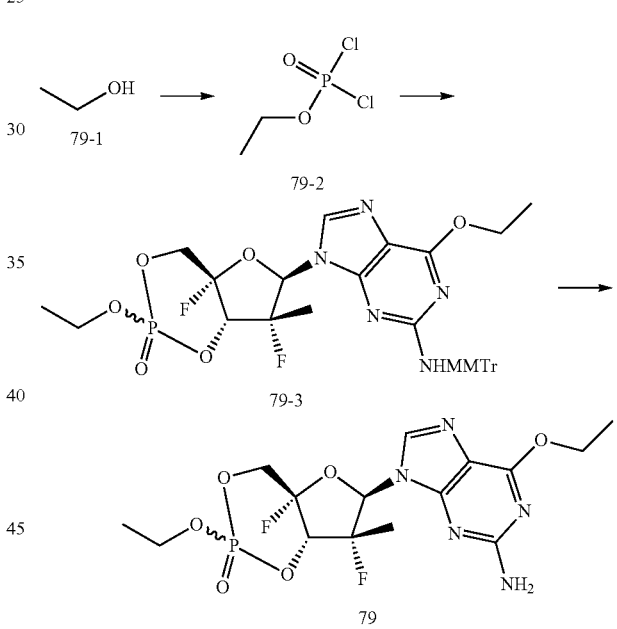

A solution of 79-1 (16.70 g, 0.363 mol) and TEA (36.66 g, 0.363 mol) in CH$_2$Cl$_2$ (150 mL) was added dropwise to a stirred solution of POCl$_3$ (55.65 g, 0.363 mol) in DCM (100 mL) over 25 mins at –78° C. After the mixture was stirred for 2 h. at R.T., the triethylamine hydrochloride salt was filtered, and washed with CH$_2$Cl$_2$ (100 mL). The filtrate was concentrated at low pressure, and the residue was distilled under high vacuum (~10 mm Hg) with a cow-head fraction collector. The product was collected between 45° C. (distillation head temperature) as a colorless liquid (30.5 g, 50% yield). $^1$H-NMR (400 MHz, CDCl$_3$) δ=4.44 (dq, J=10.85, 7.17 Hz, 2H), 1.44-1.57 (m, 3H); $^{31}$P-NMR (162 MHz, CDCl$_3$) δ=6.75 (br. s., 1P).

To a stirred suspension of 83-A (93 mg, 0.15 mmol) in CH$_2$Cl$_2$ (1 mL) was added TEA (61 mg, 0.15 mmol) at R.T. The mixture was cooled to –20° C., and then was treated with a 79-2 (35 mg, 0.21 mmol) solution dropwise over a period of 10 mins. The mixture was stirred at this temperature for 15 min., and then was treated with NMI (27 mg, 0.33 mmol). The mixture was stirred at −20° C., and then slowly warmed to R.T. The mixture was stirred overnight. The mixture was suspended in EA (15 mL), washed with brine (10 mL) and dried over anhydrous sodium sulfate. The solution was concentrated at low pressure, and the residue was purified by chromatography (DCM:MeOH=100:1) to give 79-3 (60 mg, yield: 56%) as a solid.

A solution of 79-3 (60 mg, 0.085 mmol) in 80% AcOH aqueous (2 mL) was stirred at R.T. for 2 h. The mixture was concentrated under reduced pressure, and the residue was purified by a silica gel column eluting DCM/MeOH=50/1and prep-HPLC to give compound 79 (23 mg, 62%) as a white solid. ESI-MS: m/z 436.3 [M+H]$^+$.

Example 56

Compound 80 with 80-2 (134 mg, 0.7 mmol). The mixture was stirred at this temperature for 15 mins and then was treated with NMI (90 mg, 1.1 mmol). The mixture was stirred at −20° C. for 1 h., and then slowly warmed to R.T. overnight. The mixture was suspended in EA (15 mL), washed with brine (10 mL), and dried over anhydrous sodium sulfate. The organic phase was concentrated at low pressure, and the residue was purified by silica column gel (DCM:MeOH=100:1) to give 80-3 (310 mg, yield: 84%) as a solid.

A solution of 80-3 (310 mg, 0.43 mmol) in 80% AcOH aqueous (4 mL) was stirred at R.T. for 2 h. The mixture was concentrated at low pressure, and the residue was purified by a silica gel column eluting DCM/MeOH=50/1 and prep-HPLC to give compound 80 (79 mg, 50%) as a white solid. ESI-MS: m/z 464.0 [M+H]$^+$.

Example 57

Compound 81

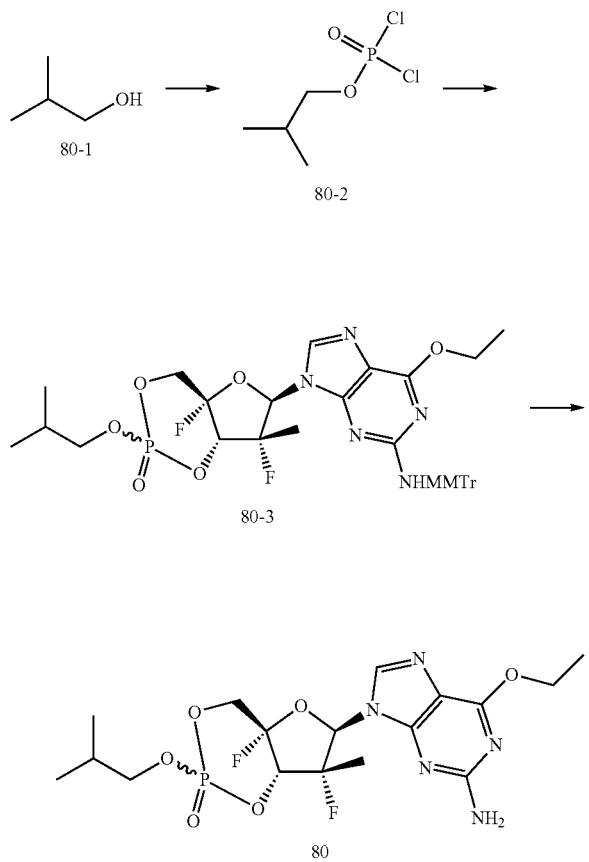

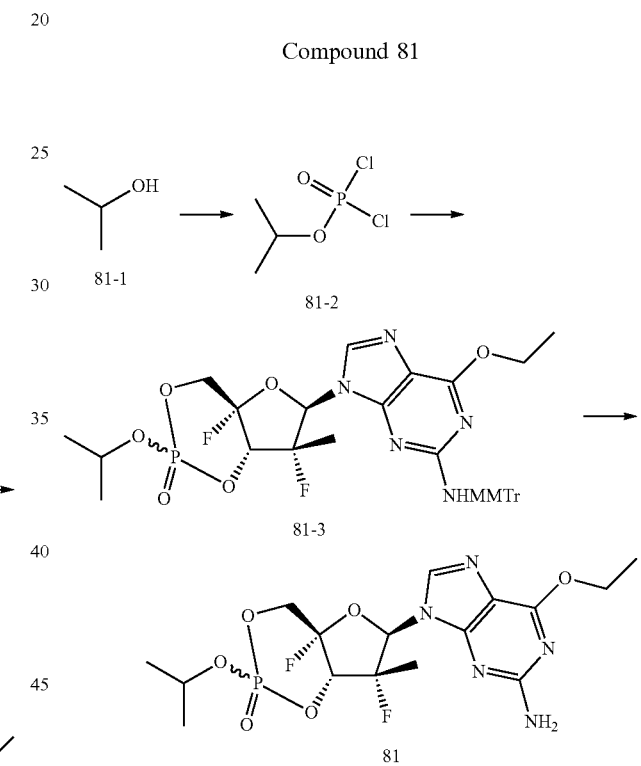

Compound 80-2 was prepared using a similar procedure as for the preparation of 79-2 using a solution of iso-butanol (23.9 g, 322.98 mmol) and POCl$_3$ (49.5 g, 322.98 mmol). Compound 80-2 (26 g, 42% yield) was obtained as a colorless liquid. $^1$H-NMR (400 MHz, CDCl$_3$) δ=4.10 (dd, J=9.04, 6.39 Hz, 2H), 2.09 (dq, J=13.24, 6.67, 6.67, 6.67, 6.67 Hz, 1H), 1.01 (d, J=6.62 Hz, 6H); $^{31}$P-NMR (162 MHz, CDCl$_3$) δ=7.06 (br. s., 1P).

To a stirred suspension of 83-A (310 mg, 0.5 mmol) in CH$_2$Cl$_2$ (3 mL) was added TEA (202 mg, 2 mmol) at R.T. The mixture was cooled to −20° C., and then was treated Compound 81-2 was prepared using a similar procedure as for the preparation of 79-2 using a solution of isopropyl alcohol (21 g, 350 mmol) and POCl$_3$ (53.6 g, 350 mmol). Compound 81-2 (40.5 g, 65% yield) was obtained as a colorless liquid. $^1$H-NMR (400 MHz, CDCl$_3$) δ=4.94-5.10 (m, 1H), 1.48 (d, J=6.17 Hz, 6H); $^{31}$P-NMR (162 MHz, CDCl$_3$) δ=5.58 (br. s., 1P).

Compound 81-3 was prepared using a similar procedure as for the preparation of 80-3 using 81-2 (124 mg, 0.7 mmol) and 83-A (310 mg, 0.5 mmol). Compound 81-3 (300 mg, 83%) was obtained as a solid.

Compound 81 was prepared using a similar procedure as for the preparation of compound 80 using 81-3 (300 mg, 0.41 mmol) in 80% AcOH aqueous (4 mL). Compound 81 (80 mg, 43%) was obtained as a white solid. ESI-MS: m/z 450.0 [M+H]$^+$.

Example 58
Compound 82
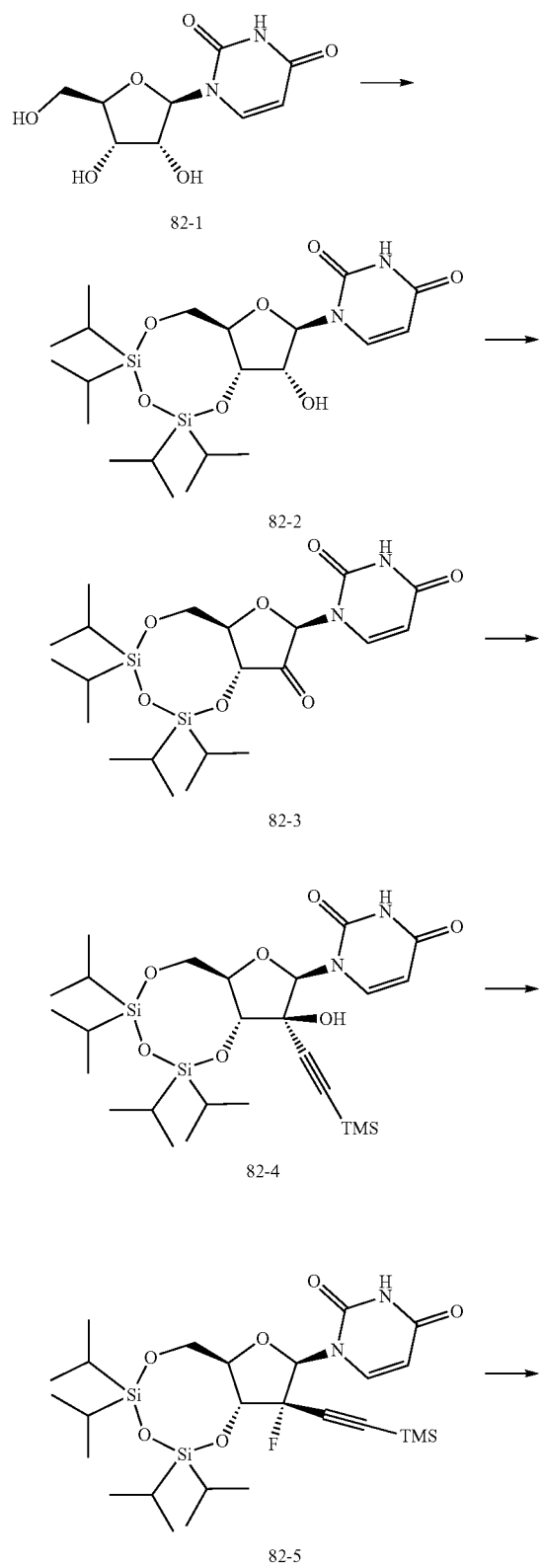
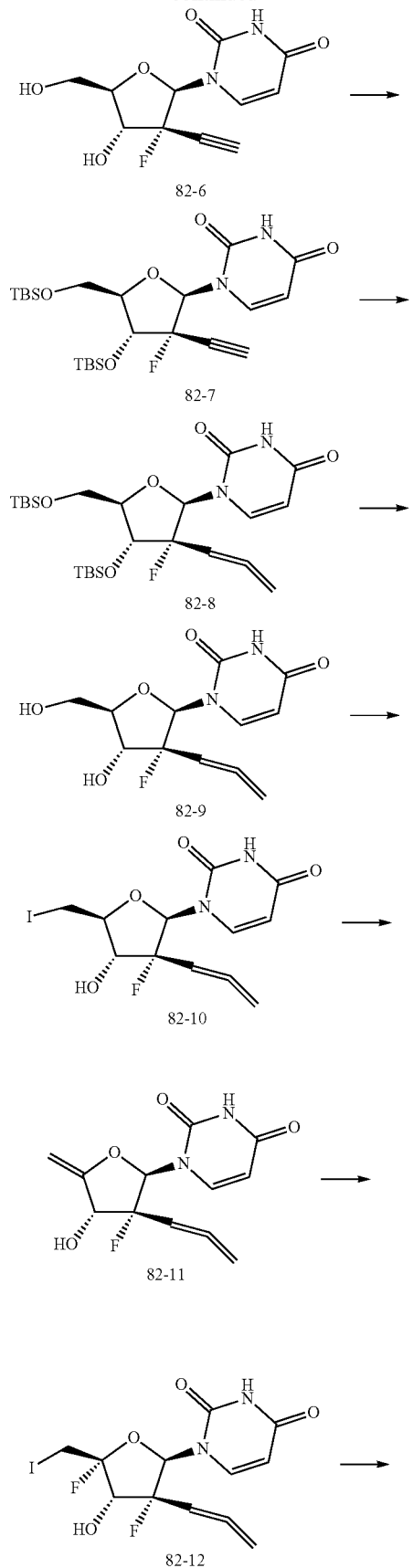

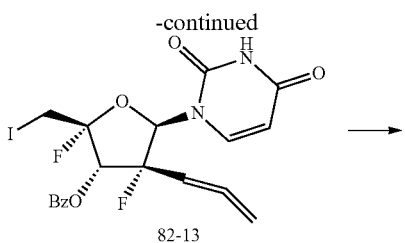

82-13

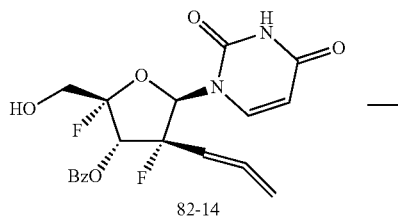

82-14

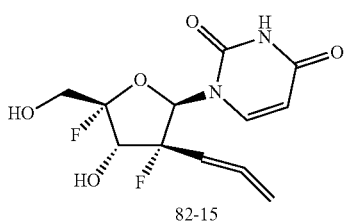

82-15

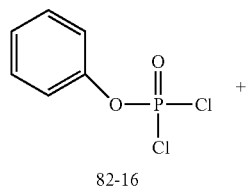

82-16

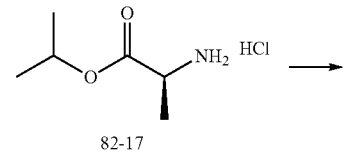

82-17

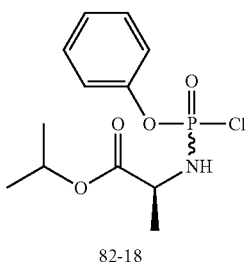

82-18

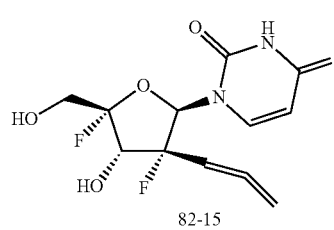

82-15

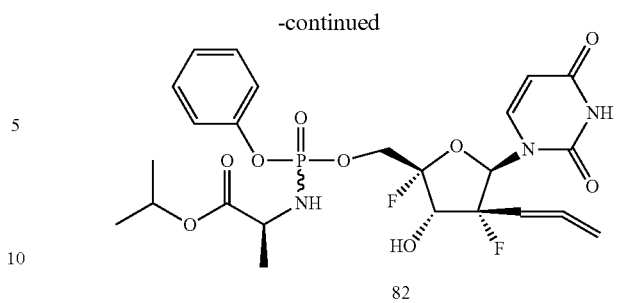

82

To an ice cooled solution of 82-1 (50 g, 204.9 mmol) in dry Py (400 mL) was added TIPDSCl (70.78 g, 225.4 mmol) dropwise. The mixture was stirred at R.T. for 16 h, and then concentrated at low pressure. The residue was purified by chromatography using 20% EA in PE to generate 82-2 (111.5 g, 100%) as a white solid.

To a solution of 82-2 (50 g, 103 mmol) in anhydrous $CH_3CN$ (400 mL) was added IBX (43 g, 153 mmol) at R.T. The mixture was refluxed overnight and monitored by TLC (PE:EA=1:1). The precipitate was filtered off, and the filtrate was concentrated to give the crude 82-3 (50 g, 99%) as a white solid.

To a solution of trimethylsilylacetylene (20 g, 200 mmol) in anhydrous THF (400 mL) was added dropwise n-BuLi (80 mL, 200 mL) at −78° C. The mixture was stirred at −78° C. for 30 mins, and then warmed to R.T for 10 mins. Compound 82-3 (30 g, 60 mmol) in THF (100 mL) was added to the mixture dropwise at −78° C. The mixture was stirred at −78° C. for 1 h and then slowly warmed to R.T. The mixture was stirred for 20 mins, and then the reaction was quenched with a sat. $NH_4Cl$ solution at −78° C. The mixture was diluted with EA. The organic phase was washed with brine, dried over anhydrous $Na_2SO_4$, and concentrated at low pressure. The residue was purified by silica gel column chromatography (15% EA in PE) to give 82-4 as a white solid (14 g, 50%).

Compound 82-4 (14 g, 24 mmol) was dissolved in anhydrous toluene (100 mL) under $N_2$ and cooled to −78° C. DAST (19 g, 120 mmol) was added dropwise at −78° C. and stirring was continued for 1.5 h. The mixture was diluted with EA and poured into a sat. $NaHCO_3$ solution. The organic layer was washed with brine, dried over anhydrous $Na_2SO_4$, and concentrated at low pressure. The residue was purified by silica gel chromatography (20% EA in PE) to give 82-5 as a white solid (12 g, 81%).

A mixture of 82-5 (12 g, 20 mmol) and $NH_4F$ (11 g, 30 mmol) in MeOH (150 mL) was refluxed for 2 h. After cooling to R.T, the mixture was concentrated at low pressure, and the residue was purified by silica gel column chromatography (5% MeOH in DCM) to give 82-6 (3.1 g, 58%) as a white solid.

To a solution of 82-6 (3.1 g, 11.6 mmol) in dry Py (50 mL) was added imidazole (3.1 g, 46.4 mmol) and TBSCl (5.2 g, 34.8 mmol). The mixture was stirred at 50-60° C. for 3 h. The mixture was concentrated at low pressure, and the residue was dissolved in EA (100 mL). The solution was washed with brine, dried over anhydrous $Na_2SO_4$, and concentrated at low pressure. The residue was purified by silica gel chromatography (20% EA in PE) to give 82-7 as a white solid (5 g, 86%).

To a solution of 82-7 (4.5 g, 9 mmol) in 1,4-dioxane (45 mL) was added CuBr (643 mg, 4.5 mmol), dicyclohexylamine (3.3 g, 18 mmol) and paraformaldehyde (675 mg, 22.5 mmol). The mixture was refluxed for 24 h and then cooled to R.T. The reaction was quenched with a sat. NH₄Cl solution. The mixture was extracted with EA (3×100 mL). The organic layer was washed with brine, dried over anhydrous Na₂SO₄, and concentrated at low pressure. The residue was purified by silica gel column chromatography (15% EA in PE) to give 82-8 as a white solid (2.0 g, 43%).

A mixture of 82-8 (2 g, 4 mmol) and NH₄F (2.2 g, 60 mmol) in MeOH (20 mL) was refluxed overnight. After cooling to R.T., the mixture was concentrated at low pressure, and the residue was purified by silica gel column chromatography (5% MeOH in DCM) to give 82-9 (946 mg, 83%) as a white solid.

To a stirred suspension of 82-9 (946 mg, 3.33 mmol), PPh₃ (1.3 g, 5 mmol), imidazole (453 mg, 6.66 mmol) and pyridine (3 mL) in anhydrous THF (12 mL) was added a solution of I₂ (1 g, 4.33 mmol) in THF (4 mL) dropwise at 0° C. The mixture was warmed to R.T. and stirred for 16 h. The reaction was quenched with a sat. Na₂S₂O₃ aq. solution and extracted with EA (3×60 mL). The organic layer was dried over Na₂SO₄ and concentrated at low pressure. The residue was purified on a silica gel column (2% MeOH in DCM to 5% MeOH in DCM) to afford 82-10 (2.1 g, crude) as a white solid.

To a solution of 82-10 (2.1 g, 5.3 mmol) in THF (15 mL) was added DBU (15 g, 100 mmol) and the mixture stirred for 30 mins. The mixture was diluted with EA and neutralized with acetic acid. The solution was washed with brine, dried over anhydrous Na₂SO₄, and concentrated at low pressure. The residue was purified by silica gel column chromatography (1.5% MeOH in DCM) to give 82-11 as a white solid (800 mg, 90%).

To an ice-cooled solution of 82-11 (800 mg, 3 mmol) in dry MeCN (1.5 mL) was added NEt₃·3HF (484 mg, 3 mmol) and NIS (1.68 g, 7.5 mmol). The mixture was stirred at R.T. for 30 mins., and the reaction was monitored by LCMS. The reaction was quenched with sat. Na₂S₂O₃ and sat. NaHCO₃ solution, and extracted with EA (3×50 mL). The organic layer was dried over anhydrous Na₂SO₄, and concentrated at low pressure. The residue was purified by a silica gel column (25% EA in PE) to afford 82-12 (850 mg, 68%) as a white solid.

To a solution of 82-12 (850 mg, 2 mmol) in dry DCM (10 mL) was added DMAP (488 mg, 4 mmol) and BzCl (422 mg, 3 mol). The mixture was stirred for 4-5 h at R.T., and the reaction was monitored by LCMS. The mixture was diluted with CH₂Cl₂ (40 mL), and washed with a sat. NaHCO₃ solution. The organic layer was dried over anhydrous Na₂SO₄, and filtered. The filtrate was evaporated at low pressure, and the residue was purified by silica gel column chromatography (20% EA in PE) to give 82-13 (900 mg, 87%) as a white foam.

Tetra-butylammonium hydroxide (21 mL as 54-56% aqueous solution, 42 mmol, 24 eq.) was adjusted with TFA to pH ~4 (~3.5 mL), and the solution was treated with a solution of 82-13 (900 mg, 1.7 mmol) in DCM (21 mL). m-Cloroperbenzoic acid (2.1 g, 60-70%, ~8.75 mmol, ~5 eq.) was added portionwise under vigorous stirring, and the mixture was stirred overnight. The mixture was diluted with CH₂Cl₂ (30 mL), and washed with a saturated NaHCO₃ solution. The organic layer was washed with brine, dried over anhydrous magnesium sulfate and concentrated under reduced pressure. The residue was purified by column chromatography in (40-70% EA in PE) to give 82-14 as an oil. The residue was purified by TLC (50% EA in PE) to give pure 82-14 (350 mg 50%).

Compound 82-14 (350 mg, 0.86 mg) was treated with 7N NH₃ in MeOH (15 mL). The mixture was stirred for 2-3 h and monitored by TLC. The mixture was concentrated at low pressure, and the residue was purified by silica gel column chromatography (5% isopropanol in DCM) to give 82-15 (250 mg, 96%) as a white solid. ¹H NMR (CD₃OD, 400 MHz) δ=7.75 (d, J=7.9 Hz, 1H), 6.60-6.35 (m, 1H), 5.72 (d, J=8.2 Hz, 1H), 5.37-5.25 (m, 1H), 5.17-5.06 (m, 1H), 5.04-4.94 (m, 1H), 4.59-4.29 (m, 1H), 3.87-3.70 (m, 2H).

To a stirred solution of 82-16 (3.79 g, 18 mmol) and 82-17 (3 g, 18 mmol) in anhydrous DCM (60 mL) was added with a solution of TEA (4 g, 39 mmol) in DCM (40 mL) dropwise at −78° C., and the mixture was stirred for 2 h. The mixture was concentrated at low pressure, and the residue was dissolved in methyl-butyl ether. The precipitate was removed by filtration, and the filtrate was concentrated to give the crude product. The residue was purified by dry column chromatography (anhydrous DCM) to give pure 82-18 as a colorless oil (3 g, 54%).

Compound 82-15 (200 mg, 0.66 mmol) was coevaporated with toluene 3 times to remove H₂O. Compound 82-15 was treated with MeCN (1.5 mL) and NMI (541 mg, 6.6 mmol). The mixture was stirred at R.T., and then 82-18 (403 mg, 1.32 mmol) in MeCN (0.5 mL) was added. The residue was purified by a silica gel column (5% iPrOH in DCM) to give the crude product, which was purified by HPLC (0.1% HCOOH in water and MeCN) to give compound 82 (33 mg, 9%). ESI-LCMS: m/z 594 [M+Na]⁺.

Example 59

Compound 84

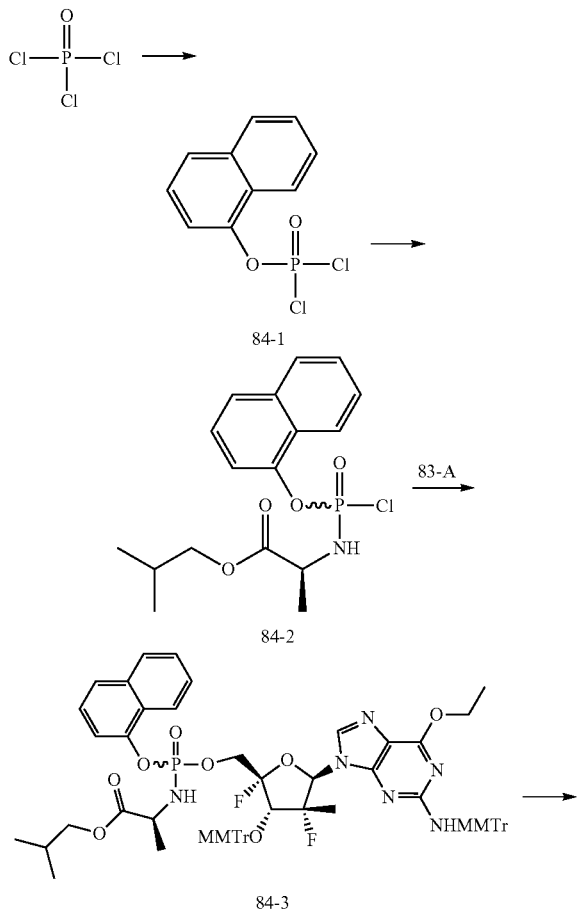

84-1

84-2

84-3

-continued

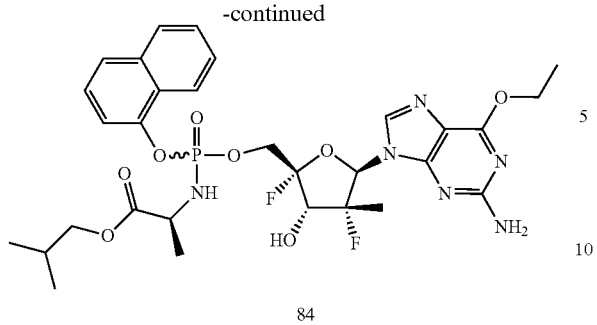

84

To a stirred solution of POCl₃ (2.0 g, 13 mmol) in anhydrous DCM (10 mL) was added 1-naphthol (1.88 g, 13 mmol) at −70° C. and TEA (1.31 g, 13 mmol) in DCM (3 mL) dropwise at −70° C. The mixture was gradually warmed to R.T., and stirred for 1 h. A crude solution of 84-1 was obtained.

To a stirred solution of (S)-isobutyl 2-aminopropanoate hydrochloride (2.35 g, 13 mmol) in DCM (20 mL) was added TEA (2.63 g, 26 mmol) and a crude solution of 84-1 at −70° C. The mixture was gradually warmed to R.T., and stirred for 2 h. The reaction was monitored by LCMS and quenched with n-propylamine. The solvent was evaporated at low pressure, and the residue was purified by chromatography (PE:MTBE=5:11:1) to give pure 84-2 (1.8 g, 37%).

To a solution of 83-A (300 mg, 0.337 mmol) and NMI (276 mg, 3.37 mmol) in anhydrous CH₃CN (4 mL) was added 84-2 (249 mg, 0.674 mol, in DCM (5 mL)) at 0° C. The mixture was stirred at R.T. for 10 h. The reaction was monitored by LCMS, and then quenched with H₂O. The mixture was extracted with CH₂Cl₂ (3×20 mL). The organic phase was dried over anhydrous MgSO₄, and concentrated at low pressure. The residue was purified by chromatography using PE:EA=5:1-2:1 as the eluent to give 84-3 (360 mg, 87%).

Compound 84-3 (360 mg, 0.294 mmol) was dissolved in CH₃COOH (80%, 8 mL), and stirred at 40-50° C. for 2.5 h. The reaction was monitored by LCMS and then quenched with MeO. The mixture was concentrated at low pressure, and the residue was purified by chromatography using PE:EA=1:1 as the eluent to generate crude compound 84. The product purified by prep-HPLC (neutral system, NH₄HCO₃) to give compound 84 (70 mg, 75%) as a white solid. ESI-MS: m/z 679.2 [M+H]⁺.

Example 60

Compound 85

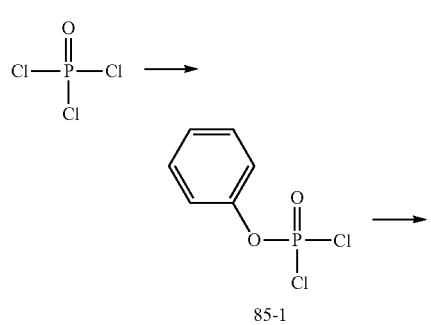

85-1

-continued

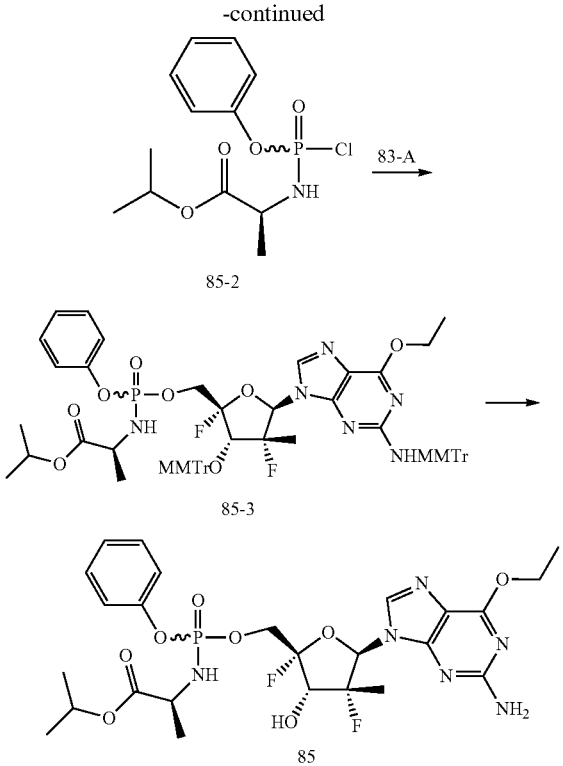

To a stirred solution of POCl₃ (2.0 g, 13 mmol) in anhydrous DCM (10 mL) was added phenol (1.22 g, 13 mmol) at −70° C. and TEA (1.31 g, 13 mmol) in DCM (3 mL) dropwise at −70° C. The mixture was gradually warmed to R.T., and stirred for 1 h. A crude solution of 85-1 was obtained.

Compound 85 was prepared using a similar procedure as for the preparation of compound 84 using 85-2 (205 mg, 0.674 mol, in DCM (5 mL) obtained from (S)-isopropyl 2-aminopropanoate hydrochloride and 85-1) and 83-A (300 mg, 0.337 mmol). Compound 85 (50 mg, 74%) was obtained as a white solid. ESI-MS: m/z 615.2 [M+H]⁺.

Example 61

Compound 86

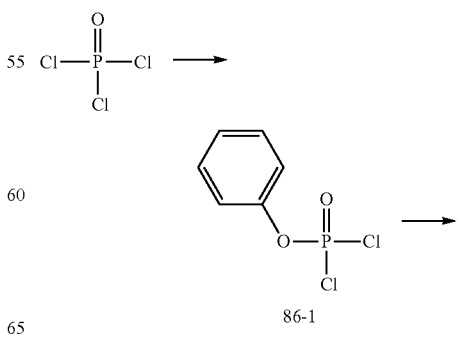

86-1

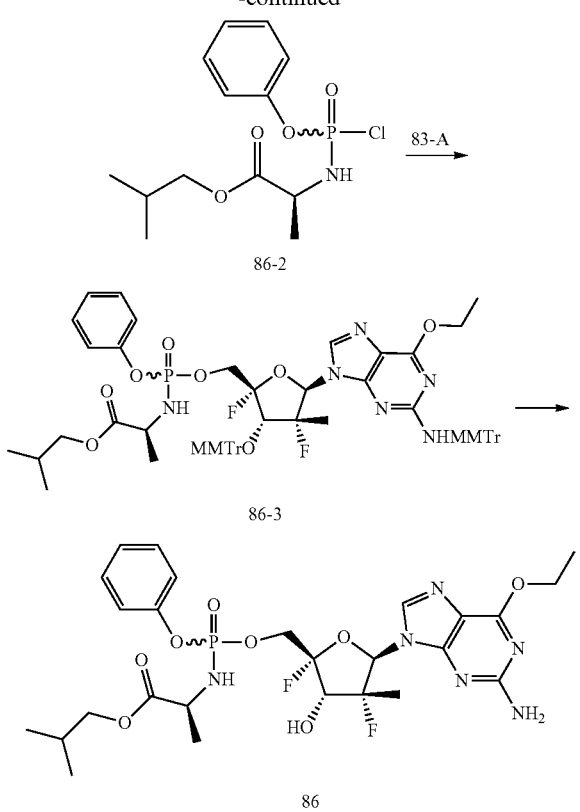

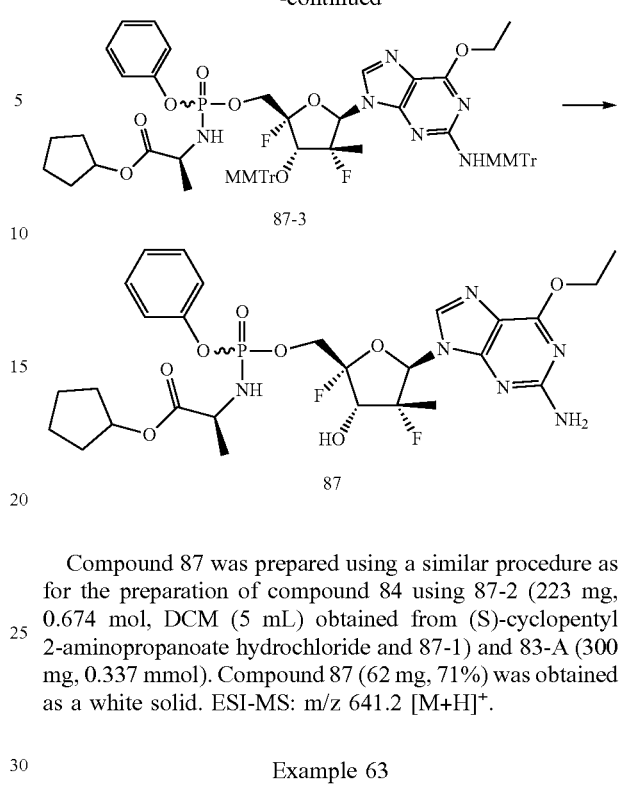

Compound 86 was prepared using a similar procedure as for the preparation of compound 84 using 86-2 (214 mg, 0.674 mol, in DCM (5 mL) obtained from (S)-isobutyl 2-aminopropanoate hydrochloride and 86-1) and 83-A (300 mg, 0.337 mmol). Compound 86 (70 mg, 87%) was obtained as a white solid. ESI-MS: m/z 629.2 [M+H]$^+$.

Example 62

Compound 87

Compound 87 was prepared using a similar procedure as for the preparation of compound 84 using 87-2 (223 mg, 0.674 mol, DCM (5 mL) obtained from (S)-cyclopentyl 2-aminopropanoate hydrochloride and 87-1) and 83-A (300 mg, 0.337 mmol). Compound 87 (62 mg, 71%) was obtained as a white solid. ESI-MS: m/z 641.2 [M+H]$^+$.

Example 63

Compound 88

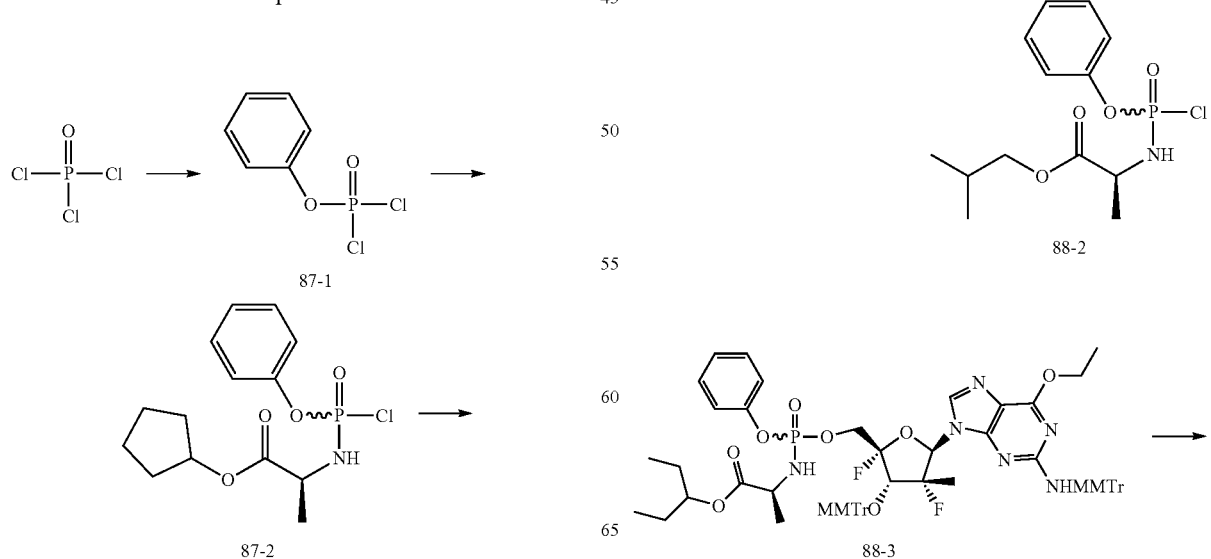

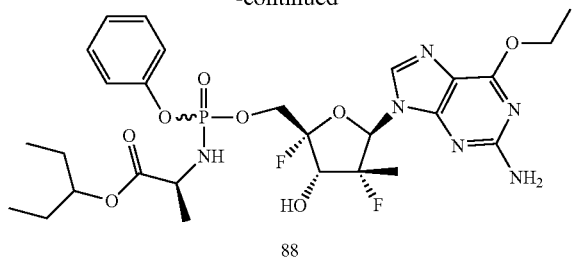

88

Compound 88 was prepared using a similar procedure as for the preparation of compound 84 using 88-2 (223 mg, 0.674 mol, DCM (5 mL), obtained from (S)-3-pentyl 2-aminopropanoate hydrochloride and 88-1) and 83-A (300 mg, 0.337 mmol). Compound 88 (42 mg, 60%) was obtained as a white solid. ESI-MS: m/z 643.2 [M+H]$^+$.

Example 64

Compound 89

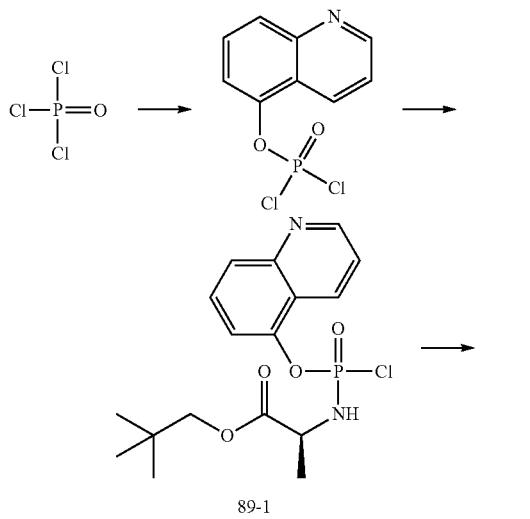

89-1

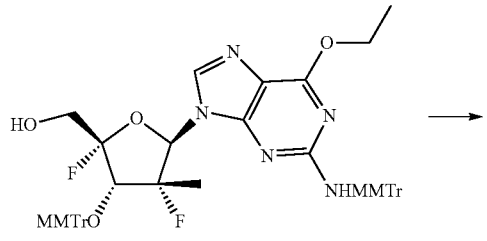

89-2

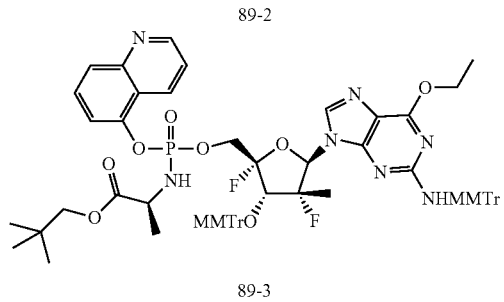

89-3

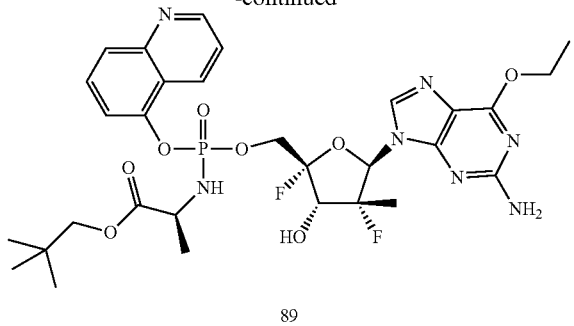

89

A stirred solution of phosphoryl trichloride (1.00 g, 6.58 mmol) and 5-quinoline (955 mg, 6.58 mmol) in anhydrous DCM (50 mL) was treated with a solution of TEA (665 mg, 6.58 mmol) in DCM (10 mL) at −78° C. The mixture was gradually warmed to R.T., and stirred for 2 h. The solution was cooled to −78° C. and then treated with (S)-neopentyl 2-aminopropanoate hydrochloride (1.28 g, 6.58 mmol). TEA (1.33 g, 13.16 mmol) was added dropwise at −78° C. The mixture was gradually warmed to R.T., and stirred for 2 h. The mixture was concentrated at low pressure, and the residue was dissolved in methyl-butyl ether. The precipitate was filtered off, and the filtrate was concentrated at low pressure. The residue was purified by a silica gel column (pure AcOEt) to give 89-1 as colorless oil (500 mg, 20%).

To a solution of 89-2 (300 mg, 0.337 mmol) and NMI (276.6 mg, 3.37 mmol) in anhydrous CH$_3$CN (0.9 mL) was added 89-1 (388 mg, 1.011 mmol) in CH$_3$CN (0.3 mL) dropwise at 0° C. The mixture was stirred at R.T. overnight. The reaction was quenched with water, and extracted with AcOEt. The organic phase was washed with brine, dried over anhydrous sodium sulfate, and concentrated at low pressure. The residue was purified by silica gel column (33% EA in PE) to give 89-3 as a yellow powder (300 mg, 71.9%).

Compound 89-3 (300 mg, 0.243 mmol) was dissolved in 80% CH$_3$COOH (3 mL), and the mixture was stirred at 60° C. for 2.5 h. The mixture was partitioned between AcOEt and water. The organic layer phase was washed by brine, dried over sodium sulfate and concentrated at low pressure. The residue was purified by silica gel column (50% EA in PE) to give compound 89 as a yellow powder (81 mg, crude product). The crude product (81 mg) was purified by RP HPLC to give compound 89 as a white solid. (28.7 mg, 17.1%). ESI-LCMS: m/z 694.1 [M+H]$^+$.

Example 65

Compound 90

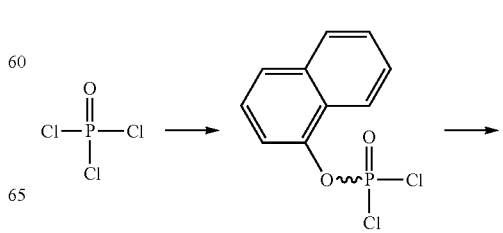

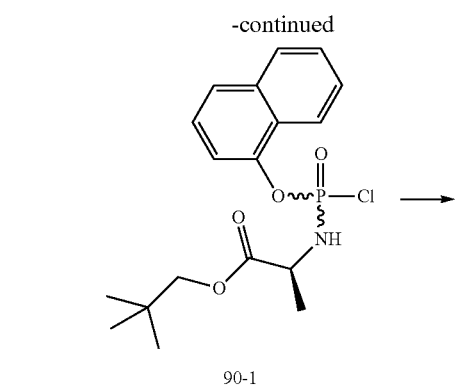

90-1

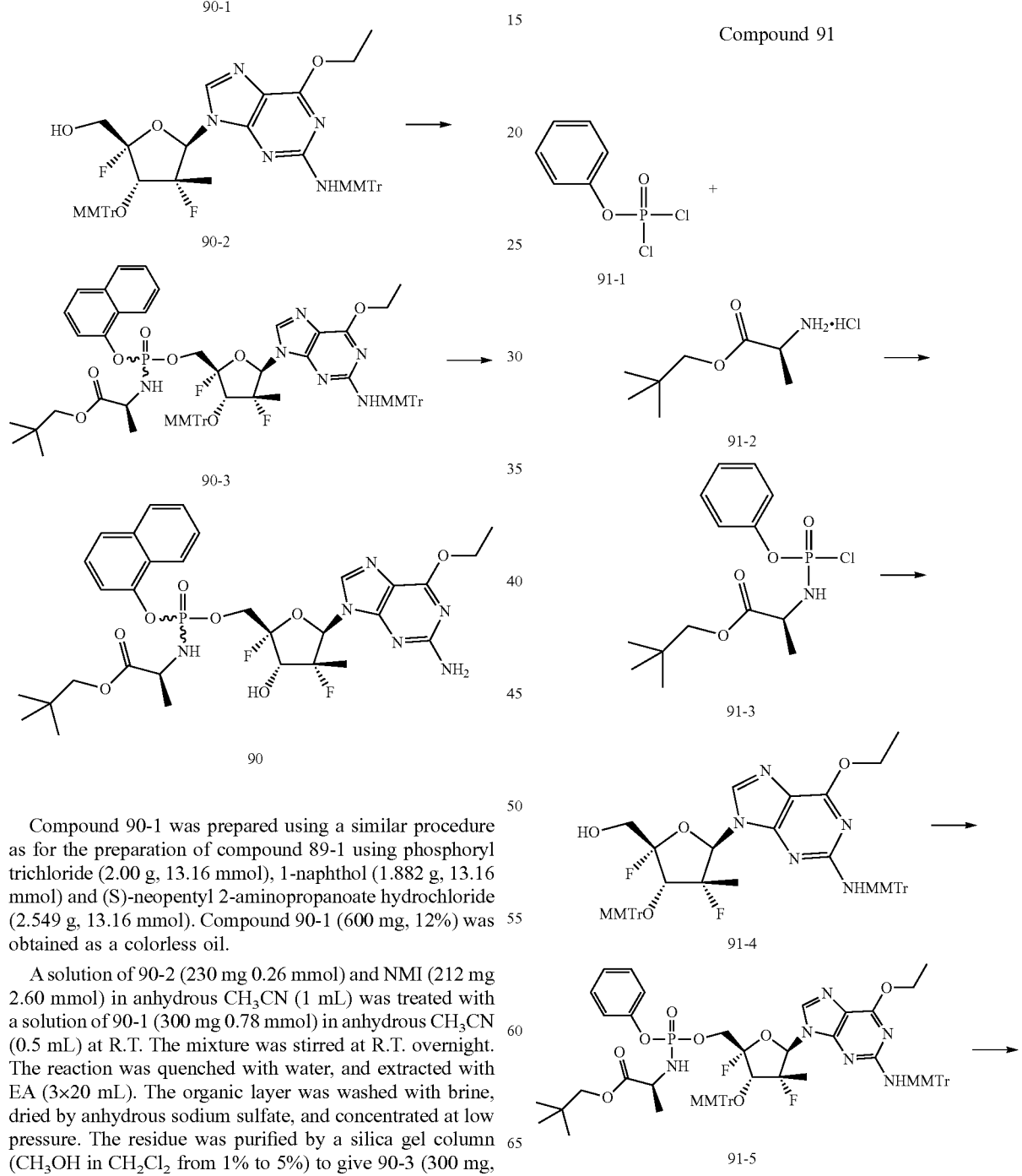

Compound 90-1 was prepared using a similar procedure as for the preparation of compound 89-1 using phosphoryl trichloride (2.00 g, 13.16 mmol), 1-naphthol (1.882 g, 13.16 mmol) and (S)-neopentyl 2-aminopropanoate hydrochloride (2.549 g, 13.16 mmol). Compound 90-1 (600 mg, 12%) was obtained as a colorless oil.

A solution of 90-2 (230 mg 0.26 mmol) and NMI (212 mg 2.60 mmol) in anhydrous $CH_3CN$ (1 mL) was treated with a solution of 90-1 (300 mg 0.78 mmol) in anhydrous $CH_3CN$ (0.5 mL) at R.T. The mixture was stirred at R.T. overnight. The reaction was quenched with water, and extracted with EA (3×20 mL). The organic layer was washed with brine, dried by anhydrous sodium sulfate, and concentrated at low pressure. The residue was purified by a silica gel column ($CH_3OH$ in $CH_2Cl_2$ from 1% to 5%) to give 90-3 (300 mg, 93%) as a white solid.

Compound 90-3 (300 mg, 0.24 mmol) was dissolved in $CH_3COOH$ (80%, 5 mL). The mixture was stirred at 60° C. for 2.5 h. The mixture was diluted with EA (30 mL) and washed with brine. The organic phase was dried over anhydrous sodium sulfate, and concentrated at low pressure. The residue was purified by a silica gel column ($CH_3OH$ in $CH_2Cl_2$ from 1% to 5%) to give crude compound 90 (105 mg). The crude product was purified by HPLC (0.1% $NH_4HCO_3$ in water and $CH_3CN$) to give compound 90 (45 mg, 26%) as a white solid. ESI-LCMS: m/z 693.2 $[M+H]^+$.

Example 66

Compound 91

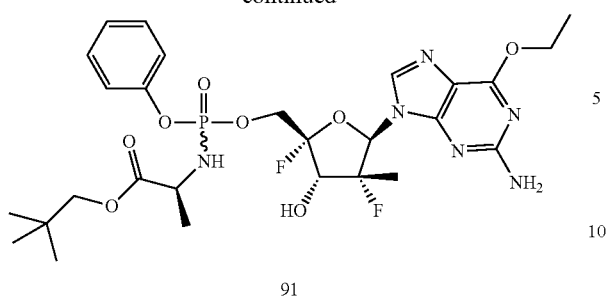

91

A stirred solution of 91-1 (2.00 g, 13.99 mmol) and 91-2 (2.00 g, 13.99 mmol) in anhydrous DCM (8 mL) was treated with a solution of TEA (3.11 g, 30.8 mmol) in DCM (20 mL) dropwise at −78° C. The mixture was stirred for 2 h. at −78° C. and then gradually warmed to R.T. The organic solvent was removed at low pressure, and the residue was dissolved in methyl-butyl ether. The precipitate was filtered off, and the filtrate was concentrated at low pressure. The residue was purified on a silica gel column (dry DCM) to give 91-3 as colorless oil (1 g, 20.96%).

Compound 91-4 (260 mg, 0.29 mmol) was coevaporated with toluene 3 times to remove H$_2$O. Dried 91-4 was treated with MeCN (0.8 mL) and NMI (240 mg, 2.9 mmol) and then stirred for 10 mins. The mixture was treated with a solution of 91-3 (291 mg, 0.87 mmol) in MeCN (0.4 mL), and then concentrated at low pressure. The residue was purified on a silica gel column (75% EA in PE)) to give 91-5 (300 mg, 86%) as a white solid.

Compound 91-5 (300 mg, 0.25 mmol) was treated with CH$_3$COOH (5 mL, 80%), and stirred at 50° C. for 3 h. The mixture was diluted with EA. The solution was washed with brine, dried over anhydrous Na$_2$SO$_4$, and concentrated at low pressure. The residue was purified by silica gel column chromatography (67% EA in PE) to give crude compound 91, which was purified by HPLC. The product was dried by lyophilization to give compound 91 (30 mg, 18.5%) as a white solid. ESI-LCMS: m/z 643 [M+H]$^+$.

Example 67

Compound 77

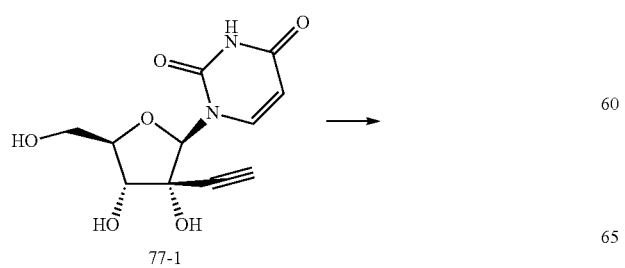

77-1

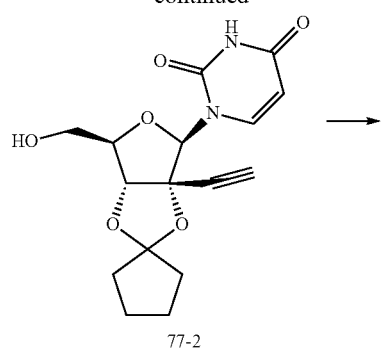

77-2

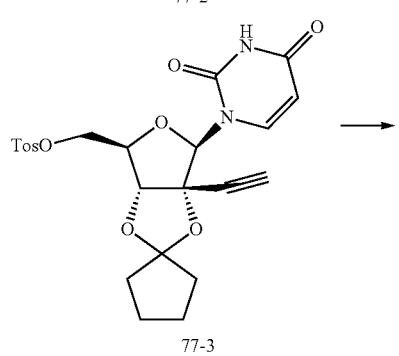

77-3

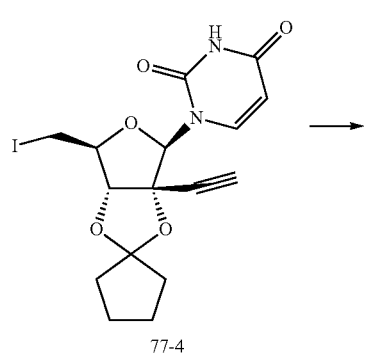

77-4

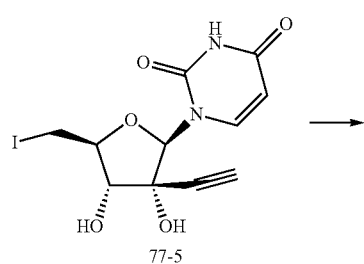

77-5

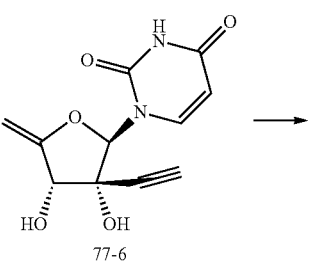

77-6

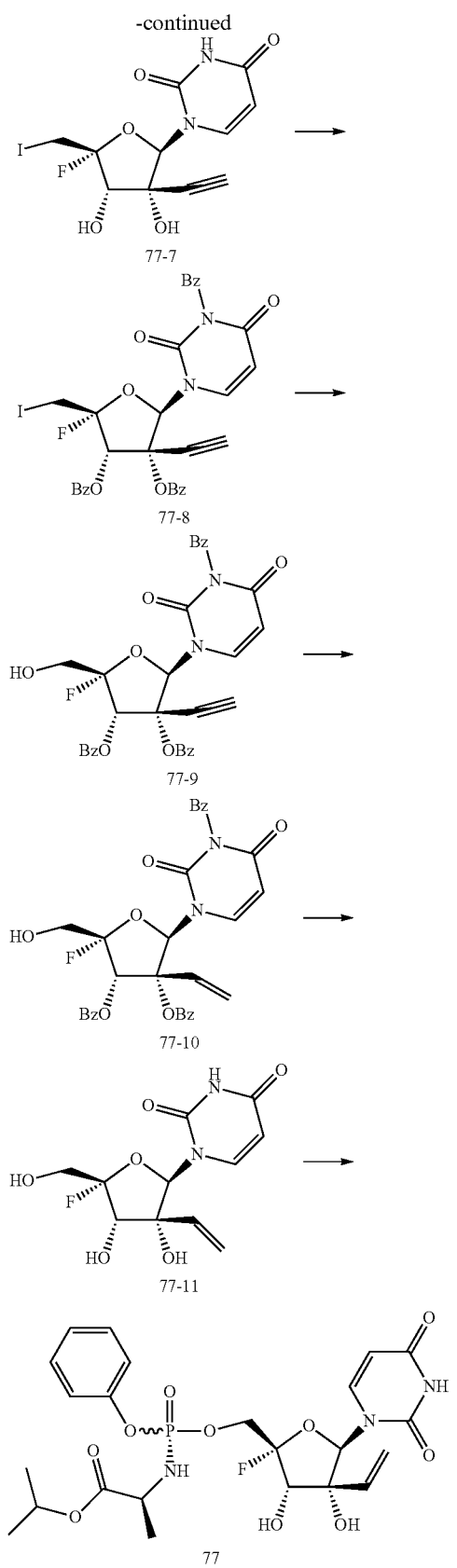

To a solution of 1,1-dimethoxycyclopentane (19.3 g, 148.52 mmol) and 77-1 (10.0 g, 37.13 mmol) in DCE (100 mL) was added TsOH.H₂O (0.7 g, 3.71 mmol). The mixture was stirred at 50° C. for 12 h. The mixture was neutralized with Et₃N, and concentrated at low pressure. The residue was purified by silica gel column chromatography (1-10% MeOH in DCM) to give 77-2 (8.7 g, 70.1%) as a white solid.

Compound 77-2 (20.0 g, 0.06 mol) was coevaporated with anhydrous pyridine 3 times to remove H₂O. To an ice-cold solution of 77-2 in anhydrous pyridine (100 mL) was added TsCl (22.8 g, 0.12 mol) at 0° C., and the mixture was stirred overnight. The reaction was monitored by LCMS and TLC. The reaction was quenched with H₂O, and the mixture extracted with EA (3×200 mL). The solution was dried over anhydrous Na₂SO₄ and evaporated at low pressure. The residue was purified by silica gel column chromatography (DCM:MeOH=100:1 to 15:1) to give 77-3 (20.0 g, 69.0%) as a white solid.

To a solution of 77-3 (20.0 g, 0.04 mol) in acetone (200 mL) was added NaI (31.0 g, 0.2 mol), and the mixture was heated to reflux overnight. The reaction was monitored by LCMS. The reaction was quenched with a sat. Na₂S₂O₃ solution. The solution was extracted with EA (3×200 mL). The organic layer was dried over anhydrous Na₂SO₄, and evaporated at low pressure. The residue was purified by silica gel column chromatography (DCM:MeOH=100:1 to 15:1) to give 77-4 (15.0 g, 83.3%) as a white solid.

Compound 77-4 (13.4 g, 30.16 mmol) was treated with HCOOH (80%) in H₂O at R.T. The solution was stirred at 60° C. for 2 h. The mixture was concentrated at low pressure. The residue was purified by column chromatography (1%-10% MeOH in DCM) to give 77-5 (9.1 g, 80.0%) as a white solid.

To a solution of 77-5 (5.0 g, 13.22 mmol) in anhydrous CH₃CN/THF (50 mL, 1:1, v:v) was added DBU (6.0 g, 39.66 mmol) at R.T. The solution was stirred at 50° C. for 1.5 h. The reaction was quenched with HCOOH at 0° C., and then concentrated at low pressure. The residue was purified by column chromatography (50%-70% EA in PE) to give 77-6 (3.3 g, 48.1%) as a white solid.

To an ice-cold solution of 77-6 (2.1 g, 8.39 mmol) in anhydrous MeCN (21 mL) was added NIS (2.4 g, 10.49 mmol) and TEA.3HF (1.0 g, 6.29 mmol) under N₂. The mixture was stirred at R.T. for 1 h. The reaction was quenched with sat. NaHCO₃ and sat. Na₂SO₃ solution, and extracted with EA (3×100 mL). The organic phase was dried over anhydrous Na₂SO₄, and evaporated to dryness at low pressure. The residue was purified on a silica gel column (30%-50% EA in PE) to give 77-7 (1.3 g, 39.3%) as a light yellow solid.

To a stirred solution of 77-7 (3.2 g, 8.08 mmol) in anhydrous DCM (32 mL) was added DMAP (2.5 g, 20.20 mmol) and Et₃N (2.5 g, 24.24 mmol) at R.T. The mixture was treated with BzCl (3.7 g, 26.66 mmol) at 0° C. and then stirred at R.T. overnight. The reaction was quenched with water, and extracted with EA (3×60 mL). The organic phase was concentrated at low pressure, and the residue was purified by column chromatography (20%-30% EA in PE) to give 77-8 (1.8 g, 31.6%) as a white solid.

Bu₄NOH (8.0 g, 13.74 mL, 55% in H₂O) was adjusted to pH=3-4 with TFA, and then cooled to R.T. To a solution of 77-8 (600 mg, 0.85 mmol) in DCM (10 mL) was added the Bu₄NOH solution and m-CPBA (917 mg, 4.25 mmol, 80%) at R.T. The mixture was stirred at 25° C. for 48 h and then washed with a sat. NaHCO₃ solution. The organic layer was directly passed through basic Al₂O₃ column, and the solvent was concentrated at low pressure. The residue was purified by a silica gel column (20%-30% EA in PE) to give 77-9 (123 mg, 24.3%) as a white solid.

To a solution of 77-9 (300 mg, 0.50 mmol) in EA/hexane (20 mL, 1:1, v:v) was added Lindlar catalyst (200 mg) under $N_2$. The mixture was stirred under H2 (40 Psi) at 2° C. for 1.5 h. The suspension was filtered, and the filtrate was treated with Lindlar catalyst (200 mg) under Na, and stirred under H2 (40 Psi) at 25° C. for 1.5 h. The mixture was filtered, and the filtrate was concentrated at low pressure to give crude 77-10 (287 mg) as a white solid.

Compound 77-10 (287 mg, 0.48 mmol) was dissolved in $NH_3$/MeOH (30 mL, 7 M). The mixture was stirred at R.T. for 24 h under Na and then concentrated at low pressure. The residue was purified by prep-HPLC (0.1% HCOOH in water and MeCN) to give 77-11 (50 mg, 34.7% over two steps) as a white solid. $^1$H-NMR (CD$_3$OD, 400 MHz) δ=7.86 (d, J=8.0 Hz 1H), 6.26 (s, 1H), 5.62-5.86 (m, 1H), 5.49 (d, J=17.1 Hz, 1H), 5.30 (d, J=10.5 Hz, 1H), 4.41 (d, J=19.3 Hz, 1H), 3.71-3.86 (m, 1H).

Compound 77-11 (113 mg, 0.39 mmol) was co-evaporated with toluene 3 times to remove $H_2O$. To a stirred solution of 77-11 (113 mg, 0.39 mmol) in a mixture of MeCN (0.5 mL) and NMI (320 mg, 3.90 mmol) was added a solution of 73-C (256 mg, 0.66 mmol) in MeCN (0.5 mL) at 0° C. The mixture was stirred at R.T. overnight and then concentrated at low pressure. The residue was purified on a silica gel column (5% MeOH in DCM) to give crude compound 77, which purified by prep-HPLC (0.1% HCOOH in water and MeCN) to give compound 77 (45 mg, 20.1%) as a white solid. ESI-MS: m/z 538.2 [M−F]$^+$ ESI-MS: m/z 580.2 [M+Na]$^+$.

Example 68

Compound 78

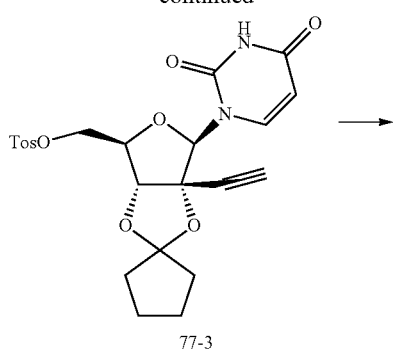

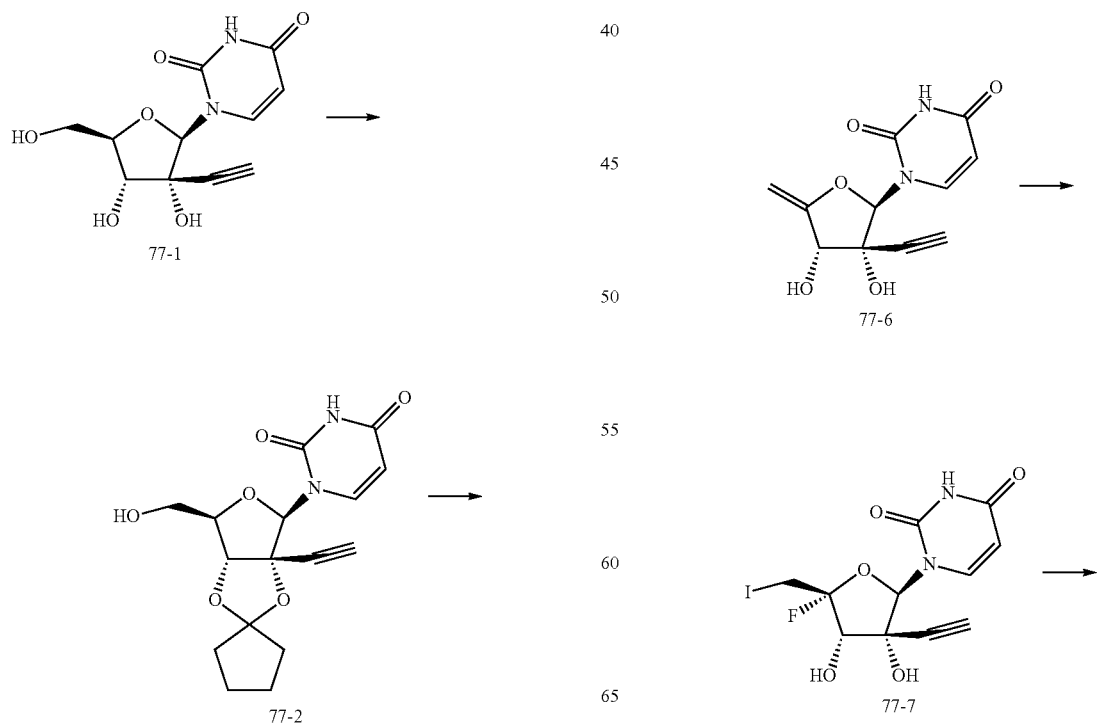

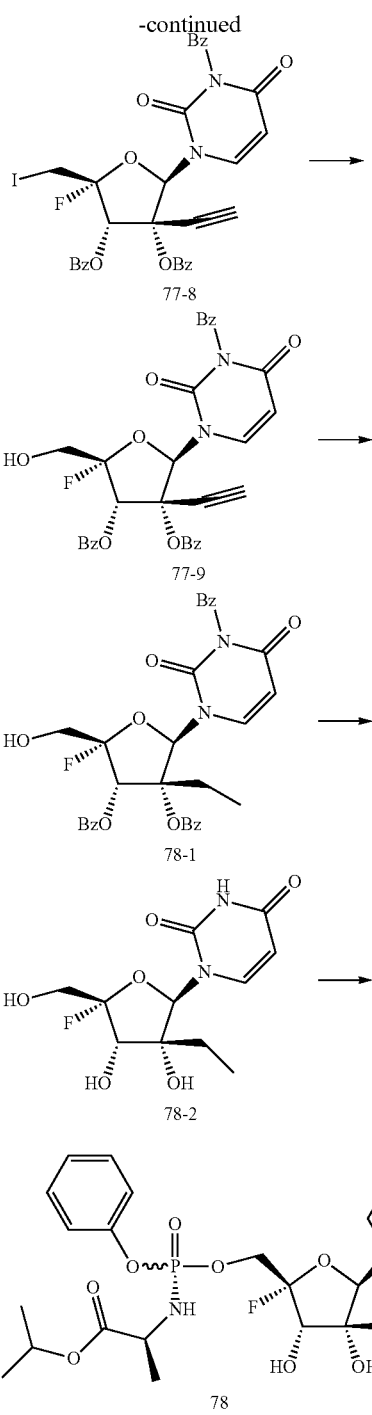

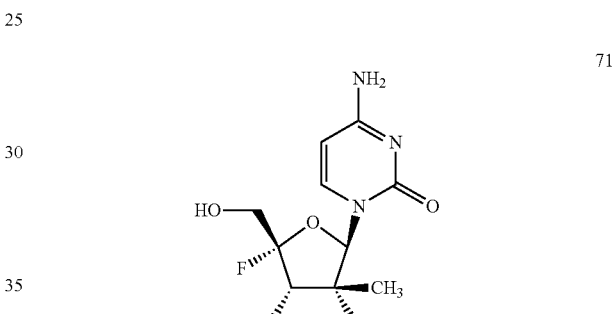

To a solution of 77-9 (300 mg, 0.50 mmol) in MeOH (30 mL) was added wet Pd/C (300 mg, 10%) under $N_2$. The mixture was stirred under H2 (1 atm) at 25° C. for 1.5 h. The suspension was filtered, and then concentrated at low pressure to give crude 78-1 (307 mg) as a white solid.

Compound 78-1 (307 mg, 0.48 mmol) was dissolved in $NH_3$/MeOH (30 mL, 7 M). The mixture was stirred at R.T. for 24 h under $N_2$ then concentrated at low pressure. The residue was purified by prep-HPLC (0.1% HCOOH in water and MeCN) to give 78-2 (30 mg, 21% over two steps) as a white solid.

Compound 78-2 (91 mg, 0.31 mmol) was co-evaporated with toluene 3 times to remove $H_2O$. To a stirred solution of 78-2 (91 mg, 0.31 mmol) in a mixture of MeCN (0.5 mL) and NMI (254 mg, 3.90 mmol) was added a solution 73-C (203 mg, 0.66 mmol) in MeCN (0.5 mL) at 0° C. The mixture was stirred at R.T. overnight and then concentrated at low pressure. The residue was purified on a silica gel column (5% MeOH in DCM) to the crude compound 78, which purified by prep-HPLC (0.1% HCOOH in water and MeCN) to give compound 78 (30 mg, 17%) as a white solid. ESI-MS: m/z 540.1 [M-F]$^+$.

Example 69

Additional Compounds of Formula (I)

The foregoing syntheses are exemplary and can be used as a starting point to prepare a large number of additional compounds. Examples of compounds of Formula (I) that can be prepared in various ways, including those synthetic schemes shown and described herein, are provided below. Those skilled in the art will be able to recognize modifications of the disclosed syntheses and to devise routes based on the disclosures herein; all such modifications and alternate routes are within the scope of the claims.

Example 70

HCV Replicon Assay

Cells

Huh-7 cells containing the self-replicating, subgenomic HCV replicon with a stable luciferase (LUC) reporter were cultured in Dulbecco's modified Eagle's medium (DMEM) containing 2 mM L-glutamine and supplemented with 10% heat-inactivated fetal bovine serum (FBS), 1% penicillin-streptomyocin, 1% nonessential amino acids, and 0.5 mg/mL G418.

Determination of Anti-HCV Activity

Determination of 50% inhibitory concentration ($EC_{50}$) of compounds in HCV replicon cells were performed by the following procedure. On the first day, 5,000 HCV replicon cells were plated per well in a 96-well plate. On the following day, test compounds were solubilized in 100% DMSO to 100× the desired final testing concentration. Each compound was then serially diluted (1:3) up to 9 different concentrations. Compounds in 100% DMSO are reduced to 10% DMSO by diluting 1:10 in cell culture media. The compounds were diluted to 10% DMSO with cell culture media, which were used to dose the HCV replicon cells in 96-well format. The final DMSO concentration was 1%. The HCV replicon cells were incubated at 37° C. for 72 h. At 72 h, cells were processed when the cells are still subconfluent. Compounds that reduce the LUC signal are determined by Bright-Glo Luciferase Assay (Promega, Madison, Wis.). % Inhibition was determined for each compound concentration in relation to the control cells (untreated HCV replicon) to calculate the $EC_{50}$.

Compounds of Formula (I) are active in the replicon assay. The antiviral activity of exemplary compounds is shown in Table 2, where 'A' indicates an $EC_{50}<1$ μM, 'B' indicates an $EC_{50} \geq 1$ μM and <10 μM, and 'C' indicates an $EC_{50} \geq 10$ μM and <100 μM.

TABLE 2

| Compound # | $EC_{50}$ |
| --- | --- |
| 2 | A |
| 3 | A |
| 5 | A |
| 11 | A |
| 13 | B |
| 14 | A |
| 16 | A |
| 17 | A |
| 18 | A |
| 19 | A |
| 20 | A |
| 21 | A |
| 22 | A |
| 27 | C |
| 28 | A |
| 29 | C |
| 30 | A |
| 31 | A |
| 32 | A |
| 33 | A |
| 34 | A |
| 35 | A |
| 36 | A |
| 37 | A |
| 40 | B |
| 41 | B |
| 42 | A |
| 43 | A |
| 49 | A |
| 51 | B |
| 52 | A |
| 53 | A |
| 54 | A |
| 55 | A |
| 56 | A |
| 57 | A |
| 58 | A |
| 59 | C |
| 60 | C |
| 61 | A |
| 62 | A |
| 66 | A |
| 67 | B |
| 70 | B |
| 73 | B |
| 77 | B |
| 79 | A |
| 80 | B |
| 81 | A |
| 83 | A |
| 84 | A |
| 85 | A |
| 86 | A |
| 87 | A |
| 88 | A |
| 89 | A |
| 90 | A |
| 91 | A |

Example 71

NS5B Inhibition Assay

The enzyme activity of NS5B570-Con1 (Delta-21) was measured as an incorporation of tritiated NMP into acid-insoluble RNA products. The complementary IRES (cIRES) RNA sequence was used as a template, corresponding to 377 nucleotides from the 3'-end of HCV (−) strand RNA of the Con-1 strain, with a base content of 21% Ade, 23% Ura, 28% Cyt, and 28% Gua. The cIRES RNA was transcribed in vitro using a T7 transcription kit (Ambion, Inc.) and purified using the Qiagen RNeasy maxi kit. HCV polymerase reactions contained 50 nM NS5B570-Con1, 50 nM cIRES RNA, about 0.5 μCi tritiated NTP, 1 μM of competing cold NTP, 20 mM NaCl, 40 mM Tris-HCl (pH 8.0), 4 mM dithiothreitol, and 4 mM $MgCl_2$. Standard reactions were incubated for 2 h at 37° C., in the presence of increasing concentration of inhibitor. At the end of the reaction, RNA was precipitated with 10% TCA, and acid-insoluble RNA products were filtered on a size exclusion 96-well plate. After washing of the plate, scintillation liquid was added and radio labeled RNA products were detected according to standard procedures with a Trilux Topcount scintillation counter. The compound concentration at which the enzyme-catalyzed rate was reduced by 50% ($IC_{50}$) was calculated by fitting the data to a non-linear regression (sigmoidal). The $IC_{50}$ values were derived from the mean of several independent experiments and are shown in Table 3. Compounds of Formula (I) showed activity in this assay. A value of 'A' in the table below indicates an $IC_{50}$ of <1 μM, a value of '13' indicates an $IC_{50} \geq 1$ μM and <10 μM, and a value of 'C' indicates an $IC_{50}$ value of $\geq 10$ μM and <100 μM.

TABLE 3

| Compound # | $IC_{50}$ |
| --- | --- |
| 6 | A |
| 7a | A |
| 7b | B |
| 9 | A |
| 12 | A |
| 15 | A |
| 26 | A |
| 28 | A |
| 38 | A |
| 44 | A |
| 46 | A |
| 50 | A |
| 63 | A |
| 64 | A |
| 69 | A |
| 76 | A |

Example 72

Assessment of Inhibition of Mitochondrial Function

Drug-associated dysfunction of mitochondria is believed to play a role in the etiology of the various adverse symptoms that occur in patients treated with antiviral nucleoside/nucleotides. For this reason, evaluation of compounds for their potential to inhibit mitochondrial function is useful. To assess the potential for nucleotide/nucleoside analogs to interfere with normal mitochondrial functions and exhibit mitochondrial toxicity, the following were measured: (1) the ability of nucleotides to be incorporated by human mitochondrial RNA polymerase in vitro and (2) the cellular inhibition of the synthesis of the mitochondrial DNA (mtDNA)-encoded protein, cytochrome c oxidase (COX-I), relative to the nuclear DNA (nDNA)-encoded mitochondrial protein succinate dehydrogenase subunit A (SDH-A) in HepG2 cells. Control compounds and compounds of Formula (I) were studied in these assays.

Biochemical Assay

Arnold et al. "Sensitivity of Mitochondrial Transcription and Resistance of RNA Polymerase II Dependent Nuclear Transcription to Antiviral Ribonucleosides" PLoS Pathog (2012) 8(11): e1003030. doi:10.1371/journal.ppat.1003030, which is hereby incorporated by reference in its entirety.

Assessment of Incorporation of Nucleotides by Human Mitochondrial RNA Polymerase (HMRP)

DdRp Assay with Human Mitochondrial RNA Polymerase

The DdRp assay with human mitochondrial RNA polymerase was performed under single turnover conditions where enzyme concentration is in excess of the primer/template. The $^{33}$P-RNA/DNA primer/template was used at a concentration of 100 nM, together with 320 nM enzyme. The standard 10-4, reactions were carried out at 30° C. for 1 minute with 100 μM of each nucleotide 5'-triphosphate (NTP), 10 mM $MgCl_2$, 50 mM NaCl, 40 mM Tris, pH 7.5, and 1 mM DTT. The reaction was stopped by adding 20 μL of formamide loading dye containing 50 mM EDTA. RNA products were resolved by electrophoresis on 22.5% TBE Urea polyacrylamide sequencing gels that were scanned using a TYPHOON PhosphorImager.

Results

As shown in both FIGS. 10 and 11, the appropriate natural nucleotides were shown to be good substrates for incorporation by HMRP in each template. The template in FIG. 10 was designed to measure incorporation of UTP analogs. Primer/Template: (SEQ ID NO: 1) UUUUGCCGCGCC and (SEQ ID NO: 2) GGGAATGCTAGGCGCGGC. In the control water lanes, wherein no nucleotides were added, no incorporation was observed as indicated by the lack of product band. As shown in FIG. 10, UTP and 3'-deoxy-UTP were efficient substrates for incorporation as indicated by the prominent product band. The potential for misincorporation was assessed using the control nucleotide CTP. As provided in FIG. 10, CTP was incorporated to a lesser extent relative to UTP. In contrast to UTP and 3'-deoxy-UTP, compounds of Formula (I) and 2'-Me-2'-F-UTP were not efficient substrates for incorporation by HMRP as demonstrated by the lack of product band.

The template strand shown in FIG. 11 was designed to measure the incorporation of GTP analogs. Primer/Template: (SEQ ID NO: 3) UUUUGCCGCGCC and (SEQ ID NO: 4) GGGAATGCACGGCGCGGC. In the control water lanes, no incorporation was observed as indicated by the lack of product band. GTP and 3'-deoxy-GTP were found to be efficient substrates for incorporation as demonstrated by the significant product bands. The potential for misincorporation was assessed using the control nucleotide ATP. As shown by the lack of product band in FIG. 11, control ATP was a poor substrate for incorporation. Nucleotide analog 2'-Me-GTP (the nucleotide metabolite of monophosphate prodrug INX-0189/BMS-986094) was tested and found to be a good substrate for incorporation by HMRP as indicated by the product band. Nucleotide analog 2'-Me-2'-F-GTP (nucleotide metabolite of monophosphate prodrug GS-938) was tested and also found to be incorporated by HMRP. In contrast, compounds of Formula (I) were not efficient substrates for incorporation into the template strand by HMRP as indicated by the lack of product bands in FIG. 11.

Assessment of Inhibition of Mitochondrial Protein Synthesis—Cell Based Assay

Assay Principle

MitoBiogenesis™ In Cell ELISA kits (Cat. #M5643) were obtained from Mitosciences, OR, USA. The MitoBiogenesis™ In Cell ELISA kit is a duplexing 96 well assay that ratios both an mtDNA and an nDNA encoded mitochondrial protein. Cells were seeded in 96 microplates and after exposure to compounds for several cell doublings, the levels of the two mitochondrial proteins were measured simultaneously in each well. The two proteins assayed were each subunits of different oxidative phosphorylation enzyme complexes, one protein being subunit I of Complex IV (cytochrome c oxidase; COX I) that is mtDNA encoded and the other being the 70 kDa subunit of Complex II (succinate dehydrogenase subunit A; SDH A) that is nDNA encoded. Complex IV includes several proteins that are encoded by the mtDNA while the proteins of Complex II are entirely encoded by nDNA. To control for the density of cells present at the end of the culture period, the number of cells were assessed by staining with Janus Green and the levels of COX I/SDH A normalized to the final cell density.

96 Well Plate Assay Format for HepG2 Cells

On the first day, 1000 HepG2 cells per well were plated in a 96 well plate. On the following day, compounds to be tested were solubilized in 100% DMSO to 100× the desired final testing concentration. Each compound was serially diluted (1:3) up to 9 distinct concentrations. Compounds in 100% DMSO were reduced to 10% (v/v) DMSO by diluting 1:10 in cell culture media. A 10 μL aliquot of the compounds diluted to 10% (v/v) DMSO with cell culture media was used to dose the cells in duplicate. The final DMSO concentration was 1% (v/v). Untreated cells and wells containing no cells were included on the plate to serve as controls. Cells were then incubated with compounds and observed for 8 days at 37° C. and 5% $CO_2$. Plates were processed as described below in the assay procedure.

Batch Assay Format for HepG2 Cells

An alternate cell culture procedure was employed to test the potential to mediate mitochondrial toxicity at higher concentrations than achievable in the 96 well plate format. HepG2 cells were grown either in media/DMSO alone or in a series of compound concentrations in 15 $cm^2$ dishes or 6 well plates at an initial cell seeding density of $5×10^6$ and $5×10^4$ cells/mL, respectively. Cells were then incubated and observed for 8 days at 37° C. and 5% $CO_2$. After 8 days, the cells were harvested by trypsinization, counted, and seeded in 96 well plates at a density of 25,000 cells/well in 16 replicate wells. Cells were allowed to adhere overnight and then the plates were processed as described below in the assay procedure.

Assay Procedure

Figure 12B:
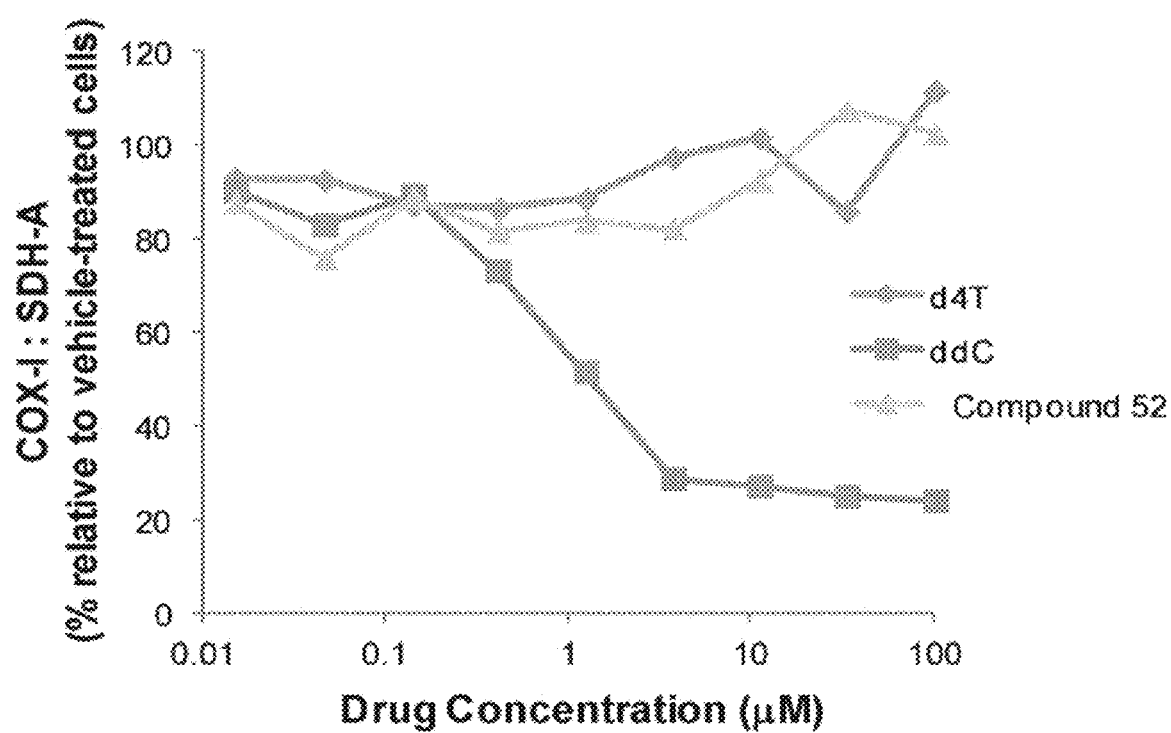
Figure 12C:
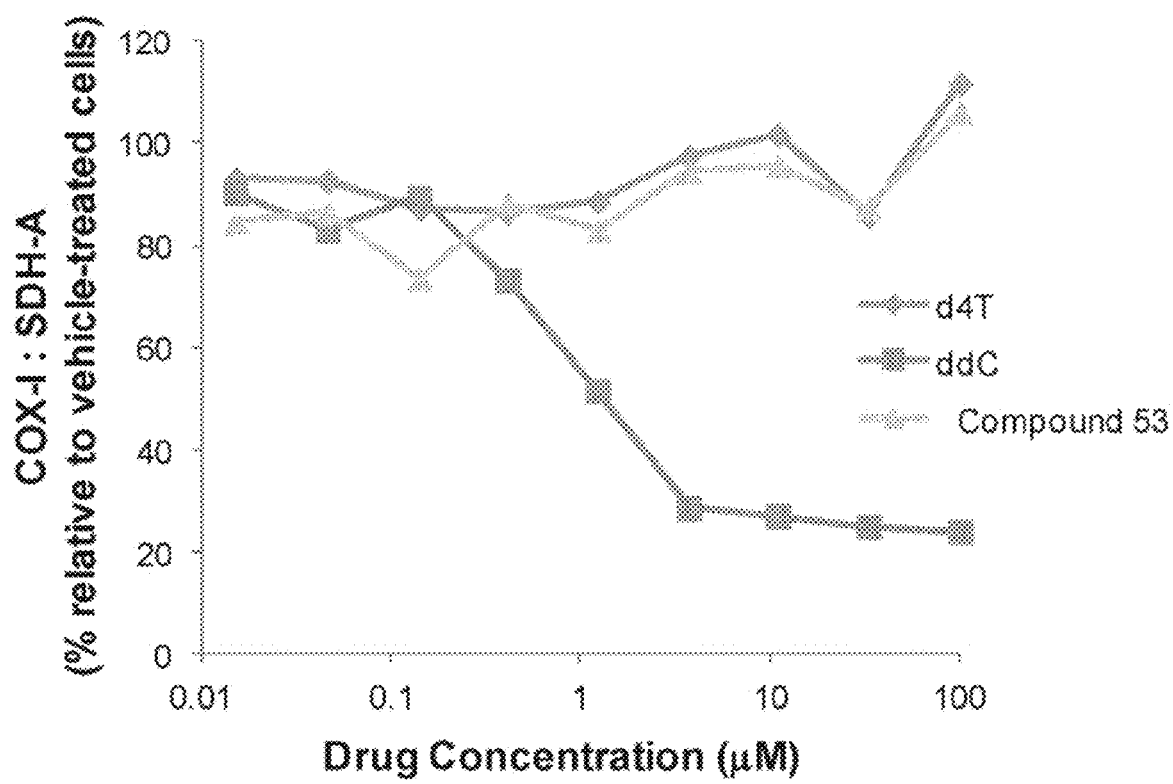
Figure 12D:
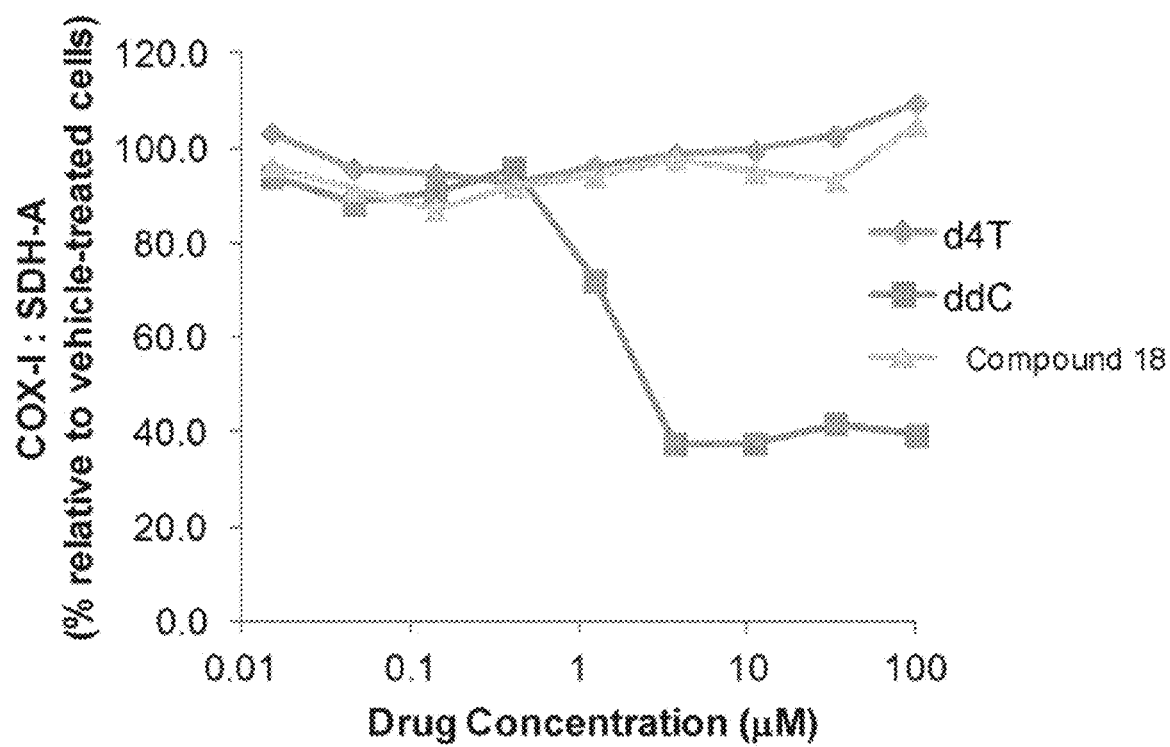

The assay was performed according to the manufacturer's instructions. Briefly, after the end of the culture period the cell culture media was gently aspirated from the wells of the plate and replaced with 100 μL of 4% (v/v) paraformaldehyde solution in phosphate buffered saline (PBS, Electron Microscopy Sciences Cat. #15713). After a 20 mins incubation at R.T., the solution was removed and the wells washed 3× with 300 μL of PBS. After the final wash, the PBS was removed and the wells overlayed with 100 μL PBS. The plates were then sealed and stored at 4° C. until used. To perform the assay, the PBS overlay was removed by blotting on a paper towel and 100 μL of 0.5% (v/v) acetic acid added to each well to block endogenous alkaline phosphatase activity. After a 5 mins incubation at R.T., the acetic acid solution was removed and the cells washed once with 200 μL PBS. Then, 100 μL of permeabilization buffer (0.1% (v/v) Triton X 100) was added to each well. After 30 mins incubation at R.T., the permeabilization buffer was removed and each well was blocked with 200 μL of 2× blocking solution for 2 h at R.T. The 2× blocking solution was then removed and 100 μL of primary antibody solution containing anti COX I and anti SDH A antibodies in 1× blocking solution was added to each well. Plates were then sealed and incubated overnight at 4° C. The primary antibody/blocking solution was removed and the plate washed 3× with 250 μL 0.05% (v/v) Tween 20 in PBS. Then, 100 μL of secondary antibody solution containing alkaline phosphatase (AP) labeled anti SDH A antibody and horseradish peroxidase (HRP) labeled anti COX I antibody was added and incubated for 1 h at R.T. The plate was then washed 4× with 250 μL 0.05% (v/v) Tween 20 in PBS. After blotting the plate dry 100 μL of AP detection reagent was added to each well, and the plate incubated in the dark for 30 mins at R.T. The optical density of each well was then measured at 405 nm. The AP detection reagent was then removed and replaced with 100 μL of HRP detection reagent, and the plate incubated in the dark for a further 30 mins at R.T. The optical density of each well was then measured at 600 nm. The HRP detection reagent was then removed and each well was then stained with 50 μL of 1× Janus Green Stain for 5 mins at R.T. After removal of the dye, the plates were washed 5× in ultrapure water to remove any remaining dye. The Janus Green stain was then solubilized by the addition of 100 μL of 0.5 M HCl and incubated for 10 mins. The optical density of each well was then measured at 595 nm.
Data Analysis The average of all replicate background measurements from each experimental condition was calculated and subtracted from the experimental values of the same condition. The SDH A and COX I signals were then plotted as a ratio (COX I/SDH A) and normalized to the Janus Green staining intensity to correct for differences in cell density.
Results Control compound d4T was tested and found not to inhibit mitochondrial protein synthesis at concentrations up to 100 μM as shown in FIGS. 12A-D. Control compound ddC was tested and found to strongly inhibit mitochondrial protein synthesis. See FIGS. 12A-D. As demonstrated in FIG. 12A, nucleoside monophosphate prodrug INX-08189/BMS-986094 (which delivers 2'-Me-GTP) was tested in the assay and found to strongly inhibit mitochondrial protein synthesis. In contrast, compounds of Formula (I) were tested and found to not inhibit mitochondrial protein synthesis at concentrations up to 100 μM as shown in FIGS. 12B-D.

Example 73

Combination of Compounds

Combination Testing

Two or more test compounds were tested in combination with each other using an HCV genotype 1b HCV replicon harbored in Huh7 cells with a stable luciferase (LUC) reporter. Cells were cultured under standard conditions in Dulbecco's modified Eagle's medium (DMEM; Mediatech Inc, Herndon, Va.) containing 10% heat-inactivated fetal bovine serum (FBS; Mediatech Inc, Herndon, Va.) 2 mM L-glutamine, and nonessential amino acids (JRH Biosciences). HCV replicon cells were plated in a 96-well plate at a density of $10^4$ cells per well in DMEM with 10% FBS. On the following day, the culture medium was replaced with DMEM containing either no compound as a control, the test compounds serially diluted in the presence of 2% FBS and 0.5% DMSO, or a combination of compound 18 with one or more test compounds serially diluted in the presence of 2% FBS and 0.5% DMSO. The cells were incubated with no compound as a control, with the test compounds, or the combination of compounds for 72 h. The direct effects of the combination of the test compounds were examined using a luciferase (LUC) based reporter as determined by the Bright-Glo Luciferase Assay (Promega, Madison, Wis.). Dose-response curves were determined for individual compounds and fixed ratio combinations of two or more test compounds.

The method utilized for evaluating combination effects used a program called MacSynergy II. MacSynergy II software was kindly provided by Dr. M. Prichard (University of Michigan). The Prichard Model allows for a three-dimensional examination of drug interactions and a calculation of the synergy volume (units: μMN) generated from running the replicon assay using a checkerboard combination of two or more inhibitors. The volumes of synergy (positive volumes) or antagonism (negative volumes) represent the relative quantity of synergism or antagonism per change in the concentrations of the two drugs. Synergy and antagonism volumes are defined based on the Bliss independence model. In this model, synergy volumes of less than −25 indicate antagonistic interactions, volumes in the −25-25 range indicate additive behavior, volumes in the 25-100 range indicate synergistic behavior and volumes >100 indicate strong synergistic behavior. Determination of in vitro additive, synergistic and strongly synergistic behavior for combinations of compounds can be of utility in predicting therapeutic benefits for administering the combinations of compounds in vivo to infected patients.

The synergy volume results for the combinations are provided in Table 4.

TABLE 4

| Combination Compound | Synergy Volume ($\mu m^2$ %) | Determination |
|---|---|---|
| ANA-598 (3002) | 29.46 | Synergistic |
| HCV-796 (3004) | 81.72 | Synergistic |
| Ribavirin (5012) | 6.77 | Additive |
| Filibuvir (3007) | 23.51 | Additive |
| VX-222 (3003) | 32.35 | Synergistic |
| BMS-790052 (4001) | 38.01 | Synergistic |
| VX-950 (1001) | 32.28 | Synergistic |
| TMC-435 (1013) | 97.17 | Synergistic |

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A pharmaceutical composition comprising a compound of Formula (I), or a pharmaceutically acceptable salt thereof, having the structure:

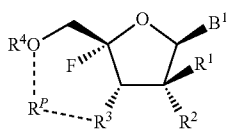
(I)

wherein:

$B^1$ is selected from the group consisting of

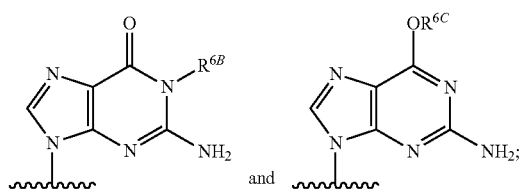
and $R^1$ is selected from the group consisting of an unsubstituted $C_{1-6}$ alkyl and an unsubstituted $C_{2-6}$ alkynyl;
each -------- is absent;
$R^2$ is fluoro;
$R^P$ is absent;
$R^3$ is OH;
$R^4$ is hydrogen or

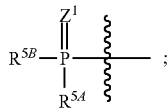
;

$R^{5A}$ is selected from the group consisting of OH,

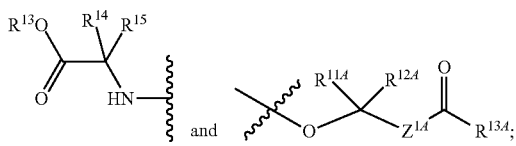

$R^{5B}$ is selected from the group consisting of an OH, —O-unsubstituted phenyl, —O-unsubstituted naphthyl,

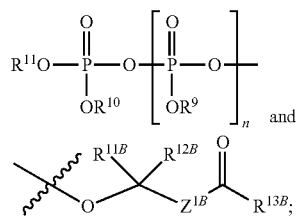

$R^{6B}$ and $R^{6C}$ are each independently selected from the group consisting of hydrogen and an unsubstituted $C_{1-6}$ alkyl;

$R^{11A}$, $R^{12A}$, $R^{11B}$ and $R^{12B}$ are each hydrogen;
$R^{13}$ is selected from the group consisting of an unsubstituted $C_{1-6}$ alkyl and an unsubstituted $C_{3-6}$ cycloalkyl;
$R^{14}$ and $R^{15}$ are each independently selected from the group consisting of hydrogen and an unsubstituted $C_{1-6}$ alkyl;
$R^{13A}$ and $R^{13B}$ are each an unsubstituted —O—$C_{1-4}$ alkyl;
n is 0 or 1;
$R^9$, $R^{10}$ and $R^{11}$ are each hydrogen; and
$Z^1$, $Z^{1A}$ and $Z^{1B}$ are each O,
and a pharmaceutically acceptable carrier, diluent, excipient or combination thereof.

2. The pharmaceutical composition of claim 1, wherein $R^1$ is an unsubstituted $C_{1-6}$ alkyl.

3. The pharmaceutical composition of claim 1, wherein $R^1$ is methyl.

4. The pharmaceutical composition of claim 1, wherein $R^1$ is ethynyl.

5. The pharmaceutical composition of claim 1, wherein $R^4$ is hydrogen.

6. The pharmaceutical composition of claim 1, wherein $R^4$ is

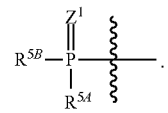
.

7. The pharmaceutical composition of claim 6, wherein $R^{5B}$ is an —O-unsubstituted phenyl; and $R^{5A}$ is

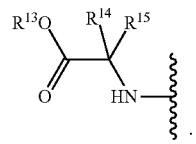
.

8. The pharmaceutical composition of claim 6, wherein $R^{5A}$ is

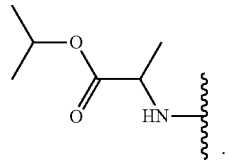 [SMILES: *NC(C)C(=O)OC(C)C]
.

9. The pharmaceutical composition of claim 6, wherein $R^{5A}$ is

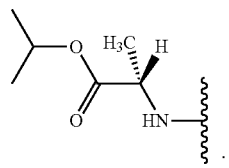 [SMILES: *N[C@@H](C)C(=O)OC(C)C]
.

10. The pharmaceutical composition of claim 6, wherein $R^{5A}$ is

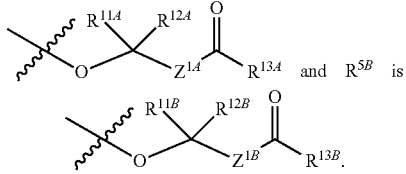

and $R^{5B}$ is

11. The pharmaceutical composition of claim 10, wherein $R^{13A}$ and $R^{13B}$ are each —O-isopropyl.

12. The pharmaceutical composition of claim 1, wherein $B^1$ is

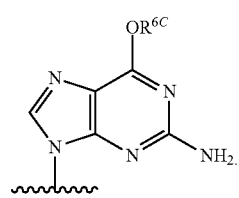

13. The pharmaceutical composition of claim 1, wherein $R^{6C}$ is ethyl.

14. The pharmaceutical composition of claim 1, wherein the compound of Formula (I), or a pharmaceutically acceptable salt thereof, has a structure selected from the group consisting of:

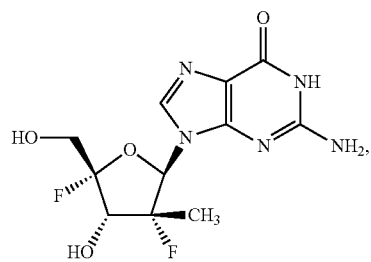

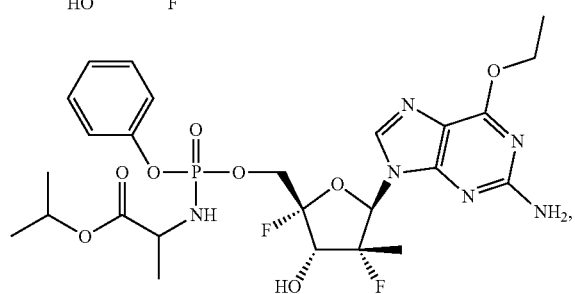

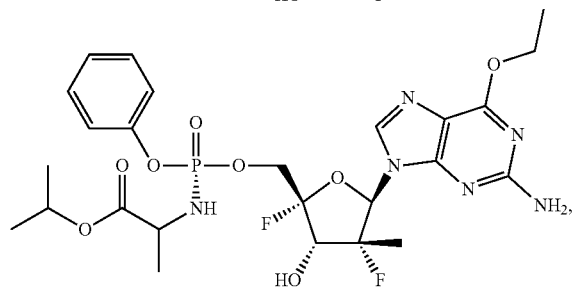

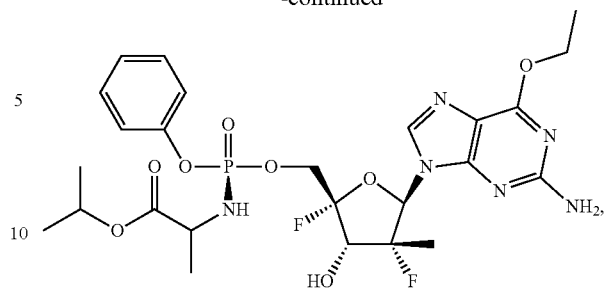

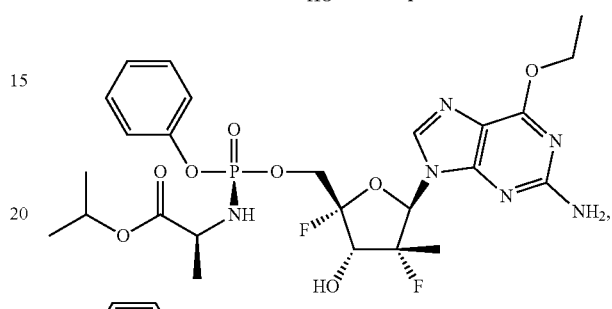

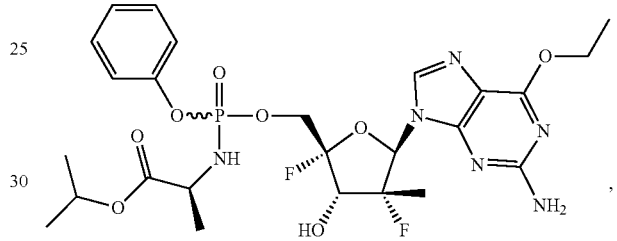

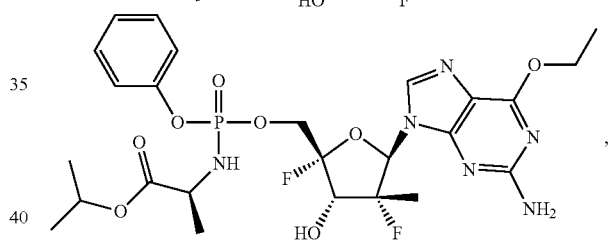

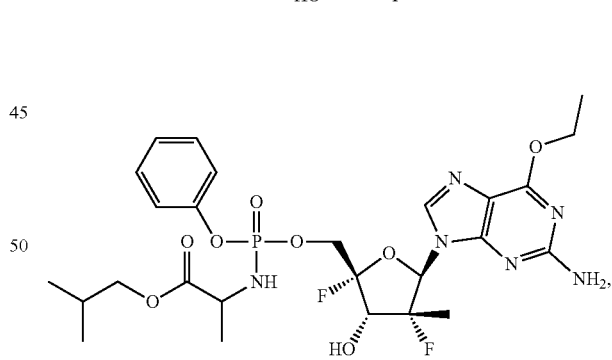

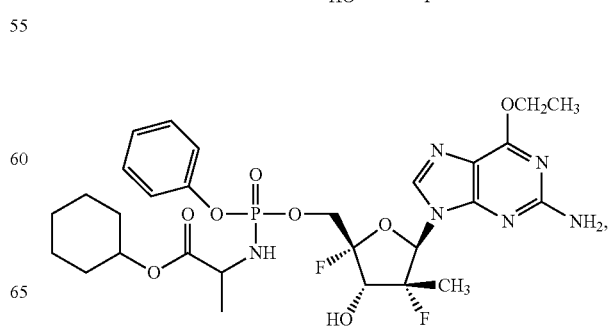

-continued

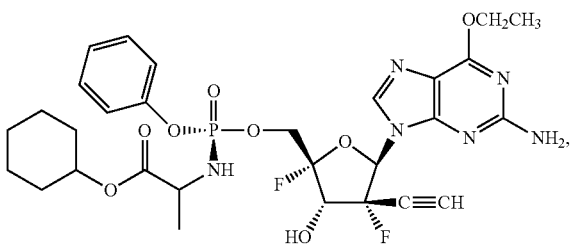

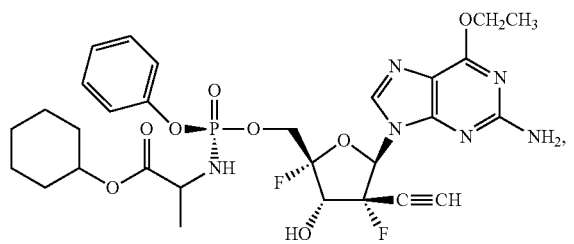

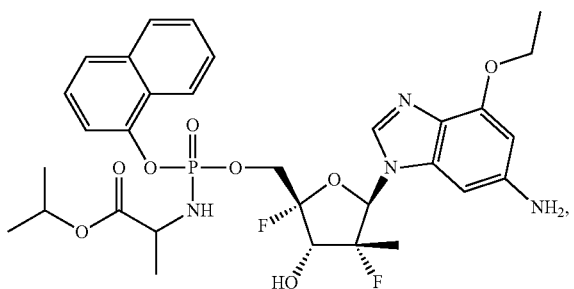

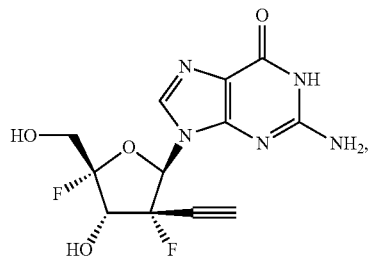

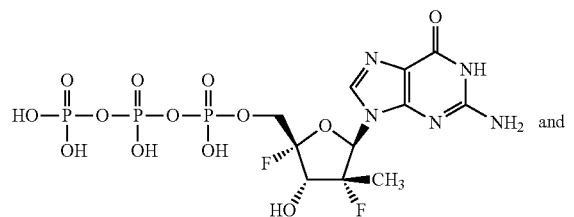

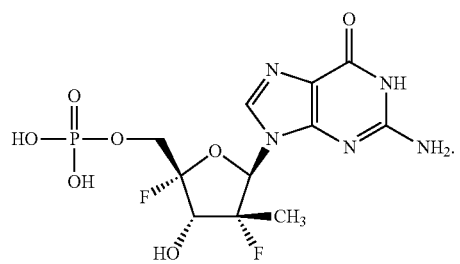

15. The pharmaceutical composition of claim 1, wherein the compound of Formula (I), or a pharmaceutically acceptable salt thereof, has the structure

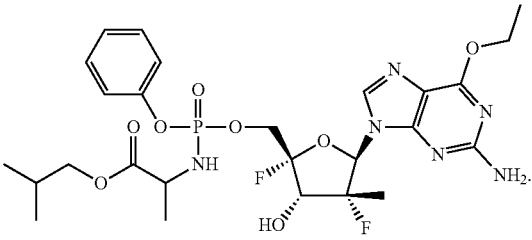 [SMILES: CCOc1nc(N)nc2c1ncn2[C@@H]1O[C@](F)(COP(=O)(NC(C)C(=O)OCC(C)C)Oc2ccccc2)[C@@H](O)[C@@]1(C)F]

16. The pharmaceutical composition of claim 1, wherein the compound of Formula (I), or a pharmaceutically acceptable salt thereof, has the structure

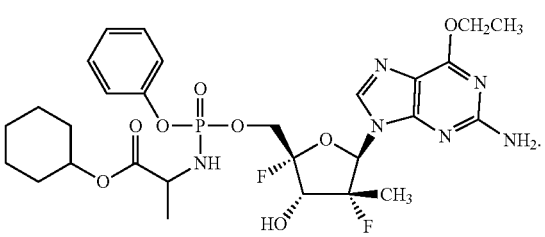 [SMILES: CCOc1nc(N)nc2c1ncn2[C@@H]1O[C@](F)(COP(=O)(NC(C)C(=O)OC2CCCCC2)Oc2ccccc2)[C@@H](O)[C@@]1(C)F]

17. The pharmaceutical composition of claim 1, wherein the compound of Formula (I), or a pharmaceutically acceptable salt thereof, has a structure selected from the group consisting of:

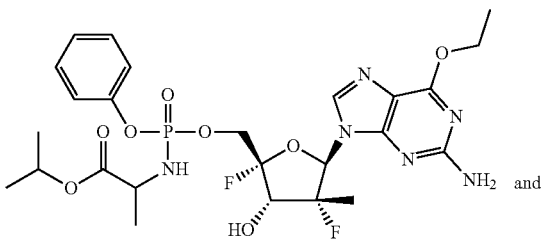

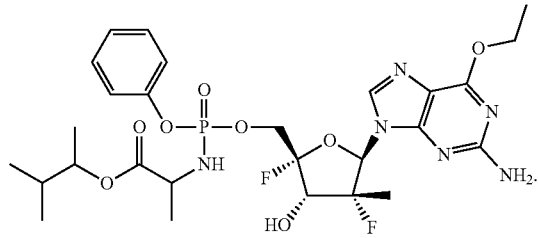

18. The pharmaceutical composition of claim 1, wherein the compound of Formula (I), or a pharmaceutically acceptable salt thereof, has a structure selected from the group consisting of:

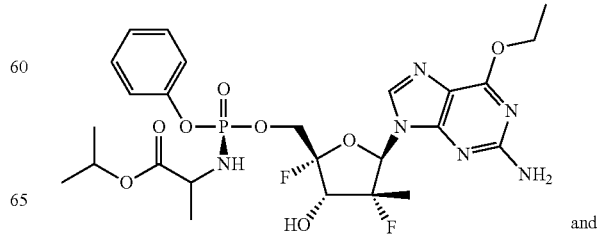

and

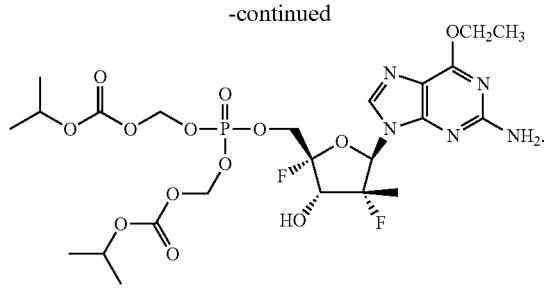
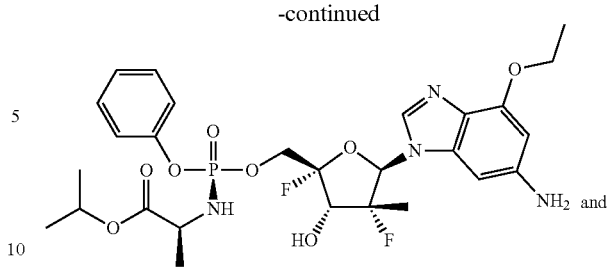
19. The pharmaceutical composition of claim 1, wherein the compound of Formula (I), or a pharmaceutically acceptable salt thereof, has a structure selected from the group consisting of:
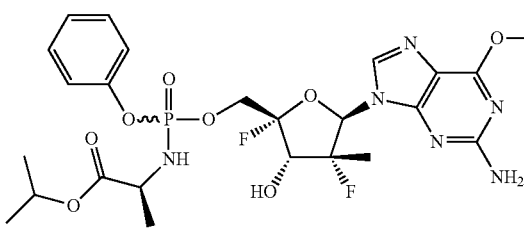,
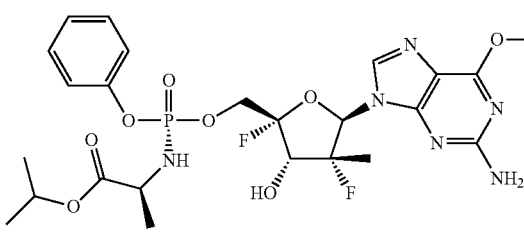,
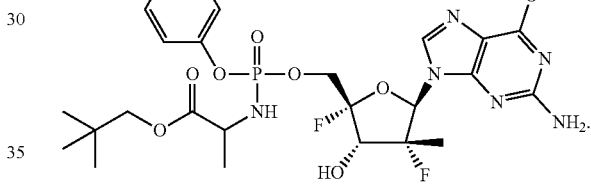,
20. The pharmaceutical composition of claim 1, wherein the compound of Formula (I), or a pharmaceutically acceptable salt thereof, has the structure
* * * * *